United States Patent
Vlahov et al.

(10) Patent No.: US 10,624,972 B2
(45) Date of Patent: Apr. 21, 2020

(54) CONJUGATES FOR TREATING DISEASES

(71) Applicant: ENDOCYTE, INC., West Lafayette, IN (US)

(72) Inventors: Iontcho Radoslavov Vlahov, West Lafayette, IN (US); Christopher Paul Leamon, West Lafayette, IN (US); Longwu Qi, West Lafayette, IN (US); Yingcai Wang, West Lafayette, IN (US); Kevin Yu Wang, Zionsville, IN (US); Ning Zou, West Lafayette, IN (US); Albert E. Felten, Lafayette, IN (US)

(73) Assignee: Endocyte, Inc., West Lafayette, IN (US)

( * ) Notice: Subject to any disclaimer, the term of this patent is extended or adjusted under 35 U.S.C. 154(b) by 0 days.

(21) Appl. No.: 15/557,703

(22) PCT Filed: Mar. 13, 2015

(86) PCT No.: PCT/US2015/020397
§ 371 (c)(1),
(2) Date: Sep. 12, 2017

(87) PCT Pub. No.: WO2016/148674
PCT Pub. Date: Sep. 22, 2016

(65) Prior Publication Data
US 2018/0228914 A1 Aug. 16, 2018

(51) Int. Cl.
*A61K 47/65* (2017.01)
*A61K 47/55* (2017.01)

(52) U.S. Cl.
CPC ............ *A61K 47/65* (2017.08); *A61K 47/551* (2017.08)

(58) Field of Classification Search
None
See application file for complete search history.

(56) References Cited

U.S. PATENT DOCUMENTS

| | | | |
|---|---|---|---|
| 4,691,024 A | 9/1987 | Kunikatsu et al. | |
| 5,672,486 A | 9/1997 | Soulillou | |
| 6,106,864 A | 8/2000 | Dolan et al. | |
| 6,548,505 B1 | 4/2003 | Martin et al. | |
| 7,601,332 B2 | 10/2009 | Vlahov et al. | |
| 9,138,484 B2 | 9/2015 | Leamon et al. | |
| 9,549,992 B2 | 1/2017 | Leamon et al. | |
| 2006/0019911 A1 | 1/2006 | Papisov | |
| 2010/0074863 A1 | 3/2010 | Wang et al. | |
| 2012/0238731 A1* | 9/2012 | Fishkin | C07K 16/30 530/391.9 |
| 2013/0028917 A1 | 1/2013 | Howard et al. | |
| 2013/0267522 A1* | 10/2013 | Knapp | A61K 31/519 514/249 |
| 2014/0088089 A1 | 3/2014 | Chari | |
| 2015/0315196 A1 | 11/2015 | Howard et al. | |

FOREIGN PATENT DOCUMENTS

| | | |
|---|---|---|
| WO | WO1991007418 | 5/1991 |
| WO | WO1991011172 | 8/1991 |
| WO | WO1994002518 | 2/1994 |
| WO | WO1998055148 | 12/1998 |
| WO | WO2000035298 | 6/2000 |
| WO | WO2000012507 | 8/2000 |
| WO | WO2008098368 | 8/2008 |
| WO | WO2011/130598 | 10/2011 |
| WO | WO2011130598 | 10/2011 |
| WO | WO2011146707 | 11/2011 |
| WO | WO2014/062697 | 4/2014 |
| WO | WO2014/078484 | 5/2014 |
| WO | WO2014078484 | 5/2014 |
| WO | WO2014062697 | 6/2014 |
| WO | WO2016040723 | 3/2016 |
| WO | WO2016085967 | 6/2016 |
| WO | WO2016148674 | 9/2016 |
| WO | WO2017172930 | 10/2017 |

OTHER PUBLICATIONS

Tyagi et al. ("Binding of an indole alkaloid, vinblastine to double stranded DNA: A spectroscopic insight in to nature and strength of interaction," Journal of Photochemistry and Photobiology B: Biology 108 (2012) 48-52) (Year: 2012).*
PCT Search Report and Written Opinion for PCT/US2015/020397, dated May 9, 2015.
D. E. Thurston and D. S. Bose, *Chem. Rev.*, 1994, 94, 433-465.
W. Leimgruber, V. Stefanovié, F. Schenker, A. Karr and J. Berger, *J. Am. Chem. Soc.*, 1965, 87, 5791-5793.
M. D. Tendler and S. Korman, *Nature*, 1963, 199, 501.
J. Mantaj, P. J. M. Jackson, K. M. Rahman and D. E. Thurston, *Angew. Chem. Int. Ed*, 2017, 56, 462-488.
J. Mantaj, P. J. M. Jackson, K. Karu, K. M. Rahman and D. E. Thurston, *PLoS ONE*, 2016, 11, e0152303.
K. M. Rahman, D. B. Corcoran, T. T. T. Bui, P. J. M. Jackson and D. E. Thurston, *PLoS ONE*, 2014, 9, e105021.
M. L. Kopka, D. S. Goodsell, I. Baikalov, K. Grzeskowiak, D. Cascio and R. E. Dickerson, *Biochemistry*, 1994, 33, 13593-13610.
J. A. Hartley and D. Hochhauser, *Curr. Opin. in Pharmacol.*, 2012, 12, 398-402.
D. Antonow and D. E. Thurston, *Chem. Rev.*, 2011, 111, 2815-2864.
I. R. Vlahov, S. Hahn, K. Wang, H. K. R. Santhapuram, A. Felten, J. Vaughn and C. Leamon, From Abstracts of Papers, 252nd ACS National Meeting & Exposition, Philadelphia, PA, United States, 2016, MEDI-39.

(Continued)

*Primary Examiner* — Christina Bradley
(74) *Attorney, Agent, or Firm* — Barnes & Thornburg, LLP

(57) ABSTRACT

The present disclosure relates to pyrrolobenzodiazepine (PBD) prodrugs and conjugates thereof. The present disclosure also relates to pharmaceutical compositions of the conjugates described herein, methods of making and methods of using the same.

25 Claims, 3 Drawing Sheets
Specification includes a Sequence Listing.

(56) References Cited

OTHER PUBLICATIONS

I. R. Saunders, A. J. Bankovich, W. C. Anderson, M. A. Aujay, S. Bheddah, K. Black, R. Desai, P. A. Escarpe, J. Hampl, A. Laysang, D. Liu, J. Lopez-Molina, M. Milton, A. Park, M. A. Pysz, H. Shao, B. Slingerland, M. Torgov, S. A. Williams, O. Foord, P. Howard, J. Jassem, A. Badzio, P. Czapiewski, D. H. Harpole, A. Dowlati, P. P. Massion, W. D. Travis, M. C. Pietanza, J. T. Poirier, C. M. Rudin, R. A. Stull and S. J. Dylla, *Sci. Transl. Med.*, 2015, 7, 302ra136.
S. C. Jeffrey, P. J. Burke, R. P. Lyon, D. W. Meyer, D. Sussman, M. Anderson, J. H. Hunter, C. I. Leiske, J. B. Miyamoto, N. D. Nicholas, N. M. Okeley, R. J. Sanderson, I. J. Stone, W. Zeng, S. J. Gregson, L. Masterson, A. C. Tiberghien, P. W. Howard, D. E. Thurston, C.-L. Law and P. D. Senter, *Bioconjugate Chem.*, 2013, 24, 1256-1263.
A. C. Tiberghien, J.-N. Levy, L. A. Masterson, N. V. Patel, L. R. Adams, S. Corbett, D. G. Williams, J. A. Hartley and P. W. Howard, Med. Chem. Lett, 2016, 7, 983-987.
M. J. Sagnou, P. W. Howard, S. J. Gregson, E. Eno-Amooquaye, P. J. Burke and D. E. Thurston, *Bioorg. Med. Chem. Lett.*, 2000, 10, 2083-2086.
M. P. VanBrunt, K. Shanebeck, Z. Caldwell, J. Johnson, P. Thompson, T. Martin, H. F. Dong, G. R. Li, H. Y. Xu, F. D'Hooge, L. Masterson, P, Bariola, A. Tiberghien, E. Ezeadi, D. G. Williams, J. A. Hartley, P. W. Howard, K. H. Grabstein, M. K. Bowen and M. Marelli, *Bioconjugate Chem.*, 2015, 26, 2249-2260.
S. C. Jeffrey, J. B. Andreyka, S. X. Bemhardt, K. M. Kissler, T. Kline, J. S. Lenox, R. F. Moser, M. T. Nguyen, N. M. Okeley, I. J. Stone, X. Zhang and P. D. Senter, *Bioconjugate Chem.*, 2006, 17, 831-840.
S. C. Jeffrey, M. T. Nguyen, J. B. Andreyka, D. L. Meyer, S. O. Doronina and P. D. Senter, *Bioorg. Med. Chem. Lett.*, 2006, 16, 358-362.
M. Tanaka, S. Oishi, H. Ohno and N. Fujii, *Int. J. Pept. Res. Ther.*, 2007, 13, 271-279.
I. R. Vlahov, H. K. Santhapuram, P. J. Kleindl, S. J. Howard, K. M. Stanford and C. P. Leamon, *Bioorg. Med. Chem. Lett.*, 2006, 16, 5093-5096.
I. R. Vlahov, F. You and P. J. Kleindl, in *Encyclopedia of Reagents for Organic Synthesis*, ed. P. L. Fuchs, John Wiley & Sons, Ltd, New Jersey, 2001, pp. 1-6.
I. R. Vlahov, H. K. R. Santhapuram, F. You, Y. Wang, P. J. Kleindl, S. J. Hahn, J. F. Vaughn, D. S. Reno and C. P. Leamon, *J. Org. Chem.*, 2010, 75, 3685-3691.
M. L. Miller, N. E. Fishkin, W. Li, K. R. Whiteman, Y. Kovtun, E. E. Reid, K. E. Archer, E. K. Maloney, C. A. Audette, M. F. Mayo, A. Wilhelm, H. A. Modafferi, R. Singh, J. Pinkas, V. Goldmacher, J. M. Lambert and R. V. J. Chari, *Mol. Cancer Ther.*, 2016, 15, 1870-1878.
A. Kamal, G. Ramesh, O. Srinivas, P. Ramulu, N. Laxman, T. Rehana, M. Deepak, M. S. Achary and H. A. Nagarajaram, *Bioorg. Med Chem.*, 2004, 12, 5427-5436.
M. Oh, J.-H. Jang, S.-J. Choo, S.-O. Kim, J. W. Kim, S.-K. Ko, N.-K. Soung, J.-S. Lee, C.-J. Kim, H. Oh, Y.-S. Hong, M. Ueki, H. Hirota, H. Osada, B. Y. Kim and J. S. Ahn, *Bioorg. Med. Chem. Lett.*, 2014, 24, 1802-1804.
A. Kamal, M. V. Rao and B. Satyanarayana Reddy, *Chem. Heterocycl. Compd.*, 1998, 34, 1342-1358.
K. D. Harshman and P. B. Dervan, *Nucleic Acids Res.*, 1985, 13, 4825-4835.
D. K. Kolmel and E. T. Kool, *Chem. Rev.*, 2017, 117, 10358-10376.
Melby, E.L., *Cancer Res.*, 53(8), pp. 1755-1760.
Boger, D. L.; Hughes, T. V.; Hedrick, H. P. *J. Org. Chem.* 2001, 66, 2207-2216.
Wang, Y.; Li, L.; Tian, Z.; Jiang, W.; Larrick, J. W. *Bioorg. Med Chem.* 2006, 19, 7854-7861.
Lee et al., "BMS-247550: a novel epothilone analog with a mode of action similar to paclitaxel but possessing superior antitumor efficacy" *Clin Cancer Res* 7:1429-1437 (2001).

* cited by examiner

```
                         SEQUENCE LISTING

<160> NUMBER OF SEQ ID NOS: 5

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N5-((2S,3R,4R,5R)-2,3,4,5,6-pentahydroxyhexyl)
      -L-glutamine
<220> FEATURE:
<221> NAME/KEY: MOD_RES
<222> LOCATION: (3)..(3)
<223> OTHER INFORMATION: N5-((2S,3R,4R,5R)-2,3,4,5,6-pentahydroxyhexyl)
      -L-glutamine
<220> FEATURE:
<221> NAME/KEY: MOD_RES
<222> LOCATION: (5)..(5)
<223> OTHER INFORMATION: N5-((2S,3R,4R,5R)-2,3,4,5,6-pentahydroxyhexyl)
      -L-glutamine

<400> SEQUENCE: 1

Gln Glu Gln Glu Gln Cys
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Arg Asp Asp Cys
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: (S,E)-2-amino-3-(4-(1-(2-(6-(2,5-dioxo-2,5-
      dihydro-1H-pyrrol-1-yl)hexanoyl)hydrazineylidene)ethyl)
      phenyl)propanoic acid

<400> SEQUENCE: 3

Asp Glu Xaa Asp Cys
```

```
<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: (S)-3-(4-acetylphenyl)-2-aminopropanoic acid

<400> SEQUENCE: 4

Asp Glu Xaa Asp Cys
1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Arg Asp Asp
1
```

CONJUGATES FOR TREATING DISEASES

CROSS REFERENCE TO RELATED APPLICATIONS

This application is a U.S. national stage application under 35 U.S.C. § 371(b) of International Application No. PCT/US2015/020397 filed Mar. 13, 2015, the disclosure of Change(s) which is hereby incorporated herein by reference.

SEQUENCE LISTING

The instant application contains a Sequence Listing which has been submitted electronically in ASCII format and is hereby incorporated by reference in its entirety. Said ASCII copy, created on Apr. 26, 2018, is named 20150-269425 SL.txt and is 1,852 bytes in size.

TECHNICAL FIELD

The present disclosure relates to pyrrolobenzodiazepine (PBD) prodrugs and conjugates thereof. The present disclosure also relates to pharmaceutical compositions of the conjugates described herein, methods of making and methods of using the same.

BACKGROUND

The mammalian immune system provides a means for the recognition and elimination of pathogenic cells, such as tumor cells, and other invading foreign pathogens. While the immune system normally provides a strong line of defense, there are many instances where pathogenic cells, such as cancer cells, and other infectious agents evade a host immune response and proliferate or persist with concomitant host pathogenicity. Chemotherapeutic agents and radiation therapies have been developed to eliminate, for example, replicating neoplasms. However, many of the currently available chemotherapeutic agents and radiation therapy regimens have adverse side effects because they lack sufficient selectivity to preferentially destroy pathogenic cells, and therefore, may also harm normal host cells, such as cells of the hematopoietic system, and other non-pathogenic cells. The adverse side effects of these anticancer drugs highlight the need for the development of new therapies selective for pathogenic cell populations and with reduced host toxicity.

Researchers have developed therapeutic protocols for destroying pathogenic cells by targeting cytotoxic compounds to such cells. Many of these protocols utilize toxins conjugated to antibodies that bind to antigens unique to or overexpressed by the pathogenic cells in an attempt to minimize delivery of the toxin to normal cells. Using this approach, certain immunotoxins have been developed consisting of antibodies directed to specific antigens on pathogenic cells, the antibodies being linked to toxins such as ricin, *Pseudomonas* exotoxin, Diptheria toxin, and tumor necrosis factor. These immunotoxins target pathogenic cells, such as tumor cells, bearing the specific antigens recognized by the antibody (Olsnes, S., *Immunol. Today*, 10, pp. 291-295, 1989; Melby, E. L., *Cancer Res.*, 53(8), pp. 1755-1760, 1993; Better, M. D., PCT Publication Number WO 91/07418, published May 30, 1991).

Another approach for targeting populations of pathogenic cells, such as cancer cells or foreign pathogens, in a host is to enhance the host immune response against the pathogenic cells to avoid the need for administration of compounds that may also exhibit independent host toxicity. One reported strategy for immunotherapy is to bind antibodies, for example, genetically engineered multimeric antibodies, to the surface of tumor cells to display the constant region of the antibodies on the cell surface and thereby induce tumor cell killing by various immune-system mediated processes (De Vita, V. T., *Biologic Therapy of Cancer*, 2d ed. Philadelphia, Lippincott, 1995; Soulillou, J. P., U.S. Pat. No. 5,672,486). However, these approaches have been complicated by the difficulties in defining tumor-specific antigens.

Folate plays important roles in nucleotide biosynthesis and cell division, intracellular activities which occur in both malignant and certain normal cells. The folate receptor has a high affinity for folate, which, upon binding the folate receptor, impacts the cell cycle in dividing cells. As a result, folate receptors have been implicated in a variety of cancers (e.g., ovarian, endometrial, lung and breast) which have been shown to demonstrate high folate receptor expression. In contrast, folate receptor expression in normal tissues is limited (e.g., kidney, liver, intestines and placenta). This differential expression of the folate receptor in neoplastic and normal tissues makes the folate receptor an ideal target for small molecule drug development. The development of folate conjugates represents one avenue for the discovery of new treatments that take advantage of differential expression of the folate receptor. There is a great need for the development of folate conjugates, methods to identify folate receptor positive cancers, and methods to treat patients with folate receptor positive cancers.

SUMMARY

In one aspect, the present disclosure provides conjugates comprising a binding ligand, a linker and a drug, having the formula

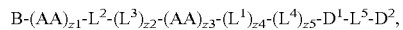

$$B\text{-}(AA)_{z1}\text{-}L^2\text{-}(L^3)_{z2}\text{-}(AA)_{z3}\text{-}(L^1)_{z4}\text{-}(L^4)_{z5}\text{-}D^1\text{-}L^5\text{-}D^2,$$

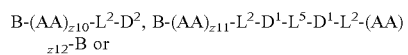

$$B\text{-}(AA)_{z10}\text{-}L^2\text{-}D^2, B\text{-}(AA)_{z11}\text{-}L^2\text{-}D^1\text{-}L^5\text{-}D^1\text{-}L^2\text{-}(AA)_{z12}\text{-}B \text{ or}$$

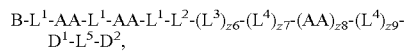

$$B\text{-}L^1\text{-}AA\text{-}L^1\text{-}AA\text{-}L^1\text{-}L^2\text{-}(L^3)_{z6}\text{-}(L^4)_{z7}\text{-}(AA)_{z8}\text{-}(L^4)_{z9}\text{-}D^1\text{-}L^5\text{-}D^2,$$

wherein each of B, AA, $L^1$, $L^2$, $L^3$, $L^4$, $L^5$, $D^1$, $D^2$, z1, z2, z3, z4, z5, z6, z7, z8, z9, z10, z11 and z12 are defined as described herein; or a pharmaceutically acceptable salt thereof.

In another aspect, the disclosure provides pharmaceutical compositions comprising a therapeutically effective amount of the conjugates described herein, or a pharmaceutically acceptable salt thereof, and at least on excipient.

In another aspect, the disclosure provides a method of treating abnormal cell growth in a mammal, including a human, the method comprising administering to the mammal any of the conjugates or compositions described herein.

The conjugates of the present disclosure can be described as embodiments in any of the following enumerated clauses. It will be understood that any of the embodiments described herein can be used in connection with any other embodiments described herein to the extent that the embodiments do not contradict one another.

1. A conjugate comprising a binding ligand, a linker and a drug, having the formula

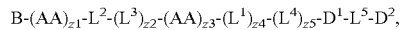

$$B\text{-}(AA)_{z1}\text{-}L^2\text{-}(L^3)_{z2}\text{-}(AA)_{z3}\text{-}(L^1)_{z4}\text{-}(L^4)_{z5}\text{-}D^1\text{-}L^5\text{-}D^2,$$

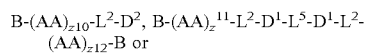

$$B\text{-}(AA)_{z10}\text{-}L^2\text{-}D^2, B\text{-}(AA)_z{}^{11}\text{-}L^2\text{-}D^1\text{-}L^5\text{-}D^1\text{-}L^2\text{-}(AA)_{z12}\text{-}B \text{ or}$$

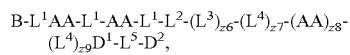

$$B\text{-}L^1AA\text{-}L^1\text{-}AA\text{-}L^1\text{-}L^2\text{-}(L^3)_{z6}\text{-}(L^4)_{z7}\text{-}(AA)_{z8}\text{-}(L^4)_{z9}D^1\text{-}L^5\text{-}D^2,$$

wherein
each z1, z10, z11 and z12 is each independently 2, 3, 4 or 5;
z2 is 0, 1 or 2;
z3 is 0, 1, 2, 3 or 4;
z4 is 0, 1 or 2; and
z5 is 0, 1 or 2
z6 is 0, 1 or 2;
z7 is 0, 1 or 2;
z8 is 0, 1, 2, 3 or 4;
z9 is 0, 1 or 2;
B is of the formula I

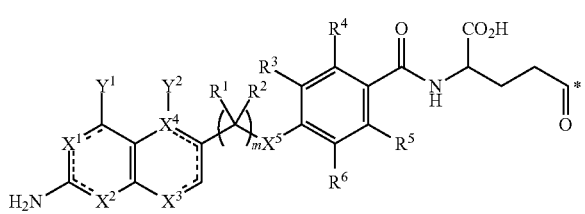

wherein $R^1$ and $R^2$ in each instance are independently selected from the group consisting of H, D, halogen, $C_1$-$C_6$ alkyl, $C_2$-$C_6$ alkenyl, $C_2$-$C_6$ alkynyl, —$OR^7$, —$SR^7$ and —$NR^7R^{7'}$, wherein each hydrogen atom in $C_1$-$C_6$ alkyl, $C_2$-$C_6$ alkenyl and $C_2$-$C_6$ alkynyl is independently optionally substituted by halogen, —$OR^8$, —$SR^8$, —$NR^8R^{8'}$, —$C(O)R^8$, —$C(O)OR^8$ or —$C(O)NR^8R^{8'}$;

$R^3$, $R^4$, $R^5$ and $R^6$ are each independently selected from the group consisting of H, D, halogen, $C_1$-$C_6$ alkyl, $C_2$-$C_6$ alkenyl, $C_2$-$C_6$ alkynyl, —CN, —$NO_2$, —NCO, —$OR^9$, —$SR^9$, —$NR^9R^{9'}$, —$C(O)R^9$, —$C(O)OR^9$ and —$C(O)NR^9R^{9'}$, wherein each hydrogen atom in $C_1$-$C_6$ alkyl, $C_2$-$C_6$ alkenyl and $C_2$-$C_6$ alkynyl is independently optionally substituted by halogen, —$OR^{10}$, —$SR^{10}$, —$NR^{10}R^{10'}$, —$C(O)R^{10}$, —$C(O)OR^{10}$ or —$C(O)NR^{10}R^{10'}$;

each $R^7$, $R^{7'}$, $R^8$, $R^{8'}$, $R^9$, $R^{9'}$, $R^{10}$ and $R^{10'}$ is independently H, D, $C_1$-$C_6$ alkyl, $C_2$-$C_6$ alkenyl or $C_2$-$C_6$ alkynyl;

$X^1$ is —$NR^{11}$—, =N—, —N=, —$C(R^{11})$= or =$C(R^{11})$—;

$X^2$ is —$NR^{11'}$— or =N—;

$X^3$ is —$NR^{11''}$—, —N= or —$C(R^{11'})$=;

$X^4$ is —N= or —C=;

$X^5$ is $NR^{12}$ or $CR^{12}R^{12'}$;

$Y^1$ is H, D, —$OR^{13}$, —$SR^{13}$ or —$NR^{13}R^{13'}$ when $X^1$ is —N= or —$C(R^{11})$=, or $Y^1$ is =O when $X^1$ is —$NR^{11}$—, =N— or =$C(R^{11})$—;

$Y^2$ is H, D, $C_1$-$C_6$ alkyl, $C_2$-$C_6$ alkenyl, —$C(O)R^{14}$, —$C(O)OR^{14}$, —$C(O)NR^{14}R^{14'}$ when $X^4$ is —C=, or $Y^2$ is absent when $X^4$ is —N=;

$R^{11}$, $R^{11'}$, $R^{11''}$, $R^{12}$, $R^{12'}$, $R^{13}$, $R^{13'}$, $R^{14}$ and $R^{14'}$ are each independently selected from the group consisting of H, D, $C_1$-$C_6$ alkyl, —$C(O)R^{15}$, —$C(O)OR^{15}$ and —$C(O)NR^{15}R^{15'}$;

$R^{15}$ and $R^{15'}$ are each independently H or $C_1$-$C_6$ alkyl;

m is 1, 2, 3 or 4;

AA is an amino acid;

$L^1$ is a linker of the formula II

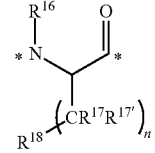

wherein $R^{16}$ is selected from the group consisting of H, D, $C_1$-$C_6$ alkyl, $C_2$-$C_6$ alkenyl, $C_2$-$C_6$ alkynyl, —$C(O)R^{19}$, —$C(O)OR^{19}$ and —$C(O)NR^{19}R^{19'}$, wherein each hydrogen atom in $C_1$-$C_6$ alkyl, $C_2$-$C_6$ alkenyl and $C_2$-$C_6$ alkynyl is independently optionally substituted by halogen, $C_1$-$C_6$ alkyl, $C_2$-$C_6$ alkenyl, and $C_2$-$C_6$ alkynyl, —$OR^{20}$, —$OC(O)R^{20}$, —$OC(O)NR^{20}R^{20'}$, —$OS(O)R^{20}$, —$OS(O)_2R^{20}$, —$SR^{20}$, —$S(O)R^{20}$, —$S(O)_2R^{20}$, —$S(O)NR^{20}R^{20'}$, —$S(O)_2NR^{20}R^{20'}$, —$OS(O)NR^{20}R^{20'}$, —$OS(O)_2NR^{20}R^{20'}$, —$NR^{20}R^{20'}$, —$NR^{20}C(O)R^{21}$, —$NR^{20}C(O)OR^{21}$, —$NR^{20}C(O)NR^{21}R^{21'}$, —$NR^{20}S(O)R^{21}$, —$NR^{20}S(O)_2R^{21}$, —$NR^{20}S(O)NR^{21}R^{21'}$, —$NR^{20}S(O)_2NR^{21}R^{21'}$, —$C(O)R^{20}$, —$C(O)OR^{20}$ or —$C(O)NR^{20}R^{20'}$;

each $R^{17}$ and $R^{17'}$ is independently selected from the group consisting of H, D, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{22}$, —$OC(O)R^{22}$, —$OC(O)NR^{22}R^{22'}$, —$OS(O)R^{22}$, —$OS(O)_2R^{22}$, —$SR^{22}$, —$S(O)R^{22}$, —$S(O)_2R^{22}$, —$S(O)NR^{22}R^{22'}$, —$S(O)_2NR^{22}R^{22'}$, —$OS(O)NR^{22}R^{22'}$, —$OS(O)_2NR^{22}R^{22'}$, —$NR^{22}R^{22'}$, —$NR^{22}C(O)R^{23}$, —$NR^{22}C(O)OR^{23}$, —$NR^{22}C(O)NR^{23}R^{23'}$, —$NR^{22}S(O)R^{23}$, —$NR^{22}S(O)_2R^{23}$, —$NR^{22}S(O)NR^{23}R^{23'}$, —$NR^{22}S(O)_2NR^{23}R^{23'}$, —$C(O)R^{22}$, —$C(O)OR^{22}$, and —$C(O)NR^{22}R^{22'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by halogen, $C_1$-$C_6$ alkyl, $C_2$-$C_6$ alkenyl, $C_2$-$C_6$ alkynyl, —$OR^{24}$, —$OC(O)R^{24}$, —$OC(O)NR^{24}R^{24'}$, —$OS(O)R^{24}$, —$OS(O)_2R^{24}$, —$SR^{24}$, —$S(O)R^{24}$, —$S(O)_2R^{24}$, —$S(O)NR^{24}R^{24'}$, —$S(O)_2NR^{24}R^{24'}$, —$OS(O)NR^{24}R^{24'}$, —$OS(O)_2NR^{24}R^{24'}$, —$NR^{24}R^{24'}$, —$NR^{24}C(O)R^{25}$, —$NR^{24}C(O)OR^{25}$, —$NR^{24}C(O)NR^{25}R^{25'}$, —$NR^{24}S(O)R^{25}$, —$NR^{24}S(O)_2R^{25}$, —$NR^{24}S(O)NR^{25}R^{25'}$, —$NR^{24}S(O)_2NR^{25}R^{25'}$, —$C(O)R^{24}$, —$C(O)OR^{24}$ or —$C(O)NR^{24}R^{24'}$; or $R^{17}$ and $R^{17'}$ may combine to form a $C_4$-$C_6$ cycloalkyl or a 4- to 6-membered heterocycle, wherein each hydrogen atom in $C_4$-$C_6$ cycloalkyl or 4- to 6-membered heterocycle is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{24}$, —$OC(O)R^{24}$, —$OC(O)NR^{24}R^{24'}$, —$OS(O)R^{24}$, —$OS(O)_2R^{24}$, —$SR^{24}$, —$S(O)R^{24}$, —$S(O)_2R^{24}$, —$S(O)NR^{24}R^{24'}$, —$S(O)_2NR^{24}R^{24'}$, —$OS(O)NR^{24}R^{24'}$, —$OS(O)_2NR^{24}R^{24'}$, —$NR^{24}R^{24'}$, —$NR^{24}C(O)R^{25}$, —$NR^{24}C(O)OR^{25}$, —$NR^{24}C(O)NR^{25}R^{25'}$, —$NR^{24}S(O)R^{25}$, —$NR^{24}S(O)_2R^{25}$, —$NR^{24}S(O)NR^{25}R^{25'}$, —$NR^{24}S(O)_2NR^{25}R^{25'}$, —$C(O)R^{24}$, —$C(O)OR^{24}$ or —$C(O)NR^{24}R^{24'}$;

$R^{18}$ is selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{26}$, —$OC(O)R^{26}$, —$OC(O)NR^{26}R^{26'}$, —$OS(O)R^{26}$, —$OS(O)_2R^{26}$, —$SR^{26}$, —$S(O)R^{26}$, —$S(O)_2R^{26}$, —$S(O)NR^{26}R^{26'}$, —$S(O)_2NR^{26}R^{26'}$, —$OS(O)NR^{26}R^{26'}$, —$OS(O)_2NR^{26}R^{26'}$, —$NR^{26}R^{26'}$, —$NR^{26}C(O)

$R^{27}$, —$NR^{26}C(O)OR^{27}$, —$NR^{26}C(O)NR^{27}R^{27'}$, —$NR^{26}C(=NR^{26''})NR^{27}R^{27'}$, —$NR^{26}S(O)R^{27}$, —$NR^{26}S(O)_2R^{27}$, —$NR^{26}S(O)NR^{27}R^{27'}$, —$NR^{26}S(O)_2NR^{27}R^{27'}$, —$C(O)R^{26}$, —$C(O)OR^{26}$ and —$C(O)NR^{26}R^{26'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by halogen, $C_1$-$C_6$ alkyl, $C_2$-$C_6$ alkenyl, —$(CH_2)_pOR^{28}$, —$(CH_2)_p(OCH_2)_qOR^{28}$, —$(CH_2)_p(OCH_2CH_2)_qOR^{28}$, —$OR^{29}$, —$OC(O)R^{29}$, —$OC(O)NR^{29}R^{29'}$, —$OS(O)R^{29}$, —$OS(O)_2R^{29}$, —$(CH_2)_pOS(O)OR^{29}$, —$OS(O)_2OR^{29}$, —$SR^{29}$, —$S(O)R^{29}$, —$S(O)_2R^{29}$, —$S(O)NR^{29}R^{29'}$, —$S(O)_2NR^{29}R^{29'}$, —$OS(O)NR^{29}R^{29'}$, —$OS(O)_2NR^{29}R^{29'}$, —$NR^{29}R^{29'}$, —$NR^{29}C(O)R^{30}$, —$NR^{29}C(O)OR^{30}$, —$NR^{29}C(O)NR^{30}R^{30'}$, —$NR^{29}S(O)R^{30}$, —$NR^{29}S(O)_2R^{30}$, —$NR^{29}S(O)NR^{30}R^{30'}$, —$NR^{29}S(O)_2NR^{30}R^{30'}$, —$C(O)R^{29}$, —$C(O)OR^{29}$ or —$C(O)NR^{29}R^{29'}$;

each $R^{19}$, $R^{19'}$, $R^{20}$, $R^{20'}$, $R^{21}$, $R^{21'}$, $R^{22}$, $R^{22'}$, $R^{23}$, $R^{23'}$, $R^{24}$, $R^{24'}$, $R^{25}$, $R^{25'}$, $R^{26}$, $R^{26'}$, $R^{26''}$, $R^{29}$, $R^{29'}$, $R^{30}$ and $R^{30'}$ is independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, —OH, —SH, —$NH_2$ or —$CO_2H$;

$R^{27}$ and $R^{27'}$ are each independently selected from the group consisting of H, $C_1$-$C_9$ alkyl, $C_2$-$C_9$ alkenyl, $C_2$-$C_9$ alkynyl, $C_3$-$C_6$ cycloalkyl, —$(CH_2)_p$(sugar), —$(CH_2)_p(OCH_2CH_2)_q$-(sugar) and —$(CH_2)_p(OCH_2CH_2CH_2)_q$(sugar);

$R^{28}$ is a H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, 5- to 7-membered heteroaryl or sugar;

n is 1, 2, 3, 4 or 5;
p is 1, 2, 3, 4 or 5;
q is 1, 2, 3, 4 or 5;
$L^2$ is a releasable linker;
$L^3$ is selected from the group consisting of $C_1$-$C_6$ alkyl, —$(CR^{39}R^{39'})_rC(O)$—, —$(CR^{39}R^{39'})_rOC(O)$—, —$NR^{39}R^{39'}C(O)(CR^{39}R^{39'})_r$—, —$(CH_2)_rNR^{39}$—, —$(OCR^{39}R^{39'}CR^{39}R^{39'})_rC(O)$—, and —$(OCR^{39}R^{39'}CR^{39}R^{39'}CR^{39}R^{39'})_rC(O)$—, wherein
each $R^{39}$ and $R^{39'}$ is independently selected from the group consisting of H, D, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{40}$, —$OC(O)R^{40}$, —$OC(O)NR^{40}R^{40'}$, —$OS(O)R^{40}$, —$OS(O)_2R^{40}$; —$SR^{40}$, —$S(O)R^{40}$, —$S(O)_2R^{40}$, —$S(O)NR^{40}R^{40'}$, —$S(O)_2NR^{40}R^{40'}$, —$OS(O)NR^{40}R^{40'}$, —$OS(O)_2NR^{40}R^{40'}$, —$NR^{40}R^{40'}$, —$NR^{40}C(O)R^{41}$, —$NR^{40}C(O)OR^{41}$, —$NR^{40}C(O)NR^{41}R^{41'}$, —$NR^{40}S(O)R^{41}$, —$NR^{40}S(O)_2R^{41}$, —$NR^{40}S(O)NR^{41}R^{41'}$, —$NR^{40}S(O)_2NR^{41}R^{41'}$, —$C(O)R^{40}$, —$C(O)OR^{40}$ and —$C(O)NR^{40}R^{40'}$;

$R^{40}$, $R^{40'}$, $R^{41}$ and $R^{41'}$ are each independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl; and r in each instance is 1, 2, 3, 4, or 5;
$L^4$ is selected from the group consisting of —$C(O)(CR^{44}R^{44'})_t$—, —$(OCR^{44}R^{44'}CR^{44}R^{44'})_t$—, —$(OCR^{44}R^{44'}CR^{44}R^{44'})_t$—, —$(OCR^{44}R^{44'}CR^{44}R^{44'})_tC(O)$—, —$NR^{42}CR^{43}R^{43'}CR^{43}R^{43'}$, —$NR^{42}CR^{43}R^{43'}CR^{43}R^{43'}$, —$(CR^{44}=CR^{44})_t$—, and —$NR^{42}C_6$-$C_{10}$ aryl($C_1$-$C_6$ alkyl)OC(O)$—;

wherein
$R^{42}$ is selected from the group consisting of H, D, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{45}$, —$OC(O)R^{45}$, —$OC(O)NR^{45}R^{45'}$, —$OS(O)R^{45}$, —$OS(O)_2R^{45}$, —$SR^{45}$, —$S(O)R^{45}$, —$S(O)_2R^{45}$, —$S(O)NR^{45}R^{45'}$, —$S(O)_2NR^{45}R^{45'}$, —$OS(O)NR^{45}R^{45'}$, —$OS(O)_2NR^{45}R^{45'}$, —$NR^{45}R^{45'}$, —$NR^{45}C(O)R^{46}$, —$NR^{45}C(O)OR^{46}$, —$NR^{45}C(O)NR^{46}R^{46'}$, —$NR^{45}S(O)R^{46}$, —$NR^{45}S(O)_2R^{46}$, —$NR^{45}S(O)NR^{46}R^{46'}$, —$NR^{45}S(O)_2NR^{46}R^{46'}$, —$C(O)R^{45}$, —$C(O)OR^{45}$ or —$C(O)NR^{45}R^{45'}$, each $R^{43}$, $R^{43'}$, $R^{44}$ and $R^{44'}$ is independently selected from the group consisting of H, D, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{47}$, —$OC(O)R^{47}$, —$OC(O)NR^{47}R^{47'}$, —$OS(O)R^{47}$, —$OS(O)_2R^{47}$, —$SR^{47}$, —$S(O)R^{47}$, —$S(O)_2R^{47}$, —$S(O)NR^{47}R^{47'}$, —$S(O)_2NR^{47}R^{47'}$, —$OS(O)NR^{47}R^{47'}$, —$OS(O)_2NR^{47}R^{47'}$, —$NR^{47}R^{47'}$, —$NR^{47}C(O)R^{48}$, —$NR^{47}C(O)OR^{48}$, —$NR^{47}C(O)NR^{48}R^{48'}$, —$NR^{47}S(O)R^{48}$, —$NR^{47}S(O)_2R^{48}$, —$NR^{47}S(O)NR^{48}R^{48'}$, —$NR^{47}S(O)_2NR^{48}R^{48'}$, —$C(O)R^{47}$, —$C(O)OR^{47}$ or —$C(O)NR^{47}R^{47'}$;

$R^{45}$, $R^{45'}$, $R^{46}$, $R^{46'}$, $R^{47}$, $R^{47'}$, $R^{48}$ and $R^{48'}$ are each independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl;

t is in each instance 1, 2, 3, 4, or 5;
$L^5$ is selected from the groups consisting of $C_1$-$C_{10}$ alkyl, —$(CR^{49}=CR^{49'})_u$—, —$(CR^{49}R^{49'})_uC(O)$—, —$CH_2CH_2(OCR^{49}R^{49'}CR^{49}R^{49'})_u$—, —$CH_2CH_2CH_2(OCR^{49}R^{49'}CR^{49}R^{49'}CR^{49}R^{49'})_u$—, —$CH_2CH_2(OCR^{49}R^{49'}CR^{49}R^{49'})_uC(O)$— and —$CH_2CH_2(OCR^{49}R^{49'}CR^{49}R^{49'}CR^{49}R^{49'})_uC(O)$—, wherein each $R^{49}$ and $R^{49'}$ is independently selected from the group consisting of H, D, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{50}$, —$OC(O)R^{50}$, —$OC(O)NR^{50}R^{50'}$, —$OS(O)R^{50}$, —$OS(O)_2R^{50}$, —$SR^{50}$, —$S(O)R^{50}$, —$S(O)_2R^{50}$, —$S(O)NR^{50}R^{50'}$, —$S(O)_2NR^{50}R^{50'}$, —$OS(O)NR^{50}R^{50'}$, —$OS(O)_2NR^{50}R^{50'}$, —$NR^{50}R^{50'}$, —$NR^{50}C(O)R^{51}$, —$NR^{50}C(O)OR^{51}$, —$NR^{50}C(O)NR^{51}R^{51'}$, —$NR^{50}S(O)R^{51}$, —$NR^{50}S(O)_2R^{51}$, —$NR^{50}S(O)NR^{51}R^{51'}$, —$NR^{50}S(O)_2NR^{51}R^{51'}$, —$C(O)R^{50}$, —$C(O)OR^{50}$ or —$C(O)NR^{50}R^{50'}$;

$R^{50}$, $R^{50'}$, $R^{51}$ and $R^{51'}$ are each independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl;

u is in each instance 0, 1, 2, 3, 4 or 5;
$D^1$ is a PBD prodrug; and
$D^2$ is a DNA binding agent;
or a pharmaceutically acceptable salt thereof.

2. The conjugate of clause 1, wherein $D^1$ is of the formula III

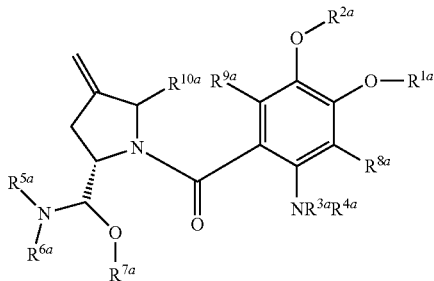

wherein $R^{1a}$, $R^{2a}$, $R^{3a}$ and $R^{4a}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —C(O)$R^{11a}$, —C(O)O$R^{11a}$, and —C(O)N$R^{11a}R^{11a'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{11a}$, —OC(O)$R^{11a}$, —OC(O)N$R^{11a}R^{11a'}$, —OS(O)$R^{11a}$, —OS(O)$_2R^{11a}$, —S$R^{11a}$, —S(O)$R^{11a}$, —S(O)$_2NR^{11a}$, —S(O)N$R^{11a}R^{11a'}$, —S(O)$_2NR^{11a}R^{11a'}$, —OS(O)N$R^{11a}R^{11a'}$, —OS(O)$_2NR^{11a}R^{11a'}$, —N$R^{11a}R^{11a'}$, —N$R^{11a}$C(O)$R^{12a}$, —N$R^{11a}$C(O)O$R^{12a}$, —N$R^{11a}$C(O)N$R^{12a}R^{12a'}$, —N$R^{11a}$S(O)$R^{12a}$, —N$R^{11a}$S(O)$_2R^{12a}$, —N$R^{11a}$S(O)N$R^{12a}R^{12a'}$, —N$R^{11a}$S(O)$_2NR^{12a}R^{12a'}$, —C(O)$R^{11a}$, —C(O)O$R^{11a}$ or —C(O)N$R^{11a}R^{11a'}$; or $R^{1a}$ is a bond; or $R^{4a}$ is a bond;

$R^{5a}$, $R^{6a}$ and $R^{7a}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —C(O)$R^{13a}$, —C(O)O$R^{13a}$ and —C(O)N$R^{13a}R^{13a'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{14a}$, —OC(O)$R^{14a}$, —OC(O)N$R^{14a}R^{14a'}$, —OS(O)$R^{14a}$, —OS(O)$_2R^{14a}$, —S$R^{14a}$, —S(O)$R^{14a}$, —S(O)$_2R^{14a}$, —S(O)N$R^{14a}R^{14a'}$, —S(O)$_2NR^{14a}R^{14a'}$, —OS(O)N$R^{14a}R^{14a'}$, —OS(O)$_2NR^{14a}R^{14a'}$, —N$R^{14a}R^{14a'}$, —N$R^{14a}$C(O)$R^{15a}$, —N$R^{14a}$C(O)O$R^{15a}$, —N$R^{14a}$C(O)N$R^{15a}R^{15a'}$, —N$R^{14a}$S(O)$R^{15a}$, —N$^{14a}$S(O)$_2R^{15a}$, —N$R^{14a}$S(O)N$R^{15a}R^{15a'}$, —N$R^{14a}$S(O)$_2NR^{15a}R^{15a'}$, —C(O)$R^{14a}$, —C(O)O$R^{14a}$ or —C(O)N$R^{14a}R^{14a'}$; wherein $R^{6a}$ and $R^{7a}$ taken together with the atoms to which they are attached optionally combine to form a 3- to 7-membered heterocycloalkyl, or $R^{5a}$ and $R^{6a}$ taken together with the atoms to which they are attached optionally combine to form a 3- to 7-membered heterocycloalkyl or 5- to 7-membered heteroaryl, wherein each hydrogen atom in 3- to 7-membered heterocycloalkyl or 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{16a}$, —OC(O)$R^{16a}$, —OC(O)N$R^{16a}R^{16a'}$, —OS(O)$R^{16a}$, —OS(O)$_2R^{16a}$, —S$R^{16a}$, —S(O)$R^{16a}$, —S(O)$_2R^{16a}$, —S(O)N$R^{16a}R^{16a'}$, —S(O)$_2NR^{16a}R^{16a'}$, —OS(O)N$R^{16a}R^{16a'}$, —OS(O)$_2NR^{16a}R^{16a'}$, —N$R^{16a}R^{16a'}$, —N$R^{16a}$C(O)$R^{17a}$, —N$R^{16a}$C(O)CH$_2$CH$_2$—, —N$R^{16a}$C(O)O$R^{17a}$, —N$R^{16a}$C(O)N$R^{17a}R^{17a'}$, —N$R^{16a}$S(O)$R^{17a}$, —N$R^{16a}$S(O)$_2R^{17a}$, —N$R^{16a}$S(O)N$R^{17a}R^{17a'}$, —N$R^{16a}$S(O)$_2NR^{17a}R^{17a'}$, —C(O)$R^{16a}$, —C(O)O$R^{16a}$ or —C(O)N$R^{16a}R^{16a'}$, and wherein one hydrogen atom in 5- to 7-membered heteroaryl is optionally a bond, or $R^{5a}$ is a bond;

$R^{8a}$ and $R^{9a}$ are each independently selected from the group consisting of H, D, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —CN, —NO$_2$, —NCO, —O$R^{18a}$, —OC(O)$R^{18a}$, —OC(O)N$R^{18a}R^{18a'}$, —OS(O)$R^{18a}$, —OS(O)$_2R^{18a}$, —S$R^{18a}$, —S(O)$R^{18a}$, —S(O)$_2R^{18a}$, —S(O)N$R^{18a}R^{18a'}$, —S(O)$_2NR^{18a}R^{18a'}$, —OS(O)N$R^{18a}R^{18a'}$, —OS(O)$_2NR^{18a}R^{18a'}$, —N$R^{18a}R^{18a'}$, —N$R^{18a}$C(O)$R^{19a}$, —N$R^{18a}$C(O)O$R^{19a}$, —N$R^{18a}$C(O)N$R^{19a}R^{19a'}$, —N$R^{18a}$S(O)$R^{19a}$, —N$R^{18a}$S(O)$_2R^{19a}$, —N$R^{18a}$S(O)N$R^{19a}R^{19a'}$, —N$R^{18a}$S(O)$_2NR^{19a}R^{19a'}$, —C(O)$R^{18a}$, —C(O)O$R^{18a}$ and —C(O)N$R^{18a}R^{18a'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{20a}$, —OC(O)$R^{20a}$, —OC(O)N$R^{20a}R^{20a'}$, —OS(O)$R^{20a}$, —OS(O)$_2R^{20a}$, —S$R^{20a}$, —S(O)$R^{20a}$, —S(O)$_2R^{20a}$, —S(O)N$R^{20a}R^{20a'}$, —S(O)$_2NR^{20a}R^{20a'}$, —OS(O)N$R^{20a}R^{20a'}$, —OS(O)$_2NR^{20a}R^{20a'}$, —N$R^{20a}R^{20a'}$, —N$R^{20a}$C(O)$R^{21a}$, —N$R^{20a}$C(O)O$R^{21a}$, —N$R^{20a}$C(O)N$R^{21a}R^{21a'}$, —N$R^{20a}$S(O)$R^{21a}$, —N$R^{20a}$S(O)$_2R^{21a}$, —N$R^{20a}$S(O)N$R^{21a}R^{21a'}$, —N$R^{20a}$S(O)$_2NR^{21a}R^{21a'}$, —C(O)$R^{20a}$, —C(O)O$R^{20a}$ or —C(O)N$R^{20a}R^{20a'}$;

$R^{10a}$ is selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{22a}$, —OC(O)$R^{22a}$, —OC(O)N$R^{22a}R^{22a'}$, —OS(O)$R^{22a}$, —OS(O)$_2R^{22a}$, —S$R^{22a}$, —S(O)$R^{22a}$, —S(O)$_2R^{22a}$, —S(O)N$R^{22a}R^{22a'}$, —S(O)$_2NR^{22a}R^{22a'}$, —OS(O)N$R^{22a}R^{22a'}$, —OS(O)$_2NR^{22a}R^{22a'}$, —N$R^{22a}R^{22a'}$, —N$R^{22a}$C(O)$R^{23a}$, —N$R^{22a}$C(O)O$R^{23a}$, —N$R^{22a}$C(O)N$R^{23a}R^{23a'}$, —N$R^{22a}$S(O)$R^{23a}$, —N$R^{22a}$S(O)$_2R^{23a}$, —N$R^{22a}$S(O)N$R^{23a}R^{23a'}$, —N$R^{22a}$S(O)$_2NR^{23a}R^{23a'}$, —C(O)$R^{22a}$, —C(O)O$R^{23a}$ and —C(O)N$R^{22a}R^{22a'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{24a}$, —OC(O)$R^{24a}$, —OC(O)N$R^{24a}R^{24a'}$, —OS(O)$R^{24a}$, —OS(O)$_2R^{24a}$, —S$R^{24a}$, —S(O)$R^{24a}$, —S(O)$_2R^{24a}$, —S(O)N$R^{24a}R^{24a'}$, —S(O)$_2NR^{24a}R^{24a'}$, —OS(O)N$R^{24a}R^{24a'}$, —OS(O)$_2NR^{24a}R^{24a'}$, —N$R^{24a}R^{24a'}$, —N$R^{24a}$C(O)$R^{25a}$, —N$R^{24a}$C(O)O$R^{25a}$, —N$R^{24a}$C(O)N$R^{25a}R^{25a'}$, —N$R^{24a}$S(O)$R^{25a}$, —N$R^{24a}$S(O)$_2R^{25a}$, —N$R^{24a}$S(O)N$R^{25a}R^{25a'}$, —N$R^{24a}$S(O)$_2NR^{25a}R^{25a'}$, —C(O)$R^{24a}$, —C(O)O$R^{24a}$ or —C(O)N$R^{24a}R^{24a'}$; and each $R^{11a}$, $R^{11a'}$, $R^{12a}$, $R^{12a'}$, $R^{13a}$, $R^{13a'}$, $R^{14a}$, $R^{14a'}$, $R^{15a}$, $R^{15a'}$, $R^{16a}$, $R^{16a'}$, $R^{17a}$, $R^{17a'}$, $R^{18a}$, $R^{18a'}$, $R^{19a}$, $R^{19a'}$, $R^{20a}$, $R^{20a'}$, $R^{21a}$, $R^{21a'}$, $R^{22a}$, $R^{22a'}$, $R^{23a}$, $R^{23a'}$, $R^{24a}$, $R^{24a'}$, $R^{25a}$ and $R^{25a'}$ is independently selected from the group consisting of H, D, $C_1$-$C_7$ alkyl, $C_2$-$C_7$ alkenyl, $C_2$-$C_7$ alkynyl, $C_3$-$C_{13}$ cycloalkyl, 3- to 7-membered heterocycloalkyl, $C_6$-$C_{10}$ aryl, and 5- to 7-membered heteroaryl;

provided that at least two of $R^{1a}$, $R^{4a}$, and $R^{5a}$ are a bond, or when $R^{5a}$ and $R^{6a}$ taken together with the atoms to which they are attached optionally combine to form a 3- to 7-membered heterocycloalkyl or 5- to 7-membered heteroaryl, one hydrogen atom in 5- to 7-membered heteroaryl is a bond and one of $R^{1a}$ or $R^{4a}$ is a bond; or a pharmaceutically acceptable salt thereof.

3. The conjugate of clause 1 or 2, wherein $D^2$ is a minor groove binding drug; or a pharmaceutically acceptable salt thereof.

4. The conjugate of any one of clauses 1 to 3, wherein $D^2$ is of the formula selected from the group consisting of

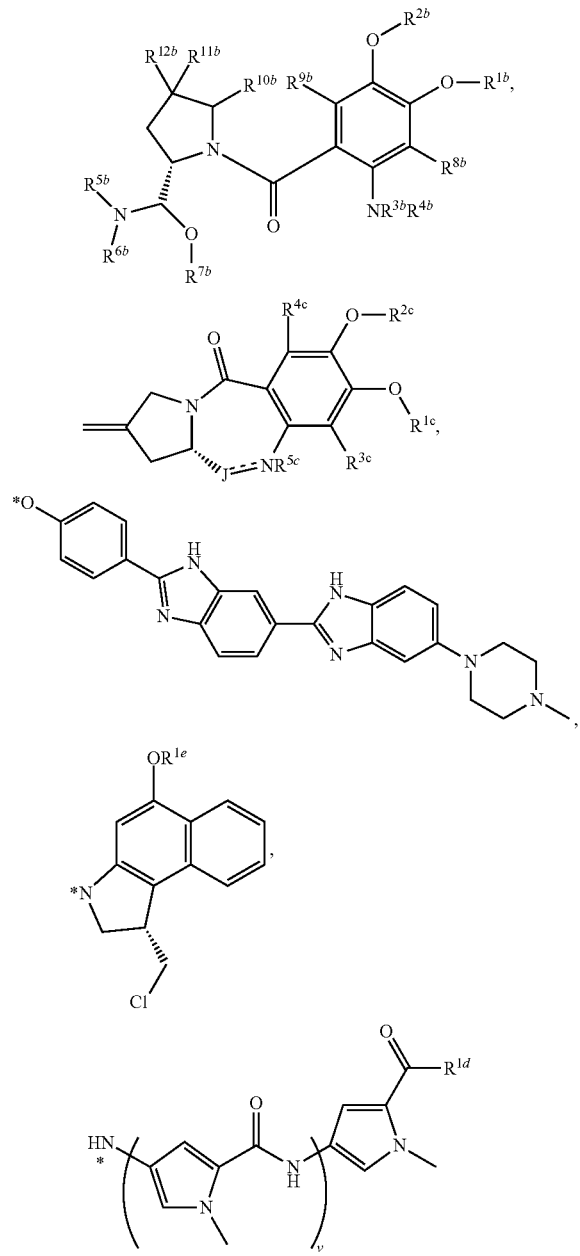

wherein $R^{1b}$, $R^{2b}$, $R^{3b}$ and $R^{4b}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —C(O)$R^{13b}$, —C(O)O$R^{13b}$, and —C(O)N$R^{13b}R^{13b'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{13b}$, —OC(O)$R^{13b}$, —OC(O)N$R^{13b}R^{13b'}$, —OS(O)$R_{13b}$, —OS(O)$_2R^{13b}$, —S$R^{13b}$, —S(O)$R^{13b}$, —S(O)$_2R^{13b}$, —S(O)N$R^{13b}R^{13b'}$, —S(O)$_2$N$R^{13b}R^{13b'}$, —OS(O)N$R^{13b}R^{13b'}$, —OS(O)$_2$N$R^{13b}R^{13b'}$, —N$R^{13b}R^{13b'}$, —N$R^{13b}$C(O)$R^{14b}$, —N$R^{13b}$C(O)O$R^{14b}$, —N$R^{13b}$C(O)N$R^{14b}R^{14b'}$, —N$R^{13b}$S(O)$R^{14b}$, —N$R^{13b}$S(O)$_2R^{14b}$, —N$R^{13b}$S(O)N$R^{14b}R^{14b'}$, —N$R^{13b}$S(O)$_2$N$R^{14b}R^{14b'}$, —C(O)$R^{13b}$, —C(O)O$R^{13b}$ or —C(O)N$R^{13b}R^{13b'}$; or any one of $R^{1b}$, $R^{2b}$, $R^{3b}$ and $R^{4b}$ is a bond;

$R^{5b}$, $R^{6b}$ and $R^{7b}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —C(O)$R^{15b}$, —C(O)O$R^{15b}$, and —C(O)N$R^{15b}R^{15b'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, -$L^4$H, -$L^3$H, —O$R^{15b}$, —OC(O)$R^{15b}$, —OC(O)N$R^{15b}R^{15b'}$, —OS(O)$R^{15b}$, —OS(O)$_2R^{15b}$, —S$R^{15b}$, —S(O)$R^{15b}$, —S(O)$_2R^{15b}$, —S(O)N$R^{15b}R^{15b'}$, —S(O)$_2$N$R^{15b}R^{15b'}$, —OS(O)N$R^{15b}R^{15b'}$, —OS(O)$_2$N$R^{15b}R^{15b'}$, —N$R^{15b}$C(O)$R^{16b}$, —N$R^{15b}$C(O)O$R^{16b}$, —N$R^{15b}$C(O)N$R^{16b}R^{16b'}$, —N$R^{15b}$S(O)$R^{16b}$, —N$R^{15b}$S(O)$_2R^{16b}$, —N$R^{15b}$S(O)N$R^{16b}R^{16b'}$, —N$R^{15b}$S(O)$^2$N$R^{16b}R^{16b'}$, —C(O)$R^{15b}$, —C(O)O$R^{15b}$ or —C(O)N$R^{15b}R^{15b'}$; wherein $R^{6b}$ and $R^{7b}$ taken together with the atoms to which they are attached optionally combine to form a 3- to 7-membered heterocycloalkyl, or $R^{5b}$ and $R^{6b}$ taken together with the atoms to which they are attached optionally combine to form a 3- to 7-membered heterocycloalkyl or 5- to 7-membered heteroaryl, wherein each hydrogen atom in 3- to 7-membered heterocycloalkyl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heteroaryl, $C_6$-$C_{10}$ aryl, 5- to 7-membered heteroaryl, —OR$^{17b}$, —OC(O)R$^{17b}$, —OC(O)NR$^{17b}$R$^{17b'}$, —OS(O)R$^{17b}$, —OS(O)$_2$R$^{17b}$, —SR$^{17b}$, —S(O)R$^{17b}$, —S(O)$_2$R$^{17b}$, —S(O)NR$^{17b}$R$^{17b'}$, —S(O)$_2$NR$^{17b}$R$^{17b'}$, —OS(O) NR$^{17b}$R$^{17b'}$, —OS(O)$_2$NR$^{17b}$R$^{17b'}$, —NR$^{17b}$R$^{17b'}$, —NR$^{17b}$C(O)R$^{18b}$, —NR$^{17b}$C(O)OR$^{18b}$, —NR$^{17b}$C(O) NR$^{18b}$R$^{18b'}$, —NR$^{17b}$S(O)R$^{18b}$, —NR$^{17b}$S(O)$_2$R$^{18b}$, —NR$^{17b}$S(O)NR$^{18b}$R$^{18b'}$, —NR$^{17b}$S(O)$_2$NR$^{18b}$R$^{18b'}$, —C(O)R$^{17b}$, —C(O)OR$^{17b}$ or —C(O)NR$^{17b}$R$^{17b}$; or any one of R$^{5b}$, R$^{6b}$ or R$^{7b}$ is a bond;

R$^{8b}$ and R$^{9b}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —CN, —NO$_2$, —NCO, —OR$^{19b}$, —OC(O)R$^{19b}$, —OC(O) NR$^{19b}$R$^{19b'}$, —OS(O)R$^{19b}$, —OS(O)$_2$R$^{19b}$, —SR$^{19b}$, —S(O)R$^{19b}$, —S(O)$_2$R$^{19b}$, —S(O)NR$^{19b}$R$^{19b'}$, —S(O)$_2$NR$^{19b}$R$^{19b'}$, —OS(O)NR$^{19b}$R$^{19b'}$, —OS(O)$_2$NR$^{19b}$R$^{19b'}$, —NR$^{19b}$R$^{19b'}$, —NR$^{19b}$C(O)R$^{20b}$, —NR$^{19b}$C(O)OR$^{20b}$, —NR$^{19b}$C(O)NR$^{20b}$R$^{2b'}$, —NR$^{19b}$S(O)R$^{20b}$, —NR$^{b}$S(O)$_2$R$^{20b}$, —NR$^{19b}$S(O)NR$^{20b}$R$^{20b'}$, —NR$^{19b}$S(O)$_2$NR$^{20b}$R$^{20b'}$, —C(O)R$^{19b}$, —C(O)OR$^{19b}$ and —C(O) NR$^{19b}$R$^{19b'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —OR$^{21b}$, —OC(O)R$^{21b}$, —OC(O) NR$^{21b}$R$^{21b'}$, —OS(O)R$^{21b}$, —OS(O)$_2$R$^{21b}$, —SR$^{21b}$, —S(O)R$^{21b}$, —S(O)$_2$R$^{21b}$, —S(O)NR$^{21b}$R$^{21b'}$, —S(O)$_2$NR$^{21b}$R$^{21b'}$, —OS(O)NR$^{21b}$R$^{21b'}$, —OS(O)$_2$NR$^{21b}$R$^{21b'}$, —NR$^{21b}$R$^{21b'}$, —NR$^{21b}$C(O)R$^{22b}$, —NR$^{21b}$C(O)OR$^{22b}$, —NR$^{21b}$C(O)NR$^{22b}$R$^{22b'}$, —NR$^{21b}$S(O)R$^{22b}$, —NR$^{21b}$S(O)$_2$R$^{22b}$, —NR$^{21b}$S(O)NR$^{22b}$R$^{22b'}$, —NR$^{21b}$S(O)$_2$NR$^{22b}$R$^{22b'}$, —C(O)R$^{21b}$, —C(O)OR$^{21b}$ or —C(O) NR$^{21b}$R$^{21b'}$;

R$^{10b}$, R$^{11b}$ and R$^{12b}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —OR$^{23b}$, —OC(O)R$^{23b}$, —OC(O)NR$^{23b}$R$^{23b'}$, —OS(O) R$^{23b}$, —OS(O)$_2$R$^{23b}$, —SR$^{23b}$, —S(O)R$^{23b}$, —S(O)$_2$R$^{23b}$, —S(O)NR$^{23b}$R$^{23b'}$, —S(O)$_2$NR$^{23b}$R$^{23b'}$, —OS(O) NR$^{23b}$R$^{23b'}$, —OS(O)$_2$NR$^{23b}$R$^{23b'}$, —NR$^{23b}$R$^{23b'}$, —NR$^{23b}$C(O)R$^{24b}$, —NR$^{23b}$C(O)OR$^{24b}$, —NR$^{23b}$C(O) NR$^{24b}$R$^{24b'}$, —NR$^{23b}$S(O)R$^{24b}$, —NR$^{23b}$S(O)$_2$R$^{24b}$, —NR$^{23b}$S(O)NR$^{24b}$R$^{24b'}$, —NR$^{23b}$S(O)$_2$NR$^{24b}$R$^{24b'}$, —C(O)R$^{23b}$, —C(O)OR$^{23b}$ and —C(O)NR$^{23b}$R$^{23b'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —OR$^{25b}$, —OC(O)R$^{25b}$, —OC(O)NR$^{25b}$R$^{25b'}$, —OS(O) R$^{25b}$, —OS(O)$_2$R$^{25b}$, —SR$^{25b}$, —S(O)R$^{25b}$, —S(O)$_2$R$^{25b}$, —S(O)NR$^{25b}$R$^{25b'}$, —S(O)$_2$NR$^{25b}$R$^{25b'}$, —OS(O) NR$^{25b}$R$^{25b'}$, —OS(O)$_2$NR$^{25b}$R$^{25b'}$, —NR$^{25b}$R$^{25b'}$, —NR$^{25b}$C(O)R$^{26b}$, —NR$^{25b}$C(O)OR$^{26b}$, —NR$^{25b}$C(O) NR$^{26b}$R$^{26b'}$, —NR$^{25b}$S(O)R$^{26b}$, —NR$^{25b}$S(O)$_2$R$^{26b}$, —NR$^{25b}$S(O)NR$^{26b}$R$^{26b'}$, —NR$^{25b}$S(O)$_2$NR$^{26b}$R$^{26b'}$, —C(O)R$^{25b}$, —C(O)OR$^{25b}$ or —C(O)NR$^{25b}$R$^{25b}$, or R$^{10b}$ and R$^{11b}$ taken together with the carbon atoms to which they are attached optionally combine to form a $C_6$-$C_{10}$ aryl, or R$^{11b}$ and R$^{12b}$ taken together with the carbon atom to which they are attached optionally combine to form an exomethylene; or R$^{12b}$ is absent;

each R$^{13b}$, R$^{13b'}$, R$^{14b}$, R$^{14b'}$, R$^{15b}$, R$^{15b'}$, R$^{16b}$, R$^{16b'}$, R$^{17b}$, R$^{17b'}$, R$^{18b}$, R$^{18b'}$, R$^{19b}$, R$^{19b'}$ R$^{20b}$, R$^{20b'}$, R$^{21b}$, R$^{21b'}$, R$^{22b}$, R$^{22b'}$, R$^{23b}$, R$^{23b'}$, R$^{24b}$, R$^{24b'}$, R$^{25b}$, R$^{25b'}$, R$^{26b}$ and R$^{26b'}$ is independently selected from the group consisting of H, D, $C_1$-$C_7$ alkyl, $C_2$-$C_7$ alkenyl, $C_2$-$C_7$ alkynyl, $C_3$-$C_{13}$ cycloalkyl, 3- to 7-membered heterocycloalkyl, $C_6$-$C_{10}$ aryl, $C_1$-$C_6$ alkyl($C_6$-$C_{10}$ aryl) and 5- to 7-membered heteroaryl, wherein each hydrogen atom in $C_6$-$C_{10}$ aryl, $C_1$-$C_6$ alkyl ($C_6$-$C_{10}$ aryl) and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —CN, —NO$_2$, —NCO, —OH, —SH, —NH$_2$, —SO$_3$H, —C(O)OH and —C(O)NH$_2$;

provided that one of R$^{1b}$, R$^{2b}$, R$^{3b}$, R$^{4b}$, R$^{5b}$, R$^{6b}$ and R$^{7b}$ is a bond;

R$^{1c}$, R$^{2c}$ and R$^{5c}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —C(O) R$^{6c}$, —C(O)OR$^{6c}$ and —C(O)NR$^{6c}$R$^{6c'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —OR$^{7c}$, —OC(O)R$^{7c}$, —OC(O)NR$^{7c}$R$^{7c'}$, —OS(O)R$^{7c}$, —OS(O)$_2$R$^{7c}$, —SR$^{7c}$, —S(O)R$^{7c}$, —S(O)$_2$R$^{7c}$, —S(O)$_2$OR$^{7c}$, —S(O)NR$^{7c}$R$^{7c'}$, —S(O)$_2$NR$^{7c}$R$^{7c'}$, —OS(O)NR$^{7c}$R$^{7c'}$, —OS(O)$_2$NR$^{7c}$R$^{7c'}$, —NR$^{7c}$R$^{7c'}$, —NR$^{7c}$C(O)R$^{8c}$, —NR$^{7c}$C(O)OR$^{8c}$, —NR$^{7c}$C(O)NR$^{8c}$R$^{8c'}$, —NR$^{7c}$S(O)R$^{8c}$, —NR$^{7c}$S(O)$_2$R$^{8c}$, —NR$^{7c}$S(O)NR$^{8c}$R$^{8c'}$, —NR$^{7c}$S(O)$_2$NR$^{8c}$R$^{8c'}$, —C(O)R$^{7c}$, —C(O)OR$^{7c}$ or —C(O) NR$^{7c}$R$^{7c'}$; or when J is —CR$^{13c}$═, R$^{5C}$ is absent; provided that one of R$^{1c}$ or R$^{2c}$ is a bond;

R$^{3c}$ and R$^{4c}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —CN, —NO$_2$, —NCO, —OR$^{9c}$, —OC(O)R$^{9c}$, —OC(O)NR$^{9c}$R$^{9c'}$, —OS(O)R$^{9c}$, —OS(O)$_2$R$^{9c}$, —SR$^{9c}$, —S(O)R$^{9c}$, —S(O)$_2$R$^{9c}$, —S(O)NR$^{9c}$R$^{9c'}$, —S(O)$_2$NR$^{9c}$R$^{9c'}$, —OS(O) NR$^{9c}$R$^{9c'}$, —OS(O)$_2$NR$^{9c}$R$^{9c'}$, —NR$^{9c}$R$^{9c'}$, —NR$^{9c}$C(O) R$^{10c}$, —NR$^{9c}$C(O)OR$^{10c}$, —NR$^{9c}$C(O)NR$^{10c}$R$^{10c'}$, —NR$^{9c}$S(O)R$^{10c}$, —NR$^{9c}$S(O)$_2$R$^{10c}$, —NR$^{9c}$S(O)NR$^{10c}$R$^{10c'}$, —NR$^{9c}$S(O)$_2$NR$^{10c}$R$^{10c'}$, —C(O)R$^{9c}$, —C(O)OR$^{9c}$ and —C(O)NR$^{9c}$R$^{9c'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —OR$^{11c}$, —OC(O)R$^{11c}$, —OC(O) NR$^{11c}$R$^{11c'}$, —OS(O)R$^{11c}$, —OS(O)$_2$R$^{11c}$, —SR$^{11c}$, —S(O) R$^{11c}$, —S(O)$_2$R$^{11c}$, —S(O)NR$^{11c}$R$^{11c'}$, —S(O)$_2$NR$^{11c}$R$^{11c'}$, —OS(O)NR$^{11c}$R$^{11c'}$, —OS(O)$_2$NR$^{11c}$R$^{11c'}$, —NR$^{11c}$R$^{11c'}$, —NR$^{11c}$C(O)R$^{12c}$, —NR$^{11c}$C(O)OR$^{12c}$, —NR$^{11c}$C(O) NR$^{12c}$R$^{12c'}$, —NR$^{11c}$S(O)R$^{12c}$, —NR$^{11c}$S(O)$_2$R$^{12c}$, —NR$^{11c}$S(O)NR$^{12c}$R$^{12c'}$, —NR$^{11c}$S(O)$_2$NR$^{12c}$R$^{12c'}$, —C(O)R$^{11c}$, —C(O)OR$^{11c}$ or —C(O)NR$^{11c}$R$^{11c}$;

J is —C(O)—, —CR$^{13c}$═ or —(CR$^{13c}$R$^{13c'}$)— each R$^{6c}$, R$^{6c'}$, R$^{7c}$, R$^{7c'}$, R$^{8c}$, R$^{8c'}$, R$^{9c}$, R$^{9c'}$, R$^{10c}$, R$^{10c'}$, R$^{11c}$, R$^{11c'}$, R$^{12c}$, R$^{12c'}$, R$^{13c}$ and R$^{13c'}$ is independently selected from the group consisting of H, D, $C_1$-$C_7$ alkyl, $C_2$-$C_7$ alkenyl, $C_2$-$C_7$alkynyl, $C_3$-$C_6$ cycloalkyl, 3- to 7-membered heterocycloalkyl, $C_6$-$C_{10}$aryl and 5- to 7-membered heteroaryl;

$R^{1d}$ is selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{2d}$, —$SR^{2d}$ and —$NR^{2d}R^{2d'}$, $R^{2d}$ and $R^{2d'}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is optionally substituted by —$OR^{3d}$, —$SR^{3d}$, and —$NR^{3d}R^{3d'}$;

$R^{3d}$ and $R^{3d'}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl;

$R^{1e}$ is selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{2e}$, —$OC(O)R^{2e}$, —$OC(O)NR^{2e}R^{2e'}$, —$OS(O)R^{2e}$, —$OS(O)_2R^{2e}$, —$SR^{2e}$, —$S(O)R^{2e}$, —$S(O)_2R^{2e}$, —$S(O)NR^{2e}R^{2e'}$, —$S(O)_2NR^{2e}R^{2e'}$, —$OS(O)NR^{2e}R^{2e'}$, —$OS(O)_2NR^{2e}R^{2e'}$, —$NR^{2e}R^{2e'}$, —$NR^{2e}C(O)R^{3e}$, —$NR^{2e}C(O)OR^{3e}$, —$NR^{2e}C(O)NR^{3e}R^{3e'}$, —$NR^{2e}S(O)R^{3e}$, —$NR^{2e}S(O)_2R^{3e}$, —$NR^{2e}S(O)NR^{2e}R^{2e'}$, —$NR^{2e}S(O)_2NR^{3e}R^{3e'}$, —$C(O)R^{2e}$, —$C(O)OR^{2e}$ or —$C(O)NR^{2e}R^{2e}$;

each $R^{2e}$, $R^{2e'}$, $R^{3e}$ and $R^{3e'}$ is independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is optionally substituted by —$OR^{4e}$, —$SR^{4e}$ or —$NR^{4e}R^{4e'}$;

$R^{4e}$ and $R^{4e'}$ are independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl;

v is 1, 2 or 3; and

\* is a covalent bond;

or a pharmaceutically acceptable salt thereof.

5. The conjugate of any one of clauses 1 to 4, wherein each AA is independently selected from the group consisting of L-lysine, L-asparagine, L-threonine, L-serine, L-isoleucine, L-methionine, L-proline, L-histidine, L-glutamine, L-arginine, L-glycine, L-aspartic acid, L-glutamic acid, L-alanine, L-valine, L-phenylalanine, L-leucine, L-tyrosine, L-cysteine, L-tryptophan, L-phosphoserine, L-sulfocysteine, L-arginosuccinic acid, L-hydroxyproline, L-phosphoethanolamine, L-sarcosine, L-taurine, L-carnosine, L-citrulline, L-anserine, L-1,3-methyl-histidine, L-alpha-amino-adipic acid, D-lysine, D-asparagine, D-threonine, D-serine, D-isoleucine, D-methionine, D-proline, D-histidine, D-glutamine, D-arginine, D-glycine, D-aspartic acid, D-glutamic acid, D-alanine, D-valine, D-phenylalanine, D-leucine, D-tyrosine, D-cysteine, D-tryptophan, D-citrulline and D-carnosine, or a pharmaceutically acceptable salt thereof.

6. The conjugate of any one of clauses 1 to 5, wherein $R^{16}$ is H; or a pharmaceutically acceptable salt thereof.

7. The conjugate of any one of clauses 1 to 6, wherein each $R^{17}$ and $R^{17'}$ is independently selected from the group consisting of H, $C_1$-$C_6$ alkyl and —$OR^{22}$, wherein each hydrogen atom in $C_1$-$C_6$ alkyl is independently optionally substituted by —$OR^{24}$; or $R^{17}$ and $R^{17'}$ may combine to form a $C_4$-$C_6$ cycloalkyl or a 4- to 6-membered heterocycle, wherein each hydrogen atom in $C_4$-$C_6$ cycloalkyl or 4- to 6-membered heterocycle is independently optionally substituted by halogen, $C_1$-$C_6$ alkyl or —$OR^{24}$; or a pharmaceutically acceptable salt thereof.

8. The conjugate of any one of clauses 1 to 7, wherein $R^{18}$ is selected from the group consisting of H, $C_1$-$C_6$ alkyl, 5- to 7-membered heteroaryl, —$OR^{26}$, —$NR^{26}C(O)R^{27}$, —$NR^{26}C(O)NR^{27}R^{27'}$, —$NR^{26}C(=NR^{26''})NR^{27}R^{27'}$, and —$C(O)NR^{26}R^{26'}$, wherein each hydrogen atom in $C_1$-$C_6$ alkyl and 5- to 7-membered heteroaryl is independently optionally substituted by $C_1$-$C_6$ alkyl, —$OR^{29}$, —$(CH_2)_pOS(O)_2OR^{29}$, —$OS(O)_2OR^{29}$, or —$C(O)NR^{29}R^{29'}$;

each $R^{26}$, $R^{26'}$, $R^{26''}$, $R^{29}$ and $R^{29'}$ is independently H or $C_1$-$C_7$ alkyl, wherein each hydrogen atom in $C_1$-$C_7$ alkyl, is independently optionally substituted by halogen, —OH, —SH, —$NH_2$ or —$CO_2H$;

$R^{27}$ and $R^{27'}$ are each independently selected from the group consisting of H, $C_1$-$C_9$ alkyl, $C_2$-$C_9$ alkenyl, $C_2$-$C_9$ alkynyl, $C_3$-$C_6$ cycloalkyl, —$(CH_2)_p$(sugar), —$(CH_2)_p$($OCH_2CH_2)_q$-(sugar) and —$(CH_2)_p$($OCH_2CH_2CH_2)_q$(sugar);

n is 2, 3, 4 or 5;

p is 1, 2, 3, 4 or 5;

q is 1, 2, 3, 4 or 5;

or a pharmaceutically acceptable salt thereof.

9. The conjugate of any one of clauses 1 to 8, wherein each $L^1$ is selected from the group consisting of

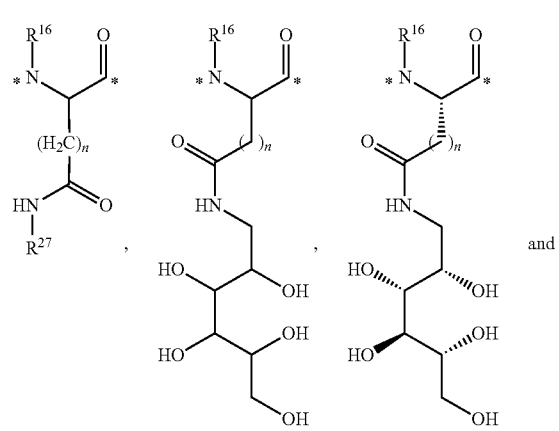

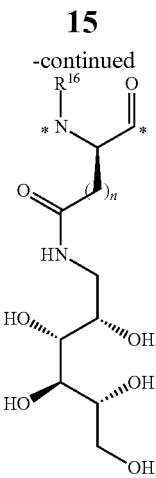

wherein $R^{16}$ is H, and * is a covalent bond; or a pharmaceutically acceptable salt thereof.

10. The conjugate of any one of clauses 1 to 9, wherein $R^1$ and $R^2$ in each instance are H; $R^3$, $R^4$, $R^5$ and $R^6$ are H; $X^1$ is —$NR^{11}$—; $X^2$ is =N—; $X^3$ is —N=; $X^4$ is —N=; $X^5$ is $NR^{12}$; $Y^1$ is is =O; $Y^2$ is absent; $R^{11}$ and $R^{12}$ are H; m is 1, 2, 3 or 4; and * is a covalent bond; or a pharmaceutically acceptable salt thereof.

11. The conjugate of any one of clauses 1 to 10, having the formula

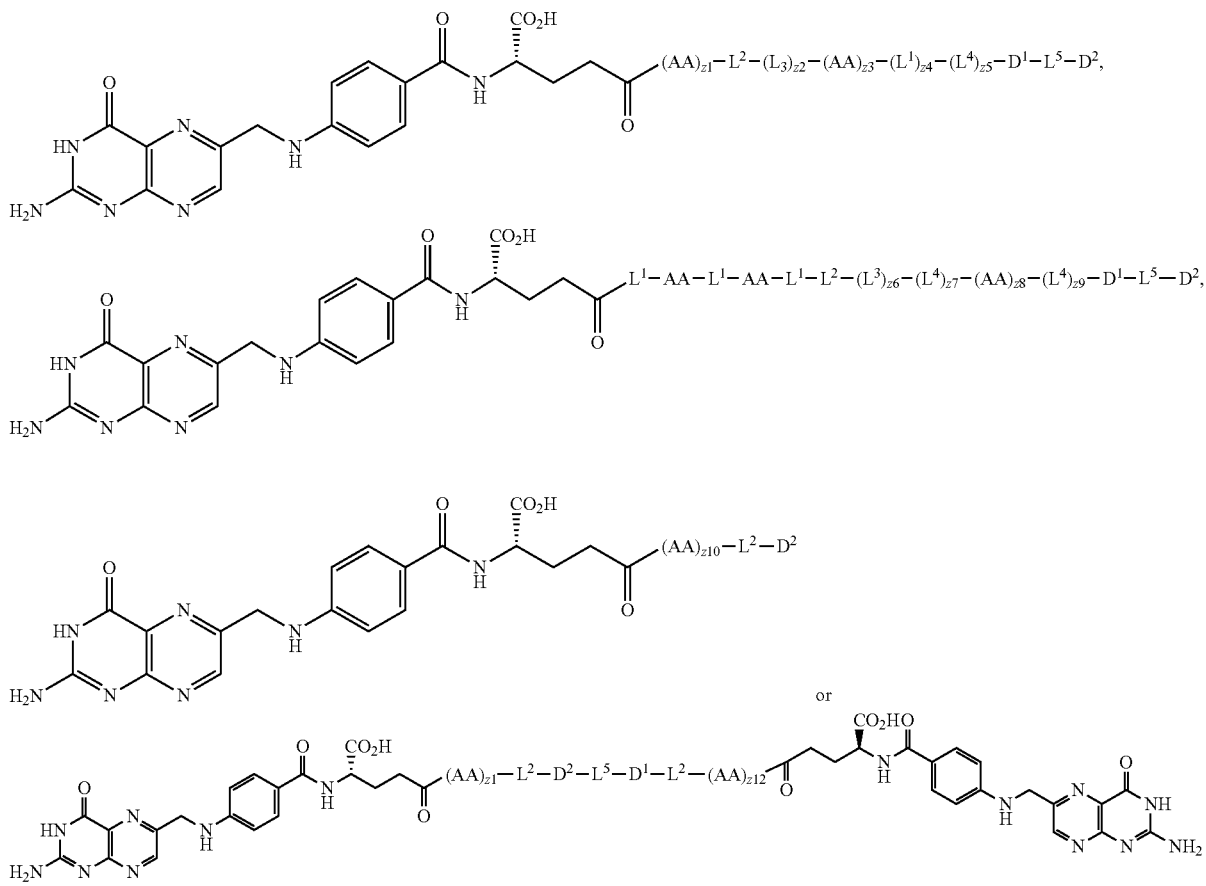

or a pharmaceutically acceptable salt thereof.

12. The conjugate of any one of clauses 1 to 11, having the formula
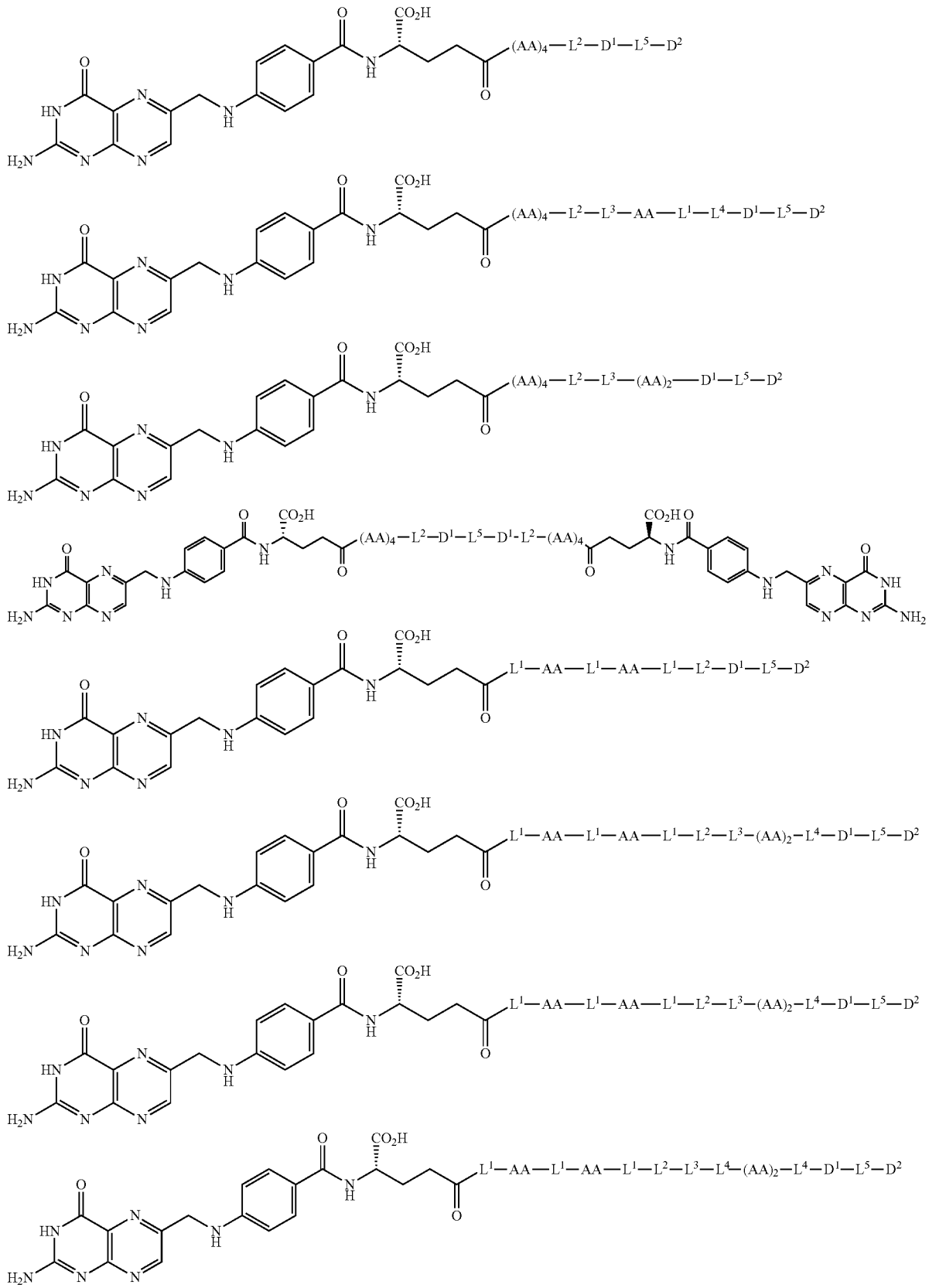

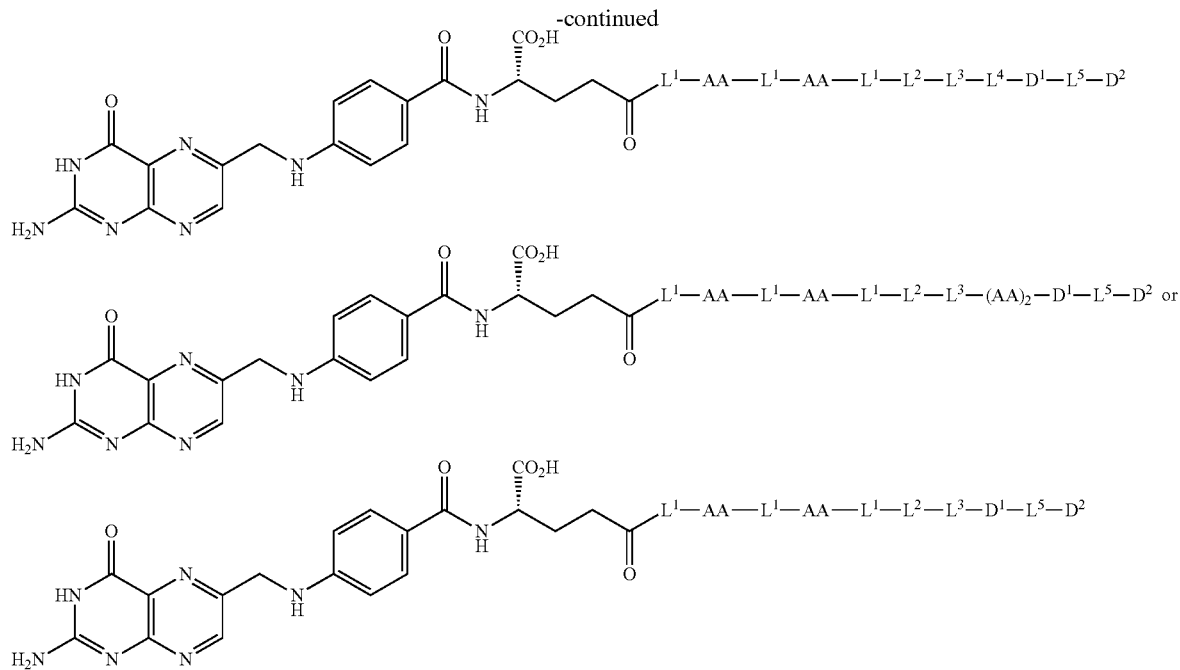

or a pharmaceutically acceptable salt thereof.

13. The conjugate of any one of clauses 1 to 12, wherein the sequence of -(AA)$_4$- is -Asp-Arg-Asp-Asp- (SEQ ID NO: 5); or a pharmaceutically acceptable salt thereof.
14. The conjugate of any one of clauses 1 to 13, wherein the sequence of -(AA)$_2$- is Val-CIT; or a pharmaceutically acceptable salt thereof.
15. The conjugate of any one of clauses 1 to 14, wherein L$^2$ is selected from the group consisting of

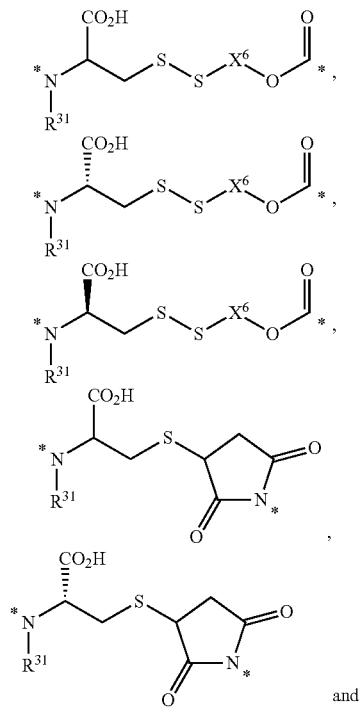

and wherein

R$^{31}$ is selected from the group consisting of H, D, C$_1$-C$_6$ alkyl, C$_2$-C$_6$ alkenyl, C$_2$-C$_6$ alkynyl and C$_3$-C$_6$ cycloalkyl, wherein each hydrogen atom in C$_1$-C$_6$ alkyl, C$_2$-C$_6$ alkenyl, C$_2$-C$_6$ alkynyl and C$_3$-C$_6$ cycloalkyl is independently optionally substituted by halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{32}$, —OC(O)R$^{32}$, —OC(O)NR$^{32}$R$^{32'}$, —OS(O)R$^{32}$, —OS(O)$_2$R$^{32}$, —SR$^{32}$, —S(O)R$^{32}$, —S(O)$_2$R$^{32}$, —S(O)NR$^{32}$R$^{32'}$, —S(O)$_2$NR$^{32}$R$^{32'}$, —OS(O)NR$^{32}$R$^{32'}$, —OS(O)$_2$NR$^{32}$R$^{32'}$, —NR$^{32}$R$^{32'}$, —NR$^{32}$C(O)R$^{33}$, —NR$^{32}$C(O)OR$^{33}$, —NR$^{32}$C(O)NR$^{33}$R$^{33'}$, —NR$^{32}$S(O)R$^{33}$, —NR$^{32}$S(O)$_2$R$^{33}$, —NR$^{32}$S(O)NR$^{33}$R$^{33'}$, —NR$^{32}$S(O)$_2$NR$^{33}$R$^{33'}$, —C(O)R$^{32}$, —C(O)OR$^{32}$ or —C(O)NR$^{32}$R$^{32'}$;

X$^6$ is C$_1$-C$_6$ alkyl or C$_6$-C$_{10}$ aryl(C$_1$-C$_6$ alkyl), wherein each hydrogen atom in C$_1$-C$_6$ alkyl and C$_6$-C$_{10}$ aryl(C$_1$-C$_6$ alkyl) is independently optionally substituted by halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{34}$, —OC(O)R$^{34}$, —OC(O)NR$^{34}$R$^{34'}$, —OS(O)R$^{34}$, —OS(O)$_2$R$^{34}$, —SR$^{34}$, —S(O)R$^{34}$, —S(O)$_2$R$^{34}$, —S(O)NR$^{34}$R$^{34'}$, —S(O)$_2$NR$^{34}$R$^{34'}$, —OS(O)NR$^{34}$R$^{34'}$, —OS(O)$_2$NR$^{34}$R$^{34'}$, —NR$^{34}$R$^{34'}$, —NR$^{34}$C(O)R$^{35}$, —NR$^{34}$C(O)OR$^{35}$, —NR$^{34}$C(O)NR$^{35}$R$^{35'}$, —NR$^{34}$S(O)R$^{35}$, —NR$^{34}$S(O)$_2$R$^{35}$, —NR$^{34}$S(O)NR$^{35}$R$^{35'}$, —NR$^{34}$S(O)$_2$NR$^{35}$R$^{35'}$, —C(O)R$^{34}$, —C(O)OR$^{34}$ or —C(O)NR$^{34}$R$^{34'}$;

each R$^{32}$, R$^{32'}$, R$^{33}$, R$^{33'}$, R$^{34}$, R$^{34'}$, R$^{35}$ and R$^{35'}$ are independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl;

$R^{36}$ is independently selected from the group consisting of H, D, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{37}$, —$OC(O)R^{37}$, —$OC(O)NR^{37}R^{37'}$, —$OS(O)R^{37}$, —$OS(O)_2R^{37}$, —$SR^{37}$, —$S(O)R^{37}$, —$S(O)_2R^{37}$, —$S(O)NR^{37}R^{37'}$, —$S(O)_2NR^{37}R^{37'}$, —$OS(O)NR^{37}R^{37'}$, —$OS(O)_2NR^{37}R^{37'}$, —$NR^{37}R^{37'}$, —$NR^{37}C(O)R^{38}$, —$NR^{37}C(O)OR^{38}$, —$NR^{37}C(O)NR^{38}R^{38'}$, —$NR^{37}S(O)R^{38}$, —$NR^{37}S(O)_2R^{38}$, —$NR^{37}S(O)NR^{38}R^{38'}$, —$NR^{37}S(O)_2NR^{38}R^{38'}$, —$C(O)R^{37}$, —$C(O)OR^{37}$ or —$C(O)NR^{37}R^{37'}$;

$R^{37}$, $R^{37'}$, $R^{38}$ and $R^{38'}$ are each independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl; and

* is a covalent bond;

or a pharmaceutically acceptable salt thereof.

16. The conjugate of any one of clauses 1 to 15, wherein $L^2$ is of the formula

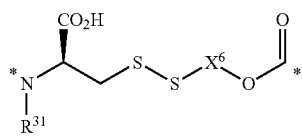

wherein $R^{31}$ is H; and $X^6$ is $C_1$-$C_6$ alkyl; or a pharmaceutically acceptable salt thereof.

17. The conjugate of any one of clauses 1 to 15, wherein $L^2$ is of the formula

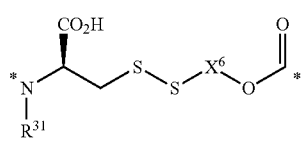

wherein $R^{31}$ is H; and $X^6$ is $C_6$-$C_{10}$ aryl($C_1$-$C_6$ alkyl); or a pharmaceutically acceptable salt thereof.

18. The conjugate of any one of clauses 1 to 15, wherein $L^2$ is of the formula

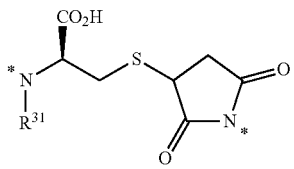

wherein $R^{36}$ is independently selected from the group consisting of H, D, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{37}$, —$OC(O)R^{37}$, —$OC(O)NR^{37}R^{37'}$, —$OS(O)R^{37}$, —$OS(O)_2R^{37}$, —$SR^{37}$, —$S(O)R^{37}$, —$S(O)_2R^{37}$, —$S(O)NR^{37}R^{37'}$, —$S(O)_2NR^{37}R^{37'}$, —$OS(O)NR^{37}R^{37'}$, —$OS(O)_2NR^{37}R^{37'}$, —$NR^{37}R^{37'}$, —$NR^{37}C(O)R^{38}$, —$NR^{37}C(O)OR^{38}$, —$NR^{37}C(O)NR^{38}R^{38'}$, —$NR^{37}S(O)R^{38}$, —$NR^{37}S(O)_2R^{38}$, —$NR^{37}S(O)NR^{38}R^{38'}$, —$NR^{37}S(O)_2NR^{38}R^{38'}$, —$C(O)R^{37}$, —$C(O)OR^{37}$ or —$C(O)NR^{37}R^{37'}$;

$R^{37}$, $R^{37'}$, $R^{38}$ and $R^{38'}$ are each independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl; and

* is a covalent bond.

19. The conjugate of any one of clauses 1 to 15, wherein $R^{36}$ is H; or a pharmaceutically acceptable salt thereof.

20. The conjugate of any one of clauses 1 to 15, 18 or 19, wherein the linker is of the formula (SEQ ID NO: 1 is included in the structure below)

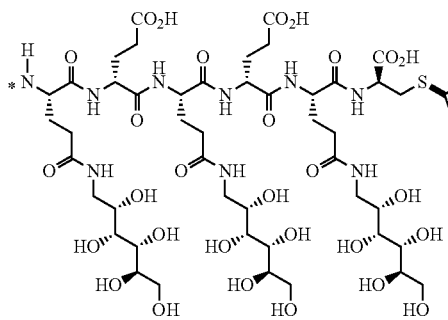

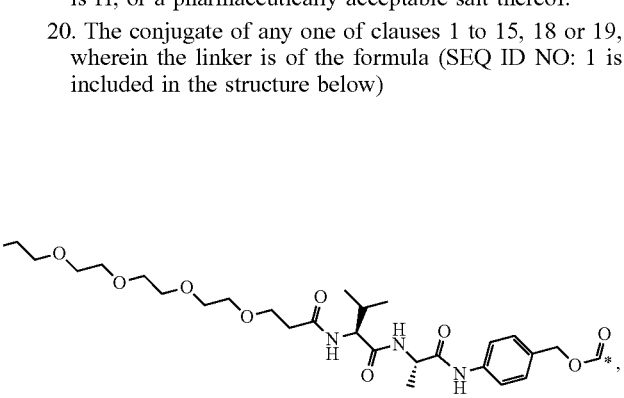

wherein * is a bond; or a pharmaceutically acceptable salt thereof.

21. The conjugate of any one of clauses 1 to 15, 18 or 19, wherein the linker is of the formula (SEQ ID NO: 1 is included in the structure below)

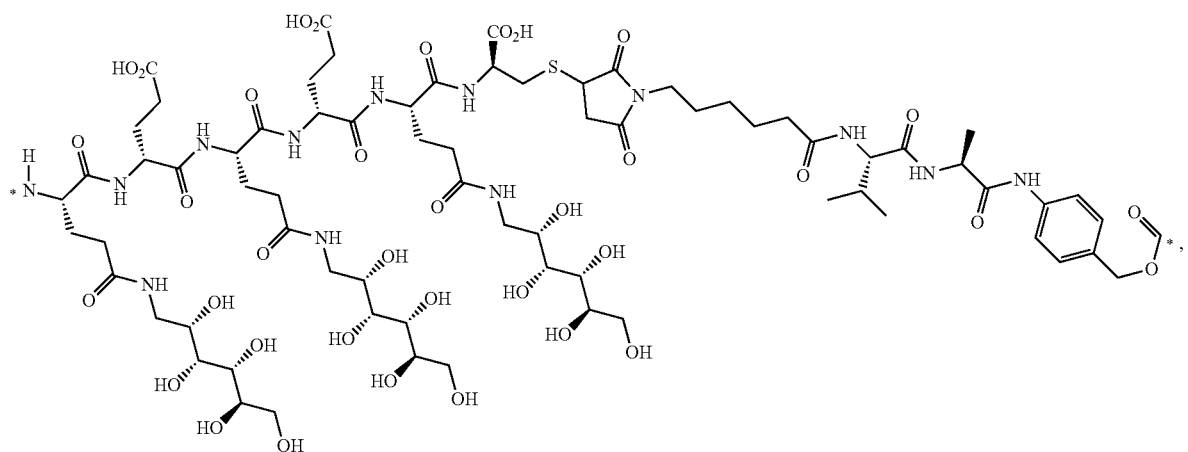 [SMILES: CC(C)[C@H](NC(=O)CCCCCN1C(=O)CC(SC[C@@H](NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)[C@@H](CCC(=O)O)NC(=O)[C@@H](N)CCC(=O)NC[C@H](O)[C@@H](O)[C@H](O)[C@H](O)CO)C(=O)O)C1=O)C(=O)N[C@@H](C)C(=O)Nc1ccc(COC=O)cc1]

wherein * is a bond; or a pharmaceutically acceptable salt thereof.

22. The conjugate of any one of clauses 1 to 16, wherein the linker is of the formula (SEQ ID NO: 1 is included in the structure below)

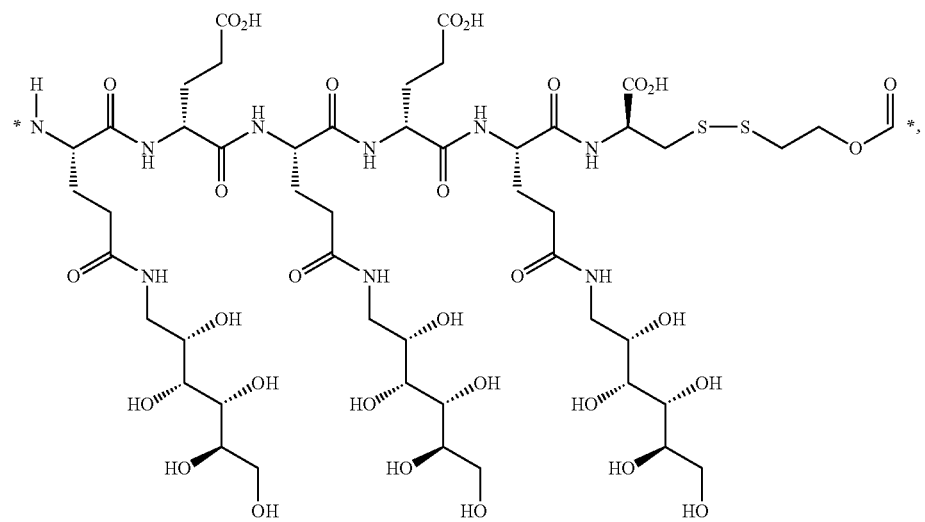 [SMILES: N[C@@H](CCC(=O)NC[C@H](O)[C@@H](O)[C@H](O)[C@H](O)CO)C(=O)N[C@H](CCC(=O)O)C(=O)N[C@@H](CCC(=O)NC[C@H](O)[C@@H](O)[C@H](O)[C@H](O)CO)C(=O)N[C@H](CCC(=O)O)C(=O)N[C@@H](CCC(=O)NC[C@H](O)[C@@H](O)[C@H](O)[C@H](O)CO)C(=O)N[C@H](CSSCCOC=O)C(=O)O]

wherein * is a bond; or a pharmaceutically acceptable salt thereof.

23. The conjugate of any one of clauses 1 to 16, wherein the linker is of the formula (SEQ ID NO: 2 is included in the structure below)

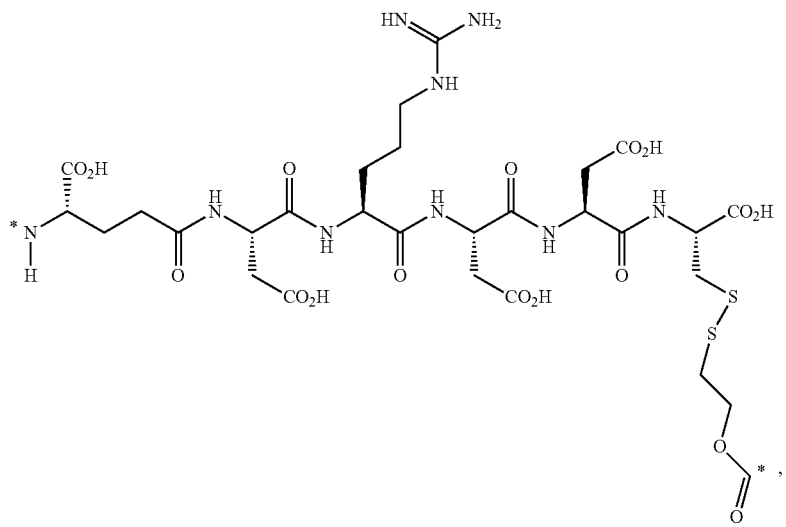 [SMILES: N=C(N)NCCC[C@H](NC(=O)[C@H](CC(=O)O)NC(=O)CC[C@H](N)C(=O)O)C(=O)N[C@@H](CC(=O)O)C(=O)N[C@@H](CC(=O)O)C(=O)N[C@@H](CSSCCOC=O)C(=O)O]

wherein * is a bond; or a pharmaceutically acceptable salt thereof.

24. The conjugate of any one of clauses 1 to 15 or 16, wherein the linker is of the formula (SEQ ID NO: 2 is included in the structure below)

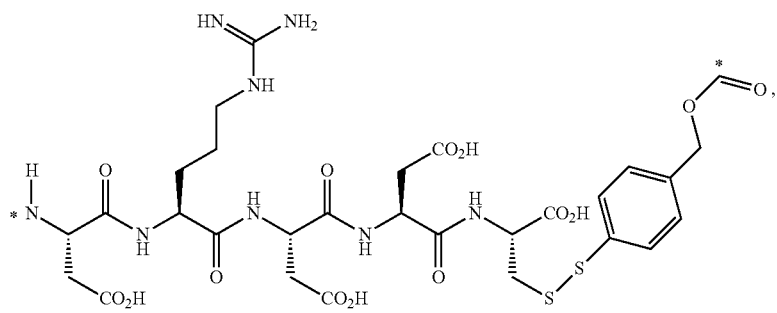 [SMILES: N=C(N)NCCC[C@H](NC(=O)[C@@H](N)CC(=O)O)C(=O)N[C@@H](CC(=O)O)C(=O)N[C@@H](CC(=O)O)C(=O)N[C@@H](CSSc1ccc(COC=O)cc1)C(=O)O]

wherein * is a bond; or a pharmaceutically acceptable salt thereof.

25. The conjugate of any one of clauses 1 to 15, 18 or 19, wherein the linker is of the formula (SEQ ID NO: 1 is included in the structure below)

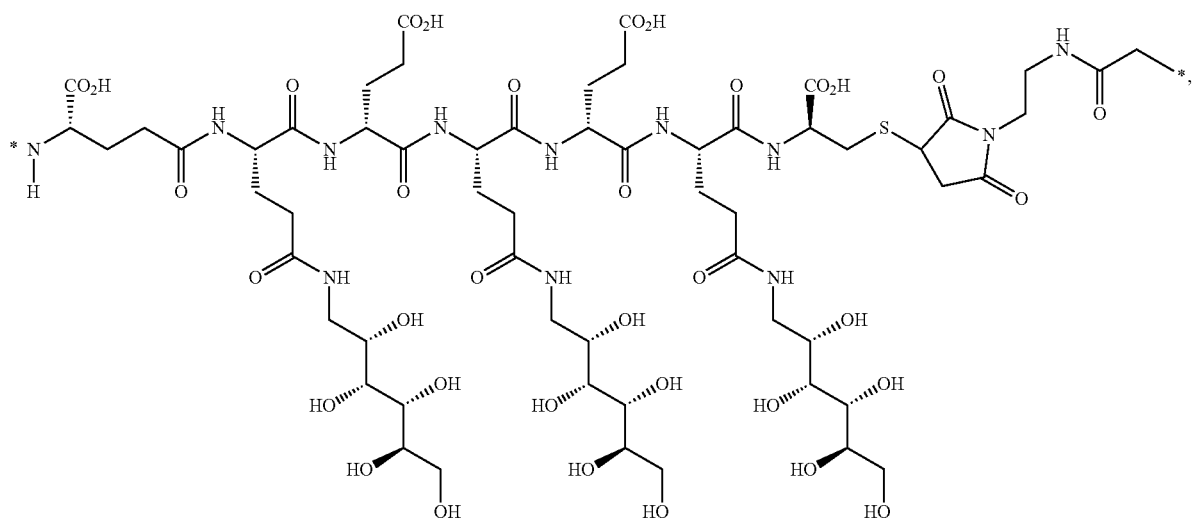 [SMILES: CCC(=O)NCCN1C(=O)CC(SC[C@@H](NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)CC[C@H](N)C(=O)O)C(=O)O)C1=O]

wherein * is a bond; or a pharmaceutically acceptable salt thereof.

26. The conjugate of any one of clauses 1 to 15, 18 or 19, wherein the linker is of the formula (SEQ ID NO: 2 is included in the structure below)

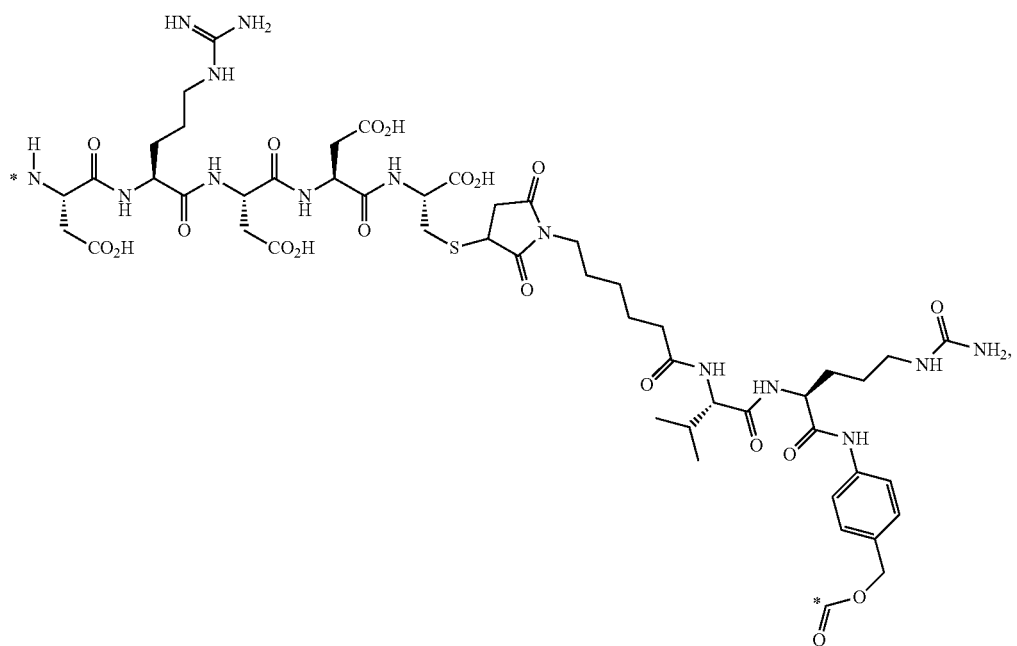 [SMILES: CC(C)[C@H](NC(=O)CCCCCN1C(=O)CC(SC[C@H](NC(=O)[C@H](CC(=O)O)NC(=O)[C@H](CC(=O)O)NC(=O)[C@H](CCCNC(=N)N)NC(=O)[C@@H](N)CC(=O)O)C(=O)O)C1=O)C(=O)N[C@@H](CCCNC(N)=O)C(=O)Nc1ccc(COC=O)cc1]

wherein * is a bond; or a pharmaceutically acceptable salt thereof.

27. The conjugate of any one of clauses 1 to 15, 18 or 19, wherein the linker is of the formula (SEQ ID NO: 2 is included in the structure below)

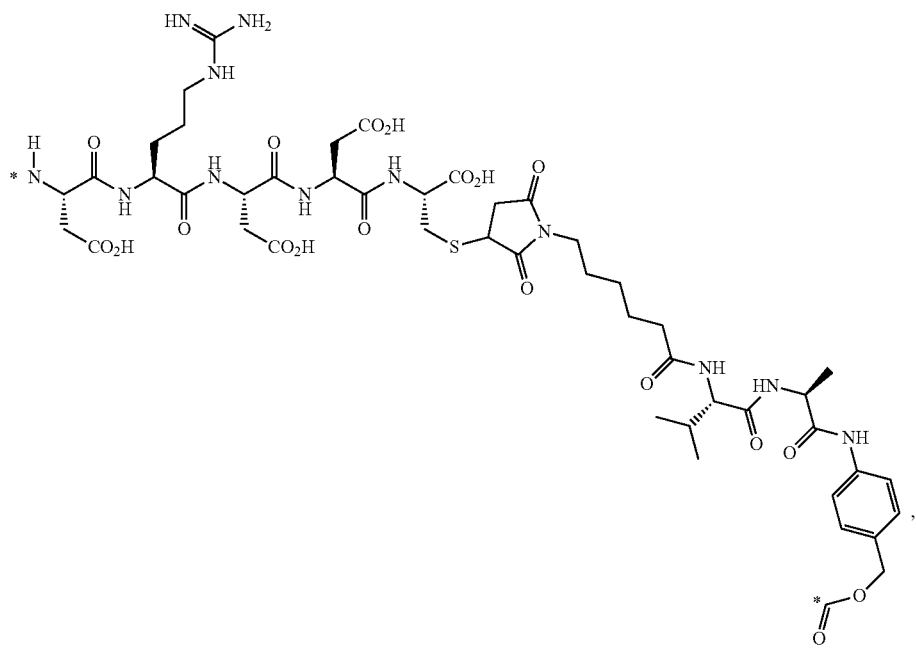 [SMILES: CC(C)[C@H](NC(=O)CCCCCN1C(=O)CC(SC[C@H](NC(=O)[C@H](CC(=O)O)NC(=O)[C@H](CC(=O)O)NC(=O)[C@H](CCCNC(=N)N)NC(=O)[C@@H](N)CC(=O)O)C(=O)O)C1=O)C(=O)N[C@@H](C)C(=O)Nc1ccc(COC=O)cc1]
wherein * is a bond, or a pharmaceutically acceptable salt thereof.
28. The conjugate of any one of clauses 1 to 15, 18 or 19, wherein the linker is of the formula (SEQ ID NO: 1 is included in the structure below)
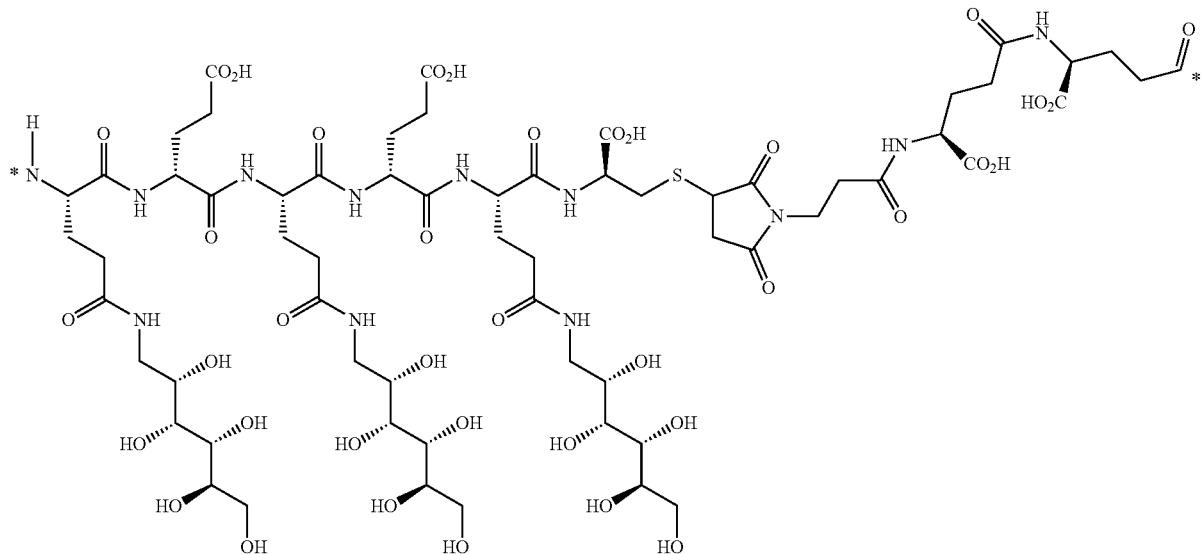 [SMILES: N[C@@H](CCC(=O)NC[C@H](O)[C@@H](O)[C@H](O)[C@H](O)CO)C(=O)N[C@H](CCC(=O)O)C(=O)N[C@@H](CCC(=O)NC[C@H](O)[C@@H](O)[C@H](O)[C@H](O)CO)C(=O)N[C@H](CCC(=O)O)C(=O)N[C@@H](CCC(=O)NC[C@H](O)[C@@H](O)[C@H](O)[C@H](O)CO)C(=O)N[C@H](CSC1CC(=O)N(CCC(=O)N[C@@H](CCC(=O)N[C@@H](CCC=O)C(=O)O)C(=O)O)C1=O)C(=O)O]
wherein * is a bond, or a pharmaceutically acceptable salt thereof.
29. The conjugate of any of clauses 1-28, wherein -D$^1$-L$^5$-D$^2$ is of the formula

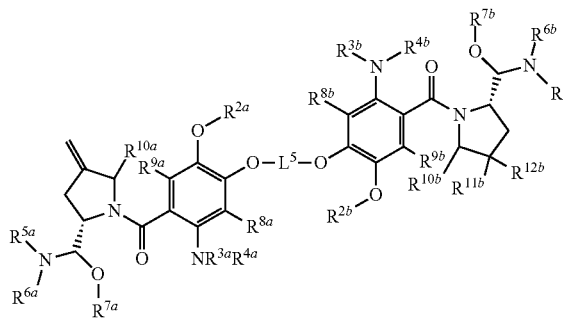

wherein $R^{2a}$, $R^{3a}$, $R^{4a}$, $R^{8a}$, $R^{9a}$, $R^{10a}$, $R^{2b}$, $R^{3b}$, $R^{4b}$, $R^{8b}$ and $R^{9b}$ are H; or a pharmaceutically acceptable salt thereof.

30. The conjugate of any of clause 29, wherein $R^{2a}$, $R^{3a}$, $R^{4a}$, $R^{8a}$, $R^{9a}$, $R^{10a}$, $R^{2b}$, $R^{3b}$, $R^{4b}$, $R^{8b}$ and $R^{9b}$ are H, $L^5$ is $C_1$-$C_{10}$ alkyl or —$(CR^{49}R^{49'})_u C(O)$—, each $R^{49}$ and $R^{49'}$ is H, and u is 1, 2, 3, or 4; or a pharmaceutically acceptable salt thereof.

31. The conjugate of any of clauses 1-28, wherein -$D^1$-$L^5$-$D^2$ is of the formula

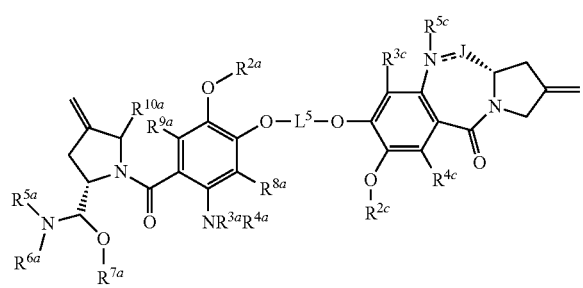

wherein $R^{2a}$, $R^{3a}$, $R^{4a}$, $R^{5a}$, $R^{6a}$, $R^{7a}$, $R^{8a}$, $R^{9a}$, $R^{10a}$, $R^{2c}$, $R^{3c}$, $R^{4c}$, $R^{5c}$ are H; or a pharmaceutically acceptable salt thereof.

32. The conjugate of any of clause 31, wherein, $L^5$ is $C_1$-$C_{10}$ alkyl or —$(CR^{49}R^{49'})_u C(O)$—, wherein each $R^{49}$ and $R^{49'}$ is H, and u is 1, 2, 3, 4 or 5; or a pharmaceutically acceptable salt thereof.

33. The conjugate of any of clauses 1-28, wherein -$D^1$-$L^5$-$D^2$ is of the formula

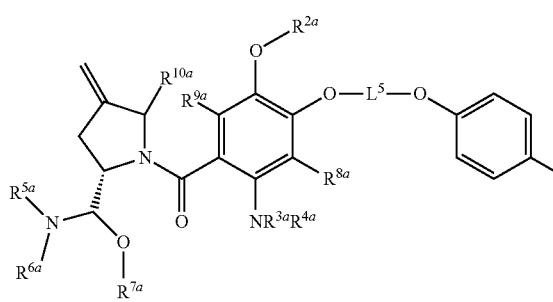

wherein, $R^{2a}$, $R^{3a}$, $R^{4a}$, $R^{5a}$, $R^{6a}$, $R^{7a}$, $R^{8a}$, $R^{9a}$ and $R^{10a}$ are H; or a pharmaceutically acceptable salt thereof.

34. The conjugate of clause 33, wherein, $L^5$ is $C_1$-$C_{10}$ alkyl or —$(CR^{49}R^{49'})_u C(O)$—, wherein each $R^{49}$ and $R^{49'}$ is H, and u is 1, 2, 3, 4 or 5; or a pharmaceutically acceptable salt thereof.

35. The conjugate of any of clauses 1-28, wherein -$D^1$-$L^5$-$D^2$ is of the formula

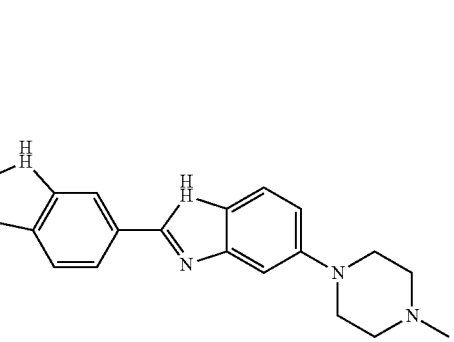

wherein, $R^{2a}$, $R^{3a}$, $R^{4a}$, $R^{5a}$, $R^{6a}$, $R^{7a}$, $R^{8a}$, $R^{9a}$, $R^{10a}$ and $R^{11a}$ are H; or a pharmaceutically acceptable salt thereof.

36. The conjugate of clause 35, wherein $L^5$ is $C_1$-$C_{10}$ alkyl or —$(CR^{49}R^{49'})_u C(O)$—, wherein each $R^{49}$ and $R^{49'}$ is H, and u is 1, 2, 3, 4 or 5; or a pharmaceutically acceptable salt thereof.

37. The conjugate of any of claims 1-28, wherein -$D^1$-$L^5$-$D^2$ is of the formula

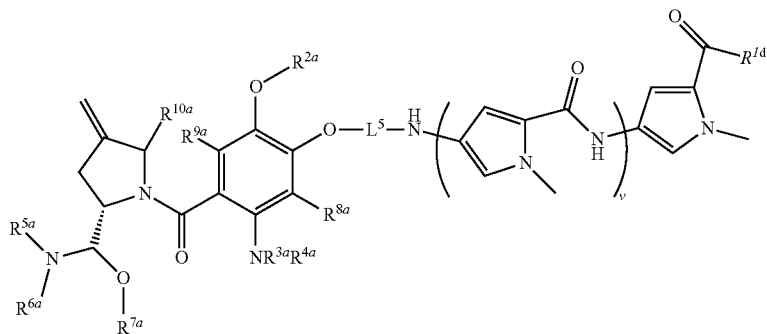

wherein $R^{2a}$, $R^{3a}$, $R^{4a}$, $R^{5a}$, $R^{6a}$, $R^{7a}$, $R^{8a}$, $R^{9a}$, $R^{10a}$, $R^{1d}$ are H; or a pharmaceutically acceptable salt thereof.

38. The conjugate of clause 37, wherein $L^5$ is $C_1$-$C_{10}$ alkyl or —$(CR^{49}R^{49'})_uC(O)$—, wherein each $R^{49}$ and $R^{49'}$ is H, and u is 1, 2, 3, 4 or 5; or a pharmaceutically acceptable salt thereof.

39. The conjugate of any of clauses 1-28, wherein -$D^1$-$L^5$-$D^2$ is of the formula

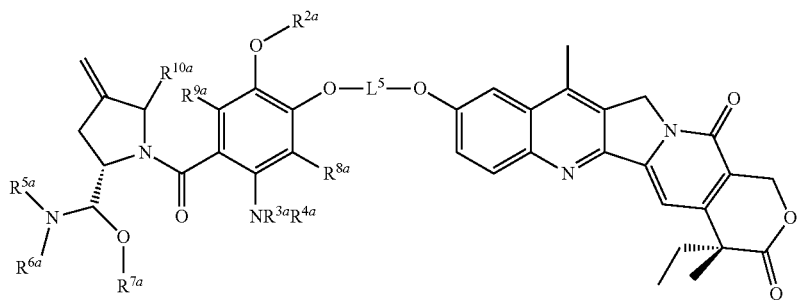

wherein $R^{2a}$, $R^{3a}$, $R^{4a}$, $R^{5a}$, $R^{6a}$, $R^{7a}$, $R^{8a}$, $R^{9a}$ and $R^{10a}$ are H; or a pharmaceutically acceptable salt thereof.

40. The conjugate of clause 39, wherein $L^5$ is $C_1$-$C_{10}$ alkyl or —$(CR^{49}R^{49'})_uC(O)$—, wherein each $R^{49}$ and $R^{49'}$ is H, and u is 1, 2, 3, 4 or 5; or a pharmaceutically acceptable salt thereof.

41. The conjugate of any of clauses 1-28, wherein -$D^1$-$L^5$-$D^2$ is of the formula

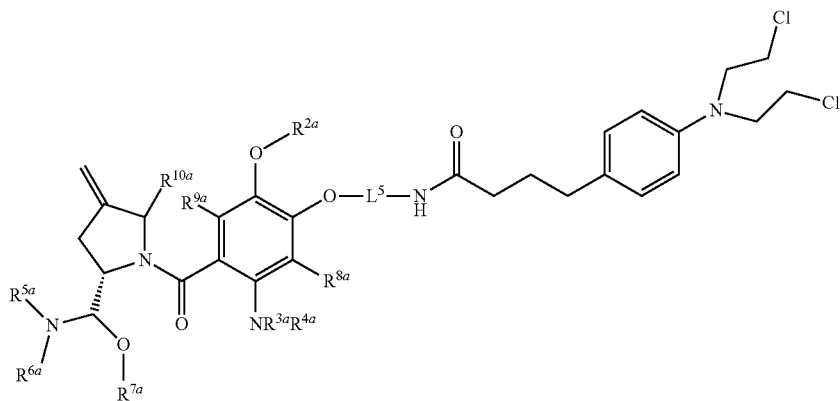

wherein $R^{2a}$, $R^{3a}$, $R^{4a}$, $R^{5a}$, $R^{6a}$, $R^{7a}$, $R^{8a}$, $R^{9a}$ and $R^{10a}$ are H; or a pharmaceutically acceptable salt thereof.

42. The conjugate of clause 41, wherein $L^5$ is $C_1$-$C_{10}$ alkyl or —$(CR^{49}R^{49'})_uC(O)$—, wherein each $R^{49}$ and $R^{49'}$ is H, and u is 1, 2, 3, 4 or 5; or a pharmaceutically acceptable salt thereof.

43. The conjugate of any of clauses 1-28, wherein -$D^1$-$L^5$-$D^2$ is of the formula

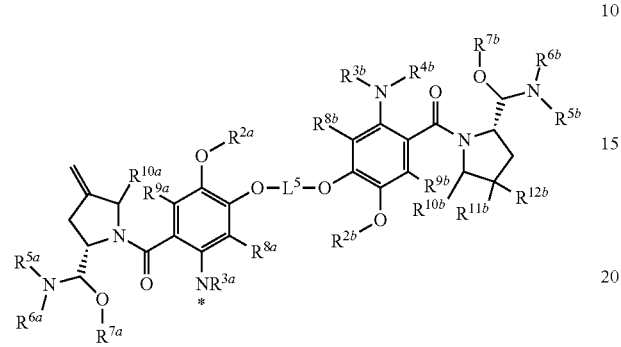

wherein $R^{2a}$, $R^{3a}$, $R^{5a}$, $R^{6a}$, $R^{7a}$, $R^{8a}$, $R^{9a}$, $R^{10a}$, $R^{2b}$, $R^{3b}$, $R^{4b}$, $R^{5b}$, $R^{6b}$, $R^{7b}$, $R^{8b}$, $R^{9b}$, $R^{10b}$, $R^{11b}$ and $R^{12b}$ are H; or a pharmaceutically acceptable salt thereof.

44. The conjugate of clause 43, wherein $L^5$ is $C_1$-$C_{10}$ alkyl or $(CR^{49}R^{49'})_uC(O)$—, wherein each $R^{49}$ and $R^{49'}$ is H, and u is 1, 2, 3, 4 or 5; or a pharmaceutically acceptable salt thereof.

45. A conjugate of the formula (SEQ ID NO: 1 is included in the structure below)

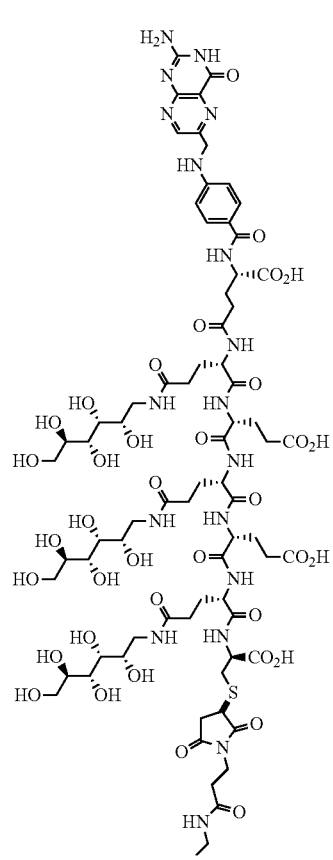

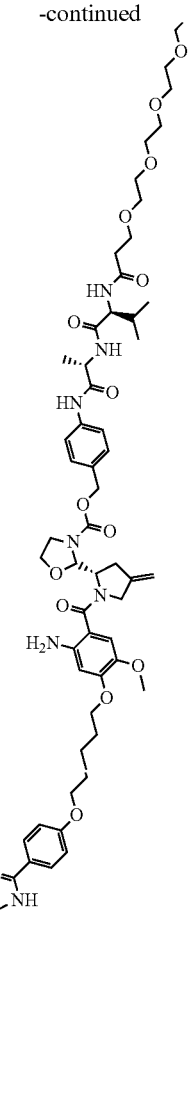

or a pharmaceutically acceptable salt thereof.

46. A pharmaceutical composition comprising a therapeutically effective amount of a conjugate according to any one of clauses 1-45, or a pharmaceutically acceptable salt thereof, and at least on excipient.

47. A method of treating abnormal cell growth in a mammal, including a human, the method comprising administering to the mammal a conjugate of any one of clauses 1-45.

48. The method of clause 47, wherein the abnormal cell growth is cancer

49. The method of clause 48, wherein the cancer is lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said method, said abnormal cell growth is a benign proliferative disease, including, but not limited to, psoriasis, benign prostatic hypertrophy or restinosis.

50. Use of a conjugate according to any one of clauses 1-45 in the preparation of a medicament for the treatment of cancer.

BRIEF DESCRIPTION OF THE DRAWINGS

FIG. 2 also shows and that EC1788 (▲) dosed at 0.2 µmol/kg TIW for two weeks decreases KB tumors in test animals compared to untreated control (●), and that EC1788 gave a complete response. The dotted line indicates the last dosing day.

FIG. 3 also shows and that EC1879 (c) dosed at 2 µmol/kg TIW for 1 week decreases KB tumors in test animals compared to untreated control (a), and that EC1879 gave a partial response. FIG. 3 also shows and that EC1788 (b) dosed at 0.4 µmol/kg BIW for 2 weeks decreases KB tumors in test animals compared to untreated control (a), and that EC1788 gave a complete response, and cure. The dotted line indicates the last dosing day.

DEFINITIONS

Figure 1:
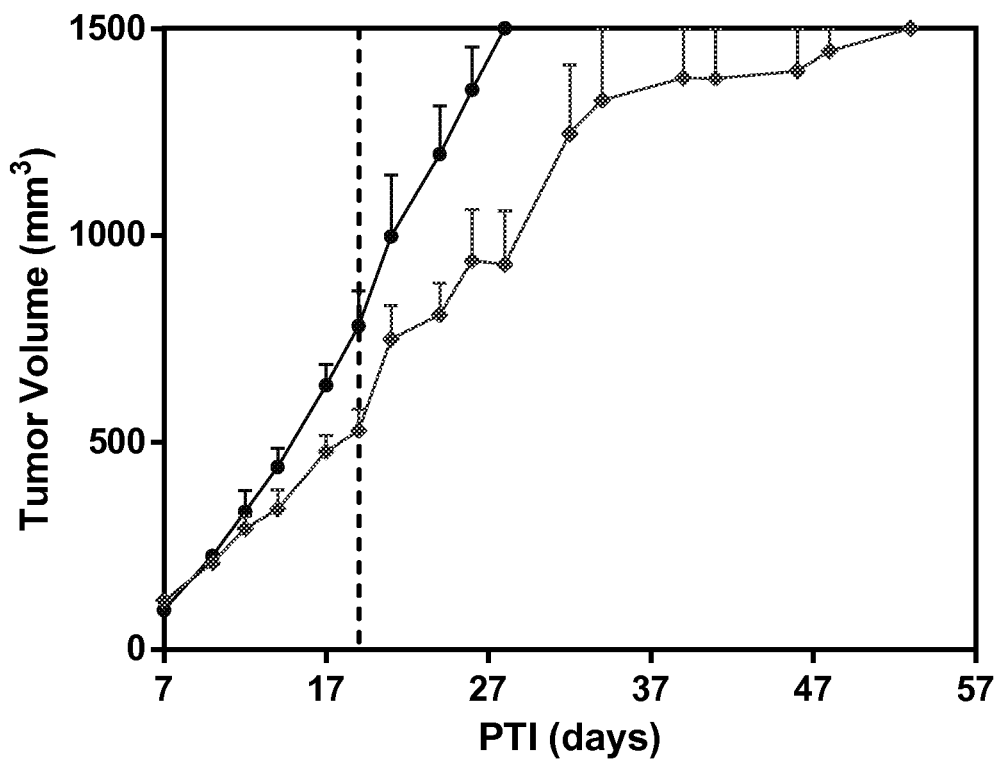
FIG. 1 shows that EC1629 (♦) dosed at 2 µmol/kg TIW for two weeks decreases KB tumors in test animals compared to untreated control (●). The dotted line indicates the last dosing day.

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$, Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (=O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like.

As used herein, the term "alkenyl" includes a chain of carbon atoms, which is optionally branched, and contains from 2 to 20 carbon atoms, and also includes at least one carbon-carbon double bond (i.e. C=C). It will be understood that in certain embodiments, alkenyl may be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkenyl groups, including $C_2$-$C_8$, $C_2$-$C_7$, $C_2$-$C_6$, and $C_2$-$C_4$ may be referred to as lower alkenyl. Alkenyl may be unsubstituted, or substituted as described for alkyl or as described in the various embodiments provided herein. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e. C≡C). It will be understood that in certain embodiments alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkynyl groups, including $C_2$-$C_8$, $C_2$-$C_7$, $C_2$-$C_6$, and $C_2$-$C_4$ may be referred to as lower alkynyl. Alkenyl may be unsubstituted, or substituted as described for alkyl or as described in the various embodiments provided herein. Illustrative alkenyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthalenyl and anthracenyl. The aryl group may be unsubstituted, or substituted as described for alkyl or as described in the various embodiments provided herein.

As used herein, the term "cycloalkyl" refers to a 3 to 15 member all-carbon monocyclic ring, an all-carbon 5-member/6-member or 6-member/6-member fused bicyclic ring, or a multicyclic fused ring (a "fused" ring system means that each ring in the system shares an adjacent pair of carbon atoms with each other ring in the system) group where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_6$, $C_3$-$C_6$ and $C_4$-$C_6$. Cycloalkyl may be unsubstituted, or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, adamantyl, norbornyl, norbornenyl, 9H-fluoren-9-yl, and the like.

As used herein, the term "heterocycloalkyl" refers to a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. Heterocycloalkyl may also have one of more double bonds, including double bonds to nitrogen (e.g. C=N or N=N) but does not contain a completely conjugated pi-electron system. It will be understood that in certain embodiments, heterocycloalkyl may be advantageously of limited size such as 3- to 7-membered heterocycloalkyl, 5- to 7-membered heterocycloalkyl, and the like. Heterocycloalkyl may be unsubstituted, or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1,2,3,4-tetrahydropyridinyl, and the like.

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazoloyl, and the like.

As used herein, "hydroxy" or "hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "aryloxy" refers to an —O-aryl or an —O-heteroaryl group. Representative examples include, but are not limited to, phenoxy, pyridinyloxy, furanyloxy, thienyloxy, pyrimidinyloxy, pyrazinyloxy, and the like, and the like.

As used herein, "mercapto" refers to an —SH group.

As used herein, "alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "halo" or "halogen" refers to fluorine, chlorine, bromine or iodine.

As used herein, "trihalomethyl" refers to a methyl group having three halo substituents, such as a trifluoromethyl group.

As used herein, "cyano" refers to a —CN group.

As used herein, "sulfinyl" refers to a —S(O)R" group, where R" is any R group as described in the various embodiments provided herein, or R" may be a hydroxyl group.

As used herein, "sulfonyl" refers to a —S(O)$_2$R" group, where R" is any R group as described in the various embodiments provided herein, or R" may be a hydroxyl group.

As used herein, "S-sulfonamido" refers to a —S(O)$_2$NR"R" group, where R" is any R group as described in the various embodiments provided herein.

As used herein, "N-sulfonamido" refers to a —NR"S(O)$_2$R" group, where R" is any R group as described in the various embodiments provided herein.

As used herein, "O-carbamyl" refers to a —OC(O)NR"R" group, where R" is any R group as described in the various embodiments provided herein.

As used herein, "N-carbamyl" refers to an R"OC(O)NR"— group, where R" is any R group as described in the various embodiments provided herein.

As used herein, "O-thiocarbamyl" refers to a —OC(S)NR"R" group, where R" is any R group as described in the various embodiments provided herein.

As used herein, "N-thiocarbamyl" refers to a R"OC(S)NR"— group, where R" is any R group as described in the various embodiments provided herein.

As used herein, "amino" refers to an —NR"R" group, where R" is any R group as described in the various embodiments provided herein.

As used herein, "C-amido" refers to a —C(O)NR"R" group, where R" is any R group as described in the various embodiments provided herein.

As used herein, "N-amido" refers to a R"C(O)NR"— group, where R" is any R group as described in the various embodiments provided herein.

As used herein, "nitro" refers to a $NO_2$ group.

As used herein, "bond" refers to a covalent bond.

As used herein, "optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocycle group is not substituted with the alkyl group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, the term "pharmaceutically acceptable salt" refers to those salts which counter ions which may be used in pharmaceuticals. Such salts include:

(1) acid addition salts, which can be obtained by reaction of the free base of the parent conjugate with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or (2) salts formed when an acidic proton present in the parent conjugate either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like.

Pharmaceutically acceptable salts are well known to those skilled in the art, and any such pharmaceutically acceptable salt may be contemplated in connection with the embodiments described herein As used herein, "amino acid" (a.k.a. "AA") means any molecule that includes an alpha-carbon atom covalently bonded to an amino group and an acid group. The acid group may include a carboxyl group. "Amino acid" may include molecules having one of the formulas:

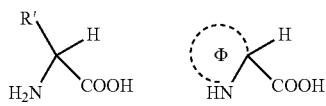

wherein R' is a side group and Ψ includes at least 3 carbon atoms. "Amino acid" includes stereoisomers such as the D-amino acid and L-amino acid forms. Illustrative amino acid groups include, but are not limited to, the twenty endogenous human amino acids and their derivatives, such as lysine (Lys), asparagine (Asn), threonine (Thr), serine (Ser), isoleucine (Ile), methionine (Met), proline (Pro), histidine (His), glutamine (Gln), arginine (Arg), glycine (Gly), aspartic acid (Asp), glutamic acid (Glu), alanine (Ala), valine (Val), phenylalanine (Phe), leucine (Leu), tyrosine (Tyr), cysteine (Cys), tryptophan (Trp), phosphoserine (PSER), sulfo-cysteine, arginosuccinic acid (ASA), hydroxyproline, phosphoethanolamine (PEA), sarcosine (SARC), taurine (TAU), carnosine (CARN), citrulline (CIT), anserine (ANS), 1,3-methyl-histidine (ME-HIS), alpha-amino-adipic acid (AAA), beta-alanine (BALA), ethanolamine (ETN), gamma-amino-butyric acid (GABA), beta-amino- isobutyric acid (BAIA), alpha-amino-butyric acid (BABA), L-allo-cystathionine (cystathionine-A; CYSTA-A), L-cystathionine (cystathionine-B; CYSTA-B), cystine, allo-isoleucine (ALLO-ILE), DL-hydroxylysine (hydroxylysine (I)), DL-allo-hydroxylysine (hydroxylysine (2)), ornithine (ORN), homocystine (HCY), and derivatives thereof. It will be appreciated that each of these examples are also contemplated in connection with the present disclosure in the D-configuration as noted above. Specifically, for example, D-lysine (D-Lys), D-asparagine (D-Asn), D-threonine (D-Thr), D-serine (D-Ser), D-isoleucine (D-Ile), D-methionine (D-Met), D-proline (D-Pro), D-histidine (D-His), D-glutamine (D-Gln), D-arginine (D-Arg), D-glycine (D-Gly), D-aspartic acid (D-Asp), D-glutamic acid (D-Glu), D-alanine (D-Ala), D-valine (D-Val), D-phenylalanine (D-Phe), D-leucine (D-Leu), D-tyrosine (D-Tyr), D-cysteine (D-Cys), D-tryptophan (D-Trp), D-citrulline (D-CIT), D-carnosine (D-CARN), and the like. In connection with the embodiments described herein, amino acids can be covalently attached to other portions of the conjugates described herein through their alpha-amino and carboxy functional groups (i.e. in a peptide bond configuration), or through their side chain functional groups (such as the side chain carboxy group in glutamic acid) and either their alpha-amino or carboxy functional groups. It will be understood that amino acids, when used in connection with the conjugates described herein, may exist as zwitterions in a conjugate in which they are incorporated.

As used herein, "sugar" refers to carbohydrates, such as monosaccharides, disaccharides, or oligosaccharides. In connection with the present disclosure, monosaccharides are preferred. Non-limiting examples of sugars include erythrose, threose, ribose, arabinose, xylose, lyxose, allose, altrose, glucose, mannose, galactose, ribulose, fructose, sorbose, tagatose, and the like. It will be undertsood that as used in connection with the present disclosure, sugar includes cyclic isomers of amino sugars, deoxy sugars, acidic sugars, and combinations thereof. Non-limiting examples of such sugars include, galactosamine, glucosamine, deoxyribose, fucose, rhamnose, glucuronic acid, ascorbic acid, and the like. In some embodiments, sugars for use in connection with the present disclosure include

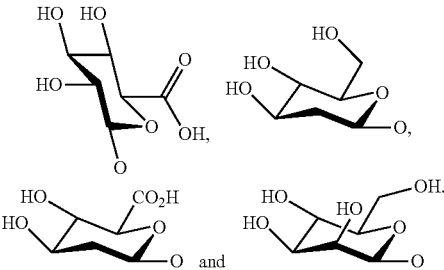

As used herein, "prodrug" refers to a compound that can be administered to a subject in a pharmacologically inactive form which then can be converted to a pharmacologically active form through a normal metabolic process, such as hydrolysis of an oxazolidine. It will be understood that the metabolic processes through which a prodrug can be converted to an active drug include, but are not limited to, one or more spontaneous chemical reaction(s), enzyme-catalyzed chemical reaction(s), and/or other metabolic chemical reaction(s), or a combination thereof. It will be appreciated that understood that a variety of metabolic processes are known in the art, and the metabolic processes through which the prodrugs described herein are converted to active drugs are non-limiting. A prodrug can be a precursor chemical compound of a drug that has a therapeutic effect on a subject.

Au used herein, the term "therapeutically effective amount" refers to an amount of a drug or pharmaceutical agent that elicits the biological or medicinal response in a subject (i.e. a tissue system, animal or human) that is being sought by a researcher, veterinarian, medical doctor or other clinician, which includes, but is not limited to, alleviation of the symptoms of the disease or disorder being treated. In one aspect, the therapeutically effective amount is that amount of an active which may treat or alleviate the disease or symptoms of the disease at a reasonable benefit/risk ratio applicable to any medical treatment. In another aspect, the therapeutically effective amount is that amount of an inactive prodrug which when converted through normal metabolic processes to produce an amount of active drug capable of eliciting the biological or medicinal response in a subject that is being sought.

It is also appreciated that the dose, whether referring to monotherapy or combination therapy, is advantageously selected with reference to any toxicity, or other undesirable side effect, that might occur during administration of one or more of the conjugates described herein. Further, it is appreciated that the co-therapies described herein may allow for the administration of lower doses of conjugates that show such toxicity, or other undesirable side effect, where those lower doses are below thresholds of toxicity or lower in the therapeutic window than would otherwise be administered in the absence of a cotherapy.

As used herein, "administering" includes all means of introducing the conjugates and compositions described herein to the host animal, including, but are not limited to, oral (po), intravenous (iv), intramuscular (im), subcutaneous (sc), transdermal, inhalation, buccal, ocular, sublingual, vaginal, rectal, and the like. The conjugates and compositions described herein may be administered in unit dosage forms and/or formulations containing conventional nontoxic pharmaceutically-acceptable carriers, adjuvants, and/or vehicles.

As used herein "pharmaceutical composition" or "composition" refers to a mixture of one or more of the conjugates described herein, or pharmaceutically acceptable salts, solvates, hydrates thereof, with other chemical components, such as pharmaceutically acceptable excipients. The purpose of a pharmaceutical composition is to facilitate administration of a conjugate to a subject. Pharmaceutical compositions suitable for the delivery of conjugates described and methods for their preparation will be readily apparent to those skilled in the art. Such compositions and methods for their preparation may be found, for example, in 'Remington's Pharmaceutical Sciences', 19th Edition (Mack Publishing Company, 1995).

A "pharmaceutically acceptable excipient" refers to an inert substance added to a pharmaceutical composition to further facilitate administration of a conjugate such as a diluent or a carrier.

DETAILED DESCRIPTION

In each of the foregoing and each of the following embodiments, it is to be understood that the formulae include and represent not only all pharmaceutically acceptable salts of the conjugates, but also include any and all hydrates and/or solvates of the conjugate formulae. It is appreciated that certain functional groups, such as the hydroxy, amino, and like groups form complexes and/or coordination conjugates with water and/or various solvents, in the various physical forms of the conjugates. Accordingly, the above formulae are to be understood to include and represent those various hydrates and/or solvates. It is also to be understood that the non-hydrates and/or non-solvates of the conjugate formulae are described by such formula, as well as the hydrates and/or solvates of the conjugate formulae.

The conjugates described herein can be expressed by the generalized descriptors B, L and Drug, where B is a cell surface receptor binding ligand (a.k.a. a "binding ligand"), L is a linker that may include a releasable portion (i.e. a releasable linker) and L may be described by one or more of the groups AA, $L^1$, $L^2$, $L^3$, $L^4$ or $L^5$ as defined herein, and Drug represents one or more drugs (e.g. $D^1$ and $D^2$) covalently attached to the conjugate.

The conjugates described herein can be described according to various embodiments including but not limited to B-$(AA)_{z1}$-$L^2$-$(L^3)_{z2}$-$(AA)_{z3}$-$(L^1)_{z4}$-$(L^4)_{z5}$-$D^1$-$L^5$-$D^2$ B-$L^1$-AA-$L^1$-AA-$L^1$-$L^2$-$(L^3)_{z6}$-$(L^4)_{z7}$-$(AA)_{z8}$-$(L^4)_{z9}$-$D^1$-$L^5$-$D^2$ B-$(AA)_{z10}$-$L^2$-$D^2$ B-$(AA)_{z11}$-$L^2$-$D^1$-$L^5$-$D^1$-$L^2$-$(AA)_{z12}$-B

B-$(AA)_4$-$L^2$-$D^1$-$L^5$-$D^2$

B-$(AA)_4$-$L^2$-$L^3$-AA-$L^1$-$L^4$-$D^1$-$L^5$-$D^2$

B-$(AA)_4$-$L^2$-$L^3$-$(AA)_2$-$D^1$-$L^5$-$D^2$

B-$(AA)_4$-$L^2$-$D^2$

B-$(AA)_4$-$L^2$-$D^1$-$L^5$-$D^1$-$L^2$-$(AA)_4$-B

B-$L^1$-AA-$L^1$-AA-$L^1$-$L^2$-$D^1$-$L^5$-$D^2$

B-L1-AA-L1-AA-L1-L2-L3-$(AA)_2$-L4-D1-L5-D2

B-$L^1$-AA-$L^1$-AA-$L^1$-$L^2$-$L^3$-$L^4$-$(AA)_2$-$L^4$-$D^1$-$L^5$-$D^2$

B-$L^1$-AA-$L^1$-AA-$L^1$-$L^2$-$L^3$-$L^4$-$D^1$-$L^5$-$D^2$

B-$L^1$-AA-$L^1$-AA-$L^1$-$L^2$-$L^3$-$(AA)_2$-$D^1$-$L^5$-$D^2$

B-$L^1$-AA $L^1$-AA-$L^1$-$L^2$-$L^3$-$D^1$-$L^5$-$D^2$ wherein B, AA, $L^1$, $L^2$, $L^3$, $L^4$, $L^5$, $D^1$ and $D^2$ are defined by the various embodiments described herein, and z1 is 2, 3, 4 or 5; z2 is 0, 1 or 2; z3 is 0, 1, 2, 3 or 4; z4 is 0, 1 or 2; z5 is 0, 1 or 2; y1 is 0, 1 or 2; y2 is 0, 1 or 2; y3 is 0, 1, 2, 3 or 4; and y4 is 0, 1 or 2.

As used herein, the term cell surface receptor binding ligand (aka a "binding ligand"), generally refers to compounds that bind to and/or target receptors that are found on cell surfaces, and in particular those that are found on, over-expressed by, and/or preferentially expressed on the surface of pathogenic cells. Illustrative ligands include, but are not limited to, vitamins and vitamin receptor binding compounds.

Illustrative vitamin moieties include carnitine, inositol, lipoic acid, pyridoxal, ascorbic acid, niacin, pantothenic acid, folic acid, riboflavin, thiamine, biotin, vitamin $B_{12}$, and the lipid soluble vitamins A, D, E and K. These vitamins, and their receptor-binding analogs and derivatives, constitute the targeting entity covalently attachment to the linker. Illustrative biotin analogs that bind to biotin receptors include, but are not limited to, biocytin, biotin sulfoxide, oxybiotin, and the like).

In some embodiments, the B is folate or derivative thereof. In some embodiments, the B is of the formula I

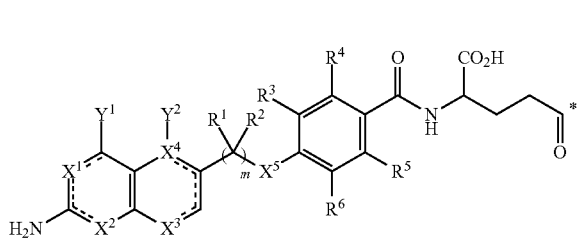

wherein $R^1$ and $R^2$ in each instance are independently selected from the group consisting of H, D, halogen, $C_1$-$C_6$ alkyl, $C_2$-$C_6$ alkenyl, $C_2$-$C_6$ alkynyl, —$OR^7$, —$SR^7$ and —$NR^7R^{7'}$, wherein each hydrogen atom in $C_1$-$C_6$ alkyl, $C_2$-$C_6$ alkenyl and $C_2$-$C_6$ alkynyl is independently optionally substituted by halogen, —$OR^8$, —$SR^8$, —$NR^8R^{8'}$, —$C(O)R^8$, —$C(O)OR^8$ or —$C(O)NR^8R^{8'}$;

$R^3$, $R^4$, $R^5$ and $R^6$ are each independently selected from the group consisting of H, D, halogen, $C_1$-$C_6$ alkyl, $C_2$-$C_6$ alkenyl, $C_2$-$C_6$ alkynyl, —CN, —$NO_2$, —NCO, —$OR^9$, —$SR^9$, —$NR^9R^{9'}$, —$C(O)R^9$, —$C(O)OR^9$ and —$C(O)NR^9R^{9'}$, wherein each hydrogen atom in $C_1$-$C_6$ alkyl, $C_2$-$C_6$ alkenyl and $C_2$-$C_6$ alkynyl is independently optionally substituted by halogen, —$OR^{10}$, —$SR^{10}$, —$NR^{10}R^{10'}$, —$C(O)R^{10}$, —$C(O)OR^{10}$ or —$C(O)NR^{10}R^{10'}$;

each $R^7$, $R^{7'}$, $R^8$, $R^{8'}$, $R^9$, $R^{9'}$, $R^{10}$ and $R^{10'}$ is independently H, D, $C_1$-$C_6$ alkyl, $C_2$-$C_6$ alkenyl or $C_2$-$C_6$ alkynyl;

$X^1$ is —$NR^{11}$—, =N—, —N=, —$C(R^{11})$= or =$C(R^{11})$—;

$X^2$ is —$NR^{11'}$— or =N—;

$X^3$ is —$NR^{11''}$—, —N= or —$C(R^{11''})$=;

$X^4$ is —N= or —C=;

$X^5$ is $NR^{12}$ or $CR^{12}R^{12'}$;

$Y^1$ is H, D, —$OR^{13}$, —$SR^{13}$ or —$NR^{13}R^{13'}$ when $X^1$ is —N= or —$C(R^{11})$=, or $Y^1$ is =O when $X^1$ is —$NR^{11}$—, =N— or =$C(R^{11})$—;

$Y^2$ is H, D, $C_1$-$C_6$ alkyl, $C_2$-$C_6$ alkenyl, —$C(O)R^{14}$, —$C(O)OR^{14}$, —$C(O)NR^{14}R^{14'}$ when $X^4$ is —C=, or $Y^2$ is absent when $X^4$ is —N=;

$R^{11}$, $R^{11'}$, $R^{11''}$, $R^{12}$, $R^{12'}$, $R^{13}$, $R^{13'}$, $R^{14}$ and $R^{14'}$ are each independently selected from the group consisting of H, D, $C_1$-$C_6$ alkyl, —$C(O)R^{15}$, —$C(O)OR^{15}$ and —$C(O)NR^{15}R^{15'}$;

$R^{15}$ and $R^{15'}$ are each independently H or $C_1$-$C_6$ alkyl;

m is 1, 2, 3 or 4; and

* is a covalent bond.

It will be appreciate that when B is described according to the formula I, that both the D- and L-forms are contemplated. In some embodiments, B is of the formula Ia or Ib

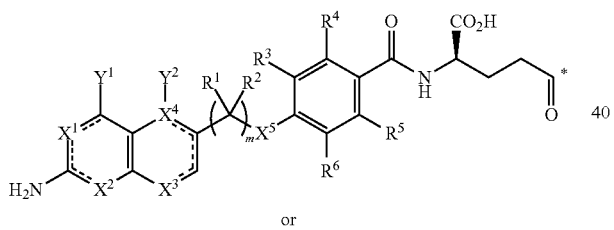

Ia or

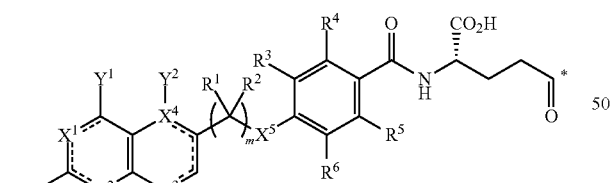

Ib where each of $R^1$, $R^2$, $R^3$, $R^4$, $R^5$, $R^6$, $Y^1$, $Y^2$, $X^1$, $X^2$, $X^3$, $X^4$, $X^5$, m and * are as defined for the formula I.

In some embodiments described herein, $R^1$ and $R^2$ are H. In some embodiments described herein, m is 1. In some embodiments described herein, $R^3$ is H. In some embodiments described herein, $R^4$ is H. In some embodiments described herein, $R^5$ is H. In some embodiments described herein, $R^6$ is H. In some embodiments described herein, $R^3$, $R^4$, $R^5$ and $R^6$ are H. In some embodiments described herein, $X^1$ is —$NR^{11}$, and $R^{11}$ is H. In some embodiments described herein, $X^2$ is =N—. In some embodiments described herein, $X^3$ is —N=. In some embodiments described herein, $X^4$ is —N=. In some embodiments described herein, $X^1$ is —$NR^{11}$, and $R^{11}$ is H; $X^2$ is =N—; $X^3$ is —N=; and $X^4$ is —N=. In some embodiments described herein, $X^5$ is $NR^{12}$, and $R^{12}$ is H. In some embodiments, $Y^1$ is =O. In some embodiments, $Y^2$ is absent. In some embodiments, B is of the formula Ic

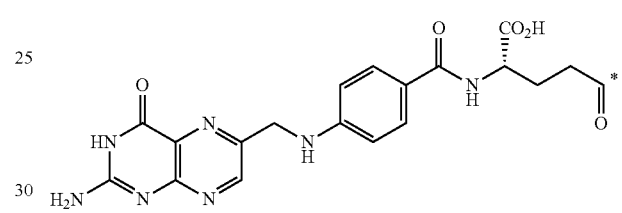

Ic wherein * is defined for formula I.

In some embodiments, B is of the formula Id

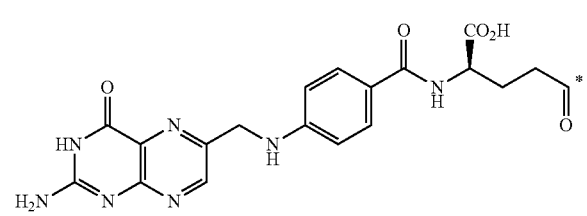

Id wherein * is defined for formula I.

It will be appreciated that in certain embodiments, the conjugates described herein can be represented by the exemplary formulae

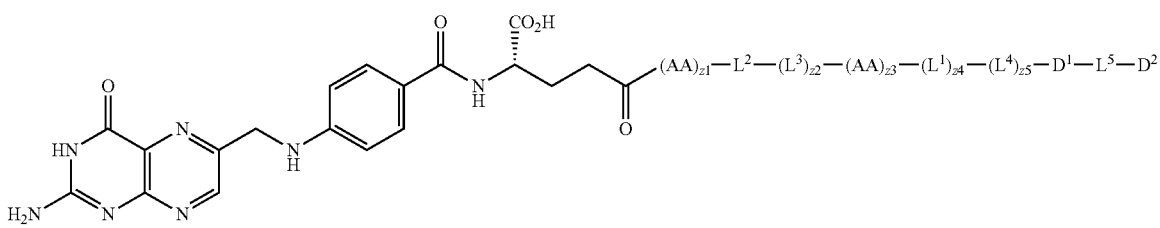

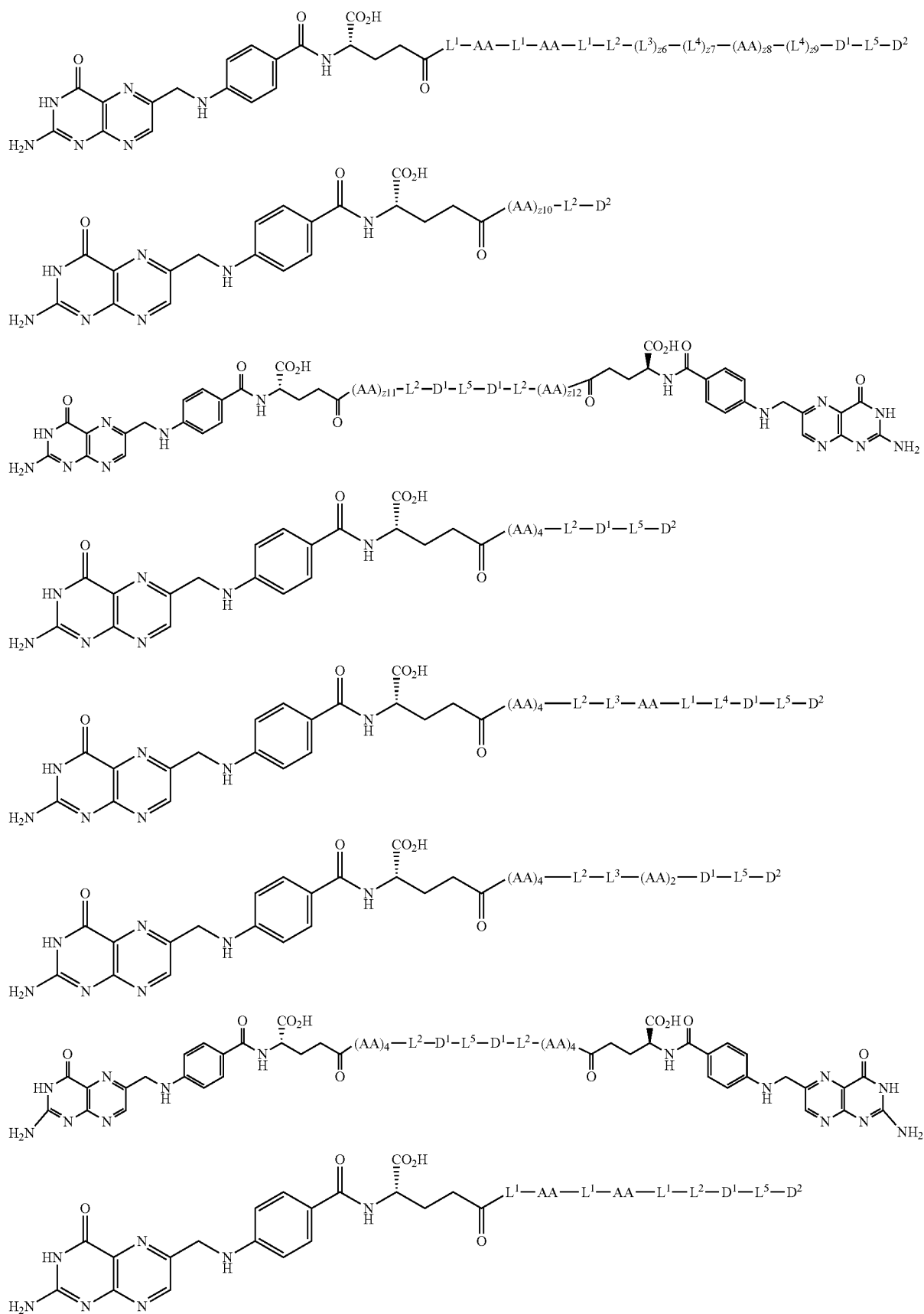

-continued

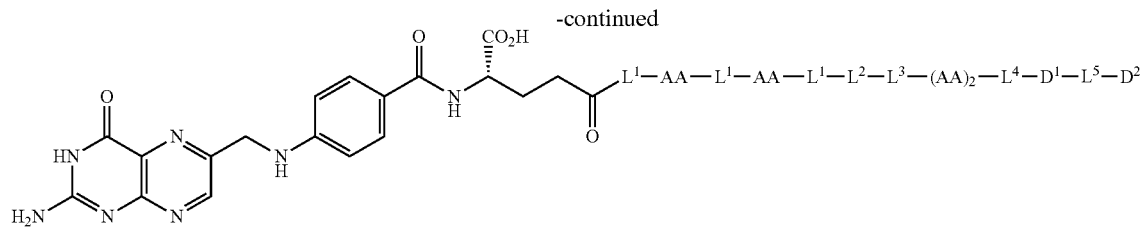

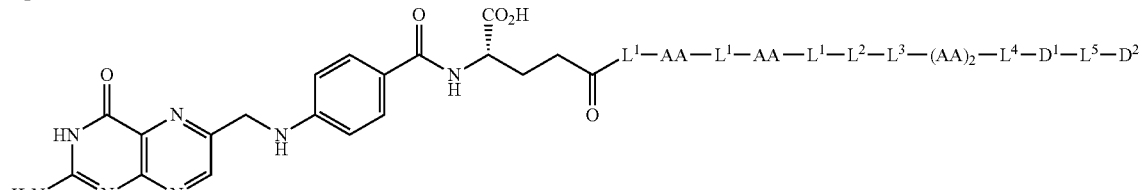

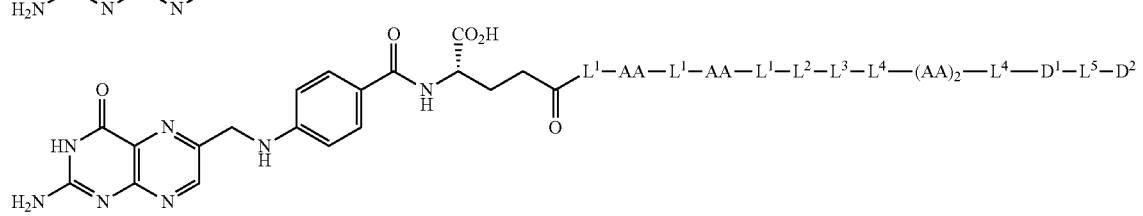

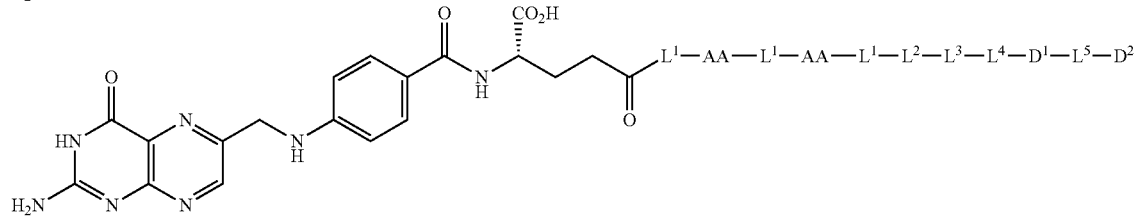

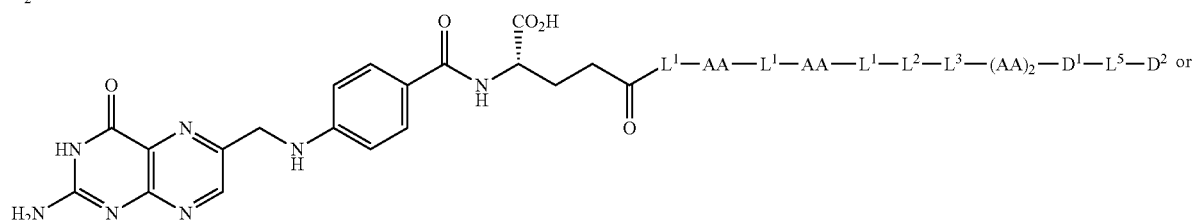

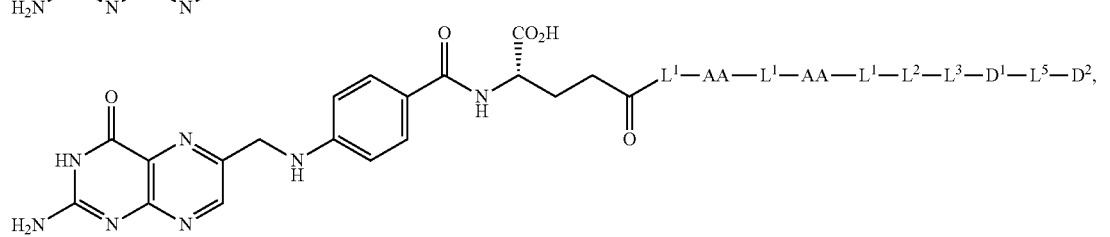

or a pharmaceutically acceptable salt thereof.

The linker for connected B and Drug in the conjugates described herein can be represented by the groups AA, $L^1$, $L^2$, $L^3$, $L^4$ or $L^5$.

AA is an amino acid as defined herein. In certain embodiments, AA is a naturally occurring amino acid. In certain embodiments, AA is in the L-form. In certain embodiments, AA is in the D-form. It will be appreciated that in certain embodiments, the conjugates described herein will comprise more than one amino acid as portions of the linker, and the amino acids can be the same or different, and can be selected from a group of amino acids. It will be appreciated that in certain embodiments, the conjugates described herein will comprise more than one amino acid as portions of the linker, and the amino acids can be the same or different, and can be selected from a group of amino acids in D- or L-form. In some embodiments, each AA is independently selected from the group consisting of L-lysine, L-asparagine, L-threonine, L-serine, L-isoleucine, L-methionine, L-proline, L-histidine, L-glutamine, L-arginine, L-glycine, L-aspartic acid, L-glutamic acid, L-alanine, L-valine, L-phenylalanine, L-leucine, L-tyrosine, L-cysteine, L-tryptophan, L-phosphoserine, L-sulfo-cysteine, L-arginosuccinic acid, L-hydroxyproline, L-phosphoethanolamine, L-sarcosine, L-taurine, L-carnosine, L-citrulline, L-anserine, L-1,3-methyl-histidine, L-alpha-amino-adipic acid, D-lysine, D-asparagine, D-threonine, D-serine, D-isoleucine, D-methionine, D-proline, D-histidine, D-glutamine, D-arginine, D-glycine, D-aspartic acid, D-glutamic acid, D-alanine, D-valine, D-phenylalanine, D-leucine, D-tyrosine, D-cysteine, D-tryptophan, D-citrulline and D-carnosine.

In some embodiments, each AA is independently selected from the group consisting of L-asparagine, L-arginine, L-glycine, L-aspartic acid, L-glutamic acid, L-glutamine, L-cysteine, L-alanine, L-valine, L-leucine, L-isoleucine, L-citrulline, D-asparagine, D-arginine, D-glycine, D-aspartic acid, D-glutamic acid, D-glutamine, D-cysteine, D-alanine, D-valine, D-leucine, D-isoleucine and D-citrulline. In some embodiments, each AA is independently selected from the group consisting of Asp, Arg, Val, Ala, Cys and CIT. In some embodiments, each AA is independently selected from the group consisting of Asp, Arg, Val, Ala, D-Cys and CIT. In some embodiments, each AA is independently selected from the group consisting of Asp, Arg, Val, Ala and CIT. In some embodiments, z1 is 4 and the sequence of AA therein is -Asp-Arg-Asp-Asp- (SEQ ID NO: 5). In some embodiments, z3 is 2 and the sequence of AA therein is Val-Ala. In some embodiments, z3 is 2 and the sequence of AA therein is Val-CIT. In some embodiments, z1 is 4 and the sequence of AA therein is -Asp-Arg-Asp-Asp- (SEQ ID NO: 5), and z3 is 2 and the sequence of AA therein is Val-Ala. In some embodiments, z1 is 4 and the sequence of AA therein is -Asp-Arg-Asp-Asp- (SEQ ID NO: 5), and z3 is 2 and the sequence of AA therein is Val-CIT.

In some embodiments, z8 is 3. In some embodiments, z8 is 2. In some embodiments, z8 is 2, and the sequence of AA therein is Val-Ala. In some embodiments, z10 is 5. In some embodiments, z10 is 4. In some embodiments, z10 is 3. In some embodiments, z10 is 4 and the sequence of AA therein is -Asp-Arg-Asp-Asp- (SEQ ID NO: 5). In some embodiments, z11 is 5. In some embodiments, z11 is 4. In some embodiments, z11 is 3. In some embodiments, z11 is 4 and the sequence of AA therein is -Asp-Arg-Asp-Asp- (SEQ ID NO: 5). In some embodiments, z12 is 5. In some embodiments, z12 is 4. In some embodiments, z12 is 3. In some embodiments, z12 is 4 and the sequence of AA therein is -Asp-Asp-Arg-Asp- (SEQ ID NO: 5). In some embodiments, z11 is 4 and z12 is 4. In some embodiments, z11 is 4 and the sequence of AA therein is -Asp-Arg-Asp-Asp- (SEQ ID NO: 5), and z12 is 4 and the sequence of AA therein is -Asp-Asp-Arg-Asp- (SEQ ID NO: 5). In some embodiments, z8 is 2, and the sequence of AA is Glu-Glu-, wherein the amino acids are covalently attached at their alpha-amino functionality and their side chain carboxylate.

$L^1$ can be present or absent in the conjugates described herein. When $L^1$ is present, $L^1$ can be any group covalently attaching portions of the linker to the binding ligand, portions of the linker to one another, or to $D^1$, or to $D^2$. It will be understood that the structure of $L^1$ is not particularly limited in any way. It will be further understood that $L^1$ can comprise numerous functionalities well known in the art to covalently attach portions of the linker to the binding ligand, portions of the linker to one another, or to $D^1$, or to $D^2$, including but not limited to, alkyl groups, ether groups, amide groups, carboxy groups, sulfonate groups, alkenyl groups, alkynyl groups, cycloalkyl groups, aryl groups, heterocycloalkyl, heteroaryl groups, and the like. In some embodiments, $L^1$ is a linker of the formula II

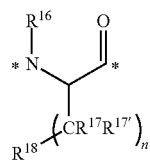

II wherein
$R^{16}$ is selected from the group consisting of H, D, $C_1$-$C_6$ alkyl, $C_2$-$C_6$ alkenyl, $C_2$-$C_6$ alkynyl, —C(O)$R^{19}$, —C(O)OR$^{19}$ and —C(O)NR$^{19}$R$^{19'}$, wherein each hydrogen atom in $C_1$-$C_6$ alkyl, $C_2$-$C_6$ alkenyl and $C_2$-$C_6$ alkynyl is independently optionally substituted by halogen, $C_1$-$C_6$ alkyl, $C_2$-$C_6$ alkenyl, and $C_2$-$C_6$ alkynyl, —OR$^{20}$, —OC(O)R$^{20}$, —OC(O)NR$^{20}$R$^{20'}$, —OS(O)R$^{20}$, —OS(O)$_2$R$^{20}$, —SR$^{20}$, —S(O)R$^{20}$, —S(O)$_2$R$^{20}$, —S(O)NR$^{20}$R$^{20'}$, —S(O)$_2$NR$^{20}$R$^{20'}$, —OS(O)NR$^{20}$R$^{20'}$, —OS(O)$_2$NR$^{20}$R$^{20'}$, —NR$^{20}$R$^{20'}$, —NR$^{20}$C(O)R$^{21}$, —NR$^{20}$C(O)OR$^{21}$, —NR$^{20}$C(O)NR$^{21}$R$^{21'}$, —NR$^{20}$S(O)R$^{21}$, —NR$^{20}$S(O)$_2$R$^{21}$, —NR$^{20}$S(O)NR$^{21}$R$^{21'}$, —NR$^{20}$S(O)$_2$NR$^{21}$R$^{21'}$, —C(O)R$^{20}$, —C(O)OR$^{20}$ or —C(O)NR$^{20}$R$^{20'}$;

each $R^{17}$ and $R^{17'}$ is independently selected from the group consisting of H, D, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —OR$^{22}$, —OC(O)R$^{22}$, —OC(O)NR$^{22}$R$^{22'}$, —OS(O)R$^{22}$, —OS(O)$_2$R$^{22}$, —SR$^{22}$, —S(O)R$^{22}$, —S(O)$_2$R$^{22}$, —S(O)NR$^{22}$R$^{22'}$, —S(O)$_2$NR$^{22}$R$^{22'}$, —OS(O)NR$^{22}$R$^{22'}$, —OS(O)$_2$NR$^{22}$R$^{22'}$, —NR$^{22}$R$^{22'}$, —NR$^{22}$C(O)R$^{23}$, —NR$^{22}$C(O)OR$^{23}$, —NR$^{22}$C(O)NR$^{23}$R$^{23'}$, —NR$^{22}$S(O)R$^{23}$, —NR$^{22}$S(O)$_2$R$^{23}$, —NR$^{22}$S(O)NR$^{23}$R$^{23'}$, —NR$^{22}$S(O)$_2$NR$^{23}$R$^{23'}$, —C(O)R$^{22}$, —C(O)OR$^{22}$, and —C(O)NR$^{22}$R$^{22'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by halogen, $C_1$-$C_6$ alkyl, $C_2$-$C_6$ alkenyl, $C_2$-$C_6$ alkynyl, —OR$^{24}$, —OC(O)R$^{24}$, —OC(O)NR$^{24}$R$^{24'}$, —OS(O)R$^{24}$, —OS(O)$_2$R$^{24}$, —SR$^{24}$, —S(O)R$^{24}$, —S(O)$_2$R$^{24}$, —S(O)NR$^{24}$R$^{24'}$, —S(O)$_2$NR$^{24}$R$^{24'}$, —OS(O)NR$^{24}$R$^{24'}$, —OS(O)$_2$NR$^{24}$R$^{24'}$, —NR$^{24}$R$^{24'}$, —NR$^{24}$C(O)R$^{25}$, —NR$^{24}$C(O)OR$^{25}$, —NR$^{24}$C(O)NR$^{25}$R$^{25'}$, —NR$^{24}$S(O)R$^{25}$, —NR$^{24}$S(O)$_2$R$^{25}$, —NR$^{24}$S(O)NR$^{25}$R$^{25'}$, —NR$^{24}$S(O)$_2$NR$^{25}$R$^{25'}$, —C(O)R$^{24}$, —C(O)OR$^{24}$ or —C(O)NR$^{24}$R$^{24'}$; or $R^{17}$ and $R^{17'}$ may combine to form a $C_4$-$C_6$ cycloalkyl or a 4- to 6-membered heterocycle, wherein each hydrogen atom in $C_4$-$C_6$ cycloalkyl or 4- to 6-membered heterocycle is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —OR$^{24}$, —OC(O)R$^{24}$, —OC(O)NR$^{24}$R$^{24'}$, —OS(O)R$^{24}$, —OS(O)$_2$R$^{24}$, —SR$^{24}$, —S(O)R$^{24}$, —S(O)$_2$R$^{24}$, —S(O)NR$^{24}$R$^{24'}$, —S(O)$_2$NR$^{24}$R$^{24'}$, —OS(O)NR$^{24}$R$^{24'}$, —OS(O)$_2$NR$^{24}$R$^{24'}$, —NR$^{24}$R$^{24'}$, —NR$^{24}$C(O)R$^{25}$, —NR$^{24}$C(O)OR$^{25}$, —NR$^{24}$C(O)NR$^{25}$R$^{25'}$, —NR$^{24}$S(O)R$^{25}$, —NR$^{24}$S(O)$_2$R$^{25}$, —NR$^{24}$S(O)NR$^{25}$R$^{25'}$, —NR$^{24}$S(O)$_2$NR$^{25}$R$^{25'}$, —C(O)R$^{24}$, —C(O)OR$^{24}$ or —C(O)NR$^{24}$R$^{24'}$;

$R^{18}$ is selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —OR$^{26}$, —OC(O)R$^{26}$, —OC(O)NR$^{26}$R$^{26'}$, —OS(O)R$^{26}$, —OS(O)$_2$R$^{26}$, —SR$^{26}$, —S(O)R$^{26}$, —S(O)$_2$R$^{26}$, —S(O)NR$^{26}$R$^{26'}$, —S(O)$_2$NR$^{26}$R$^{26'}$, —OS(O)NR$^{26}$R$^{26'}$, —OS(O)$_2$NR$^{26}$R$^{26'}$, —NR$^{26}$R$^{26'}$, —NR$^{26}$C(O)R$^{27}$, —NR$^{26}$C(O)OR$^{27}$, —NR$^{26}$C(O)NR$^{27}$R$^{27'}$, —NR$^{26}$C(=NR$^{26''}$)NR$^{27}$R$^{27'}$, —NR$^{26}$S(O)R$^{27}$, —NR$^{26}$S(O)$_2$R$^{27}$, —NR$^{26}$S(O)NR$^{27}$R$^{27'}$, —NR$^{26}$S(O)$_2$NR$^{27}$R$^{27'}$, —C(O)R$^{26}$, —C(O)OR$^{26}$ and —C(O)NR$^{26}$R$^{26'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by halogen, $C_1$-$C_6$ alkyl, $C_2$-$C_6$ alkenyl, —(CH$_2$)$_p$OR$^{28}$, —(CH$_2$)$_q$(OCH$_2$)$_q$OR$^{28}$, —(CH$_2$)$_p$(OCH$_2$CH$_2$)$_q$OR$^{28}$, —OR$^{29}$, —OC(O)R$^{29}$, —OC(O)NR$^{29}$R$^{29'}$, —OS(O)R$^{29}$, —OS(O)$_2$R$^{29}$, —(CH$_2$)$_p$OS(O)$_2$OR$^{29}$, —OS(O)$_2$OR$^{29}$, —SR$^{29}$, —S(O)R$^{29}$, —S(O)$_2$R$^{29}$, —S(O)NR$^{29}$R$^{29'}$, —S(O)$_2$NR$^{29}$R$^{29'}$, —OS(O)NR$^{29}$R$^{29'}$, —OS(O)₂NR²⁹R²⁹', —NR²⁹R²⁹', —NR²⁹C(O)R³⁰, —NR²⁹C(O)OR³⁰, —NR²⁹C(O)NR³⁰R³⁰', —NR²⁹S(O)R³⁰, —NR²⁹S(O)₂R³⁰, —NR²⁹S(O)NR³⁰R³⁰', —NR²⁹S(O)₂NR³⁰R³⁰', —C(O)R²⁹, —C(O)OR²⁹ or —C(O)NR²⁹R²⁹';

each $R^{19}, R^{19'}, R^{20}, R^{20'}, R^{21}, R^{21'}, R^{22}, R^{22'}, R^{23}, R^{23'}, R^{24}, R^{24'}, R^{25}, R^{25'}, R^{26}, R^{26'}, R^{26''}, R^{29}, R^{29'}, R^{30}$ and $R^{30'}$ is independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, —OH, —SH, —NH₂ or —CO₂H;

$R^{27}$ and $R^{27'}$ are each independently selected from the group consisting of H, $C_1$-$C_9$ alkyl, $C_2$-$C_9$ alkenyl, $C_2$-$C_9$ alkynyl, $C_3$-$C_6$ cycloalkyl, —(CH₂)$_p$(sugar), —(CH₂)$_p$(OCH₂CH₂)$_q$-(sugar) and —(CH₂)$_p$(OCH₂CH₂CH₂)$_q$(sugar);

$R^{28}$ is a H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, 5- to 7-membered heteroaryl or sugar;

n is 1, 2, 3, 4 or 5;

p is 1, 2, 3, 4 or 5;

q is 1, 2, 3, 4 or 5; and

* is a covalent bond.

It will be appreciate that when L¹ is described according to the formula II, that both the R- and S-configurations are contemplated. In some embodiments, L¹ is of the formula IIa or IIb IIa

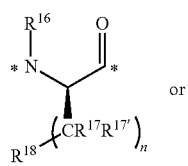

or

IIb

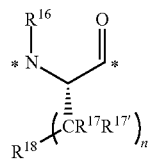

where each of $R^{16}, R^{17}, R^{17'}, R^{18}$, n and * are nd are as defined for the formula II.

In some embodiments, each L¹ is selected from the group consisting of

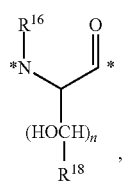,

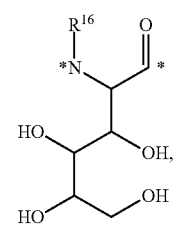

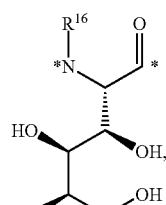,

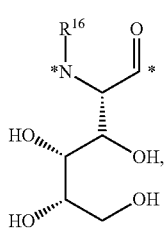,

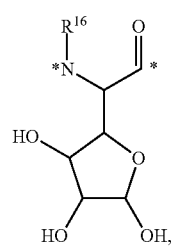

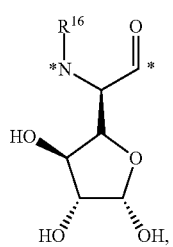,

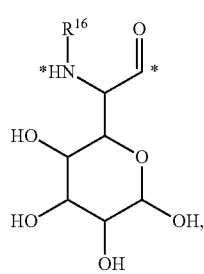

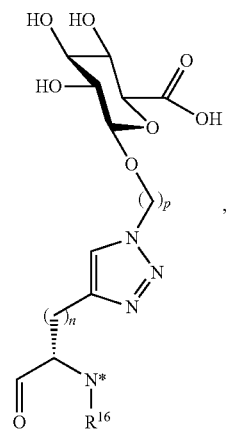

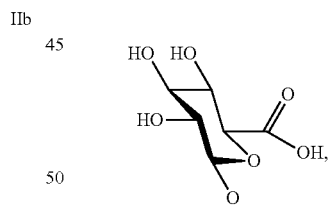

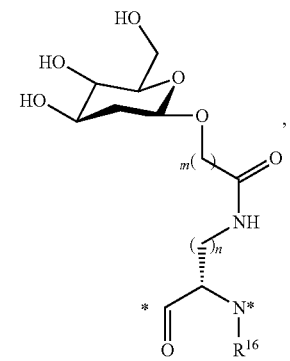

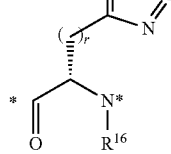
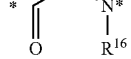

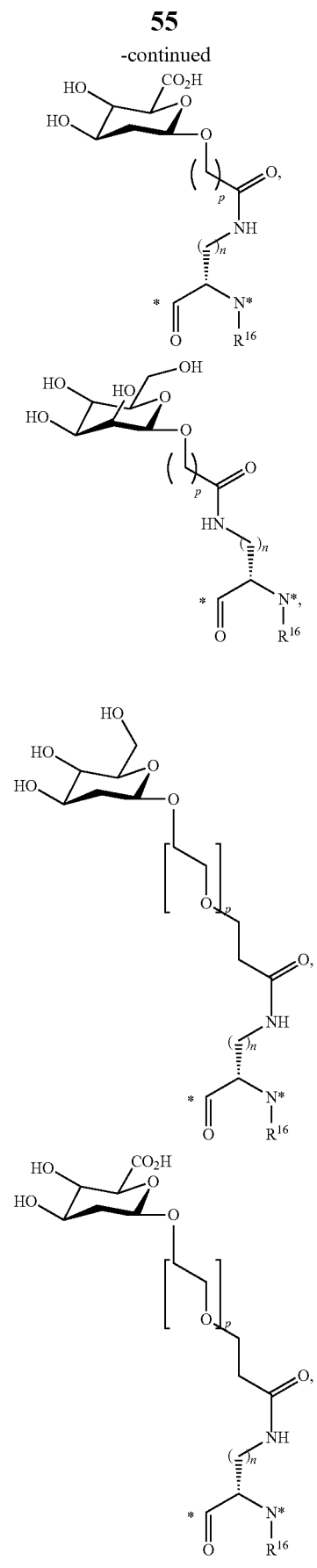
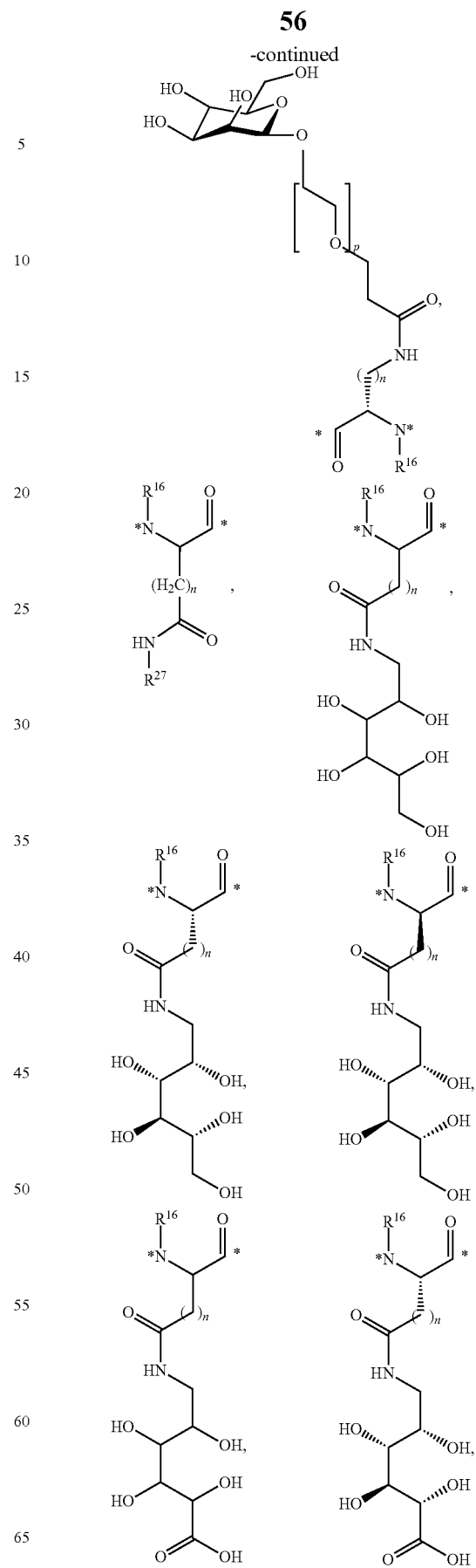

-continued

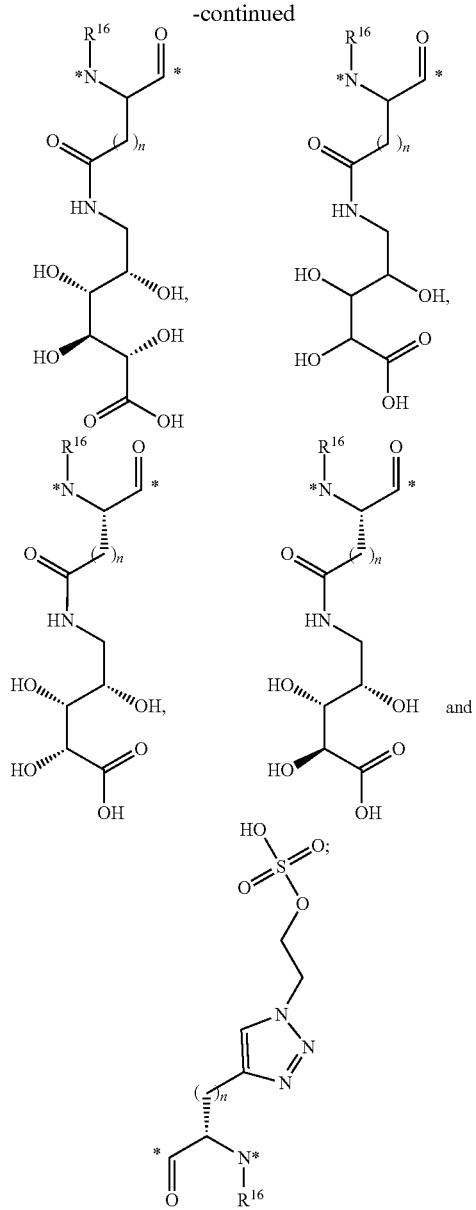

and combinations thereof,
wherein

R$^{16}$ is selected from the group consisting of H, D, C$_1$-C$_6$ alkyl, C$_2$-C$_6$ alkenyl, C$_2$-C$_6$ alkynyl, —C(O)R$^{19}$, —C(O)OR$^{19}$ and —C(O)NR$^{19}$R$^{19'}$, wherein each hydrogen atom in C$_1$-C$_6$ alkyl, C$_2$-C$_6$ alkenyl and C$_2$-C$_6$ alkynyl is independently optionally substituted by halogen, C$_1$-C$_6$ alkyl, C$_2$-C$_6$ alkenyl, and C$_2$-C$_6$ alkynyl, —OR$^{20}$, —OC(O)R$^{20}$, —OC(O)NR$^{20}$R$^{20'}$, —OS(O)R$^{20}$, —OS(O)$_2$R$^{20}$, —SR$^{20}$, —S(O)R$^{20}$, —S(O)$_2$R$^{20}$, —S(O)NR$^{20}$R$^{20'}$, —S(O)$_2$NR$^{20}$R$^{20'}$, —OS(O)NR$^{20}$R$^{20'}$, —OS(O)$_2$NR$^{20}$R$^{20'}$, —NR$^{20}$R$^{20'}$, —NR$^{20}$C(O)R$^{21}$, —NR$^{20}$C(O)OR$^{21}$, —NR$^{20}$C(O)NR$^{21}$R$^{21'}$, —NR$^{20}$S(O)R$^{21}$, —NR$^{20}$S(O)$_2$R$^{21}$, —NR$^{20}$S(O)NR$^{21}$R$^{21'}$, —NR$^{20}$S(O)$_2$NR$^{21}$R$^{21'}$, —C(O)R$^{20}$, —C(O)OR$^{20}$ or —C(O)NR$^{20}$R$^{20'}$;

R$^{18}$ is selected from the group consisting of H, D, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{26}$, —OC(O)R$^{26}$, —OC(O)NR$^{26}$R$^{26'}$, —OS(O)R$^{26}$, —OS(O)$_2$R$^{26}$, —SR$^{26}$, —S(O)R$^{26}$, —S(O)$_2$R$^{26}$, —S(O)NR$^{26}$R$^{26'}$, —S(O)$_2$NR$^{26}$R$^{26'}$, —OS(O)NR$^{26}$R$^{26'}$, —OS(O)$_2$NR$^{26}$R$^{26'}$, —NR$^{26}$R$^{26'}$, —NR$^{26}$C(O)R$^{27}$, —NR$^{26}$C(O)OR$^{27}$, —NR$^{26}$C(O)NR$^{27}$R$^{27'}$, —NR$^{26}$C(=NR$^{26''}$)NR$^{27}$R$^{27'}$, —NR$^{26}$S(O)R$^{27}$, —NR$^{26}$S(O)$_2$R$^{27}$, —NR$^{26}$S(O)NR$^{27}$R$^{27'}$, —NR$^{26}$S(O)$_2$NR$^{27}$R$^{27'}$, —C(O)R$^{26}$, —C(O)OR$^{26}$ and —C(O)NR$^{26}$R$^{26'}$, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl is independently optionally substituted by halogen, C$_1$-C$_6$ alkyl, C$_2$-C$_6$ alkenyl, —(CH$_2$)$_p$OR$^{28}$, —(CH$_2$)$_p$(OCH$_2$)$_q$OR$^{28}$, —(CH$_2$)$_p$(OCH$_2$CH$_2$)$_q$OR$^{28}$, —OR$^{29}$, —OC(O)R$^{29}$, —OC(O)NR$^{29}$R$^{29'}$, —OS(O)R$^{29}$, —OS(O)$_2$R$^{29}$, —(CH$_2$)$_p$OS(O)$_2$R$^{29}$, —OS(O)$_2$OR$^{29}$, —SR$^{29}$, —S(O)R$^{29}$, —S(O)$_2$R$^{29}$, —S(O)NR$^{29}$R$^{29'}$, —S(O)$_2$NR$^{29}$R$^{29'}$, —OS(O)NR$^{29}$R$^{29'}$, —OS(O)$_2$NR$^{29}$R$^{29'}$, —NR$^{29}$R$^{29'}$, —NR$^{29}$C(O)R$^{30}$, —NR$^{29}$C(O)OR$^{30}$, —NR$^{29}$C(O)NR$^{30}$R$^{30'}$, —NR$^{29}$S(O)R$^{30}$, —NR$^{29}$S(O)$_2$R$^{30}$, —NR$^{29}$S(O)NR$^{30}$R$^{30'}$, —NR$^{29}$S(O)$_2$NR$^{30}$R$^{30'}$, —C(O)R$^{29}$, —C(O)OR$^{29}$ or —C(O)NR$^{29}$R$^{29'}$;

each each R$^{19}$, R$^{19'}$, R$^{20}$, R$^{20'}$, R$^{21}$, R$^{21'}$, R$^{26}$, R$^{26'}$, R$^{26''}$, R$^{29}$, R$^{29'}$, R$^{30}$ and R$^{30'}$ is independently selected from the group consisting of H, D, C$_1$-C$_7$ alkyl, C$_2$-C$_7$ alkenyl, C$_2$-C$_7$ alkynyl, C$_3$-C$_6$ cycloalkyl, 3- to 7-membered heterocycloalkyl, C$_6$-C$_{10}$ aryl and 5- to 7-membered heteroaryl, wherein each hydrogen atom in C$_1$-C$_7$ alkyl, C$_2$-C$_7$ alkenyl, C$_2$-C$_7$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by halogen, —OH, —SH, —NH$_2$ or —CO$_2$H;

R$^{27}$ and R$^{27'}$ are each independently selected from the group consisting of H, C$_1$-C$_9$ alkyl, C$_2$-C$_9$ alkenyl, C$_2$-C$_9$ alkynyl, C$_3$-C$_6$ cycloalkyl, —(CH$_2$)$_p$(sugar), —(CH$_2$)$_p$(OCH$_2$CH$_2$)$_q$-(sugar) and —(CH$_2$)$_p$(OCH$_2$CH$_2$CH$_2$)$_q$(sugar);

R$^{28}$ is H, D, C$_1$-C$_7$ alkyl, C$_2$-C$_7$ alkenyl, C$_2$-C$_7$ alkynyl, C$_3$-C$_6$ cycloalkyl, 3- to 7-membered heterocycloalkyl, C$_6$-C$_{10}$ aryl, 5- to 7-membered heteroaryl or sugar;

n is 1, 2, 3, 4 or 5;

p is 1, 2, 3, 4 or 5;

q is 1, 2, 3, 4 or 5; and

* is a covalent bond.

In some embodiments, each L$^1$ is selected from the group consisting of

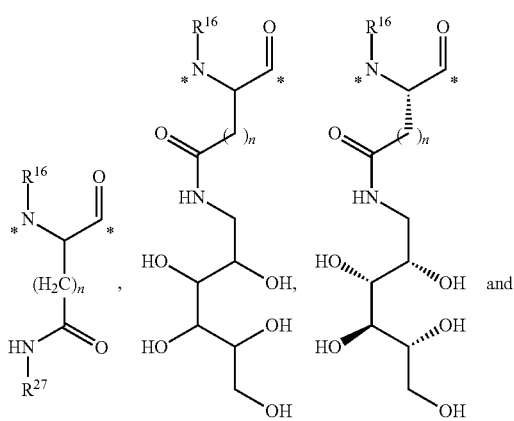

-continued

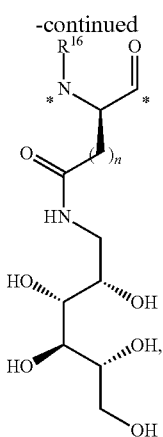

wherein R[16] is defined as described herein, and * is a covalent bond.

In some embodiments, R[16] is H. In some embodiments, R[18] is selected from the group consisting of H, 5- to 7-membered heteroaryl, —OR[26], —NR[26]C(O)R[27], —NR[26]C(O)NR[27]R[27'], —NR[26]C(=NR[26''])NR[27]R[27'], and —C(O)NR[26]R[26'], wherein each hydrogen atom 5- to 7-membered heteroaryl is independently optionally substituted by halogen, $C_1$-$C_6$ alkyl, $C_2$-$C_6$ alkenyl, —(CH$_2$)$_p$OR[28], —(CH$_2$)$_p$(OCH$_2$)$_q$OR[28], —(CH$_2$)$_p$(OCH$_2$CH$_2$)$_q$OR[28], —OR[29], —OC(O)R[29], —OC(O)NR[29]R[29'], —OS(O)R[29], —OS(O)$_2$R[29], —(CH$_2$)$_p$OS(O)$_2$OR[29], —OS(O)$_2$OR[29], —SR[29], —S(O)R[29], —S(O)$_2$R[29], —S(O)NR[29]R[29'], —S(O)$_2$NR[29]R[29'], —OS(O)NR[29]R[29'], —OS(O)$_2$NR[29]R[29'], —NR[29]R[29'], —NR[29]C(O)R[30], —NR[29]C(O)OR[30], —NR[29]C(O)NR[30]R[30'], —NR[29]S(O)R[30], —NR[29]S(O)$_2$R[30], —NR[29]S(O)NR[30]R[30'], —NR[29]S(O)$_2$NR[30]R[30'], —C(O)R[29], —C(O)OR[29] or —C(O)NR[29]R[29'];

each R[26], R[26'], R[26''], R[29], R[29'], R[30] and R[30'] is independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, —OH, —SH, —NH$_2$ or —CO$_2$H;

R[27] and R[27'] are each independently selected from the group consisting of H, $C_1$-$C_9$ alkyl, $C_2$-$C_9$ alkenyl, $C_2$-$C_9$ alkynyl, $C_3$-$C_6$ cycloalkyl, —(CH$_2$)$_p$(sugar), —(CH$_2$)$_p$(OCH$_2$CH$_2$)$_q$-(sugar) and —(CH$_2$)$_p$(OCH$_2$CH$_2$CH$_2$)$_q$(sugar);

R[28] is a H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, 5- to 7-membered heteroaryl or sugar;

n is 1, 2, 3, 4 or 5;
p is 1, 2, 3, 4 or 5;
q is 1, 2, 3, 4 or 5; and
* is a covalent bond.

In some embodiments, R[18] is selected from the group consisting of H, 5- to 7-membered heteroaryl, —OR[26], —NR[26]C(O)R[27], —NR[26]C(O)NR[27]R[27'], —NR[26]C(=NR[26''])NR[27]R[27'], and —C(O)NR[26]R[26'], wherein each hydrogen atom 5- to 7-membered heteroaryl is independently optionally substituted by —(CH$_2$)$_p$OR[28], —OR[29], —(CH$_2$)$_p$OS(O)$_2$OR[29] and —OS(O)$_2$OR[29], each R[26], R[26'], R[26''] and R[29] is independently H or $C_1$-$C_7$ alkyl, wherein each hydrogen atom in $C_1$-$C_7$ alkyl is independently optionally substituted by halogen, —OH, —SH, —NH$_2$ or —CO$_2$H;

R[27] and R[27'] are each independently selected from the group consisting of H, —(CH$_2$)$_p$(sugar), —(CH$_2$)$_p$(OCH$_2$CH$_2$)$_q$(sugar) and —(CH$_2$)$_p$(OCH$_2$CH$_2$CH$_2$)$_q$(sugar);

R[28] is H or sugar;
n is 1, 2, 3, 4 or 5;
p is 1, 2, 3, 4 or 5;
q is 1, 2, 3, 4 or 5; and
* is a covalent bond.

In some embodiments, each L[1] is selected from the group consisting of

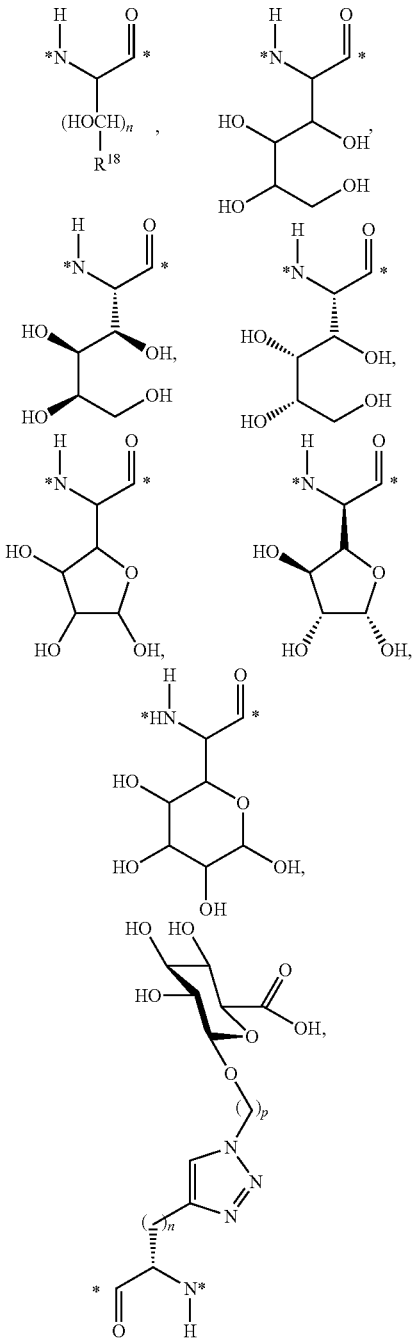

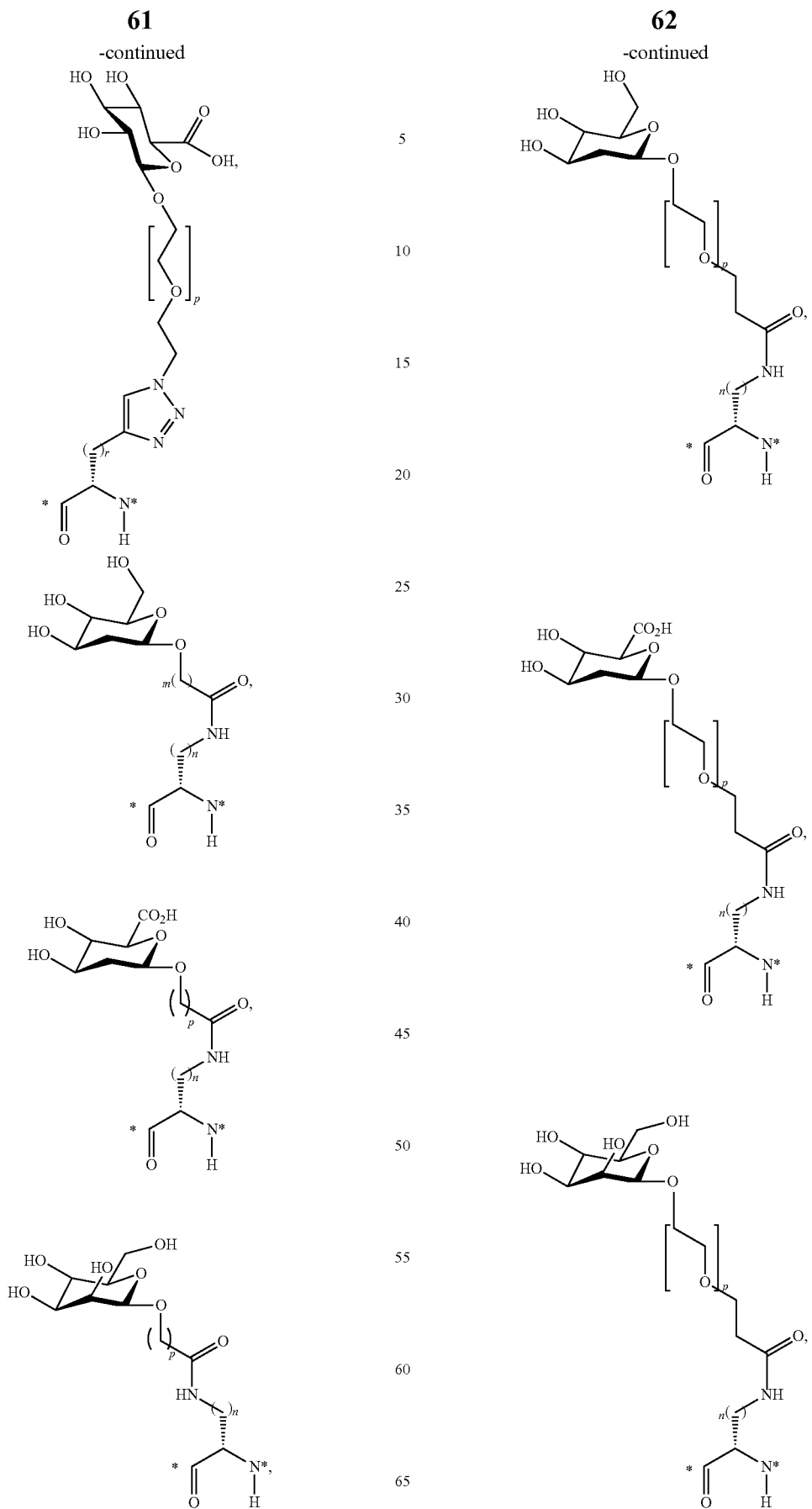

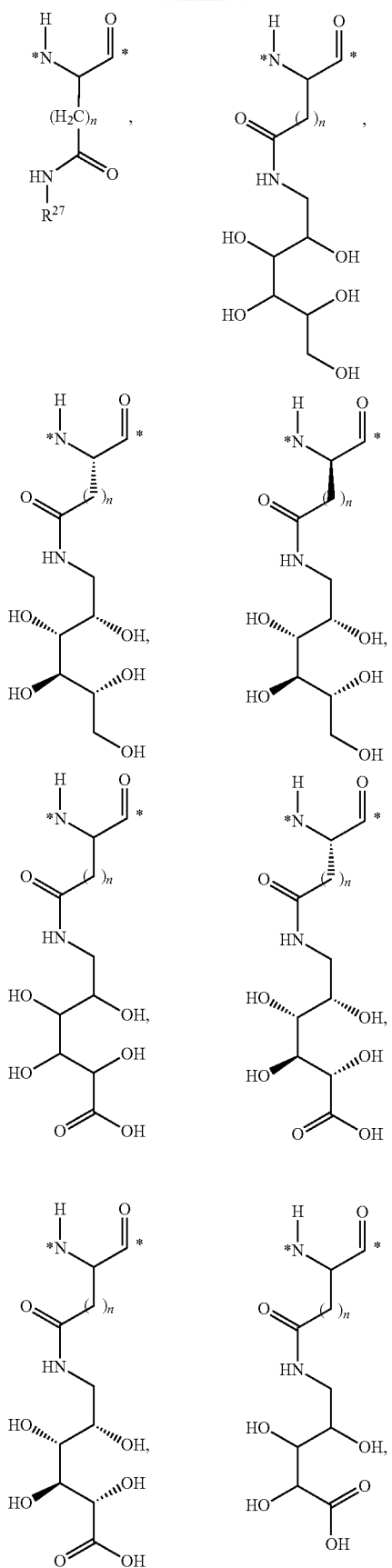
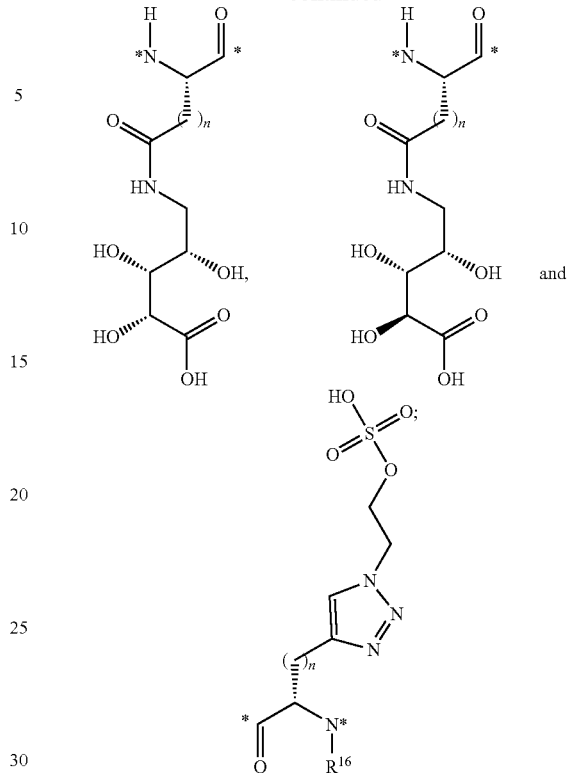

and combinations thereof,
wherein
$R^{18}$ is selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{26}$, —$OC(O)R^{26}$, —$OC(O)NR^{26}R^{26'}$, —$OS(O)R^{26}$, —$OS(O)_2R^{26}$, —$SR^{26}$, —$S(O)R^{26}$, —$S(O)_2R^{26}$, —$S(O)NR^{26}R^{26'}$, —$S(O)_2NR^{26}R^{26'}$, —$OS(O)NR^{26}R^{26'}$, —$OS(O)_2NR^{26}R^{26'}$, —$NR^{26}R^{26'}$, —$NR^{26}C(O)R^{27}$, —$NR^{26}C(O)OR^{27}$, —$NR_{26}C(O)NR^{27}R^{27'}$, —$NR_{26}C(=NR^{26''})NR^{27}R^{27'}$, —$NR^{26}S(O)R^{27}$, —$NR^{26}S(O)_2R^{27}$, —$NR^{26}S(O)NR^{27}R^{27'}$, —$NR^{26}S(O)_2NR^{27}R^{27'}$, —$C(O)R_{26}$, —$C(O)OR^{26}$ and —$C(O)NR^{26}R^{26'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by halogen, $C_1$-$C_6$ alkyl, $C_2$-$C_6$ alkenyl, —$(CH_2)_pOR^{28}$, —$(CH_2)_p(OCH_2)_qOR^{28}$, —$(CH_2)_p(OCH_2CH_2)_qOR^{28}$, —$OR^{29}$, —$OC(O)R^{29}$, —$OC(O)NR^{29}R^{29'}$, —$OS(O)R^{29}$, —$OS(O)_2R^{29}$, —$(CH_2)_pOS(O)_2OR^{29}$, —$OS(O)_2OR^{29}$, —$SR^{29}$, —$S(O)R^{29}$, —$S(O)_2R^{29}$, —$S(O)NR^{29}R^{29'}$, —$S(O)_2NR^{29}R^{29'}$, —$OS(O)NR^{29}R^{29'}$, —$OS(O)_2NR^{29}R^{29'}$, —$NR^{29}R^{29'}$, —$NR^{29}C(O)R^{30}$, —$NR^{29}C(O)OR^{30}$, —$NR^{29}C(O)NR^{30}R^{30'}$, —$NR^{29}S(O)R^{30}$, —$NR^{29}S(O)_2R^{30}$, —$NR^{29}S(O)NR^{30}R^{30'}$, —$NR^{29}S(O)_2NR^{30}R^{30'}$, —$C(O)R^{29}$, —$C(O)OR^{29}$ or —$C(O)NR^{29}R^{29'}$;

each $R^{26}$, $R^{26'}$, $R^{26''}$, $R^{29}$, $R^{29'}$, $R^{30}$ and $R^{30'}$ is independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, —OH, —SH, —$NH_2$ or —$CO_2H$;

$R^{27}$ and $R^{27'}$ are each independently selected from the group consisting of H, $C_1$-$C_9$ alkyl, $C_2$-$C_9$ alkenyl, $C_2$-$C_9$ alkynyl, $C_3$-$C_6$ cycloalkyl, —$(CH_2)_p$(sugar), —$(CH_2)_p$(OCH$_2$CH$_2$)$_q$-(sugar) and —$(CH_2)_p$(OCH$_2$CH$_2$CH$_2$)$_q$(sugar);

$R^{28}$ is a H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, 5- to 7-membered heteroaryl or sugar;

n is 1, 2, 3, 4 or 5;
p is 1, 2, 3, 4 or 5;
q is 1, 2, 3, 4 or 5; and
* is a covalent bond.

In some embodiments, $R^{18}$ is selected from the group consisting of H, 5- to 7-membered heteroaryl, —$OR^{26}$, —$NR^{26}C(O)R^{27}$, —$NR^{26}C(O)NR^{27}R^{27'}$, —$NR^{26}C(=NR^{26''})NR^{27}R^{27'}$, and —$C(O)NR^{26}R^{26'}$, wherein each hydrogen atom 5- to 7-membered heteroaryl is independently optionally substituted by halogen, $C_1$-$C_6$ alkyl, $C_2$-$C_6$ alkenyl, —$(CH_2)_p OR^{28}$, —$(CH_2)_p(OCH_2)_q OR^{28}$, —$(CH_2)_p(OCH_2CH_2)_q OR^{28}$, —$OR^{29}$, —$OC(O)R^{29}$, —$OC(O)NR^{29}R^{29'}$, —$OS(O)R^{29}$, —$OS(O)_2R^{29}$, —$(CH_2)_p OS(O)_2 OR^{29}$, —$OS(O)_2 OR^{29}$, —$SR^{29}$, —$S(O)R^{29}$, —$S(O)_2R^{29}$, —$S(O)NR^{29}R^{29'}$, —$S(O)_2NR^{29}R^{29'}$, —$OS(O)NR^{29}R^{29'}$, —$OS(O)_2NR^{29}R^{29'}$, —$NR^{29}R^{29'}$, —$NR^{29}C(O)R^{30}$, —$NR^{29}C(O)OR^{30}$, —$NR^{29}C(O)NR^{30}R^{30'}$, —$NR^{29}S(O)R^{30}$, —$NR^{29}S(O)_2R^{30}$, —$NR^{29}S(O)NR^{30}R^{30'}$, —$NR^{29}S(O)_2NR^{30}R^{30'}$, —$C(O)R^{29}$, —$C(O)OR^{29}$ or —$C(O)NR^{29}R^{29'}$;

each $R^{26}$, $R^{26'}$, $R^{26''}$, $R^{29}$, $R^{29'}$, $R^{30}$ and $R^{30'}$ is independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, —OH, —SH, —$NH_2$ or —$CO_2H$;

$R^{27}$ and $R^{27'}$ are each independently selected from the group consisting of H, $C_1$-$C_9$ alkyl, $C_2$-$C_9$ alkenyl, $C_2$-$C_9$ alkynyl, $C_3$-$C_6$ cycloalkyl, —$(CH_2)_p$(sugar), —$(CH_2)_p$(OCH$_2$CH$_2$)$_q$-(sugar) and —$(CH_2)_p$(OCH$_2$CH$_2$CH$_2$)$_q$(sugar);

$R^{28}$ is a H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, 5- to 7-membered heteroaryl or sugar;

n is 1, 2, 3, 4 or 5;
p is 1, 2, 3, 4 or 5;
q is 1, 2, 3, 4 or 5; and
* is a covalent bond.

In some embodiments, $R^{18}$ is selected from the group consisting of H, 5- to 7-membered heteroaryl, —$OR^{26}$, —$NR^{26}C(O)R^{27}$, —$NR^{26}C(O)NR^{27}R^{27'}$, —$NR^{26}C(=NR^{26''})NR^{27}R^{27'}$, and —$C(O)NR^{26}R^{26'}$, wherein each hydrogen atom 5- to 7-membered heteroaryl is independently optionally substituted by —$(CH_2)_p OR^{28}$, —$OR^{29}$, —$(CH_2)_p OS(O)_2 OR^{29}$ and —$OS(O)_2 OR^{29}$, each $R^{26}$, $R^{26'}$, $R^{26''}$ and $R^{29}$ is independently H or $C_1$-$C_7$ alkyl, wherein each hydrogen atom in $C_1$-$C_7$ alkyl is independently optionally substituted by halogen, —OH, —SH, —$NH_2$ or —$CO_2H$;

$R^{27}$ and $R^{27'}$ are each independently selected from the group consisting of H, —$(CH_2)_p$(sugar), —$(CH_2)_p$(OCH$_2$CH$_2$)$_q$(sugar) and —$(CH_2)_p$(OCH$_2$CH$_2$CH$_2$)$_q$(sugar);

$R^{28}$ is H or sugar;
n is 1, 2, 3, 4 or 5;
p is 1, 2, 3, 4 or 5;

q is 1, 2, 3, 4 or 5; and
* is a covalent bond.

In some embodiments of the conjugates described herein, $L^1$ is present. In some embodiments of the conjugates described herein, $L^1$ is absent. In some embodiments, z4 is 0. In some embodiments, z4 is 1. In some embodiments, z4 is 2.

$L^2$ is a releasable linker. As used herein, the term "releasable linker" refers to a linker that includes at least one bond that can be broken under physiological conditions, such as a pH-labile, acid-labile, base-labile, oxidatively labile, metabolically labile, biochemically labile, or enzyme-labile bond. It is appreciated that such physiological conditions resulting in bond breaking do not necessarily include a biological or metabolic process, and instead may include a standard chemical reaction, such as a hydrolysis reaction, for example, at physiological pH, or as a result of compartmentalization into a cellular organelle such as an endosome having a lower pH than cytosolic pH.

It is understood that a cleavable bond can connect two adjacent atoms within the releasable linker and/or connect other linkers or B, $D^1$ and/or $D^2$, as described herein, at either or both ends of the releasable linker. In the case where a cleavable bond connects two adjacent atoms within the releasable linker, following breakage of the bond, the releasable linker is broken into two or more fragments. Alternatively, in the case where a cleavable bond is between the releasable linker and another moiety, such as another linker, a drug or binding ligand, the releasable linker becomes separated from the other moiety following breaking of the bond.

The lability of the cleavable bond can be adjusted by, for example, substituents at or near the cleavable bond, such as including alpha-branching adjacent to a cleavable disulfide bond, increasing the hydrophobicity of substituents on silicon in a moiety having silicon-oxygen bond that may be hydrolyzed, homologating alkoxy groups that form part of a ketal or acetal that may be hydrolyzed, and the like.

Illustrative releasable linkers described herein include linkers that include hemiacetals and sulfur variations thereof, acetals and sulfur variations thereof, hemiaminals, aminals, and the like, and can be formed from methylene fragments substituted with at least one heteroatom, 1-alkoxyalkylene, 1-alkoxycycloalkylene, 1-alkoxyalkylenecarbonyl, 1-alkoxycycloalkylenecarbonyl, and the like. Illustrative releasable linkers described herein include linkers that include carbonylarylcarbonyl, carbonyl(carboxyaryl)carbonyl, carbonyl(biscarboxyaryl)carbonyl, haloalkylenecarbonyl, and the like. Illustrative releasable linkers described herein include linkers that include alkylene(dialkylsilyl), alkylene(alkylarylsilyl), alkylene(diarylsilyl), (dialkylsilyl)aryl, (alkylarylsilyl)aryl, (diarylsilyl)aryl, and the like. Illustrative releasable linkers described herein include oxycarbonyloxy, oxycarbonyloxyalkyl, sulfonyloxy, oxysulfonylalkyl, and the like. Illustrative releasable linkers described herein include linkers that include iminoalkylidenyl, carbonylalkylideniminyl, iminocycloalkylidenyl, carbonylcycloalkylideniminyl, and the like. Illustrative releasable linkers described herein include linkers that include alkylenethio, alkylenearylthio, and carbonylalkylthio, and the like.

In some embodiments, $L^2$ is selected from the group consisting of

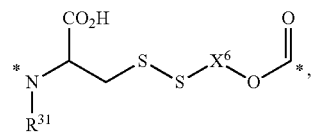

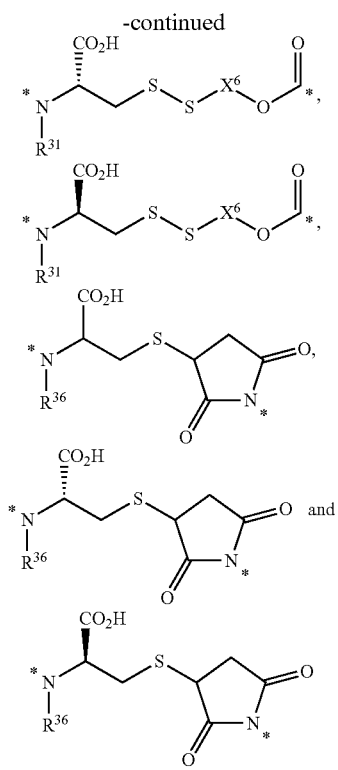

wherein $R^{31}$ is selected from the group consisting of H, D, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, —$OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

$X^6$ is $C_1$-$C_6$ alkyl or $C_6$-$C_{10}$ aryl($C_1$-$C_6$ alkyl), wherein each hydrogen atom in $C_1$-$C_6$ alkyl and $C_6$-$C_{10}$ aryl($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{34}$, —$OC(O)R^{34}$, —$OC(O)NR^{34}R^{34'}$, —$OS(O)R^{34}$, —$OS(O)_2R^{34}$, —$SR^{34}$, —$S(O)R^{34}$, —$S(O)_2R^{34}$, —$S(O)NR^{34}R^{34'}$, —$S(O)_2NR^{34}R^{34'}$, —$OS(O)NR^{34}R^{34'}$, —$OS(O)_2NR^{34}R^{34'}$, —$NR^{34}R^{34'}$, —$NR^{34}C(O)R^{35}$, —$NR^{34}C(O)OR^{35}$, —$NR^{34}C(O)NR^{35}R^{35'}$, —$NR^{34}S(O)R^{35}$, —$NR^{34}S(O)_2R^{35}$, —$NR^{34}S(O)NR^{35}R^{35'}$, —$NR^{34}S(O)_2NR^{35}R^{35'}$, —$C(O)R^{34}$, —$C(O)OR^{34}$ or —$C(O)NR^{34}R^{34'}$;

each $R^{32}$, $R^{32'}$, $R^{33}$, $R^{33'}$, $R^{34}$, $R^{34'}$, $R^{35}$ and $R^{35'}$ are independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl;

$R^{36}$ is independently selected from the group consisting of H, D, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{37}$, —$OC(O)R^{37}$, —$OC(O)NR^{37}R^{37'}$, —$OS(O)R^{37}$, —$OS(O)_2R^{37}$, —$SR^{37}$, —$S(O)R^{37}$, —$S(O)_2R^{37}$, —$S(O)NR^{37}R^{37'}$, —$S(O)_2NR^{37}R^{37'}$, —$OS(O)NR^{37}R^{37'}$, —$OS(O)_2NR^{37}R^{37'}$, —$NR^{37}R^{37'}$, —$NR^{37}C(O)R^{38}$, —$NR^{37}C(O)OR^{38}$, —$NR^{37}C(O)NR^{38}R^{38'}$, —$NR^{37}S(O)R^{38}$, —$NR^{37}S(O)_2R^{38}$, —$NR^{37}S(O)NR^{38}R^{38'}$, —$NR^{37}S(O)_2NR^{38}R^{38'}$, —$C(O)R^{37}$, —$C(O)OR^{37}$ or —$C(O)NR^{37}R^{37'}$;

$R^{37}$, $R^{37'}$, $R^{38}$ and $R^{38'}$ are each independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl; and

* is a covalent bond.

In some embodiments, $R^{31}$ is H. In some embodiments, $R^{36}$ is H. In some embodiments, $X^6$ is $C_1$-$C_6$ alkyl. In some embodiments, $X^6$ is $C_1$-$C_6$ alkyl. $C_6$-$C_{10}$ aryl($C_1$-$C_6$ alkyl).

In some embodiments, $L^2$ is

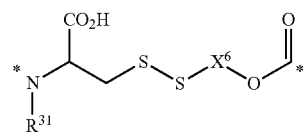

wherein $R^{31}$ is selected from the group consisting of H, D, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, —$OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

$X^6$ is $C_1$-$C_6$ alkyl or $C_6$-$C_{10}$ aryl($C_1$-$C_6$ alkyl), wherein each hydrogen atom in $C_1$-$C_6$ alkyl and $C_6$-$C_{10}$ aryl($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{34}$, —$OC(O)R^{34}$, —$OC(O)NR^{34}R^{34'}$, —$OS(O)R^{34}$, —$OS(O)_2R^{34}$, —$SR^{34}$, —$S(O)R^{34}$, —$S(O)_2R^{34}$, —$S(O)NR^{34}R^{34'}$, —$S(O)_2NR^{34}R^{34'}$, —$OS(O)NR^{34}R^{34'}$, —$OS(O)_2NR^{34}R^{34'}$, —$NR^{34}R^{34'}$, —$NR^{34}C(O)R^{35}$, —$NR^{34}C(O)OR^{35}$, —$NR^{34}C(O)NR^{35}R^{35'}$, —$NR^{34}S(O)R^{35}$, —$NR^{34}S(O)_2R^{35}$, —$NR^{34}S(O)NR^{35}R^{35'}$, —$NR^{34}S(O)_2NR^{35}R^{35'}$, —$C(O)R^{34}$, —$C(O)OR^{34}$ or —$C(O)NR^{34}R^{34'}$;

each $R^{32}$, $R^{32'}$, $R^{33}$, $R^{33'}$, $R^{34}$, $R^{34'}$, $R^{35}$ and $R^{35'}$ are independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl; and

* is a covalent bond.

In some embodiments, $R^{31}$ is H, and $X^6$ is $C_1$-$C_6$ alkyl. In some embodiments, $R^{31}$ is H, and $X^6$ is $C_6$-$C_{10}$ aryl($C_1$-$C_6$ alkyl).

In some embodiments, $L^2$ is

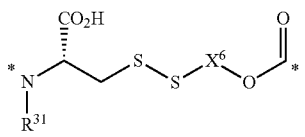

wherein $R^{31}$ is selected from the group consisting of H, D, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, —$OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

$X^6$ is $C_1$-$C_6$ alkyl or $C_6$-$C_{10}$ aryl($C_1$-$C_6$ alkyl), wherein each hydrogen atom in $C_1$-$C_6$ alkyl and $C_6$-$C_{10}$ aryl($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{34}$, —$OC(O)R^{34}$, —$OC(O)NR^{34}R^{34'}$, —$OS(O)R^{34}$, —$OS(O)_2R^{34}$, —$SR^{34}$, —$S(O)R^{34}$, —$S(O)_2R$, —$S(O)NR^{34}R^{34'}$, —$S(O)_2NR^{34}R^{34'}$, —$OS(O)NR^{34}R^{34'}$, —$OS(O)_2NR^{34}R^{34'}$, —$NR^{34}R^{34'}$, —$NRC(O)R^{35}$, —$NRC(O)OR^{35}$, —$NRC(O)NR^{35}R^{35'}$, —$NR^{34}S(O)R^{35}$, —$NR^{34}S(O)_2R^{35}$, —$NR^{34}S(O)NR^{35}R^{35'}$, —$NRS(O)_2NR^{35}R^{35'}$, —$C(O)R^{34}$, —$C(O)OR^{34}$ or —$C(O)NR^{34}R^{34'}$;

each $R^{32}$, $R^{32'}$, $R^{33}$, $R^{33'}$, $R^{34}$, $R^{34'}$, $R^{35}$ and $R^{35'}$ are independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl; and

* is a covalent bond.

In some embodiments, $R^{31}$ is H, and $X^6$ is $C_1$-$C_6$ alkyl. In some embodiments, $R^{31}$ is H, and $X^6$ is $C_6$-$C_{10}$ aryl($C_1$-$C_6$ alkyl).

In some embodiments, $L^2$ is

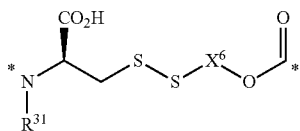

wherein $R^{31}$ is selected from the group consisting of H, D, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, —$OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

$X^6$ is $C_1$-$C_6$ alkyl or $C_6$-$C_{10}$ aryl($C_1$-$C_6$ alkyl), wherein each hydrogen atom in $C_1$-$C_6$ alkyl and $C_6$-$C_{10}$ aryl($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{34}$, —$OC(O)R^{34}$, —$OC(O)NR^{34}R^{34'}$, —$OS(O)R^{34}$, —$OS(O)_2R^{34}$, —$SR^{34}$, —$S(O)R^{34}$, —$S(O)_2R^{34}$, —$S(O)NR^{34}R^{34'}$, —$S(O)_2NR^{34}R^{34'}$, —$OS(O)NR^{34}R^{34'}$, —$OS(O)_2NR^{34}R^{34'}$, —$NR^{34}R^{34'}$, —$NR^{34}C(O)R^{35}$, —$NR^{34}C(O)OR^{35}$, —$NR^{34}C(O)NR^{35}R^{35'}$, —$NR^{34}S(O)R^{35}$, —$NR^{34}S(O)_2R^{35}$, —$NR^{34}S(O)NR^{35}R^{35'}$, —$NR^{34}S(O)_2NR^{35}R^{35'}$, —$C(O)R^{34}$, —$C(O)OR^{34}$ or —$C(O)NR^{34}R^{34'}$;

each $R^{32}$, $R^{32'}$, $R^{33}$, $R^{33'}$, $R^{34}$, $R^{34'}$, $R^{35}$ and $R^{35'}$ are independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl; and

* is a covalent bond.

In some embodiments, $R^{31}$ is H, and $X^6$ is $C_1$-$C_6$ alkyl. In some embodiments, $R^{31}$ is H, and $X^6$ is $C_6$-$C_{10}$ aryl($C_1$-$C_6$ alkyl).

In some embodiments, $L^2$ is

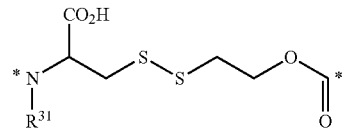

$R^{31}$ is selected from the group consisting of H, D, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, —$OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

each $R^{32}$, $R^{32'}$, $R^{33}$ and $R^{33'}$ are independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl; and

* is a covalent bond. In some embodiments, $R^{31}$ is H.

In some embodiments, $L^2$ is

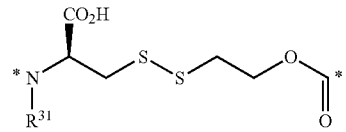

$R^{31}$ is selected from the group consisting of H, D, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, —$OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

each $R^{32}$, $R^{32'}$, $R^{33}$ and $R^{33'}$ are independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl; and

* is a covalent bond. In some embodiments, $R^{31}$ is H.

In some embodiments, $L^2$ is

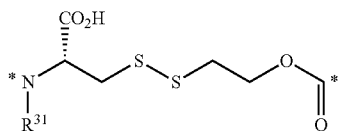

$R^{31}$ is selected from the group consisting of H, D, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, —$OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

each $R^{32}$, $R^{32'}$, $R^{33}$ and $R^{33'}$ are independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl; and

* is a covalent bond. In some embodiments, $R^{31}$ is H.

In some embodiments, $L^2$ is

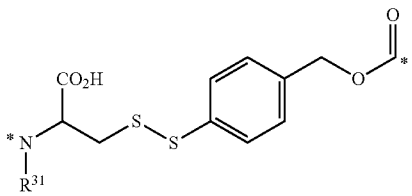

$R^{31}$ is selected from the group consisting of H, D, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, —$OC(O)R^{32}$, —$OC(O)NR^{32}R^{32'}$, —$OS(O)R^{32}$, —$OR^{32}$, —$OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

each $R^{32}$, $R^{32'}$, $R^{33}$ and $R^{33'}$ are independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl; and

* is a covalent bond. In some embodiments, $R^{31}$ is H.

In some embodiments, $L^2$ is

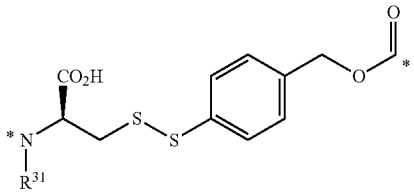

$R^{31}$ is selected from the group consisting of H, D, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, —$OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

each $R^{32}$, $R^{32'}$, $R^{33}$ and $R^{33'}$ are independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl; and

* is a covalent bond. In some embodiments, $R^{31}$ is H.

In some embodiments, $L^2$ is

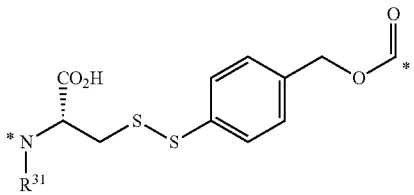

$R^{31}$ is selected from the group consisting of H, D, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, —$OC(O)R^{32}$, —$OC(O)NR^{32}R^{32'}$, —$OS(O)R^{32}$, —OS(O)$_2$R$^{32}$, —SR$^{32}$, —S(O)R$^{32}$, —S(O)$_2$R$^{32}$, —S(O)NR$^{32}$R$^{32'}$, —S(O)$_2$NR$^{32}$R$^{32'}$, —OS(O)NR$^{32}$R$^{32'}$, —OS(O)$_2$NR$^{32}$R$^{32'}$, —NR$^{32}$R$^{32'}$, —NR$^{32}$C(O)R$^{33}$, —NR$^{32}$C(O)OR$^{33}$, —NR$^{32}$C(O)NR$^{33}$R$^{33'}$, —NR$^{32}$S(O)R$^{33}$, —NR$^{32}$S(O)$_2$R$^{33}$, —NR$^{32}$S(O)NR$^{33}$R$^{33'}$, —NR$^{32}$S(O)$_2$NR$^{33}$R$^{33'}$, —C(O)R$^{32}$, —C(O)OR$^{32}$ or —C(O)NR$^{32}$R$^{32'}$;

each R$^{32}$, R$^{32'}$, R$^{33}$ and R$^{33'}$ are independently selected from the group consisting of H, D, C$_1$-C$_7$ alkyl, C$_2$-C$_7$ alkenyl, C$_2$-C$_7$ alkynyl, C$_3$-C$_6$ cycloalkyl, 3- to 7-membered heterocycloalkyl, C$_6$-C$_{10}$ aryl, and 5- to 7-membered heteroaryl; and

* is a covalent bond. In some embodiments, R$^{31}$ is H.

In some embodiments, L$^2$ is

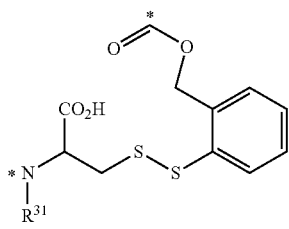

R$^{31}$ is selected from the group consisting of H, D, C$_1$-C$_6$ alkyl, C$_2$-C$_6$ alkenyl, C$_2$-C$_6$ alkynyl and C$_3$-C$_6$ cycloalkyl, wherein each hydrogen atom in C$_1$-C$_6$ alkyl, C$_2$-C$_6$ alkenyl, C$_2$-C$_6$ alkynyl and C$_3$-C$_6$ cycloalkyl is independently optionally substituted by halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{32}$, —OC(O)R$^{32}$, —OC(O)NR$^{32}$R$^{32'}$, —OS(O)R$^{32}$, —OS(O)$_2$R$^{32}$, —SR$^{32}$, —S(O)R$^{32}$, —S(O)$_2$R$^{32}$, —S(O)NR$^{32}$R$^{32'}$, —S(O)$_2$NR$^{32}$R$^{32'}$, —OS(O)NR$^{32}$R$^{32'}$, —OS(O)$_2$NR$^{32}$R$^{32'}$, —NR$^{32}$R$^{32'}$, —NR$^{32}$C(O)R$^{33}$, —NR$^{32}$C(O)OR$^{33}$, —NR$^{32}$C(O)NR$^{33}$R$^{33'}$, —NR$^{32}$S(O)R$^{33}$, —NR$^{32}$S(O)$_2$R$^{33}$, —NR$^{32}$S(O)NR$^{33}$R$^{33'}$, —NR$^{32}$S(O)$_2$NR$^{33}$R$^{33'}$, —C(O)R$^{32}$, —C(O)OR$^{32}$ or —C(O)NR$^{32}$R$^{32'}$;

each R$^{32}$, R$^{32'}$, R$^{33}$ and R$^{33'}$ are independently selected from the group consisting of H, D, C$_1$-C$_7$ alkyl, C$_2$-C$_7$ alkenyl, C$_2$-C$_7$ alkynyl, C$_3$-C$_6$ cycloalkyl, 3- to 7-membered heterocycloalkyl, C$_6$-C$_{10}$ aryl, and 5- to 7-membered heteroaryl; and

* is a covalent bond. In some embodiments, R$^{31}$ is H.

In some embodiments, L$^2$ is

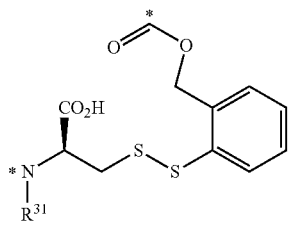

R$^{31}$ is selected from the group consisting of H, D, C$_1$-C$_6$ alkyl, C$_2$-C$_6$ alkenyl, C$_2$-C$_6$ alkynyl and C$_3$-C$_6$ cycloalkyl, wherein each hydrogen atom in C$_1$-C$_6$ alkyl, C$_2$-C$_6$ alkenyl, C$_2$-C$_6$ alkynyl and C$_3$-C$_6$ cycloalkyl is independently optionally substituted by halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{32}$, —OC(O)R$^{32}$, —OC(O)NR$^{32}$R$^{32'}$, —OS(O)R$^{32}$, —OS(O)$_2$R$^{32}$, —SR$^{32}$, —S(O)R$^{32}$, —S(O)$_2$R$^{32}$, —S(O)NR$^{32}$R$^{32'}$, —S(O)$_2$NR$^{32}$R$^{32'}$, —OS(O)NR$^{32}$R$^{32'}$, —OS(O)$_2$NR$^{32}$R$^{32'}$, —NR$^{32}$R$^{32'}$, —NR$^{32}$C(O)R$^{33}$, —NR$^{32}$C(O)OR$^{33}$, —NR$^{32}$C(O)NR$^{33}$R$^{33'}$, —NR$^{32}$S(O)R$^{33}$, —NR$^{32}$S(O)$_2$R$^{33}$, —NR$^{32}$S(O)NR$^{33}$R$^{33'}$, —NR$^{32}$S(O)$_2$NR$^{33}$R$^{33'}$, —C(O)R$^{32}$, —C(O)OR$^{32}$ or —C(O)NR$^{32}$R$^{32'}$;

each R$^{32}$, R$^{32'}$, R$^{33}$ and R$^{33'}$ are independently selected from the group consisting of H, D, C$_1$-C$_7$ alkyl, C$_2$-C$_7$ alkenyl, C$_2$-C$_7$ alkynyl, C$_3$-C$_6$ cycloalkyl, 3- to 7-membered heterocycloalkyl, C$_6$-C$_{10}$ aryl, and 5- to 7-membered heteroaryl; and

* is a covalent bond. In some embodiments, R$^{31}$ is H.

In some embodiments, L$^2$ is

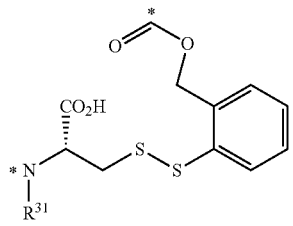

R$^{31}$ is selected from the group consisting of H, D, C$_1$-C$_6$ alkyl, C$_2$-C$_6$ alkenyl, C$_2$-C$_6$ alkynyl and C$_3$-C$_6$ cycloalkyl, wherein each hydrogen atom in C$_1$-C$_6$ alkyl, C$_2$-C$_6$ alkenyl, C$_2$-C$_6$ alkynyl and C$_3$-C$_6$ cycloalkyl is independently optionally substituted by halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl,

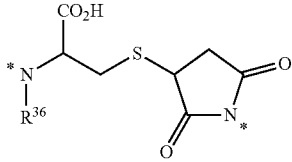

R$^{36}$ is independently selected from the group consisting of H, D, C$_1$-C$_6$ alkyl, C$_2$-C$_6$ alkenyl, C$_2$-C$_6$ alkynyl and C$_3$-C$_6$ cycloalkyl, wherein each hydrogen atom in C$_1$-C$_6$ alkyl, C$_2$-C$_6$ alkenyl, C$_2$-C$_6$ alkynyl and C$_3$-C$_6$ cycloalkyl is independently optionally substituted by halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{37}$, —OC(O)R$^{37}$, —OC(O)NR$^{37}$R$^{37'}$, —OS(O)R$^{37}$, —OS(O)$_2$R$^{37}$, —SR$^{37}$, —S(O)R$^{37}$, —S(O)$_2$R$^{37}$, —S(O)NR$^{37}$R$^{37'}$, —S(O)$_2$NR$^{37}$R$^{37'}$, —OS(O)NR$^{37}$R$^{37'}$, —OS(O)$_2$NR$^{37}$R$^{37'}$, —NR$^{37}$R$^{37'}$, —NR$^{37}$C(O)R$^{38}$, —NR$^{37}$C(O)OR$^{38}$, —NR$^{37}$C(O)NR$^{38}$R$^{38'}$, —NR$^{37}$S(O)R$^{38}$, —NR$^{37}$S(O)$_2$R$^{38}$, —NR$^{37}$S(O)NR$^{38}$R$^{38'}$, —NR$^{37}$S(O)$_2$NR$^{38}$R$^{38'}$, —C(O)R$^{37}$, —C(O)OR$^{37}$ or —C(O)NR$^{37}$R$^{37'}$;

R$^{37}$, R$^{37'}$, R$^{38}$ and R$^{38'}$ are each independently selected from the group consisting of H, D, C$_1$-C$_7$ alkyl, C$_2$-C$_7$ alkenyl, C$_2$-C$_7$ alkynyl, C$_3$-C$_6$ cycloalkyl, 3- to 7-membered heterocycloalkyl, C$_6$-C$_{10}$ aryl and 5- to 7-membered heteroaryl; and

* is a covalent bond. In some embodiments, R$^{36}$ is H.

In some embodiments, L$^2$ is

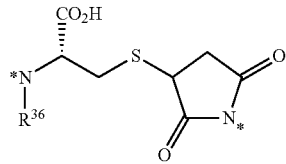

R$^{36}$ is independently selected from the group consisting of H, D, C$_1$-C$_6$ alkyl, C$_2$-C$_6$ alkenyl, C$_2$-C$_6$ alkynyl and C$_3$-C$_6$ cycloalkyl, wherein each hydrogen atom in C$_1$-C$_6$ alkyl, C$_2$-C$_6$ alkenyl, C$_2$-C$_6$ alkynyl and C$_3$-C$_6$ cycloalkyl is independently optionally substituted by halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{37}$, —OC(O)R$^{37}$, —OC(O)NR$^{37}$R$^{37'}$, —OS(O)R$^{37}$, —OS(O)$_2$R$^{37}$, —SR$^{37}$, —S(O)R$^{37}$, —S(O)$_2$R$^{37}$, —S(O)NR$^{37}$R$^{37'}$, —S(O)$_2$NR$^{37}$R$^{37'}$, —OS(O)NR$^{37}$R$^{37'}$, —OS(O)$_2$NR$^{37}$R$^{37'}$, —NR$^{37}$R$^{37'}$, —NR$^{37}$C(O)R$^{38}$, —NR$^{37}$C(O)OR$^{38}$, —NR$^{37}$C(O)NR$^{38}$R$^{38'}$, —NR$^{37}$S(O)R$^{38}$, —NR$^{37}$S(O)$_2$R$^{38}$, —NR$^{37}$S(O)NR$^{38}$R$^{38'}$, —NR$^{37}$S(O)$_2$NR$^{38}$R$^{38'}$, —C(O)R$^{37}$, —C(O)OR$^{37}$ or —C(O)NR$^{37}$R$^{37'}$;

R$^{37}$, R$^{37'}$, R$^{38}$ and R$^{38'}$ are each independently selected from the group consisting of H, D, C$_1$-C$_7$ alkyl, C$_2$-C$_7$ alkenyl, C$_2$-C$_7$ alkynyl, C$_3$-C$_6$ cycloalkyl, 3- to 7-membered heterocycloalkyl, C$_6$-C$_{10}$ aryl and 5- to 7-membered heteroaryl; and

* is a covalent bond. In some embodiments, R$^{36}$ is H.

In some embodiments, L$^2$ is

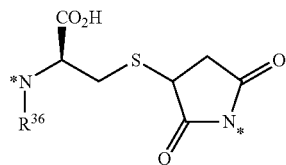

R$^{36}$ is independently selected from the group consisting of H, D, C$_1$-C$_6$ alkyl, C$_2$-C$_6$ alkenyl, C$_2$-C$_6$ alkynyl and C$_3$-C$_6$ cycloalkyl, wherein each hydrogen atom in C$_1$-C$_6$ alkyl, C$_2$-C$_6$ alkenyl, C$_2$-C$_6$ alkynyl and C$_3$-C$_6$ cycloalkyl is independently optionally substituted by halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{37}$, —OC(O)R$^{37}$, —OC(O)NR$^{37}$R$^{37'}$, —OS(O)R$^{37}$, —OS(O)$_2$R$^{37}$, —SR$^{37}$, —S(O)R$^{37}$, —S(O)$_2$R$^{37}$, —S(O)NR$^{37}$R$^{37'}$, —S(O)$_2$NR$^{37}$R$^{37'}$, —OS(O)NR$^{37}$R$^{37'}$, —OS(O)$_2$NR$^{37}$R$^{37'}$, —NR$^{37}$R$^{37'}$, —NR$^{37}$C(O)R$^{38}$, —NR$^{37}$C(O)OR$^{38}$, —NR$^{37}$C(O)NR$^{38}$R$^{38'}$, —NR$^{37}$S(O)R$^{38}$, —NR$^{37}$S(O)$_2$R$^{38}$, —NR$^{37}$S(O)NR$^{38}$R$^{38'}$, —NR$^{37}$S(O)$_2$NR$^{38}$R$^{38'}$, —C(O)R$^{37}$, —C(O)OR$^{37}$ or —C(O)NR$^{37}$R$^{37'}$;

R$^{37}$, R$^{37'}$, R$^{38}$ and R$^{38'}$ are each independently selected from the group consisting of H, D, C$_1$-C$_7$ alkyl, C$_2$-C$_7$ alkenyl, C$_2$-C$_7$ alkynyl, C$_3$-C$_6$ cycloalkyl, 3- to 7-membered heterocycloalkyl, C$_6$-C$_{10}$ aryl and 5- to 7-membered heteroaryl; and

* is a covalent bond. In some embodiments, R$^{36}$ is H.

L$^3$ can be present or absent in the conjugates described herein. When L$^3$ is present, L$^3$ can be any group covalently attaching portions of the linker to one another, or to D$^1$, or to D$^2$. It will be understood that the structure of L$^3$ is not particularly limited in any way. It will be further understood that L$^3$ can comprise numerous functionalities well known in the art to covalently attach portions of the linker to one another, or to D$^1$, or to D$^2$, including but not limited to, alkyl groups, ether groups, amide groups, carboxy groups, sulfonate groups, alkenyl groups, alkynyl groups, cycloalkyl groups, aryl groups, heterocycloalkyl, heteroaryl groups, and the like. In some embodiments, L$^3$ is selected from the group consisting of C$_1$-C$_6$ alkyl, —(CR$^{39}$R$^{39'}$)$_r$C(O)—, —(CR$^{39}$R$^{39'}$)$_r$OC(O)—, —NR$^{39}$R$^{39'}$C(O)(CR$^{39}$R$^{39'}$)$_r$—, —(CH$_2$)$_r$NR$^{39}$—, —(OCR$^{39}$R$^{39'}$CR$^{39}$R$^{39'}$)$_r$C(O)—, and —(OCR$^{39}$R$^{39'}$CR$^{39}$R$^{39'}$CR$^{39}$R$^{39'}$)—$_r$C(O)—, wherein each R$^{39}$ and R$^{39'}$ is independently selected from the group consisting of H, D, halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{40}$, —OC(O)R$^{40}$, —OC(O)NR$^{40}$R$^{40'}$, —OS(O)R$^{40}$, —OS(O)$_2$R$^{40}$, —SR$^{40}$, —S(O)R$^{40}$, —S(O)$_2$R$^{40}$, —S(O)NR$^{40}$R$^{40'}$, —S(O)$_2$NR$^{40}$R$^{40'}$, —OS(O)NR$^{40}$R$^{40'}$, —OS(O)$_2$NR$^{40}$R$^{40'}$, —NR$^{40}$R$^{40'}$, —NR$^{40}$C(O)R$^{41}$, —NR$^{40}$C(O)OR$^{41}$, —NR$^{40}$C(O)NR$^{41}$R$^{41'}$, —NR$^{40}$S(O)R$^{41}$, —NR$^{40}$S(O)$_2$R$^{41}$, —NR$^{40}$S(O)NR$^{41}$R$^{41'}$, —NR$^{40}$S(O)$_2$NR$^{41}$R$^{41'}$, —C(O)R$^{40}$, —C(O)OR$^{40}$ and —C(O)NR$^{40}$R$^{40'}$;

R$^{40}$, R$^{40'}$, R$^{41}$ and R$^{41'}$ are each independently selected from the group consisting of H, D, C$_1$-C$_7$ alkyl, C$_2$-C$_7$ alkenyl, C$_2$-C$_7$ alkynyl, C$_3$-C$_6$ cycloalkyl, 3- to 7-membered heterocycloalkyl, C$_6$-C$_{10}$ aryl, and 5- to 7-membered heteroaryl; and r in each instance is 1, 2, 3, 4, or 5. In some embodiments of the conjugates described herein, L$^3$ is present. In some embodiments of the conjugates described herein, L$^3$ is absent. In some embodiments, z2 is 0. In some embodiments, z2 is 1. In some embodiments, z2 is 2. In some embodiments, z6 is 0. In some embodiments, z6 is 1. In some embodiments, z6 is 2. In some embodiments, r is 5. In some embodiments, r is 4. In some embodiments, r is 3. In some embodiments, r is 5, each R$^{39}$ is H, and each R$^{39'}$ is H. In some embodiments, r is 4, each R$^{39}$ is H, and each R$^{39'}$ is H. In some embodiments, r is 3, each R$^{39}$ is H, and each R$^{39'}$ is H.

In some embodiments, L$^3$ is —(CR$^{39}$R$^{39'}$)$_r$C(O)—. In some embodiments, L$^3$ is —(CR$^{39}$R$^{39'}$)$_r$C(O)—, r is 5, each R$^{39}$ is H, and each R$^{39'}$ is H. In some embodiments, L$^3$ is —(CR$^{39}$R$^{39'}$)$_r$C(O)—, r is 4, each R$^{39}$ is H, and each R$^{39'}$ is H. In some embodiments, L$^3$ is —(CR$^{39}$R$^{39'}$)$_r$C(O)—, r is 3, each R$^{39}$ is H, and each R$^{39'}$ is H.

In some embodiments, L$^3$ is —(CR$^{39}$R$^{39'}$)$_r$OC(O)—, r is 5, each R$^{39}$ is H, and each R$^{39'}$ is H. In some embodiments, L$^3$ is —(CR$^{39}$R$^{39'}$)$_r$OC(O)—, r is 4, each R$^{39}$ is H, and each R$^{39'}$ is H. In some embodiments, L$^3$ is —(CR$^{39}$R$^{39'}$)$_r$OC(O)—, r is 3, each R$^{39}$ is H, and each R$^{39'}$ is H.

In some embodiments, L$^3$ is —NR$^{39}$R$^{39'}$C(O)(CR$^{39}$R$^{39'}$)$_r$—, r is 5, each R$^{39}$ is H, and each R$^{39'}$ is H. In some embodiments, $L^3$ is —$NR^{39}R^{39'}C(O)(CR^{39}R^{39'})_r$—, r is 4, each $R^{39}$ is H, and each $R^{39'}$ is H. In some embodiments, $L^3$ is —$NR^{39}R^{39'}C(O)(CR^{39}R^{39'})_r$—, r is 3, each $R^{39}$ is H, and each $R^{39'}$ is H.

In some embodiments, $L^3$ is —$(CH_2)_rNR^{39}$—, r is 5 and $R^{39}$ is H. In some embodiments, $L^3$ is —$(CH_2)_rNR^{39}$—, r is 4 and $R^{39}$ is H. In some embodiments, $L^3$ is —$(CH_2)_rNR^{39}$—, r is 3 and $R^{39}$ is H. In some embodiments, $L^3$ is —$(CH_2)_rNR^{39}$—, r is 2 and $R^{39}$ is H.

In some embodiments, $L^3$ is —$(OCR^{39}R^{39'}CR^{39}R^{39'})_rC(O)$—, r is 5, each $R^{39}$ is H, and each $R^{39'}$ is H. In some embodiments, $L^3$ is —$(OCR^{39}R^{39'}CR^{39}R^{39'})_rC(O)$—, r is 4, each $R^{39}$ is H, and each $R^{39'}$ is H. In some embodiments, $L^3$ is —$(OCR^{39}R^{39'}CR^{39}R^{39'})_rC(O)$—, r is 3, each $R^{39}$ is H, and each $R^{39'}$ is H.

$L^4$ can be present or absent in the conjugates described herein. When $L^4$ is present, $L^4$ can be any group covalently attaching portions of the linker to one another, or to $D^1$, or to $D^2$. It will be understood that the structure of $L^4$ is not particularly limited in any way. It will be further understood that $L^4$ can comprise numerous functionalities well known in the art to covalently attach portions of the linker to one another, or to $D^1$, or to $D^2$, including but not limited to, alkyl groups, ether groups, amide groups, carboxy groups, sulfonate groups, alkenyl groups, alkynyl groups, cycloalkyl groups, aryl groups, heterocycloalkyl, heteroaryl groups, and the like. In some embodiments, $L^4$ is selected from the group consisting of —$C(O)(CR^{44}R^{44'})_t$—, —$NR^{42}CR^{43}R^{43'}CR^{43}R^{43'}(OCR^{44}R^{44'}CR^{44}R^{44'})_t$—, —$NR^{42}CR^{43}R^{43'}CR^{43}R^{43'}(OCR^{44}R^{44'}CR^{44}R^{44'})_t$—, —$NR^{42}CR^{43}R^{43'}CR^{43}R^{43'}(OCR^{44}R^{44'}CR^{44}R^{44'})_tC(O)$—, —$NR^{42}CR^{43}R^{43'}CR^{43}R^{43'}(CR^{44}=CR^{44'})_t$—, and —$NR^{42}C_6$-$C_{10}$ aryl($C_1$-$C_6$ alkyl)OC(O)—;

wherein $R^{42}$ is selected from the group consisting of H, D, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{45}$, —$OC(O)R^{45}$, —$OC(O)NR^{45}R^{45'}$, —$OS(O)R^{45}$, —$OS(O)_2R^{45}$, —$SR^{45}$, —$S(O)R^{45}$, —$S(O)_2R^{45}$, —$S(O)NR^{45}R^{45'}$, —$S(O)_2NR^{45}R^{45'}$, —$OS(O)NR^{45}R^{45'}$, —$OS(O)_2NR^{45}R^{45'}$, —$NR^{45}R^{45'}$, —$NR^{45}C(O)R^{46}$, —$NR^{45}C(O)OR^{46}$, —$NR^{45}C(O)NR^{46}R^{46'}$, —$NR^{45}S(O)R^{46}$, —$NR^{45}S(O)_2R^{46}$, —$NR^{45}S(O)NR^{46}R^{46'}$, —$NR^{45}S(O)_2NR^{46}R^{46'}$, —$C(O)R^{45}$, —$C(O)OR^{45}$ or —$C(O)NR^{45}R^{45'}$, each $R^{43}$, $R^{43'}$, $R^{44}$ and $R^{44'}$ is independently selected from the group consisting of H, D, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{47}$, —$OC(O)R^{47}$, —$OC(O)NR^{47}R^{47'}$, —$OS(O)R^{47}$, —$OS(O)_2R^{47}$, —$SR^{47}$, —$S(O)R^{47}$, —$S(O)_2R^{47}$, —$S(O)NR^{47}R^{47'}$, —$S(O)_2NR^{47}R^{47'}$, —$OS(O)NR^{47}R^{47'}$, —$OS(O)_2NR^{47}R^{47'}$, —$NR^{47}C(O)R^{48}$, —$NR^{47}C(O)OR^{48}$, —$NR^{47}C(O)NR^{48}R^{48'}$, —$NR^{47}S(O)R^{48}$, —$NR^{47}S(O)_2R^{48}$, —$NR^{47}S(O)NR^{48}R^{48'}$, —$NR^{47}S(O)_2NR^{48}R^{48'}$, —$C(O)R^{47}$, —$C(O)OR^{47}$ or —$C(O)NR^{47}R^{47'}$;

$R^{45}$, $R^{45'}$, $R^{46}$, $R^{46'}$, $R^{47}$, $R^{47'}$, $R^{48}$ and $R^{48'}$ are each independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl;

t is in each instance 1, 2, 3, 4, or 5; and

* is a covalent bond.

In some embodiments of the conjugates described herein, $L^4$ is present. In some embodiments of the conjugates described herein, $L^4$ is absent. In some embodiments, z5 is 0. In some embodiments, z5 is 1. In some embodiments, z5 is 2. In some embodiments, z7 is 0. In some embodiments, z7 is 1. In some embodiments, z7 is 2. In some embodiments, z9 is 0. In some embodiments, z9 is 1. In some embodiments, z9 is 2. In some embodiments, z7 is 0 and z9 is 0. In some embodiments, z7 is 0 and z9 is 1. In some embodiments, z7 is 1 and z9 is 1. In some embodiments, z7 is 1 and z9 is 0.

In some embodiments, $L^4$ is —$NR^{42}C_6$-$C_{10}$ aryl($C_1$-$C_6$ alkyl)OC(O)—, wherein $R^{42}$ is H. In some embodiments, z5 is 1, and $L^4$ is —$NR^{42}C_6$-$C_{10}$ aryl($C_1$-$C_6$ alkyl)OC(O)—, wherein $R^{42}$ is H. In some embodiments, z7 is 1, and $L^4$ is —$NR^{42}C_6$-$C_{10}$ aryl($C_1$-$C_6$ alkyl)OC(O)—, wherein $R^{42}$ is H. In some embodiments, z9 is 1, and $L^4$ is —$NR^{42}C_6$-$C_{10}$ aryl($C_1$-$C_6$ alkyl)OC(O)—, wherein $R^{42}$ is H. In some embodiments, $L^4$ is —$NR^{42}CR^{43}R^{43'}CR^{43}R^{43'}(OCR^{44}R^{44'}CR^{44}R^{44'})_tC(O)$— wherein each $R^{42}$, $R^{43}$, $R^{43'}$, $R^{44}$ and $R^{44'}$ is H, and t is 4. In some embodiments, $L^4$ is —$NR^{42}CR^{43}R^{43'}CR^{43}R^{43'}(OCR^{44}R^{44'}CR^{44}R^{44'})_tC(O)$— or —$NR^{42}C_6$-$C_{10}$ aryl($C_1$-$C_6$ alkyl)OC(O)—, wherein each $R^{42}$, $R^{43}$, $R^{43'}$, $R^{44}$ and $R^{44'}$ is H, $z_7$ is 1, $z_9$ is 1, and t is 4.

In some embodiments, -$L^3$-$L^4$- is —$(CH_2)_rNR^{39}C(O)(CR^{44}R^{44'})_t$—, wherein r is 2, t is 2, $R^{39}$ is H, each $R^{44}$ is H, and each $R^{44'}$ is H. In some embodiments, -$L^3$-$L^4$-$(AA)_2$ is —$(CR^{39}R^{39'})_rC(O)$—$NR^{42}CR^{43}R^{43'}CR^{43}R^{43'}(OCR^{44}R^{44'}CR^{44}R^{44'})_tC(O)$-Val-Ala-, -$L^3$-$L^4$-$(AA)_2$-$L^4$ is —$(CR^{39}R^{39'})_rC(O)$—$NR^{42}CR^{43}R^{43'}CR^{43}R^{43'}(OCR^{44}R^{44'}CR^{44}R^{44'})_tC(O)$-Val-Ala-$NR^{42}C_6$-$C_{10}$ aryl($C_1$-$C_6$ alkyl)OC(O)—, wherein each $R^{39}$, $R^{39'}$, $R^{42}$, $R^{43}$, $R^{43'}$, $R^{44}$ and $R^{44'}$ is H, r is 2 and t is 4.

$L^5$ can be present or absent in the conjugates described herein. When $L^5$ is present, $L^5$ can be any group covalently attaching $D^1$ to $D^2$. It will be understood that the structure of $L^5$ is not particularly limited in any way. It will be further understood that $L^5$ can comprise numerous functionalities well known in the art to covalently attach $D^1$ to $D^2$, including but not limited to, alkyl groups, ether groups, amide groups, carboxy groups, sulfonate groups, alkenyl groups, alkynyl groups, cycloalkyl groups, aryl groups, heterocycloalkyl, heteroaryl groups, and the like. In some embodiments, $L^5$ is selected from the group consisting of $C_1$-$C_{10}$ alkyl, —$(CR^{49}=CR^{49'})_u$—, —$(CR^{49}R^{49'})_uC(O)$—, —$CH_2CH_2(OCR^{49}R^{49'}CR^{49}R^{49'})_u$—, —$CH_2CH_2CH_2(OCR^{49}R^{49'}CR^{49}R^{49'}CR^{49}R^{49'})_u$—, —$CH_2CH_2(OCR^{49}R^{49'}CR^{49}R^{49'})_uC(O)$— and —$CH_2CH_2(OCR^{49}R^{49'}CR^{49}R^{49'}CR^{49}R^{49'})_uC(O)$—, wherein each $R^{49}$ and $R^{49'}$ is independently selected from the group consisting of H, D, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{50}$, —$OC(O)R^{50}$, —$OC(O)NR^{50}R^{50'}$, —$OS(O)R^{50}$, —$OS(O)_2R^{50}$, —$SR^{50}$, —$S(O)R^{50}$, —$S(O)_2R^{50}$, —$S(O)NR^{50}R^{50'}$, —$S(O)_2NR^{50}R^{50'}$, —$OS(O)NR^{50}R^{50'}$, —$OS(O)_2NR^{50}R^{50'}$, —$NR^{50}R^{50'}$, —$NR^{50}C(O)R^{51}$, —$NR^{50}C(O)OR^{51}$, —$NR^{50}C(O)NR^{51}R^{51'}$, —$NR^{50}S(O)R^{51}$, —$NR^{50}S(O)_2R^{51}$, —$NR^{50}S(O)NR^{51}R^{51'}$, —$NR^{50}S(O)_2NR^{51}R^{51'}$, —$C(O)R^{50}$, —$C(O)OR^{50}$ or —$C(O)NR^{50}R^{50'}$;

$R^{50}$, $R^{50'}$, $R^{51}$ and $R^{51'}$ are each independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl;

u is in each instance 0, 1, 2, 3, 4 or 5; and

* is a covalent bond.

In some embodiments of the conjugates described herein, $L^5$ is present. In some embodiments of the conjugates described herein, $L^5$ is absent. In some embodiments, $L^5$ is $C_1$-$C_6$ alkyl. In some embodiments, $L^5$ is —$(CR^{49}R^{49'})_uC(O)$—, wherein each $R^{49}$ and $R^{49'}$ is H, and u is 3. In some embodiments, $L^5$ is —$(CR^{49}R^{49'})_uC(O)$—, wherein each $R^{49}$ and $R^{49'}$ is H, and u is 4. In some embodiments, $L^5$ is —$(CR^{49}R^{49'})_uC(O)$—, wherein each $R^{49}$ and $R^{49'}$ is H, and u is 5.

In some embodiments, the linker is of the formula -(AA)$_{z1}$-$L^2$-($L^3$)$_{z2}$-(AA)$_{z3}$-($L^1$)$_{z4}$-($L^4$)$_{z5}$-, wherein AA, $L^1$, $L^2$, $L^3$, $L^4$, z1, z2, z3, z4 and z5 are defined as described herein. In some embodiments, the linker is of the formula -$L^1$-AA-$L^1$-AA-$L^1$-$L^2$-($L^3$)$_{z6}$-($L^4$)$_{z7}$-(AA)$_{z8}$-($L^4$)$_{z9}$-, wherein AA, $L^1$, $L^2$, $L^3$, $L^4$, z6, z7, z8 and z9 are defined as described herein. In some embodiments, the linker is of the formula -(AA)$_{z10}$-$L^2$-, wherein AA, $L^2$ and z10 are defined as described herein. In some embodiments, the linker is of the formula -(AA)$_{z11}$-$L^2$-, wherein AA, $L^2$, and z11 are defined as described herein. In some embodiments, the linker is of the formula -$L^2$-(AA)$_{z12}$-, wherein AA, $L^2$, and z12 are defined as described herein. In some embodiments, the linker is of the formula -(AA)$_4$-$L^2$-, wherein AA and $L^2$ are defined as described herein. In some embodiments, the linker is of the formula -(AA)$_4$-$L^2$-, wherein the sequence of -(AA)$_4$- is -Asp-Arg-Asp-Asp- (SEQ ID NO: 5), and $L^2$ is defined as described herein. In some embodiments, the linker is of the formula -(AA)$_4$-$L^2$-$L^3$-AA-$L^1$-$L^4$-, wherein the sequence of -(AA)$_4$- is -Asp-Arg-Asp-Asp- (SEQ ID NO: 5), and AA, $L^1$, $L^2$, $L^3$ and $L^4$ are defined as described herein. In some embodiments, the linker is of the formula -(AA)$_4$-$L^2$-$L^3$-(AA)$_2$-, wherein AA, $L^1$, $L^2$ and $L^3$ are defined as described herein. In some embodiments, the linker is of the formula -(AA)$_4$-$L^2$-$L^3$-(AA)$_2$-, wherein the sequence of -(AA)$_4$- is -Asp-Arg-Asp-Asp- (SEQ ID NO: 5), the sequence of -(AA)$_2$- is Val-Ala, and $L^1$, $L^2$ and $L^3$ are defined as described herein. In some embodiments, the linker is of the formula -(AA)$_4$-$L^2$-$L^3$-(AA)$_2$-, wherein the sequence of -(AA)$_4$- is -Asp-Arg-Asp-Asp- (SEQ ID NO: 5), the sequence of -(AA)$_2$- is Val-CIT, and $L^1$, $L^2$ and $L^3$ are defined as described herein. In some embodiments, the linker is of the formula -$L^1$-AA-$L^1$-AA-$L^1$-$L^2$-, wherein AA, $L^1$ and $L^2$ are defined as described herein. In some embodiments, the linker is of the formula -L1-AA-L1-AA-L1-L2-L3-(AA)$_2$-L4-, wherein AA, $L^1$, $L^2$, $L^3$ and $L^4$ are defined as described herein. In some embodiments, the linker is of the formula -$L^1$-AA-$L^1$-AA-$L^1$-$L^2$-$L^3$-$L^4$-(AA)$_2$-$L^4$-, wherein AA, $L^1$, $L^2$, $L^3$ and $L^4$ are defined as described herein. In some embodiments, the linker is of the formula -$L^1$-AA-$L^1$-AA-$L^1$-$L^2$-$L^3$-$L^4$-, AA, $L^1$, $L^2$, $L^3$ and $L^4$ are defined as described herein. In some embodiments, the linker is of the formula -L1-AA-L1-AA-$L^1$-$L^2$-$L^3$-(AA)$_2$-, wherein AA, $L^1$, $L^2$ and $L^3$ are defined as described herein. -L1-AA-L1-AA-$L^1$-$L^2$-$L^3$-, wherein AA, $L^1$, $L^2$ and $L^3$ are defined as described herein.

In some embodiments, the linker is of the formula (SEQ ID NO: 1 is included in the structure below)

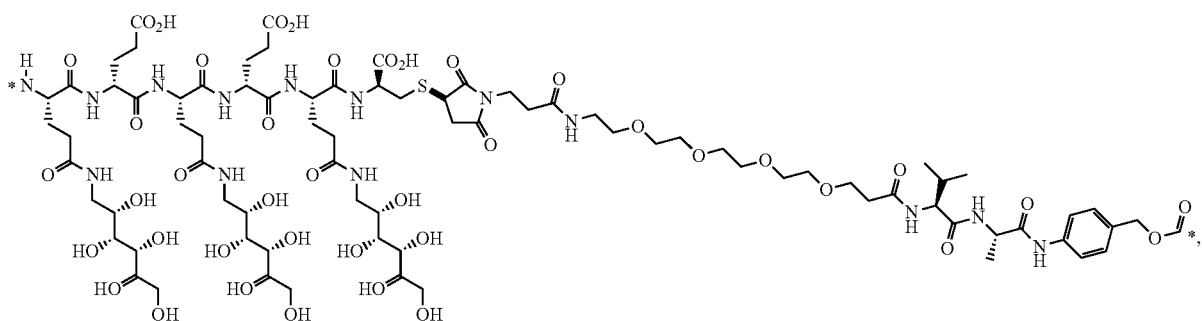

wherein * is a bond.

In some embodiments, the linker is of the formula (SEQ ID NO: 1 is included in the structure below)

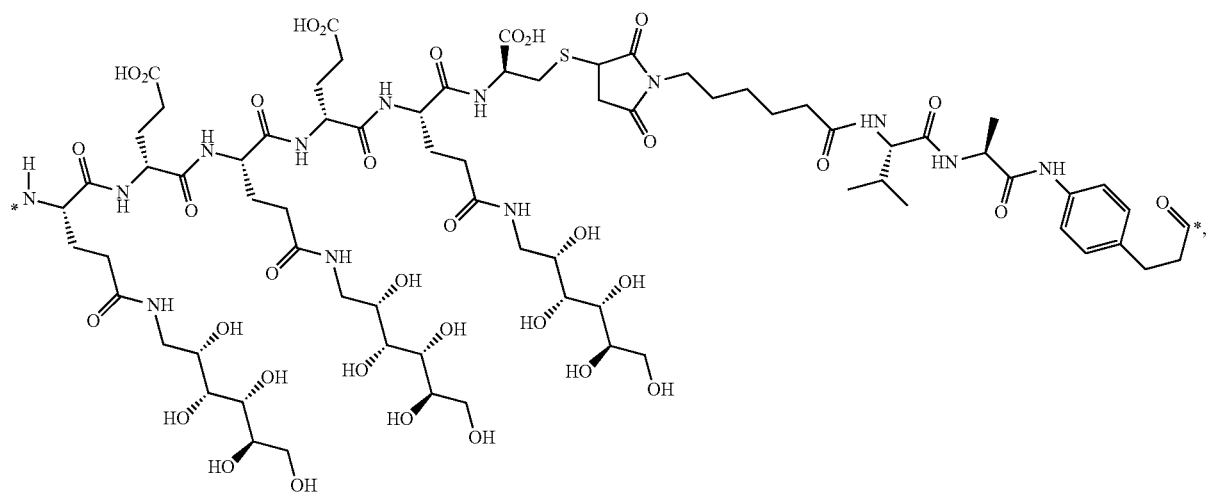 [SMILES: CC(C)[C@H](NC(=O)CCCCCN1C(=O)CC(SC[C@@H](NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)[C@@H](CCC(=O)O)NC(=O)[C@@H](N)CCC(=O)NC[C@H](O)[C@@H](O)[C@H](O)[C@H](O)CO)C(=O)O)C1=O)C(=O)N[C@@H](C)C(=O)Nc1ccc(CCC=O)cc1]
wherein * is a bond.
In some embodiments, the linker is of the formula (SEQ ID NO: 1 is included in the structure below)
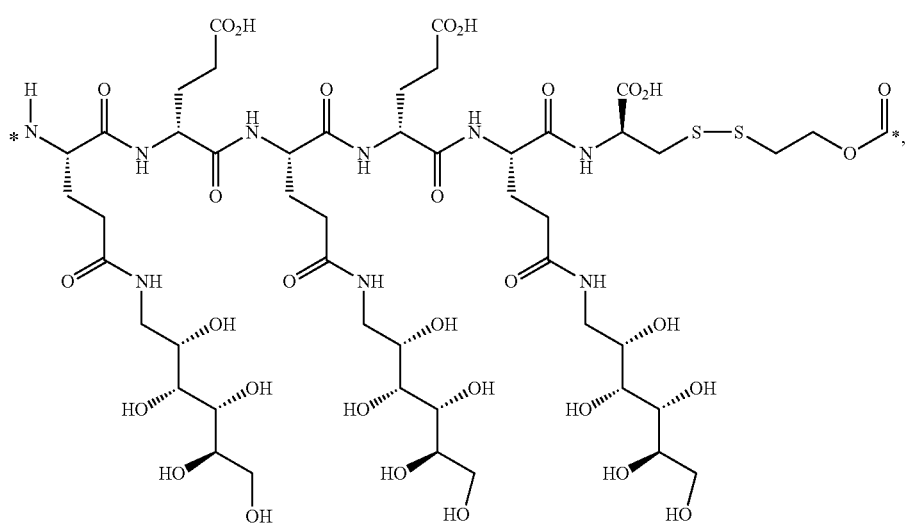 [SMILES: N[C@@H](CCC(=O)NC[C@H](O)[C@@H](O)[C@H](O)[C@H](O)CO)C(=O)N[C@H](CCC(=O)O)C(=O)N[C@@H](CCC(=O)NC[C@H](O)[C@@H](O)[C@H](O)[C@H](O)CO)C(=O)N[C@H](CCC(=O)O)C(=O)N[C@@H](CCC(=O)NC[C@H](O)[C@@H](O)[C@H](O)[C@H](O)CO)C(=O)N[C@H](CSSCCOC=O)C(=O)O]
wherein * is a bond.
In some embodiments, the linker is of the formula (SEQ ID NO: 2 is included in the structure below)

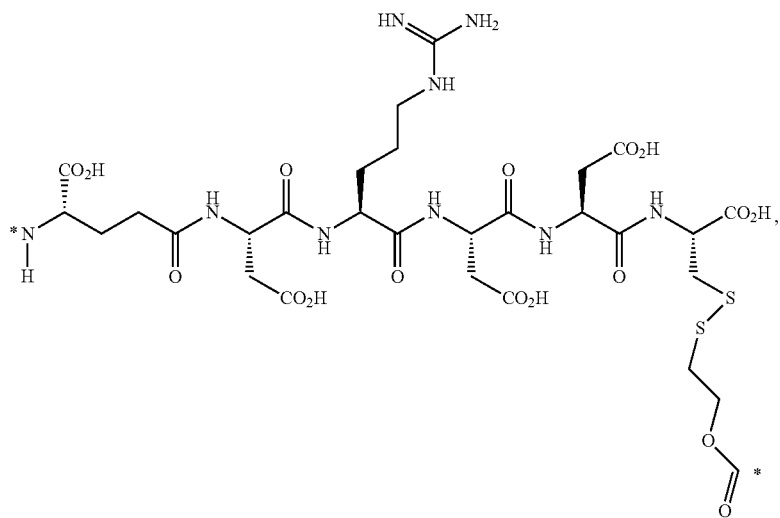 [SMILES: N=C(N)NCCC[C@H](NC(=O)[C@H](CC(=O)O)NC(=O)CC[C@H](N)C(=O)O)C(=O)N[C@@H](CC(=O)O)C(=O)N[C@@H](CC(=O)O)C(=O)N[C@@H](CSSCCOC=O)C(=O)O]
wherein * is a bond.
In some embodiments, the linker is of the formula (SEQ ID NO: 2 is included in the structure below)
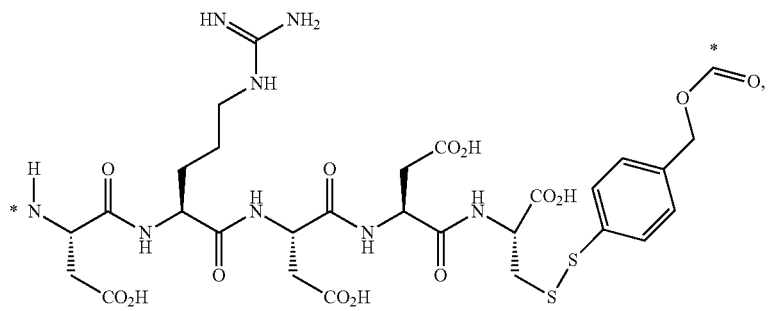 [SMILES: N=C(N)NCCC[C@H](NC(=O)[C@@H](N)CC(=O)O)C(=O)N[C@@H](CC(=O)O)C(=O)N[C@@H](CC(=O)O)C(=O)N[C@@H](CSSc1ccc(COC=O)cc1)C(=O)O]
wherein * is a bond.
In some embodiments, the linker is of the formula (SEQ ID NO: 1 is included in the structure below)
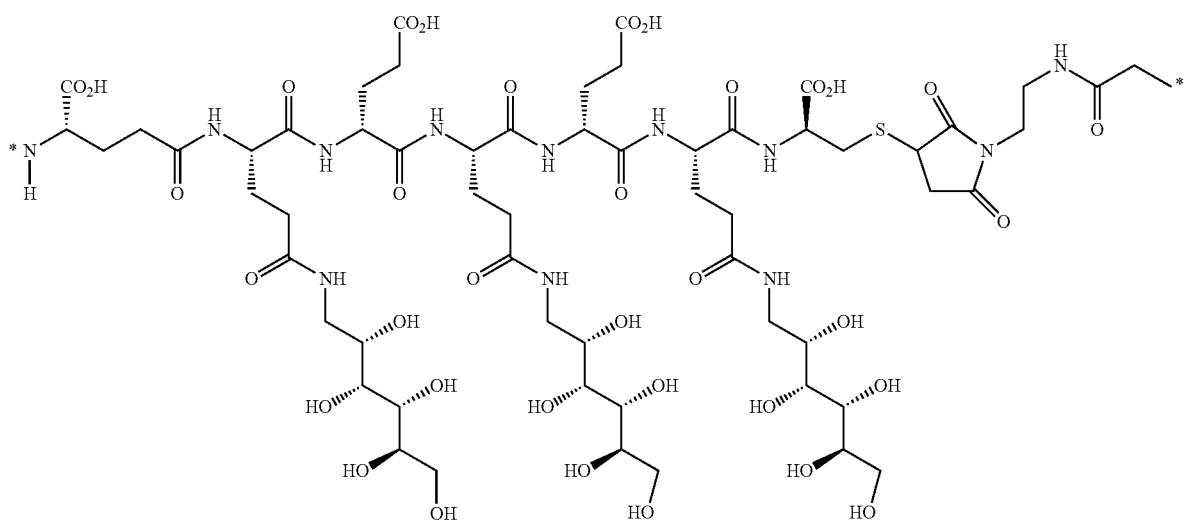 [SMILES: CCC(=O)NCCN1C(=O)CC(SC[C@@H](NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)CC[C@H](N)C(=O)O)C(=O)O)C1=O]
wherein * is a bond.

In some embodiments, the linker is of the formula (SEQ ID NO: 2 is included in the structure below)
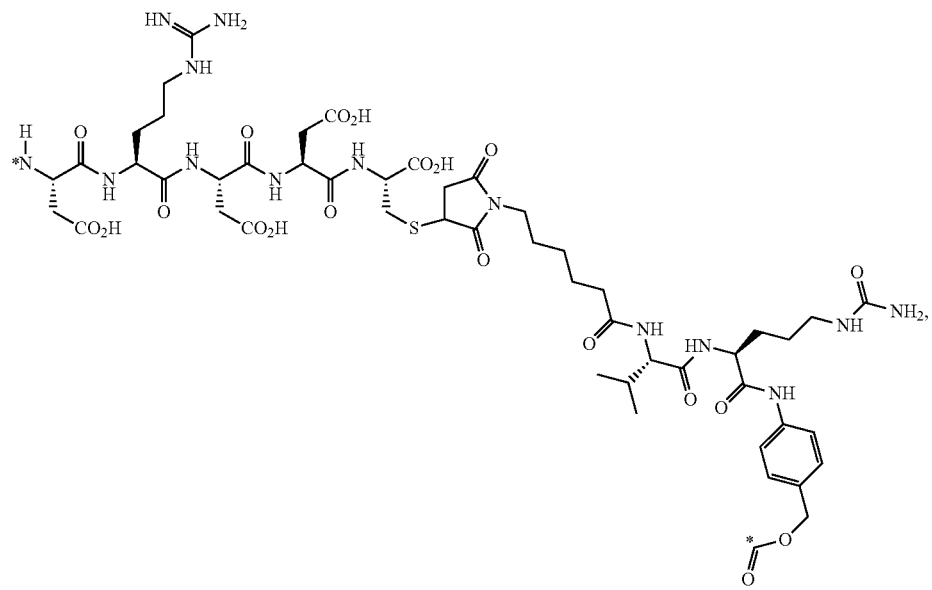 [SMILES: CC(C)[C@H](NC(=O)CCCCCN1C(=O)CC(SC[C@H](NC(=O)[C@H](CC(=O)O)NC(=O)[C@H](CC(=O)O)NC(=O)[C@H](CCCNC(=N)N)NC(=O)[C@@H](N)CC(=O)O)C(=O)O)C1=O)C(=O)N[C@@H](CCCNC(N)=O)C(=O)Nc1ccc(COC=O)cc1]
wherein * is a bond.
In some embodiments, the linker is of the formula (SEQ ID NO: 2 is included in the structure below)
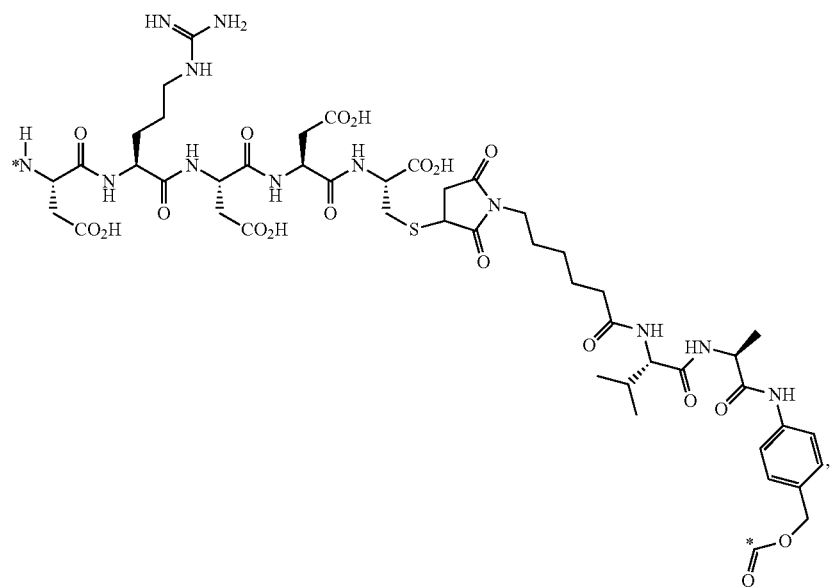 [SMILES: CC(C)[C@H](NC(=O)CCCCCN1C(=O)CC(SC[C@H](NC(=O)[C@H](CC(=O)O)NC(=O)[C@H](CC(=O)O)NC(=O)[C@H](CCCNC(=N)N)NC(=O)[C@@H](N)CC(=O)O)C(=O)O)C1=O)C(=O)N[C@@H](C)C(=O)Nc1ccc(COC=O)cc1]
wherein * is a bond.
In some embodiments, the linker is of the formula (SEQ ID NO: 1 is included in the structure below)

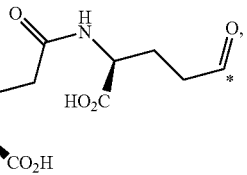

wherein * is a bond.

In the conjugates described herein, Drug describes one or two drugs selected $D^1$ and/or $D^2$, covalently attached to one or more linker portions of the conjugate. In some embodiments, both $D^1$ and $D^2$ are present. In some embodiments, D comprises the structure -$D^1$-$L^5$-$D^2$. In some embodiments, Drug comprises the structure -$D^1$-$L^5$-$D^1$-.

Certain of the drugs $D^1$ and $D^2$ described herein comprise pyrrolobenzodiazepine (PBD) prodrugs. It will be understood that such PBD prodrugs undergo conversion to a therapeutically active PBD compound through processes in the body after delivery of a conjugate as decribed herein. In some embodiments, at least one of the drugs incorporated into conjugates decribed herein is a PBD prodrug as described herein.

$D^1$ can be described as a PBD prodrug of the formula III

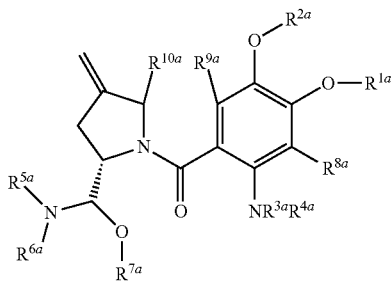

wherein $R^{1a}$, $R^{2a}$, $R^{3a}$ and $R^{4a}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —C(O)$R^{11a}$, —C(O)O$R^{11a}$, and —C(O)NR$^{11a}R^{11a'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —OR$^{11a}$, —OC(O)R$^{11a}$, —OC(O)NR$^{11a}R^{11a'}$, —OS(O)R$^{11a}$, —OS(O)$_2$R$^{11a}$, —SR$^{11a}$, —S(O)R$^{11a}$, —S(O)$_2$R$^{11a}$, —S(O)$_2$NR$^{11a}R^{11a'}$, —OS(O)NR$^{11a}R^{11a'}$, —OS(O)$_2$NR$^{11a}R^{11a'}$, —NR$^{11a}R^{11a'}$, —NR$^{11a}$C(O)R$^{12a}$, —NR$^{11a}$C(O)OR$^{12a}$, —NR$^{11a}$S(O)NR$^{12a}R^{12a'}$, —NR$^{11a}$S(O)R$^{12a}$, —NR$^{11a}$S(O)$_2$R$^{12a}$, —NR$^{11a}$S(O)NR$^{12a}R^{12a'}$, —NR$^{11a}$S(O)$_2$NR$^{12a}R^{12a'}$, —C(O)R$^{11a}$, —C(O)OR$^{11a}$ or —C(O)NR$^{11a}R^{11a'}$; or $R^{1a}$ is a bond; or $R^{4a}$ is a bond;

$R^{5a}$, $R^{6a}$ and $R^{7a}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —C(O)R$^{13a}$, —C(O)OR$^{13a}$ and —C(O)NR$^{13a}R^{13a'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —OR$^{14a}$, —OC(O)R$^{14a}$, —OC(O)NR$^{14a}R^{14a'}$, —OS(O)R$^{14a}$, —OS(O)$_2$R$^{14a}$, —SR$^{14a}$, —S(O)R$^{14a}$, —S(O)$_2$R$^{14a}$, —S(O)NR$^{14a}R^{14a'}$, —S(O)$_2$NR$^{14a}R^{14a'}$, —OS(O)NR$^{14a}R^{14a'}$, —OS(O)$_2$NR$^{14a}R^{14a'}$, —NR$^{14a}R^{14a'}$, —NR$^{14a}$C(O)R$^{15a}$, —NR$^{14a}$C(O)OR$^{15a}$, —NR$^{14a}$C(O)NR$^{15a}R^{15a'}$, —NR$^{14a}$S(O)R$^{15a}$, —NR$^{14a}$S(O)$_2$R$^{15a}$, —NR$^{14a}$S(O)NR$^{15a}R^{15a'}$, —NR$^{14a}$S(O)$_2$NR$^{15a}R^{15a'}$, —C(O)R$^{14a}$, —C(O)OR$^{14a}$ or —C(O)NR$^{14a}R^{14a'}$; wherein $R^{6a}$ and $R^{7a}$ taken together with the atoms to which they are attached optionally combine to form a 3- to 7-membered heterocycloalkyl, or $R^{5a}$ and $R^{6a}$ taken together with the atoms to which they are attached optionally combine to form a 3- to 7-membered heterocycloalkyl or 5- to 7-membered heteroaryl, wherein each hydrogen atom in 3- to 7-membered heterocycloalkyl or 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —OR$^{16a}$, —OC(O)R$^{16a}$, —OC(O)NR$^{16a}R^{16a'}$, —OS(O)R$^{16a}$, —OS(O)$_2$R$^{16a}$, —SR$^{16a}$, —S(O)R$^{16a}$, —S(O)$_2$R$^{16a}$, —S(O)NR$^{16a}R^{16a'}$, —S(O)$_2$NR$^{16a}R^{16a'}$, —OS(O)NR$^{16a}R^{16a'}$, —OS(O)$_2$NR$^{16a}R^{16a'}$, —NR$^{16a}R^{16a'}$, —NR$^{16a}$C(O)R$^{17a}$, —NR$^{16a}$C(O)CH$_2$CH$_2$—, —NR$^{16a}$C(O)OR$^{17a}$, —NR$^{16a}$C(O)

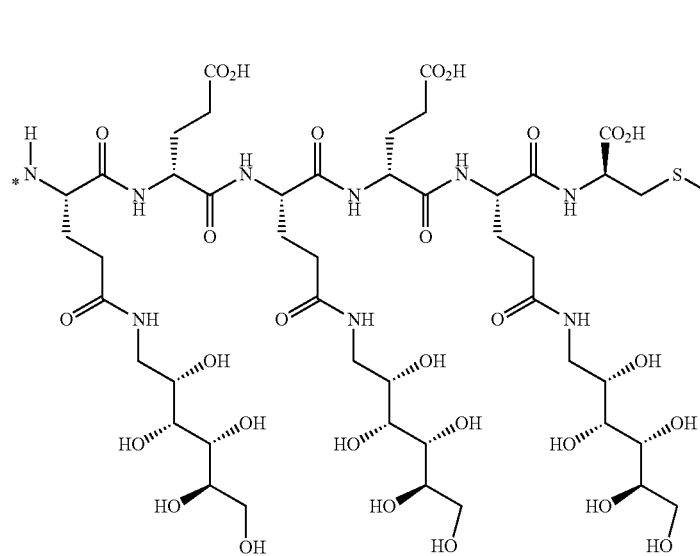

$NR^{17a}R^{17a'}$, —$NR^{16a}S(O)R^{17a}$, —$NR^{16a}S(O)_2R^{17a}$, —$NR^{16a}S(O)NR^{17a}R^{17a'}$, —$NR^{16a}S(O)_2NR^{17a}R^{17a'}$, —$C(O)R^{16a}$, —$C(O)OR_{16a}$ or —$C(O)NR^{16a}R^{16a'}$, and wherein one hydrogen atom in 5- to 7-membered heteroaryl is optionally a bond, or $R^{5a}$ is a bond;

$R^{8a}$ and $R^{9a}$ are each independently selected from the group consisting of H, D, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —CN, —$NO_2$, —NCO, —$OR^{18a}$, —$OC(O)R^{18a}$, —$OC(O)NR^{18a}R^{18a'}$, —$OS(O)R^{18a}$, —$OS(O)_2R^{18a}$, —$SR^{18a}$, —$S(O)R^{18a}$, —$S(O)_2R^{18a}$, —$S(O)NR^{18a}R^{18a'}$, —$S(O)_2NR^{18a}R^{18a'}$, —$OS(O)NR^{18a}R^{18a'}$, —$OS(O)_2NR^{18a}R^{18a'}$, —$NR^{18a}R^{18a'}$, —$NR^{18a}C(O)R^{19a}$, —$NR^{18a}C(O)OR^{19a}$, —$NR^{18a}C(O)NR^{19a}R^{19a'}$, —$NR^{18a}S(O)R^{19a}$, —$NR^{18a}S(O)_2R^{19a}$, —$NR^{18a}S(O)NR^{19a}R^{19a'}$, —$NR^{18a}S(O)_2NR^{19a}R^{19a'}$, —$C(O)R^{18a}$, —$C(O)OR^{18a}$ and —$C(O)NR^{18a}R^{18a'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{20a}$, —$OC(O)R^{20a}$, —$OC(O)NR^{20a}R^{20a'}$, —$OS(O)R^{20a}$, —$OS(O)_2R^{20a}$, —$SR^{20a}$, —$S(O)R^{20a}$, —$S(O)_2R^{20a}$, —$S(O)NR^{20a}R^{20a'}$, —$S(O)_2NR^{20a}R^{20a'}$, —$OS(O)NR^{20a}R^{20a'}$, —$OS(O)_2NR^{20a}R^{20a'}$, —$NR^{20a}R^{20a'}$, —$NR^{20a}C(O)R^{21a}$, —$NR^{20a}C(O)OR^{21a}$, —$NR^{20a}C(O)NR^{21a}R^{21a'}$, —$NR^{20a}S(O)R^{21a}$, —$NR^{20a}S(O)_2R^{21a}$, —$NR^{20a}S(O)NR^{21a}R^{21a'}$, —$NR^{20a}S(O)_2NR^{21a}R^{21a'}$, —$C(O)R^{20a}$, —$C(O)OR^{20a}$ or —$C(O)NR^{20a}R^{20a'}$;

$R^{10a}$ is selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{22a}$, —$OC(O)R^{22a}$, —$OC(O)NR^{22a}R^{22a'}$, —$OS(O)R^{22a}$, —$OS(O)_2R^{22a}$, —$SR^{22a}$, —$S(O)R^{22a}$, —$S(O)_2R^{22a}$, —$S(O)NR^{22a}R^{22a'}$, —$S(O)_2NR^{22a}R^{22a'}$, —$OS(O)NR^{22a}R^{22a'}$, —$OS(O)_2NR^{22a}R^{22a'}$, —$NR^{22a}R^{22a'}$, —$NR^{22a}C(O)R^{23a}$, —$NR^{22a}C(O)OR^{23a}$, —$NR^{22a}C(O)NR^{23a}R^{23a'}$, —$NR^{22a}S(O)R^{23a}$, —$NR^{22a}S(O)_2R^{23a}$, —$NR^{22a}S(O)NR^{23a}R^{23a'}$, —$NR^{22a}S(O)_2NR^{23a}R^{23a'}$, —$C(O)R^{22a}$, —$C(O)OR^{23a}$ and —$C(O)NR^{22a}R^{22a'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{24a}$, —$OC(O)R^{24a}$, —$OC(O)NR^{24a}R^{24a'}$, —$OS(O)R^{24a}$, —$OS(O)_2R^{24a}$, —$SR^{24a}$, —$S(O)R^{24a}$, —$S(O)_2R^{24a}$, —$S(O)NR^{24a}R^{24a'}$, —$S(O)_2NR^{24a}R^{24a'}$, —$OS(O)NR^{24a}R^{24a'}$, —$OS(O)_2NR^{24a}R^{24a'}$, —$NR^{24a}R^{24a'}$, —$NR^{24a}C(O)R^{25a}$, —$NR^{24a}C(O)OR^{25a}$, —$NR^{24a}C(O)NR^{25a}R^{25a'}$, —$NR^{24a}S(O)R^{25a}$, —$NR^{24a}S(O)_2R^{25a}$, —$NR^{24a}S(O)NR^{25a}R^{25a'}$, —$NR^{24a}S(O)_2NR^{25a}R^{25a'}$, —$C(O)R^{24a}$, —$C(O)OR^{24a}$ or —$C(O)NR^{24a}R^{24a'}$; and each $R^{11a}R^{11a'}$, $R^{12a}$, $R^{12a'}$, $R^{13a}$, $R^{13a'}$, $R^{14a}$, $R^{14a'}$, $R^{15a}$, $R^{15a'}$, $R^{16a}$, $R^{16a'}$, $R^{17a}$, $R^{17a'}$, $R^{18a}$, $R^{18a'}$, $R^{19a}$, $R^{19a'}$, $R^{20a}$, $R^{20a'}$, $R^{21a}$, $R^{21a'}$, $R^{22a}$, $R^{22a'}$, $R^{23a}$, $R^{23a'}$, $R^{24a}$, $R^{24a'}$, $R^{25a}$ and $R^{25a'}$ is independently selected from the group consisting of H, D, $C_1$-$C_7$ alkyl, $C_2$-$C_7$ alkenyl, $C_2$-$C_7$ alkynyl, $C_3$-$C_{13}$ cycloalkyl, 3- to 7-membered heterocycloalkyl, $C_6$-$C_{10}$ aryl, and 5- to 7-membered heteroaryl;

provided that at least two of $R^{1a}$, $R^{4a}$ and $R^{5a}$ are a bond, or when $R^{5a}$ and $R^{6a}$ taken together with the atoms to which they are attached optionally combine to form a 3- to 7-membered heterocycloalkyl or 5- to 7-membered heteroaryl, one hydrogen atom in 5- to 7-membered heteroaryl is a bond and one of $R^{1a}$ or $R^{4a}$ is a bond.

In some embodiments, $R^{1a}$ is a bond, and $R^{5a}$ is a bond. In some embodiments, $R^{1a}$ is a bond, and $R^{4a}$ is a bond. In some embodiments, $R^{1a}$ is a bond, and $R^{2a}$ is $C_1$-$C_6$ alkyl. In some embodiments, $R^{1a}$ is a bond, $R^{3a}$ is H, and $R^{4a}$ is H. In some embodiments, $R^{1a}$ is a bond, and $R^{2a}$ is $C_1$-$C_6$ alkyl. In some embodiments, $R^{1a}$ is a bond, $R^{2a}$ is $C_1$-$C_6$ alkyl, $R^{3a}$ is H, and $R^{4a}$ is H. In some embodiments, $R^{1a}$ is a bond, $R^{5a}$ is a bond, and $R^{6a}$ and $R^{7a}$ taken together with the atoms to which they are attached optionally combine to form a 3- to 7-membered heterocycloalkyl. In some embodiments, $R^{1a}$ is a bond, and $R^{5a}$ and $R^{6a}$ taken together with the atoms to which they are attached optionally combine to form a 3- to 7-membered heterocycloalkyl or 5- to 7-membered heteroaryl, wherein one hydrogen atom in 5- to 7-membered heteroaryl is a bond.

In some embodiments, $R^{5a}$, $R^{6a}$ and $R^{7a}$ are each independently selected from the group consisting of H, $C_1$-$C_6$ alkyl, —$C(O)R^{13a}$, —$C(O)OR^{13a}$, wherein each hydrogen atom in $C_1$-$C_6$ alkyl is optionally substituted by —$OC(O)R^{14a}$; wherein $R^{6a}$ and $R^{7a}$ taken together with the atoms to which they are attached optionally combine to form a 3- to 7-membered heterocycloalkyl, or $R^{5a}$ and $R^{6a}$ taken together with the atoms to which they are attached optionally combine to form a 3- to 7-membered heterocycloalkyl or 5- to 7-membered heteroaryl, provided that at least two of $R^{1a}$, $R^{4a}$ and $R^{5a}$ are a bond, or when $R^{5a}$ and $R^{6a}$ taken together with the atoms to which they are attached optionally combine to form a 3- to 7-membered heterocycloalkyl or 5- to 7-membered heteroaryl, one hydrogen atom in 5- to 7-membered heteroaryl is a bond and one of $R^{1a}$ or $R^{4a}$ is a bond; and each $R^{13a}$ and $R^{14a}$ is independently H or $C_1$-$C_7$ alkyl.

In some embodiments, $D^1$ is a PBD prodrug of the formula IIIa

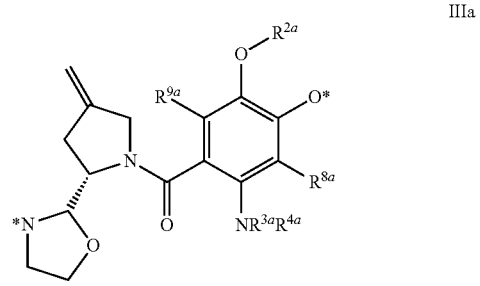

IIIa wherein $R^{2a}$, $R^{3a}$ and $R^{4a}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$C(O)R^{11a}$, —$C(O)OR^{11a}$, and —$C(O)NR^{11a}R^{11a'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, $OC(O)R^{11a}$, —$OC(O)NR^{11a}R^{11a'}$, —$OS(O)R^{11a}$, —$OS(O)_2R^{11a}$, —$SR^{11a}$, —$S(O)R^{11a}$, —$S(O)_2R^{11a}$, —$S(O)NR^{11a}R^{11a'}$, —$S(O)_2NR^{11a}R^{11a'}$, —$OS(O)NR^{11a}R^{11a'}$, —$OS(O)_2NR^{11a}R^{11a'}$, —$NR^{11a}R^{11a'}$, —$NR^{11a}C(O)R^{12a}$, —NR$^{11a}$C(O)OR$^{12a}$, —NR$^{11a}$C(O)NR$^{12a}$R$^{12a'}$, —NR$^{11a}$S(O)R$^{12a}$, —NR$^{11a}$S(O)$_2$R$^{12a}$, —NR$^{11a}$S(O)NR$^{12a}$R$^{12a'}$, —NR$^{11a}$S(O)$_2$NR$^{12a}$R$^{12a'}$, —C(O)R$^{11a}$, —C(O)OR$^{11a}$ or —C(O)NR$^{11a}$R$^{11a'}$;

R$^{8a}$ and R$^{9a}$ are each independently selected from the group consisting of H, D, halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —CN, —NO$_2$, —NCO, —OR$^{18a}$, —OC(O)R$^{18a}$, —OC(O)NR$^{18a}$R$^{18a'}$, —OS(O)R$^{18a}$, —OS(O)$_2$R$^{18a}$, —SR$^{18a}$, —S(O)R$^{18a}$, —S(O)$_2$R$^{18a}$, —S(O)NR$^{18a}$R$^{18a'}$, —S(O)$_2$NR$^{18a}$R$^{18a'}$, —OS(O)NR$^{18a}$R$^{18a'}$, —OS(O)$_2$NR$^{18a}$R$^{18a'}$, —NR$^{18a}$R$^{18a'}$, —NR$^{18a}$C(O)R$^{19a}$, —NR$^{18a}$C(O)OR$^{19a}$, —NR$^{18a}$C(O)NR$^{19a}$R$^{19a'}$, —NR$^{18a}$S(O)R$^{19a}$, —NR$^{18a}$S(O)$_2$R$^{19a}$, —NR$^{18a}$S(O)NR$^{19a}$R$^{19a'}$, —NR$^{18a}$S(O)$_2$NR$^{19a}$R$^{19a'}$, —C(O)R$^{18a}$, —C(O)OR$^{18a}$ and —C(O)NR$^{18a}$R$^{18a'}$, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl is independently optionally substituted by C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{20a}$, —OC(O)R$^{20a}$, —OC(O)NR$^{20a}$R$^{20a'}$, —OS(O)R$^{20a}$, —OS(O)$_2$R$^{20a}$, —SR$^{20a}$, —S(O)R$^{20a}$, —S(O)$_2$R$^{20a}$, —S(O)NR$^{20a}$R$^{20a'}$, —S(O)$_2$NR$^{20a}$R$^{20a'}$, —OS(O)NR$^{20a}$R$^{20a'}$, —OS(O)$_2$NR$^{20a}$R$^{20a'}$, —NR$^{20a}$R$^{20a'}$, —NR$^{20a}$C(O)R$^{21a}$, —NR$^{20a}$C(O)OR$^{21a}$, —NR$^{20a}$C(O)NR$^{21a}$R$^{21a'}$, —NR$^{20a}$S(O)R$^{21a}$, —NR$^{20a}$S(O)$_2$R$^{21a}$, —NR$^{20a}$S(O)NR$^{21a}$R$^{21a'}$, —NR$^{20a}$S(O)$_2$NR$^{21a}$R$^{21a'}$, —C(O)R$^{20a}$, —C(O)OR$^{20a}$ or —C(O)NR$^{20a}$R$^{20a'}$;

each R$^{11a}$, R$^{11a'}$, R$^{12a}$, R$^{12a'}$, R$^{18a}$, R$^{18a'}$, R$^{19a}$, R$^{19a'}$, R$^{20a}$, R$^{20a'}$, R$^{21a}$ and R$^{21a'}$ is independently selected from the group consisting of H, D, C$_1$-C$_7$ alkyl, C$_2$-C$_7$ alkenyl, C$_2$-C$_7$ alkynyl, C$_3$-C$_{13}$ cycloalkyl, 3- to 7-membered heterocycloalkyl, C$_6$-C$_{10}$ aryl, and 5- to 7-membered heteroaryl; and

* is a bond. In some embodiments, R$^{2a}$, R$^{3a}$ and R$^{4a}$ are each independently H or C$_1$-C$_6$ alkyl; R$^{8a}$ and R$^{9a}$ are each H, and * is a bond.

In some embodiments, D$^1$ is a PBD prodrug of the formula IIIb

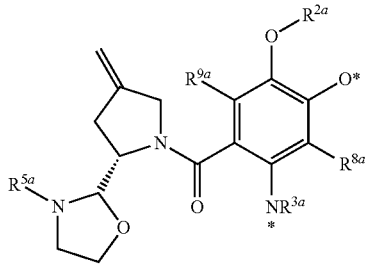

IIIb wherein

R$^{2a}$ and R$^{3a}$ are each independently selected from the group consisting of H, D, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —C(O)R$^{11a}$, —C(O)OR$^{11a}$, and —C(O)NR$^{11a}$R$^{11a'}$, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl is independently optionally substituted by C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{11a}$, —OC(O)R$^{11a}$, —OC(O)NR$^{11a}$R$^{11a'}$, —OS(O)R$^{11a}$, —OS(O)$_2$R$^{11a}$, —SR$^{11a}$, —S(O)R$^{11a}$, —S(O)$_2$R$^{11a}$, —S(O)NR$^{11a}$R$^{11a'}$, —S(O)$_2$NR$^{11a}$R$^{11a'}$, —OS(O)NR$^{11a}$R$^{11a'}$, —OS(O)$_2$NR$^{11a}$R$^{11a'}$, —NR$^{11a}$R$^{11a'}$, —NR$^{11a}$C(O)R$^{12a}$, —NR$^{11a}$C(O)OR$^{12a}$, —NR$^{11a}$C(O)NR$^{12a}$R$^{12a'}$, —NR$^{11a}$S(O)R$^{12a}$, —NR$^{11a}$S(O)$_2$R$^{12a}$, —NR$^{11a}$S(O)NR$^{12a}$R$^{12a'}$, —NR$^{11a}$S(O)$_2$NR$^{12a}$R$^{12a'}$, —C(O)R$^{11a}$, —C(O)OR$^{11a}$ or —C(O)NR$^{11a}$R$^{11a'}$;

R$^{5a}$ is selected from the group consisting of H, D, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —C(O)R$^{13a}$, —C(O)OR$^{13a}$ and —C(O)NR$^{13a}$R$^{13a'}$, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl is optionally substituted by C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{14a}$, —OC(O)R$^{14a}$, —OC(O)NR$^{14a}$R$^{14a'}$, —OS(O)R$^{14a}$, —OS(O)$_2$R$^{14a}$, —SR$^{14a}$, —S(O)R$^{14a}$, —S(O)$_2$R$^{14a}$, —S(O)NR$^{14a}$R$^{14a'}$, —S(O)$_2$NR$^{14a}$R$^{14a'}$, —OS(O)NR$^{14a}$R$^{14a'}$, —OS(O)$_2$NR$^{14a}$R$^{14a'}$, —NR$^{14a}$R$^{14a'}$, —NR$^{14a}$C(O)R$^{15a}$, —NR$^{14a}$C(O)OR$^{15a}$, —NR$^{14a}$C(O)NR$^{15a}$R$^{15a'}$, —NR$^{14a}$S(O)R$^{15a}$, —NR$^{14a}$S(O)$_2$R$^{15a}$, —NR$^{14a}$S(O)NR$^{15a}$R$^{15a'}$, —NR$^{14a}$S(O)$_2$NR$^{15a}$R$^{15a'}$, —C(O)R$^{14a}$, —C(O)OR$^{14a}$ or —C(O)NR$^{14a}$R$^{14a'}$;

R$^{8a}$ and R$^{9a}$ are each independently selected from the group consisting of H, D, halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —CN, —NO$_2$, —NCO, —OR$^{18a}$, —OC(O)R$^{18a}$, —OC(O)NR$^{18a}$R$^{18a'}$, —OS(O)R$^{18a}$, —OS(O)$_2$R$^{18a}$, —SR$^{18a}$, —S(O)R$^{18a}$, —S(O)$_2$R$^{18a}$, —S(O)NR$^{18a}$R$^{18a'}$, —S(O)$_2$NR$^{18a}$R$^{18a'}$, —OS(O)NR$^{18a}$R$^{18a'}$, —OS(O)$_2$NR$^{18a}$R$^{18a'}$, —NR$^{18a}$R$^{18a'}$, —NR$^{18a}$C(O)R$^{19a}$, —NR$^{18a}$C(O)OR$^{19a}$, —NR$^{18a}$C(O)NR$^{19a}$R$^{19a'}$, —NR$^{18a}$S(O)R$^{19a}$, —NR$^{18a}$S(O)$_2$R$^{19a}$, —NR$^{18a}$S(O)NR$^{19a}$R$^{19a'}$, —NR$_{18a}$S(O)$_2$NR$^{19a}$R$^{19a'}$, —C(O)R$^{18a}$, —C(O)OR$^{18a}$ and —C(O)NR$^{18a}$R$^{18a'}$, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl is independently optionally substituted by C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{20a}$, —OC(O)R$^{20a}$, —OC(O)NR$^{20a}$R$^{20a'}$, —OS(O)R$^{20a}$, —OS(O)$_2$R$^{20a}$, —SR$^{20a}$, —S(O)R$^{20a}$, —S(O)$_2$R$^{20a}$, —S(O)NR$^{20a}$R$^{20a'}$, —S(O)$_2$NR$^{20a}$R$^{20a'}$, —OS(O)NR$^{20a}$R$^{20a'}$, —OS(O)$_2$NR$^{20a}$R$^{20a'}$, —NR$^{20a}$R$^{20a'}$, —NR$^{20a}$C(O)R$^{21a}$, —NR$^{20a}$C(O)OR$^{21a}$, —NR$^{20a}$C(O)NR$^{21a}$R$^{21a'}$, —NR$^{20a}$S(O)R$^{21a}$, —NR$^{20a}$S(O)$_2$R$^{21a}$, —NR$^{20a}$S(O)NR$^{21a}$R$^{21a'}$, —NR$^{20a}$S(O)$_2$NR$^{21a}$R$^{21a'}$, —C(O)R$^{20a}$, —C(O)OR$^{20a}$ or —C(O)NR$^{20a}$R$^{20a'}$;

each R$^{11a}$R$^{11a'}$, R$^{12a}$, R$^{12a'}$, R$^{13a}$, R$^{13a'}$, R$^{14a}$, R$^{14a'}$, R$^{15a}$, R$^{15a'}$, R$^{18a}$, R$^{18a'}$, R$^{19a}$, R$^{19a'}$, R$^{20a}$, R$^{20a'}$, R$^{21a}$ and R$^{21a'}$ is independently selected from the group consisting of H, D, C$_1$-C$_7$ alkyl, C$_2$-C$_7$ alkenyl, C$_2$-C$_7$alkynyl, C$_3$-C$_{13}$ cycloalkyl, 3- to 7-membered heterocycloalkyl, C$_6$-C$_{10}$ aryl, and 5- to 7-membered heteroaryl; and * is a bond. In some embodiments, R$^{2a}$ and R$^{3a}$ are each independently H or C$_1$-C$_6$ alkyl; R$^{5a}$ is selected from the group consisting of H, C$_1$-C$_6$ alkyl, —C(O)R$^{13a}$, and —C(O)OR$^{13a}$, wherein each hydrogen atom in C$_1$-C$_6$ alkyl is optionally substituted by C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{14a}$, —OC(O)R$^{14a}$, R$^{13a}$ and R$^{14a}$ are each independently selected from the group consisting of H, D, C$_1$-C$_7$ alkyl, C$_2$-C$_7$ alkenyl, C$_2$-C$_7$alkynyl, $C_3$-$C_{13}$ cycloalkyl, 3- to 7-membered heterocycloalkyl, $C_6$-$C_{10}$ aryl, and 5- to 7-membered heteroaryl; $R^{8a}$ and $R^{9a}$ are each H, and * is a bond.

In some embodiments, $D^1$ is a PBD prodrug of the formula IIIc

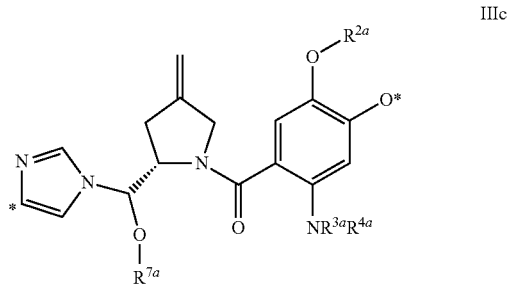

IIIc wherein $R^{2a}$, $R^{3a}$ and $R^{4a}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —C(O)$R^{11a}$, —C(O)O$R^{11a}$, and —C(O)N$R^{11a}R^{11a'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{11a}$, —OC(O)$R^{11a}$, —OC(O)N$R^{11a}R^{11a'}$, —OS(O)$R^{11a}$, —OS(O)$_2R^{11a}$, —S$R^{11a}$, —S(O)$R^{11a}$, —S(O)$_2R^{11a}$, —S(O)N$R^{11a}R^{11a'}$, —S(O)$_2$N$R^{11a}R^{11a'}$, —OS(O)N$R^{11a}R^{11a'}$, —OS(O)$_2$N$R^{11a}R^{11a'}$, —N$R^{11a}R^{11a'}$, —N$R^{11a}$C(O)$R^{12a}$, —N$R^{11a}$C(O)O$R^{12a}$, —N$R^{11a}$C(O)N$R^{12a}R^{12a'}$, —N$R^{11a}$S(O)$R^{12a}$, —N$R^{11a}$S(O)$_2R^{12a}$, —N$R^{11a}$S(O)N$R^{12a}R^{12a'}$, —N$R^{11a}$S(O)$_2$N$R^{12a}R^{12a'}$, —C(O)$R^{11a}$, —C(O)O$R^{11a}$ or —C(O)N$R^{11a}R^{11a'}$;

$R^{7a}$ is selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —C(O)$R^{13a}$, —C(O)O$R^{13a}$ and —C(O)N$R^{13a}R^{13a'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{14a}$, —OC(O)$R^{14a}$, —OC(O)N$R^{14a}R^{14a'}$, —OS(O)$R^{14a}$, —OS(O)$_2R^{14a}$, —S$R^{14a}$, —S(O)$R^{14a}$, —S(O)$_2R^{14a}$, —S(O)N$R^{14a}R^{14a'}$, —S(O)$_2$N$R^{14a}R^{14a'}$, —OS(O)N$R^{14a}R^{14a'}$, —OS(O)$_2$N$R^{14a}R^{14a'}$, —N$R^{14a}R^{14a'}$, —N$R^{14a}$C(O)$R^{15a}$, —N$R^{14a}$C(O)O$R^{15a}$, —N$R^{14a}$C(O)N$R^{15a}R^{15a'}$, —N$R^{14a}$S(O)$R^{15a}$, —N$R^{14a}$S(O)$_2R^{15a}$, —N$R^{14a}$S(O)N$R^{15a}R^{15a'}$, —N$R^{14a}$S(O)$_2$N$R^{15a}R^{15a'}$, —C(O)$R^{14a}$, —C(O)O$R^{14a}$ or —C(O)N$R^{14a}R^{14a'}$;

each $R^{11a}$, $R^{11a'}$, $R^{12a}$, $R^{12a'}$, $R^{13a}$, $R^{13a'}$, $R^{14a}$, $R^{14a'}$, $R^{15a}$, $R^{15a'}$, $R^{18a}$, $R^{18a'}$, $R^{19a}$, $R^{19a'}$, $R^{20a}$, $R^{20a'}$, $R^{21a}$ and $R^{21a'}$ is independently selected from the group consisting of H, D, $C_1$-$C_7$ alkyl, $C_2$-$C_7$ alkenyl, $C_2$-$C_7$alkynyl, $C_3$-$C_{13}$ cycloalkyl, 3- to 7-membered heterocycloalkyl, $C_6$-$C_{10}$ aryl, and 5- to 7-membered heteroaryl; and * is a bond. In some embodiments, $R^{2a}$, $R^{3a}$ and $R^{4a}$ are each independently H or $C_1$-$C_6$ alkyl; $R^{7a}$ is H or $C_1$-$C_6$ alkyl; $R^{8a}$ and $R^{9a}$ are each H, and * is a bond.

Where, for example, $D^1$ is a PBD prodrug as described herein, $D^2$ can be any other drug useful for eliciting a desired biological effect. It will be understood that the identity of $D^2$ is not particularly limited, and a variety of drugs known in the art can be used in connection with the conjugates described herein as $D^2$. In certain embodiments, $D^2$ can be a DNA binding agent. In certain embodiments, $D^2$ can be a DNA alkylating agent. It will be understood that DNA binding agents and DNA alkylating agents are well known in the art and the identity of such DNA binding agents and DNA alkylating agents is not limited. In some embodiments, $D^2$ can be a DNA minor groove binding drug.

In some embodiments, $D^2$ is selected from the group consisting of

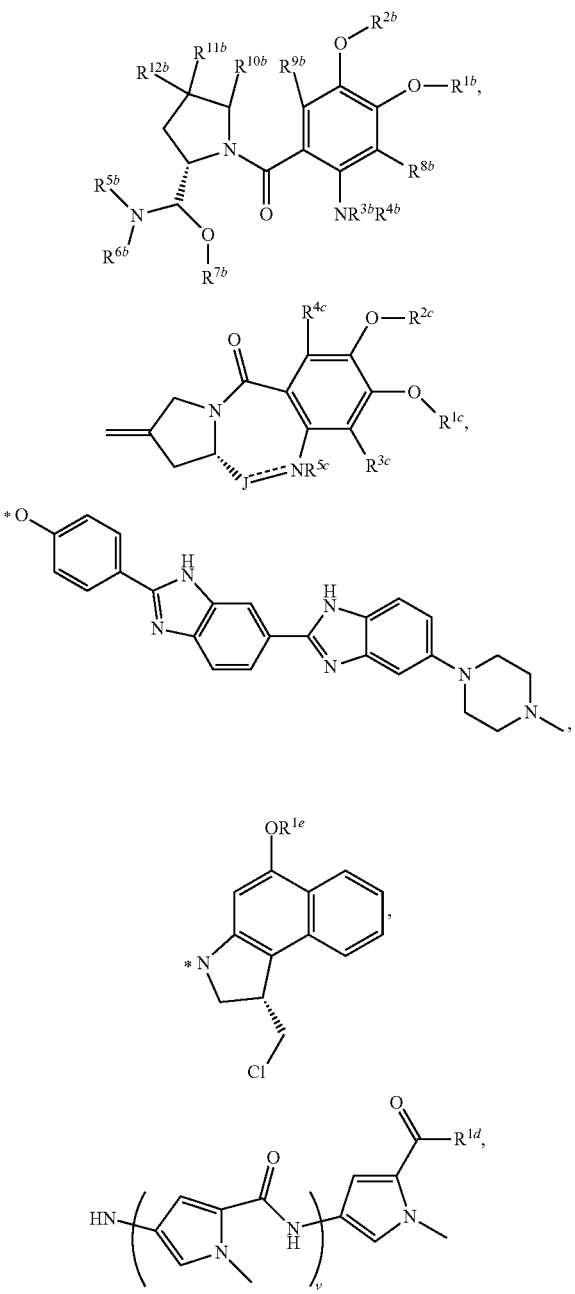

-continued

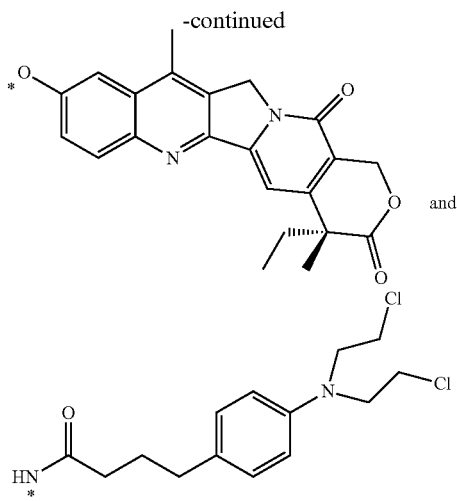

and wherein $R^{1b}$, $R^{2b}$, $R^{3b}$ and $R^{4b}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —C(O)$R^{13b}$, —C(O)O$R^{13b}$, and —C(O)N$R^{13b}R^{13b'}$ wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{13b}$, —OC(O)$R^{13b}$, —OC(O)N$R^{13b}R^{13b'}$, —OS(O)$R^{13b}$, —OS(O)$_2R^{13b}$, —S$R^{13b}$, —S(O)$R^{13b}$, —S(O)$_2R^{13b}$, —S(O)N$R^{13b}R^{13b'}$, —S(O)$_2$N$R^{13b}R^{13b'}$, —OS(O)N$R^{13b}R^{13b'}$, —OS(O)$_2$N$R^{13b}R^{13b'}$, —N$R^{13b}R^{13b'}$, —N$R^{13b}$C(O)$R^{14b}$, —N$R^{13b}$C(O)O$R^{14b}$, —N$R^{13b}$C(O)N$R^{14b}R^{14b'}$, —N$R^{13b}$S(O)$R^{14b}$, —N$R^{13b}$S(O)$_2R^{14b}$, —N$R^{13b}$S(O)N$R^{14b}R^{14b'}$, —N$R^{13b}$S(O)$_2$N$R^{14b}R^{14b'}$, C(O)$R^{13b}$, —C(O)O$R^{13b}$ or —C(O)N$R^{13b}R^{13b'}$; or any one of $R^{1b}$, $R^{2b}$, $R^{3b}$ and $R^{4b}$ is a bond;

$R^{5b}$, $R^{6b}$ and $R^{7b}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —C(O)$R^{15b}$, —C(O)O$R^{15b}$, and —C(O)N$R^{15b}R^{15b'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, -$L^4$H, -$L^3$H, —O$R^{15b}$, —OC(O)$R^{15b}$, —OC(O)N$R^{15b}R^{15b'}$, —OS(O)$R^{15b}$, —OS(O)$_2R^{15b}$, —S$R^{15b}$, —S(O)$R^{15b}$, —S(O)$_2R^{15b}$, —S(O)N$R^{15b}R^{15'}$, —S(O)$_2$N$R^{15b}R^{15'}$, —OS(O)N$R^{15b}R^{15b'}$, —OS(O)$_2$N$R^{15b}R^{15b'}$, —N$R^{15b}R^{15b}$; —N$R^{15b}$C(O)$R^{16b}$, —N$R^{15b}$C(O)O$R^{16b}$, —N$R^{15b}$C(O)N$R^{16b}R^{16b'}$, —N$R^{15b}$S(O)$R^{16b}$, —N$R^{15b}$S(O)$_2R^{16b}$, —N$R^{15b}$S(O)N$R^{16b}R^{16b'}$, —N$R^{15b}$S(O)$_2$N$R^{16b}R^{16b'}$, —C(O)$R^{15b}$, —C(O)O$R^{15b}$ or —C(O)N$R^{15b}R^{15b'}$; wherein $R^{6b}$ and $R^{7b}$ taken together with the atoms to which they are attached optionally combine to form a 3- to 7-membered heterocycloalkyl, or $R^{5b}$ and $R^{6b}$ taken together with the atoms to which they are attached optionally combine to form a 3- to 7-membered heterocycloalkyl or 5- to 7-membered heteroaryl, wherein each hydrogen atom in 3- to 7-membered heterocycloalkyl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{17b}$, —OC(O)$R^{17b}$, —OC(O)N$R^{17b}R^{17b'}$, —OS(O)$R^{17b}$, —OS(O)$_2R^{17b}$, —S$R^{17b}$, —S(O)$R^{17b}$, —S(O)$_2R^{17b}$, —S(O)N$R^{17b}R^{17b'}$, —S(O)$_2$N$R^{17b}R^{17b'}$, —OS(O)N$R^{17b}R^{17b'}$, —OS(O)$_2$N$R^{17b}R^{17b'}$, —N$R^{17b}R^{17b'}$, —N$R^{17b}$C(O)$R^{18b}$, —N$R^{17b}$C(O)O$R^{18b}$, —N$R^{17b}$C(O)N$R^{18b}R^{18b'}$, —N$R^{17b}$S(O)$R^{18b}$, —N$R^{17b}$S(O)$_2R^{18b}$, —N$R^{17b}$S(O)N$R^{18b}R^{18b'}$, —N$R^{17b}$S(O)$_2$N$R^{18b}R^{18b'}$, —C(O)$R^{17b}$, —C(O)O$R^{17b}$ or —C(O)N$R^{17b}R^{17b'}$; or any one of $R^{5b}$, $R^{6b}$ or $R^{7b}$ is a bond;

$R^{8b}$ and $R^{9b}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —CN, —NO$_2$, —NCO, —O$R^{19b}$, —OC(O)$R^{19b}$, —OC(O)N$R^{19b}R^{19b'}$, —OS(O)$R^{19b}$, —OS(O)$_2R^{19b}$, —S$R^{19b}$, —S(O)$R^{19b}$, —S(O)$_2R^{19b}$, —S(O)N$R^{19b}R^{19b'}$, —S(O)$_2$N$R^{19b}R^{19b'}$, —OS(O)N$R^{19b}R^{19b'}$, —OS(O)$_2$N$R^{19b}R^{19b'}$, —N$R^{19b}R^{19b'}$, —N$R^{19b}$C(O)$R^{20b}$, —N$R^{19b}$C(O)O$R^{20b}$, —N$R^{19b}$C(O)N$R^{20b}R^{20b'}$, —N$R^{19b}$S(O)$R^{20b}$, —N$R^{19b}$S(O)$_2R^{20b}$, —N$R^{19b}$S(O)N$R^{20b}R^{20b'}$, —N$R^{19b}$S(O)$_2$N$R^{20b}R^{20b'}$, —C(O)$R^{19b}$, —C(O)O$R^{19b}$ and —C(O)N$R^{19b}R^{19b'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{21b}$, —OC(O)$R^{21b}$, —OC(O)N$R^{21b}R^{21b'}$, —OS(O)$R^{21b}$, —OS(O)$_2R^{21b}$, —S$R^{21b}$, —S(O)$R^{21b}$, —S(O)$_{21b}R^{21b'}$, —S(O)$_2$N$R^{21b}R^{21b'}$, —OS(O)N$R^{21b}R^{21b'}$, —OS(O)$_2$N$R^{21b}R^{21b'}$, —N$R^{21b}R^{21b'}$, —N$R^{21b}$C(O)$R^{22b}$, —N$R^{21b}$C(O)O$R^{22b}$, —N$R^{21b}$C(O)N$R^{22b}R^{22b'}$, —N$R^{21b}$S(O)$R^{22b}$, —N$R^{21b}$S(O)$_2R^{22b}$, —N$R^{21b}$S(O)N$R^{22b}R^{22b'}$, —N$R^{21b}$S(O)$_2$N$R^{22b}R^{22b'}$, —C(O)$R^{21b}$, —C(O)O$R^{21b}$ or —C(O)N$R^{21b}R^{21b'}$;

$R^{10b}$, $R^{11b}$ and $R^{12b}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{23b}$, —OC(O)$R^{23b}$, —OC(O)N$R^{23b}R^{23b'}$, —OS(O)$R^{23b}$, —OS(O)$_2R^{23b}$, —S$R^{23b}$, —S(O)$R^{23b}$, —S(O)$_2R^{23b}$, —S(O)N$R^{23b}R^{23b'}$, —S(O)$_2$N$R^{23b}R^{23b'}$, —OS(O)N$R^{23b}R^{23b'}$, —OS(O)$_2$N$R^{23b}R^{23b'}$, —N$R^{23b}R^{23b'}$, —N$R^{23b}$C(O)$R^{24b}$, —N$R^{23b}$C(O)O$R^{24b}$, —N$R^{23b}$C(O)N$R^{24b}R^{24b'}$, —N$R^{23b}$S(O)$R^{24b}$, —N$R^{23b}$S(O)$_2R^{24b}$, —N$R^{23b}$S(O)N$R^{24b}R^{24b'}$, —N$R^{23b}$S(O)$_2$N$R^{24b}R^{24b'}$, —C(O)$R^{23b}$, —C(O)O$R^{23b}$ and —C(O)N$R^{23b}R^{23b'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{25b}$, —OC(O)$R^{25b}$, —OC(O)N$R^{25b}R^{25b'}$, —OS(O)$R^{25b}$, —OS(O)$_2R^{25b}$, —S$R^{25b}$, —S(O)$R^{25b}$, —S(O)$_2R^{25b}$, —S(O)N$R^{25b}R^{25b'}$, —S(O)$_2$N$R^{25b}R^{25b'}$, —OS(O)N$R^{25b}R^{25b'}$, —OS(O)$_2$N$R^{25b}R^{25b'}$, —N$R^{25b}R^{25b'}$, —N$R^{25b}$C(O)$R^{26b}$, —N$R^{25b}$C(O)O$R^{26b}$, —N$R^{25b}$C(O)N$R^{26b}R^{26b'}$, —N$R^{25b}$S(O)$R^{26b}$, —N$R^{25b}$S(O)$_2R^{26b}$, —N$R^{25b}$S(O)N$R^{26b}R^{26b'}$, —N$R^{25b}$S(O)$_2$N$R^{26b}R^{26b'}$, —C(O)$R^{25b}$, —C(O)O$R^{25b}$ or —C(O)N$R^{25b}R^{25b'}$, or $R^{10b}$ and $R^{11b}$ taken together with the carbon atoms to which they are attached optionally combine to form a $C_6$-$C_{10}$ aryl, or $R^{11b}$ and $R^{12b}$ taken together with the carbon atom to which they are attached optionally combine to form an exomethylene; or $R^{12b}$ is absent;

each $R^{13b}$, $R^{13b'}$, $R^{14b}$, $R^{14b'}$, $R^{15b}$, $R^{15b'}$, $R^{16b}$, $R^{16b'}$, $R^{17b}$, $R^{17b'}$, $R^{18b}$, $R^{18b'}$, $R^{19b}$, $R^{19b'}$, $R^{20b}$, $R^{20b'}$, $R^{21b}$, $R^{21b'}$, $R^{22b}$, $R^{22b'}$, $R^{23b}$, $R^{23b'}$, $R^{24b}$, $R^{24b'}$, $R^{25b}$, $R^{25b'}$, $R^{26b}$ and $R^{26b'}$ is independently selected from the group consisting of H, D, $C_1$-$C_7$ alkyl, $C_2$-$C_7$ alkenyl, $C_2$-$C_7$ alkynyl, $C_3$-$C_{13}$ cycloalkyl, 3- to 7-membered heterocycloalkyl, $C_6$-$C_{10}$ aryl, $C_1$-$C_6$ alkyl($C_6$-$C_{10}$ aryl) and 5- to 7-membered heteroaryl, wherein each hydrogen atom in $C_6$-$C_{10}$ aryl, $C_1$-$C_6$ alkyl ($C_6$-$C_{10}$ aryl) and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —CN, —NO$_2$, —NCO, —OH, —SH, —NH$_2$, —SO$_3$H, —C(O)OH and —C(O)NH$_2$;

provided that one of $R^{1b}$, $R^{2b}$, $R^{3b}$, $R^{4b}$, $R^{5b}$, $R^{6b}$ is a bond;

$R^{1c}$, $R^{2c}$ and $R^{5c}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —C(O)$R^{6c}$, —C(O)O$R^{6c}$ and —C(O)N$R^{6c}R^{6c'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{7c}$, —OC(O)$R^{7c}$, —OC(O)N$R^{7c}R^{7c'}$, —OS(O)$R^{7c}$, —OS(O)$_2R^{7c}$, —S$R^{7c}$, —S(O)$R^{7c}$, —S(O)$_2R^{7c}$, —S(O)$_2$O$R^{7c}$, —S(O)N$R^{7c}R^{7c'}$, —S(O)$_2$N$R^{7c}R^{7c'}$, —OS(O)N$R^{7c}R^{7c'}$, —OS(O)$_2$N$R^{7c}R^{7c'}$, —N$R^{7c}R^{7c'}$, —N$R^{7c}$C(O)$R^{8c}$, —N$R^{7c}$C(O)O$R^{8c}$, —N$R^{7c}$C(O)N$R^{8c}R^{8c'}$, —N$R^{7c}$S(O)$R^{8c}$, —N$R^{7c}$S(O)$_2R^{8c}$, —N$R^{7c}$S(O)N$R^{8c}R^{8c'}$, —N$R^{7c}$S(O)$_2$N$R^{8c}R^{8c'}$, —C(O)$R^{7c}$, —C(O)O$R^{7c}$ or —C(O)N$R^{7c}R^{7c'}$; or when J is —C$R^{13c}$═, $R^{5c}$ is absent; provided that one of $R^{1c}$ or $R^{2c}$ is a bond;

$R^{3c}$ and $R^{4c}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —CN, —NO$_2$, —NCO, —O$R^{9c}$, —OC(O)$R^{9c}$, —OC(O)N$R^{9c}R^{9c'}$, —OS(O)$R^{9c}$, —OS(O)$_2R^{9c}$, —S$R^{9c}$, —S(O)$R^{9c}$, —S(O)$_2R^{9c}$, —S(O)N$R^{9c}R^{9c'}$, —S(O)$_2$N$R^{9c}R^{9c'}$, —OS(O)N$R^{9c}R^{9c'}$, —OS(O)$_2$N$R^{9c}R^{9c'}$, —N$R^{9c}R^{9c'}$, —N$R^{9c}$C(O)$R^{10c}$, —N$R^{9c}$C(O)O$R^{10c}$, —N$R^{9c}$C(O)N$R^{10c}R^{10c'}$, —N$R^{9c}$S(O)$R^{10c}$, —N$R^{9c}$S(O)$_2R^{10c}$, —N$R^{9c}$S(O)N$R^{10c}R^{10c'}$, —N$R^{9c}$S(O)$_2$N$R^{10c}R^{10c'}$, —C(O)$R^{9c}$, —C(O)O$R^{9c}$ and —C(O)N$R^{9c}R^{9c'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{11c}$, —OC(O)$R^{11c}$, —OC(O)N$R^{11c}R^{11c'}$, —OS(O)$R^{11c}$, —OS(O)$_2R^{11c}$, —S$R^{11c}$, —S(O)$R^{11c}$, —S(O)$_2R^{11c}$, —S(O)N$R^{11c}R^{11c'}$, —S(O)$_2$N$R^{11c}R^{11c'}$, —OS(O)N$R^{11c}R^{11c'}$, —OS(O)$_2$N$R^{11c}R^{11c'}$, —N$R^{11c}R^{11c'}$, —N$R^{11c}$C(O)$R^{12c}$, —N$R^{11c}$C(O)O$R^{12c}$, —N$R^{11c}$C(O)N$R^{12c}R^{12c'}$, —N$R^{11c}$S(O)$R^{12c}$, —N$R^{11c}$S(O)$_2R^{12c}$, —N$R^{11c}$S(O)N$R^{12c}R^{12c'}$, —N$R^{11c}$S(O)$_2$N$R^{12c}R^{12c'}$, —C(O)$R^{11c}$, —C(O)O$R^{11c}$ or —C(O)N$R^{11c}R^{11c'}$;

J is —C(O)—, —C$R^{13c}$═ or —(C$R^{13c}R^{13c'}$)— each $R^{6c}$, $R^{6c'}$, $R^{7c}$, $R^{7c'}$, $R^{8c}$, $R^{8c'}$, $R^{9c}$, $R^{9c'}$, $R^{10c}$, $R^{10c'}$, $R^{11c}$, $R^{11c'}$, $R^{12c}$, $R^{12c'}$, $R^{13c}$ and $R^{13c'}$ is independently selected from the group consisting of H, D, $C_1$-$C_7$ alkyl, $C_2$-$C_7$ alkenyl, $C_2$-$C_7$alkynyl, $C_3$-$C_6$ cycloalkyl, 3- to 7-membered heterocycloalkyl, $C_6$-$C_{10}$ aryl and 5- to 7-membered heteroaryl;

$R^{1d}$ is selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{2d}$, —S$R^{2d}$ and —N$R^{2d}R^{2d'}$;

$R^{2d}$ and $R^{2d'}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is optionally substituted by —O$R^{3d}$, —S$R^{3d}$, and —N$R^{3d}R^{3d'}$;

$R^{3d}$ and $R^{3d'}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl;

$R^{1e}$ is selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{2e}$, —OC(O)$R^{2e}$, —OC(O)N$R^{2e}R^{2e'}$, —OS(O)$R^{2e}$, —OS(O)$_2R^{2e}$, —S$R^{2e}$, —S(O)$R^{2e}$, —S(O)$_2R^{2e}$, —S(O)N$R^{2e}R^{2e'}$, —S(O)$_2$N$R^{2e}R^{2e'}$, —OS(O) N$R^{2e}R^{2e'}$, —OS(O)$_2$N$R^{2e}R^{2e'}$, —N$R^{2e}R^{2e'}$, —N$R^{2e}$C(O) $R^{3e}$, —N$R^{2e}$C(O)O$R^{3e}$, —N$R^{2e}$C(O)N$R^{3e}R^{3e'}$, —N$R^{2e}$S(O) $R^{3e}$, —N$R^{2e}$S(O)$_2R^{3e}$, —N$R^{2e}$S(O)N$R^{2e}R^{2e'}$, —N$R^{2e}$S(O)$_2$N$R^{3e}R^{3e'}$, —C(O)$R^{2e}$, —C(O)O$R^{2e}$ or —C(O)N$R^{2e}R^{2e'}$;

each $R^{2e}$, $R^{2e'}$, $R^{3e}$ and $R^{3e'}$ is independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is optionally substituted by O$R^{4e}$, —S$R^{4e}$ or —N$R^{4e}R^{4e'}$;

$R^{4e}$ and $R^{4e'}$ are independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl;

v is 1, 2 or 3; and

* is a covalent bond.

In some embodiments, Drug can be described by the general formula -$D^1$-$L^5$-$D^2$. In some embodiments, Drug can be described by the formula

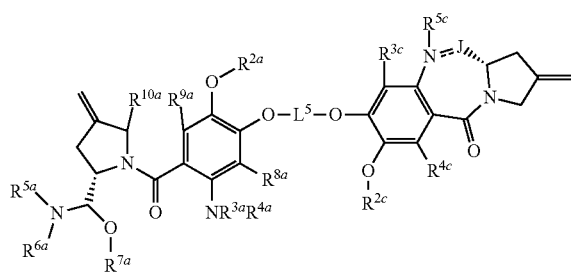

wherein, $L^5$, $R^{2a}$, $R^{3a}$, $R^{4a}$, $R^{5a}$, $R^{6a}$, $R^{7a}$, $R^{8a}$, $R^{9a}$, $R^{10a}$, $R^{2b}$, $R^{3b}$, $R^{4b}$, $R^{5b}$, $R^{6b}$, $R^{7b}$, $R^{8b}$, $R^{9b}$, $R^{10b}$, $R^{11b}$ and $R^{12b}$ are defined as described herein. In some embodiments, $R^{2a}$, $R^{3a}$, $R^{4a}$, $R^{8a}$, $R^{9a}$, $R^{10a}$, $R^{2b}$, $R^{3b}$, $R^{4b}$, $R^{8b}$ and $R^{9b}$ are H, $L^5$ is $C_1$-$C_{10}$ alkyl, $-(CR^{49}=CR^{49'})_u-$, $-(CR^{49}R^{49'})_uC(O)-$, $-CH_2CH_2(OCR^{49}R^{49'}CR^{49}R^{49'})_u-$, $-CH_2CH_2CH_2(OCR^{49}R^{49'}CR^{49}R^{49'}CR^{49}R^{49'})_u-$, $-CH_2CH_2(OCR^{49}R^{49'}CR^{49}R^{49'})_uC(O)-$ or $-CH_2CH_2(OCR^{49}R^{49'}CR^{49}R^{49'}CR^{49}R^{49'})_uC(O)-$, wherein each $R^{49}$ and $R^{49'}$ is H, and u is 1, 2, 3, 4 or 5. In some embodiments $R^{2a}$, $R^{3a}$, $R^{4a}$, $R^{8a}$, $R^{9a}$, $R^{10a}$, $R^{2b}$, $R^{3b}$, $R^{4b}$, $R^{8b}$ and $R^{9b}$ are H, and $L^5$ is $C_1$-$C_{10}$ alkyl. In some embodiments, $R^{2a}$, $R^{3a}$, $R^{4a}$, $R^{8a}$, $R^{9a}$, $R^{10a}$, $R^{2b}$, $R^{3b}$, $R^{4b}$, $R^{8b}$ and $R^{9b}$ are H, $L^5$ is $-(OCR^{49}R^{49'}CR^{49}R^{49'})_u-$, wherein each $R^{49}$ and $R^{49'}$ is H, and u is 4. In some embodiments, $R^{4a}$ is a bond, $R^{2a}R^{3a}$, $R^{8a}$, $R^{9a}$, $R^{10a}$, $R^{2b}$, $R^{3b}$, $R^{4b}$, $R^{8b}$ and $R^{9b}$ are H, $L^5$ is $C_1$-$C_{10}$ alkyl, $-(CR^{49}=CR^{49})_u-$, $-(CR^{49}R^{49'})_uC(O)-$, $-CH_2CH_2(OCR^{49}R^{49'}CR^{49}R^{49'})_u-$, $-CH_2CH_2CH_2(OCR^{49}R^{49'}CR^{49}R^{49'}CR^{49}R^{49'})_u-$, $-CH_2CH_2(OCR^{49}R^{49'}CR^{49}R^{49'})_uC(O)-$ or $-CH_2CH_2(OCR^{49}R^{49'}CR^{49}R^{49'}CR^{49}R^{49'})_uC(O)-$, wherein each $R^{49}$ and $R^{49'}$ is H and u is 1, 2, 3, 4 or 5. In some embodiments, $R^{5a}$ is a bond, $R^{2a}$, $R^{3a}$, $R^{4a}$, $R^{8a}$, $R^{9a}$, $R^{10a}$, $R^{2b}$, $R^{3b}$, $R^{4b}$, $R^{8b}$ and $R^{9b}$ are H, and $L^5$ is $C_1$-$C_{10}$ alkyl.

In some embodiments, Drug can be described by the general formula -$D^1$-$L^5$-$D^2$. In some embodiments, Drug can be described by the formula

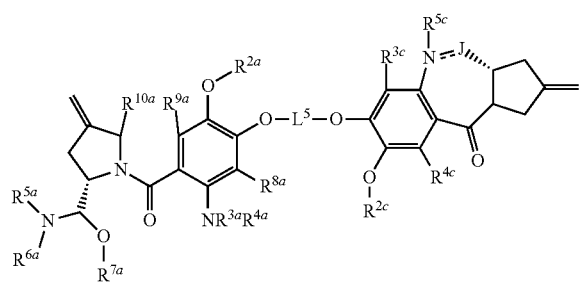

wherein $L^5$, $R^{2a}$, $R^{3a}$, $R^{4a}$, $R^{5a}$, $R^{6a}$, $R^{7a}$, $R^{8a}$, $R^{9a}$, $R^{10a}$, $R^{2c}$, $R^{3c}$, $R^{4c}$, $R^{5c}$ and are as defined herein. In some embodiments, $R^{2a}$, $R^{3a}$, $R^{4a}$, $R^{8a}$, $R^{9a}$, $R^{10a}$, $R^{2c}$, $R^{3c}$, $R^{4c}$ and $R^{5c}$ are H, $L^5$ is $C_1$-$C_{10}$ alkyl, $-(CR^{49}=CR^{49'})_u-$, $-(CR^{49}R^{49'})C(O)-$, $-CH_2CH_2(OCR^{49}R^{49'}CR^{49}R^{49'})_u-$, $-CH_2CH_2CH_2(OCR^{49}R^{49'}CR^{49}R^{49'}CR^{49}R^{49'})_u-$, $-CH_2CH_2(OCR^{49}R^{49'}CR^{49}R^{49'})C(O)-$ or $-CH_2CH_2(OCR^{49}R^{49'}CR^{49}R^{49'}CR^{49}R^{49'})C(O)-$, wherein each $R^{49}$ and $R^{49'}$ is H, and u is 1, 2, 3, 4 or 5. In some embodiments, J is $-C(O)-$, $R^{2a}$, $R^{3a}$, $R^{4a}$, $R^{8a}$, $R^{9a}$, $R^{10a}$, $R^{2c}$, $R^{3c}$, $R^{4c}$ and $R^{5c}$ are H, and $L^5$ is $C_1$-$C_{10}$ alkyl. In some embodiments, J is $-CR^{13c}=$, $R^{2a}$, $R^{3a}$, $R^{4a}$, $R^{8a}$, $R^{9a}$, $R^{10a}$, $R^{2c}$, $R^{3c}$, $R^{4c}$, $R^{5c}$ and $R^{13c}$ are H, and $L^5$ is $C_1$-$C_{10}$ alkyl. In some embodiments, J is $-(CR^{13c}R^{13c'})-$, $R^{2a}$, $R^{3a}$, $R^{4a}$, $R^{8a}$, $R^{9a}$, $R^{10a}$, $R^{2c}$, $R^{3c}$, $R^{4c}$, $R^{5c}$, $R^{13c}$ and $R^{13c'}$ are H, and $L^5$ is $C_1$-$C_{10}$ alkyl.

In some embodiments, Drug can be described by the general formula -$D^1$-$L^5$-$D^2$. In some embodiments, Drug can be described by the formula

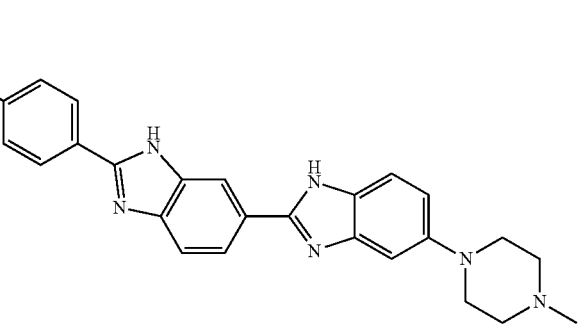

wherein, $L^5$, $R^{2a}$, $R^{3a}$, $R^{4a}$, $R^{5a}$, $R^{6a}$, $R^{7a}$, $R^{8a}$, $R^{9a}$ and $R^{10a}$ are as defined herein. In some embodiments, $R^{2a}$, $R^{3a}$, $R^{4a}$, $R^{8a}$, $R^{9a}$ and $R^{10a}$ are H, $L^5$ is $C_1$-$C_{10}$ alkyl, $-(CR^{49}=CR^{49'})_u-$, $-(CR^{49}R^{49'})C(O)-$, $-CH_2CH_2(OCR^{49}R^{49'}CR^{49}R^{49'})_u-$, $-CH_2CH_2CH_2(OCR^{49}R^{49'}CR^{49}R^{49'}CR^{49}R^{49'})_u-$, $-CH_2CH_2(OCR^{49}R^{49'}CR^{49}R^{49'})C(O)-$ or $-CH_2CH_2(OCR^{49}R^{49'}CR^{49}R^{49'}CR^{49}R^{49'})_uC(O)-$, wherein each $R^{49}$ and $R^{49'}$ is H, and u is 1, 2, 3, 4 or 5. In some embodiments, $R^{2a}$, $R^{3a}$, $R^{4a}$, $R^{8a}$, $R^{9a}$ and $R^{10a}$ are H, and $L^5$ is $C_1$-$C_{10}$ alkyl. In some embodiments, $R^{2a}$, $R^{3a}$, $R^{4a}$, $R^{8a}$, $R^{9a}$ and $R^{10a}$ are H, $L^5$ is $-(CR^{49}R^{49'})_uC(O)-$, wherein each $R^{49}$ and $R^{49'}$ is H, and u is 3. In some embodiments, $R^{2a}$, $R^{3a}$, $R^{4a}$, $R^{8a}$, $R^{9a}$ and $R^{10a}$ are H, $L^5$ is $-(CR^{49}R^{49'})C(O)-$, wherein each $R^{49}$ and $R^{49'}$ is H, and u is 4. In some embodiments, $R^{2a}$, $R^{3a}$, $R^{4a}$, $R^{8a}$, $R^{9a}$ and $R^{10a}$ are H, $L^5$ is $-(CR^{49}R^{49'})_uC(O)-$, wherein each $R^{49}$ and $R^{49'}$ is H, and u is 5.

In some embodiments, Drug can be described by the general formula -$D^1$-$L^5$-$D^2$. In some embodiments, Drug can be described by the formula

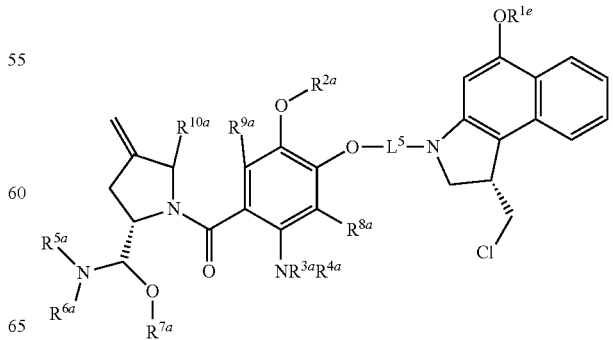

wherein, $L^5$, $R^{2a}$, $R^{3a}$, $R^{4a}$, $R^{5a}$, $R^{6a}$, $R^{7a}$, $R^{8a}$, $R^{9a}$, $R^{10a}$ and $R^{1e}$ are as defined herein. In some embodiments, $R^{2a}$, $R^{3a}$, $R^{4a}$, $R^{8a}$, $R^{9a}$, $R^{10a}$ and $R^{1e}$ are H, $L_5$ is $C_1$-$C_{10}$ alkyl, —$(CR^{49}$=$CR^{49'})_u$—, —$(CR^{49}R^{49'})_uC(O)$—, —$CH_2CH_2(OCR^{49}R^{49'}CR^{49}R^{49'})_u$—, —$CH_2CH_2(OCR^{49}R^{49'}CR^{49}R^{49'}CR^{49}R^{49'})_u$—, —$CH_2CH_2(OCR^{49}R^{49'}CR^{49}R^{49'})_uC(O)$— or —$CH_2CH_2(OCR^{49}R^{49'}CR^{49}R^{49'}CR^{49}R^{49'})_uC(O)$—, wherein each $R^{49}$ and $R^{49'}$ is H, and u is 1, 2, 3, 4 or 5. In some embodiments, $R^{2a}$, $R^{3a}$, $R^{4a}$, $R^{8a}$, $R^{9a}$, $R^{10a}$ and $R^{1e}$ are H, and $L^5$ is $C_1$-$C_{10}$ alkyl. In some embodiments, $R^{2a}$, $R^{3a}$, $R^{4a}$, $R^{8a}$, $R^{9a}$, $R^{10a}$ and $R^{1e}$ are H, $L^5$ is —$(CR^{49}_R{}^{49'})_uC(O)$—, wherein each $R^{49}$ and $R^{49'}$ is H, and u is 3. In some embodiments, $R^{2a}$, $R^{3a}$, $R^{4a}$, $R^{8a}$, $R^{9a}$, $R^{10a}$ and $R^{1e}$ are H, $L^5$ is —$(CR^{49}R^{49'})_uC(O)$—, wherein each $R^{49}$ and $R^{49'}$ is H, and u is 4. In some embodiments, $R^{2a}$, $R^{3a}$, $R^{4a}$, $R^{8a}$, $R^{9a}$, $R^{10a}$ and $R^{1e}$ are H, $L^5$ is —$(CR^{49}_R{}^{49'})_uC(O)$—, wherein each $R^{49}$ and $R^{49'}$ is H, and u is 5.

In some embodiments, Drug can be described by the general formula -$D^1$-$L^5$-$D^2$. In some embodiments, Drug can be described by the formula

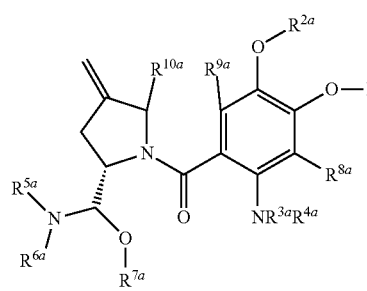

wherein $L^5$, $R^{2a}$, $R^{3a}$, $R^{4a}$, $R^{5a}$, $R^{6a}$, $R^{7a}$, $R^{8a}$, $R^{9a}$, $R^{10a}$, $R^{1d}$ and v are as defined herein. In some embodiments, $R^{2a}$, $R^{3a}$, $R^{4a}$, $R^{8a}$, $R^{9a}$, $R^{10a}$ and $R^{1e}$ are H, $L^5$ is $C_1$-$C_{10}$ alkyl, —$(CR^{49}$=$CR^{49'})_u$—, —$(CR^{49}R^{49'})_uC(O)$—, —$CH_2CH_2(OCR^{49}R^{49'}CR^{49}R^{49'})_u$—, —$CH_2CH_2CH_2(OCR^{49}R^{49'}CR^{49}R^{49'}CR^{49}R^{49'})_u$—, —$CH_2CH_2(OCR^{49}R^{49'}CR^{49}R^{49'})_uC(O)$— or —$CH_2CH_2(OCR^{49}R^{49'}CR^{49}R^{49'}CR^{49}R^{49'})_uC(O)$—, wherein each $R^{49}$ and $R^{49'}$ is H, and u is 1, 2, 3, 4 or 5. In some embodiments, $R^{2a}$, $R^{3a}$, $R^{4a}$, $R^{8a}$, $R^{9a}$, $R^{10a}$ and $R^{1e}$ are H, and $L^5$ is $C_1$-$C_{10}$ alkyl. In some embodiments, $R^{2a}$, $R^{3a}$, $R^{4a}$, $R^{8a}$, $R^{9a}$, $R^{10a}$ and $R^{1e}$ are H, $L^5$ is —$(CR^{49}R^{49'})_uC(O)$—, wherein each $R^{49}$ and $R^{49'}$ is H, and u is 4. In some embodiments, $R^{2a}$, $R^{3a}$, $R^{4a}$, $R^{8a}$, $R^{9a}$, $R^{10a}$ and $R^{1e}$ are H, $L^5$ is —$(CR^{49}R^{49'})_uC(O)$—, wherein each $R^{49}$ and $R^{49'}$ is H, and u is 5. In some embodiments, $R^{2a}$, $R^{3a}$, $R^{4a}$, $R^{8a}$, $R^{9a}$, $R^{10a}$ and $R^{1e}$ are H, $L^5$ is $C_1$-$C_{10}$ alkyl, and v is 2. In some embodiments, $R^{2a}$, $R^{3a}$, $R^{4a}$, $R^{8a}$, $R^{9a}$, $R^{10a}$ and $R^{1e}$ are H, $L^5$ is $C_1$-$C_{10}$ alkyl, and v is 3. In some embodiments, $R^{2a}$, $R^{3a}$, $R^{4a}$, $R^{8a}$, $R^{9a}$, $R^{10a}$ and $R^{1e}$ are H, $L^5$ is —$(CR^{49}_R{}^{49'})_uC(O)$—, wherein each $R^{49}$ and $R^{49'}$ is H, u is 4, and v is 2. In some embodiments, $R^{2a}$, $R^{3a}$, $R^{4a}$, $R^{8a}$, $R^{9a}$, $R^{10a}$ and $R^{1e}$ are H, $L^5$ is —$(CR^{49}R^{49'})_uC(O)$—, wherein each $R^{49}$ and $R^{49'}$ is H, u is 4, and v is 3. In some embodiments, $R^{2a}$, $R^{3a}$, $R^{4a}$, $R^{8a}$, $R^{9a}$, $R^{10a}$ and $R^{1e}$ are H, $L^5$ is —$(CR^{49}_R{}^{49'})_uC(O)$—, wherein each $R^{49}$ and $R^{49'}$ is H, u is 5, and v is 2. In some embodiments, $R^{2a}$, $R^{3a}$, $R^{4a}$, $R^{8a}$, $R^{9a}$, $R^{10a}$ and $R^{1e}$ are H, $L^5$ is —$(CR^{49}R^{49'})_uC(O)$—, wherein each $R^{49}$ and $R^{49'}$ is H, u is 5, and v is 3.

In some embodiments, Drug can be described by the general formula -$D^1$-$L^5$-$D^2$. In some embodiments, Drug can be described by the formula

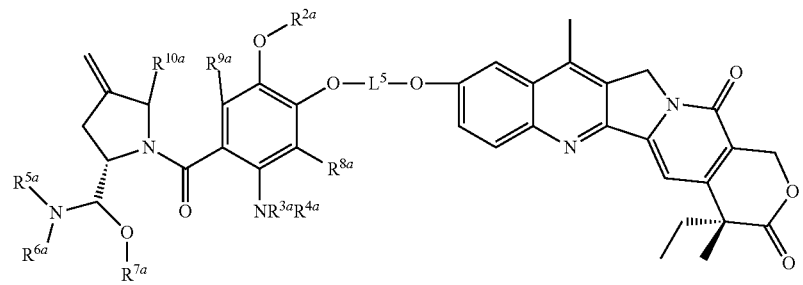

wherein $L^5$, $R^{2a}$, $R^{3a}$, $R^{4a}$, $R^{5a}$, $R^{6a}$, $R^{7a}$, $R^{8a}$, $R^{9a}$ and $R^{10a}$ are as defined herein. In some embodiments, $R^{2a}$, $R^{3a}$, $R^{4a}$, $R^{8a}$, $R^{9a}$ and $R^{10a}$ are H, $L^5$ is $C_1$-$C_{10}$ alkyl, —$(CR^{49}$=$CR^{49'})_u$—, —$(CR^{49}R^{49'})_uC(O)$—, —$CH_2CH_2(OCR^{49}R^{49'}CR^{49}R^{49'})_u$—, —$CH_2CH_2CH_2(OCR^{49}R^{49'}CR^{49}R^{49'}CR^{49}R^{49'})_u$—, —$CH_2CH_2(OCR^{49}R^{49'}CR^{49}R^{49'})_uC(O)$— or —$CH_2CH_2(OCR^{49}R^{49'}CR^{49}R^{49'}CR^{49}R^{49'})_uC(O)$—, wherein each $R^{49}$ and $R^{49'}$ is H, and u is 1, 2, 3, 4 or 5. In some embodiments, $R^{2a}$, $R^{3a}$, $R^{4a}$, $R^{8a}$, $R^{9a}$ and $R^{10a}$ are H, and $L^5$ is $C_1$-$C_{10}$ alkyl. In some embodiments, $R^{2a}$, $R^{3a}$, $R^{4a}$, $R^{8a}$, $R^{9a}$ and $R^{10a}$ are H, $L^5$ is —$(CR^{49}R^{49'})_uC(O)$—, wherein each $R^{49}$ and $R^{49'}$ is H, and u is 4. In some embodiments, $R^{2a}$, $R^{3a}$, $R^{4a}$, $R^{8a}$, $R^{9a}$ and $R^{10a}$ are H, $L^5$ is —$(CR^{49}R^{49'})_uC(O)$—, wherein each $R^{49}$ and $R^{49'}$ is H, and u is 5.

In some embodiments, Drug can be described by the general formula $-D^1-L^5-D^2$. In some embodiments, Drug can be described by the formula

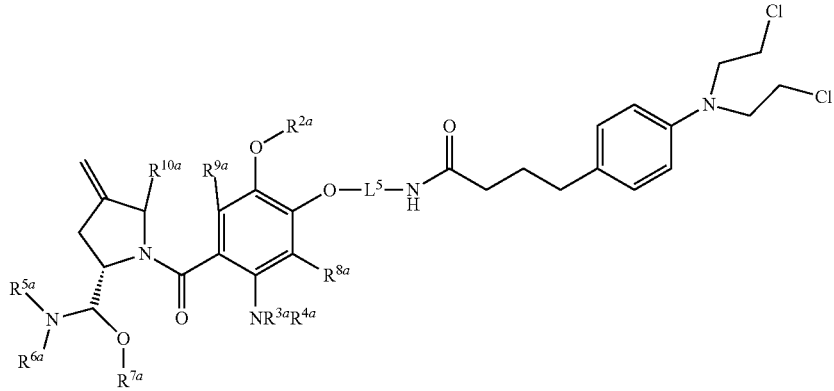

wherein $L^5$, $R^{2a}$, $R^{3a}$, $R^{4a}$, $R^{5a}$, $R^{6a}$, $R^{7a}$, $R^{8a}$, $R^{9a}$ and $R^{10a}$ are as defined herein. In some embodiments, $R^{2a}$, $R^{3a}$, $R^{4a}$, $R^{8a}$, $R^{9a}$ and $R^{10a}$ are H, $L^5$ is $C_1$-$C_{10}$ alkyl, —$(CR^{49}=CR^{49'})_u$—, —$(CR^{49}R^{49'})_uC(O)$—, —$CH_2CH_2(OCR^{49}R^{49'}CR^{49}R^{49'})_u$—, —$CH_2CH_2CH_2(OCR^{49}R^{49'}CR^{49}R^{49'}CR^{49}R^{49'})_u$—, —$CH_2CH_2(OCR^{49}R^{49'}CR^{49}R^{49'})_uC(O)$— or —$CH_2CH_2(OCR^{49}R^{49'}CR^{49}R^{49'}CR^{49}R^{49'})_uC(O)$—, wherein each $R^{49}$ and $R^{49'}$ is H, and u is 1, 2, 3, 4 or 5. In some embodiments, $R^{2a}$, $R^{3a}$, $R^{4a}$, $R^{8a}$, $R^{9a}$ and $R^{10a}$ are H, and $L^5$ is $C_1$-$C_{10}$ alkyl. In some embodiments, $R^{2a}$, $R^{3a}$, $R^{4a}$, $R^{8a}$, $R^{9a}$ and $R^{10a}$ are H, $L^5$ is —$(CR^{49}R^{49'})_uC(O)$—, wherein each $R^{49}$ and $R^{49'}$ is H, and u is 4. In some embodiments, $R^{2a}$, $R^{3a}$, $R^{4a}$, $R^{8a}$, $R^{9a}$ and $R^{10a}$ are H, $L^5$ is —$(CR^{49}R^{49'})_uC(O)$—, wherein each $R^{49}$ and $R^{49'}$ is H, and u is 5.

In some embodiments, Drug can be described by the general formula $-D^1-L^5-D^2$. In some embodiments, Drug can be described by the formula wherein $L^5$, $R^{2a}$, $R^{3a}$, $R^{5a}$, $R^{6a}$, $R^{7a}$, $R^{8a}$, $R^{9a}$, $R^{10a}$, $R^{2b}$, $R^{3b}$, $R^{4b}$, $R^{5b}$, $R^{6b}$, $R^{7b}$, $R^{8b}$, $R^{9b}$, $R^{10b}$, $R^{11b}$ and $R^{12b}$ are defined as described herein. In some embodiments, $R^{2a}$, $R^{3a}$, $R^{8a}$, $R^{9a}$, $R^{10a}$, $R^{2b}$, $R^{3b}$, $R^{4b}$, $R^{8b}$ and $R^{9b}$ are H, $L^5$ is $C_1$-$C_{10}$ alkyl, —$(CR^{49}=CR^{49'})_u$—, —$(CR^{49}R^{49'})_uC(O)$—, —$CH_2CH_2(OCR^{49}R^{49'}CR^{49}R^{49'})_u$—, —$CH_2CH_2CH_2(OCR^{49}R^{49'}CR^{49}R^{49'}CR^{49}R^{49'})_u$—, —$CH_2CH_2(OCR^{49}R^{49'}CR^{49}R^{49'})_uC(O)$— or —$CH_2CH_2(OCR^{49}R^{49'}CR^{49}R^{49'}CR^{49}R^{49'})_uC(O)$—, wherein each $R^{49}$ and $R^{49'}$ is H, and u is 1, 2, 3, 4 or 5. In some embodiments, $R^{2a}$, $R^{3a}$, $R^{4a}$, $R^{8a}$, $R^{9a}$, $R^{10a}$, $R^{2b}$, $R^{3b}$, $R^{4b}$, $R^{8b}$ and $R^{9b}$ are H, and $L^5$ is $C_1$-$C_{10}$ alkyl.

In some embodiments, $D^1$ can be absent. When $D^1$ is absent, $D^2$ is of the formula

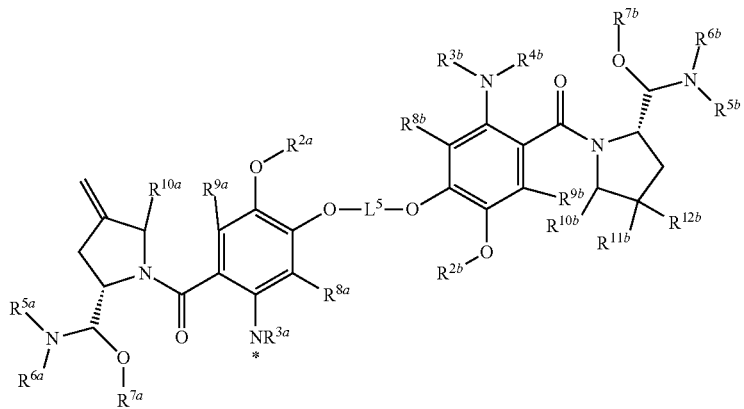

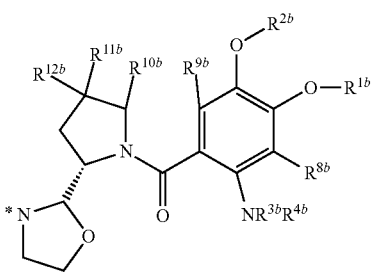

wherein $R^{1b}$, $R^{2b}$, $R^{3b}$ and $R^{4b}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —C(O)$R^{13b}$, —C(O)O$R^{13b}$, and —C(O)N$R^{13b}R^{13b'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{13b}$, —OC(O)$R^{13b}$, —OC(O)N$R^{13b}R^{13b'}$, —OS(O)$R^{13b}$, —OS(O)$_2R^{13b}$, —S$R^{13b}$, —S(O)$R^{13b}$, —S(O)$_2R^{13b}$, —S(O)N$R^{13b}R^{13b'}$, —S(O)$_2$N$R^{13b}R^{13b'}$, —OS(O)N$R^{13b}R^{13b'}$, —OS(O)$_2$N$R^{13b}R^{13b'}$, —N$R^{13b}R^{13b'}$, —N$R^{13b}$C(O)$R^{14b}$, —N$R^{13b}$C(O)O$R^{14b}$, —N$R^{13b}$C(O)N$R^{14b}R^{14b'}$, —N$R^{13b}$S(O)$R^{14b}$, —N$R^{13b}$S(O)$_2R^{14b}$, —N$R^{13b}$S(O)N$R^{14b}R^{14b'}$, —N$R^{13b}$S(O)$_2$N$R^{14b}R^{14b'}$, —C(O)$R^{13b}$, —C(O)O$R^{13b}$ or —C(O)N$R^{13b}R^{13b'}$; or any one of $R^{1b}$, $R^{2b}$, $R^{3b}$ and $R^{4b}$ is a bond;

$R^{5b}$, $R^{6b}$ and $R^{7b}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —C(O)$R^{15b}$, —C(O)O$R^{15b}$, and —C(O)N$R^{15b}R^{15b'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, -L$^4$H, -L$^3$H, —O$R^{15b}$, —OC(O)$R^{15b}$, —OC(O)N$R^{15b}R^{15b'}$, —OS(O)$R^{15b}$, —OS(O)$^2R^{15b}$, —S$R^{15b}$, —S(O)$R^{15b}$, —S(O)$_2R^{15b}$, —S(O)N$R^{15b}R^{15b'}$, —S(O)$_2$N$R^{15b}R^{15b'}$, —OS(O)N$R^{15b}R^{15b'}$, —OS(O)$_2$N$R^{15b}R^{15b'}$, —N$R^{15b}R^{15b'}$, —N$R^{15b}$C(O)$R^{16b}$, —N$R^{15b}$C(O)O$R^{16b}$, —N$R^{15b}$C(O)N$R^{16b}R^{16b'}$, —N$R^{15b}$S(O)$R^{16b}$, —N$R^{15b}$S(O)$_2R^{16b}$, —N$R^{15b}$S(O)N$R^{16b}R^{16b'}$, —N$R^{15b}$S(O)$_2$N$R^{16b}R^{16b'}$, —C(O)$R^{15b}$, —C(O)O$R^{15b}$ or —C(O)N$R^{15b}R^{15b'}$; wherein $R^{6b}$ and $R^{7b}$ taken together with the atoms to which they are attached optionally combine to form a 3- to 7-membered heterocycloalkyl, or $R^{5b}$ and $R^{6b}$ taken together with the atoms to which they are attached optionally combine to form a 3- to 7-membered heterocycloalkyl or 5- to 7-membered heteroaryl, wherein each hydrogen atom in 3- to 7-membered heterocycloalkyl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{17b}$, —OC(O)$R^{17b}$, —OC(O)N$R^{17b}R^{17b'}$, —OS(O)$R^{17b}$, —OS(O)$_2R^{17b}$, —S$R^{17b}$, —S(O)$R^{17b}$, —S(O)$_2R^{17b}$, —S(O)N$R^{17b}R^{17b'}$, —S(O)$_2$N$R^{17b}R^{17b'}$, —OS(O)N$R^{17b}R^{17b'}$, —OS(O)$_2$N$R^{17b}R^{17b'}$, —N$R^{17b}R^{17b'}$, —N$R^{17b}$C(O)$R^{18b}$, —N$R^{17b}$C(O)O$R^{18b}$, —N$R^{17b}$C(O)N$R^{18b}R^{18b'}$, —N$R^{17b}$S(O)$R^{18b}$, —N$R^{17b}$S(O)$_2R^{18b}$, —N$R^{17b}$S(O)N$R^{18b}R^{18b'}$, —N$R^{17b}$S(O)$_2$N$R^{18b}R^{18b'}$, —C(O)$R^{17b}$, —C(O)O$R^{17b}$ or —C(O)N$R^{17b}R^{17b'}$; or any one of $R^{5b}$, $R^{6b}$ or $R^{7b}$ is a bond;

$R^{8b}$ and $R^{9b}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —CN, —NO$_2$, —NCO, —O$R^{19b}$, —OC(O)$R^{19b}$, —OC(O)N$R^{19b}R^{19b'}$, —OS(O)$R^{19b}$, —OS(O)$_2R^{19b}$, —S$R^{19b}$, —S(O)$R^{19b}$, —S(O)$_2R^{19b}$, —S(O)N$R^{19b}R^{19b'}$, —S(O)$_2$N$R^{19b}R^{19b'}$, —OS(O)N$R^{19b}R^{19b'}$, —OS(O)$_2$N$R^{19b}R^{19b'}$, —N$R^{19b}R^{19b'}$, —N$R^{19b}$C(O)$R^{20b}$, —N$R^{19b}$C(O)O$R^{20b}$, —N$R^{19b}$C(O)N$R^{20b}R^{20b'}$, —N$R^{19b}$S(O)$R^{20b}$, —N$R^{19b}$S(O)$_2R^{20b}$, —N$R^{19b}$S(O)N$R^{20b}R^{20b'}$, —N$R^{19b}$S(O)N$R^{20b}R^{20b'}$, —N$R^{19b}$S(O)$_2$N$R^{20b}R^{20b'}$, —C(O)$R^{19b}$, —C(O)O$R^{19b}$ and —C(O)N$R^{19b}R^{19b'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{21b}$, —OC(O)$R^{21b}$, —OC(O)N$R^{21b}R^{21b'}$, —OS(O)$R^{21b}$, —OS(O)$_2R^{21b}$, —S$R^{21b}$, —S(O)$R^{21b}$, —S(O)$_2R^{21b}$, —S(O)N$R^{21b}R^{21b'}$, —S(O)$_2$N$R^{21b}R^{21b'}$, —OS(O)N$R^{21b}R^{21b'}$, —OS(O)$_2$N$R^{21b}R^{21b'}$, —N$R^{21b}R^{21b'}$, —N$R^{21b}$C(O)$R^{22b}$, —N$R^{21b}$C(O)O$R^{22b}$, —N$R^{21b}$C(O)N$R^{22b}R^{22b'}$, —N$R^{21b}$S(O)$R^{22b}$, —N$R^{21b}$S(O)$_2R^{22b}$, —N$R^{21b}$S(O)N$_R^{22b}R^{22b'}$, —N$R^{21b}$S(O)$_2$N$R^{22b}R^{22b'}$, —C(O)$R^{21b}$, —C(O)O$R^{21b}$ or —C(O)N$R^{21b}R^{21b'}$;

$R^{10b}$, $R^{11b}$ and $R^{12b}$ are each independently selected from the group consisting of H, D, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{23b}$, —OC(O)$R^{23b}$, —OC(O)N$R^{23b}R^{23b'}$, —OS(O)$R^{23b}$, —OS(O)$_2R^{23b}$, —S$R^{23b}$, —S(O)$R^{23b}$, —S(O)$_2R^{23b}$, —S(O)N$R^{23b}R^{23b'}$, —S(O)$_2$N$R^{23b}R^{23b'}$, —OS(O)N$R^{23b}R^{23b'}$, —OS(O)$_2$N$R^{23b}R^{23b'}$, —N$R^{23b}R^{23b'}$, —N$R^{23b}$C(O)$R^{24b}$, —N$R^{23b}$C(O)O$R^{24b}$, —N$R^{23b}$C(O)N$R^{24b}R^{24b'}$, —N$R^{23b}$S(O)$R^{24b}$, —N$R^{23b}$S(O)$_2R^{24b}$, —N$R^{23b}$S(O)N$R^{24b}R^{24b'}$, —N$R^{23b}$S(O)$_2$N$R^{24b}R^{24b'}$, —C(O)$R^{23b}$, —C(O)O$R^{23b}$ and —C(O)N$R^{23b}R^{23b'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{25b}$, —OC(O)$R^{25b}$, —OC(O)N$R^{25b}R^{25b'}$, —OS(O)$R^{25b}$, —OS(O)$_2R^{25b}$, —S$R^{25b}$, —S(O)$R^{25b}$, —S(O)$_2R^{25b}$, —S(O)N$R^{25b}R^{25b'}$, —S(O)$_2$N$R^{25b}R^{25b'}$, —OS(O)N$R^{25b}R^{25b'}$, —OS(O)$_2$N$R^{25b}R^{25b'}$, —N$R^{25b}R^{25b'}$, —N$R^{25b}$C(O)$R^{26b}$, —N$R^{25b}$C(O)O$R^{26b}$, —N$R^{25b}$C(O)N$R^{26b}R^{26b'}$, —N$R^{25b}$S(O)$R^{26b}$, —N$R^{25b}$S(O)$_2R^{26b}$, —N$R^{25b}$S(O)N$R^{26b}R^{26b'}$, —N$R^{25b}$S(O)$_2$N$R^{26b}R^{26b'}$, —C(O)$R^{25b}$, —C(O)O$R^{25b}$ or —C(O)N$R^{25b}R^{25b'}$, or $R^{10b}$ and $R^{11b}$ taken together with the carbon atoms to which they are attached optionally combine to form a $C_6$-$C_{10}$ aryl, or $R^{11b}$ and $R^{12b}$ taken together with the carbon atom to which they are attached optionally combine to form an exomethylene; or $R^{12b}$ is absent;

each $R^{13b}$, $R^{13b'}$, $R^{14b}$, $R^{14b'}$, $R^{15b}$, $R^{15b'}$, $R^{16b}$, $R^{16b'}$, $R^{17b}$, $R^{17b'}$, $R^{18b}$, $R^{18b'}$, $R^{19b}$, $R^{19b'}$, $R^{20b}$, $R^{20b'}$, $R^{21b}$, $R^{21b'}$, $R^{22b}$, $R^{22b'}$, $R^{23b}$, $R^{23b'}$, $R^{24b}$, $R^{24b'}$, $R^{25b}$, $R^{25b'}$, $R^{26b}$ and $R^{26b'}$ is independently selected from the group consisting of H, D, $C_1$-$C_7$ alkyl, $C_2$-$C_7$ alkenyl, $C_2$-$C_7$ alkynyl, $C_3$-$C_{13}$ cycloalkyl, 3- to 7-membered heterocycloalkyl, $C_6$-$C_{10}$ aryl, $C_1$-$C_6$ alkyl($C_6$-$C_{10}$ aryl) and 5- to 7-membered heteroaryl, wherein each hydrogen atom in $C_6$-$C_{10}$ aryl, $C_1$-$C_6$ alkyl ($C_6$-$C_{10}$ aryl) and 5- to 7-membered heteroaryl is independently optionally substituted by $C_1$-$C_6$ alkyl, $C_2$-$C_6$ alkenyl, $C_2$-$C_6$ alkynyl, $C_{3-}C_6$ cycloalkyl, 3- to 7-membered heterocycloalkyl, $C_6$-$C_{10}$ aryl, 5- to 7-membered heteroaryl, —CN, —NO$_2$, —NCO, —OH, —SH, —NH$_2$, —SO$_3$H, —C(O)OH and —C(O)NH$_2$; and * is a bond.

The conjugates described herein can be used for both human clinical medicine and veterinary applications. Thus, the host animal harboring the population of pathogenic cells and treated with the conjugates described herein can be human or, in the case of veterinary applications, can be a laboratory, agricultural, domestic, or wild animal. The conjugates described hereincan be applied to host animals including, but not limited to, humans, laboratory animals such rodents (e.g., mice, rats, hamsters, etc.), rabbits, monkeys, chimpanzees, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

The conjugate, compositions, methods, and uses described herein are useful for treating diseases caused at least in part by populations of pathogenic cells, which may cause a variety of pathologies in host animals. As used herein, the term "pathogenic cells" or "population of pathogenic cells" generally refers to cancer cells, infectious agents such as bacteria and viruses, bacteria- or virus-infected cells, inflammatory cells, activated macrophages capable of causing a disease state, and any other type of pathogenic cells that uniquely express, preferentially express, or overexpress cell surface receptors or cell surface anitgens that may be bound by or targeted by the conjugates described herein. Pathogenic cells can also include any cells causing a disease state for which treatment with the conjugates described herein results in reduction of the symptoms of the disease. For example, the pathogenic cells can be host cells that are pathogenic under some circumstances such as cells of the immune system that are responsible for graft versus host disease, but not pathogenic under other circumstances.

Thus, the population of pathogenic cells can be a cancer cell population that is tumorigenic, including benign tumors and malignant tumors, or it can be non-tumorigenic. The cancer cell population can arise spontaneously or by such processes as mutations present in the germline of the host animal or somatic mutations, or it can be chemically-, virally-, or radiation-induced. The conjugates described herein can be utilized to treat such cancers as carcinomas, sarcomas, lymphomas, Hodgekin's disease, melanomas, mesotheliomas, Burkitt's lymphoma, nasopharyngeal carcinomas, leukemias, and myelomas. The cancer cell population can include, but is not limited to, oral, thyroid, endocrine, skin, gastric, esophageal, laryngeal, pancreatic, colon, bladder, bone, ovarian, cervical, uterine, breast, testicular, prostate, rectal, kidney, liver, and lung cancers.

The disclosure includes all pharmaceutically acceptable isotopically-labelled conjugates, and their Drug(s) incorporated therein, wherein one or more atoms are replaced by atoms having the same atomic number, but an atomic mass or mass number different from the atomic mass or mass number which predominates in nature.

Examples of isotopes suitable for inclusion in the conjugates, and their Drug(s) incorporated therein, include isotopes of hydrogen, such as $^2$H and $^3$H, carbon, such as $^{11}$C, $^{13}$C and $^{14}$C, chlorine, such as $^{36}$Cl, fluorine, such as, $^{18}$F, iodine, such as $^{123}$I and $^{125}$I, nitrogen, such as $^{13}$N and $^{15}$N, oxygen, such as 15O, $^{17}$O and $^{18}$O, phosphorus, such as $^{32}$P, and sulfur, such as $^{35}$S.

Certain isotopically-labelled conjugates, and their Drug(s) incorporated therein, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, and $^{13}$N, can be useful in Positron Emission Topography (PET) studies for examining substrate receptor occupancy. Isotopically-labeled conjugates, and their Drug(s) incorporated therein, can generally be prepared by conventional techniques known to those skilled in the art or by processes analogous to those described in the accompanying Examples using an appropriate isotopically-labeled reagents in place of the non-labeled reagent previously employed.

The conjugates and compositions described herein may be administered orally. Oral administration may involve swallowing, so that the conjugate or composition enters the gastrointestinal tract, or buccal or sublingual administration may be employed by which the conjugate or composition enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The conjugates and compositions described herein may also be used in fast-dissolving, fast-disintegrating dosage forms such as those described in Expert Opinion in Therapeutic Patents, 11 (6), 981-986, by Liang and Chen (2001). For tablet dosage forms, depending on dose, the conjugate may make up from 1 weight % to 80 weight % of the dosage form, more typically from 5 weight % to 60 weight % of the dosage form. In addition to the conjugates and compositions described herein, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colorants, flavoring agents, preservatives and taste-masking agents. Exemplary tablets contain up to about 80% drug, from about 10 weight % to 25 about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tableting. The final formulation may comprise one or more layers and may be coated or uncoated; it may even be encapsulated. The formulation of tablets is discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a conjugate as described herein, a film-forming polymer, a binder, a solvent, a humectant, a plasticizer, a stabilizer or emulsifier, a viscosity-modifying agent and a solvent. Some components of the formulation may perform more than one function.

Solid formulations for oral administration may be formulated to be immediate and/or modified release. Modified release formulations include delayed-, sustained-, pulsed-, controlled-, targeted and programmed release. Suitable modified release formulations for the purposes of the disaclosure are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO 00/35298.

The conjugates described herein can also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous.

Suitable devices for parenteral administration include needle (including micro-needle) injectors, needle-free injectors and infusion techniques. Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art. The solubility of conjugates described herein used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus conjugates described herein can be formulated as a solid, semi-solid, or thixotropic liquid for administration as an implanted depot providing modified release of the active compound. Examples of such formulations include drug-coated stents and poly(lactic-coglycolic)acid (PGLA) microspheres. The conjugates described herein can also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated— see, for example, J. Pharm Sci, 88 (10), 955-958 by Finnin and Morgan (October 1999). Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release. The conjugates described herein can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin. The pressurized container, pump, spray, atomizer, or nebulizer contains a solution or suspension of the conjugates(s) of the present disclosure comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid. Prior to use in a dry powder or suspension formulation, the conjugate is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying. Capsules (made, for example, from gelatin or hydroxypropylmethylcellulose), blisters and cartridges for use in an inhaler or insufflator may be formulated to contain a powder mix of the conjugate described herein, a suitable powder base such as lactose or starch and a performance modifier such as Iso-leucine, mannitol, or magnesium stearate.

The lactose may be anhydrous or in the form of the monohydrate, preferably the latter. Other suitable excipients include dextran, glucose, maltose, sorbitol, xylitol, fructose, sucrose and trehalose. A typical formulation may comprise a conjugate of the present disclosure, propylene glycol, sterile water, ethanol and sodium chloride. Alternative solvents which may be used instead of propylene glycol include glycerol and polyethylene glycol.

The conjugates described here can be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present disclosure that two or more pharmaceutical compositions, at least one of which contains a conjugate as described herein, may conveniently be combined in the form of a kit suitable for co-administration of the compositions. Thus the kit of the present disclosure comprises two or more separate pharmaceutical compositions, at least one of which contains a conjugate as described herein, and means for separately retaining said compositions, such as a container, divided bottle, or divided foil packet. An example of such a kit is the familiar blister pack used for the packaging of tablets, capsules and the like. The kit of the present disclosure is particularly suitable for administering different dosage forms, for example parenteral, for administering the separate compositions at different dosage intervals, or for titrating the separate compositions against one another. To assist compliance, the kit typically comprises directions for administration and may be provided with a so-called memory aid.

Examples

Chemical Examples

It is to be understood that the conjugates described herein were prepared according to the processes described herein and/or conventional processes. Illustratively, the stereocenters of the conjugates described herein may be substantially pure (S), the substantially pure (R), or any mixture of (S) and (R) at any asymmetric carbon atom, and each may be used in the processes described herein. Similarly, the processes described in these illustrative examples may be adapted to prepare other conjugates described herein by carrying out variations of the processes described herein with routine selection of alternative starting materials and reagents.

It is also to be understood that radicals of these examples are included in the PBD prodrugs, poly-PBD prodrugs, mixed PBDs, conjugates, and conjugates described herein.

Example: Process for Preparing Intermediate Proline Derivatives

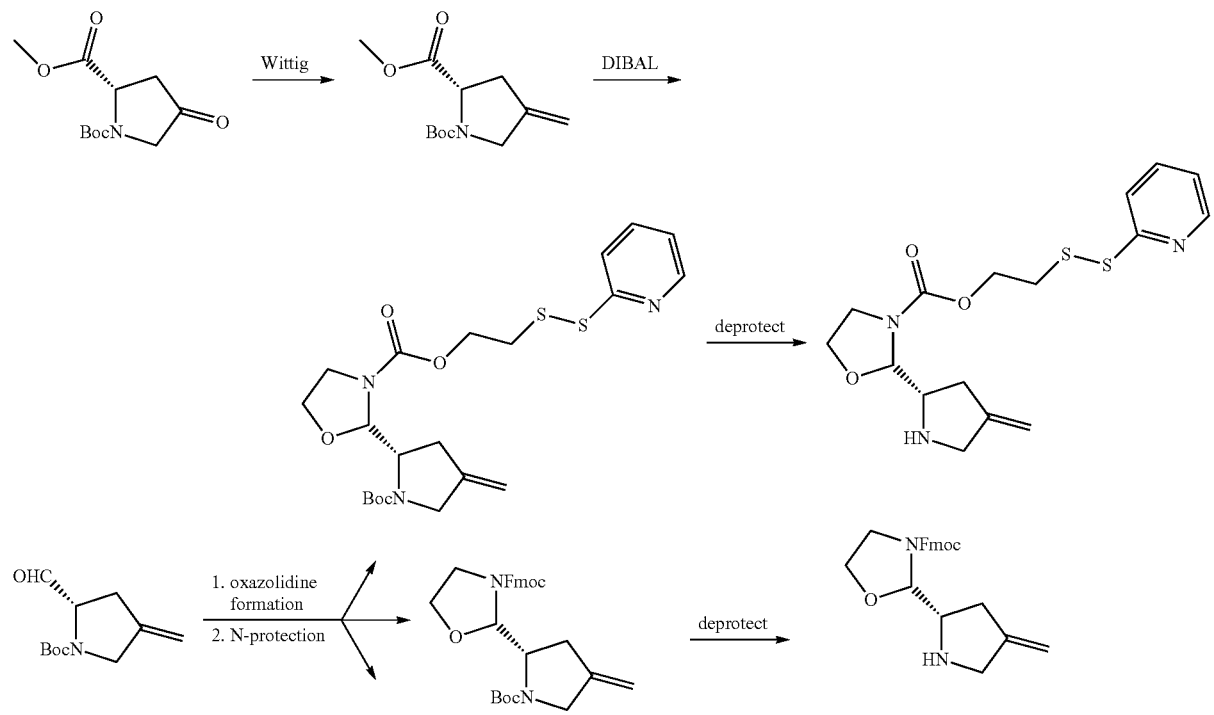

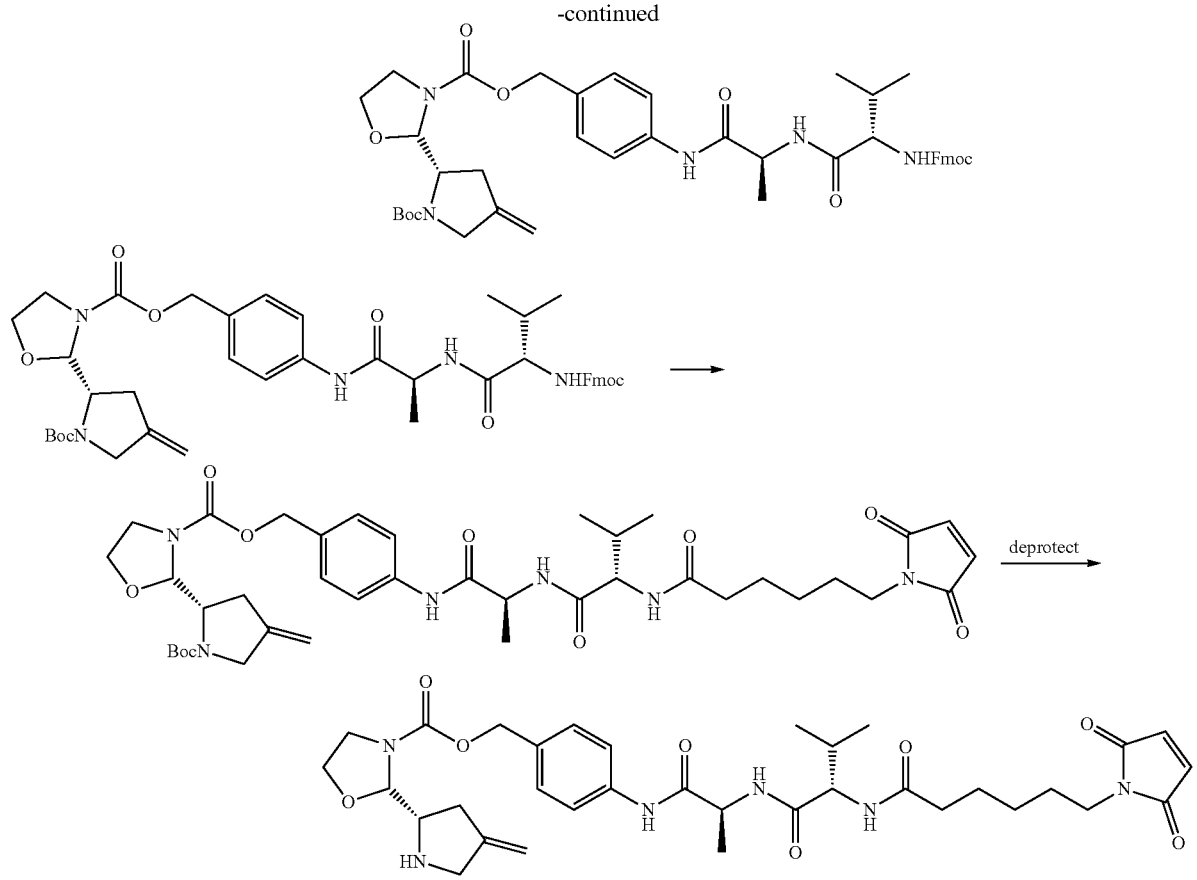
Example: Process for Preparing Intermediate Mono Fmoc-proPBD
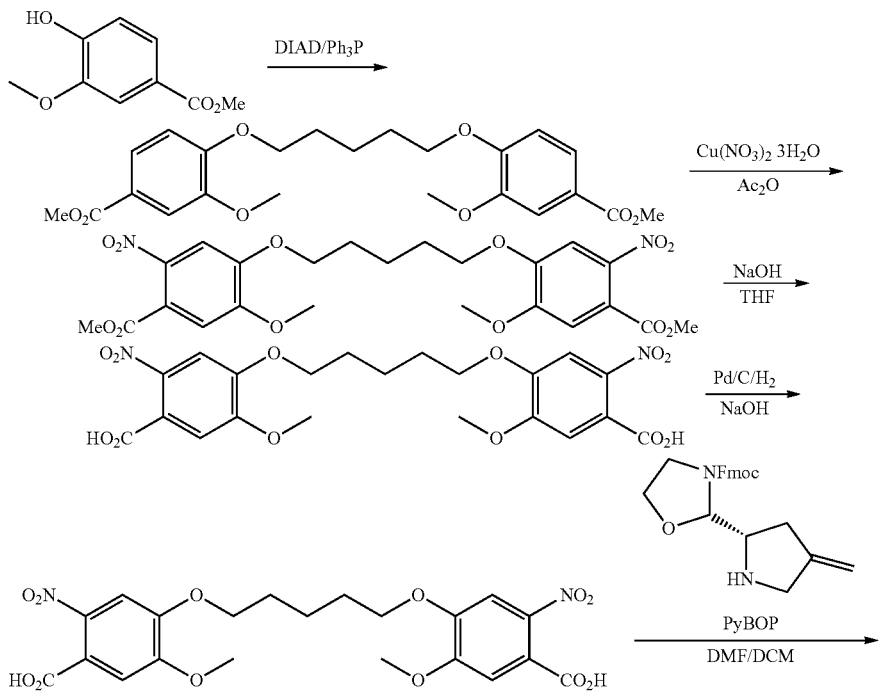

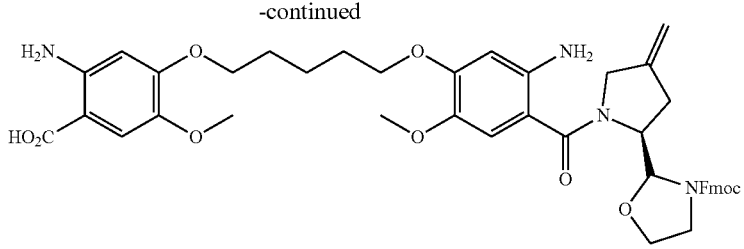
Example: Process for Preparing proPBD-SN-38
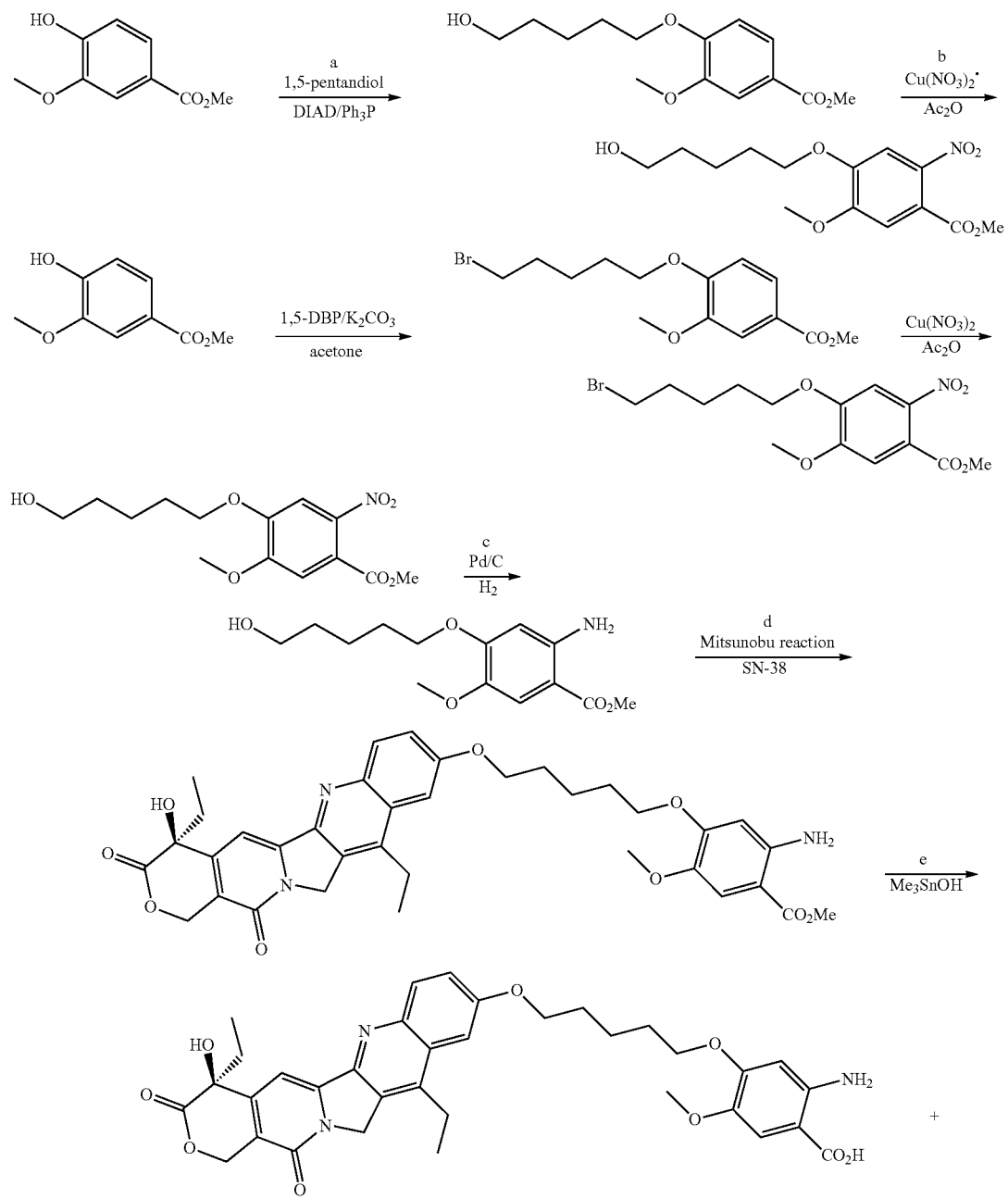

117 118
-continued
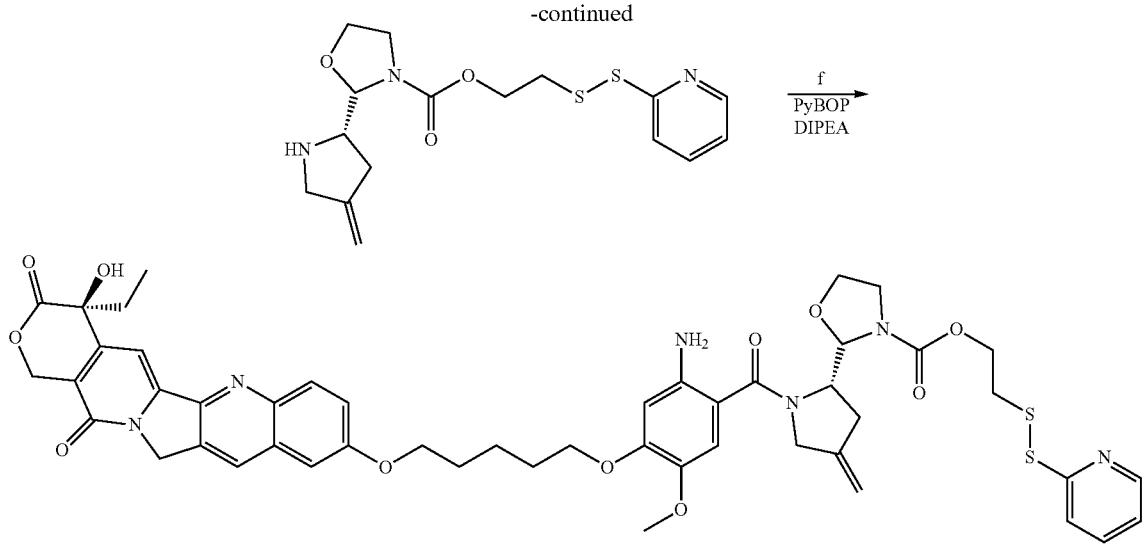
f
PyBOP
DIPEA
Example: Process for Preparing EC1879
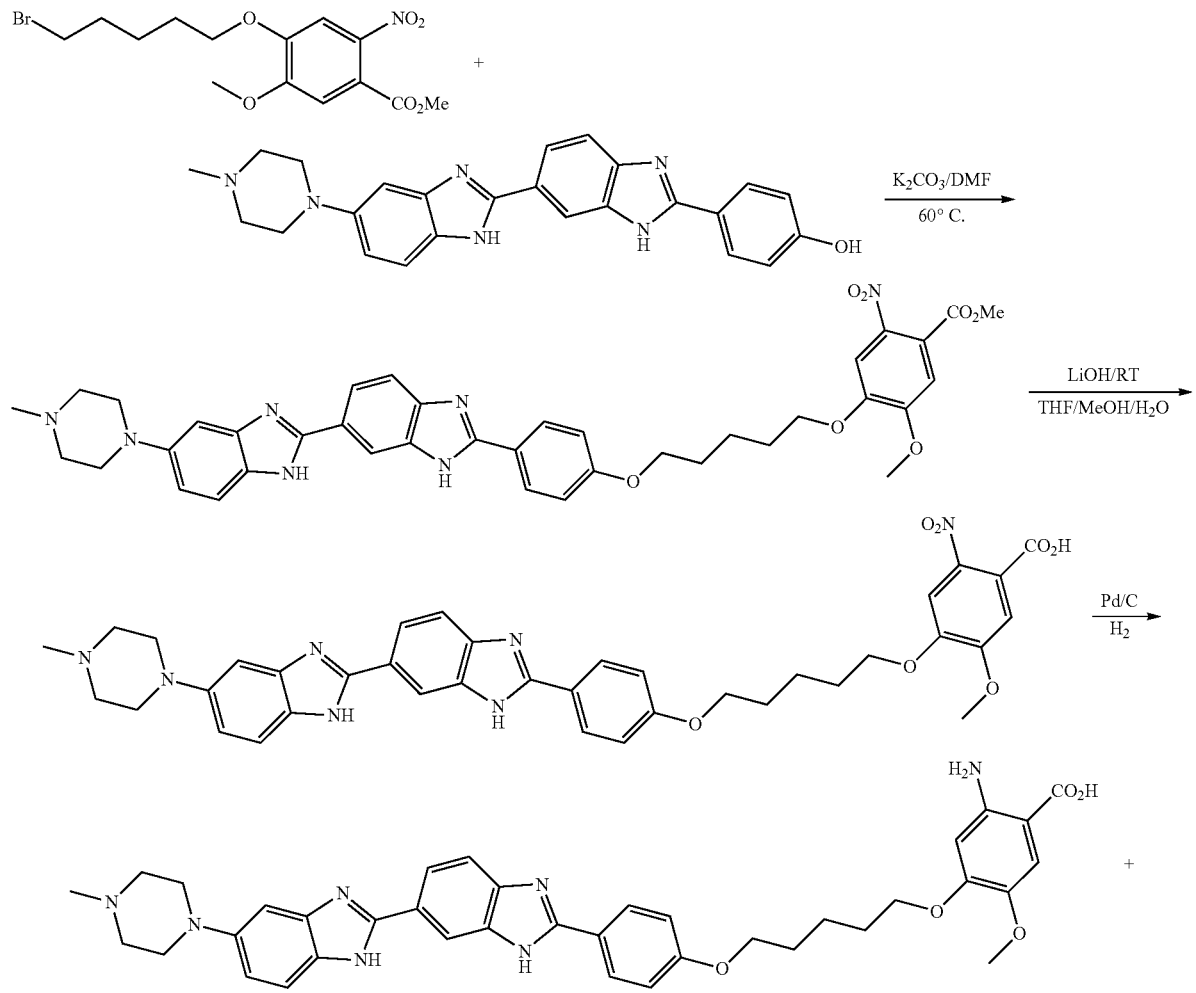

-continued
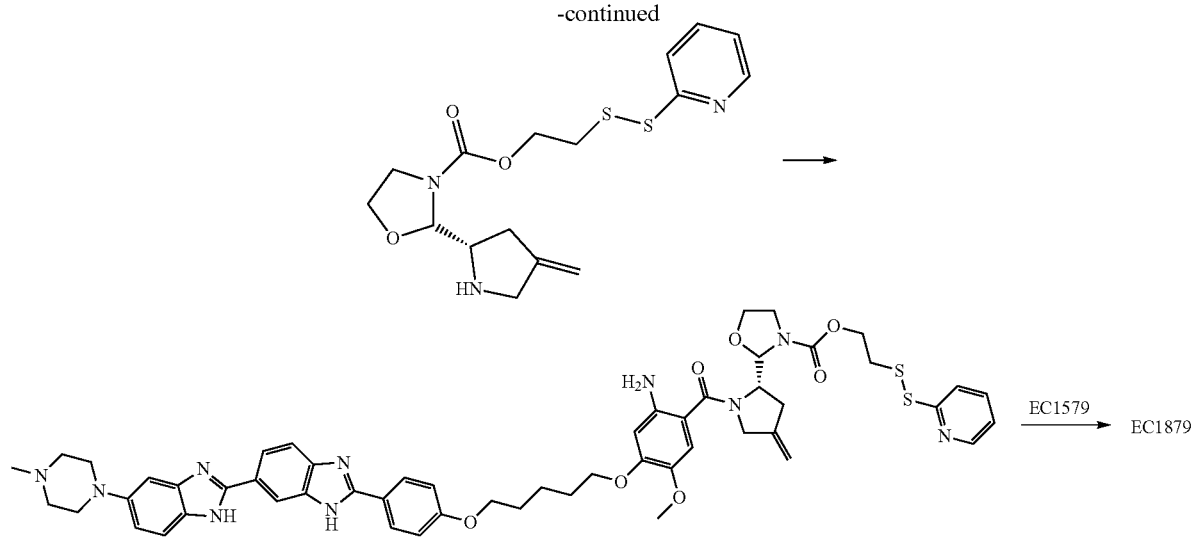
Example: Process for Preparing EC1884
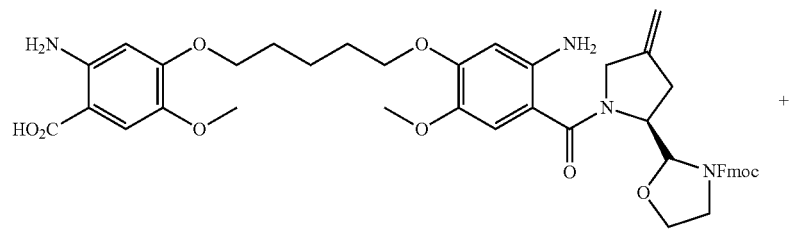
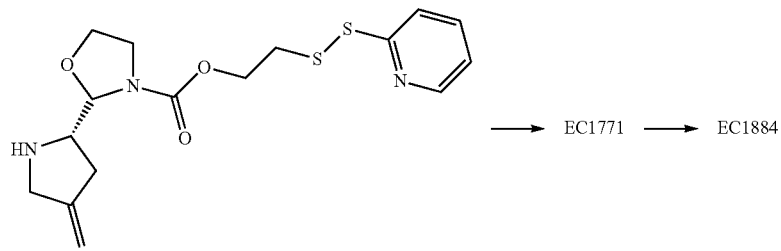
Example: Process for Preparing MC-VA-PAB Linked proPBD-FmocPBD
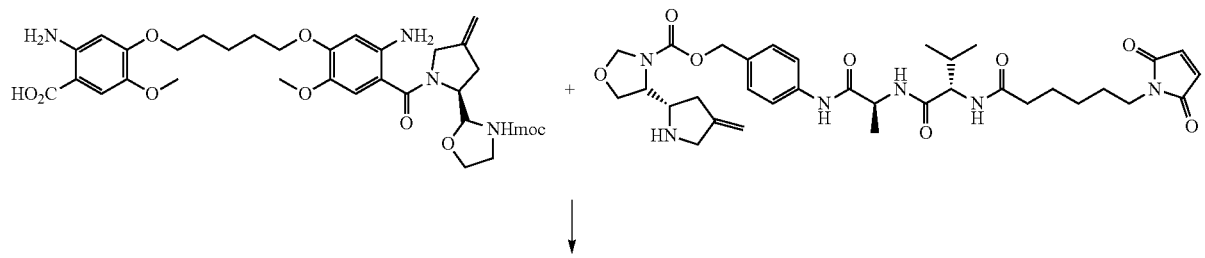

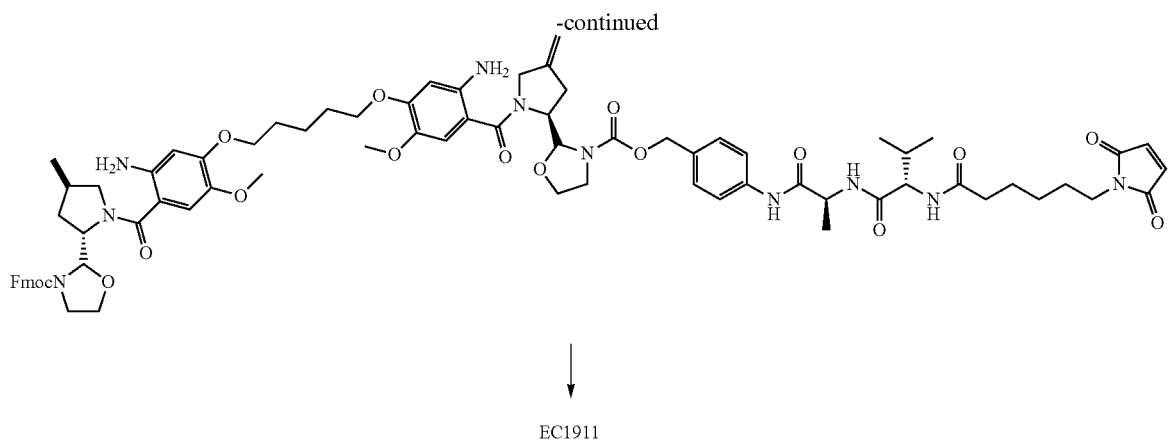

EC1911

Example: Processes for Modification of Enantiomers of Proline Derivatives

It is to be further understood that the processes described herein for particular example conjugates are illustrative of the general processes, and each may be adapted for preparing other example conjugates described herein. For example, it is to be understood that the corresponding preparations using D-proline, L-proline, or proline of varying optical mixtures, including racemic proline, is also described herein. For example, olefination and reduction of D-proline, L-proline, or proline is described herein as follows:

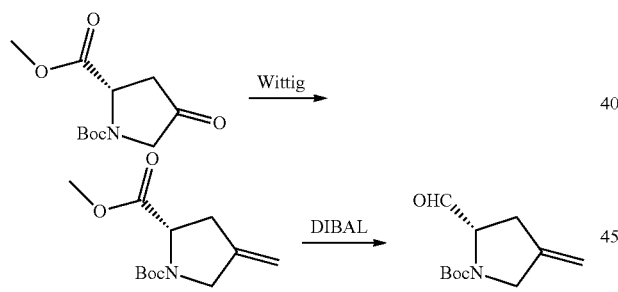

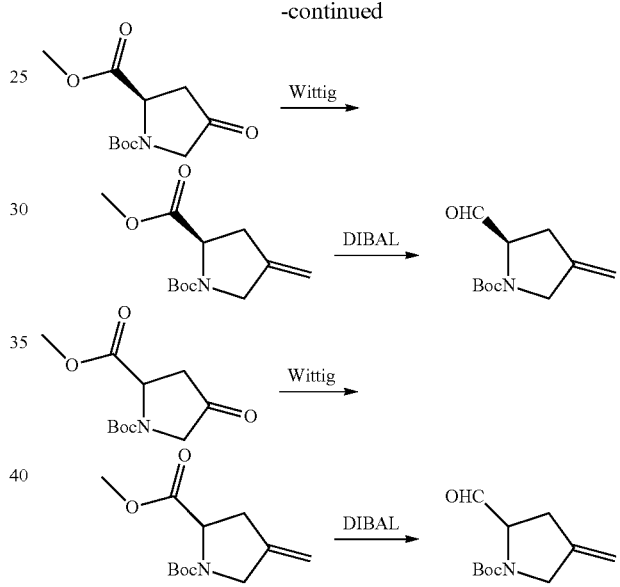

Example: Synthesis of EC2177

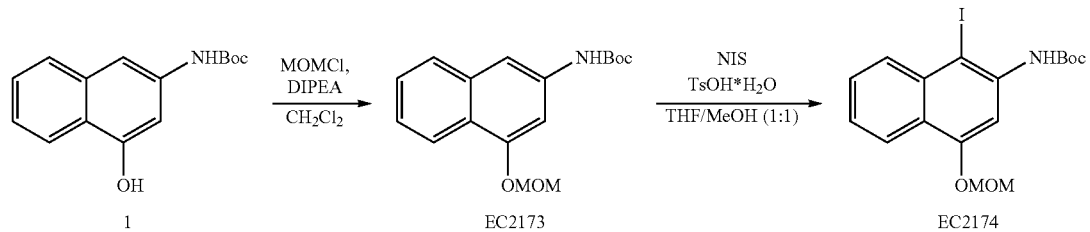

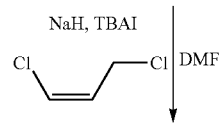

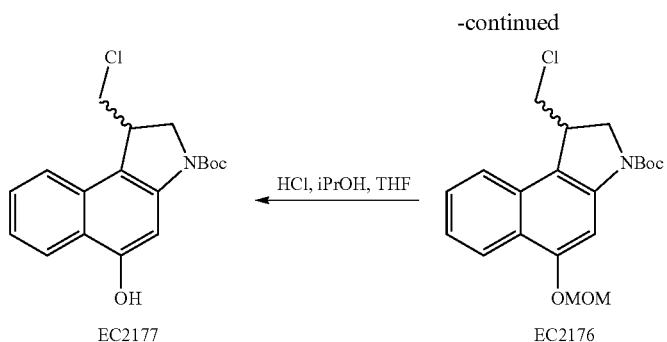

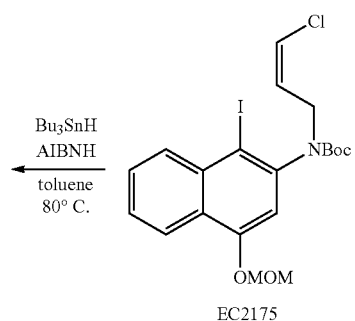

MOM ether EC2173 was synthesized in 58% yield following the procedure described in Boger, D. L.; Hughes, T. V.; Hedrick, H. P. *J. Org. Chem.* 2001, 66, 2207-2216. $^1$H NMR (500 MHz, CDCl$_3$): δ 8.20-8.09 (m, 1H), 7.74-7.66 (m, 1H), 7.43 (ddd, J=8.3, 6.8, 1.3 Hz, 1H), 7.35 (ddd, J=8.2, 6.8, 1.2 Hz, 1H), 7.05 (d, J=2.0 Hz, 1H), 6.90-6.82 (m, 1H), 6.72 (s, 1H), 5.36 (s, 2H), 3.53 (s, 3H), 1.54 (s, 9H). [M+H]$^+$=Calculated 304.16, found 304.1.

EC2174 was synthesized in 54% yield following the procedure described in Boger, D. L.; Hughes, T. V.; Hedrick, H. P. *J. Org. Chem.* 2001, 66, 2207-2216. $^1$H NMR (500 MHz, CDCl$_3$): δ 8.21 (dd, J=8.4, 1.3 Hz, 1H), 8.10-7.98 (m, 2H), 7.54 (ddd, J=8.5, 6.8, 1.4 Hz, 1H), 7.42 (ddd, J=8.2, 6.8, 1.1 Hz, 1H), 7.32-7.16 (m, 1H), 5.46 (s, 2H), 3.58 (s, 3H), 1.59 (s, 9H). [M+H]$^+$=Calculated 430.05, found 430.08.

Allyl chloride EC2175 was synthesized in 48% yield following the procedure described in Boger, D. L.; Hughes, T. V.; Hedrick, H. P. *J. Org. Chem.* 2001, 66, 2207-2216. $^1$H NMR (500 MHz, CDCl$_3$): δ 8.30-8.14 (m, 2H), 7.64-7.45 (m, 2H), 6.99 (s, 1H), 6.18-6.03 (m, 2H), 5.37 (s, 2H), 4.68-4.55 (m, 1H), 4.31 (dd, J=15.8, 6.8 Hz, 1H), 3.53 (s, 3H), 1.35 (s, 9H). [M+H]$^+$=Calculated 504.05, found 504.06.

EC2176 was synthesized in 78% yield following the procedure described in Boger, D. L.; Hughes, T. V.; Hedrick, H. P. *J. Org. Chem.* 2001, 66, 2207-2216. $^1$H NMR (500 MHz, CDCl$_3$): δ 8.29-8.20 (m, 1H), 7.92 (s, 1H), 7.67 (dd, J=24.1, 8.3 Hz, 1H), 7.49 (dddd, J=16.4, 8.3, 6.8, 1.3 Hz, 1H), 7.35 (tdd, J=8.2, 7.5, 1.2 Hz, 1H), 5.42 (s, 2H), 4.15 (ddd, J=22.0, 15.5, 10.1 Hz, 1H), 4.00-3.88 (m, 1H), 3.75-3.66 (m, 1H), 3.56 (d, J=1.5 Hz, 3H), 1.63 (s, 9H). [M+H]$^+$=Calculated 378.15, found 378.15.

EC2177 was synthesized in 64% yield following the procedure described in Boger, D. L.; Hughes, T. V.; Hedrick, H. P. *J. Org. Chem.* 2001, 66, 2207-2216. $^1$H NMR (500 MHz, CDCl$_3$): δ 8.20 (t, J=8.2 Hz, 1H), 7.81 (s, 1H), 7.65 (dd, J=24.5, 8.4 Hz, 1H), 7.53-7.41 (m, 1H), 7.37-7.28 (m, 1H), 4.22-4.05 (m, 1H), 4.00-3.87 (m, 1H), 3.83-3.64 (m, 1H), 1.61 (d, J=6.3 Hz, 9H).

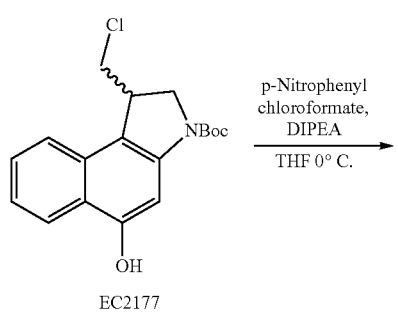

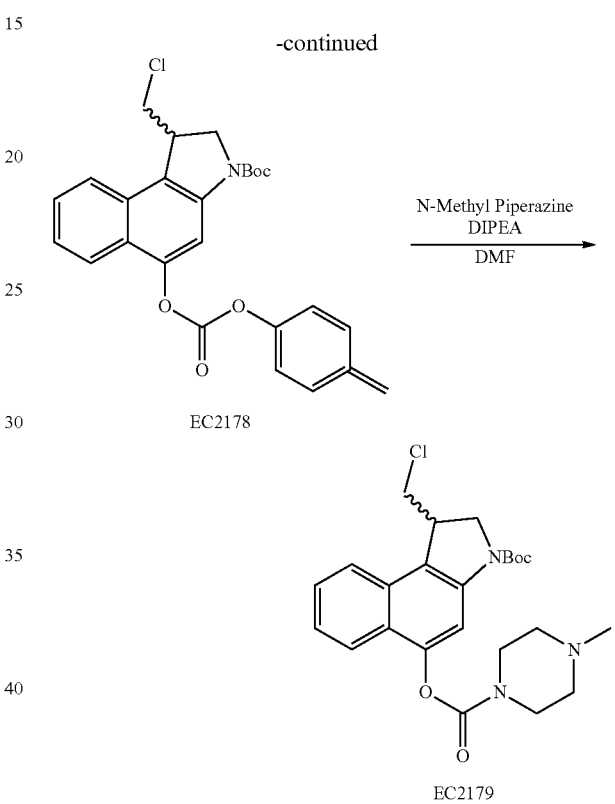

EC2178 was synthesized following the procedure described Wang, Y.; Li, L.; Tian, Z.; Jiang, W.; Larrick, J. W. *Bioorg. Med. Chem.* 2006, 14, 7854-7861. $^1$H NMR (500 MHz, CDCl$_3$): δ 8.24-8.17 (m, 2H), 8.15 (dd, J=9.2, 2.5 Hz, 2H), 7.49-7.42 (m, 2H), 7.42-7.34 (m, 1H), 7.28-7.20 (m, 1H), 4.34-4.18 (m, 1H), 4.15-4.03 (m, 1H), 3.97 (td, J=9.2, 3.8 Hz, 1H), 3.91-3.82 (m, 1H), 3.53-3.41 (m, 1H), 3.36-3.23 (m, 1H), 1.56 (s, 9H). [M+H]$^+$=Calculated 499.12, found 499.02.

EC2179 was synthesized following the procedure described in Wang, Y.; Li, L.; Tian, Z.; Jiang, W.; Larrick, J. W. *Bioorg. Med. Chem.* 2006, 14, 7854-7861. $^1$H NMR (500 MHz, CDCl$_3$): δ 7.88 (s, 1H), 7.75 (d, J=8.4 Hz, 1H), 7.57 (d, J=8.3 Hz, 1H), 7.37 (ddd, J=8.2, 6.7, 1.2 Hz, 1H), 7.30-7.22 (m, 1H), 4.23-4.08 (m, 1H), 4.01 (dd, J=11.8, 8.7 Hz, 1H), 3.95-3.84 (m, 1H), 3.81 (dd, J=11.1, 3.3 Hz, 1H), 3.74 (s, 2H), 3.54 (s, 2H), 3.37 (t, J=10.7 Hz, 1H), 2.47-2.33 (m, 4H), 2.27 (s, 3H), 1.50 (s, 9H). [M+H]$^+$=Calculated 460.98, found 460.20.

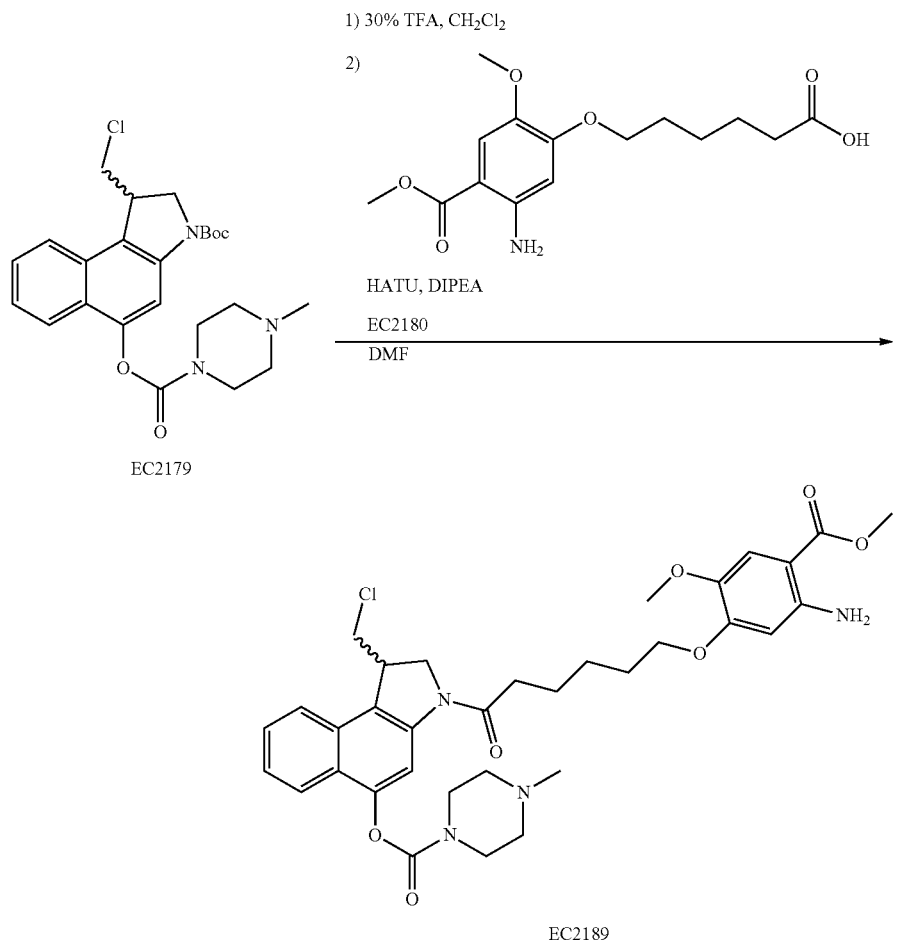
EC2189 was prepared as described herein. $^1$H NMR (500 MHz, CDCl$_3$): δ 8.37 (s, 1H), 7.87 (d, J=8.4 Hz, 1H), 7.71 (d, J=8.4 Hz, 1H), 7.52 (ddd, J=8.1, 6.7, 1.2 Hz, 1H), 7.41 (ddd, J=8.0, 6.8, 1.1 Hz, 1H), 7.06 (d, J=1.9 Hz, 1H), 7.01 (d, J=1.9 Hz, 1H), 4.37-4.18 (m, 2H), 4.06 (t, J=6.5 Hz, 3H), 3.95 (dd, J=11.2, 3.3 Hz, 1H), 3.86 (s, 3H), 3.85 (s, 3H), 3.69-3.62 (m, 2H), 3.45 (t, J=10.9 Hz, 1H), 2.56 (dt, J=24.1, 17.9 Hz, 6H), 2.40 (s, 3H), 1.84 (p, J=6.9 Hz, 5H), 1.67-1.56 (m, 2H). [M+H]$^+$=Calculated 653.28, found 653.29.
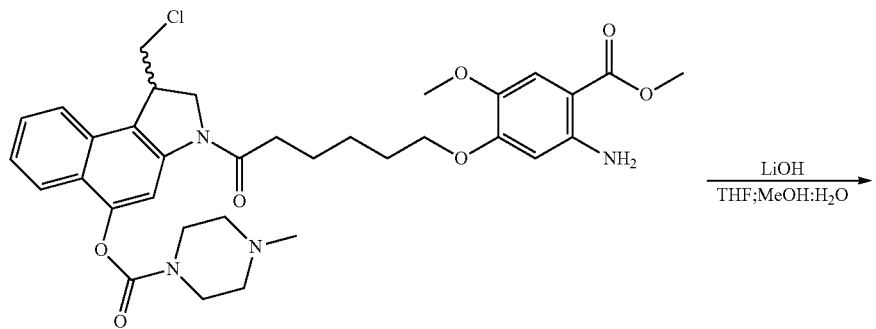

-continued

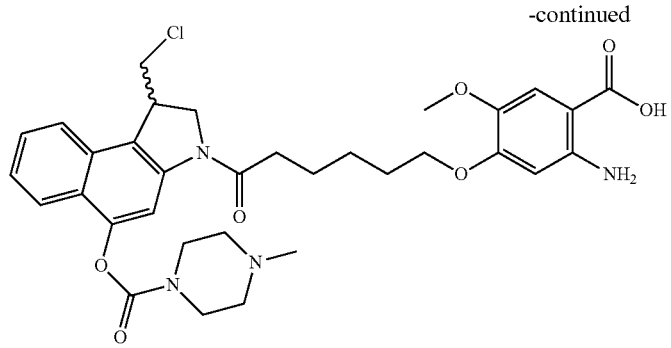
EC2190

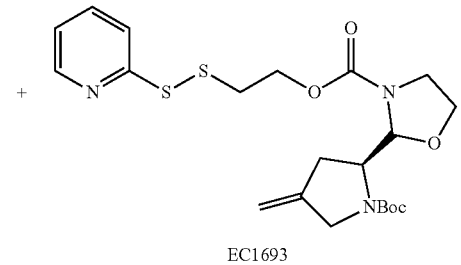
EC1693

1) 50% TFA
2) PyBop, DIPEA, DMF

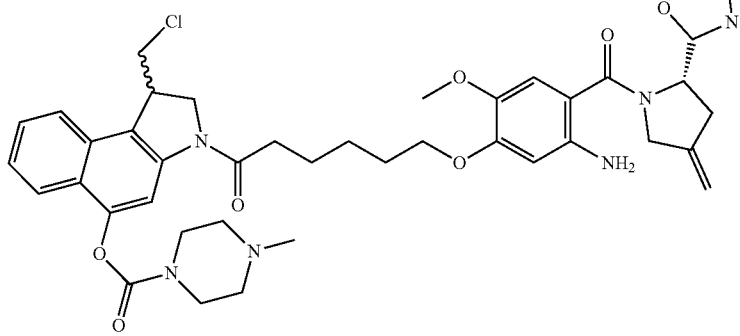
EC2191

To ester EC2189 (72 mg, 0.11 mmol) in a THF/MeOH/H$_2$O (3:1:1, 1 ml) was added LiOH (1.1 ml, 1.1 mmol). The reaction was allowed to stir at room temperature and monitored by LCMS. Upon completion the reaction mixture was acidified to pH 2 with 1M HCl and the volatile solvents were removed via reduced pressure. The product was purified by low pressure chromatography using C18 stationary phase and eluting with H$_2$O and acetonitrile, followed by lyophilization to yield the desired acid EC2190 (42 mg, 60%) as a colorless oil. $^1$H NMR (500 MHz, CDCl$_3$) Pivotal signals: δ 8.31-8.20 (m, 1H), 7.81-7.72 (m, 1H), 7.66 (d, J=8.4 Hz, 1H), 7.52-7.41 (m, 1H), 7.40-7.30 (m, 1H), 7.11-7.01 (m, 1H), 7.01-6.92 (m, 1H), 4.22 (dd, J=23.9, 10.0 Hz, 3H), 4.07-3.91 (m, 4H), 3.90-3.81 (m, 2H), 3.78 (s, 3H). [M+H]$^+$=Calculated 639.26, found 639.30.

Boc amine EC1693 (21 mg, 44.1 mol) was dissolved in a 50:50 TFA:CH$_2$Cl$_2$ solution and stirred for 30 mins. The solvent was removed in vacuo and the residue was taken in saturated NaHCO$_3$ and extracted with ethyl acetate three times. The organic extracts were combined, dried over Na$_2$SO$_4$, filtered and the solvent was removed to yield the amine. The crude amine was dissolved in DMF (2 ml) and transferred onto acid EC2190 (18.8 mg, 29.4 μmol) under Argon atmosphere. To the solution were added PyBOP (33.6 mg, 64.7 μmol), DIPEA (31.5 μl, 0.177 mmol) and left to stir for 5 hours. Upon completion, the reaction was diluted with water (10 ml), saturated NH$_4$Cl (10 ml) and extracted with ethyl acetate three times. The organic extracts were combined, dried over Na$_2$SO$_4$, filtered and the solvent was removed via reduced pressure. The product was purified using silica gel chromatography with dichloromethane and methanol as the eluent to yield the desired amide EC2191 (23 mg, 79%). $^1$H NMR (500 MHz, CDCl$_3$) Pivotal signals: δ 8.36 (s, 1H), 8.26 (s, 1H), 7.77 (d, J=8.4 Hz, 1H), 7.67-7.50 (m, 3H), 7.43 (t, J=7.6 Hz, 1H), 7.33 (t, J=7.6 Hz, 1H), 7.29-7.20 (m, 2H), 7.07-6.94 (m, 1H), 6.42 (t, J=15.6 Hz, 1H), 5.14-4.77 (m, 3H), 4.34-4.14 (m, 3H), 3.73 (s, 3H), 2.42 (s, 3H), 2.30-2.10 (m, 1H). [M+H]$^+$=Calculated 988.35, found 988.45.

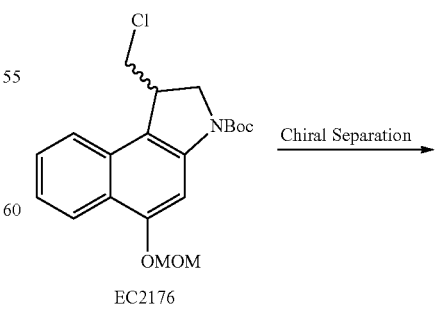
EC2176 →Chiral Separation

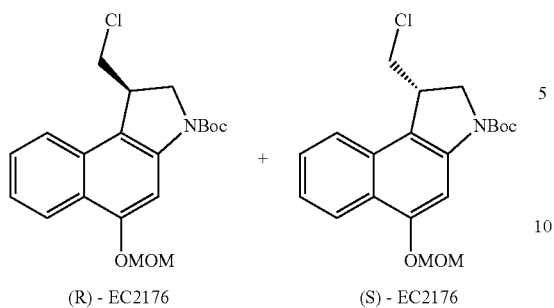
EC2176 was separated into (R)-EC2176 and (S)-EC217 using Normal phase HPLC on Chiral Stationary Phase was used for chiral separation of racemic EC 2176. Conditions as follows: Column Name: (S,S)-Whelk-01, Column Size: 250 mm×4.6 mm, Mobile Phase: Hexane/IPA (70/30).
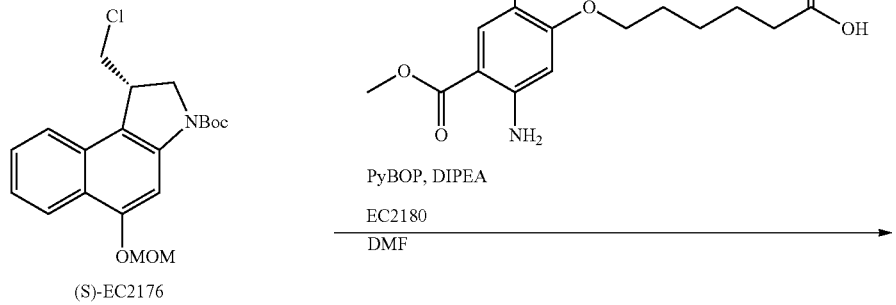
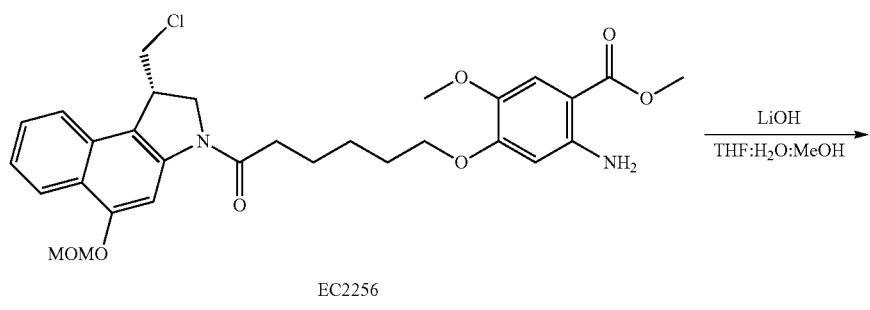

-continued

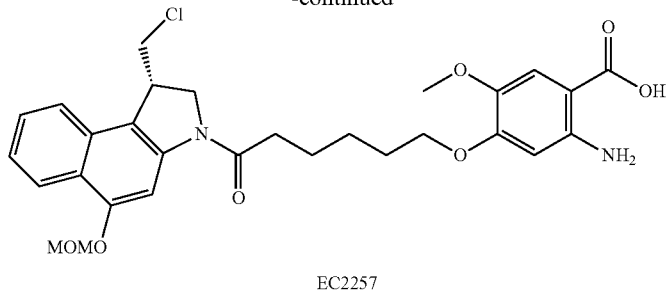

EC2257

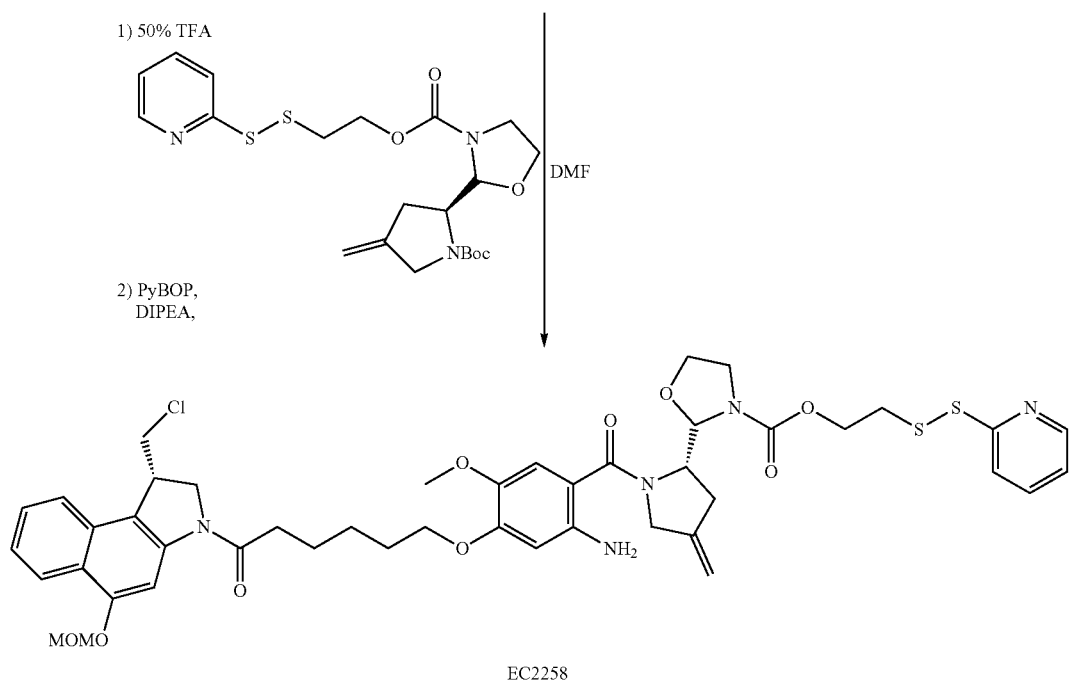

EC2258

Boc amine, (S)-EC2176 (49 mg, 0.13 mmol) was dissolved in a 30% TFA in CH$_2$Cl$_2$ solution (5 ml) at 0° C. and let stir for 3 hr. LCMS was used to monitor the reaction until complete deprotection. The reaction mixture was quenched with saturated NaHCO$_3$ and extracted three times with ethyl acetate. The organic extracts were combined, dried over Na$_2$SO$_4$, filtered and the solvent was removed under vacuum to yield the crude amine. The amine and EC2180 (40 mg, 0.13 mmol) were dissolved in DMF (1 ml) under Agron atmosphere. To the reaction mixture, PyBOP (134 mg, 0.26 mmol) was added followed by DIPEA (0.114 ml, 0.65 mmol) and the reaction mixture was stirred for 5 hours. The reaction mixture was quenched with saturated NH$_4$Cl and extracted three times with ethyl acetate. The organic extracts were combined, dried over Na$_2$SO$_4$, filtered, the solvent was removed under vacuum and EC2256 was purified using silica gel chromatography to yield the desired amide (20 mg, 28%). [M+H]$^+$=Calculated 571.21, found 571.30.

Ester EC2256 (19 mg, 0.033 mmol) was dissolved in a 3:1:1 mixture of THF:H$_2$O:MeOH (1 ml) and LiOH (0.33 ml, 0.33 mmol) was added. The reaction was monitored until full conversion was complete. The organic solvents were removed under vacuum and the crude product was purified by low pressure chromatography using C18 stationary phase and eluted with H$_2$O and ACN. Fractions of the desired product were combined, CAN was removed, the aqueous layer was extracted with ethyl acetate, dried over Na$_2$SO$_4$ and concentrated to yield acid EC2257 (17.5 mg, 94%). [M+H]$^+$=Calculated 558.03, found 557.31.

Boc amine, EC1693 (19 mg, 0.04 mmol) was dissolved in a 50% TFA in CH$_2$Cl$_2$ solution (5 ml) at 0° C. and stirred for 3 hr. LCMS was used to monitor the reaction until deprotection was complete. The reaction mixture was quneched with saturated NaHCO$_3$ and extracted three times with ethyl acetate. The organic extracts were combined, dried over Na$_2$SO$_4$, filtered and the solvent was removed under vacuum to yield the crude amine. The amine and EC2257 (17.5 mg, 0.03 mmol) were dissolved in DMF (1 ml) under Argon atmosphere. To the reaction mixture, PyBOP (36 mg, 0.07 mmol) was added followed by DIPEA (0.033 ml, 0.19 mmol), and the reaction mixture was stirred for 5 hours. The reaction mixture was quenched with saturated NH$_4$Cl and extracted three times with ethyl acetate. The organic extracts were combined, dried over Na$_2$SO$_4$, filtered, the solvent was removed under vacuum and the crude product was purified using silica gel chromatography to yield the desired amide EC2258 (22 mg, 77%). [M+H]$^+$=Calculated 906.29, found 906.47. (SEQ ID NOS 1 and 1 are included in the structures below)

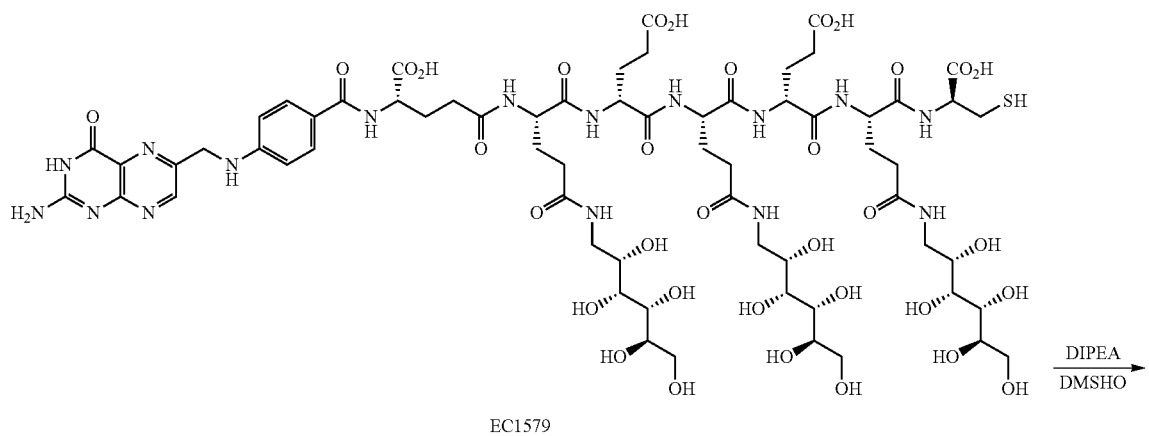

EC1579

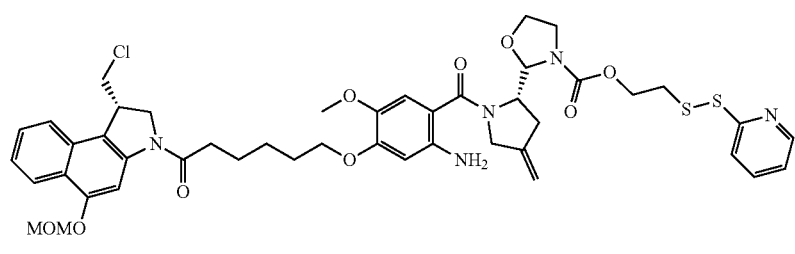

EC2258

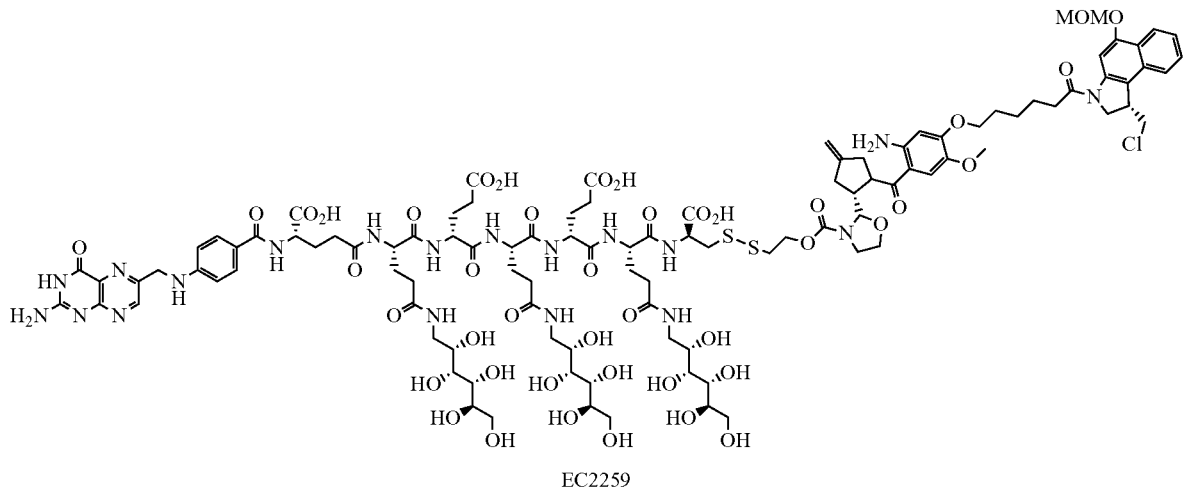

EC2259

EC2259: Disulfide EC2258 (15 mg, 0.017 mmol) and the folate spacer EC1579 (36.6 mg, 0.022 mmol) were dissolved in anhydrous DMSO under argon. DIPEA (18 μl, 0.1 mmol) was added to the reaction mixture and stirred for 2 hours. The crude product was purified by low pressure chromatography using C18 stationary phase and eluted with Ph7 buffer and acetonitrile, followed by lyophilization to produce conjugate EC2259 (12.4 mg, 30%). [M+H]$^+$=Calculated 2473.89, 1237.94, found 1238.19. (SEQ ID NOS 1 and 1 are included in the structures below)

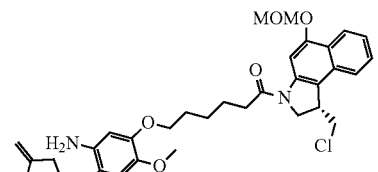

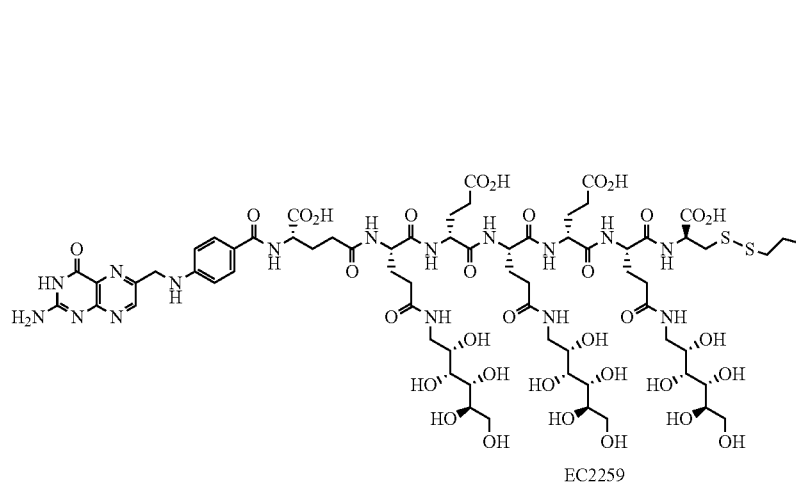

EC2259

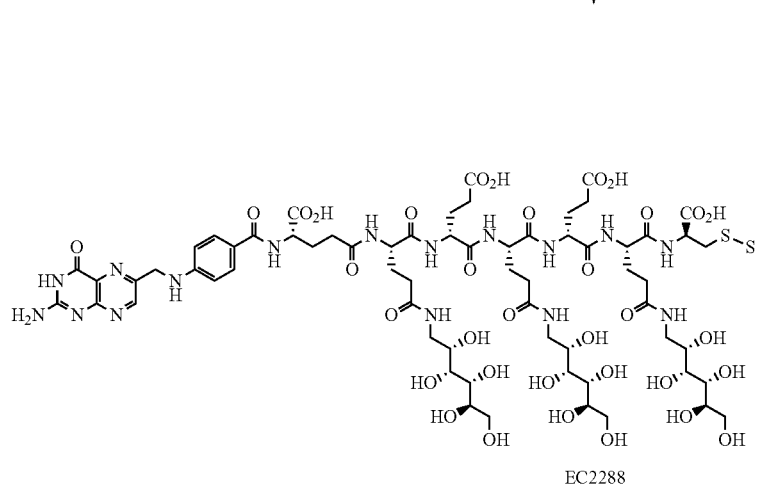

EC2288

EC2259 (7 mg, 2.83 µmol) was dissolved in DI H₂O (3 ml) with the addition of conc. HCl (6 drops). The reaction was monitored until deprotection was complete and the product purified by low pressure chromatography using C18 stationary phase and eluted with H₂O and acetonitrile, followed by lyophilization to yield the desired conjugate EC2288 (5.5 mg, 80%). [M+H]⁺=Calculated 2429.86, 1215.93, found 1215.88.

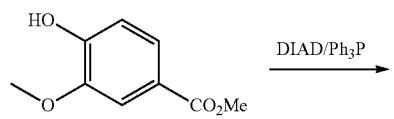

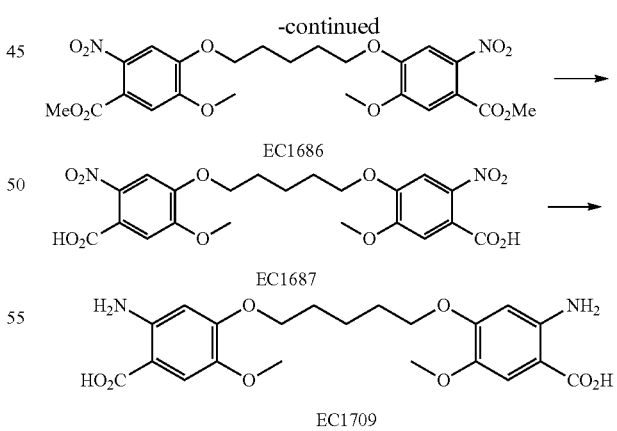

Methyl vanillate (2.18 g, 11.98 mmol) and Ph₃P (4.71 g, 17.97 mmol) in THF (20 mL) was cooled to 0° C. and to which was added DIAD (2.59 mL, 13.18 mmol) dropwise. The reaction was stirred at 0° C. for 1 hr. 1,5-petanediol (0.6 mL, 5.75 mmol) in THF (20 mL) was added over 30 min. The reaction was stirred overnight and prESlpitate formed and was collected with filtration. The filtrate was concentrated to form more solid. The solid was combined and triturated with MeOH (5 mL) to give qite clean product EC1624 1.74 g in yield of 70%. $^1$H NMR (CDCl$_3$, δ in ppm): 7.66 (m 2H), 7.62 (m, 2H), 6.87 (m, 2H), 4.10 (m, 4H), 3.89 (m, 12H), 1.95 (m, 4H), 1.69 (m, 2H). $^{13}$C NMR: 166.88, 152.50, 148.86, 132.12, 132.04, 131.88, 128.52, 128.42, 123.50, 122.55, 112.35, 111.46, 68.67, 56.03, 51.93, 28.73, 22.52, 21.92.

EC1624 (201.2 mg, 0.465 mmol) in Ac$_2$O (1.2 mL) was cooled to 0° C. and then Cu(NO$_3$)$_2$.3H$_2$O (280.3 mg, 1.16 mmol) was added slowly and after 1 hr, the ice-bath was removed. The reaction was stirred at r.t. for 4 hrs. The reaction was poured into ice water and stirred for 1 h till yellow precipitate formed and was collected with filtration. The solid was washed with more cold water (2 mL, 3×) and air-dried. 198.4 mg of EC1686 was obtained in yield of 82%. LCMS: [M+NH$_4$]$^+$ m/z=540.

EC1686 (198.4 mg) was dissolved in THF (2 mL) and treated with aq. NaOH (2 mL, 1 M) and heated to 40° C. for 3 hrs. The solvent was removed in vacuo. The aqueous phase was acidified to pH 1 with concentrated HCl to form precipitate, which was collected by filtration and was washed with H$_2$O (1 mL, 3×). The solid was air-dried to give the acid 187.7 mg of EC1687 in quantitative yield. LCMS: [M+NH$_4$]$^+$ m/z=512.

Acid EC1687 was dissolved in 0.5 M aq. NaOH (6 mL) and hydrogenation was carried out with Pd/C (10%, 4.82 mg) under H$_2$ (45 PSI) in the hydrogenation parr. The reaction was shook for 5 hrs and the filtered through a pad of celite and the filtrate was adjusted to pH 2-3 with concentrated HCl while stirring. The formed precipitate was isolated by filtration and washed with H$_2$O (1 mL, 3×). The solid was dried in a desiccator with the presence of P$_2$O$_5$ under high vacuum overnight. EC1709 was obtained 34.2 mg as a brown solid in the yield of 81%. LCMS: [M−H]$^−$ m/z=433.

(S)-1-tert-butyl 2-methyl 4-oxopyrrolidine-1,2-dicarboxylate was converted to EC1692 by Wittig reaction: Ph$_3$PCH$_3$Br (917.8 mg, 2.57 mmol) in THF (30 mL) was treated with KO$^t$Bu (1 M in THF, 2.57 μL, 2.57 mmol) at 0° C. by dropwise addition. The reaction was kept at room temperature for 2 hrs. Into the stirred solution was added the ketone (250 mg, 1.028 mmol) in THF 20 mL) at 0-10° C. The reaction was then stirred at room temperature for onvernight. The reaction was quenched with H$_2$O/EtOAc (1:1, 40 mL) after most of the THF was removed in vacuo. The aq. phase was extracted with EtOAc (20 mL, 3×) and the organic phase was washed with H$_2$O, followed by brine, and dried over anhydrous Na$_2$SO$_4$ and concentrated. The residue was purified with CombiFlash in 0-50% EtOAc/p-ether to afford the EC1692 77.2 mg, in yield of 31%. LCMS: [M-Boc+H]$^+$ m/z=142.

(S)-1-tert-butyl 2-methyl 4-methylenepyrrolidine-1,2-dicarboxylate (353.2 mg, 1.46 mmol) in DCM/toluene (1:3, 9.8 mL) was treated with Dibal (1 M in toluene, 2 eq, 2.92 mmol) dropwise at −78° C. under argon. The reaction was stirred at −78° C. for ca. 4 hrs. Then the reaction was quenched with addition of 60 μL of MeOH at −78° C. followed by 5% HCl (0.5 mL) and EtOAc (18 mL). The cold bath was removed and the reaction was stirred for 30 min. The EtOAc layer was separated and washed with brine, dried over anhydrous Na$_2$SO$_4$ and concentrated to give the crude aldehyde intermediate.

The crude aldehyde was redissolved in dry DCM (10 mL) and treated with ethanolamine (106 μL, 1.75 mmol) in the presence of anhydrous MgSO$_4$ (5 mmol, mg) at r.t. (room temperature) under Ar. The reaction was stirred for 1 hr. Then into this reaction mixture was added FmocCl (755.4 mg, 2.92 mmol) and TEA (611 μL, 4.38 mmol) and the reaction was stirred for overnight at r.t. under Ar. The reaction was purified with CombiFlash in 0-50% EtOAc/petroleum ether to provide EC1768 334.2 mg, 46% for 3 steps. LCMS: [M+H]$^+$ m/z=477. $^1$H NMR (CD$_3$OD, δ in ppm):7.81 (d, J=7.5 Hz, 2H), 7.60 (d, J=7 Hz, 2H), 7.40 (m, 2H), 7.32 (m, 2H), 4.96 (br, 2H), 4.60 (br, 1H), 4.23 (t, J=5.5 Hz, 1H), 3.97 (br, 2H), 3.73 (br, m, 3H), 2.50 (br, 2H), 1.47 (s, 1H), 1.39 (s, 9H).

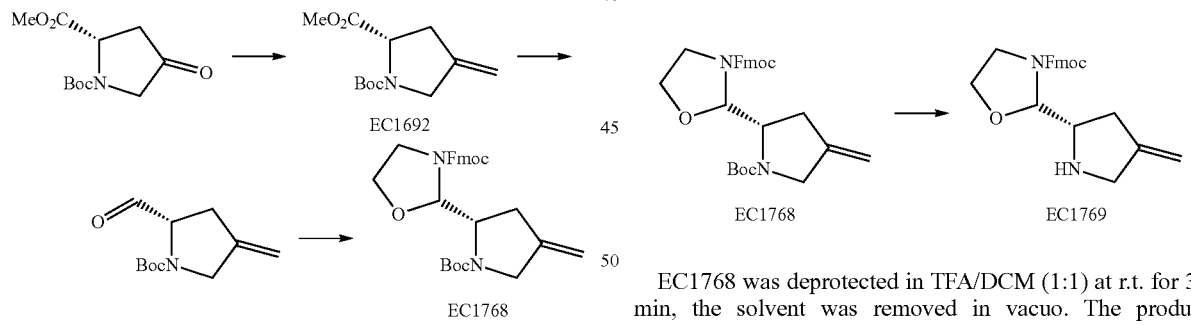

EC1768 was deprotected in TFA/DCM (1:1) at r.t. for 30 min, the solvent was removed in vacuo. The product (EC1769) was used for the coupling reaction with EC1709 without further purification. LCMS: [M+H]$^+$ m/z=377.

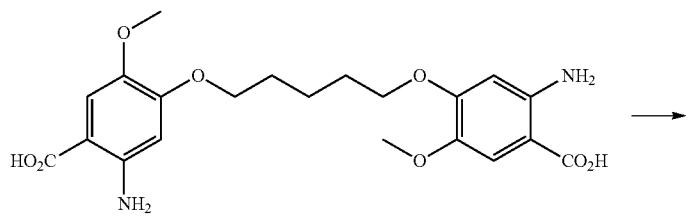

EC1709

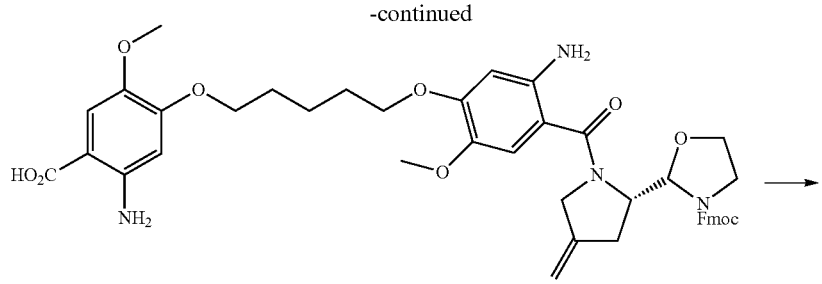

EC1770

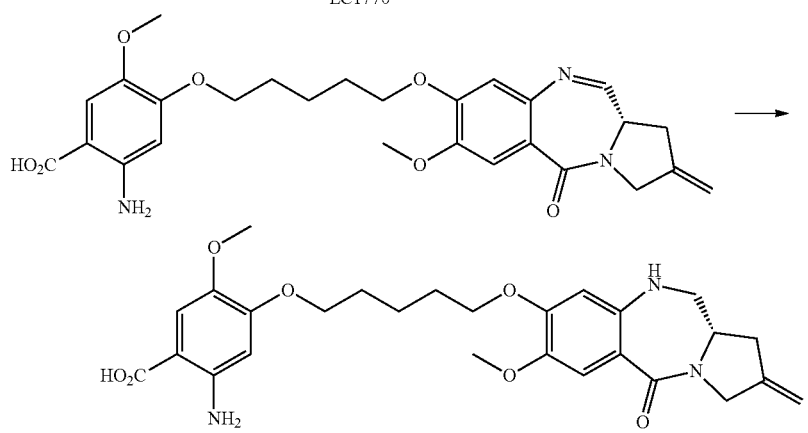

EC2170

EC1709 (42.0 mg, 0.097 mmol), EC1769 (0.053 mmol), and PyBOP (29.0 mg, 0.056 mmol) were dissolved in DMF/DCM (0.5 mL/0.5 mL) and treated with DIPEA (74 μL, 0.43 mmol) at r.t. under Ar. The reaction was completed within 1 hr, then loaded onto CombiFlash column in 0-20% MeOH/DCM to afford the pure product EC1770 (25.5 mg, 60%). LCMS: [M+H]$^+$ m/z=793. $^1$H NMR (CD$_3$OD, δ in ppm):

EC1770 (25.5 mg, 0.032 mmol) was dissolved in DCM (1 mL) was treated with diethylamine (DEA, 83.5 μL, 0.80 mmol) at r.t. under Ar. The reaction was stirred for 2 hrs, and then the solvent was removed in vacuo. This immine was redissolved in DCM (0.3 mL) and absolute ethanol (0.6 mL) and cooled to 0° C. To this cooled solution was added NaBH$_4$ (1.33 mg, 0.0352 mmol) and the reaction was stirred for 5 min at 0° C. then the ice bath was removed. The reaction was stirred at r.t. for 2 hrs. After EtOH was removed, the reaction mixture was purified with Combi-Flash in 0-15% MeOH/DCM to afford 9.9 mg of EC2170 (yield 60% for 2 steps). LCMS: [M−H]$^−$ m/z=510. $^1$H NMR (CD$_3$OD, δ in ppm): 7.41 (s, 1H), 7.31 (s, 1H), 6.32 (s, 1H), 6.26 (s, 1H), 5.07 (m, 2H), 4.27 (m, 2H), 4.00 (q, J=7 Hz, 4H), 3.75 (s, 3H), 3.73 (s, 3H), 3.57 (dd, J=1.5, 13 Hz, 1H), 2.98 (m, 1H), 2.49 (m, 1H), 1.88 (m, 4H), 1.68 (m, 2H).

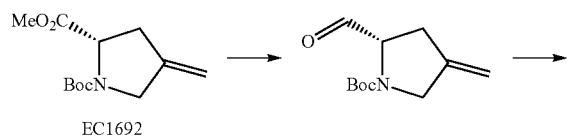

EC1692

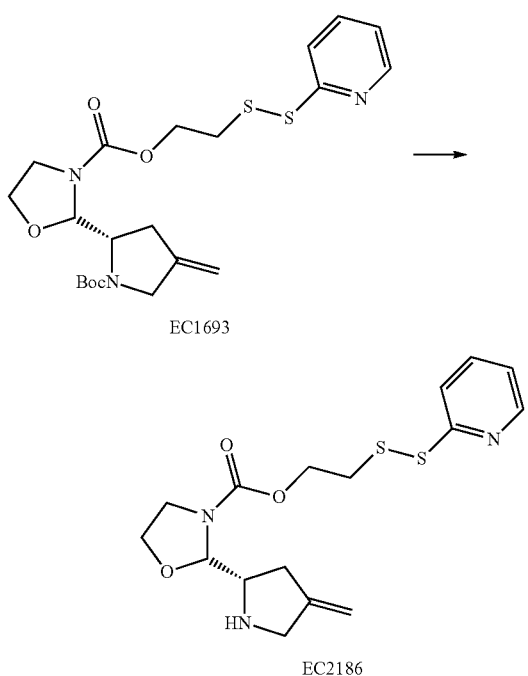

EC1693

EC2186

EC1693 was synthesized by the same methods as EC1768. LCMS: [M+H]$^+$ m/z=468. $^1$H NMR (CDCl$_3$, δ in ppm): 8.47 (d, J=5 Hz, 1H), 7.66 (m, 2H), 7.09 (m, 1H), 5.16 (br, 1H), 4.97 (br, 2H), 4.38 (br, 3H), 4.05 (br, 2H), 3.85 (br, 3H), 3.20 (m, 1H), 3.06 (br, 2H), 2.85 (br, 1H), 2.52 (m, 1H), 1.55 (s, 3H), 1.43 (s, 9H).

EC2186 was synthesized by the same methods as EC1769. LCMS: [M+H]$^+$ m/z=368.

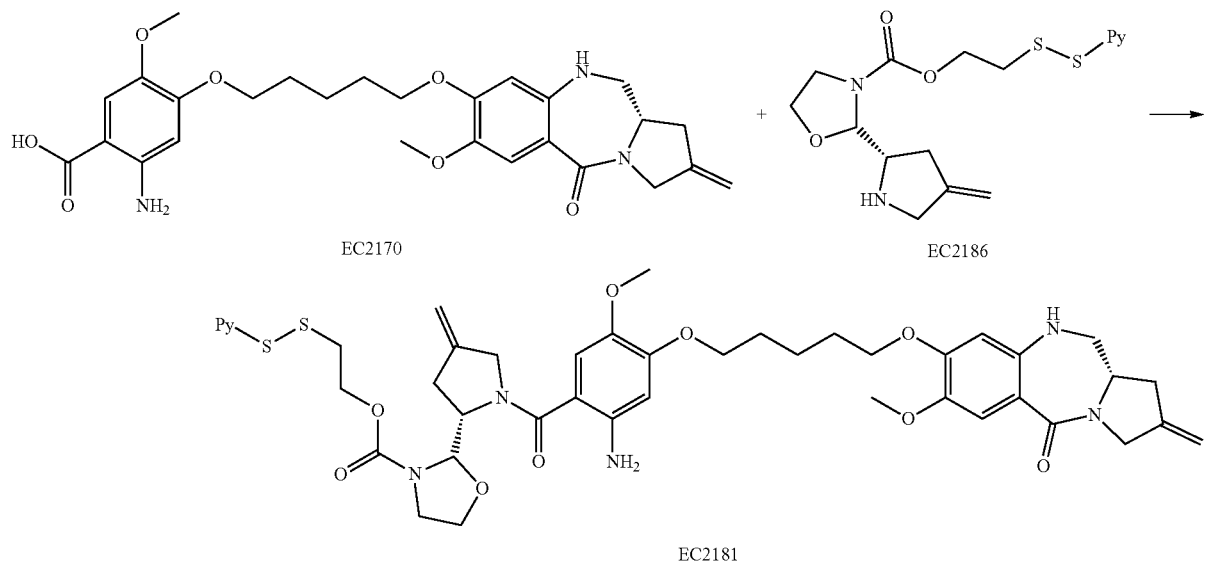

EC2181: Acid EC2170 (4.95 mg, 0.0097 mmol) was dissolved in dry DMF (0.5 mL) and was treated with PyBOP (10.1 mg, 0.0194 mmol). To the reaction mixture was added the solution of EC2186 (0.01 mmol, from 4.76 mg of EC1693) and DIPEA (30 µL, 0.17 mmol) in DCM (0.5 mL). The reaction was stirred for 5 hrs and was purified with prep-HPLC in 10-100% MeCN/pH7 buffer to give pure EC2181 2.3 mg (30% in yield). LCMS: [M+H]$^+$ m/z=861. $^1$H NMR (CD$_3$OD, δ in ppm):8.37 (s, 1H), 7.77 (m, 2H), 7.40 (s, 1H), 7.19 (s, 1H), 6.42 (s, 1H), 6.26 (s, 1H), 5.07 (m, 4H), 5.01 (s, 1H), 4.56 (d, J=1 Hz, 1H), 4.20 (m, 6H), 4.01 (m, 7H), 3.75 (s, 3H), 3.73 (s, 3H), 3.67 (d, J=11 Hz, 2H), 3.44 (m, 4H), 3.13 (br, 2H), 3.05 (m, 1H), 2.50 (, 3H), 2.48 (m, 2H), 1.85 (m, 3H) 1.26 (m, 4H). (SEQ ID NOS 1 and 1 are included in the structures below)

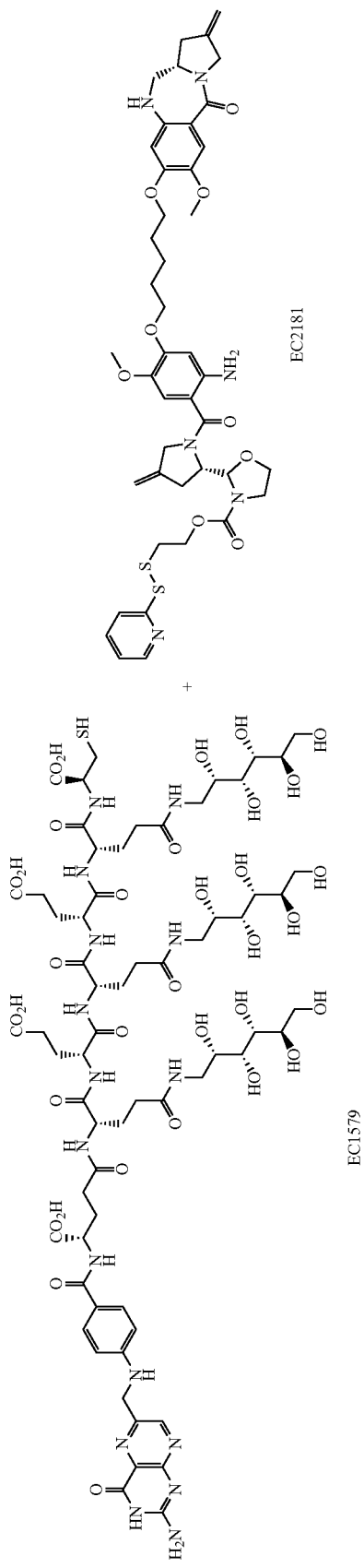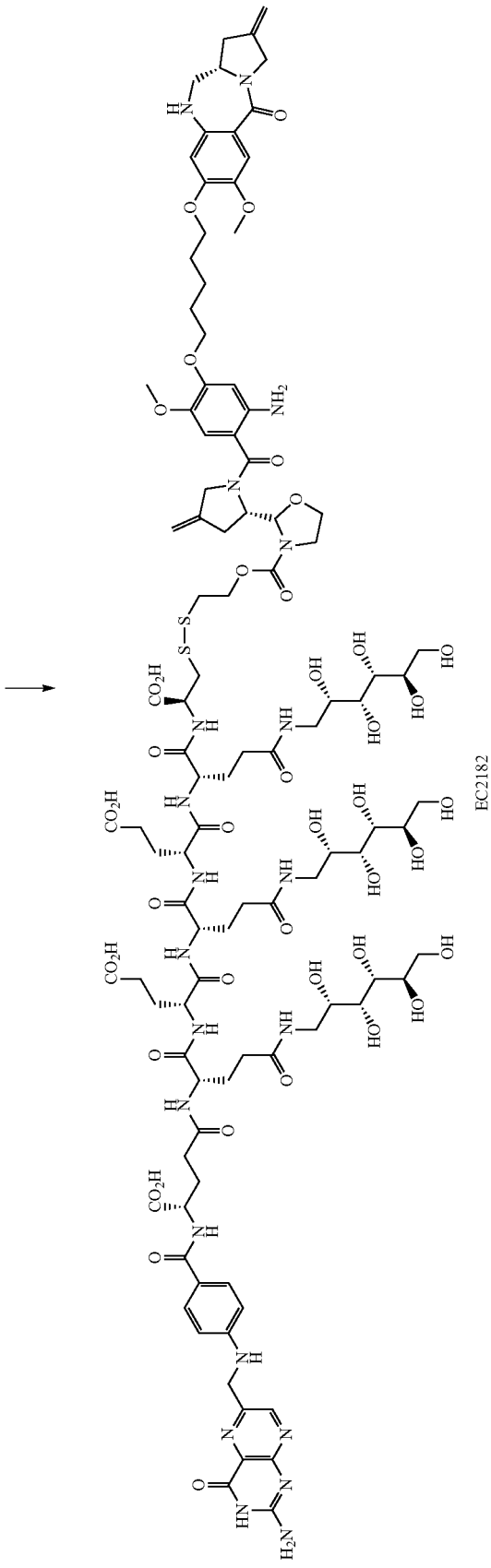

EC1579 (8.7 mg, 0.0052 mmol) in DMSO (0.5 mL) under Ar was stirred to a clear solution the solution of EC2181 (3.7 mg, 0.0043 mmol) in DMSO (0.5 mL) was added and followed by addition of TEA (3.6 μL, 0.026 mmol). The reaction was stirred for 1 hr at r.t. under Ar. The product was isolated with prep-HPLC in 10-100% MeCN/pH 7 buffer to give EC2182 6.5 mg (62% in yield) as a solid after lyophilized. LCMS: [M+3H]$^{3+}$ m/z=810. $^1$H NMR (9:1 DMSO-d6:D$_2$O, δ in ppm): 8.53 (s, 1H), 7.55 (d, J=8 Hz, 2H), 7.21 (s, 1H), 6.60 (d, J=7.5 Hz, 3H), 6.29 (s, 1H), 6.22 (s, 1H), 4.97 (s, 2H), 4.91 (s, 1H), 4.45 (s, 3H).

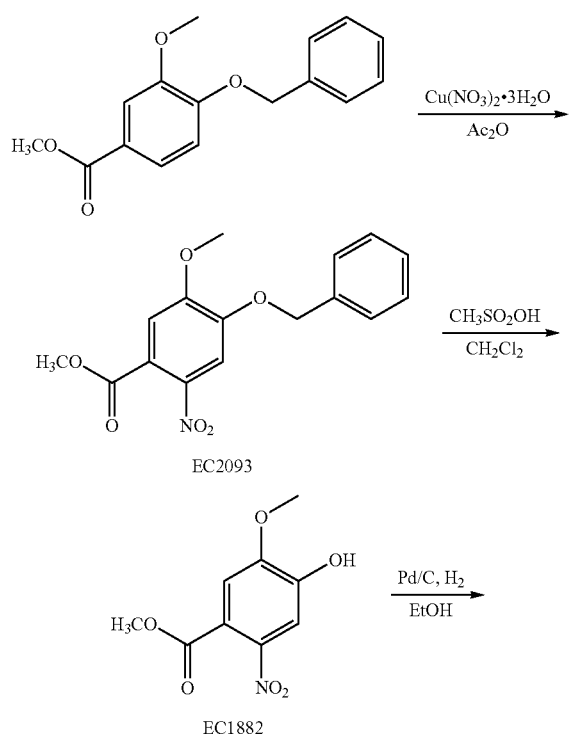

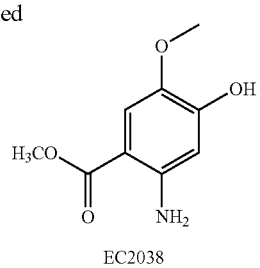

Methyl-4-Benzyloxy-3-methoxy Benzoate (5.00 g, 18.4 mmol) was dissolved in Ac$_2$O (23.5 mL) and cooled to 0° C. Cu(NO$_3$)$_2$ (5.05 g, 27.0 mmol) was added in small portions over 10 minutes. After 90 min, LCMS indicated product formation. The mixture was poured into ice-water and stirred for 45 minutes. Crude product was recovered by centrifugation, rinsed with water, and dried. The crude product was purified via silica-gel chromatography on a Combiflash system using a petroleum ether/ethyl acetate gradient. 5.80 g (99%), off-white solid. $^1$H NMR (CD$_3$OD, δ in ppm): 7.62 (s, 1H), 7.45 (d, 2H), 7.40 (t, 2H), 7.35 (m, 1H), 7.25 (s, 1H), 5.20 (s, 2H), 3.95 (s, 3H), 3.90 (s, 3H). MS (ESI-QMS): m/z=318.03 (M+H).

EC2093 (5.80 g, 18.2 mmol) was dissolved in CH$_2$Cl$_2$ (10 mL). A mixture of 2.5 mL CH$_2$Cl$_2$ and 2.5 mL of CH$_3$SO$_2$OH was added and the mixture stirred. After 3 hours, LCMS indicated product formation. The solvent was removed and the product was purified via silica-gel chromatography on a Combiflash system using a CH$_2$Cl$_2$/CH$_3$OH gradient to provide EC1882 3.46 g (84%), as off-white solid. $^1$H NMR (CD$_3$OD, δ in ppm): 7.35 (s, 1H), 7.2 (s, 1H), 3.95 (s, 3H), 3.90 (s, 3H). MS (ESI-QMS): m/z=225.78 (M−H).

EC1882 (1.0331 g, 4.55 mmol) was dissolved in ethanol (200 proof, 70 mL). Pd/C (10%, 200 mg) was added. The reaction flask was evacuated and backfilled with H$_2$ three times. H$_2$ was applied by balloon for 3 hours, at which point the flask was evacuated and backfilled with air three times. Celite was added and the product filtered through with ethanol and concentrated. Typical yield 781.0 mg, 90% recovery, brown solid. $^1$H NMR (CD$_3$OD, δ in ppm): 7.25 (s, 1H), 6.20 (s, 1H), 3.85 (s, 3H), 3.80 (s, 3H). MS (ESI): m/z=196.23 (M−H).

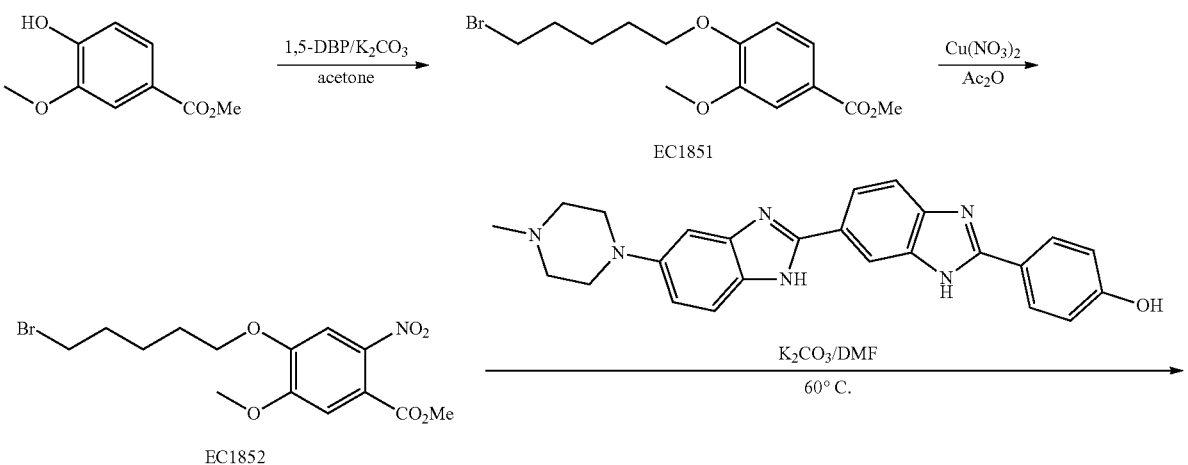

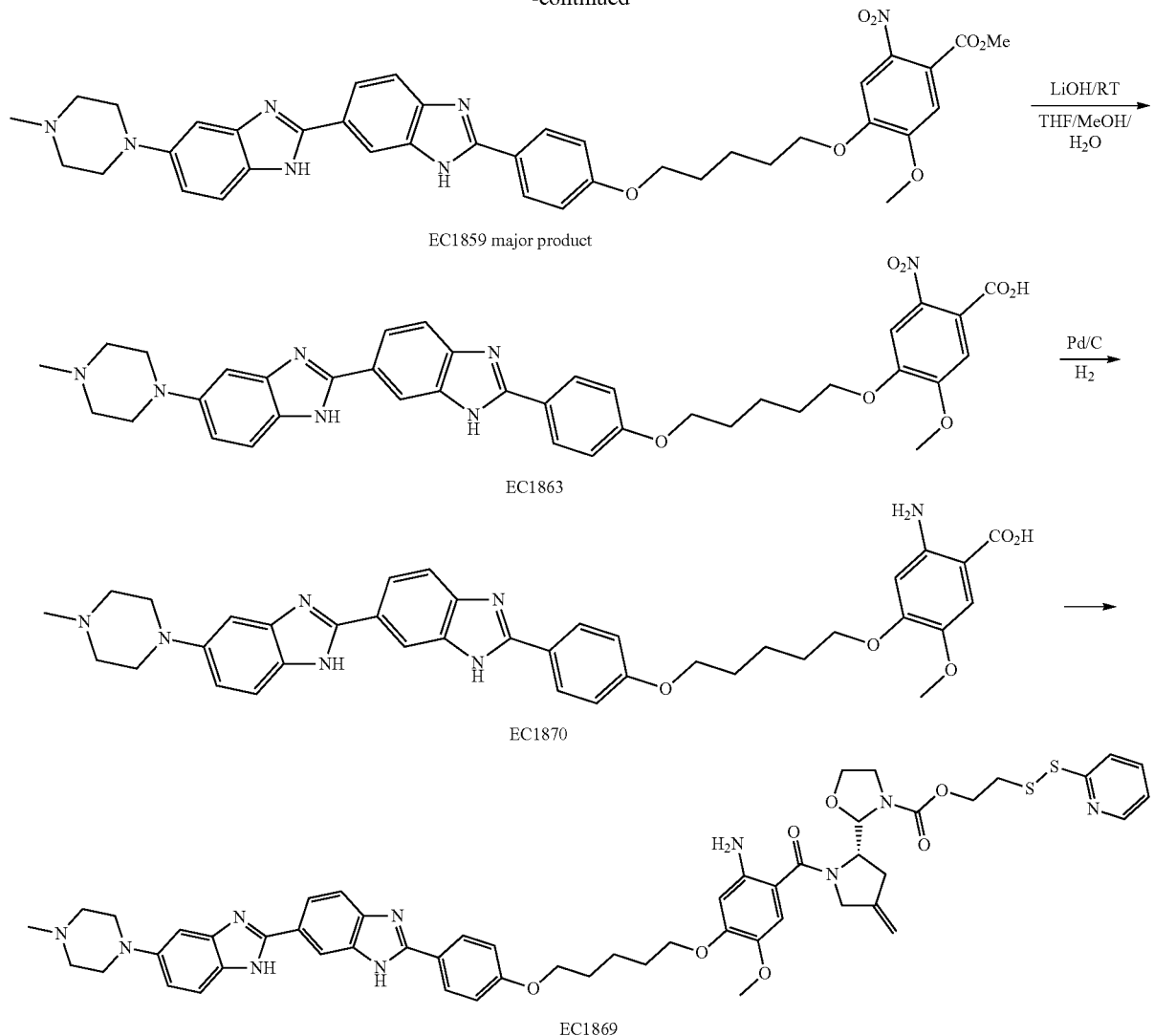

The phenol compound (2.2044 g, 12.1 mmol) was dissolved in acetone (dried through a pad of $Na_2SO_4$, 48.4 mL) and to this solution was added 1,5-dibromopentane (49.4 mL, 36.3 mmol) and $K_2CO_3$ (6.69 g, 48.4 mmol). The reaction was heated to reflux under Ar for 6 hrs. The reaction was cooled to RT and the solid was filtered out. The filtrate was concentrated and purified with CombiFlash in 0-30% EtOAc/p-ether to obtained EC1851 (3.3893 g, yield 84.5%) as a solid. LCMS: $[M+H]^+$ m/z=331. $^1$H NMR ($CDCl_3$, δ in ppm): 7.65 (dd, J=8.5, 2.0 Hz, 1H), 7.54 (d, J=2.0 Hz, 1H), 6.86 (d, J=8.50 Hz, 1H), 4.08 (t, J=6.50 Hz, 2H), 3.91 (s, 3H), 3.89 (s, 3H), 3.44 (t, J=6.5 Hz, 2H), 1.95 (m, 4H), 1.65 (m, 2H).

EC1851 (3.3893 g, 10.23 mmol) in $Ac_2O$ (52 mL) was cooled to 0° C. and treated with $Cu(NO_3)_3.3H_2O$ (2.967 g, 12.28 mmol) by slow addition. The reaction was stirred at 0° C. for 1 hr then at RT for 2 hrs. After the reaction was completed, the reaction mixture was poured into ice water and stirred for 1 hr. The resultant precipitate was collected by filtration. The product was washed with water (3×) and air-dried as EC1852 (3.7097 g, yield 96%). LCMS: $[M+H]^+$ m/z=376. $^1$H NMR ($CDCl_3$, δ in ppm): 7.41 (s, 1H), 7.05 (s, 1H), 4.08 (t, J=6.50 Hz, 2H), 3.94 (s, 3H), 3.89 (s, 3H), 3.42 (t, J=7.0 Hz, 2H), 1.93 (m, 4H), 1.63 (m, 2H).

The solution of EC1852 (37.6 mg, 0.1 mmol) and Hochest dye (53.3 mg, 0.1 mmol) in DMF (1.5 mL) under Ar was treated with $K_2CO_3$ at rt. The reaction was heated to 60° C. and kept for overnight. Then the reaction was cooled to rt and the solid was filtered out. The residue was purified with Prep-HPLC (Mobile phase A: 50 mM $NH_4HCO_3$ buffer, pH 7.0; B=ACN. Method: 10-100 B % in 30 min.) to afford EC1859 (13.1 mg, yield 18%). LCMS: $[M+H]^+$ m/z=720.71.

EC1859 (13.1 mg, 0.0182 mmol) was dissolved in THF/MeOH/$H_2O$ (3/1/1, 0.2 mL) and treated with aq. LiOH solution (1 M, 36 μL) for 4 hrs at rt under Ar. Most of the solvent was removed in vacuo and the aqueous phase was acidified with concentrated HCl to pH 2-3, the precipitate was collected as solid (EC1863, 12.8 mg, without purification) by filtration. The filtrate was washed with water (3×) and air dried for the next step. LCMS: $[M+H]^+$ m/z=706.

EC1863 (15.7 mg, 0.022 mmol) in MeOH (10 mL) was subjected to hydrogenation in a Parr shaker (10% wet Pd/C, 5% wt, 7.85 mg, $H_2$ 41 PSI) for 2 hrs. The product was isolated by filtration through a pad of celite. The solvent was removed in vacuo to give crude EC1870, LCMS: [M+H]$^+$ m/z=676.79. The crude product in DMF (0.5 mL) was mixed with the solution of EC2186 (8.81 mg, 0.024 mmol) in DCM (2.0 mL). The reaction mixture was treated with PyBOP (20.8 mg, 0.04 mmol) and DIPEA (13.9 uL, 0.08 mmol) under Ar at rt. The reaction was stirred for overnight and then purified with Prep-HPLC (Mobile phase A: 50 mM NH$_4$HCO$_3$ buffer, pH 7.0; B=ACN. Method: 10-100 B % in 30 min.) to afford 17.4 mg EC1869 in the yield of 85% for the two steps. LCMS: [M+H]$^+$ m/z=1025.9. $^1$H NMR (CD$_3$OD, δ in ppm, selected data): 8.36 (s, 1H), 8.25 (d, J=1.0 Hz, 1H), 8.03 (m, 2H), 7.96 (m, 1H), 7.77 (m, 3H), 7.69 (d, J=8.5 Hz, 1H), 7.52 (d, J=9.0 Hz, 1H), 7.16 (m, 2H), 7.06 (m, 4H), 6.43 (m, 1H). (SEQ ID NOS 1 and 1 are included in the structures below)

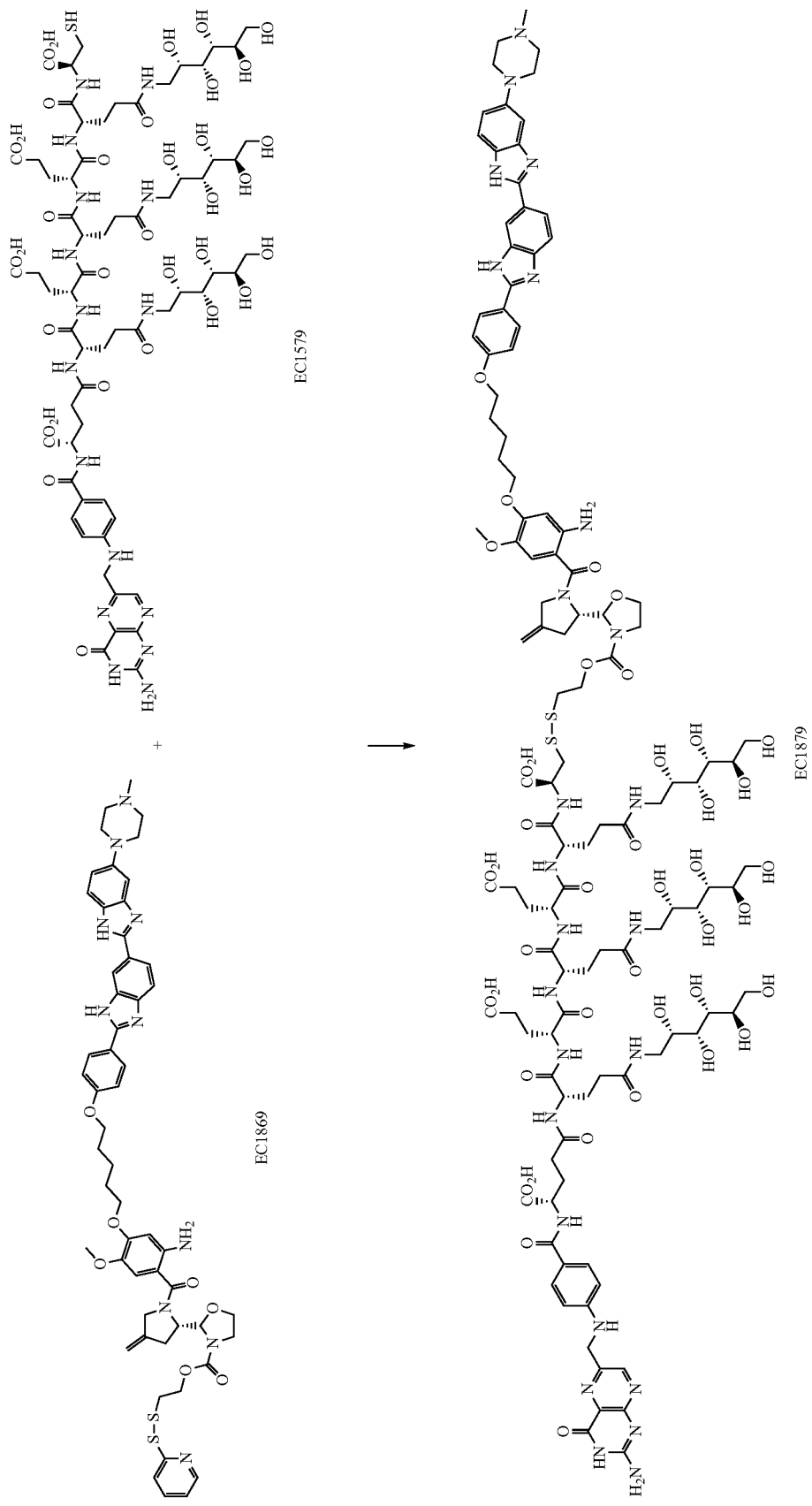

EC1579 (10.24 mg, 0.006 mmol) was dissolved in DMSO (0.3 mL) and water (0.2 mL) and bubbled with Ar at rt in an amber vial. To this solution was added a solution of EC1869 (5.0 mg, 0.0049 mmol) in DMSO (0.2 mL) and followed by addition of DIPEA (5.1 µL, 0.029 mmol). The reaction was stirred at rt under Ar for 30 min. The reaction was purified with prep-HPLC (10 to 100% ACN in 50 mM NH$_4$HCO$_3$, pH 7.4) to give the conjugate EC1879 (3.9 mg, 30% yield). LCMS: [M+2H]$^{2+}$ m/z=1297, [M+3H]$^{3+}$ m/z=865.

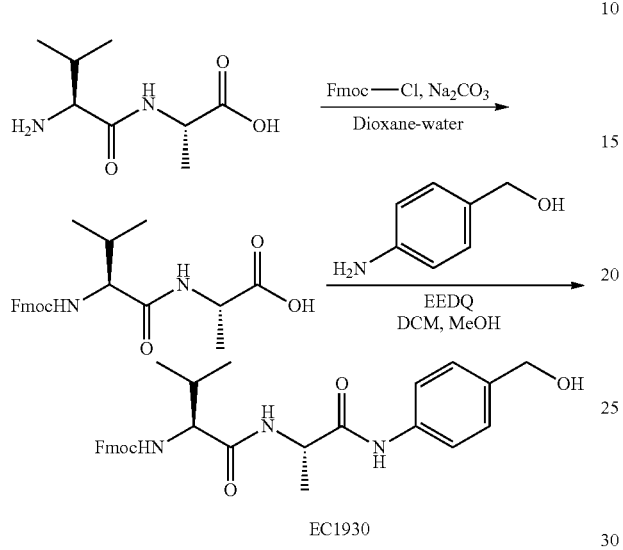

EC1930

To a solution of Val-Ala-OH (1 g, 5.31 mM) in water (40 ml) was added Na$_2$CO$_3$ (1.42 g, 13.28 mM) and cooled to 0° C. before dioxane (40 mL) was added. A solution of Fmoc-Cl (1.44 g, 5.58 mM) in dioxane (40 mL) was added dropwise over 10 min at 0° C. The reaction mixture was stirred at 0° C. for 2 h. Then the reaction mixture was allowed to stir at RT for 16 h. Dioxane was removed under vacuum, the reaction mixture diluted with water (450 mL), pH was adjusted to 2 using 1N HCl and extracted with EtOAc (3×250 mL). The combined organic layers were washed with brine, dried over MgSO$_4$, filtered, concentrated under reduced pressure and dried to yield Fmoc-Val-Ala-OH. This product was suspended in dry DCM (25 ml), PABA (0.785 g, 6.38 mM) and EEDQ (1.971 g, 7.97 mM) were added. The resulting mixture was treated under Argon with methanol until a clear solution was obtained. The reaction was stirred overnight and filtered. The filtrate was washed with diethyl ether (4×) and dried under high vacum to yield EC1930 (1.85 g, 68%). $^1$H NMR (500 MHz, CD$_3$OD): δ 7.79 (d, J$_1$=8.0 Hz, 2H), 7.65 (t, J$_1$=7.0 Hz, J$_2$=7.5 Hz, 2H), 7.54 (d, J$_1$=8.0 Hz, 2H), 7.38 (t, J$_1$=7.5 Hz, J$_2$=7.5 Hz, 2H), 7.33-7.24 (m, 4H), 4.54 (s, 2H), 4.48 (q, J$_1$=14.0 Hz, J$_2$=7.0 Hz, 1H), 4.42-4.32 (m, 2H), 4.22 (t, J$_1$=7.0 Hz, J$_2$=6.5 Hz, 1H), 3.94 (d, J$_1$=7.0 Hz, 1H), 2.07 (m, 1H), 1.43 (d, J$_1$=7.5 Hz, 3H), 0.97 (d, J$_1$=7.0 Hz, 3H), 0.95 (d, J$_1$=7.0 Hz, 3H); LCMS (ESI): (M+H)$^+$=Calculated for C$_{30}$H$_{33}$N$_3$O$_5$, 516.24; found 516.24.

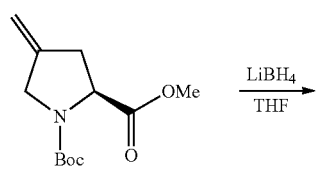

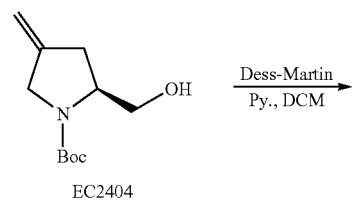

EC2404

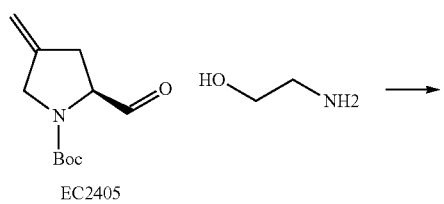

EC2405

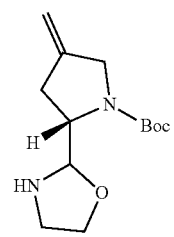

To a mixture of 1-(tert-butyl) 2-methyl (S)-4-methyl-enepyrrolidine-1,2-dicarboxylate (0.5 g, 2.07 mmol) in THF (10 mL) was added LiBH$_4$ (67.7 mg, 3.11 mmol) in portions at 0° C. under argon. The mixture was allowed to warm to room temperature over 2.5 hours. It was cooled to 0° C. and quenched with H$_2$O. The mixture was extracted with EtOAc (3×30 mL) and the organic phase was washed with H$_2$O, brine sequentially and dried over anhydrous MgSO$_4$. It was filtered and concentrated in vacuo. The crude product EC2404 was used in next step without further purification.

To a mixture of EC2404 and pyridine (0.84 ml, 10.35 mmol) in dichloromethane (8 ml) was added Dess-Martin periodinane (1.2 g, 2.90 mmol) at 0° C. It was stirred at room temperature for 2 hours. The crude product was purified with CombiFlash in 0-40% EtOAc/p-ether to afford 0.26 g of EC2405 in 59.3% yield. $^1$H NMR (500 MHz, CDCl$_3$) (rotamers): δ 9.56 and 9.49 (s, 1H), 5.03 (m, 2H), 4.35-4.20 (m, 1H), 4.13-4.02 (m, 2H), 2.86-2.71 (m, 1H), 2.67-2.64 (m, 1H), 1.49 and 1.44 (s, 9H).

A mixture of EC2405 (42.7 mg, 0.20 mmol), 2-aminoethan-1-ol (12.8 □l, 0.21 mmol) and molecular sieves in toluene (1 ml) was stirred at room temperature for 1.5 hours to generate the tert-butyl (2S)-4-methylene-2-(oxazolidin-2-yl)pyrrolidine-1-carboxylate in situ.

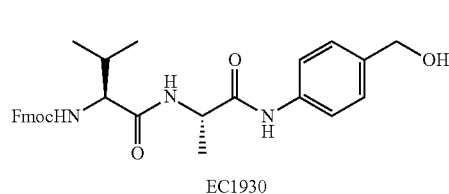

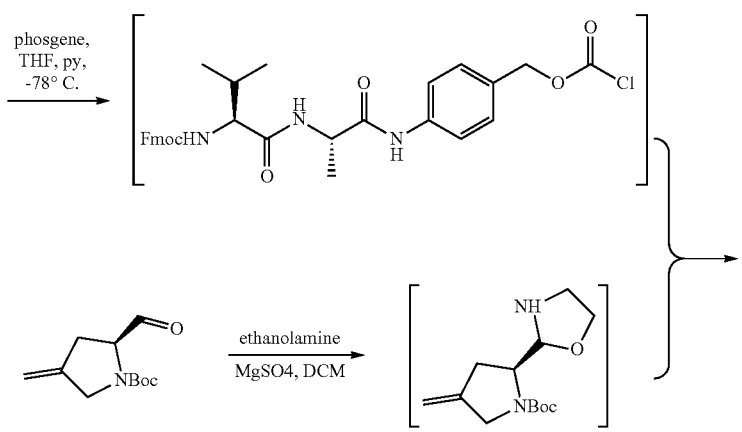

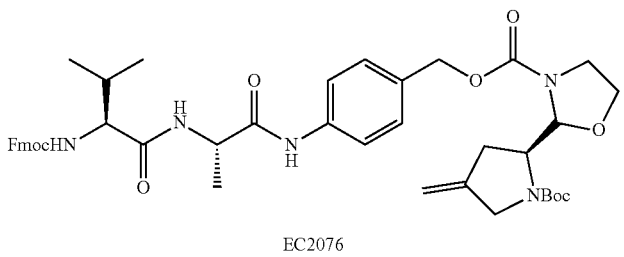

The proline derived aldehyde (550 mg, 2.6 mmol) was dissolved in DCM (10 mL), MgSO₄ (3 g) was added followed by dropwise addition of ethanolamine (0.16 mL, 2.6 mmol) in DCM (10 mL) and was added to the EC2405 mixture. The reaction was stirred at rt for 1 hr. Filtration and concentration under vacuum gave the oxazoline intermediate. In another flask, EC1930 (516 mg, 1.0 mmol) was dissolved in THF (40 mL) and pyridine was added (0.8 mL, 10 mmol). The solution was cooled to −78° C., and diphosgene (0.16 mL, 1.5 mmol) was added. The reaction was stirred at −78° C. for 1 h, DCM (20 mL) and a solution of oxazolidine intermediate was added dropwise. The reaction mixture was allowed to warm to −20° C. over several hours. LC-MS and TLC showed product formation. The reaction mixture was concentrated with silica gel and purified by flash chromatography (120 gold Redisep column, 0-100% EtOAc in petroleum ether) to give EC2076 (0.59 g, 74%). LCMS (ESI): (M+H)⁺=Calculated for $C_{44}H_{53}N_5O_9$, 796.38; found 796.74.

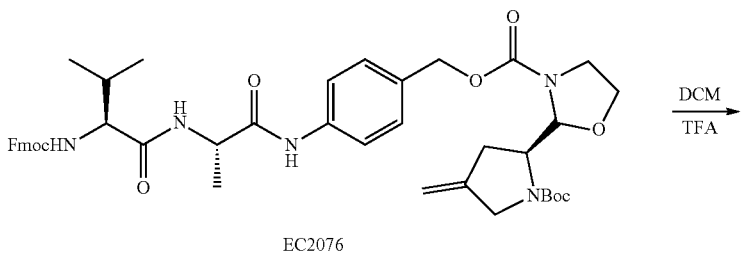

-continued

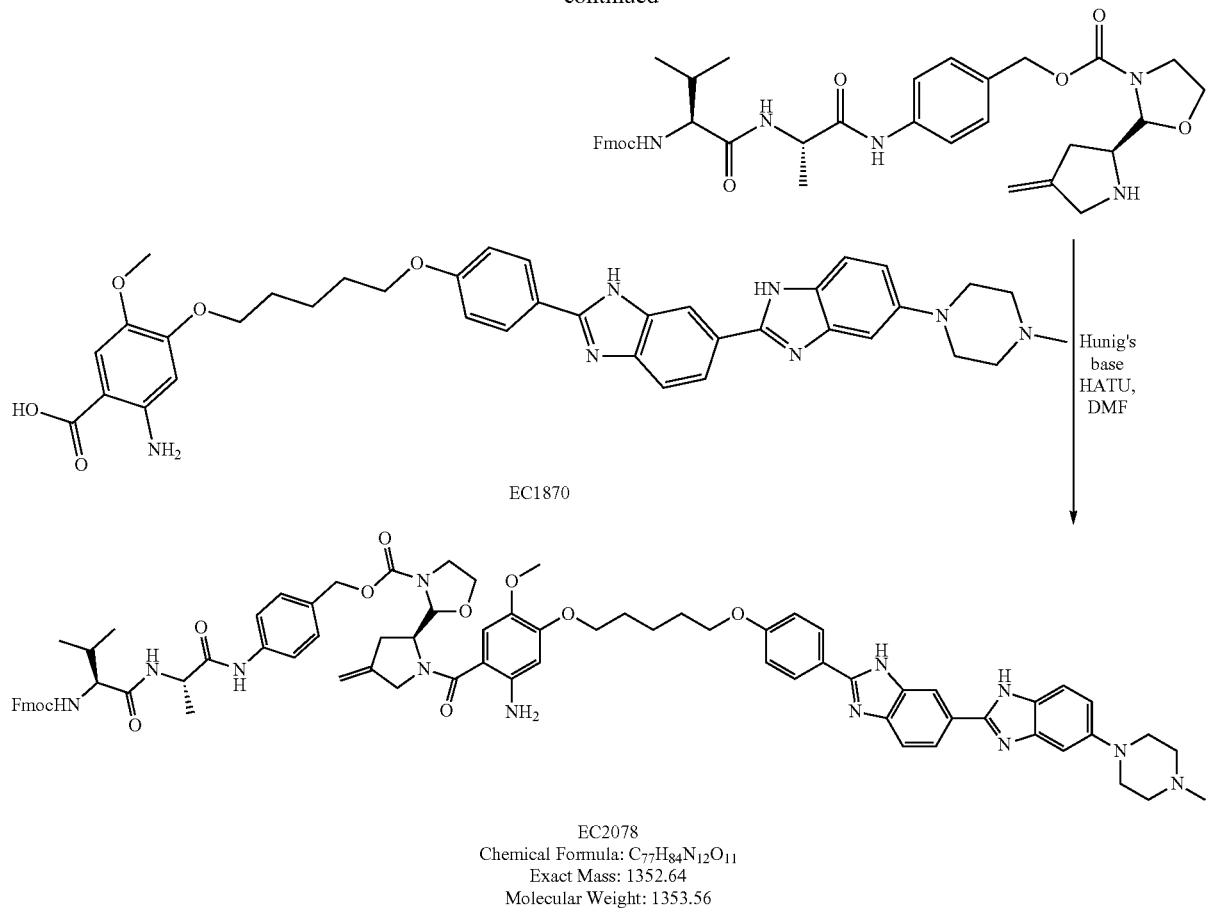

EC2078
Chemical Formula: $C_{77}H_{84}N_{12}O_{11}$
Exact Mass: 1352.64
Molecular Weight: 1353.56

EC2076 (101.0 mg, 0.127 mmol) was stirred in TFA/DCM (0.5 mL each) at rt for 30 min. LC-MS showed complete removal of Boc group. The reaction mixture was concentrated under high vacuum to remove TFA and DCM, re-dissolved in DMF (1.0 mL), and adjusted pH to 8-9 by adding Hunig's base (0.3 mL). EC1870 (86.0 mg, 0.127 mmol) was added, followed by PyBoP (84 mg, 0.16 mmol) and the reaction was stirred at rt for 2 h. LC-MS at 90 min showed that the major peak had the desired product. The reaction mixture was loaded onto a silica gel cartridge and purified by flash chromatography (12 g gold, 0-30% MeOH/DCM) to give desired product, EC2078 (140 mg, 81%). LCMS (ESI): $(M+H)^+$=Calculated for $C_{77}H_{84}N_{12}O_{11}$, 1353.64; found 1354.18.

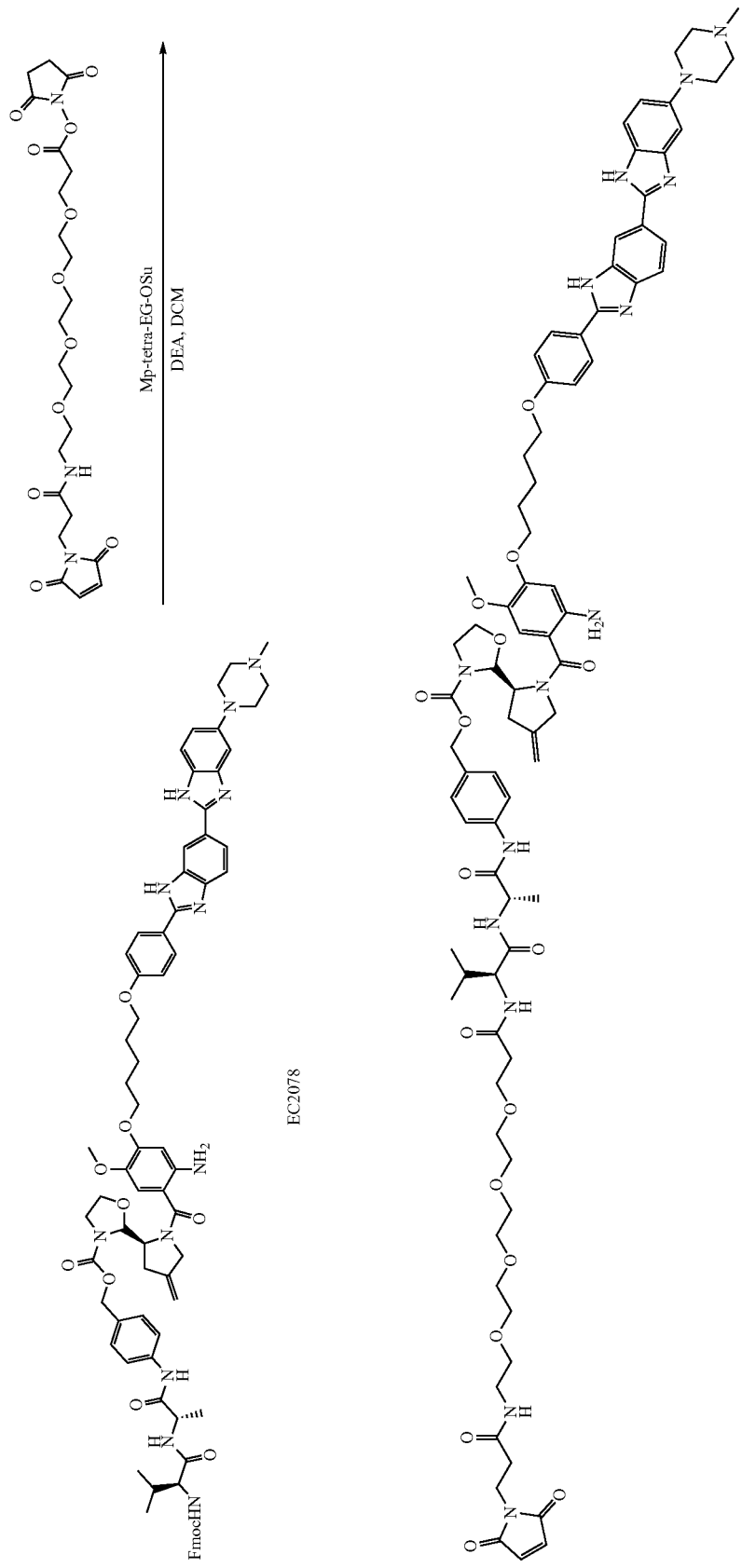

EC2078 (140 mg, 0.10 mmol) was dissolved in DEA/DCM (12/18 mL) and stirred at rt for 30 min. LC-MS showed complete removal of Fmoc group. The reaction mixture was concentrated under high vacuum to remove excess diethylamine and re-dissolved in DCM (5 mL). MP-tetra-EG-Osu (62 mg, 0.12 mmol) was added and the reaction was stirred at rt for 1 hr. The reaction mixture was concentrated, redissolved in DMSO and loaded directly to HPLC column and purified by preparative HPLC (C18 column, 5-80% ACN/pH7 buffer) giving desired product EC2079 (55.8 mg, 36%). LCMS: $[M+2H]^{2+}$ m/z=Calculated for $C_{80}H_{100}N_{14}O_{17}$, 765.37; found 765.74. (SEQ ID NOS 1 and 1 are included in the structures below)

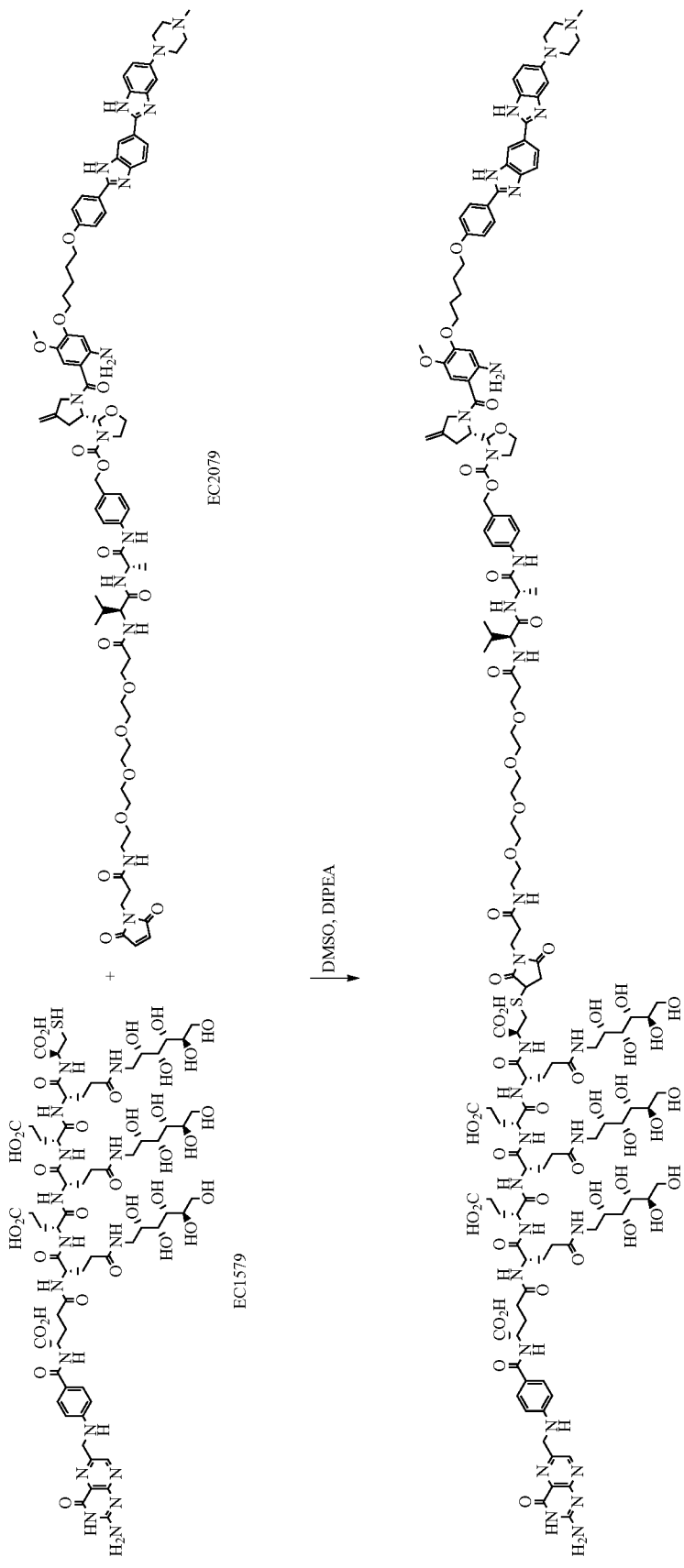

EC1579 (9.85 mg, 0.006 mmol) was stirred in DMSO (2 mL) until dissolved. DIPEA (50 uL) was added, followed by EC2079 (6.24 mg, 0.004 mmol) in DMSO (2 mL). The reaction was stirred at RT for 50 min. LC-MS analysis at 10 min showed complete conversion. The reaction mixture was directly loaded on a prep-HPLC column and purified (10-100% MeCN/Ammonium bicarbonate, pH 7 buffer) to give desired product EC2080 (5.5 mg, 42%). $^1$H NMR (500 MHz, DMSO-D$_6$+D$_2$O) (selected data): δ 8.60 (s, 1H), 8.44-8.08 (m*, 1H), 8.07 (d, J=8.5 Hz, 2H), 8.06-7.84 (m*, 2H), 7.80-7.57 (m*, 2H), 7.57 (d, J=8 Hz, 2H), 7.51 (d, J=6.5 Hz, 2H), 7.44 (m*, 1H), 7.22 (m*, 2H), 7.08 (d, J=8 Hz, 2H), 6.93 (d, J=8.5 Hz, 1H), 6.60 (d, J=8.5 Hz, 2H), 6.33 (s, 1H), 4.95 (m*, 4H), 4.45 (m*, 3H); LCMS: [M+4H]$^{4+}$ m/z=Calculated for C$_{145}$H$_{198}$N$_{30}$O$_{51}$S, 803.34; found 803.80.

* Due to diasteromeric and/or rotameric nature of the compound

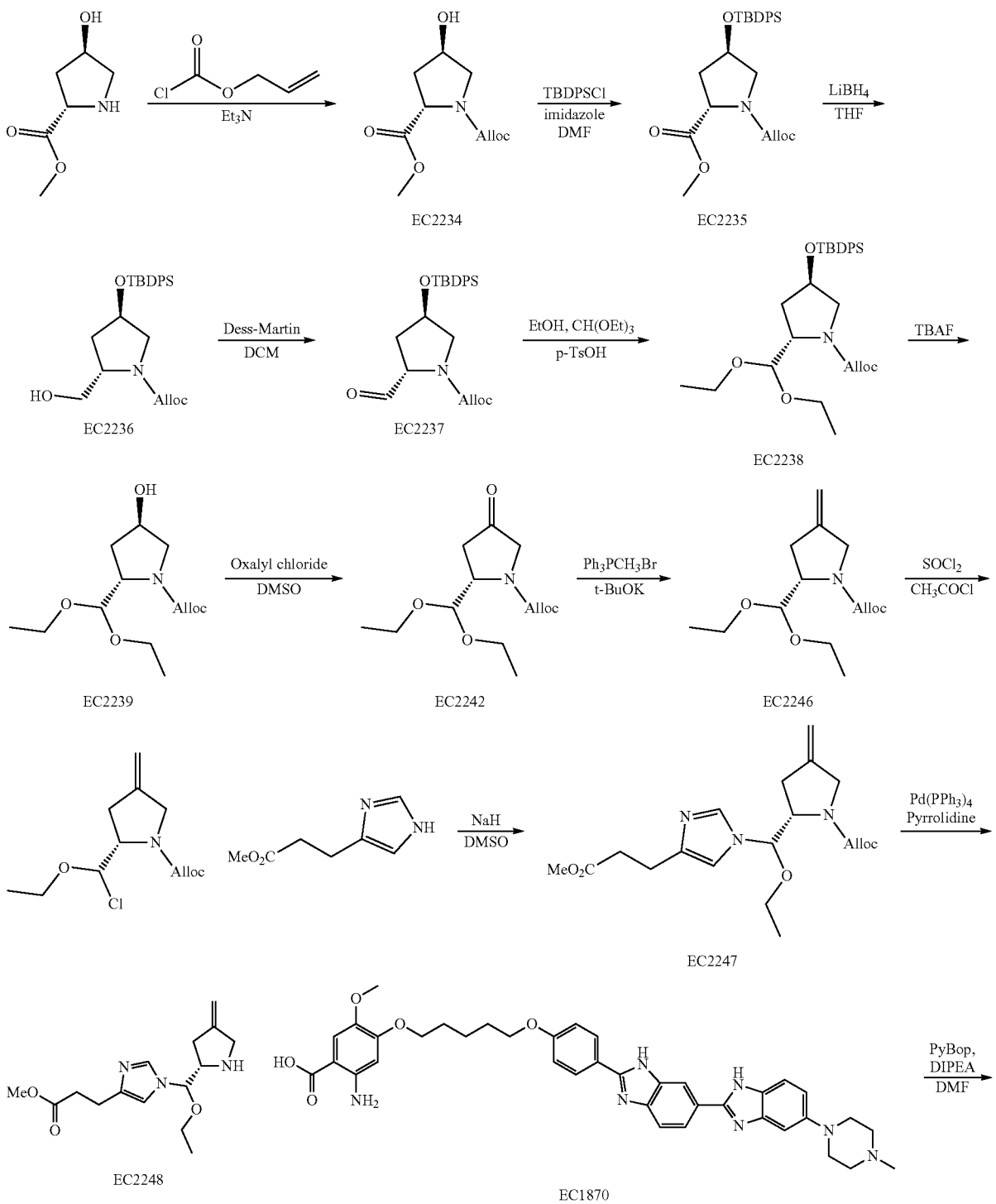

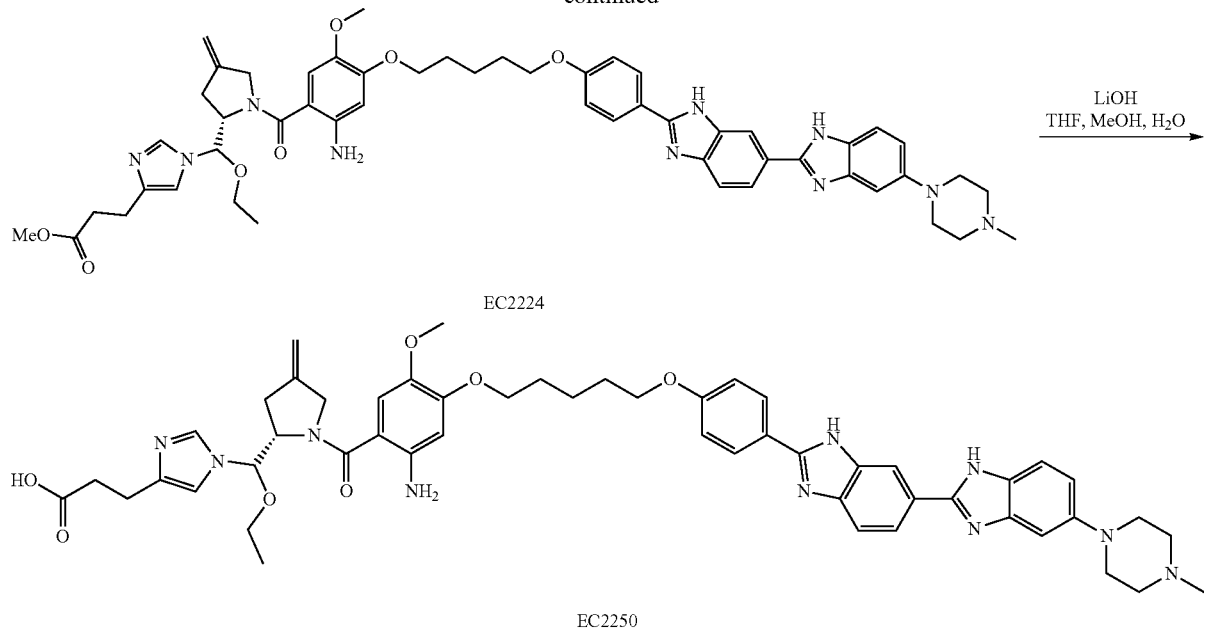

EC2234 was synthesized in 91% yield following the procedure described in Murray et al. WO2008098368 $^1$H NMR (500 MHz, CDCl$_3$) (rotamers): δ 6-5.8 (m, 1H), 5.4-5.1 (m, 2H), 4.6-4.4 (m, 4H), 3.8-3.5 (m, 2H), 2.4-2 (m, 2H).

To a mixture of EC2234 (1 g, 4.36 mmol) and imidazole (0.59 g, 8.72 mmol) in DMF was added tert-Butyldiphenylchlorosilane (1.36 ml, 5.23 mmol) dropwise at room temperature. The mixture was stirred at room temperature overnight. The reaction was quenched with water, extracted with EtOAc (3×30 ml) and the organic phase was washed with H$_2$O, brine sequentially and dried over anhydrous MgSO$_4$ and concentrated. The residue was purified with CombiFlash in 0-80% EtOAc/p-ether to afford the EC2235 1.84 g, in yield of 90%. $^1$H NMR (500 MHz, CDCl$_3$): δ 7.68-7.60 (m, 4H), 7.48-7.36 (m, 6H), 5.91 (m, 1H), 5.25 (m, 2H), 4.59 (m, 2H), 4.43 (m, 1H), 4.24-3.60 (m, 4H), 3.53 (m, 2H), 1.05 (m, 9H). LCMS: [M+H]$^+$ m/z=468.41.

To a mixture of EC2235 (0.94 g, 2.01 mmol) in THF (15 ml) was added LiBH$_4$ (65.7 mg, 3.02 mmol) in portions at 0° C. under argon. The mixture was allowed to warm to room temperature over 2.5 hours. It was cooled to 0° C. and quenched with H$_2$O. The mixture was extracted with EtOAc (3×30 ml) and the organic phase was washed with H$_2$O, brine sequentially and dried over anhydrous MgSO$_4$. It was filtered and concentrated in vacuo. The crude product was used in next step without further purification. 0.88 g of EC2236 was obtained in 99% yield. $^1$H NMR (500 MHz, CDCl$_3$): δ 7.68-7.60 (m, 4H), 7.48-7.36 (m, 6H), 5.91 (m, 1H), 5.25 (m, 2H), 4.59 (m, 2H), 4.43 (m, 1H), 4.24-3.60 (m, 4H), 3.53 (m, 2H), 1.05 (m, 9H). LCMS: [M+H]$^+$ m/z=440.41.

To a mixture of EC2236 (0.88 g, 2.0 mmol) in DCM (6 ml) was added Dess-Martin reagent (1.02 g, 2.4 mmol) at room temperature. The mixture was stirred at room temperature for 4 hours. The crude product was purified with CombiFlash in 0-40% EtOAc/p-ether to afford 0.69 g of EC2237 in 80% yield. $^1$H NMR (500 MHz, CDCl$_3$): δ 9.46 (d, J=48 Hz, 1H), 7.64-7.59 (m, 4H), 7.46-7.26 (m, 6H), 5.90 (m, 1H), 5.30 (d, J=11 Hz, 1H), 5.22 (m, 1H), 4.62 (m, 2H), 4.38 (m, 2H), 3.62 (dd, J$_1$=11 Hz, J$_2$=62.5 Hz, 1H), 3.44 (m, 2H), 2.10 (M, 1H), 1.82 (M, 2H), 1.05 (s, 9H). LCMS: [M+H]$^+$ m/z=438.35.

To a mixture of EC2237 (0.395 g, 0.9 mmol) in ethanol (5 ml) and Triethyl orthoformate (0.6 ml, 3.6 mmol) was added p-TsOH (catalytic amount) at room temperature. The mixture was stirred at room temperature for 3 hours. The crude product was purified with CombiFlash in 0-40% EtOAc/p-ether to afford 0.45 g of EC2238 in 97% yield. $^1$H NMR (500 MHz, CDCl$_3$): δ 7.63 (m, 4H), 7.37 (m, 6H), 5.93 (m, 1H), 5.30-5.19 (m, 2H), 4.77-4.49 (m, 4H), 4.11 (m, 1H), 3.67 (m, 2H), 3.54-3.42 (m, 2H), 3.37-3.23 (m, 2H), 2.22 (m, 1H), 1.98 (m, 1H), 1.19 (m, 3H), 1.04 (s, 9H), 0.98 (m, 3H). LCMS: [M+H]$^+$ m/z=512.58.

To a mixture of EC2238 (0.446 g, 0.87 mmol) in THF (6 ml) was added TBAF solution (1.05 ml g, 1.05 mmol) at room temperature under argon. The mixture was stirred at room temperature overnight. The crude product was purified with CombiFlash in 0-40% EtOAc/p-ether to afford 0.23 g of EC2239 in 95% yield. $^1$H NMR (500 MHz, CDCl$_3$): δ 5.95 (m, 1H), 5.31 (d, J=17.5 Hz, 1H), 5.21 (d, J=10.5 Hz, 1H), 4.87 (s, 1H), 4.60 (m, 3H), 4.13 (m, 1H), 3.74 (m, 2H), 3.53 (m, 5H), 2.41 (m, 1H), 1.89 (m, 1H), 1.21 (t, J$_1$=J$_2$=7.5 Hz, 3H) 1.16 (t, J$_1$=J$_2$=7.5 Hz, 3H).

To a mixture of DMSO (0.32 g, 4.51 mmol) in DCM (10 ml) was added oxalyl chloride (1.13 ml, 2 M in methylene chloride, 2.25 mmol) at −78° C. under argon. After stirring for 30 minutes, EC2239 (0.56 g, 2.05 mmol) was added at −78° C. The mixture was stirred at −78° C. for 2 hours, then it was treated with Et$_3$N (1.42 ml, 10.25 mmol). It was allowed to warm to room temperature. The reaction mixture was diluted with DCM and quenched with brine. It was washed with brine and dried over anhydrous MgSO$_4$. The crude product was purified with CombiFlash in 0-40% EtOAc/p-ether to afford 0.43 g of EC2242 in 77% yield. $^1$H NMR (500 MHz, CDCl$_3$): δ 5.95 (m, 1H), 5.35-5.22 (m, 2H), 4.70-4.58 (m, 3H), 4.40 (dd, J$_1$=9.5 Hz, J$_2$=31.5 Hz, 1H), 3.89 (m, 1H), 3.77 (m, 3H), 3.54 (m, 1H), 3.46 (m, 1H), 2.72 (d, J=18.5 Hz, 1H), 2.48 (m, 1H), 1.23 (t, $J_1=J_2=7.5$ Hz, 3H) 1.13 (t, $J_1=J_2=7.5$ Hz, 3H).

Potassium tert-butoxide (2.54 ml, 1M in THF, 2.54 mmol) was added dropwise to a suspension of methyltriphenylphosphonium bromide (0.91 g, 2.54 mmol) in THF (10 ml) at 0° C. under argon. After being stirred for 2 hours at 0° C., a solution of EC2242 (0.345 g, 1.27 mmol) g in THF (8 ml) was added dropwise, and the reaction was allowed to warm to room temperature. After being stirred overnight the reaction mixture was diluted with EtOAc and washed with $H_2O$, brine sequentially and dried over anhydrous $MgSO_4$. It was filtered and concentrated in vacuo. The crude product was purified with CombiFlash in 0-20% EtOAc/p-ether to afford 0.306 g of EC2246 in 89.5% yield. $^1$H NMR (500 MHz, $CDCl_3$): δ 5.94 (5.94, m, 1H), 5.31 (d, J=17.5 Hz, 1H), 5.20 (d, J=11 Hz, 1H), 4.91 (m, 2H), 4.71 (m, 3H), 4.14 (m, 2H), 3.94 (d, J=15 Hz, 1H), 3.72 (M, 2H), 3.48 (m, 2H), 2.79 (d, J=16.5 Hz, 1H), 2.60 (m, 1H), 1.20 (t, $J_1=J_2=7.5$ Hz, 3H), 1.14 (t, $J_1=J_2=7.5$ Hz, 3H).

A mixture of EC2246 (43.3 mg, 0.16 mmol), thionyl chloride (2.34 ml, 0.032 mmol) and acetyl chloride (18.4 ml, 0.26 mmol) was stirred at 70° C. for 2 h. It was cooled to room temperature and concentrated under reduced pressure. The crude chloro hemi-acetal was used for next step without further purification.

A mixture of methyl 3-(1H-imidazol-4-yl)propanoate (29.6 mg, 0.19 mmol) and sodium hydride (7.04 mg, 60% dispersion in mineral oil, 0.18 mmol) in DMSO was stirred at room temperature for 30 minutes. It was transferred in to a flask containing the chloro hemi-acetal and the mixture was stirred at room temperature overnight. The crude product was purified with CombiFlash in 0-100% EtOAc/p-ether to afford 23.1 mg of EC2247 in 38.3% yield. $^1$H NMR (500 MHz, $CDCl_3$) (Diastereomers): δ 7.55 (m, 1H), 7.36 (s, 1H), 6.77 (s, 1H), 6.64 (s, 1H), 5.92, (m, 2H), 5.34-5.19 (m, 2H), 5.03 (m, 2H), 4.90-4.75 (m, 2H), 4.63-4.52 (m, 4H), 4.40 (m, 2H), 4.22 (m, 2H), 3.932 (m, 2H), 3.67 (s, 6H), 3.56-3.41 (m, 6H), 3.39-2.85 (m, 4H), 2.76 (m, 2H), 2.72-2.63 (m, 6H), 1.21-1.14 (m, 6H). LCMS: $[M+H]^+$ m/z=378.68.

A mixture of EC2247 (42 mg, 0.11 mmol), Pyrrolindine (10.2 μL, 0.12 mmol) and $Pd(PPh_3)_4$ (6.4 mg, 0.0055 mmol) in DCM (0.6 ml) was stirred at room temperature for 3 hours. It was diluted with DCM, washed with $H_2O$, brine sequentially and dried over anhydrous $MgSO_4$. It was filtered and concentrated in vacuo. The crude product was used for next step without further purification. LCMS: $[M+H]^+$ m/z=294.60.

A mixture of EC2248 (10.72 mg, 0.037 mmol), EC1870 (24.7 mg, 0.037 mmol), PyBop (28.9 mg, 0.056 mmol) and DIEA (19.4 μl, 0.11 mmol) in DMSO (1 ml) was stirred at room temperature overnight. The crude product was purified with prep-HPLC (10 to 100% acetonitrile in 20 mM $NH_4HCO_3$, pH 7.4) to yield pure EC2224 (14.4 mg, 41%). LCMS: $[M+H]^+$ m/z=952.15.

To a mixture of EC2224 (16 mg, 0.017 mmol) in THF (1.5 ml), MeOH (0.5 ml) and $H_2O$ (0.5 ml) was added LiOH (85 μl, 1.0 M solution, 0.085 mmol) at room temperature. The mixture was stirred at room temperature for 4 hours. The solvent was removed under reduced pressure and the crude product was used for next step without further purification. LCMS: $[M+H]^+$ m/z=938.58. (SEQ ID NOS 1 and 1 are included in the structures below)

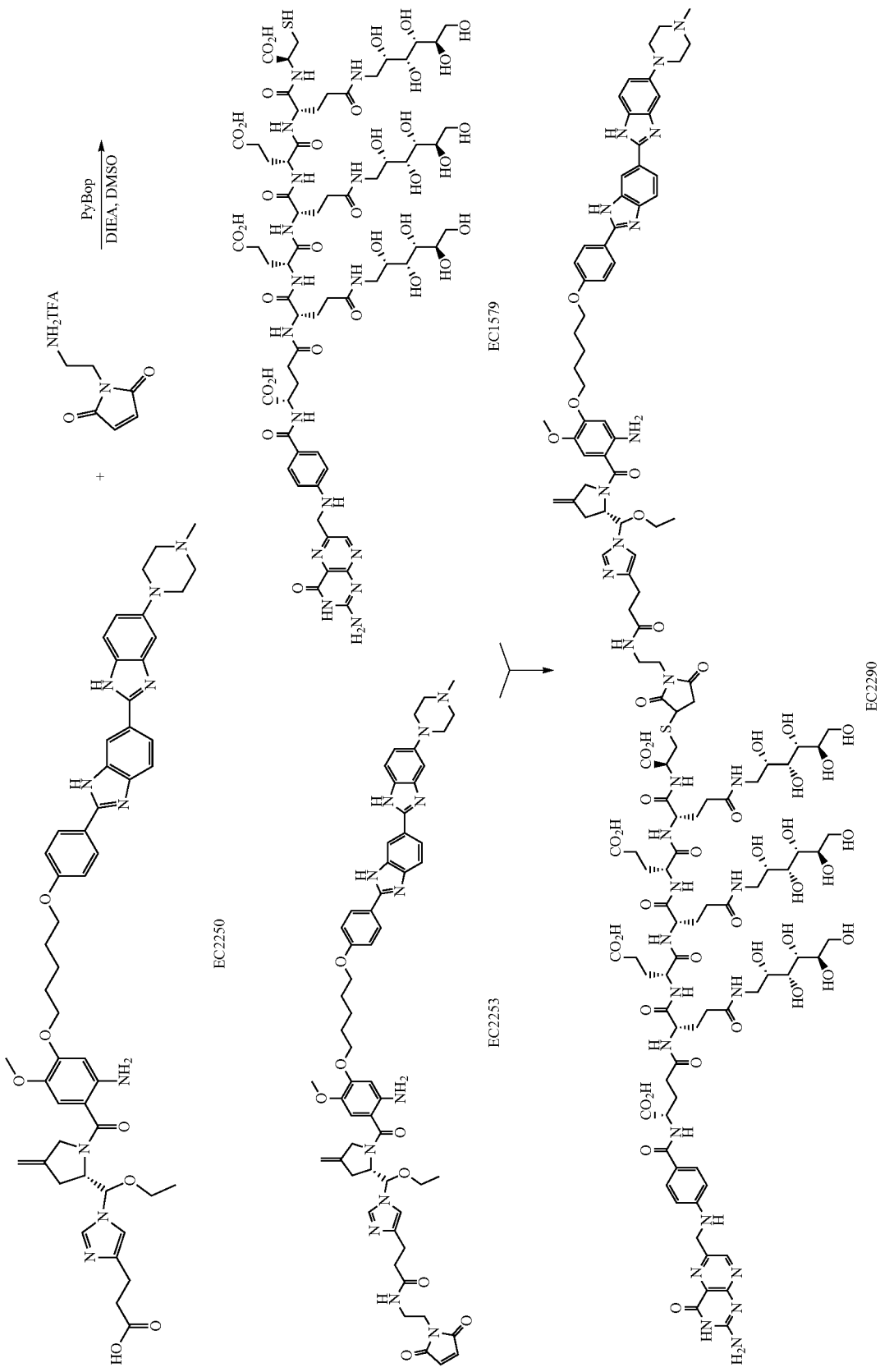

A mixture of EC2250 (12.5 mg, 0.013 mmol), 1-(2-aminoethyl)-1H-pyrrole-2,5-dione TFA salt (3.4 mg, 0.013 mmol), PyBop (10.4 mg, 0.02 mmol) and DIEA (6.8 µl, 0.04 mmol) in DMSO (1 ml) was stirred at room temperature for 1 hour. Then an aqueous solution of EC1579 was added at room temperature. To the mixture was added EC1579 (32.8 mg, 0.02 mmol) in $H_2O$ (0.5 ml) The mixture was stirred at room temperature for 30 minutes and the crude product was purified with prep-HPLC (10 to 100% acetonitrile in 20 mM $NH_4HCO_3$, pH 7.4) to yield pure EC2290 (2 mg, 5.6%). LCMS: $[M+2H]^{2+}$ m/z=1370.76. (SEQ ID NOS 4, 4 and 3 are included in the structures below)

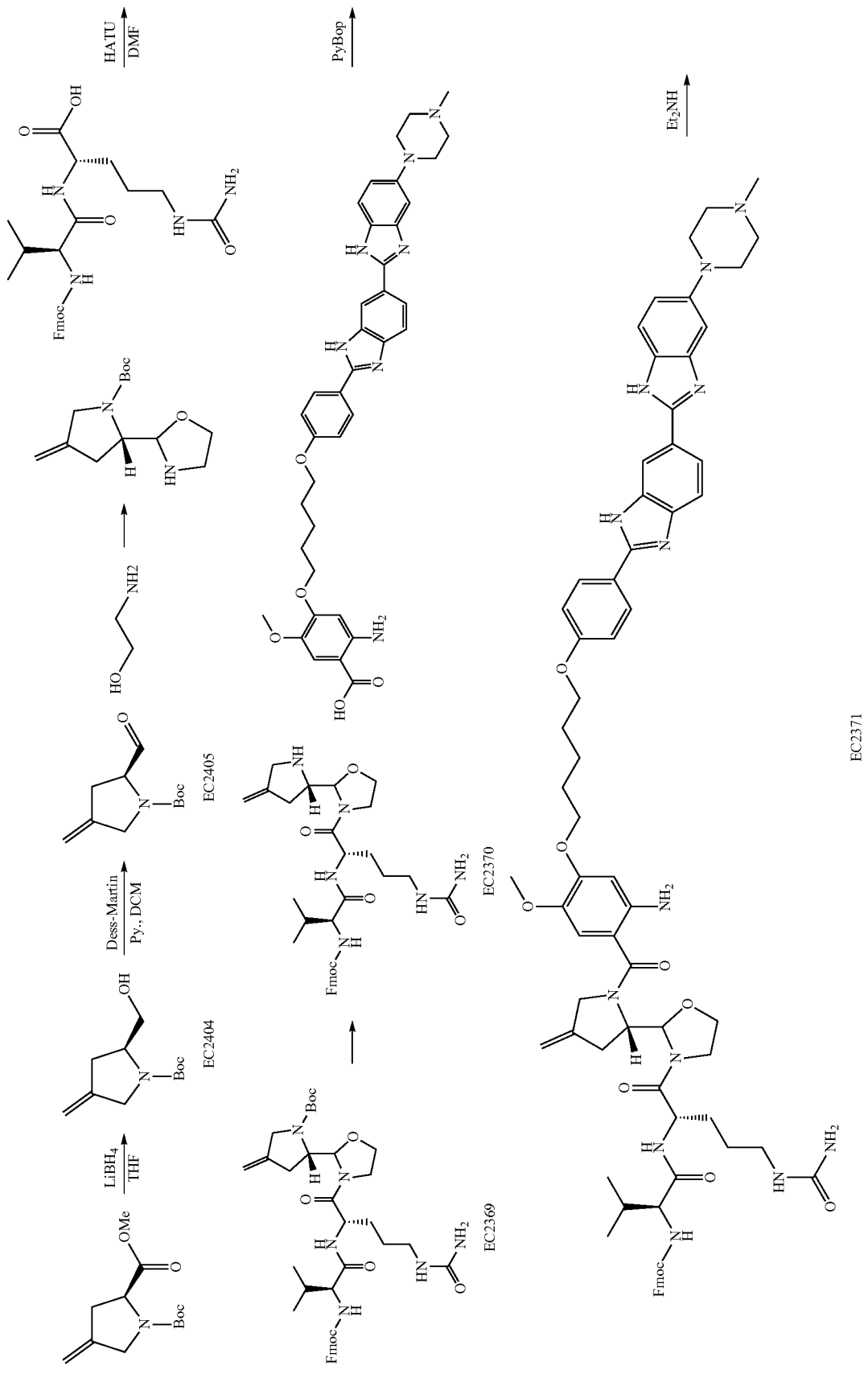

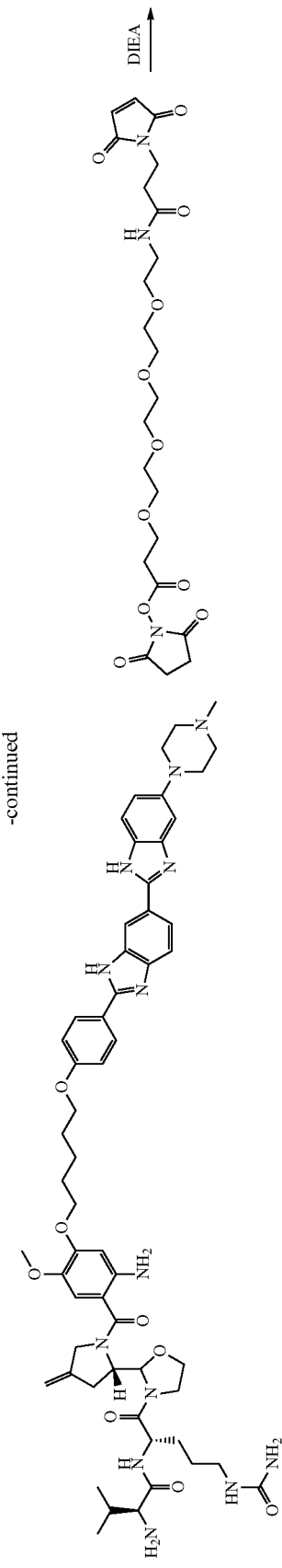
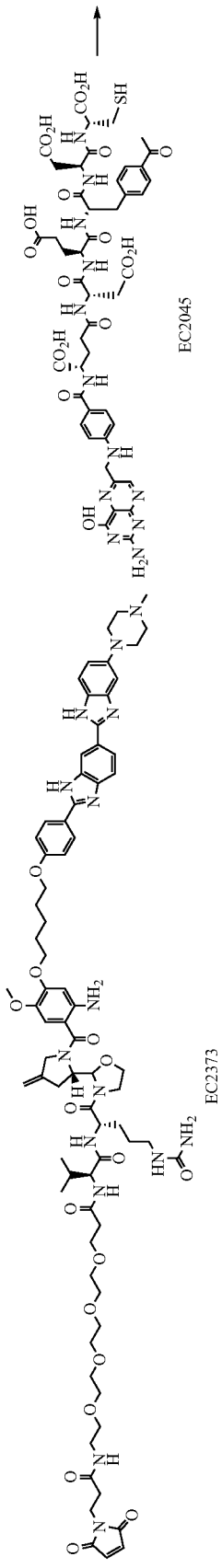
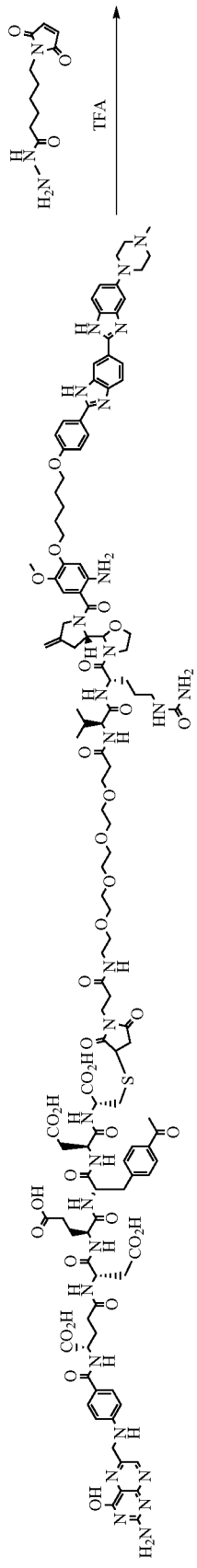
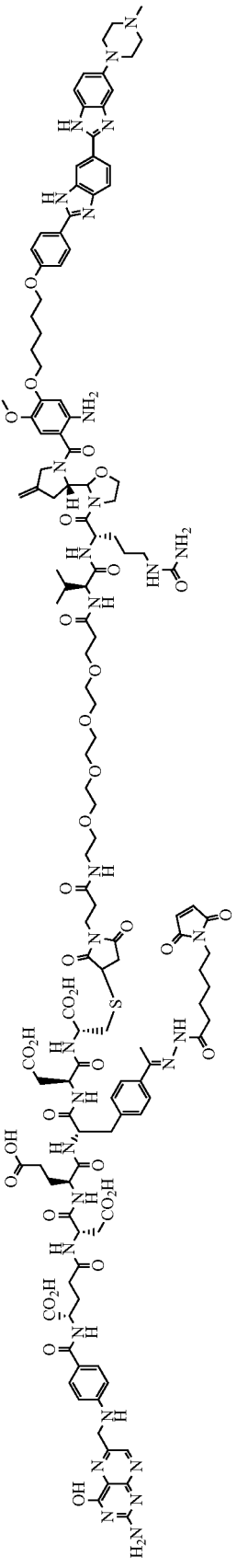

To a mixture of 1-(tert-butyl) 2-methyl (S)-4-methyl-enepyrrolidine-1,2-dicarboxylate (0.5 g, 2.07 mmol) in THF (10 mL) was added LiBH$_4$ (67.7 mg, 3.11 mmol) in portions at 0° C. under argon. The mixture was allowed to warm to room temperature over 2.5 hours. It was cooled to 0° C. and quenched with H$_2$O. The mixture was extracted with EtOAc (3×30 mL) and the organic phase was washed with H$_2$O, brine sequentially and dried over anhydrous MgSO$_4$. It was filtered and concentrated in vacuo. The crude product EC2404 was used in next step without further purification.

To a mixture of EC2404 and pyridine (0.84 ml, 10.35 mmol) in dichloromethane (8 ml) was added Dess-Martin periodinane (1.2 g, 2.90 mmol) at 0° C. It was stirred at room temperature for 2 hours. The crude product was purified with CombiFlash in 0-40% EtOAc/p-ether to afford 0.26 g of EC2405 in 59.3% yield. $^1$H NMR (500 MHz, CDCl$_3$) (rotamers): δ 9.56 and 9.49 (s, 1H), 5.03 (m, 2H), 4.35-4.20 (m, 1H), 4.13-4.02 (m, 2H), 2.86-2.71 (m, 1H), 2.67-2.64 (m, 1H), 1.49 and 1.44 (s, 9H).

A mixture of EC2405 (42.7 mg, 0.20 mmol), 2-aminoethan-1-ol (12.8 μl, 0.21 mmol) and molecular sieves in toluene (1 ml) was stirred at room temperature for 1.5 hours to generate the tert-butyl (2S)-4-methylene-2-(oxazolidin-2-yl)pyrrolidine-1-carboxylate in situ. A mixture of Fmoc-Val-Cit-OH (0.11 g, 0.22 mmol) and HATU (0.12 g, 0.30 mmol) in DMF (2 ml) was stirred at room temperature for 1 hour, then DIEA (0.11 ml, 0.61 mmol) was added. The tert-butyl (2S)-4-methylene-2-(oxazolidin-2-yl)pyrrolidine-1-carboxylate reaction mixture was transferred into this reaction mixture and stirred at room temperature overnight. The crude product was purified with CombiFlash in 0-20% MeOH/DCM to afford 40 mg of EC2369 in 24.8% yield. LCMS: [M+H]$^+$ m/z=733.73.

A mixture of EC2369 (40 mg, 0.055 mmol) in 50% TFA/DCM (1 ml) solution was stirred at room temperature for 3 hours. It was concentrated in vacuo to give the EC2370 as pale yellow solid. It was used in next step without further purification. LCMS: [M+H]$^+$ m/z=633.62.

A mixture of EC2370 (20 mg, 0.032 mmol) EC1870 (21.4 mg, 0.032 mmol), PyBop (24.7 mg, 0.047 mmol) and DIEA (16.6 μl, 0.095 mmol) in DMSO (1 ml) was stirred at room temperature for 5 hours. The crude product was purified with Combiflash in 0-20% MeOH/DCM to afford 10 mg of EC2371 in 24.5% yield. LCMS: [M+H]$^+$ m/z=1291.92.

To a mixture of EC2371 (10 mg, 0.008 mmol) in acetonitrile (1 ml) was added Et$_2$NH (12 μl, 0.116 mmol) at room temperature. The mixture was stirred at room temperature for 4 hours. It was concentrated under reduced pressure. The crude product of EC2372 was used in next step without further purification. [M+H]$^+$ m/z=1069.29.

A mixture of EC2372 (0.008 mmol), Mal-PEG4-NHS (4.1 mg, 0.008 mmol) and DIEA (4.2 μl, 0.024 mmol) in acetonitrile (1 ml) was stirred at room temperature overnight. The reaction mixture was concentrated under reduced pressure and the crude product was purified by prep-HPLC (10 to 100% acetonitrile in 20 mM NH$_4$HCO$_3$, pH 7.4) to yield pure EC2373. LCMS: [M+H]$^+$ m/z=1467.99.

A mixture of EC2373 (46.4 mg, 0.032 mmol) and EC2045 (34.5 mg, 0.032 mmol) in MeOH (0.5 ml) and DMSO (0.5 ml) was stirred at room temperature overnight. The crude product was purified by prep-HPLC (10 to 100% acetonitrile in 20 mM NH$_4$HCO$_3$, pH 7.4) to yield pure EC2374. LCMS: [M+2H]$^{2+}$ m/z=1280.63.

A mixture of EC2374 (41 mg, 0.016 mmol) and EMCH (5.4 mg, 0.016 mmol) in MeOH (0.5 ml) and DMSO (0.5 ml) was stirred at room temperature overnight. The crude product was purified by prep-HPLC (10 to 100% acetonitrile in 20 mM NH$_4$HCO$_3$, pH 7.4) to yield pure EC2375. LCMS: [M+2H]$^{2+}$ m/z=1384.71. $^1$H NMR (500 MHz, DMSO): δ 8.59 (m, 1H), 8.12 (m, 2H), 7.96 (M, 1H), 7.67-7.50 (m, 5H), 7.45 (m, 1H), 7.41-7.18 (m, 3H), 7.17-7.06 (m, 3H), 6.98-6.84 (m, 4H), 6.76-6.58 (m, 3H), 6.40-6.30 (m, 1H), 5.0-4.8 (m, 2H), 4.20-3.98 (m, 4H), 3.96-3.72 (m, 4H), 3.70-3.60 (m, 6H), 3.2-3.0 (m, 7H), 2.91 (m, 1H), 2.85 (m, 1H), 2.61-2.65 (m, 4H), 2.43 (m, 3H), 2.34-2.18 (m, 12H), 2.18-2.0 (m, 3H), 1.98-1.84 (m, 5H), 1.79 (m, 6H), 1.72 (m, 10H), 1.64-1.36 (m, 15H), 1.3-1.02 (m, 18H), 0.88-0.62 (m, 12H).

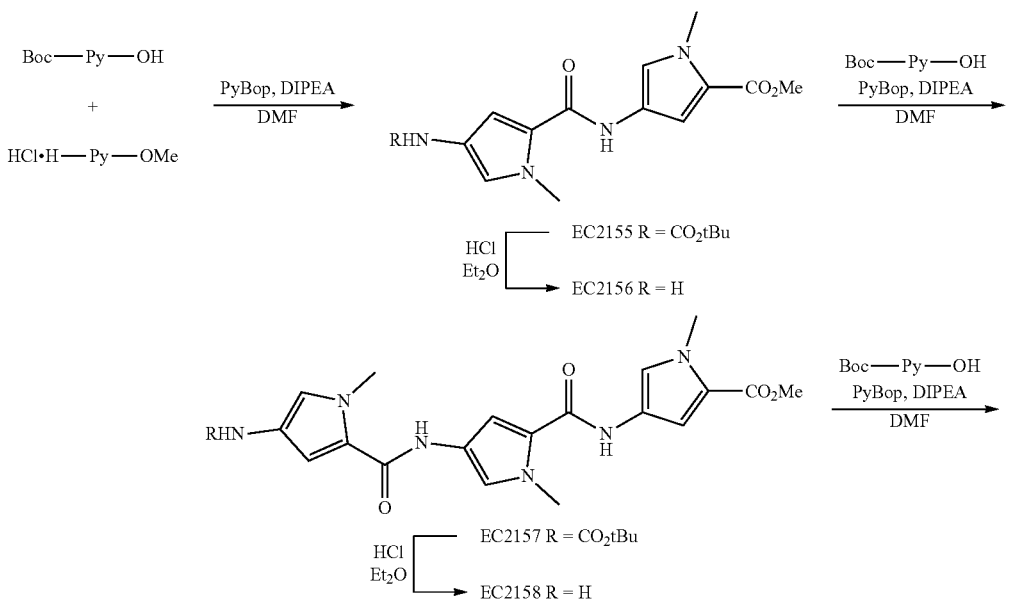

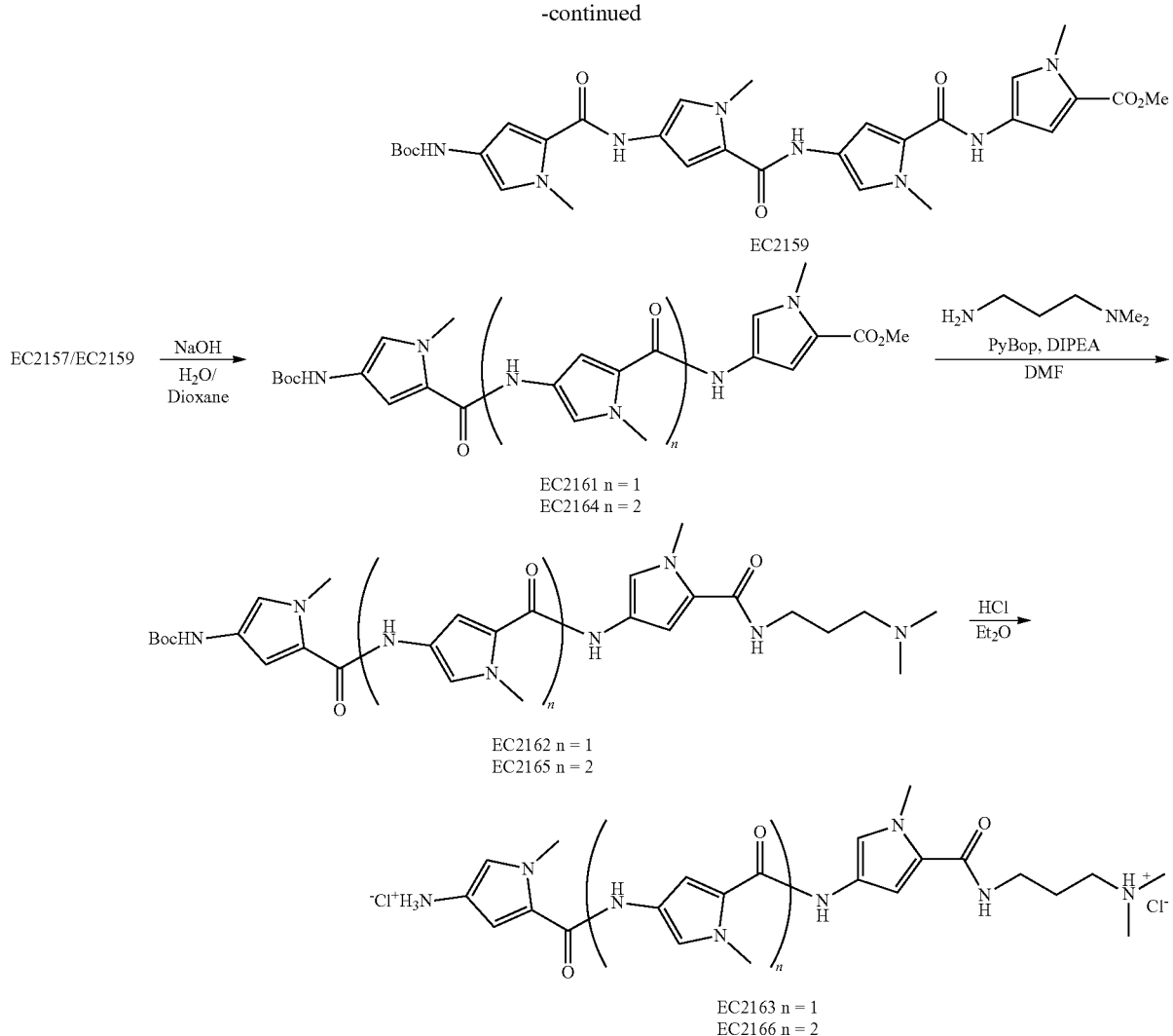

EC2159

EC2161 n = 1
EC2164 n = 2

EC2162 n = 1
EC2165 n = 2

EC2163 n = 1
EC2166 n = 2

Boc-Py-Py-OMe (EC2155): To a solution of 500 mg HCl.H-Py-OMe (2.63 mmol., 1.1 equiv), 573 mg Boc-Py-OH (2.38 mmol., 1.0 equiv), and 850 μL DIPEA (4.77 mmol., 2.0 equiv) in 5.4 mL DMF (0.44M) was added 1.24 g PyBOP (2.38 mmol., 1.0 equiv). The reaction mixture was stirred for 4 h at room temperature, and then diluted (15×) with deionized water. The precipitate that was isolated by centrifugation (4000 rpm for 10 min) and the supernatant was decanted yielding a pellet. The pellet was resuspended in deionized water and sonicated for 5 min, before the precipitate was recollected by centrifugation (repeated twice). Residual water was removed by freezing and lyophilizing from the sample to dryness. 853 mg (86.4%) of product was collected as a light brown solid. $^1$H NMR (CDCl3): δ 7.45 (s, 1H), 7.39 (s, 1H), 6.83 (s, 1H), 6.72 (s, 1H), 6.56 (s, 1H), 6.22 (s, 1H), 3.90 (s, 6H), 3.81 (s, 3H), 1.50 (s, 9H). LC/MS (ESI): m/z=377.13 (M+H).

HCl*H-Py-Py-OMe (EC2156): 38 μl (0.03M) of 2N anhydrous hydrochloric acid (HCl) in diethyl ether was added to 424 mg of EC2155 (1.13 mmol.) and stirred for 5 h at room temperature. The reaction mixture was then diluted with one volume of diethyl ether and filtered by a fritted glass funnel. The filter cake was rinsed with excess diethyl ether (5× reaction volume), and dried in vacuo to yield 343 mg (97.5%) of the product as a tan solid. $^1$H NMR (d6-DMSO): δ 10.07 (s, 1H), 9.97 (br s, 3H), 7.46 (d, J=2.0 Hz, 1H), 7.10 (d, J=2.0 Hz, 1H), 6.98 (d, J=2.0 Hz, 1H), 6.89 (d, J=2.0 Hz, 1H), 3.87 (s, 3H), 3.83 (s, 3H), 3.72 (s, 3H). LC/MS (ESI): m/z=277.07 (M+H).

Boc-Py-Py-Py-OMe (EC2157): EC2157 was synthesized accord to the same produced as EC2155. 832 mg of EC2156 yielded 1.19 g of EC2157 as a light brown solid in 89.7% yield. 1H NMR (d6-DMSO): δ 9.89 (s, 1H), 9.84 (s, 1H), 9.07 (s, 1H), 7.45 (d, J=2.0 Hz, 1H), 7.20 (d, J=1.7 Hz, 1H), 7.04 (d, J=1.5 Hz, 1H), 6.89 (m, 2H), 6.82 (s, 1H), 3.82 (s, 6H), 3.79 (s, 3H), 3.72 (s, 3H), 1.44 (s, 9H). LC/MS (ESI): m/z=499.46 (M+H)

HCl*H-Py-Py-Py-OMe (EC2158): EC2158 was synthesized accord to the same produced as EC2156. 541 mg of EC2157 yielded 343 mg of EC2158 as a tan solid in 92.1% yield. $^1$H NMR (d6-DMSO): δ 10.08 (s, 1H), 10.03 (br s, 3H), 9.93 (s, 1H), 7.44 (d, J=1.9 Hz, 1H), 7.23 (d, J=1.9 Hz, 1H), 7.09 (d, J=2.0 Hz, 1H), 7.05 (d, J=1.5 Hz, 1H), 6.99 (d, J=1.9 Hz, 1H), 6.89 (d, J=1.9 Hz, 1H), 3.88 (s, 3H), 3.83 (s, 3H), 3.82 (s, 3H), 3.72 (s, 3H). LC/MS (ESI): m/z=402.44 (M+H).

Boc-Py-Py-Py-Py-OMe (EC2159): EC2159 was synthesized accord to the same produced as EC2155. 200 mg of EC2158 yielded 267 mg of EC2159 as a light brown solid in 93.6% yield. $^1$H-NMR (d6-DMSO): δ 9.92 (s, 2H), 9.85 (s, 1H), 9.07 (s, 1H), 7.46 (d, J=2.0 Hz, 1H), 7.22 (d, J=2.0 Hz, 1H), 7.21 (d, J=1.4 Hz, 1H), 7.06 (d, J=1.9 Hz, 1H), 7.04 (d, J=1.5 Hz, 1H), 6.90 (d, J=1.9 Hz, 1H), 6.88 (s, 1H), 6.83 (s, 1H), 3.85 (s, 6H), 3.84 (s, 3H), 3.83 (s, 3H), 3.83 (s, 3H), 3.80 (s, 3H), 3.73 (s, 3H), 1.45 (s, 9H). LC/MS (ESI): m/z=621.78 (M+H).

Boc-Py-Py-Py-OH (EC2161): 316 mg (0.643 mmol.) of EC2157 was added to a solution of 12.5 mL 1,4-dioxane and 12.5 mL 1 N aqueous sodium hydroxide (0.025M). The reaction mixture was stirred for 4 h at room temperature before evaporating to dryness. The solid was dissolved in water, acidified to pH 3 with aqueous HCl, and extracted with ethyl acetate (3×). The combined organic layers were dried with sodium sulfate and concentrated to yield 290 mg of a brown/orange solid (93.1%). $^1$H NMR (CDCl$_3$) δ 7.41 (s, 1H), 7.21 (2, 2H), 6.82 (d, J=2.0 Hz, 2H), 6.74 (s, 1H), 3.89 (s, 3H), 3.86 (s, 3H), 3.85 (s, 3H), 1.48 (s, 9H). LC/MS (ESI): m/z=485.49 (M+H).

Boc-Py-Py-Py-NH(CH$_2$)$_3$N(CH$_3$)$_2$ (EC2162): To a solution of 170 mg of EC2161 (0.351 mmol., 1.0 equiv), 53.0 µl of 3-(dimethylamino)-1-propylamine (0.421 mmol., 1.2 equiv), and 125 µl of DIPEA (0.702 mmol., 2.0 equiv) in 3.5 ml of DMF (0.1M) was added 201 mg of PyBOP (0.386 mmol., 1.1 equiv). The reaction mixture was stirred for 4 h at room temperature, before it was concentrated in vacuo to yield a dark brown oil. The crude product was further purified via silica chromatography (0-10% methanol in DCM) to yield 147 mg the product as a white solid (73.6%). $^1$H NMR (d6-DMSO): δ 9.87 (s, 1H), 9.83 (s, 1H), 9.06 (s, 1H), 8.13 (t, J=1.2 Hz, 1H), 7.18 (d, J=0.3 Hz, 1H), 7.15 (d, J=1.9 Hz, 1H), 7.04 (d, J=1.5 Hz, 1H), 6.92 (d, J=1.5 Hz, 1H), 6.87 (s, 1H), 6.82 (s, 1H), 3.82 (s, 3H), 3.80 (s, 3H), 3.79 (s, 3H), 3.22 (t, J=6.1 Hz, 2H), 3.15 (d, J=2.4 Hz, 2H), 2.77 (s, 6H), 1.82 (m, 2H), 1.44 (s, 9H). LC/MS (ESI): m/z=569.67 (M+H).

2HCl*H-Py-Py-Py-NH(CH$_2$)$_3$N(CH$_3$)$_2$ (EC2163): EC2163 was synthesized accord to the same produced as EC2156. 110 mg of EC2162 yield 99 mg of EC2163 as a pale brown solid in 98% yield. $^1$H NMR (d6-DMSO): δ 10.05 (s, 1H), 9.91 (m, 4H), 9.89 (br s, 1H), 8.16 (t, J=1.2 Hz, 1H), 7.22 (d, J=1.4 Hz, 1H), 7.15 (d, J=1.9 Hz, 1H), 7.10 (d, J=1.9 Hz, 1H), 7.05 (d, J=1.5 Hz, 1H), 6.97 (d, J=1.9 Hz, 1H), 6.92 (d, J=1.5 Hz, 1H), 3.88 (s, 3H), 3.83 (s, 3H), 3.79 (s, 3H), 3.23 (m, 2H), 3.04 (m, 2H), 2.75 (s, 3H), 2.74 (s, 3H), 1.82 (m, 2H). LC/MS (ESI): m/z=469.43 (M+H).

Boc-Py-Py-Py-Py-OH (EC2164): EC2164 was synthesized accord to the same produced as EC2161. 359 mg of EC2159 yielded 340 mg of EC2164 as a brown/orange solid in 97.0% yield. $^1$H NMR (d6-DMSO): δ 9.98 (s, 1H), 9.84 (s, 1H), 9.74 (s, 1H), 9.07 (s, 1H), 7.21 (s, 2H), 7.17 (s, 1H), 7.03 (d, J=1.5 Hz, 1H), 7.00 (s, 1H), 6.87 (s, 1H), 6.82 (s, 1H), 3.83 (s, 3H), 3.82 (s, 3H), 3.81 (s, 3H), 3.79 (s, 3H), 1.44 (s, 9H). LC/MS (ESI): m/z=607.72 (M+H).

Boc-Py-Py-Py-Py-NH(CH$_2$)$_3$N(CH$_3$)$_2$ (EC2165): EC2165 was synthesized accord to the same produced as EC2162. 335 mg of EC2164 yielded 240 mg of EC2165 as a white solid in 62.9% yield. $^1$H NMR (d6-DMSO): δ 9.90 (s, 1H), 9.86 (s, 1H), 9.84 (s, 1H), 9.07 (s, 1H), 8.05 (t, J=5.7 Hz, 1H), 7.22 (d, J=2.5 Hz, 1H), 7.20 (d, J=1.4 Hz, 1H), 7.17 (d, J=2.0 Hz, 1H), 7.04 (d, J=1.5 Hz, 1H), 7.03 (d, J=1.9 Hz, 1H), 6.87 (s, 1H), 6.82 (s, 1H), 6.81 (s, 1H), 3.83 (s, 6H), 3.79 (s, 3H), 3.78 (s, 3H), 3.22 (m, 2H), 2.22 (t, J=7.2 Hz, 2H), 2.12 (s, 6H), 1.60 (m, 2H), 1.44 (s, 9H). LC/MS (ESI): m/z=691.56 (M+H).

2HCl*H-Py-Py-Py-Py-NH(CH$_2$)$_3$N(CH$_3$)$_2$ (EC2166): EC2166 was synthesized accord to the same produced as EC2156. 115 mg of EC2165 yielded 92 mg of EC2166 as a pale brown solid in 92% yield. $^1$H NMR (d6-DMSO): δ 9.89 (s, 1H), 9.85 (m, 4H), 9.58 (s, 1H), 8.03 (t, J=1.2 Hz, 1H), 7.21 (d, J=2.0 Hz, 1H), 7.18 (d, J=1.9 Hz), 7.15 (d, J=2.0 Hz, 1H), 7.01 (d, J=1.9 Hz, 1H), 7.00 (d, J=1.9 Hz, 1H), 6.80 (d, J=1.5 Hz, 1H), 6.35 (d, J=1.4 Hz, 1H), 6.24 (d, J=2.0 Hz, 1H), 3.82 (s, 6H), 3.77 (s, 3H), 3.71 (s, 3H), 3.23 (q, J=6.8, 23.3 Hz, 2H), 2.21 (t, J=7.1 Hz, 2H), 2.11 (s, 6H), 1.58 (m, 2H). LC/MS (ESI): m/z=597.67 (M+H).

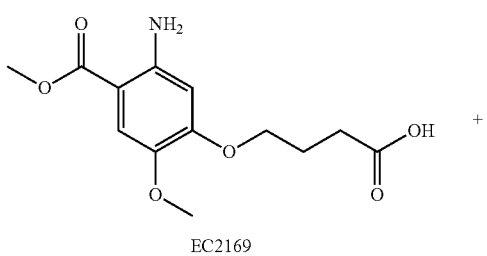

EC2169

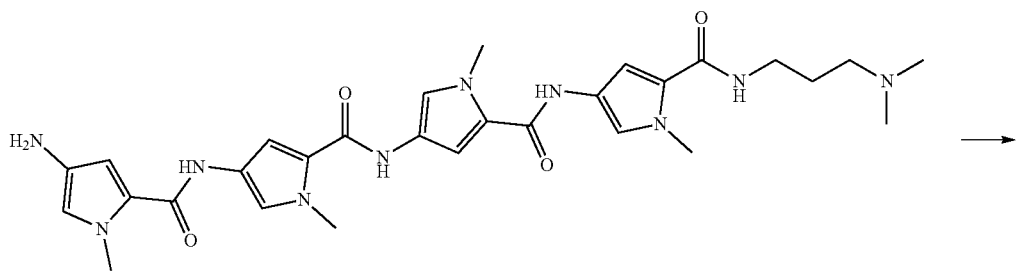

EC2166

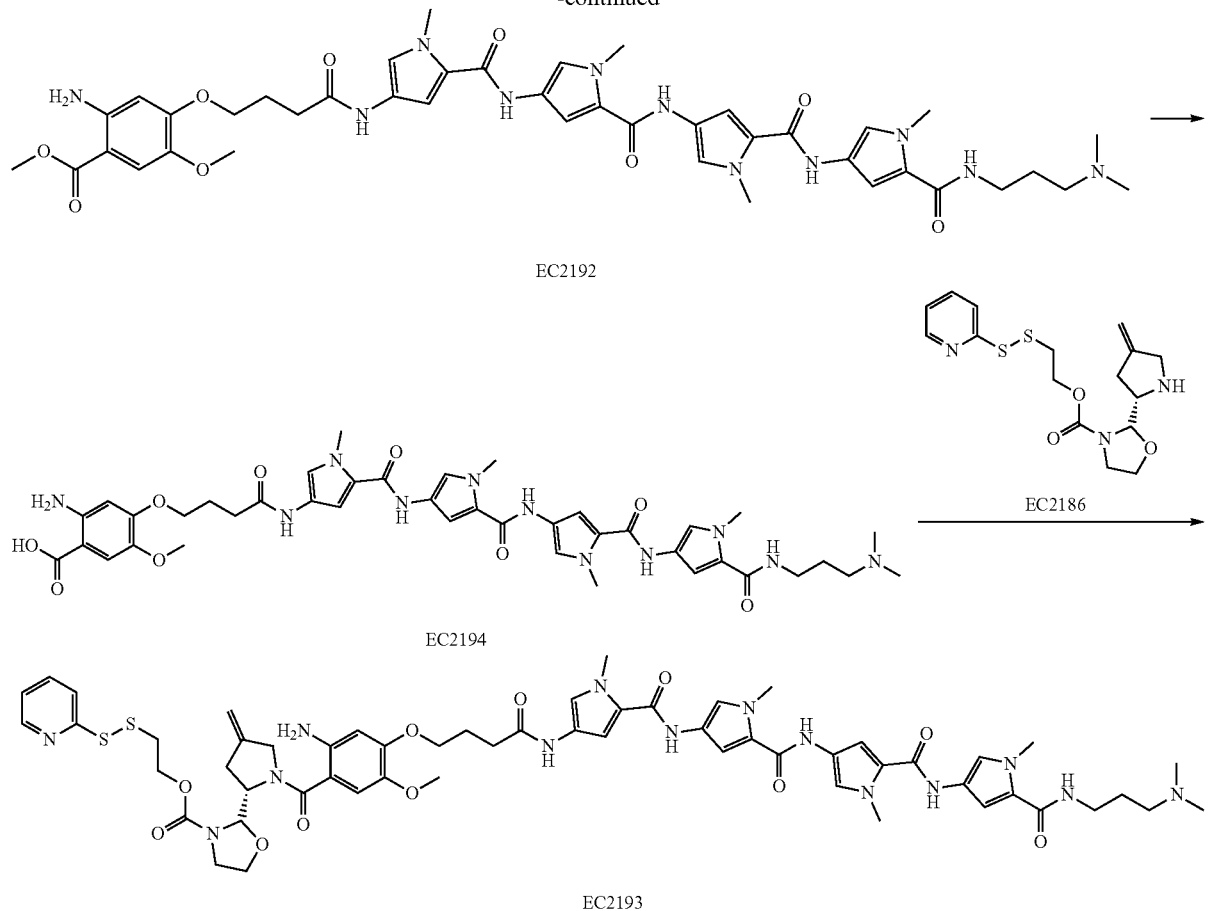

EC2192. EC2169 (28.3 mg, 0.1 mmol) and EC2166 (56.1 mg, 0.1 mmol) were dissolved in DMF (1.2 mL). The solution was treated with PyBOP (104.1 mg, 0.2 mmol) and DIPEA (69.7 µL, 0.4 mmol) at ambient temperature under Ar. The reaction was stirred for 2 h and purified with CombiFlash in 0-20% MeOH/DCM+0.1% TEA. 30.3 mg of EC2192 is obtained (35%). LCMS: [M+H]+ m/z=856.

EC2193. EC2192 (30.3 mg, 0.035 mmol) was converted to EC2194 in THF/MeOH/H2O (0.9/0.3/0.3 mL) by LiOH (1M solution, 0.3 mL) at ambient temperature. EC2194 was isolated under reduced pressure. LCMS: [M+H]+ m/z=842. EC 2186 (0.044 mmol, 25.4 mg) and EC2194 (0.035 mmol) were mixed in THF/DMF (1 mL/0.5 mL) and treated with PyBOP (36.4 mg, 0.07 mmol) and DIPEA (12.2 µL/0.07 mmol) at ambient temperature under Ar. The reaction was stirred for 2-3 h then separated with CombiFlash in 0-20% MeOH/DCM+0.1% TEA to obtain EC2193 (14.7 mg, 35%). LCMS: [M+H]+ m/z=1192.

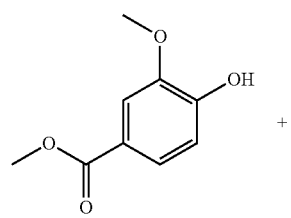

+

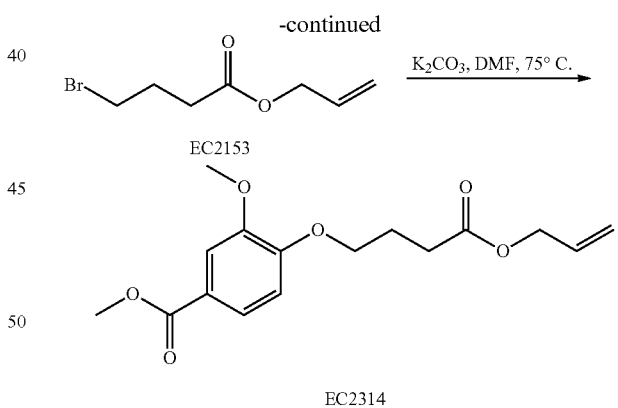

A mixture of methyl vanillate (402.2 mg, 2.21 mmol), EC2153 (502.9 mg, 2.43 mmol), and K₂CO₃ (0.6 g, 4.42 mmol) in anhydrous acetone (8.84 mL) was heated with stirring at 60° C. for 1.5 hr. The reaction was cooled to ambient temperature, the solid was filtered out, and concentrated under reduced pressure to give a residue, which was purified by CombiFlash in 0-25% EtOAc/p-ether to give 678.8 mg of EC2314 (yield 99%). LCMS: [M+H]+ m/z=309. ¹H NMR (500 MHz, CDCl₃) δ 7.64 (dd, J=8.80, 1.96 Hz, 1H), 7.53 (d, J=1.96 Hz, 1H), 5.90 (m, 1H), 5.32 (dd, J=17.60, 1.95 Hz, 1H), 5.23 (dd, J=10.27, 0.98 Hz, 1H), 4.59 (dd, J=5.87, 1.47 Hz, 2H), 4.13 (t, J=6.35 Hz, 2H), 3.90 (s, 3H), 3.89 (s, 3H), 2.58 (t, J=7.09 Hz, 2H), 2.19 (m, 2H).

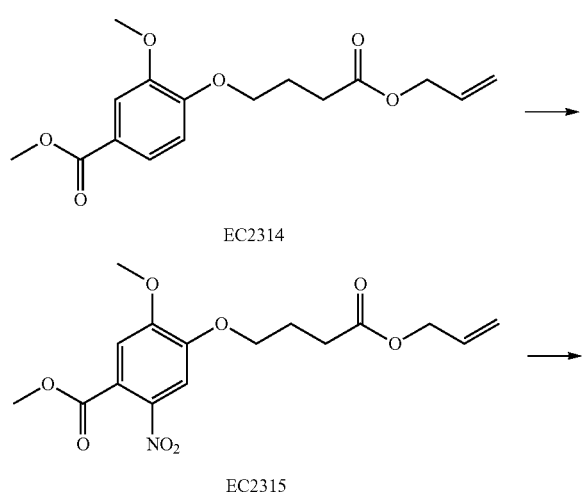

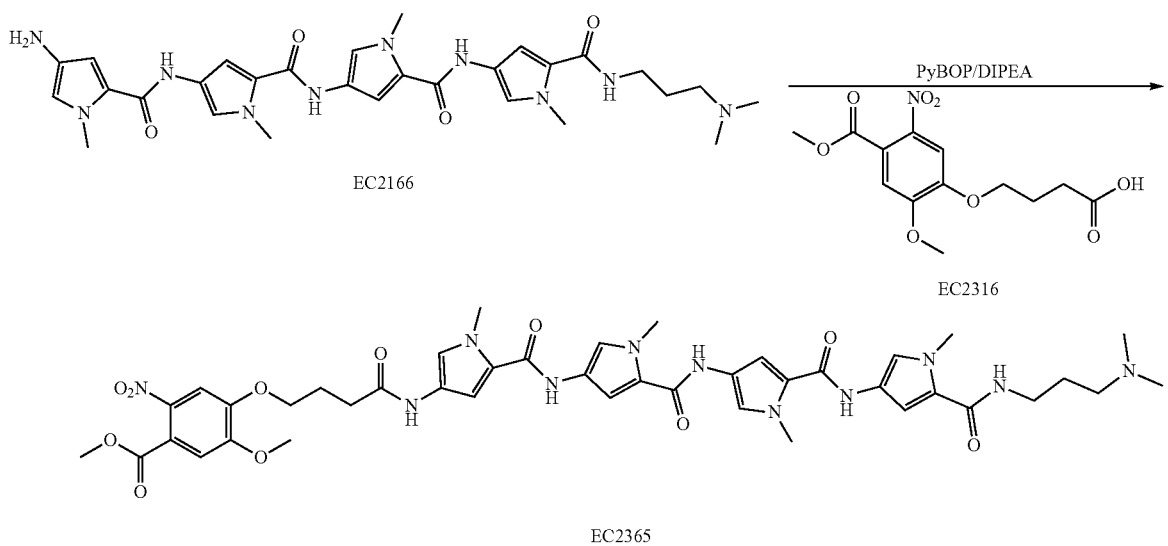

Flash system for purification (silica gel, gradient elution: 0-25% EtOAc in p-ether) to produce 559.7 mg EC2315 in a yield of 82%. LCMS: [M+H]⁺ m/z=354. ¹H NMR (500 MHz, CDCl₃) δ: 7.43 (s, 1H), 7.05 (s, 1H), 5.89 (m, 1H), 5.30 (d, J=17.1 Hz, 1H), 5.22 (d, J=10.27 Hz, 1H), 4.58 (d, J=6.84 Hz, 2H), 4.57 (t, J=6.36 Hz, 2H), 4.11 (s, 3H), 3.92 (s, 3H), 2.57 (t, J=7.34 Hz, 2H), 2.19 (m, 2H). ¹³C NMR (500 MHz, CDCl₃) δ: 172.39, 166.27, 152.78, 149.64, 141.12, 132.04, 121.62, 118.42, 110.96, 108.13, 68.41, 65.27, 56.52, 53.19, 30.38, 24.14.

The mixture of EC2315 (559.7 mg, 1.58 mmol) and Pd(PPh₃)₄ was dissolved in pre-mixed piperidine (1.1 mL, 11.06 mmol) and formic acid (417.3 μL, 11.06 mmol) in DCM (40 mL). To that solution was added water (1.0 mL) and the reaction was stirred at rt for 30 min. When the reaction was completed, the solvent was removed in vacuo, the residue was loaded to CombiFalsh in 0-20% MeOH/DCM to give the correspondent acid EC2316 as a solid (264.6 mg, yield 53%). LCMS: [M+H]⁺ m/z=314.52. ¹H NMR (500 MHz, MeOH-d4) δ: 7.55 (s, 1H), 7.23 (s, 1H), 4.15 (t, J=5.86 Hz, 2H), 3.95 (s, 3H), 3.87 (s, 3H), 2.51 (t, J=7.34 Hz, 2H), 2.11 (m, 2H).

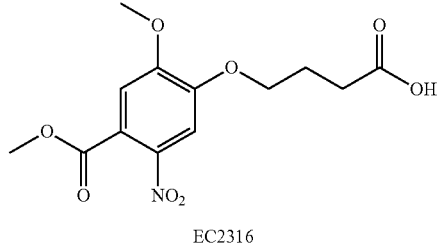

-continued

A mixture of EC2314 (598.9 mg, 1.94 mmol) in acetic anhydride (9.7 mL) was cooled to 0° C. and treated with Cu(NO₃)₂.3H₂O by slow addition. The reaction was kept at 0° C. for 1 h. The reaction was stirred at rt for 2 hrs. The reaction was poured into a stirred ice water and stirred for 1 hr. The reaction mixture in water was extracted with EtOAc (3×). The combined organic phase was washed with water and dried over anhydrous Na₂SO₄ and concentrated under reduced pressure. The residue was loaded onto a Combi- The solution of EC2166 (107.1 mg, 0.18 mmol) and EC2316 (56.8 mg, 0.18 mmol) in anhydrous DMF (1 mL) was treated with PyBOP (187.3 mg, 0.36 mmol) and DIPEA (125.4 μL, 0.72 mmol) at rt for 2 hr under Ar. The reaction was purified with CombiFalsh (silica, 0-20% MeOH/DCM) to give EC2365 (79.3 mg, yield 50%). LCMS: [M+H]⁺ m/z=886.97. ¹³C NMR (500 MHz, MeOH-d4) δ: 162.82, 152.88, 123.26, 121.89, 121.10, 119.40, 118.99, 110.81, 107.97, 105.14, 104.51, 68.59, 56.91, 55.63, 52.12, 43.94, 37.13, 35.36, 35.30, 32.21, 26.82, 24.87. ¹H NMR (500 MHz, MeOH-d4) δ:7.54 (s, 1H), 7.20 (s, 1H), 7.16 (m, 3H), 7.11 (d, J=1.95 Hz, 1H), 6.92 (m, 2H), 6.82 (d, J=1.96 Hz, 1H), 6.78 (d, J=1.96 Hz, 1H), 4.17 (t, J=5.87 Hz, 2H), 3.88 (m, 12H), 3.86 (s, 6H), 3.33 (m, 2H), 2.53 (t, J=7.34 Hz, 2H), 2.43 (m, 2H), 2.28 (s, 6H), 2.21 (m, 2H), 1.78 (m, 2H).

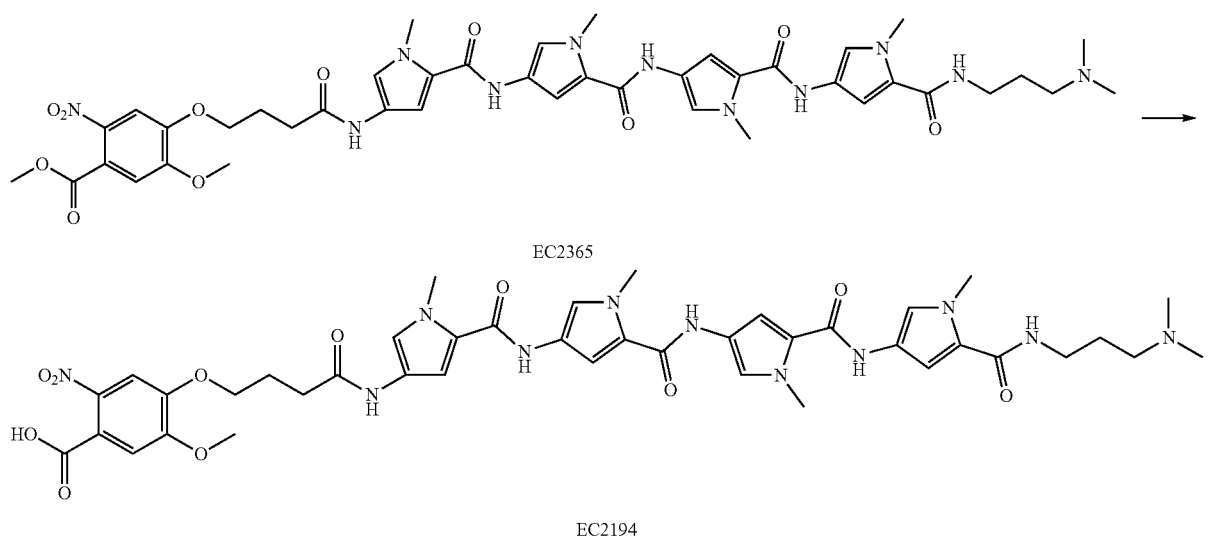

EC2363 (68.9 mg, 0.078 mmol) was dissolved in THF/MeOH/water (3:1:1, 1.6 mL) and treated with LiOH (0.33 mmol) at rt for 3 hrs. Then the reaction was diluted with MeOH (2.0 mL) and treated with Pd/C (10% wt, 10 mg) under H2 balloon at rt for overnight. The reaction was filtered through a pad of celite and concentrated in vacuo. The obtained amino acid (EC2194) was used for the next step without further purification. LCMS: [M+H]$^+$ m/z=842.85.

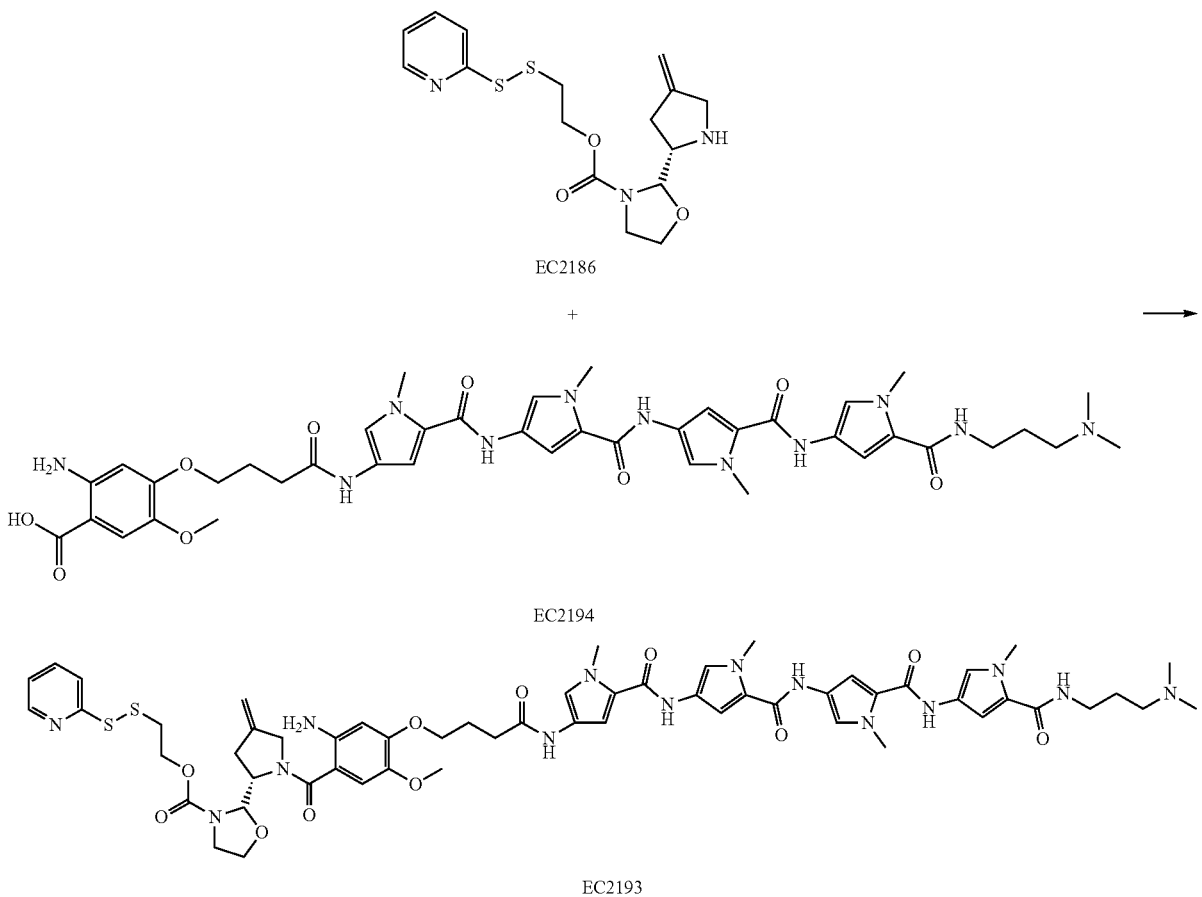

The solution of EC2194 (33.0 mg, 0.039 mmol) and EC2186 (17.3 mg, 0.047 mmol) in DMF (0.5 mL) was treated with PyBOP (40.6 mg, 0.078 mmol) and DIPEA (27.2 μL, 0.156 mmol) at rt for overnight. The reaction was purified with prep-HPLC (10 to 100% ACN in 50 mM $NH_4HCO_3$, pH 7.4) to give the product (8.4 mg, EC2193, low yield due to the instrument issue during the purification). LCMS: $[M+H]^+$ m/z=1192. (SEQ ID NOS 1 and 1 are included in the structures below)

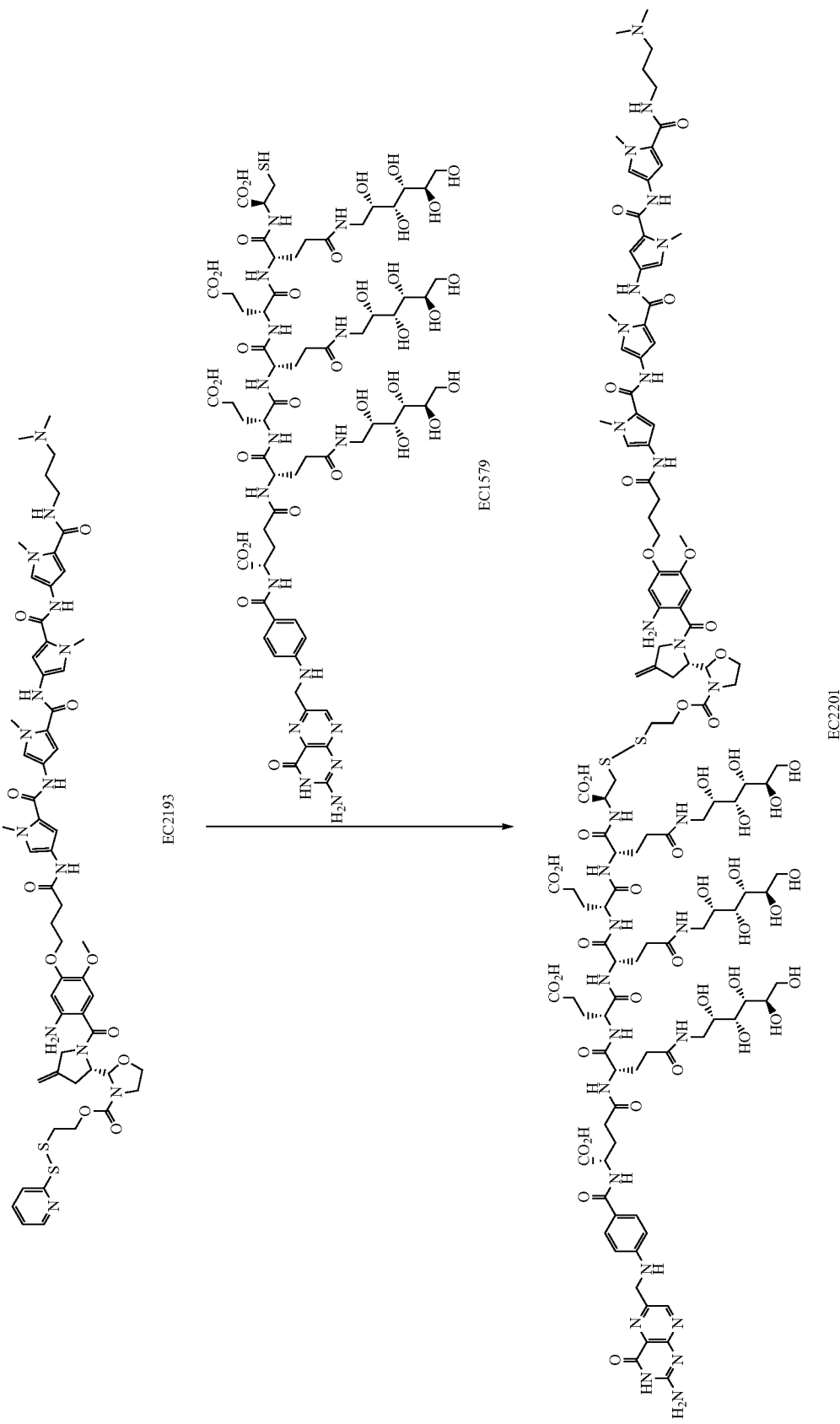

EC1579 (14.4 mg, 0.0086 mmol) was dissolved in DMSO (0.5 mL) at rt under Ar, and to which was added the solution of EC2193 (8.4 mg, 0.0071 mmol) in DMSO (0.5 mL). The reaction mixture was treated with TEA (5.9 µL, 0.043 mmoL) and stirred at rt for 30 min under Ar. The reaction was purified with prep-HPLC (10 to 100% ACN in 50 mM NH$_4$HCO$_3$, pH 7.4) to give the conjugate EC2201 (8.0 mg, 41% yield). LCMS: [M+2H]$^{2+}$ m/z=1380.56; [M+3H]$^{3+}$ m/z=921.89. $^1$H NMR (500 MHz, DMSO-d$_6$, D$_2$O drops, selected data) δ: 8.57 (s, 1H), 7.54 (d, J=8.80 Hz, 2H), 7.20 (m, 4H), 6.87 (m, 2H), 6.77 (m, 2H), 6.58 (d, J=8.80 Hz, 3H), 6.31 (d, J=13.69 Hz, 1H), 4.95 (d, br, 2H).

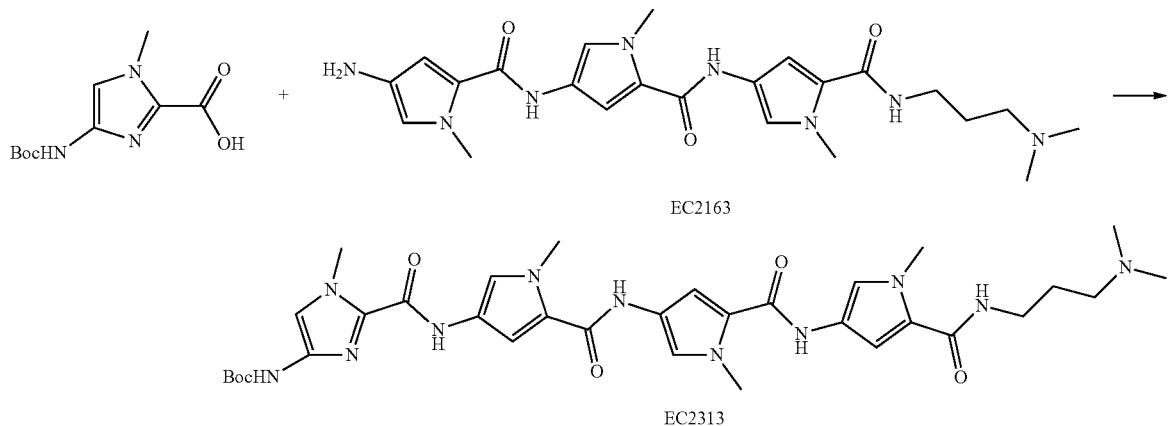

Imidazole carboxylic acid (35.03 mg, 0.145 mmol) and EC2163 (56.7 mg, 0.121 mmol) were dissolved in DMF (2 mL) and treated with PyBOP (126.0 mg, 0.242 mmol) and DIPEA (84.3 µL, 0.484 mmol) at rt under Ar. The reaction was stirred for 1 hr and then loaded to CombiFlash ((silica gel, gradient elution: 0-20% MeOH in DCM and 0.1% TEA) to give 90.1 mg of EC2313 in a yield of 93%. LCMS: [M+H]$^+$ m/z=692.9. Prior to the next step, the Boc group in EC2313 was deprotected with 50% TFA in DCM at rt for 0.5 hr to the amine TFA salt product which was used directly after the solvent and TFA were removed in vacuo.

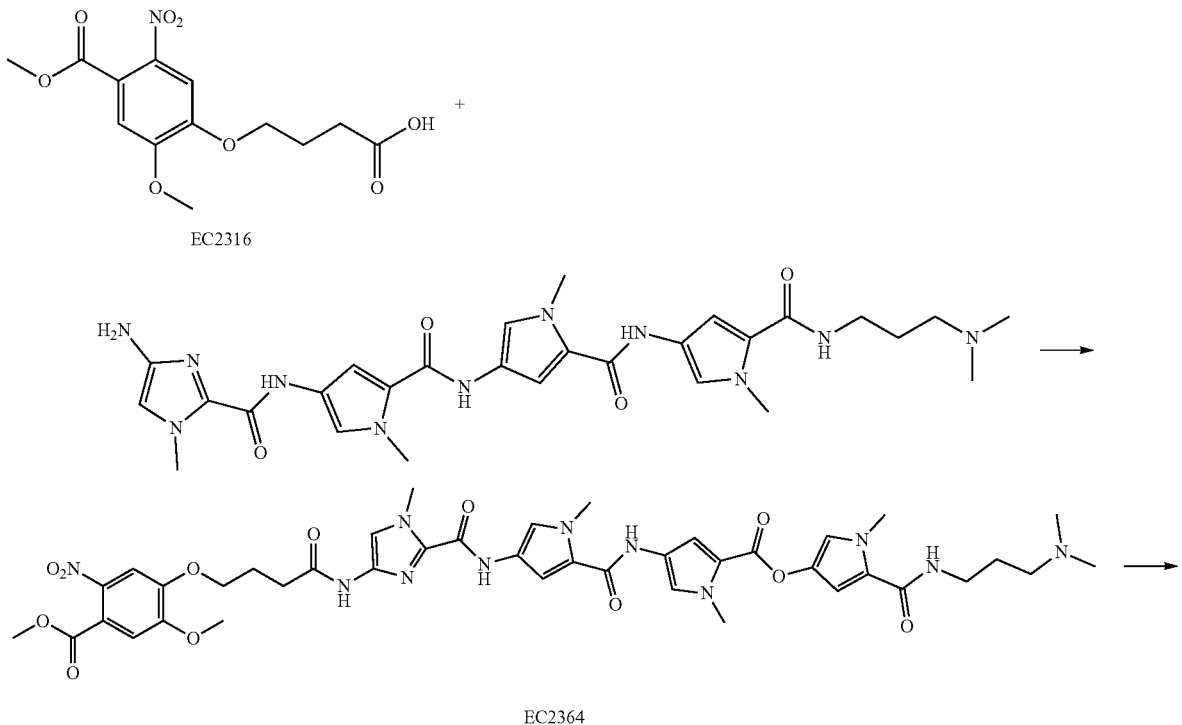

-continued

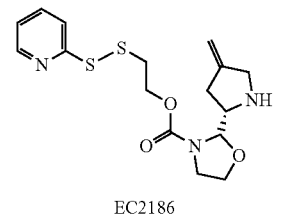

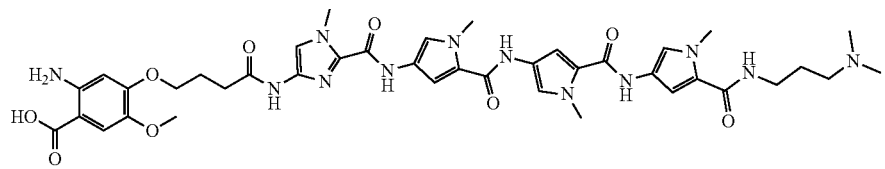

EC2367

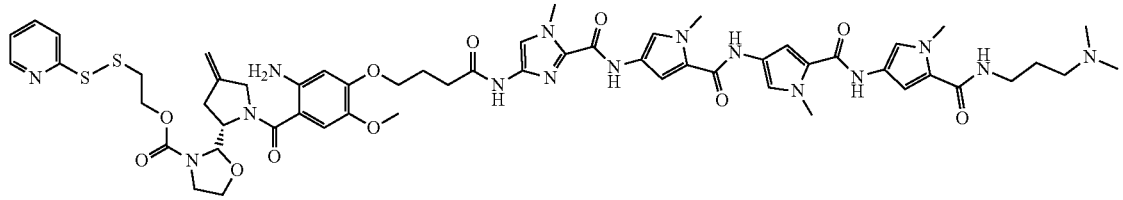

EC2366

EC2313 (90.1 mg, 0.13 mmol) was treated with 50% TFA/DCM at rt for 0.5 hr. the solvent was then removed in vacuo and redissolved in DMF (0.5 mL). To the solution was added EC2316 (40.8 mg, 0.13 mmol), PyBOP (134.3 mg, 0.26 mmol) and DIPEA (90.6 µL, 0.52 mmol). The reaction was stirred overnight at rt. The reaction was purified with prep-HPLC (10 to 100% ACN in 50 mM NH$_4$HCO$_3$, pH 7.4). 78.1 mg of the desired product EC2364 was obtained (68% yield). LCMS: [M+H]$^+$ m/z=887.8. $^1$H NMR (500 MHz, MeOH-d$_4$, selected data) δ: 7.56 (s, 1H), 7.38 (s, 1H), 7.26 (d, J=1.96 Hz, 1H) 7.21 (s, 1H), 7.19 (d, J=1.46 Hz, 1H) 7.17 (d, J=1.95 Hz, 1H), 6.95 (m, 2H), 6.85 (d, J=1.96 Hz, 1H) 4.20 (t, J=5.87 Hz, 2H), 4.03 (s, 3H), 3.93 (s, 3H), 3.91 (s, 3H) 3.89 (s, 3H), 3.88 (s, 3H), 3.87 (s, 3H) 3.85 (s, 3H).

EC2364 (78.1 mg, 0.088 mmol) was converted to an acid in THF/MeOH (0.9/0.3 mL) by LiOH (1M solution, 0.3 mL) at rt. LCMS: [M+H]$^+$ m/z=873.8. To the reaction mixture was added Pd/C (10%, wet) after flushed with H$_2$. The reaction was stirred under hydrogen balloon overnight at rt. The mixture was filtered through a pad of celite and concentrated to give the amino acid EC2367 which was used for the next step without further purification. 59.7 mg (81% yield). LCMS: [M+H]$^+$ m/z=843.8.

Amino acid EC2367 (59.7 mg, 0.071 mmol) in DMF (0.5 mL) was coupled with EC2186 (29.4 mg, 0.08 mmol) in the presence of PyBOP (73.9 mg, 0.142 mmol) and DIPEA (49.5 µL, 0.284 mmol) overnight at rt. The product was purified with prep-HPLC (10 to 100% ACN in 50 mM NH$_4$HCO$_3$, pH 7.4) to provide EC2366 (8.1 mg, 10% for 3 steps). LCMS: [M+2H]$^{2+}$ m/z=597.2. (SEQ ID NOS 1 and 1 are included in the structures below)

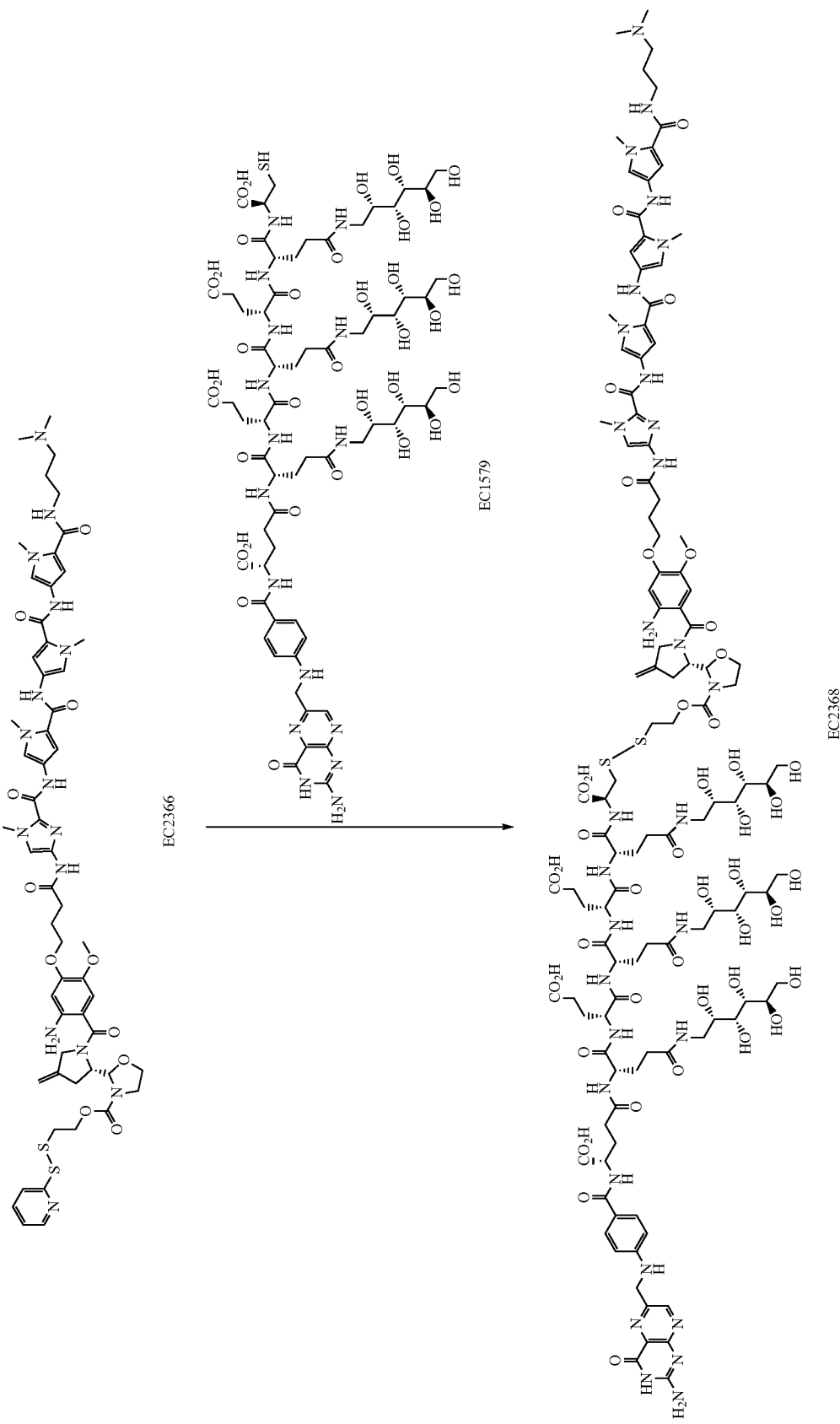

EC2366 (8.1 mg, 0.0068 mmol) in MeOH (0.5 mL) was added to the solution of EC1579 (15.0 mg, 0.0089 mmol) in DMSO (1 mL) at rt under Ar. The reaction was stirred for 0.5-1 hr. The reaction was purified with prep-HPLC (10 to 100% ACN in 50 mM NH$_4$HCO$_3$, pH 7.4) to give 3.0 mg of the product EC2368 (16% yield). LCMS: [M+3H]$^{3+}$ m/z=921, [M+2H]$^{2+}$ m/z=1382. $^1$H NMR (500 MHz, DMSO-d$_6$, D$_2$O drops, selected data) δ: 8.57 (s, br., 1H), 7.57 (s, br., 2H), 7.38 (s, 1H), 7.24 (s, 1H), 7.19 (s, 1H), 7.14 (s, 1H), 7.05 (s, 1H), 6.98 (s, 1H), 6.77 (s, 1H), 6.61 (s, br, 3H), 6.33 (s, 1H).

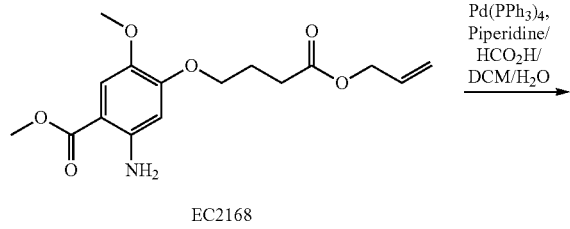

EC2168

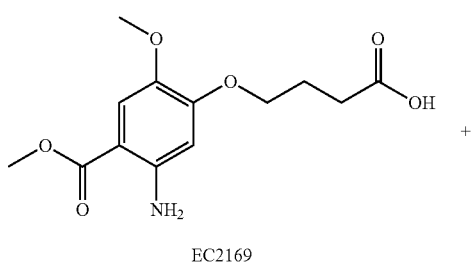

EC2169

EC2169. A mixture of EC2168 (982 mg, 3.04 mmol) and Pd(PPh$_3$)$_4$ (422 mg, 0.365 mmol) was dissolved in a pre-mixed solution of piperdine (2.10 mL)/formic acid (0.802 mL)/DCM (98.0 mL), followed by addition of water (2.0 mL). The reaction mixture was stirred at ambient temperature for 30 min, the volume was reduced to about half of the original under reduced pressure, and loaded onto a Combi-Flash system for purification (Column: silica gel. Gradient elution: 0-2% MeOH in DCM) to produce 725 mg EC2169 as a light ivory solid. MS (ESI m/z) calculated for C$_{13}$H$_{18}$NO$_6$ (M+H)$^+$: 284.11; found 284.14.

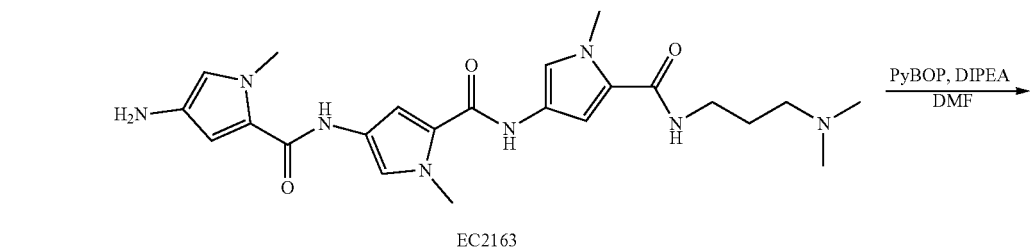

EC2163

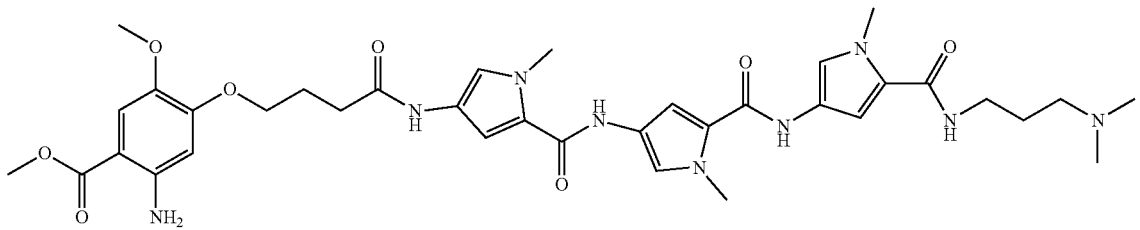

EC2184

EC2184. To a solution of EC2169 (20 mg, 0.070 mM) and EC2163 (34.4 mg, 0.060 mM) in DMF (1 mL) was added PyBop (54.6 mg, 0.105 mM) and DIPEA (0.122 mL, 0.70 mM). The reaction was allowed to stir for 30 min. LCMS analysis (20 mM NH$_4$HCO$_3$, pH 7.4) indicated that the reaction was complete. The reaction mixture was loaded onto a CombiFlash (SiO$_2$) column and eluted with 0-30% MeOH in CH$_2$Cl$_2$ to yield pure EC2184 (22 mg, 50%). LCMS (ESI): (M+H)$^+$=Calculated for C$_{36}$H$_{48}$N$_9$O$_8$, 734.35; found 734.39.

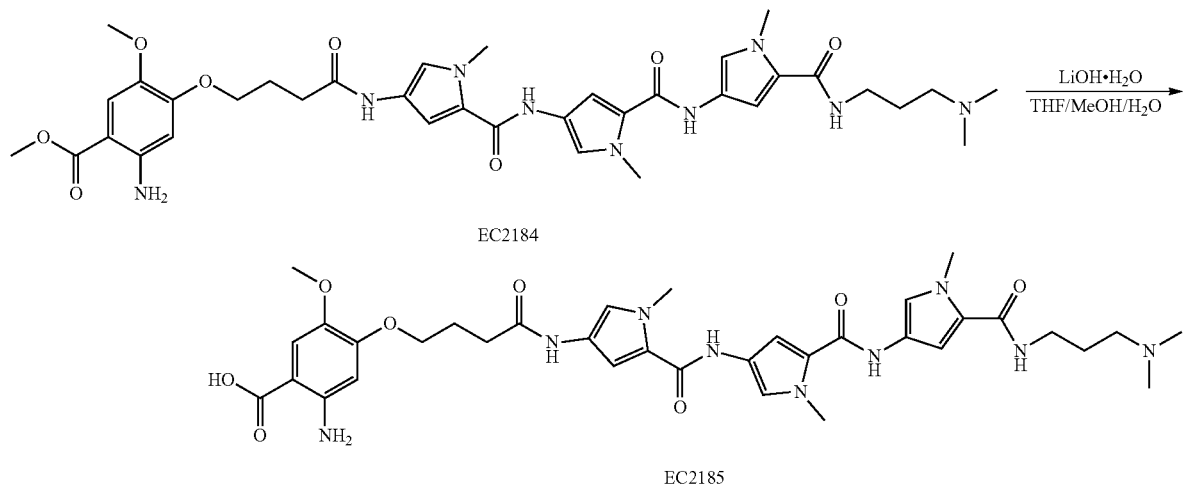

EC2184

EC2185

EC2185. To a solution of EC2184 (19 mg, 0.026 mM) in THF/MeOH (1 mL/0.33 mL) was added LiOHH$_2$O (6.5 mg, 0.155 mM) in 0.33 mL of water. The reaction was allowed to stir for 18 h. LCMS analysis (20 mM NH$_4$HCO$_3$, pH 7.4) indicated that the reaction was complete. The reaction mixture was concentrated to remove organic solvents and acidified with 2M HCl to pH 2 and freeze dried for 2 days. The isolated product was used without further purification. LCMS (ESI): (M+H)$^+$=Calculated for C$_{35}$H$_{46}$N$_9$O$_8$, 720.34; found 720.46.

the reaction was complete. The reaction mixture was loaded onto a combiflsh (SiO$_2$) column and eluted with 0-30% MeOH in CH$_2$Cl$_2$ (0.2% TEA) to yield pure EC2415 (30 mg, 37%). $^1$H NMR (500 MHz, CD$_3$OD): δ 7.51 (s, 1H), 7.17 (s, 1H), 7.14 (m, 2H), 7.10 (d, J=2 Hz, 1H), 6.89 (d, J=2 Hz, 1H), 6.80 (d, J=1.5 Hz, 1H), 6.76 (d, J=2 Hz, 1H), 4.14 (t, J$_1$=6.0 Hz, J$_2$=6.5 Hz, 2H), 3.87 (s, 6H), 3.86 (s, 3H), 3.85

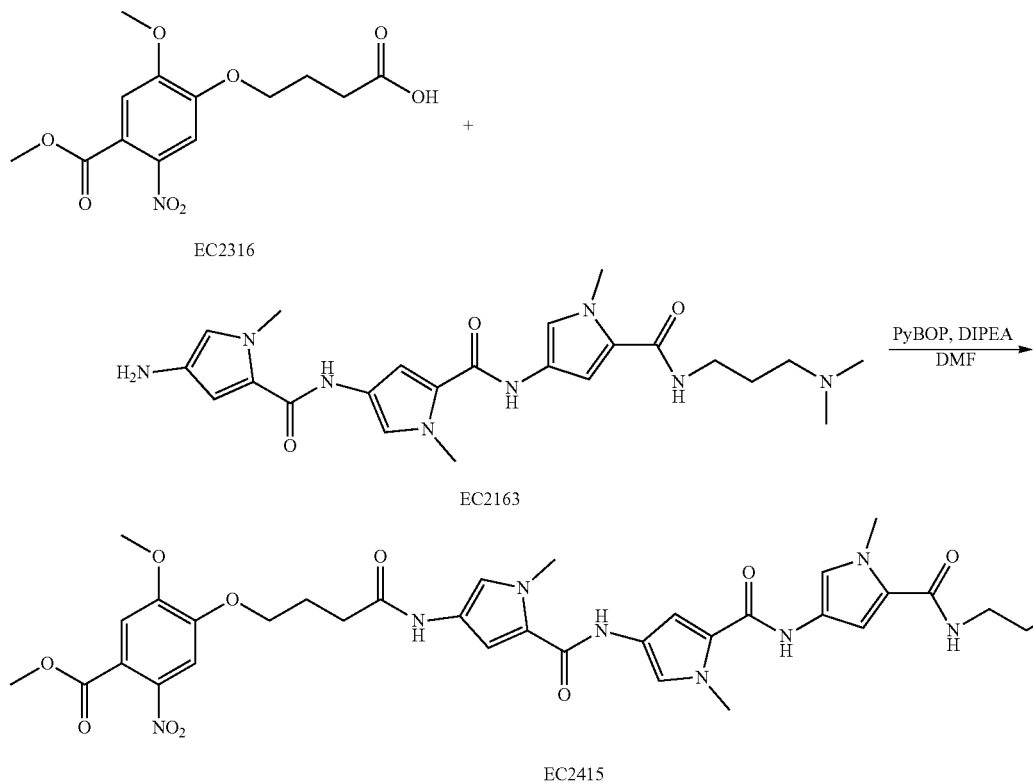

EC2316

EC2163

EC2415

To a solution of EC2316 (33.4 mg, 0.107 mM) and EC2163 (50 mg, 0.107 mM) in DMF (1 ml) was added PyBop (83.5 mg, 0.161 mM) and DIPEA (0.075 ml, 0.70 mM) respectively. The reaction was allowed to stir for 3 h. LCMS analysis (20 mM NH$_4$HCO$_3$, pH 7.4) indicated that (s, 3H), 3.84 (s, 3H), 3.31 (t, J$_1$=7.0 Hz, J$_2$=7.5 Hz, 2H), 2.52 (t, J$_1$=7.5 Hz, J$_2$=7.5 Hz, 2H), 2.39 (t, J$_1$=8.5 Hz, J$_2$=7.0 Hz, 2H), 2.25 (s, 6H), 2.17 (m, 2H), 1.75 (m, 2H); LCMS (ESI): (M+H)$^+$=Calculated for C$_{36}$H$_{45}$N$_9$O$_{10}$, 764.33; found 764.38.

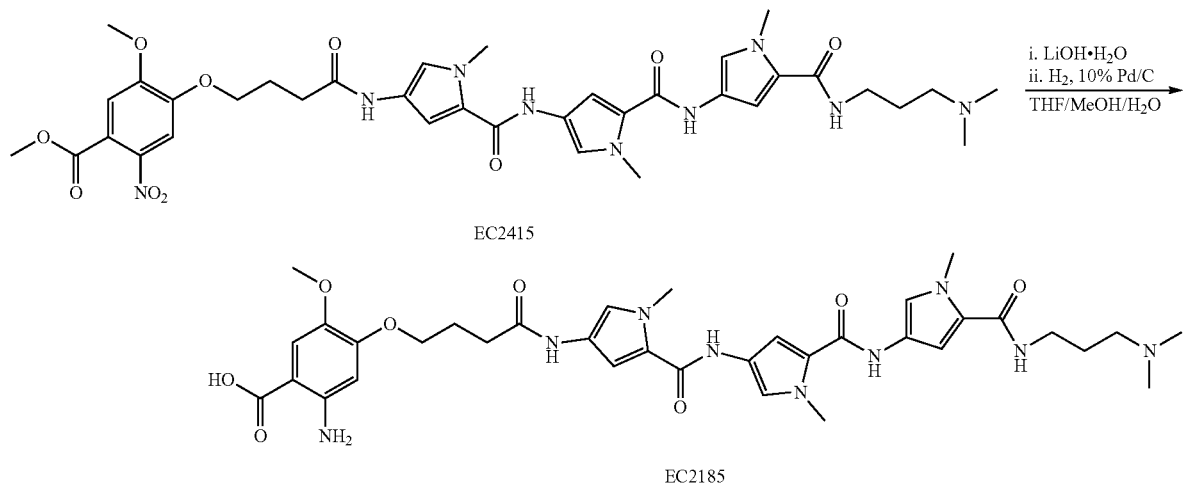

To a solution of EC2415 (30 mg, 0.039 mM) in THF/MeOH (0.6 mL/0.2 mL) was added LiOH.H₂O (4.9 mg, 0.118 mM) in 0.2 mL of water. The reaction was allowed to stir for 24 h. LCMS analysis (20 mM NH₄HCO₃, pH 7.4) indicated that the reaction was complete. The reaction mixture was diluted with methanol (1.0 mL), 10% Pd/C (6 mg) was added. Reaction mixture was stirred under H₂ atmosphere (balloon) for 24 h. LCMS analysis (20 mM NH₄HCO₃, pH 7.4) indicated that the reaction was complete (same retention time as starting material but mass is different). Reaction mixture was filtered over celite pad and concentrated. Crude product (EC2185) was dried and directly used for next reaction. LCMS (ESI): (M+H)⁺=Calculated for $C_{35}H_{45}N_9O_8$, 720.34; found 720.40.

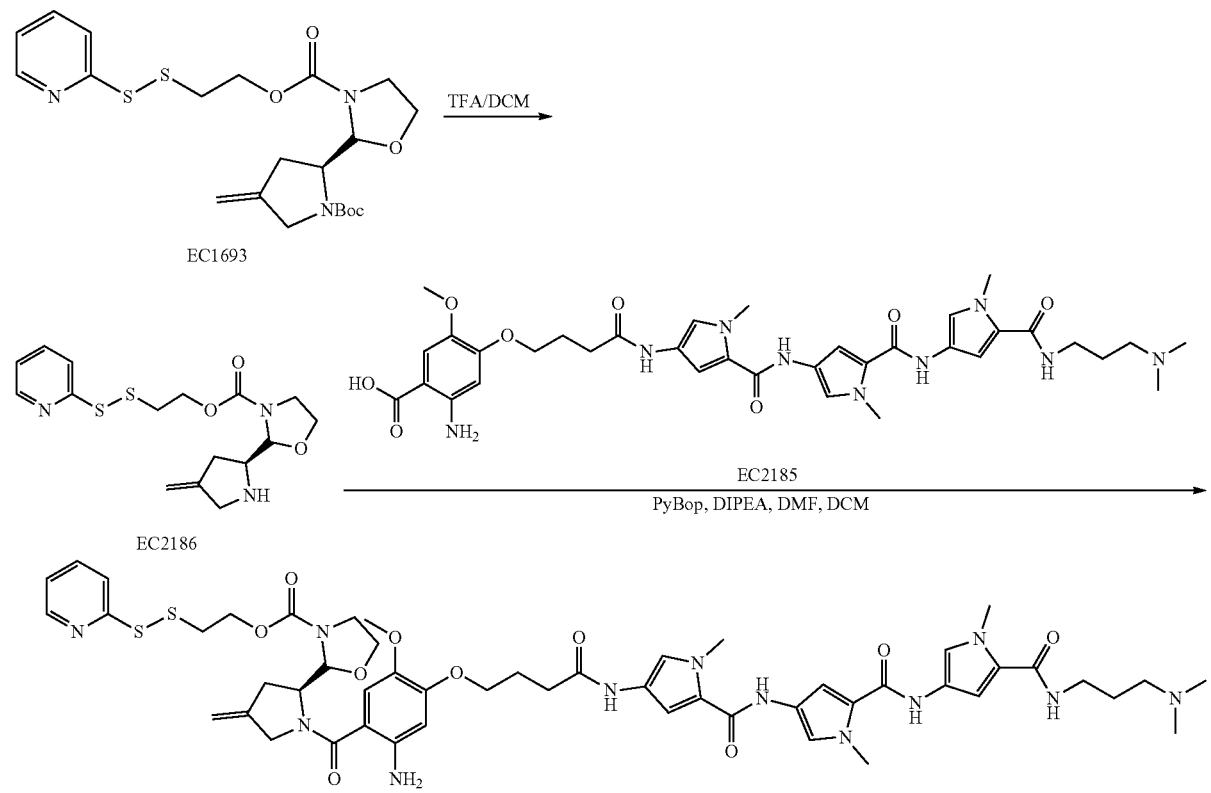

EC1693 (21 mg, 0.045 mM) was treated with the mixture of TFA/dichloromethane/TIPS (1 mL/1 mL/0.05 mL) and stirred for 30 min. LCMS analysis (20 mM NH₄HCO₃, pH 7.4) indicated that the reaction was complete. The reaction mixture was concentrated to dryness, co-evaporated with DCM (3 times) and dried under high vacuum for 1 h to yield EC2186. In another flask, EC2185 (28 mg, 0.039 mM, from previous reaction) was dissolved in dry DMF (1 mL). PyBop (40.6 mg, 0.078 mM) and DIPEA (0.136 mL, 0.78 mM) were added respectively. After the reaction mixture stirred for 5 min, EC2186 (prepared earlier) in DCM (1 mL) was added, and stirred for 1 h. LCMS analysis (20 mM $NH_4HCO_3$, pH 7.4) indicated that the reaction was complete. The reaction mixture was purified with prep-HPLC (10 to 100% acetonitrile in 20 mM $NH_4HCO_3$, pH 7.4) to yield pure EC2187 (22 mg, 53%, over 3 steps). $^1$H NMR (500 MHz, $CD_3OD$): δ 8.40 (m*, 1H), 8.37 (m*, 1H), 8.16 (m*, 1H), 7.84-7.70 (m*, 2H), 7.26-7.20 (m*, 1H), 7.17 (m*, 1H), 7.13 (d, J=1.5 Hz, 1H), 6.92 (d, J=1.5 Hz, 1H), 6.82 (dd, $J_1$=6 Hz, $J_2$=1.5 Hz, 2H), 6.42 (s, 1H), 5.14 (d, J=5 Hz, 1H) 5.10-4.94 (m*, 3H), 4.50-4.06 (m*, 5H), 4.04 (t, $J_1$=6 Hz, $J_2$=6.5 Hz, 2H), 3.90 (s, 3H), 3.88 (s, 3H), 3.87 (s, 3H), 3.85 (m*, 1H), 3.73 (s, 3H), 3.36 (t, $J_1$=6 Hz, $J_2$=7 Hz, 2H), 3.33 (m*, 1H), 3.20-3.00 (m*, 5H), 2.72 (m*, 2H), 2.55 (m*, 2H), 2.53 (s, 6H), 2.20-2.12 (m*, 2H), 1.85 (m, 2H); LCMS (ESI): $(M+H)^+$=Calculated for $C_{51}H_{65}N_{12}O_{10}S_2$, 1069.43; found 1069.60. (SEQ ID NOS 1 and 1 are included in the structures below)

* Due to diasteromeric and/or rotameric nature of the compound

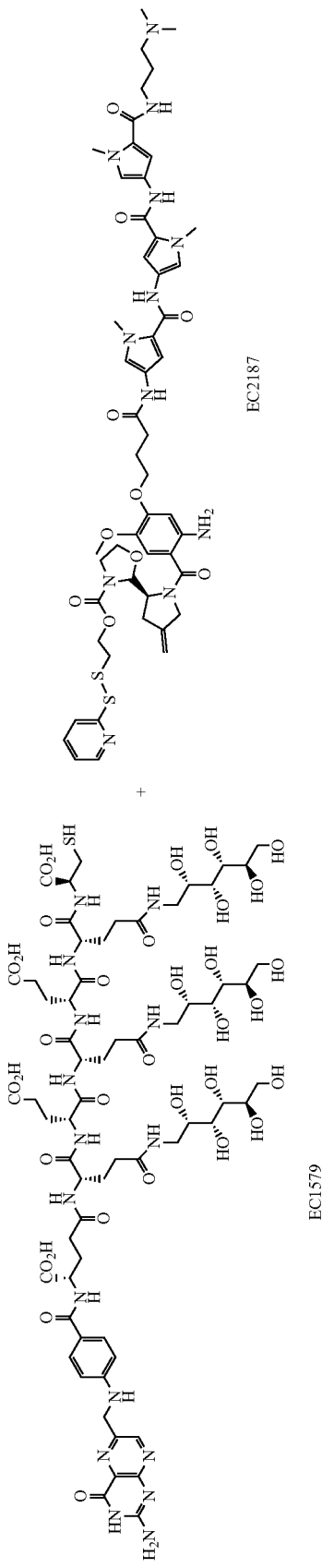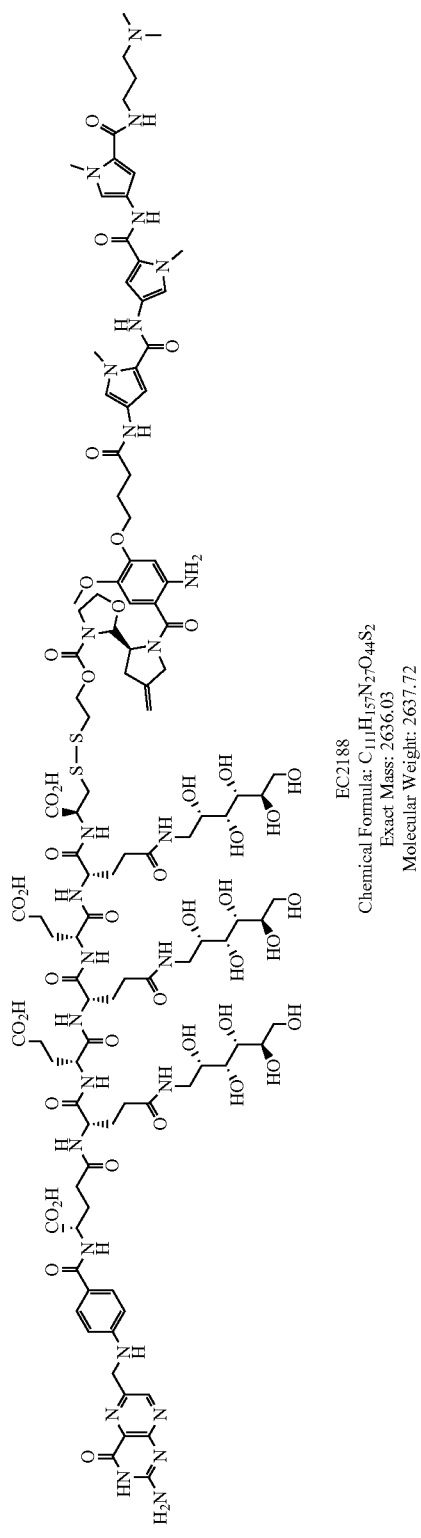

EC1579 (13.3 mg, 0.0079 mmol) in DMSO (0.5 mL) under Argon was stirred to a clear solution and to which was added the solution of EC2187 (7 mg, 0.0066 mmol) in DMSO (0.5 mL) followed by addition of DIPEA (0.023 mL, 0.131 mmol). The reaction was stirred for 1 hr at r.t. under Argon. The product was isolated with prep-HPLC in 10-100% MeCN/pH 7 buffer to give EC2188, 10.4 mg (60% in yield) as a solid after lyophilized. $^1$H NMR (500 MHz, DMSO-D$_6$+D$_2$O) (selected data): δ 8.59 (s, 1H), 7.57 (d, J=8.5 Hz, 2H), 7.20 (d, J=2 Hz, 1H), 7.16 (d, J=2 Hz, 1H), 7.13 (d, J=1.5 Hz, 1H), 6.94 (d, J=2 Hz, 1H), 6.82 (d, J=1.5 Hz, 1H), 6.77 (d, J=2 Hz, 1H), 6.60 (d, J=9 Hz, 2H), 6.58 (m, 1H), 6.33 (s, 1H), 4.97 (s, 2H), 4.93 (s, 1H), 4.45 (s, 2H); LCMS: [M+2H]$^{2+}$ m/z=Calculated for C$_{111}$H$_{157}$N$_{27}$O$_{44}$S$_2$, 1319.02; found 1319.51.

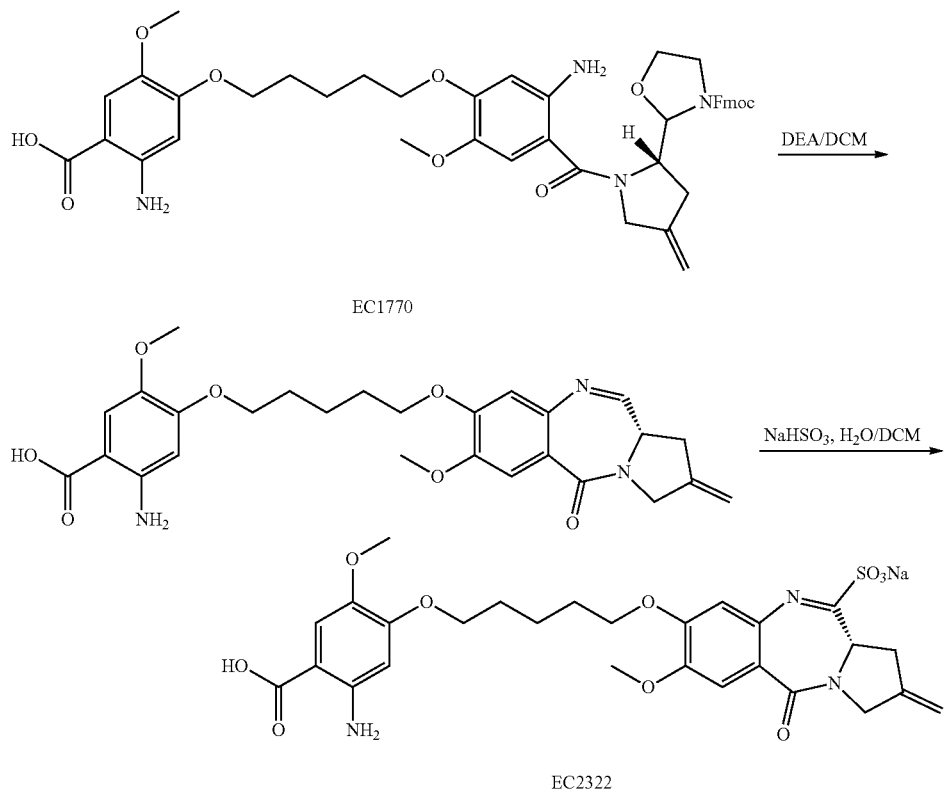

A solution of EC1770 (111 mg) and diethylamine (2.0 mL) in anhydrous DCM (5.0 mL) was stirred at ambient temperature under argon for 90 min, concentrated, co-evaporated with DCM (3 mL×3), dried under vacuum for 60 min, re-dissolved in DCM (20 mL), and mixed with a solution of NaHSO$_3$ (14.6 mg) in water (20 mL). The reaction mixture was stirred at ambient temperature for 60 min and separated. The organic layer was extracted with water (15 mL) and the combined aqueous layers were freeze-dried to yield 86.5 mg (101%) EC2322 as a beige solid. $^1$H NMR (500 MHz, 298 K, DMSO-d6) δ 7.301 (s, 1H), 6.968 (s, 1H), 6.478 (s, 1H), 6.220 (s, 1H), 5.078 (s, 1H), 5.026 (s, 1H), 4.215 (d, J=17.0 Hz, 1H), 3.953 (m, 4H), 3.884 (m, 2H), 3.714 (d, J=22.5 Hz, 1H), 3.669 (s, 3H), 3.596 (s, 3H), 3.151 (d, J=14.0 Hz, 1H), 2.830 (m, 1H), 1.757 (m, 4H), 1.525 (m, 2H). MS$^-$ (ESI m/z) calculated for C$_{27}$H$_{32}$N$_3$O$_{10}$S: 590.18; found 590.27. (SEQ ID NO: 1 is included in the structure below)

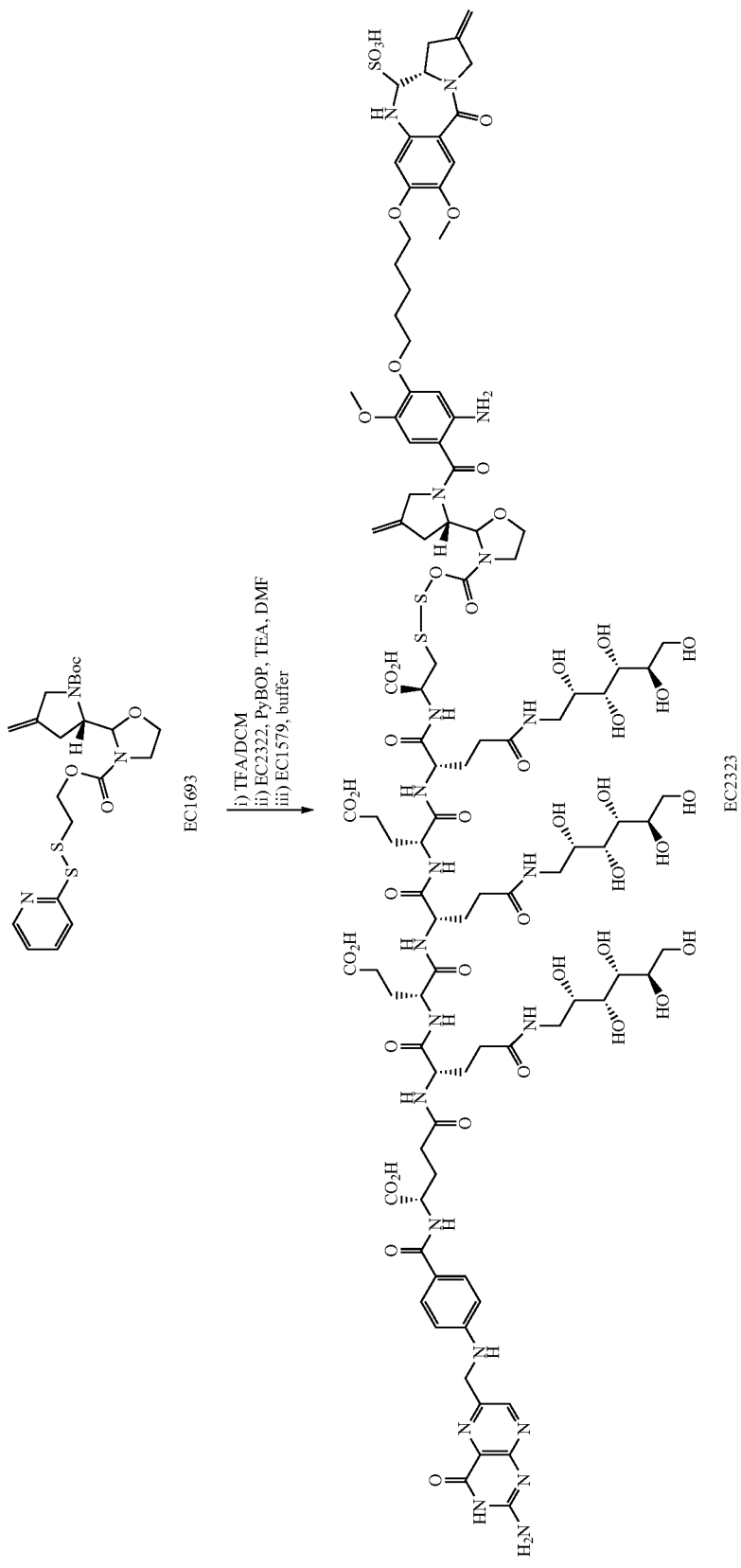

EC1693 (19.8 mg) was dissolved in a solution of TFA (0.15 mL) and DCM (0.85 mL), stirred at ambient temperature for 30 min, concentrated, co-evaporated with DCM (1 mL×3), and dried under vacuum for 60 min. The residue was dissolved in anhydrous DMF (2.5 mL) and transferred into a small vial containing EC2322 (18.3 mg) and PyBOP (19.4 mg). To the resulting solution was added TEA (32.0 μL). The reaction mixture was stirred at ambient temperature under argon for 15 min and a solution of EC1579 (76.1 mg) in buffer (50 mM $NH_4HCO_3$, pH 7.0, 7.0 mL) was added. The resulting homogeneous solution was stirred at ambient temperature under argon for 15 min and loaded directly onto a preparative HPLC (Mobile phase A: 50 mM $NH_4HCO_3$ buffer, pH 7.0; B=ACN. Method: 10-80 B % in 20 min.) for purification to produce 7.9 mg (10.6%) EC2323 as a pale yellow solid. Selective $^1$H NMR (500 MHz, 298 K, $D_2O$) δ 8.671 (s, 1H), 7.711 (b, 2H), 7.146 (s, 1H), 6.824 (b, 3H), 6.728 (s, 1H), 6.419 (b, 2H). MS⁻ (ESI m/2z) calculated for $C_{103}H_{144}N_{21}O_{46}S_3$: 1253.44; found 1253.89.

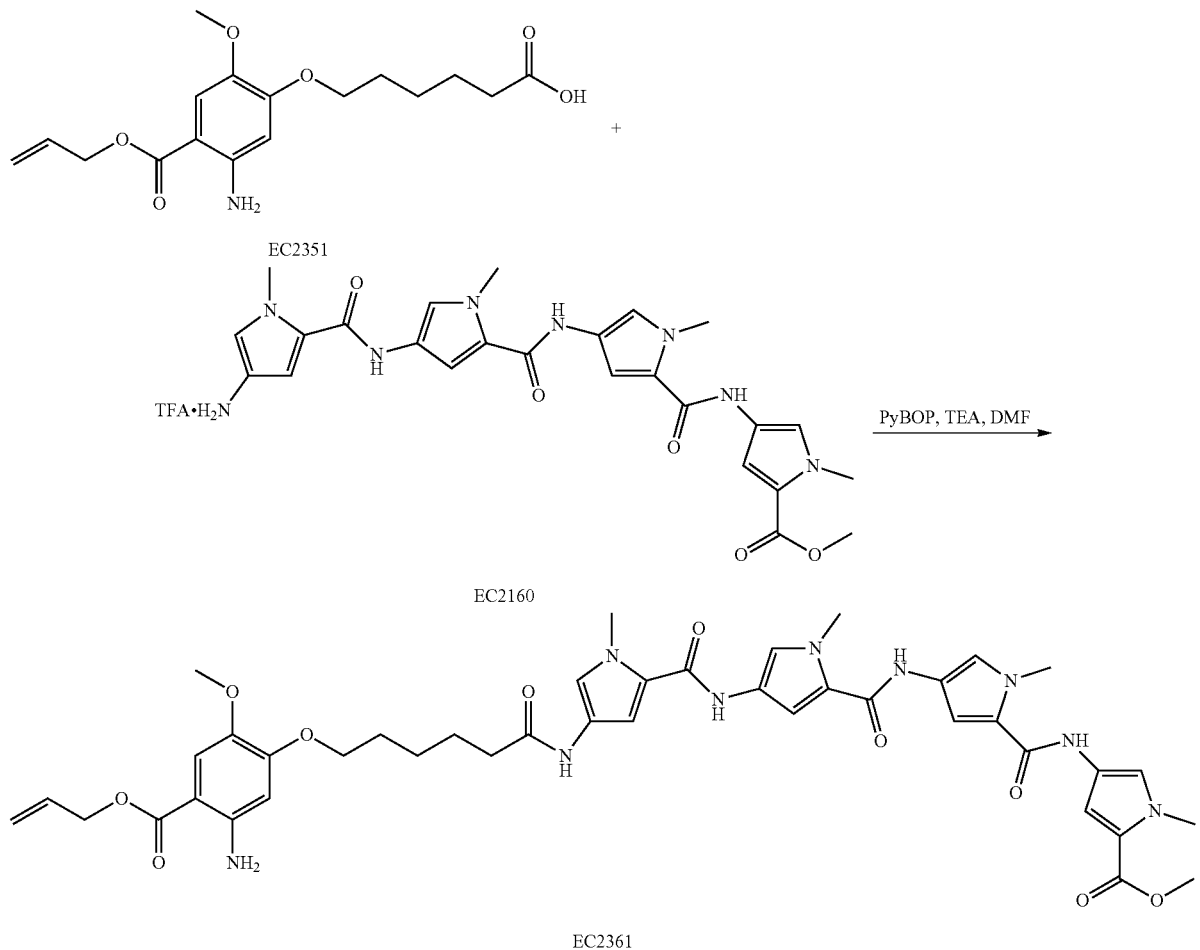

TEA (80.0 μL) was added to a solution of EC2351 (25.3 mg), EC2160 (57.1 mg), and PyBOP (42.9 mg) in anhydrous DMF (3.5 mL). The reaction mixture was stirred at ambient temperature under argon for 15 min and passed through a flash column eluting with 0-10% MeOH in DCM) to yield 62.4 mg (99.1%) crude EC2361 as a beige solid, which was used in the next step without further purification. MS⁺ (ESI m/z) calculated for $C_{42}H_{50}N_9O_{10}$: 840.37; found 840.47.

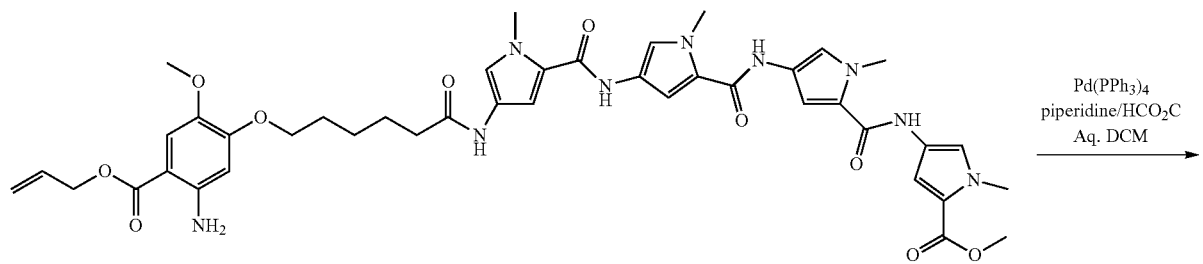

EC2361

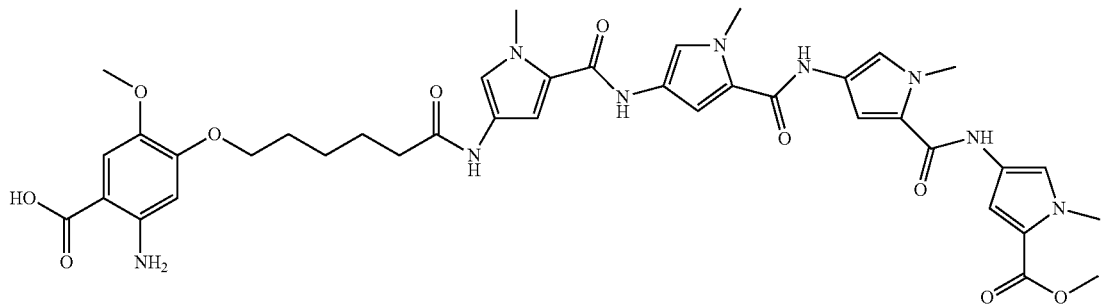

EC2362

A mixture of EC2361 (62.4 mg), Pd(PPh₃)₄ (14.7 mg), piperidine (51.4 μL), formic acid (19.6 μL), and water (30.0 μL) in DCM (3.0 mL) was stirred at ambient temperature for 25 min, then loaded directly onto a CombiFlash system (silica gel column. Gradient: 0-10% MeOH in DCM) for purification to yield 20.7 mg (34.8%) EC2362 as a beige solid. $^1$H NMR (500 MHz, 298 K, CD₃OD) δ 7.360 (s, 1H), 7.319 (s, 1H), 7.217 (s, 1H), 7.189 (s, 1H), 7.135 (s, 1H), 6.937 (s, 1H), 6.931 (s, 2H), 6.833 (s, 1H), 6.334 (s, 1H), 4.013 (t, J=6.5 Hz, 2H), 3.919 (s, 6H), 3.908 (s, 3H), 3.895 (s, 3H), 3.803 (s, 3H), 3.723 (s, 3H), 2.368 (t, J=7.0 Hz, 2H), 1.872 (m, 2H), 1.793 (m, 2H), 1.585 (m, 2H). MS⁺ (ESI m/z) calculated for $C_{39}H_{46}N_9O_{10}$: 800.34; found 840.63. (SEQ ID NO: 1 is included in the structure below)

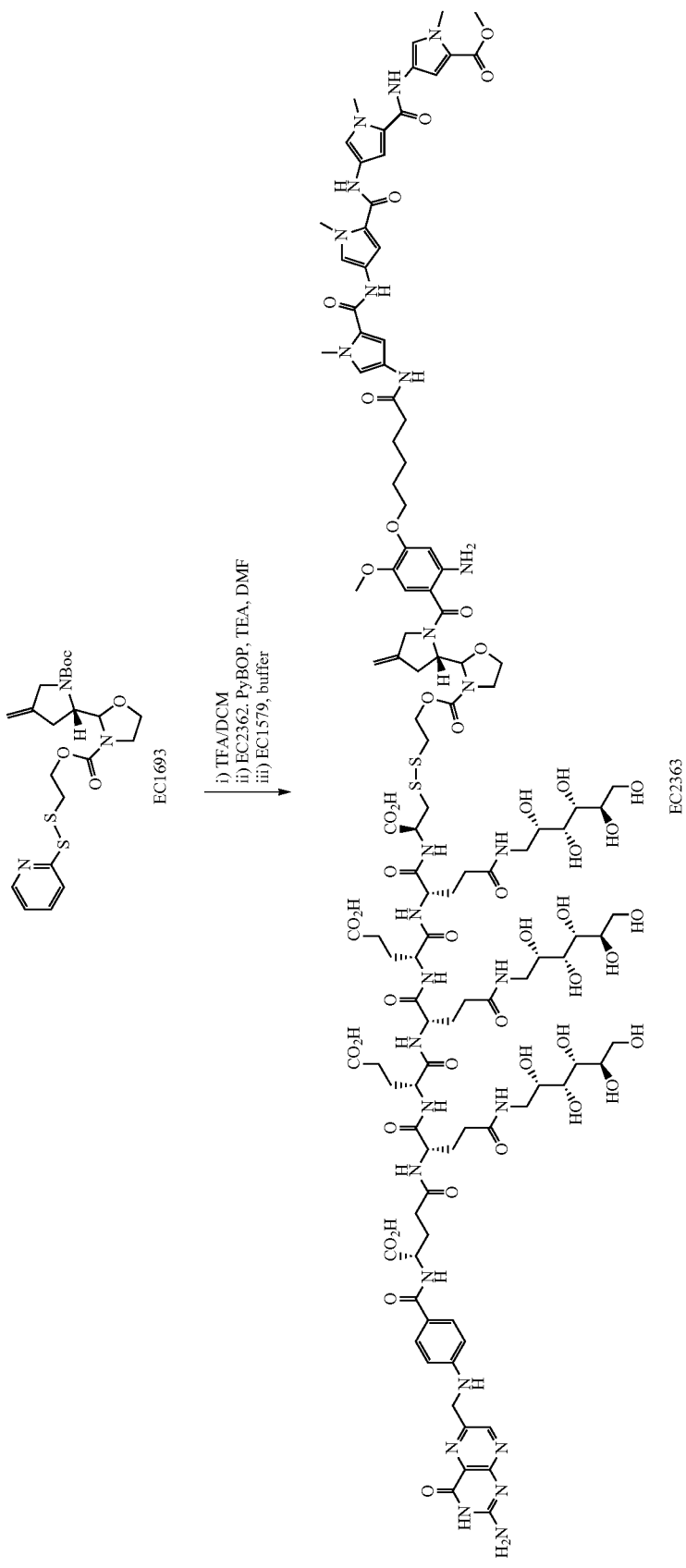

EC1693 (15.1 mg) was dissolved in a solution of TFA (0.20 mL) and DCM (1.5 mL), stirred at ambient temperature for 15 min, concentrated, co-evaporated with DCM (1.5 mL×3), and dried under vacuum for 60 min. The residue was dissolved in anhydrous DMF (1.5 mL) and transferred into a small vial containing EC2362 (20.7 mg) and PyBOP (14.8 mg). To the resulting solution was added TEA (30.0 µL). The reaction mixture was stirred at ambient temperature under argon for 10 min, diluted with DMSO (3.0 mL), and a solution of EC1579 (56.6 mg) in buffer (50 mM $NH_4HCO_3$, pH 7.0, 5.0 mL) was added. The reaction mixture was stirred at ambient temperature under argon for 10 min, at 40° C. for an additional 10 min, and loaded directly onto a preparative HPLC (Mobile phase A: 50 mM $NH_4HCO_3$ buffer, pH 7.0; B=ACN. Method: 10-80 B % in 20 min.) for purification to give 35.6 mg (50.6%) EC2363 as a pale yellow solid. Selective $^1$H NMR (500 MHz, 298 K, $D_2O$) δ 8.438 (s, 1H), 7.476 (d, J=8.0 Hz, 2H), 7.113 (s, 1H), 7.031 (s, 2H), 6.984 (s, 1H), 6.734 (s, 1H), 6.686 (s, 2H), 6.643 (s, 1H), 6.531 (d, J=9.0 Hz, 2H), 6.262 (b, 1H). MS$^-$ (ESI m/2z) calculated for $C_{115}H_{156}N_{27}O_{46}S_2$: 1357.51; found 1357.89.

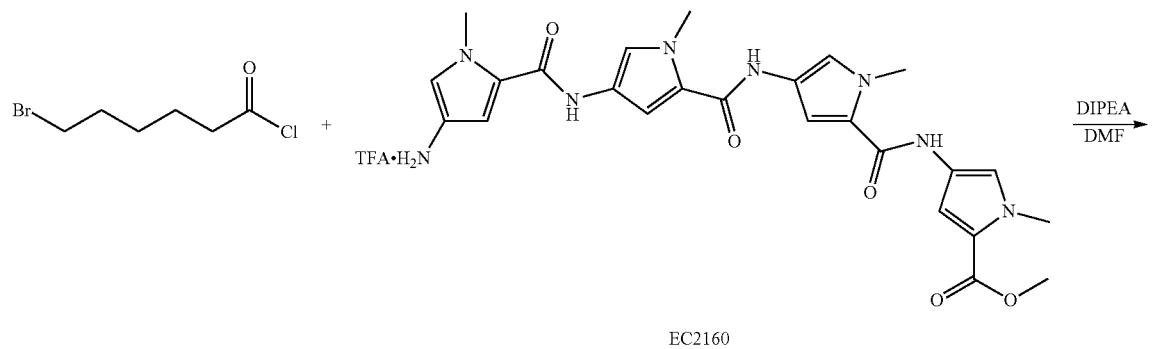

DIPEA (0.20 mL) was added dropwise to a solution of EC2160 (115.0 mg) and 6-bromohexanoyl chloride (55.0 µL) in anhydrous DMF (3.2 mL). The reaction mixture was stirred at ambient temperature under argon for 5 min, diluted with DMSO (10 mL), and loaded onto a preparative HPLC (Mobile phase A: 50 mM $NH_4HCO_3$ buffer, pH 7.0; B=ACN. Method: 10-100 B % in 20 min) for purification to give 66.5 mg EC2270 as a white solid. MS (ESI m/z) calculated for $C_{31}H_{38}BrN_8O_6$ (M+H)$^+$: 697.21; found 697.53.

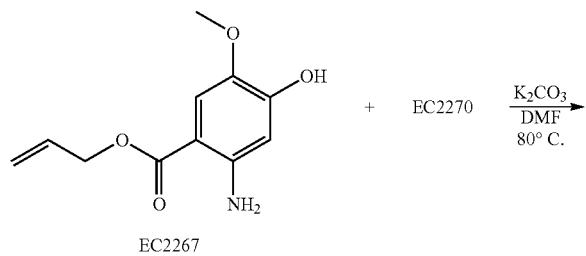

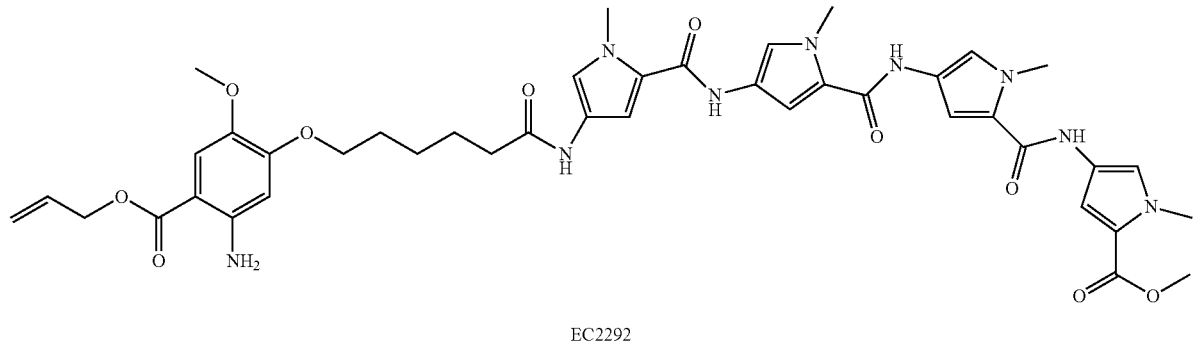

A mixture of EC2267 (15.0 mg), EC2270 (18.7 mg), and K$_2$CO$_3$ (26.1 mg) in anhydrous DMF (2.0 mL) was heated with stirring at 80° C. in a sealed vessel for 8 min, cooled in an ice-bath, diluted with DMSO (7.5 mL), filtered, and the filtrate was loaded onto a preparative HPLC (Mobile phase A: 50 mM NH$_4$HCO$_3$ buffer, pH 7.0; B=ACN. Method: 10-100 B % in 20 min) for purification to produce 11.5 mg EC2292 as a white solid. MS (ESI m/z) calculated for C$_{42}$H$_{50}$N$_9$O$_{10}$ (M+H)$^+$: 840.37; found 840.81.

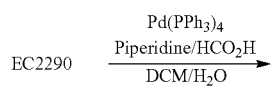

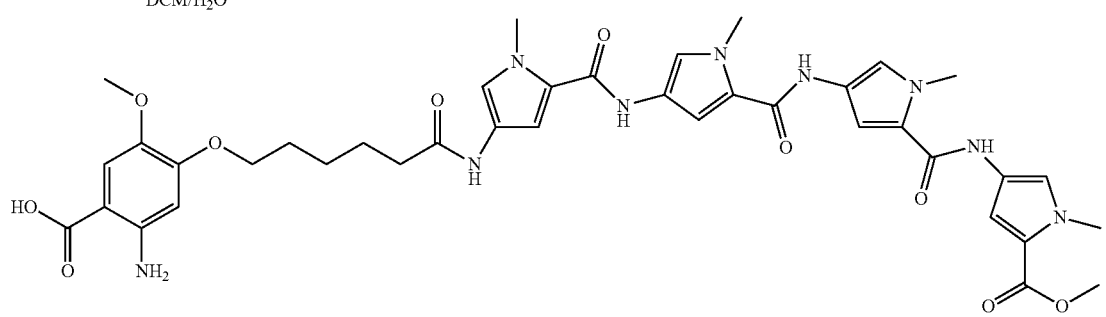

A pre-mixed solution of piperidine (2.60 μL) and formic acid (0.994 μL) in DCM (980 μL) and water (20 μL) was added to a mixture of EC2292 (3.2 mg) and Pd(PPh$_3$)$_4$ (0.70 mg) in tandem. The reaction mixture was stirred at ambient temperature under argon for 1 h and loaded directly onto a CombiFlash system (Column: silica gel. Mobile phase A: DCM; B: MeOH. Gradient: 0-10% B) for purification to give 1.2 mg EC2299 as a white solid. MS (ESI m/z) calculated for C$_{39}$H$_{46}$N$_9$O$_{10}$ (M+H)$^+$: 800.34; found 800.59. (SEQ ID NO: 1 is included in the structure below)

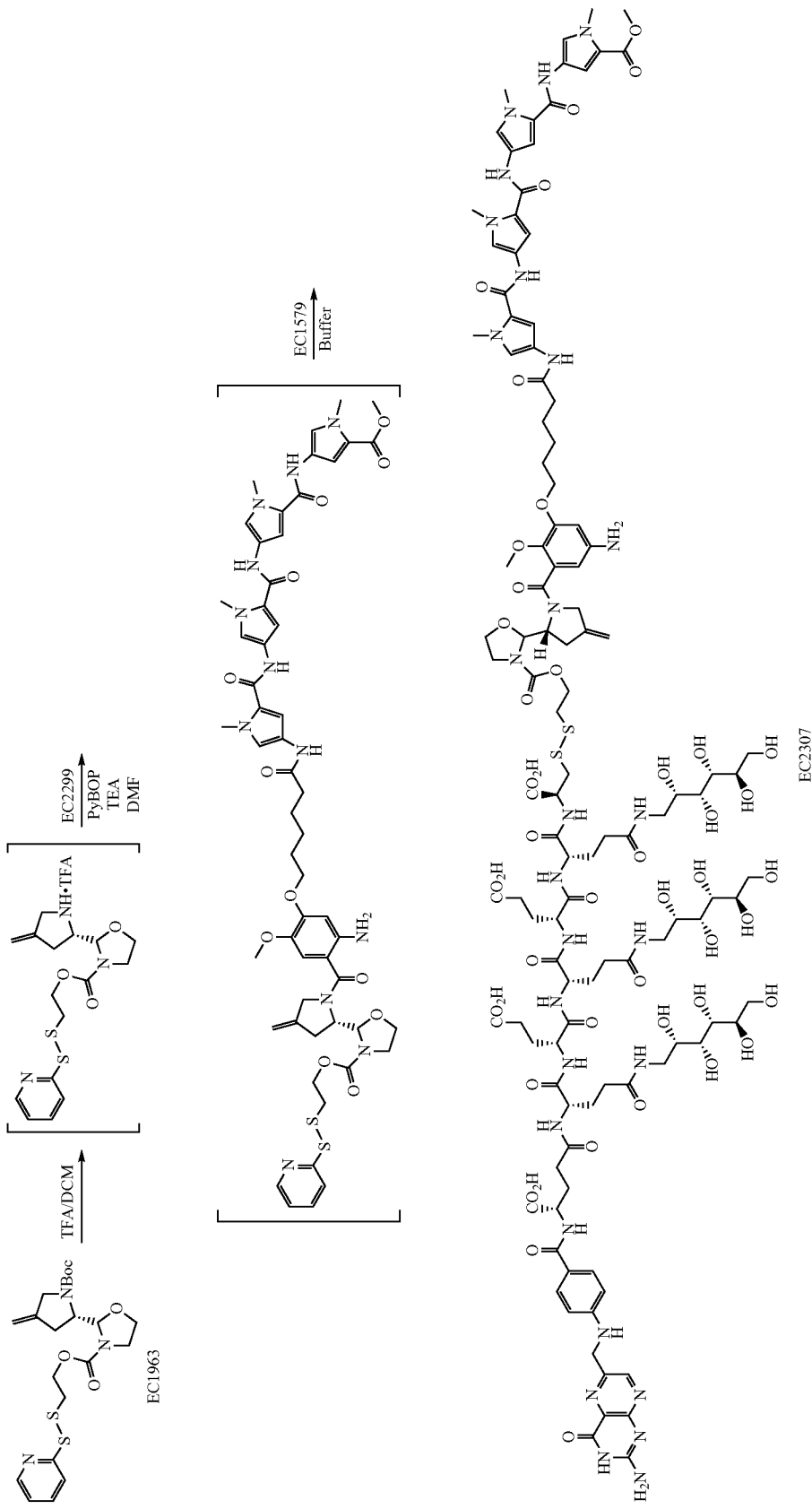

EC1963 (1.4 mg) was dissolved in a solution of TFA (50 µL) and DCM (150 µL), stirred at ambient temperature for 10 min, concentrated, co-evaporated with DCM (0.5 mL×3), and dried under vacuum for 1 h. The residue was dissolved in anhydrous DMF (350 µL) and transferred into a small vial containing EC2299 (0.50 mg) and PyBOP (1.2 mg). To the resulting solution was added TEA (1.8 µL). The reaction mixture was stirred at ambient temperature under argon for 15 min, diluted with DMSO (500 µL), and a solution of EC1579 (3.2 mg) in buffer (50 mM NH₄HCO₃, pH 7.0, 1.3 mL) was added. The resulting homogeneous solution was stirred at ambient temperature under argon for 20 min and loaded directly onto a preparative HPLC (Mobile phase A: 50 mM NH₄HCO₃ buffer, pH 7.0; B=ACN. Method: 10-100 B % in 20 min) for purification to produce 0.35 mg EC2299 as a white solid. MS (ESI m/2z) calculated for $C_{115}H_{159}N_{27}O_{46}S_2$ $[(M+2H)/2]^+$: 1359.02; found 1360.15.

A suspension of I (376 mg), 2-ethanolamine (80.6 µL), and MgSO₄ (960 mg) in DCM (20 mL) was stirred at ambient temperature under argon for 2 hr. The solid was filtered off and the filtrate was transferred into a solution of Fmoc-Glu-Oall (656 mg) and HATU (609 mg) in anhydrous DMF (6.0 mL), followed by addition of DIPEA (0.62 mL). After stirring at ambient temperature under argon for 1 hr, the reaction mixture was loaded directly onto a CombiFlash system (silica gel column. Gradient: 0-50% EtOAc in petroleum ether) for purification to produce 365 mg (42.5%) EC2407 as a white solid. ¹H NMR (500 MHz, 298 K, CDCl₃) δ 7.764 (b, 2H), 7.605 (b, 2H), 7.392 (b, 2H), 7.312 (b, 2H), 5.905 (m, 1H), 5.495-4.979 (m, 3H), 5.004-4.928 (m, 2H), 4.655-3.409 (m, 13H), 2.730-2.172 (m, 6H), 1.433 (m, 9H). MS⁺ (ESI m/z) calculated for $C_{39}H_{46}N_9O_{10}$: 800.34; found 840.63. MS⁺ (ESI m/z) calculated for $C_{36}H_{44}N_3O_8$: 646.31; found 646.50.

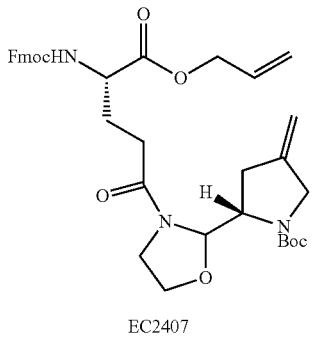

EC2407

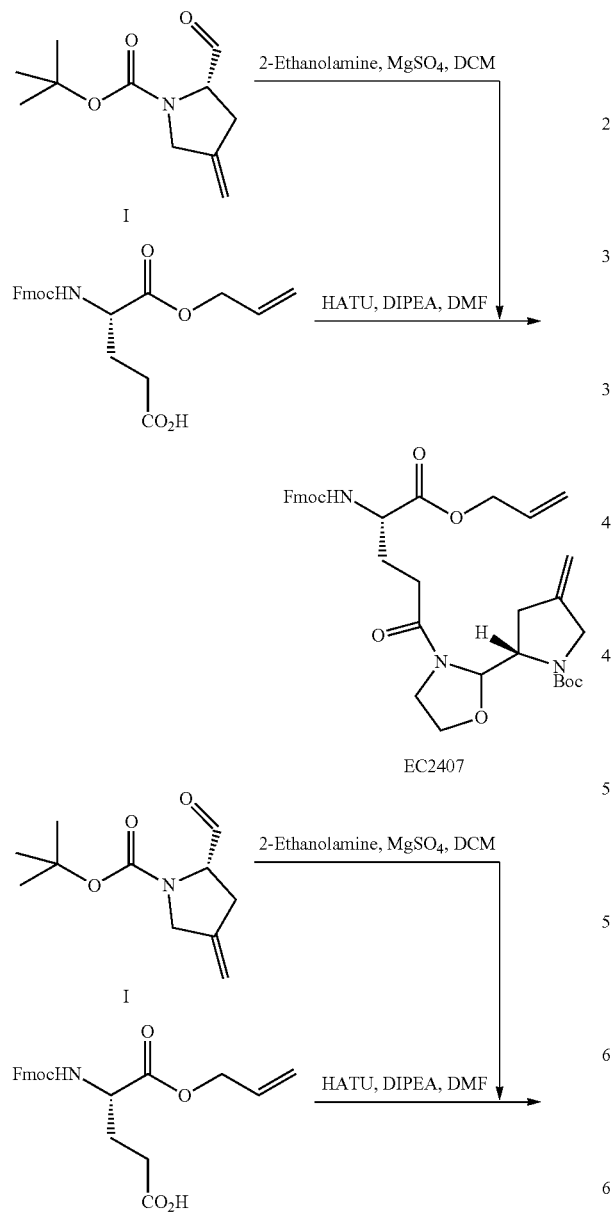

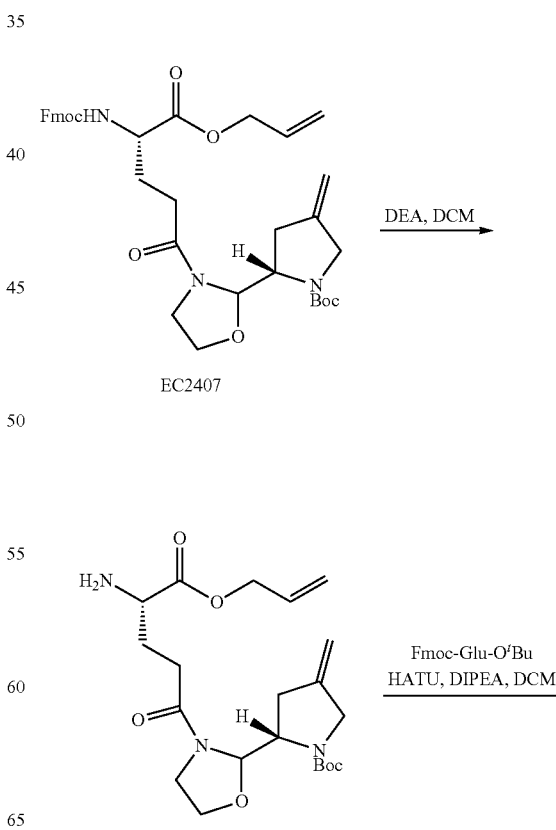

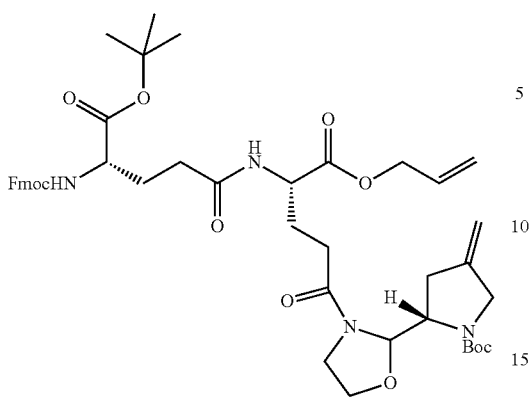

EC2438

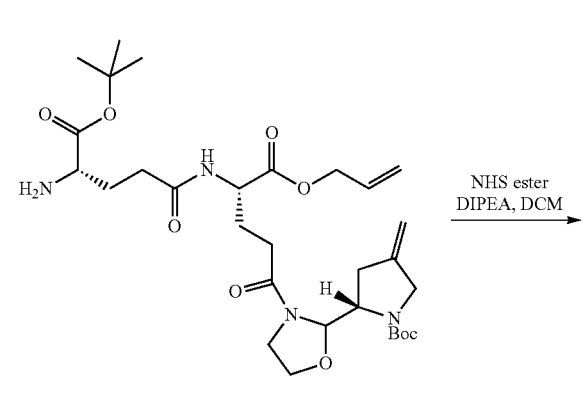

EC2439

A solution of EC2407 (365 mg) and diethylamine (4.0 mL) in anhydrous DCM (4.0 mL) was stirred at ambient temperature under argon for 3.5 hr, concentrated, co-evaporated with DCM (5 mL×3), dried under vacuum for 60 min, re-dissolved in DCM (45 mL) and DMF (1.0 mL), and added to a mixture of Fmoc-Glu-O'Bu (229 mg) and HATU (204 mg). The reaction mixture was stirred at ambient temperature under argon for 35 min, concentrated to a small volume, and loaded directly onto a CombiFlash system (silica gel column. Gradient: 0-70% EtOAc in petroleum ether) for purification to yield 300 mg (67.2%) EC2438 as a white solid. $^1$H NMR (500 MHz, 298 K, CDCl$_3$) δ 7.768 (d, J=7.5 Hz, 2H), 7.620 (d, J=7.5 Hz, 2H), 7.398 (t, J=7.5 Hz, 2H), 7.317 (t, J=7.5 Hz, 2H), 5.901 (m, 1H), 5.338 (d, J=19.5 Hz, 2H), 5.244 (m, 1H), 4.959 (m, 2H), 4.617 (m, 3H), 4.375 (m, 2H), 4.220 (m, 2H), 4.116-3.813 (m, 4H), 3.611 (b, 1H), 3.388 (m, 1H), 2.755-1.913 (m, 10H), 1.430 (m, 18H). MS$^+$ (ESI m/z) calculated for C$_{45}$H$_{59}$N$_4$O$_{11}$: 831.42; found 831.65.

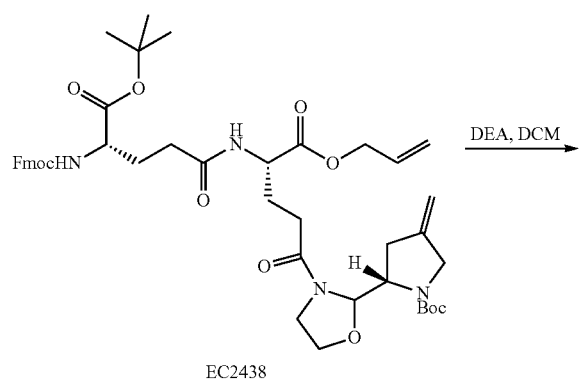

EC2438

A solution of EC2408 (300 mg) and diethylamine (10.0 mL) in anhydrous DCM (5.0 mL) was stirred at ambient temperature under argon for 1.5 hr, concentrated, co-evaporated with DCM (10 mL×3), dried under vacuum for 1 hr, and re-dissolved in DCM (10 mL). To this solution were added 3-(Maleimido)propionic acid N-succinimidyl ester (115 mg) and DIPEA (0.15 mL) in tandem. The reaction mixture was stirred at ambient temperature under argon for 50 min, concentrated to about half of the original volume, and passed through a flash column eluting with 0-100% EtOAc in petroleum ether to give 138 mg (50.3%) crude EC2439 as a white solid, which was used in the next step without further purification. MS$^+$ (ESI m/z) calculated for C$_{37}$H$_{54}$N$_5$O$_{12}$: 760.38; found 760.56.

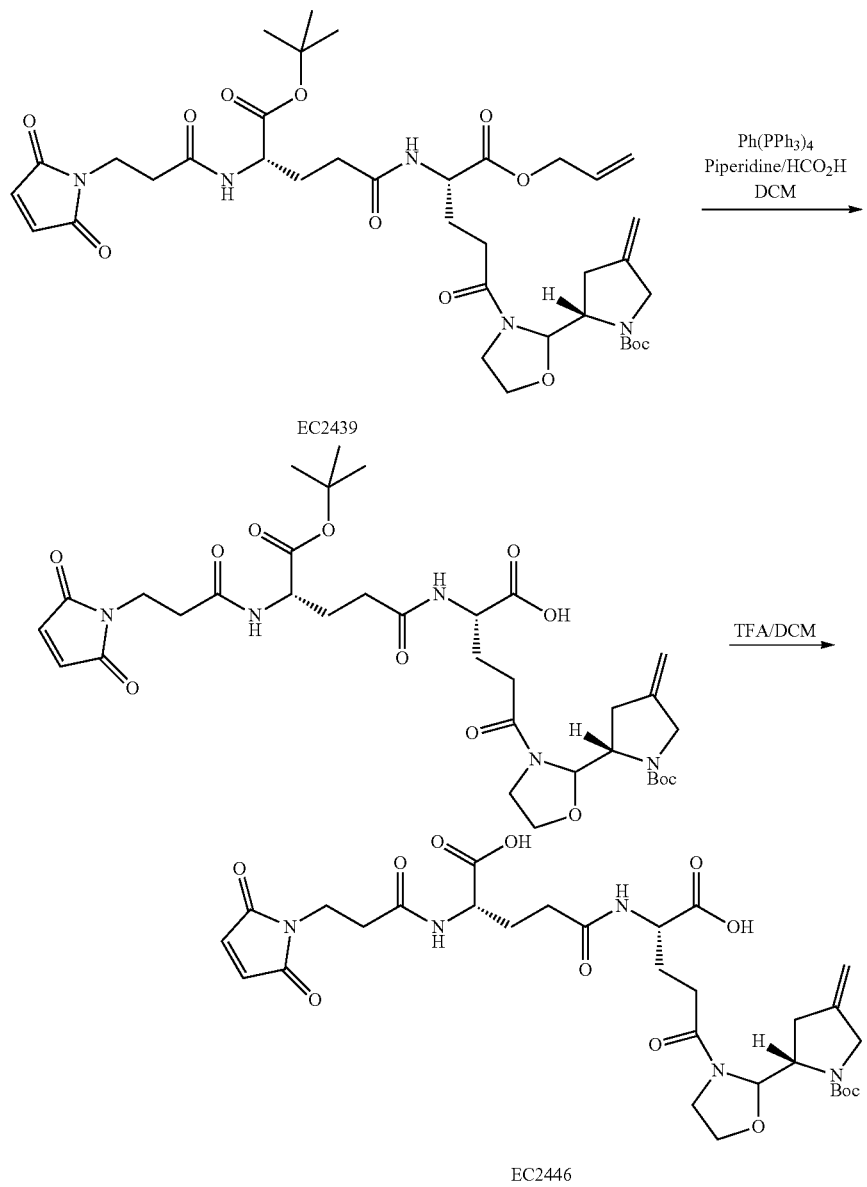

A mixture of EC2439 (192 mg), Pd(PPh$_3$)$_4$ (76.1 mg), piperidine (25.0 µL), and formic acid (9.53 µL) in DCM (5.0 mL) was stirred at ambient temperature under argon for 1 hr. To the mixture was added TFA (2.5 mL). The reaction mixture was stirred at ambient temperature under argon for 1.5 hr, concentrated, re-dissolved in DMSO (9.5 mL) and loaded directly onto a preparative HPLC (Mobile phase A: 0.1% TFA buffer; B=ACN. Method: 0-30 B % in 20 min.) for purification to afford 65.0 mg (45.6%) EC2446 as a white solid. $^1$H NMR (500 MHz, 298 K, DMSO-d6) δ 12.605 (b, 2H), 8.270 (d, J=8.0 Hz, 1H), 8.111 (d, J=8.5 Hz, 1H), 7.002 (s, 2H), 5.415 (s, 1H), 5.104 (s, 2H), 4.284 (m, 1H), 4.151 (m, 2H), 4.003 (m, 2H), 3.867 (d, J=15.0 Hz, 1H), 3.789 (m, 2H), 3.600 (m, 2H), 3.546 (m, 1H), 2.607 (m, 1H), 2.522 (m, 1H), 2.448 (m, 1H), 2.428 (m, 2H), 2.339 (m, 1H), 2.195 (m, 2H), 2.047 (m, 2H), 1.741 (m, 2H). MS$^-$ (ESI m/z) calculated for C$_{25}$H$_{32}$N$_5$O$_{10}$: 562.22; found 562.53. (SEQ ID NO: 1 is included in the structure below)

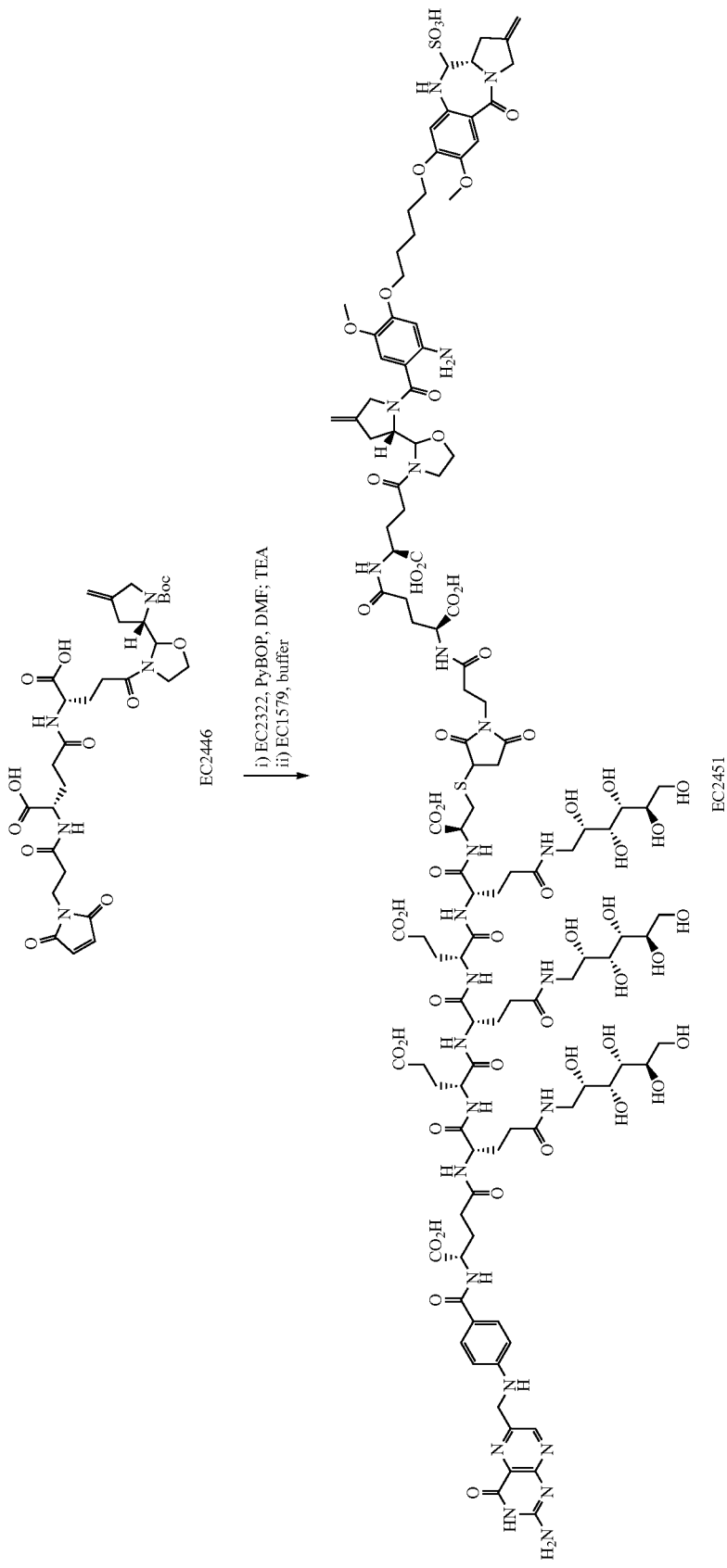

TEA (19.0 µL) was added to a solution of EC2322 (8.4 mg), EC2446 (8.4 mg), and PyBOP (7.5 mg) in anhydrous DMF (3.0 mL) and the solution was stirred at ambient temperature under argon for 60 min. To the solution was added a solution of EC1579 (25.3 mg) in buffer (50 mM $NH_4HCO_3$, pH 7.0, 6.0 mL) and the reaction mixture was stirred at ambient temperature under argon for 20 min, then loaded directly onto a preparative HPLC (Mobile phase A: 50 mM $NH_4HCO_3$ buffer, pH 7.0; B=ACN. Method: 10-80 B % in 20 min.) for purification to produce 2.3 mg (5.8%) EC2451 as a pale yellow solid. Selective $^1$H NMR (500 MHz, 298 K, $D_2O$) δ 8.688 (s, 1H), 7.699 (d, J=8.0 Hz, 2H), 7.144 (s, 1H), 6.841 (b, 3H), 6.746 (s, 1H), 6.497 (s, 1H). MS$^-$ (ESI m/2z) calculated for $C_{117}H_{161}N_{24}O_{53}S_2$: 1407.01; found 1407.69. (SEQ ID NO: 1 is included in the structure below)

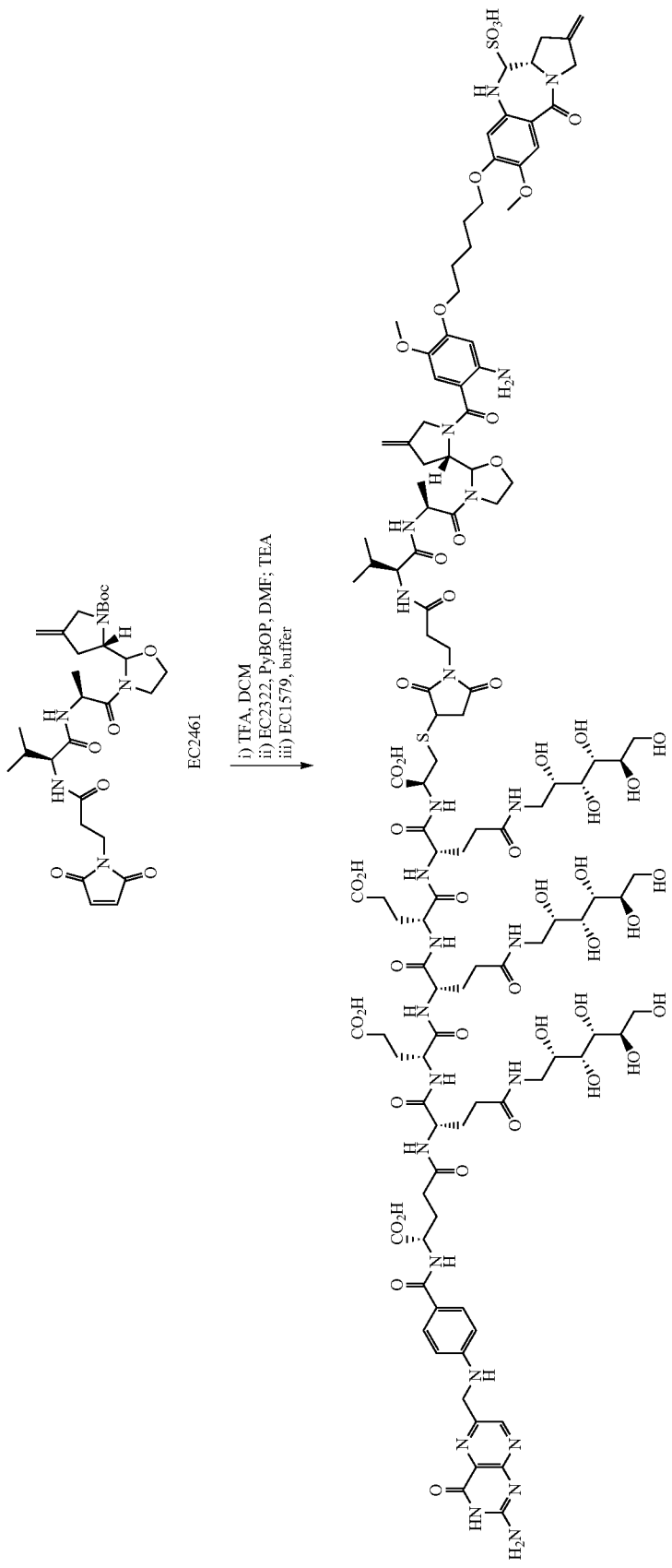

EC2461 (10.4 mg) was dissolved in a solution of TFA (0.30 mL) and DCM (1.1 mL), stirred at ambient temperature for 30 min, concentrated, co-evaporated with DCM (2 mL×3), and dried under vacuum for 60 min. The residue was dissolved in anhydrous DMF (3.0 mL) and to which are added EC2322 (9.3 mg) and PyBOP (8.1 mg), followed by TEA (21.0 µL). The reaction mixture was stirred at ambient temperature under argon for 25 min, diluted with DMF (1.5 mL), and a solution of EC1579 (32.1 mg) in buffer (50 mM $NH_4HCO_3$, pH 7.0, 5.0 mL) was added. The resulting homogeneous solution was stirred at ambient temperature under argon for 10 min and loaded directly onto a preparative HPLC (Mobile phase A: 50 mM $NH_4HCO_3$ buffer, pH 7.0; B=ACN. Method: 5-50 B % in 20 min.) for purification to yield 7.3 mg (18%) EC2464 as a pale yellow solid. Selective $^1$H NMR (500 MHz, 298 K, $D_2O$) δ 8.623 (s, 1H), 7.666 (b, 2H), 7.089 (s, 1H), 6.780 (b, 3H), 6.687 (s, 1H), 6.492 (b, 2H). MS$^-$ (ESI m/2z) calculated for $C_{115}H_{161}N_{24}O_{49}S_2$: 1363.02; found 1363.79.

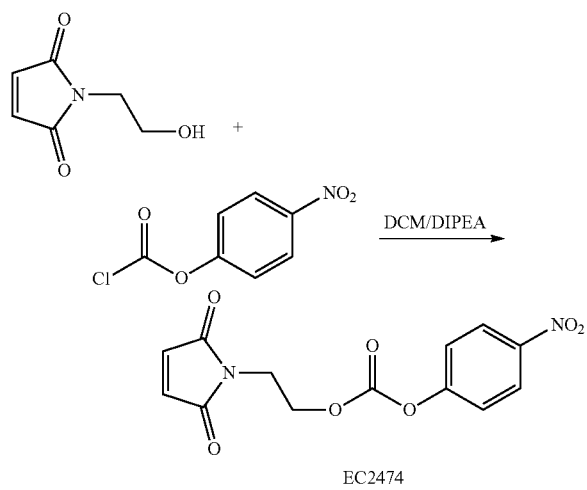

To a solution of maleimidoethanol (0.655 mg, 4.64 mM) in dry DCM (5 ml) under Argon was added p-nitrophenylchloroformate (1.12 g, 5.56 mM) and DIPEA (1.13 ml, 6.50 mM) respectively. The reaction was allowed to stir at RT for 18 h. TLC analysis (5% methanol in methylene chloride) indicated that the reaction was complete. The reaction mixture was concentrated and purified using combiflash ($SiO_2$) column and eluted with 0-100% EtOAc in petroleum ether to yield pure EC2474 (0.78 g, 55%). $^1$H NMR (500 MHz, $CDCl_3$): δ 8.28 (d, $J_1$=9.0 Hz, 2H), 7.41 ((d, $J_1$=9.0 Hz, 2H)), 6.77 (s, 2H), 4.41 (t, $J_1$=4.5 Hz, $J_2$=5.5 Hz, 2H), 3.95 (t, $J_1$=4.5 Hz, $J_2$=5.5 Hz, 2H); $^{13}$C NMR (500 MHz, $CDCl_3$): δ 170.37, 155.40, 152.40, 145.59, 134.36, 125.32, 121.99, 66.15, 36.35

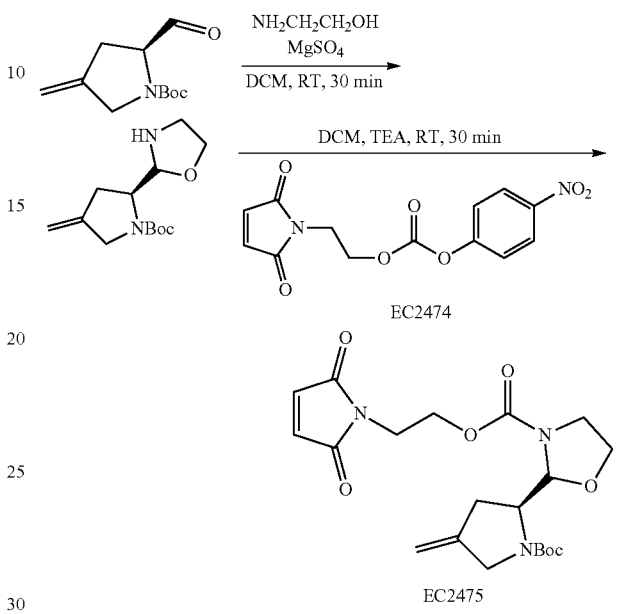

To a solution of aldehyde (158 mg, 0.75 mM) in dry DCM (2 mL) was added $MgSO_4$ (79 mg) and ethanolamine (67.83 µL, 1.13 mM) repectiveley. The reaction was allowed to stir for 1 h. In another flask, EC2474 (459 mg, 1.5 mM) was dissolved in dry DCM (2 mL) and triethyl amine (0.314 mL, 2.25 mM) was added. Above reaction mixture (step1) was slowly added to this solution and stirred for 20 h. LCMS analysis (20 mM $NH_4HCO_3$, pH 7.4) indicated that the reaction was complete (only mass no UV). TLC analysis (50% EtOAc in petroleum ether) indicated that the reaction was complete. The reaction mixture was concentrated and purified using combiflash ($SiO_2$) column eluting with 0-50% EtOAc in petroleum ether to yield pure EC2475 (158 mg, 50%). $^1$H NMR (500 MHz, $CDCl_3$): δ 6.72 (s, 2H), 4.85-5.30 (m, 3H), 3.95-4.25 (m, 5H), 3.70-3.95 (m, 5H), 3.25 (br s, 1H), 2.40-2.85 (m, 2H), 1.41 (s, 9H); LCMS (ESI): (M+H)$^+$=Calculated for $C_{20}H_{27}N_3O_7$, 422.18; found 422.39. (SEQ ID NO: 1 is included in the structure below)

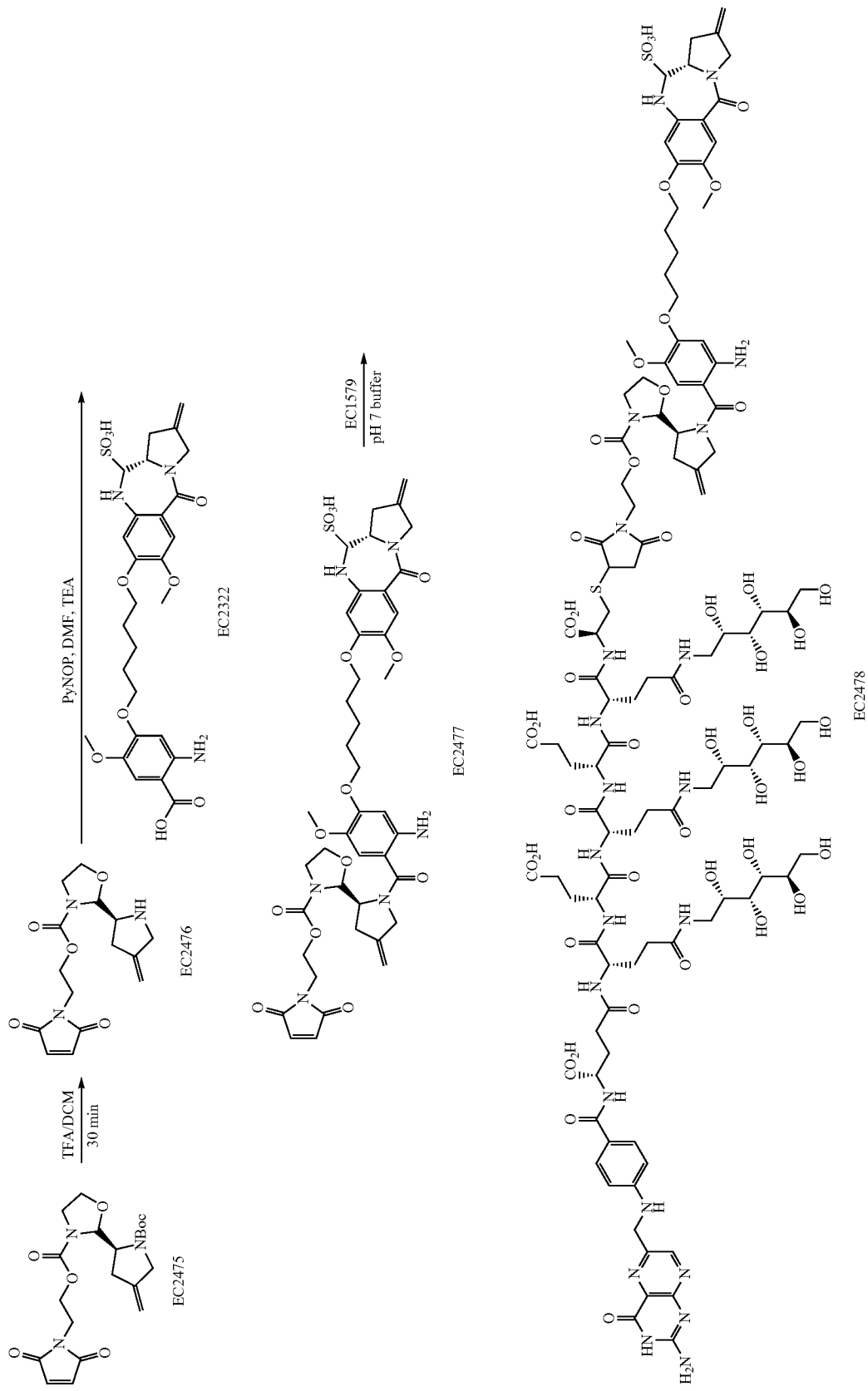

EC2475 (10.0 mg, 0.025 mM) was treated with the mixture of TFA/dichloromethane/TIPS (1.0 mL/1.0 mL/0.06 mL) and stirred for 30 min. LCMS analysis (20 mM NH$_4$HCO$_3$, pH 7.4) indicated that the reaction was complete. The reaction mixture was concentrated to dryness, co-evaporated with DCM (3 times) and dried under high vacuum for 1 h to yield EC2476. In another flask, EC2322 (13 mg, 0.02 mM) was dissolved in dry DMF (1 mL). PyBop (11 mg, 0.02 mM) and TEA (29.5 µL, 0.21 mM) were added respectively. Stirred for 5 min, EC2476 (prepared earlier) in DMF (1 mL) was added, and stirred for 1 h. LCMS analysis (20 mM NH$_4$HCO$_3$, pH 7.4) indicated that the product EC2477 was formed. EC1579 (50 mg, 0.03 mM) in phosphate buffer (2 mL) was added and stirred for 1 h. LCMS analysis (20 mM NH$_4$HCO$_3$, pH 7.4) indicated the product formation. The reaction mixture was purified with prep-HPLC (5 to 80% acetonitrile in 20 mM NH$_4$HCO$_3$, pH 7.4) to yield pure EC2478 (7.5 mg, 12%). $^1$H NMR (500 MHz, DMSO-D$_6$+D$_2$O) (selected data): δ 8.60 (s, 1H), 7.56 (d, J=8.0 Hz, 2H), 6.94 (s, 1H), 6.60 (d, J=8.5 Hz, 2H), 6.60 (s, 1H), 6.49 (s, 1H), 6.28 (br s, 1H), 5.06 (s, 1H), 5.01 (s, 1H), 4.90 (m, 2H), 4.45 (s, 4H); LCMS (ESI): [M−2H]$^{2-}$=Calculated for C$_{107}$H$_{148}$N$_{22}$O$_{48}$S$_2$, 1286.28; found 1286.31.

The following examples are also described herein. It is to be understood that radicals of these examples are included in the PBD prodrugs, poly-PBD prodrugs, mixed PBDs, conjugates, and conjugates described herein.

EC1564
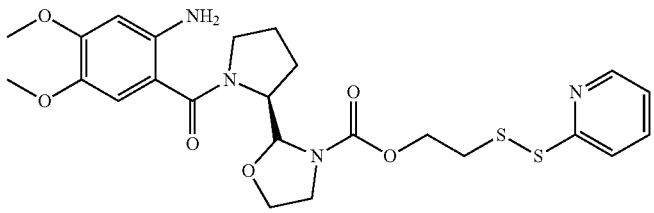

EC1592
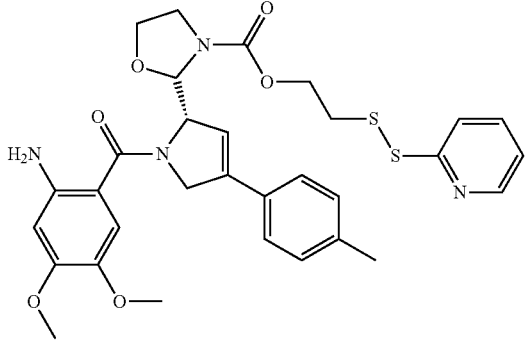

EC1593
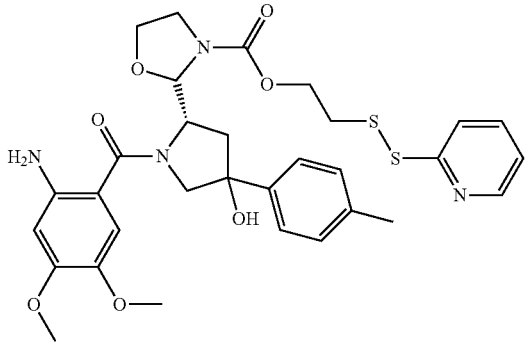

EC1627
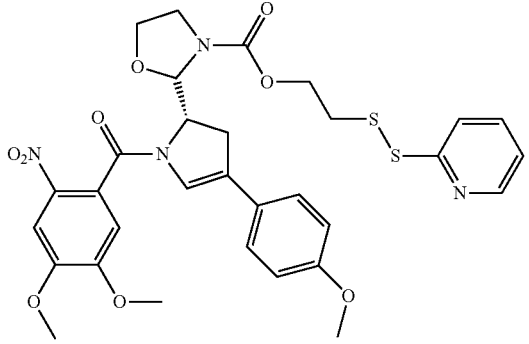

-continued
EC1628
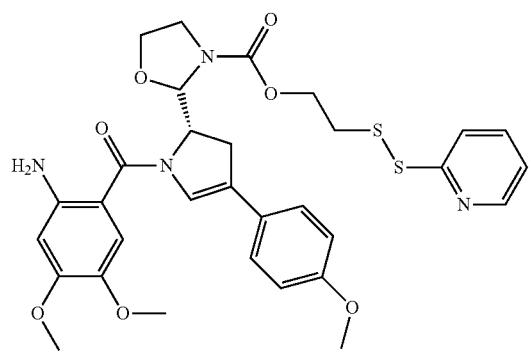
EC1660
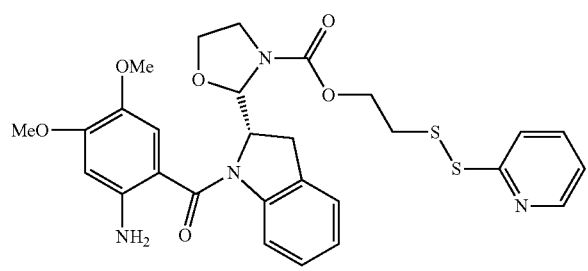
EC1672
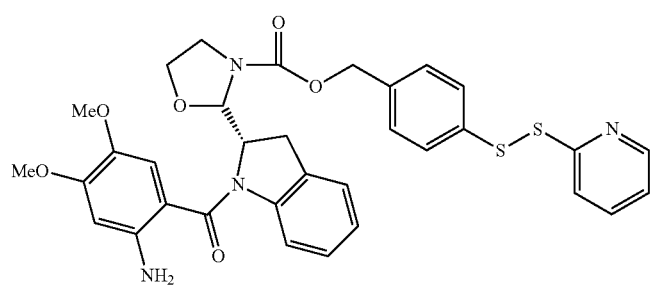
EC1741
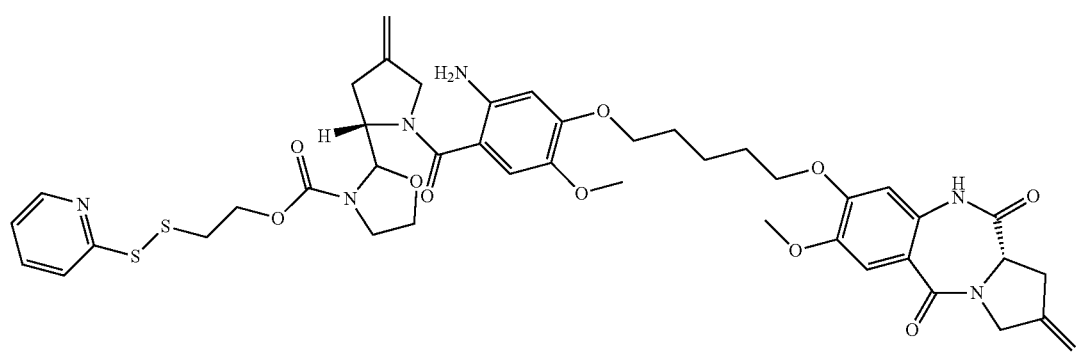
EC1771
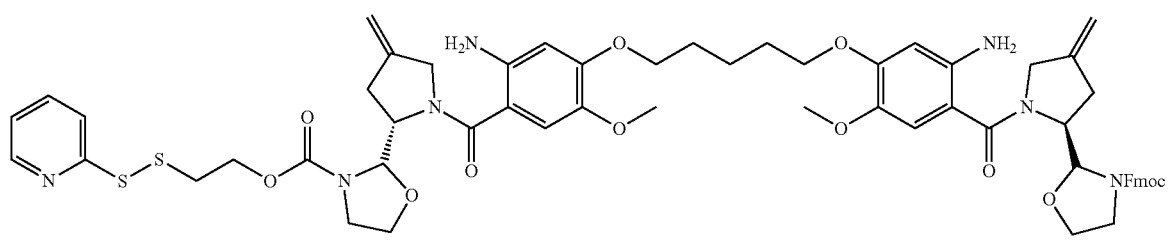

-continued
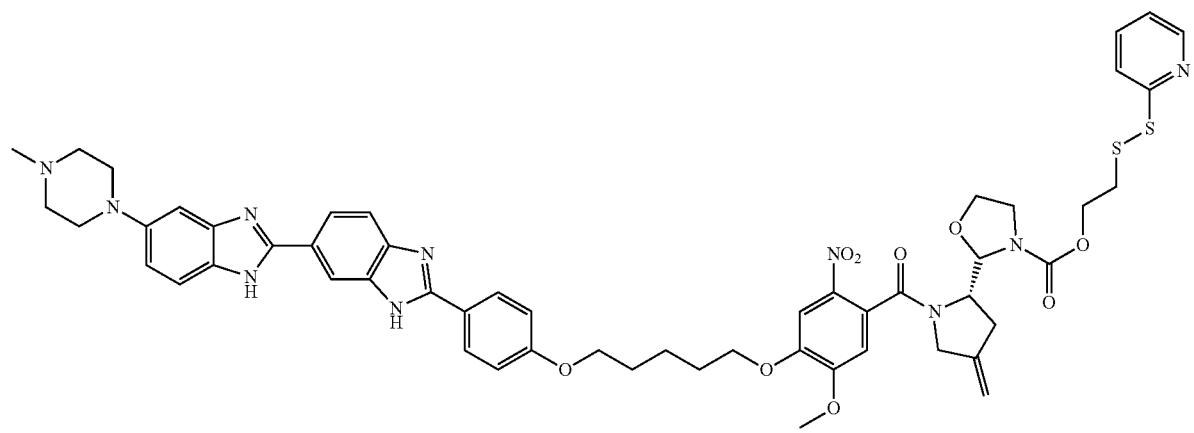
EC1864
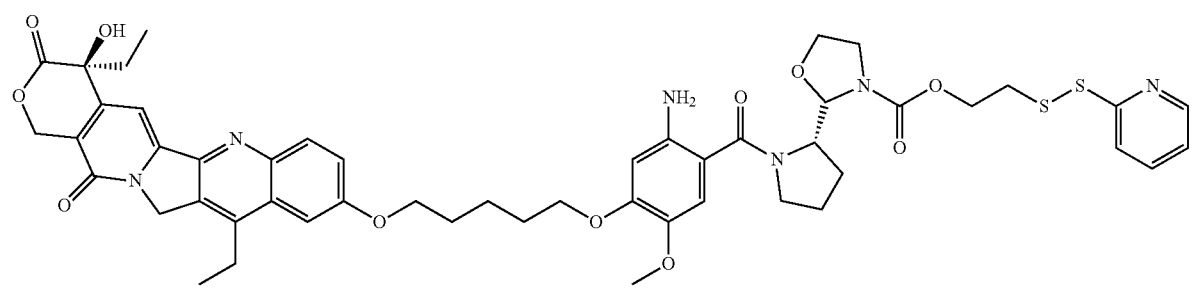
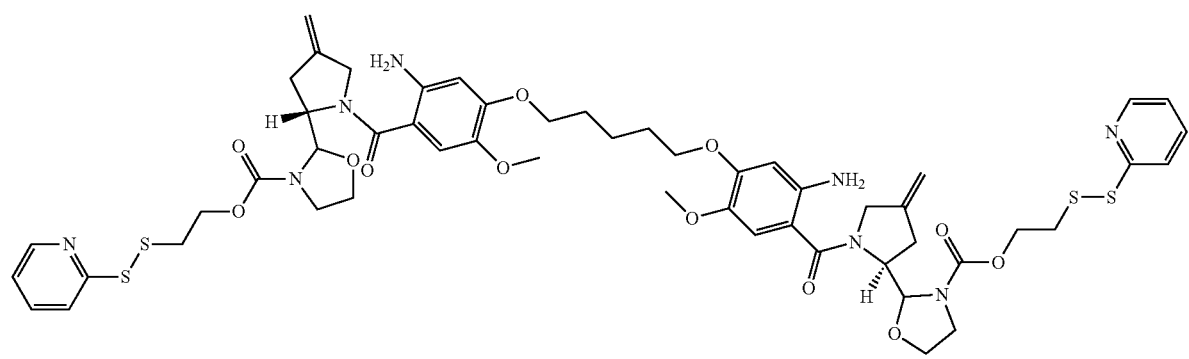
EC1695

-continued
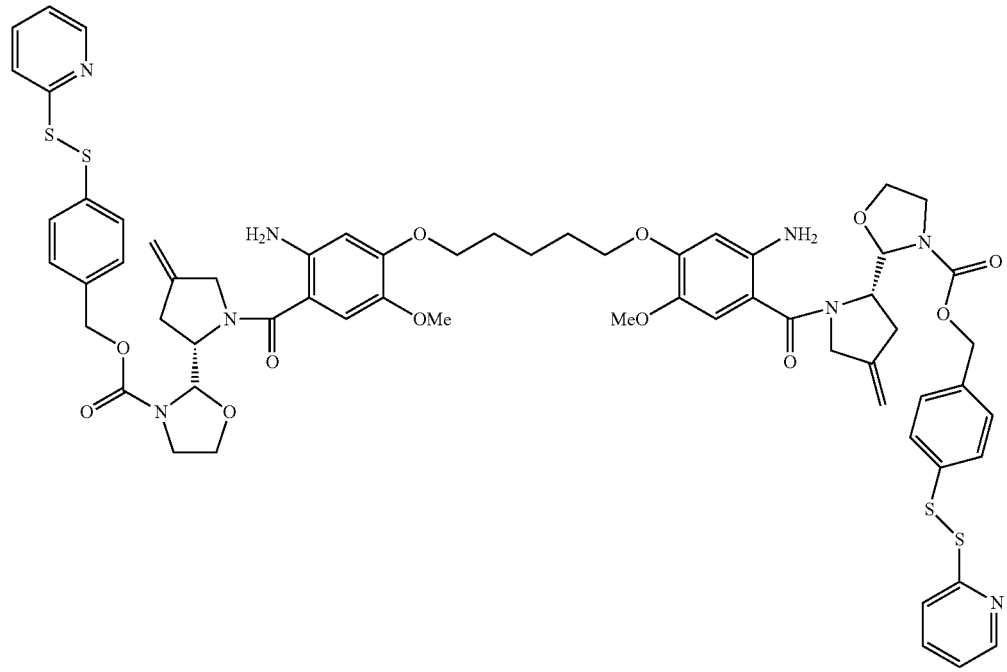
EC1703
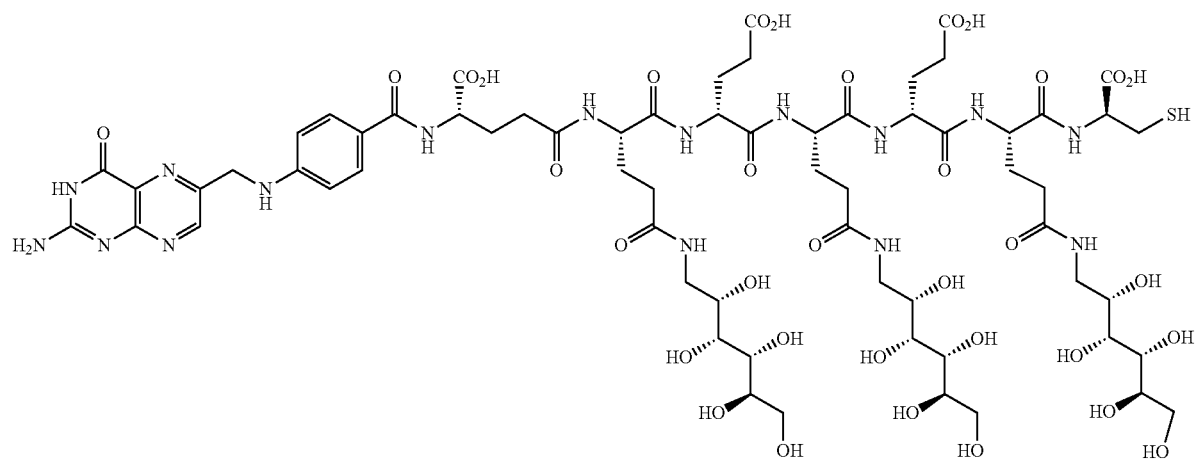 [SMILES: Nc1nc2ncc(CNc3ccc(C(=O)N[C@@H](CCC(=O)N[C@@H](CCC(=O)NC[C@H](O)[C@@H](O)[C@H](O)[C@H](O)CO)C(=O)N[C@H](CCC(=O)O)C(=O)N[C@@H](CCC(=O)NC[C@H](O)[C@@H](O)[C@H](O)[C@H](O)CO)C(=O)N[C@H](CCC(=O)O)C(=O)N[C@@H](CCC(=O)NC[C@H](O)[C@@H](O)[C@H](O)[C@H](O)CO)C(=O)N[C@H](CS)C(=O)O)C(=O)O)cc3)nc2c(=O)[nH]1]
EC1579 (SEQ ID NO: 1 is included in the structure above)

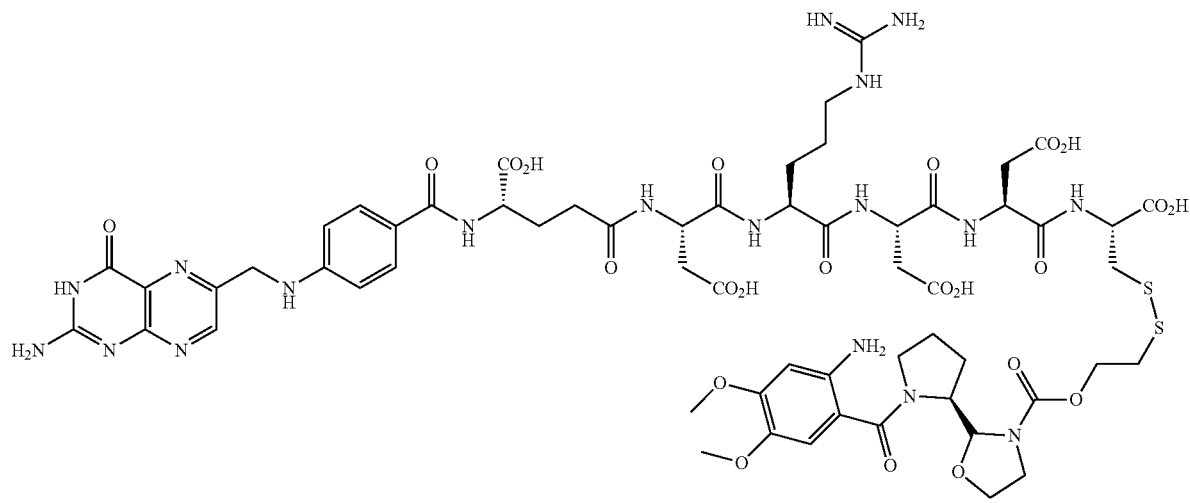 [SMILES: COc1cc(N)c(C(=O)N2CCC[C@H]2C2OCCN2C(=O)OCCSSC[C@H](NC(=O)[C@H](CC(=O)O)NC(=O)[C@H](CC(=O)O)NC(=O)[C@H](CCCNC(=N)N)NC(=O)[C@H](CC(=O)O)NC(=O)CC[C@H](NC(=O)c2ccc(NCc3cnc4nc(N)[nH]c(=O)c4n3)cc2)C(=O)O)C(=O)O)cc1OC]
EC1569 (SEQ ID NO: 2 is included in the structure above)
The following conjugates of PBD prodrugs, poly-PBD prodrugs, or mixed PBDs are described herein. The conjugates are prepared according to the processes described herein and conventional processes.
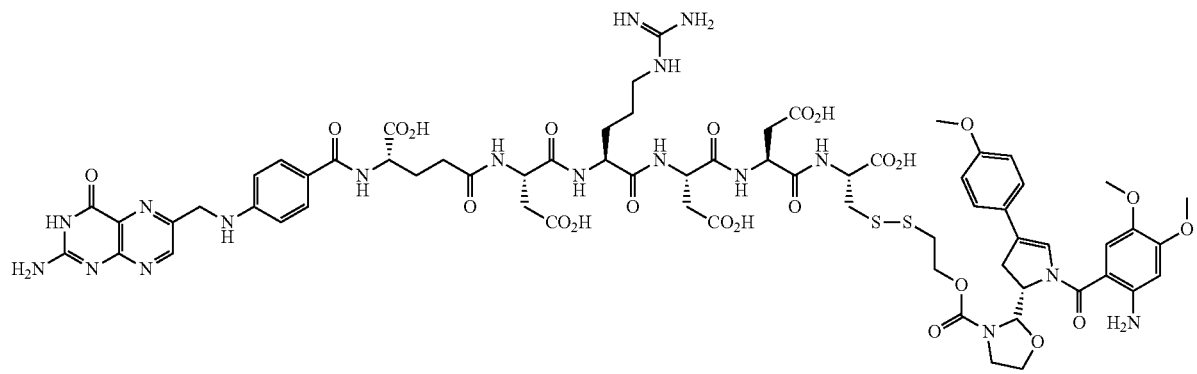 [SMILES: COc1ccc(C2=CN(C(=O)c3cc(OC)c(OC)cc3N)[C@H](C3OCCN3C(=O)OCCSSC[C@H](NC(=O)[C@H](CC(=O)O)NC(=O)[C@H](CC(=O)O)NC(=O)[C@H](CCCNC(=N)N)NC(=O)[C@H](CC(=O)O)NC(=O)CC[C@H](NC(=O)c3ccc(NCc4cnc5nc(N)[nH]c(=O)c5n4)cc3)C(=O)O)C(=O)O)C2)cc1]
EC1629 (SEQ ID NO: 2 is included in the structure above)
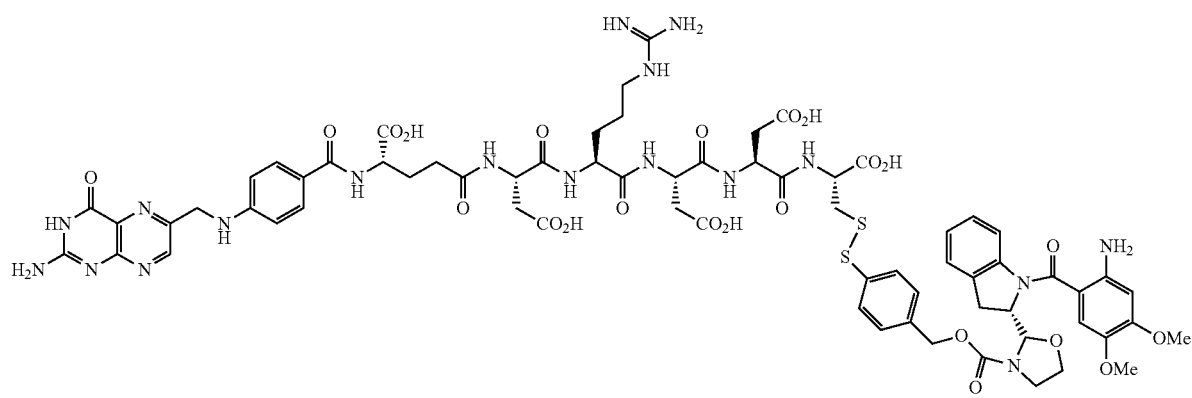 [SMILES: COc1cc(N)c(C(=O)N2c3ccccc3C[C@H]2C2OCCN2C(=O)OCc2ccc(SSC[C@H](NC(=O)[C@H](CC(=O)O)NC(=O)[C@H](CC(=O)O)NC(=O)[C@H](CCCNC(=N)N)NC(=O)[C@H](CC(=O)O)NC(=O)CC[C@H](NC(=O)c3ccc(NCc4cnc5nc(N)[nH]c(=O)c5n4)cc3)C(=O)O)C(=O)O)cc2)cc1OC]
EC1673 (SEQ ID NO: 2 is included in the structure above)

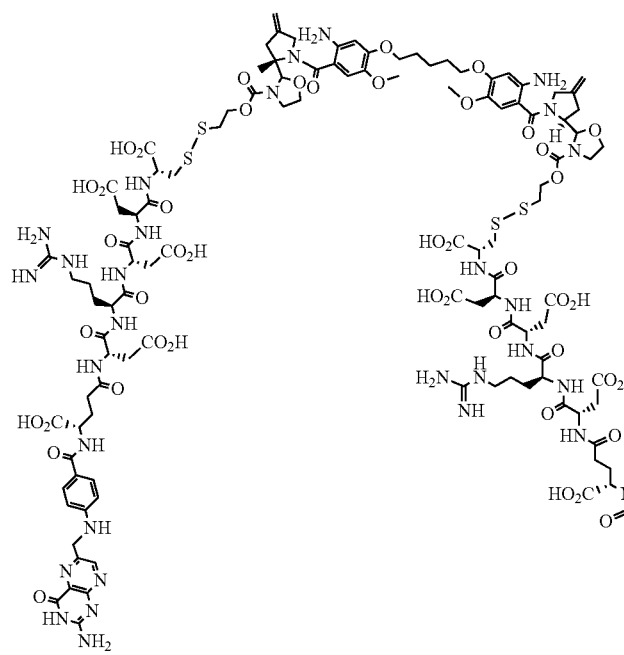
EC1866 (SEQ ID NOS 2 and 2 are included in the structures above)
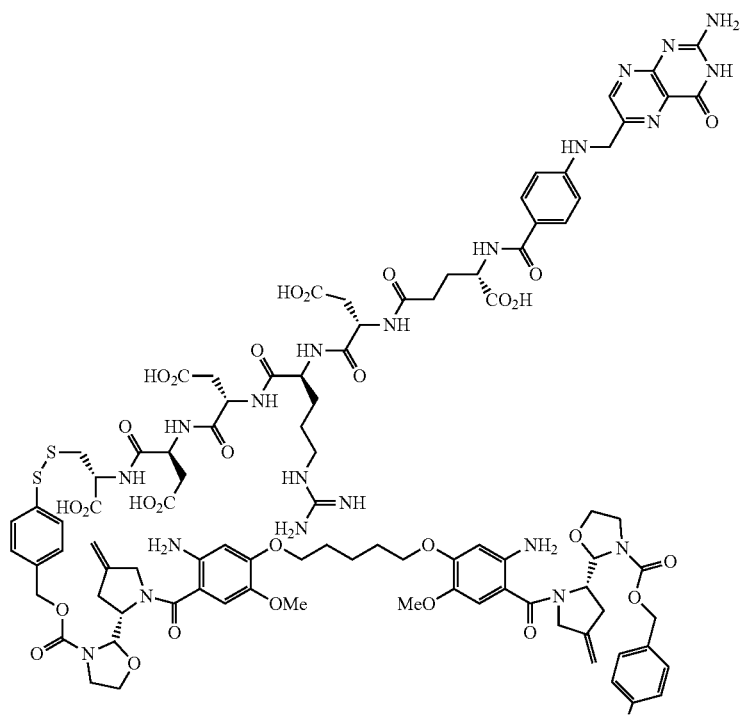

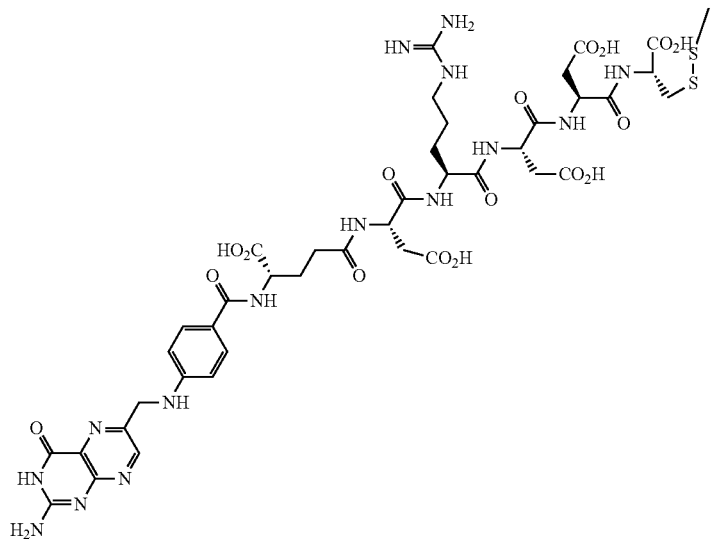
EC1704 (SEQ ID NOS 2 and 2 are included in the structures above)
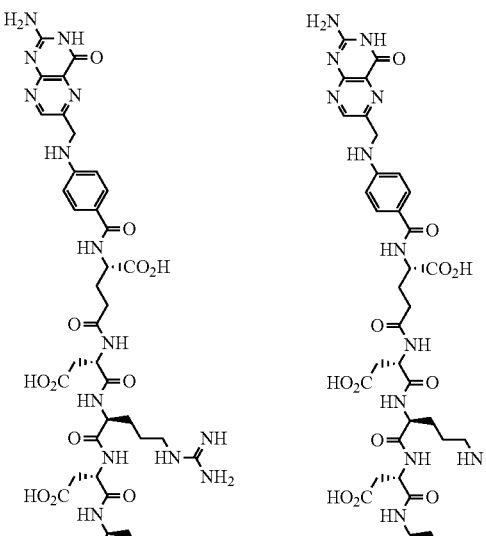
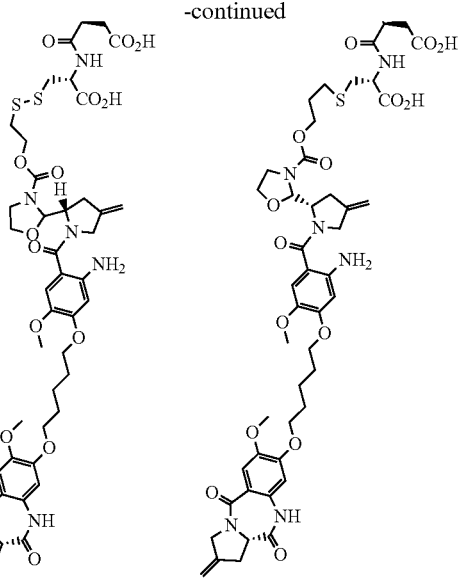
EC1744 (SEQ ID NO: 2 is included in the structure above)
EC1772 (SEQ ID NO: 2 is included in the structure above)

257    258
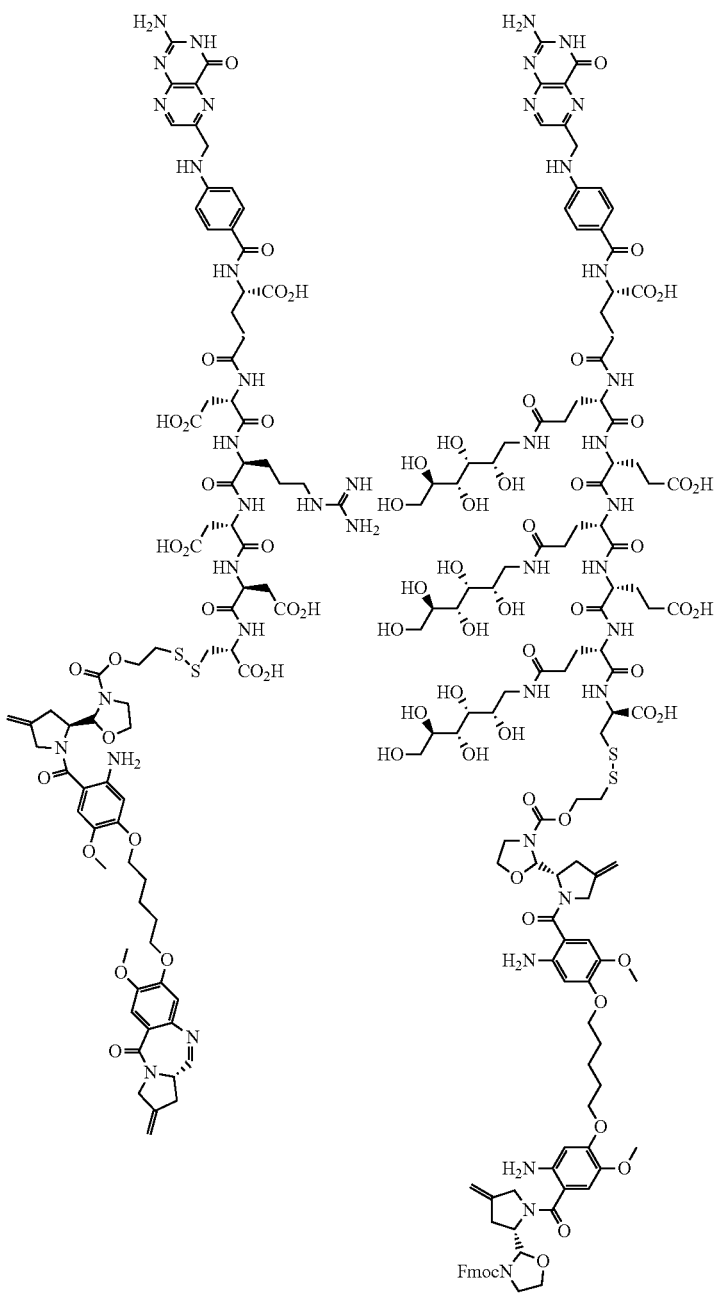
EC1788 (SEQ ID NO: 2 is included in the structure above)
EC1884 (SEQ ID NO: 1 is included in the structure above)

259 260
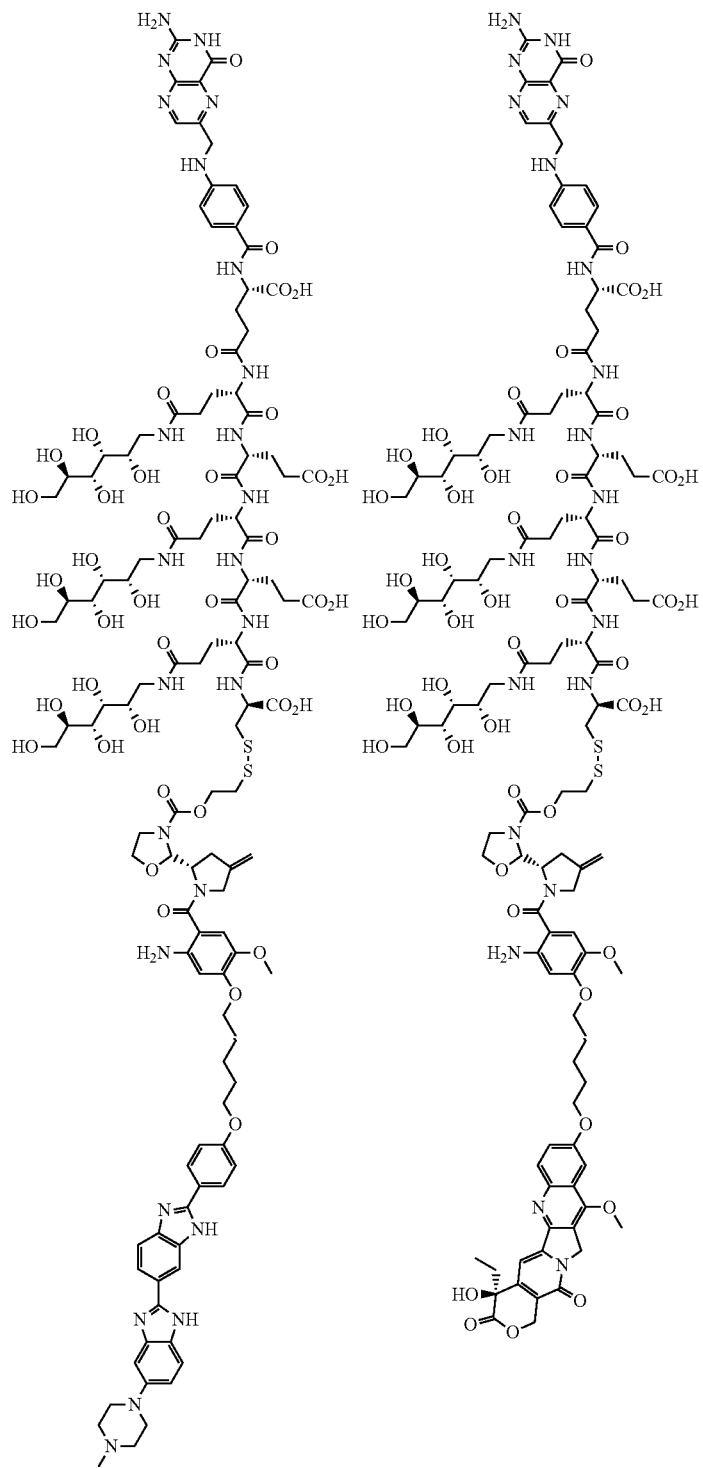
EC1879 (SEQ ID NO: 1 is included in the structure above)
EC1904 (SEQ ID NO: 1 is included in the structure above)

261 262
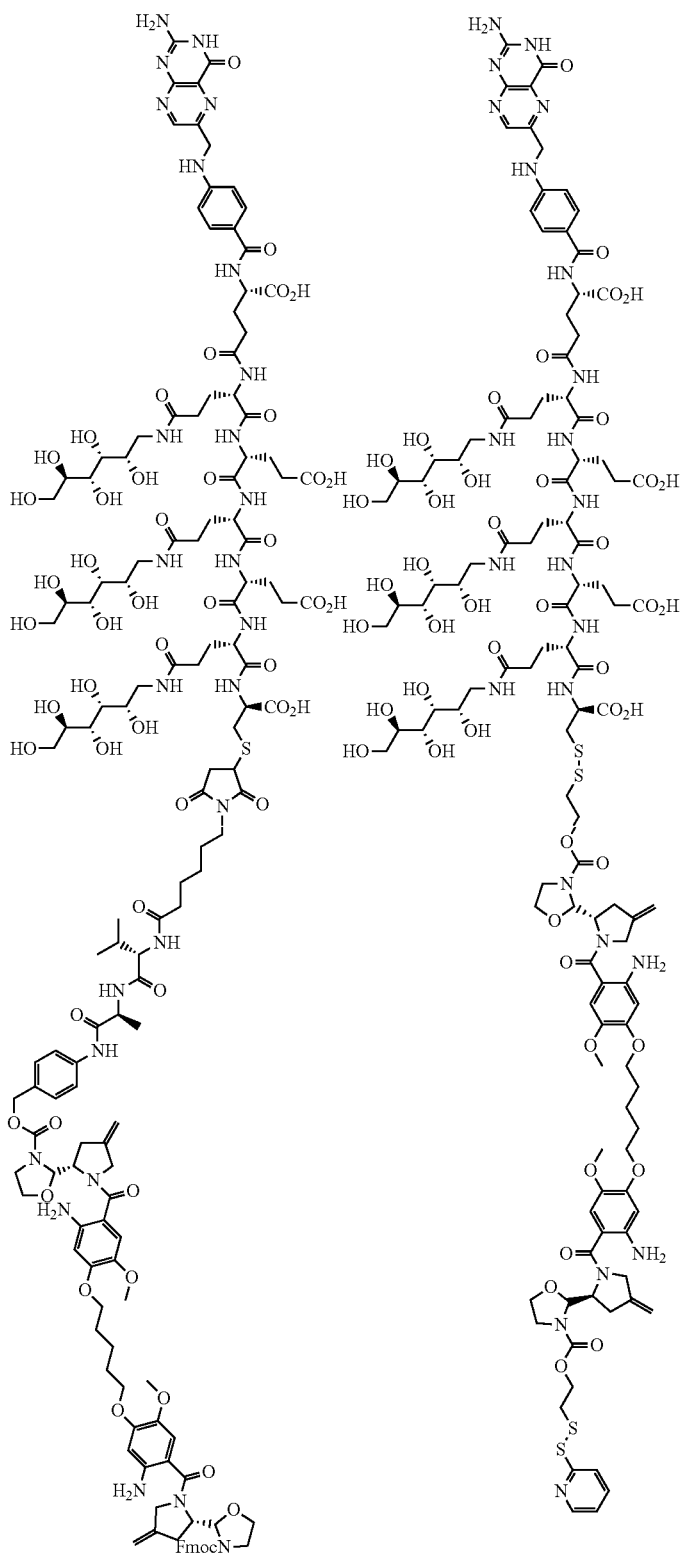
EC1911 (SEQ ID NO: 1 is included in the structure above)
EC1949 (SEQ ID NO: 1 is included in the structure above)

263
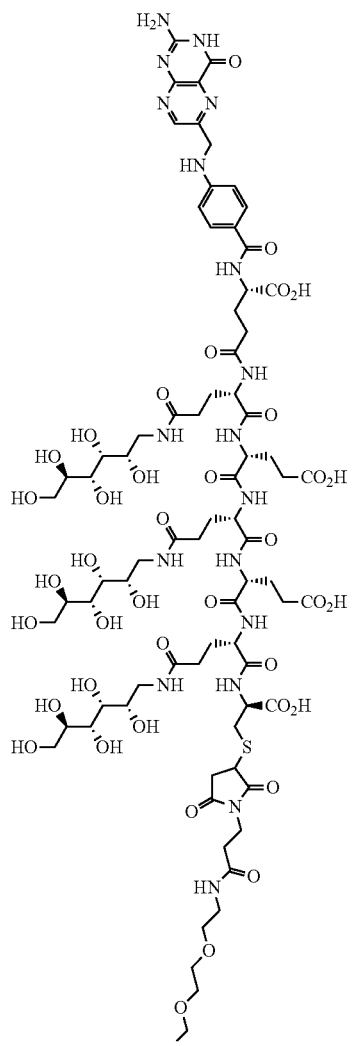
264
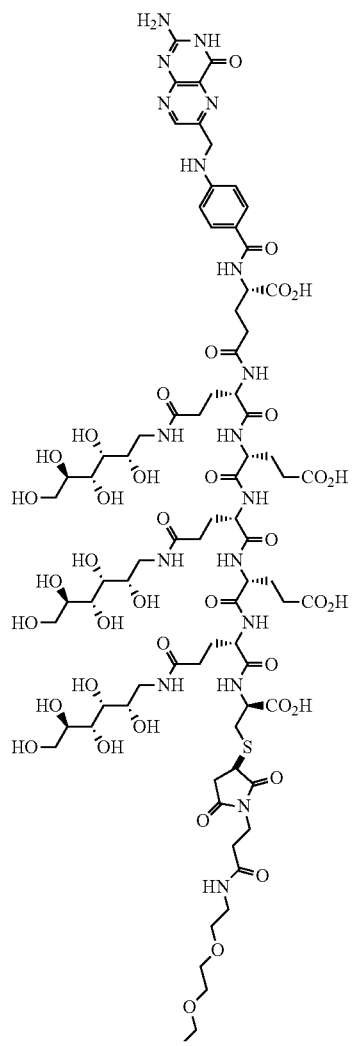

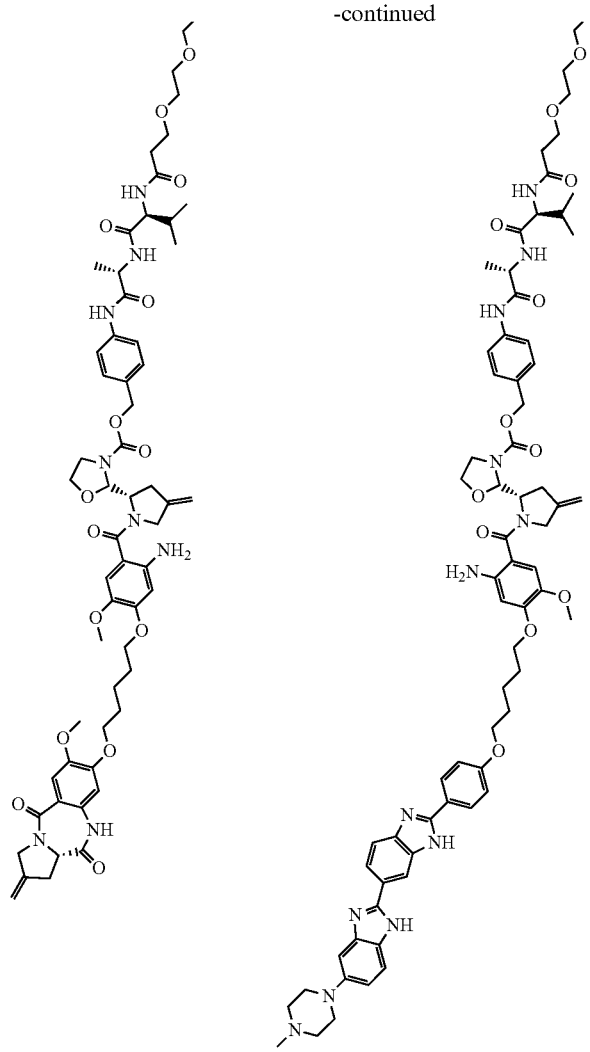
EC2074 (SEQ ID NO: 1 is included in the structure above)
EC2080 (SEQ ID NO: 1 is included in the structure above)
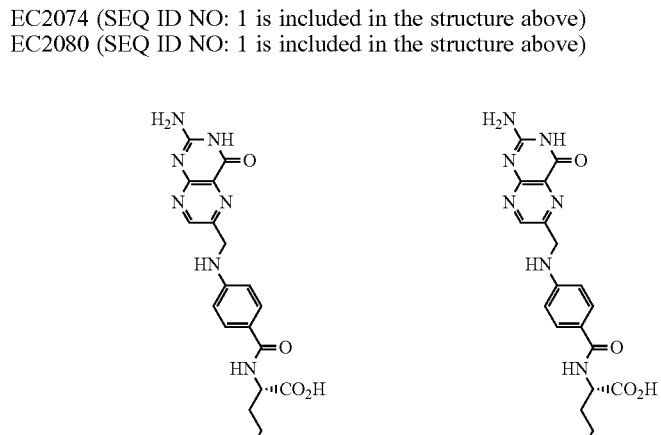

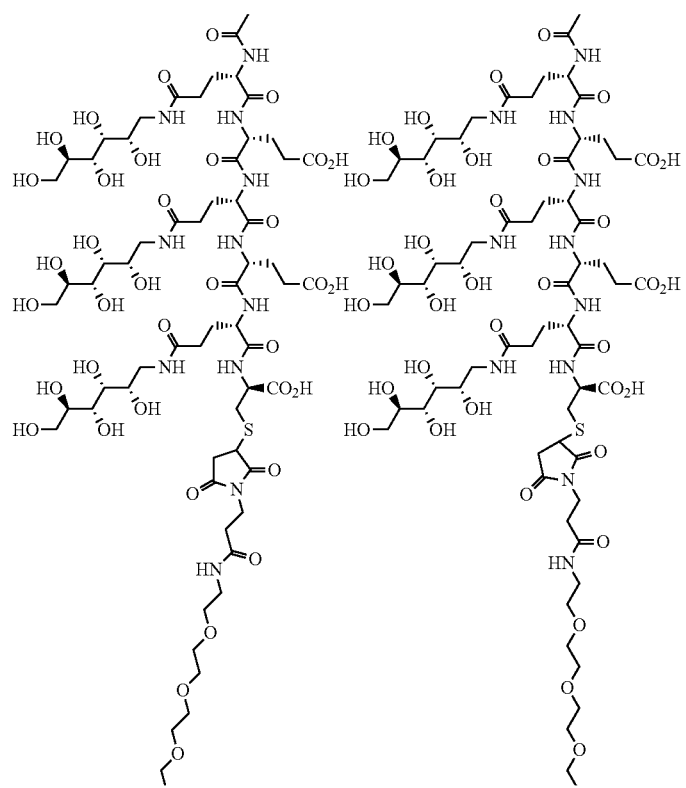

-continued
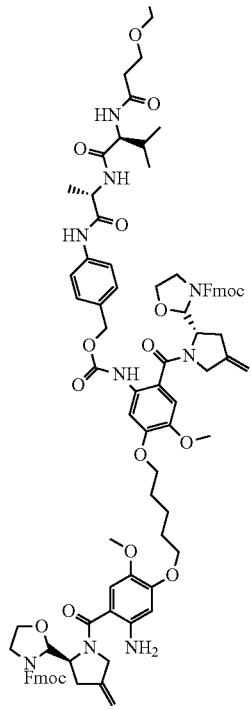
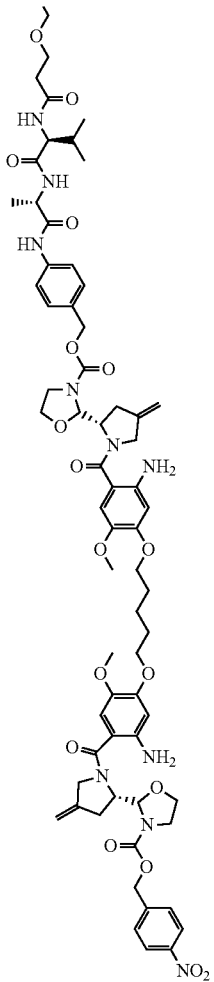
EC2103 (SEQ ID NO: 1 is included in the structure above)
EC2127 (SEQ ID NO: 1 is included in the structure above)

271                              272
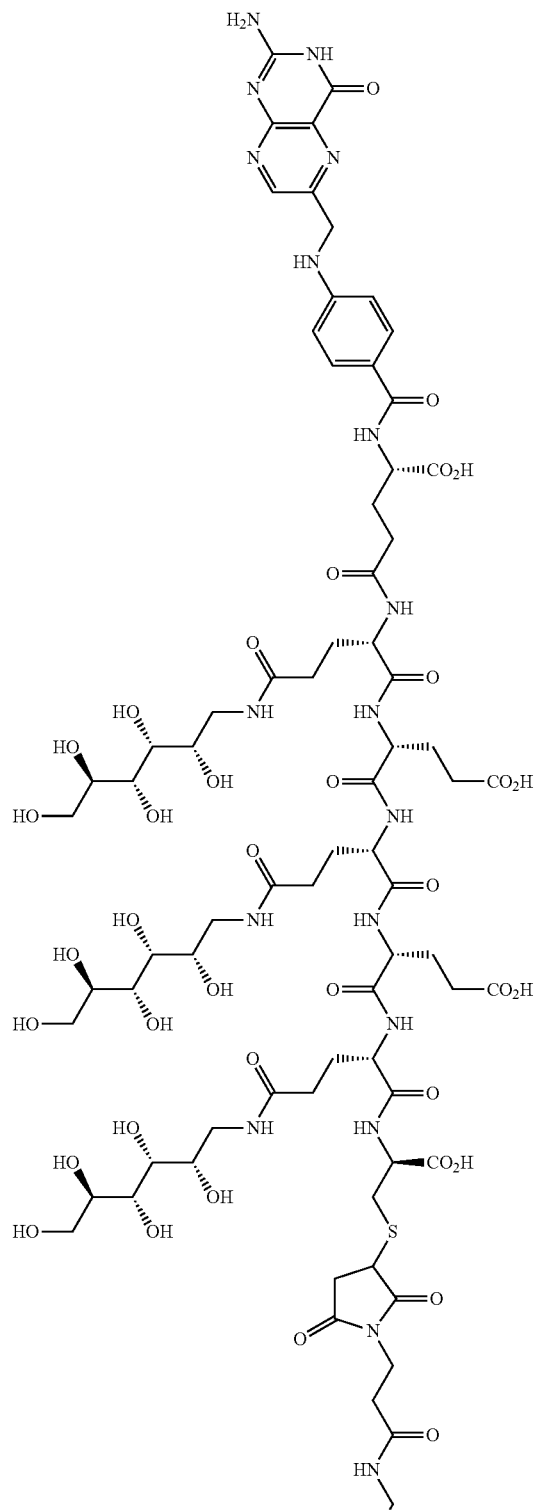
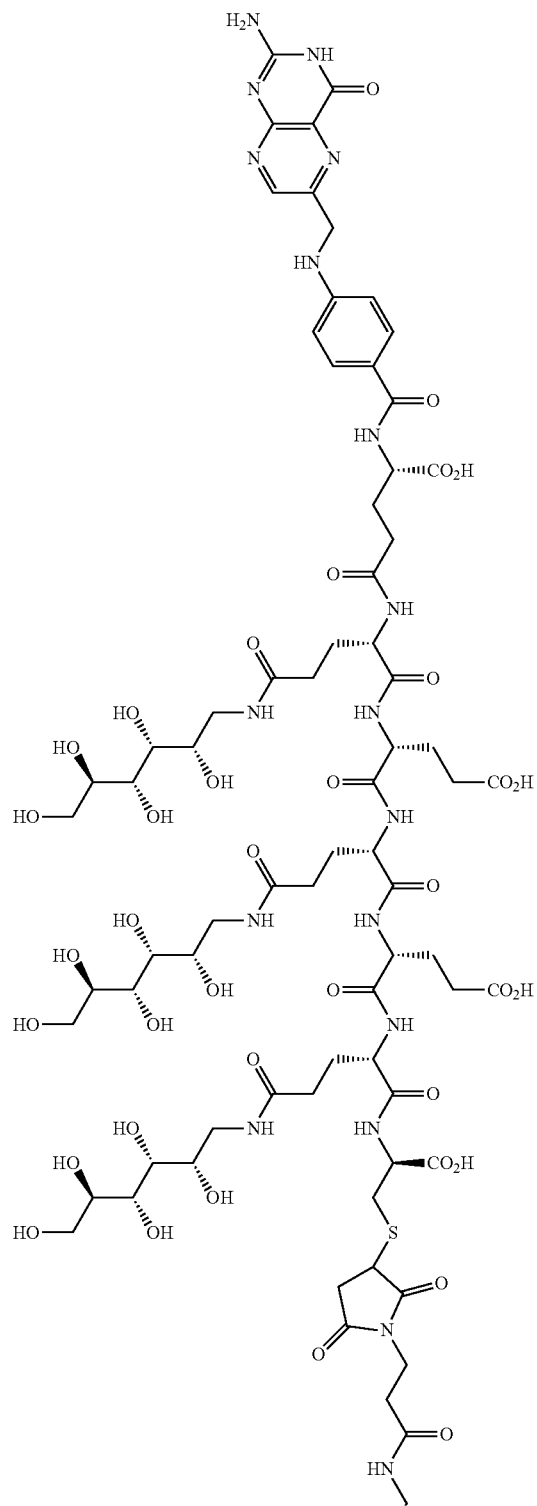

273
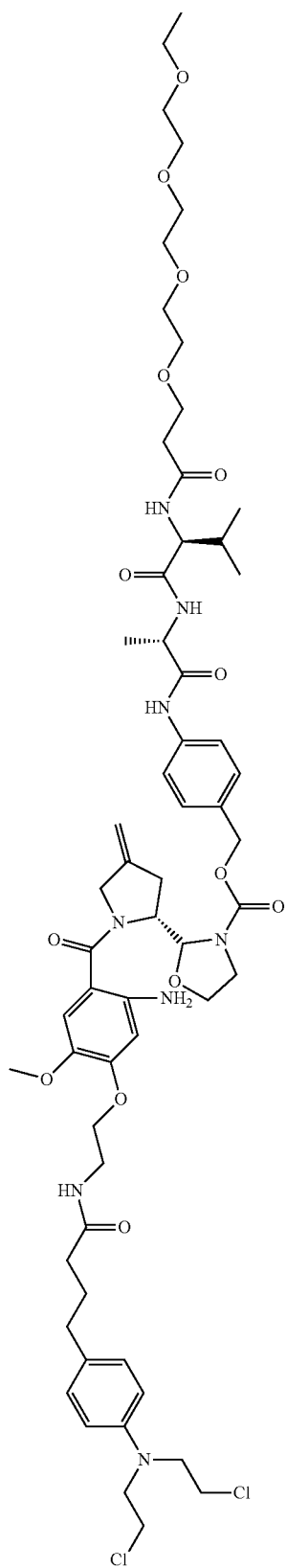
274
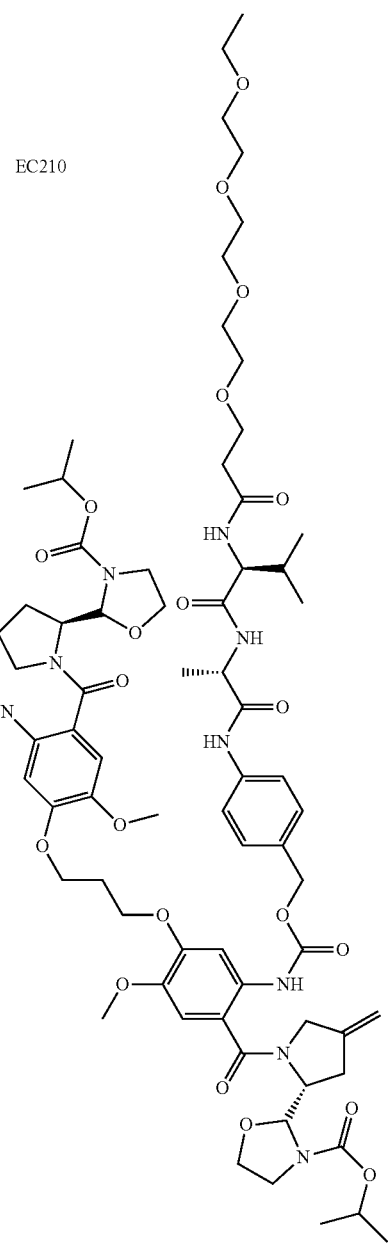
EC210
EC2130 (SEQ ID NO: 1 is included in the structure above)
EC2110 (SEQ ID NO: 1 is included in the structure above)

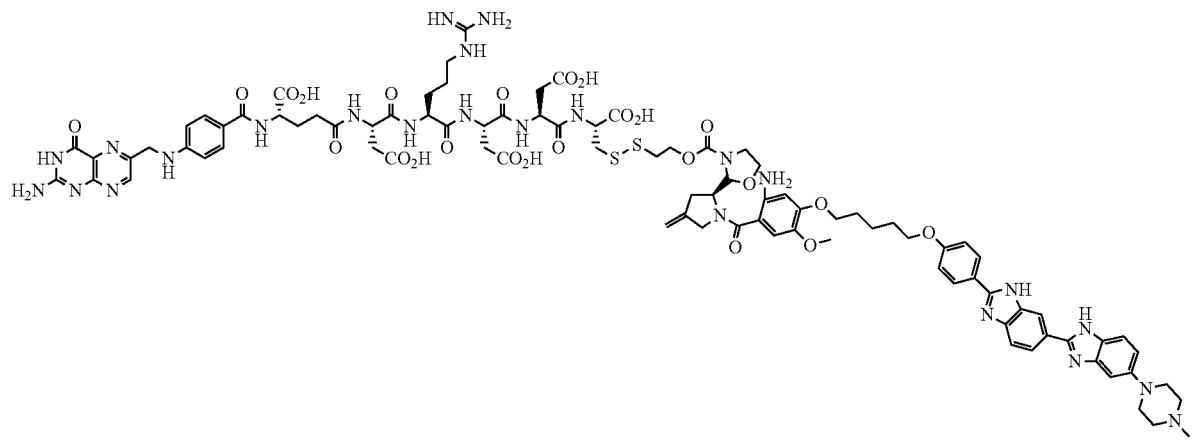 [SMILES: C=C1C[C@@H](C2OCCN2C(=O)OCCSSC[C@H](NC(=O)[C@H](CC(=O)O)NC(=O)[C@H](CC(=O)O)NC(=O)[C@H](CCCNC(=N)N)NC(=O)[C@H](CC(=O)O)NC(=O)CC[C@H](NC(=O)c2ccc(NCc3cnc4nc(N)[nH]c(=O)c4n3)cc2)C(=O)O)C(=O)O)N(C(=O)c2cc(OC)c(OCCCCCOc3ccc(-c4nc5ccc(-c6nc7cc(N8CCN(C)CC8)ccc7[nH]6)cc5[nH]4)cc3)cc2N)C1]
(SEQ ID NO: 2 is included in the structure above)
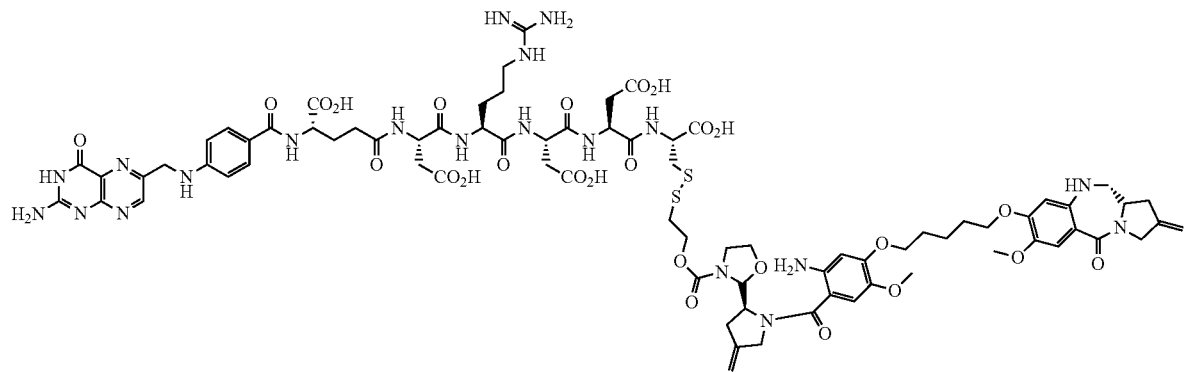
(SEQ ID NO: 2 is included in the structure above)
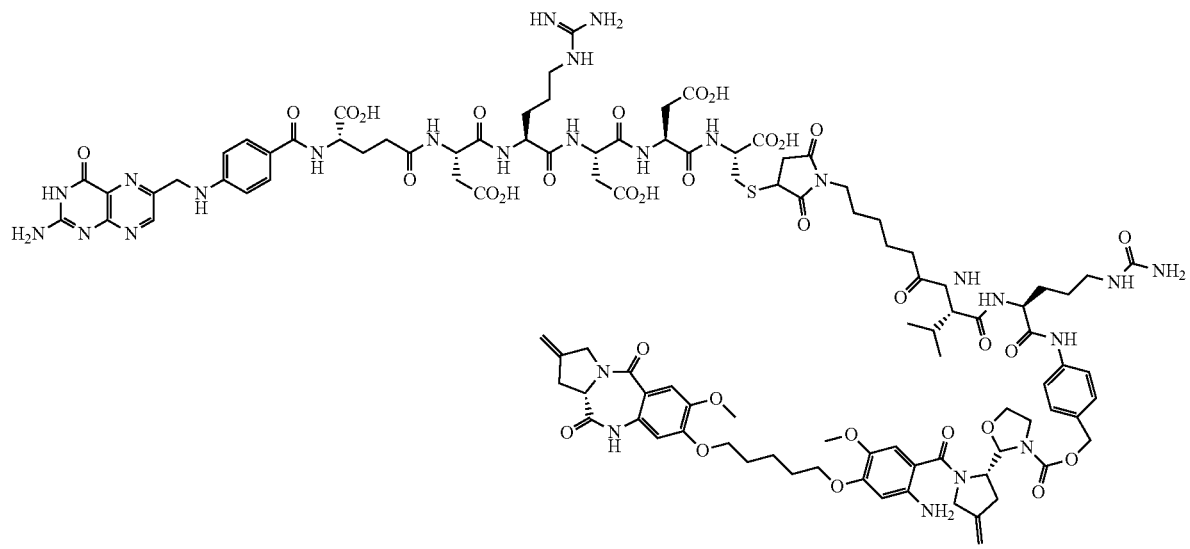
(SEQ ID NO: 2 is included in the structure above)

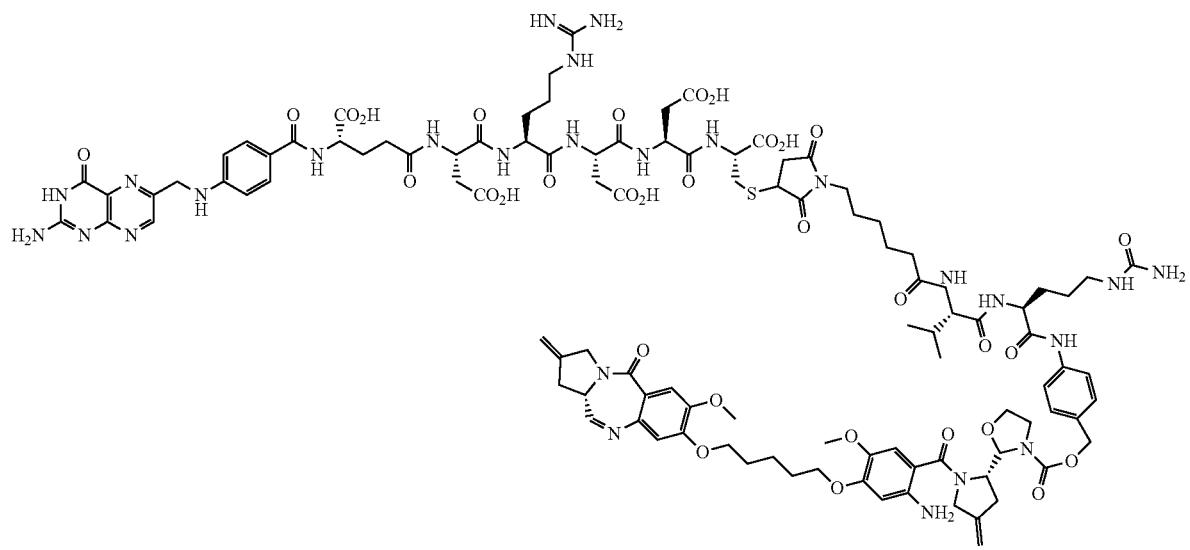
(SEQ ID NO: 2 is included in the structure above)
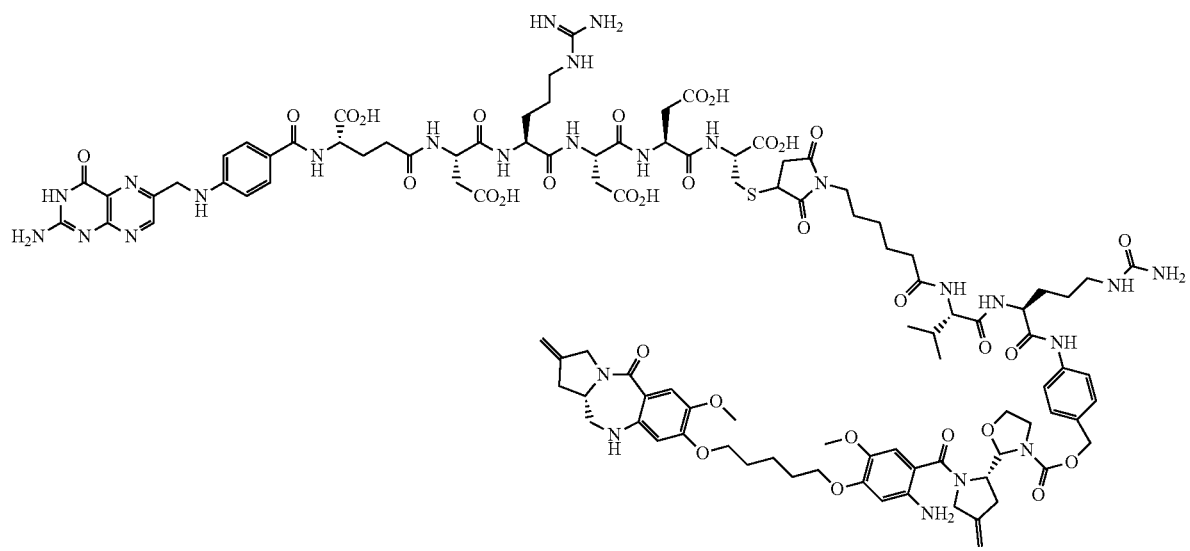 [SMILES: C=C1C[C@H]2CNc3cc(OCCCCCOc4cc(N)c(C(=O)N5CC(=C)C[C@H]5C5OCCN5C(=O)OCc5ccc(NC(=O)[C@H](CCCNC(N)=O)NC(=O)[C@@H](NC(=O)CCCCCN6C(=O)CC(SC[C@H](NC(=O)[C@H](CC(=O)O)NC(=O)[C@H](CC(=O)O)NC(=O)[C@H](CCCNC(=N)N)NC(=O)[C@H](CC(=O)O)NC(=O)CC[C@H](NC(=O)c7ccc(NCc8cnc9nc(N)[nH]c(=O)c9n8)cc7)C(=O)O)C(=O)O)C6=O)C(C)C)cc5)cc4OC)c(OC)cc3C(=O)N2C1]
(SEQ ID NO: 2 is included in the structure above)

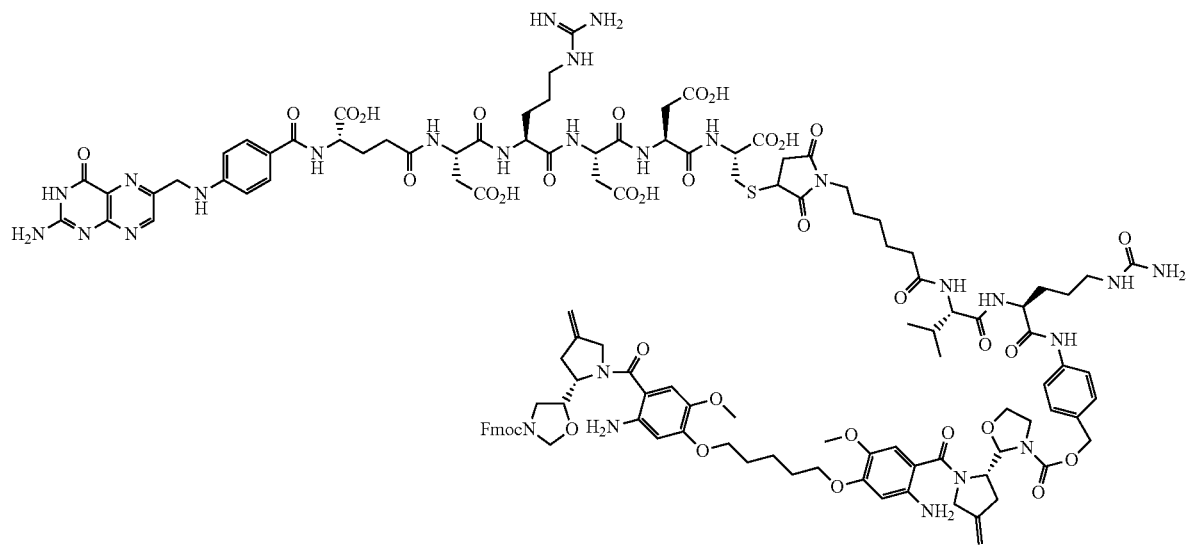
(SEQ ID NO: 2 is included in the structure above)
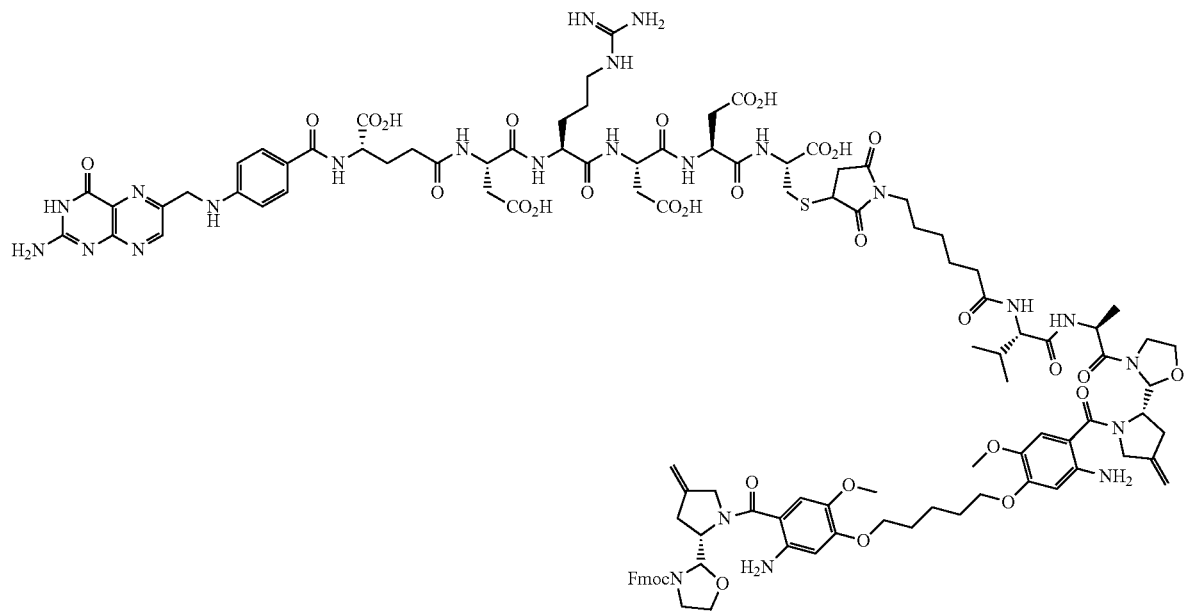
(SEQ ID NO: 2 is included in the structure above)

281
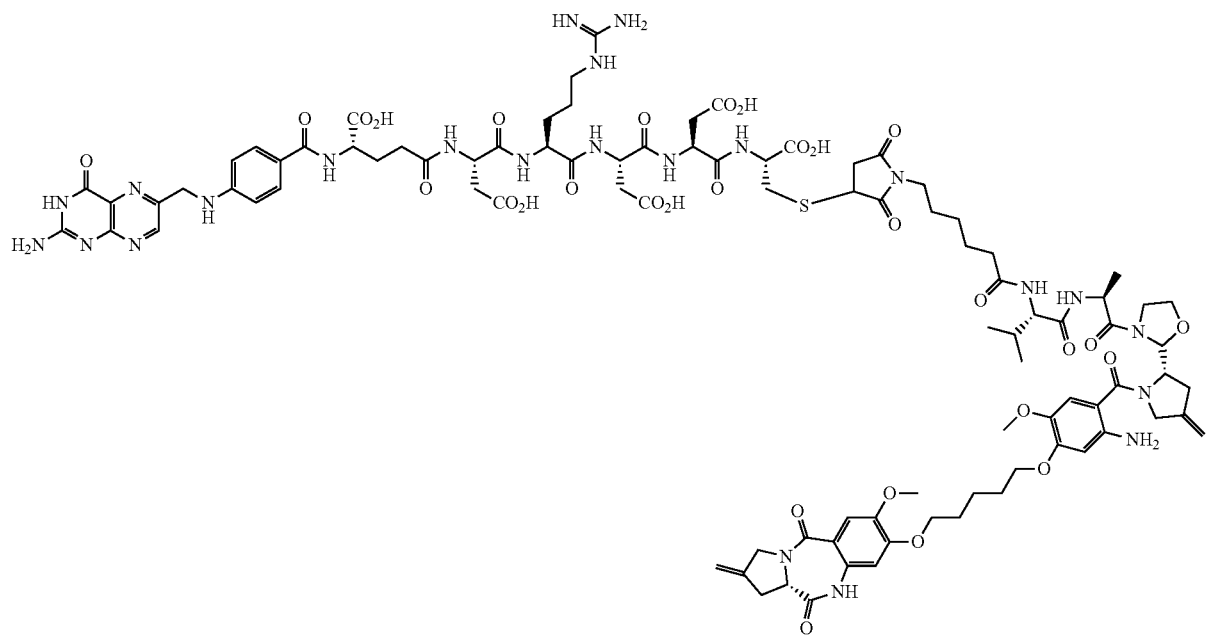 [SMILES: C=C1C[C@H]2C(=O)Nc3cc(OCCCCCOc4cc(N)c(C(=O)N5CC(=C)C[C@H]5C5OCCN5C(=O)[C@H](C)NC(=O)[C@@H](NC(=O)CCCCCN5C(=O)CC(SC[C@H](NC(=O)[C@H](CC(=O)O)NC(=O)[C@H](CC(=O)O)NC(=O)[C@H](CCCNC(=N)N)NC(=O)[C@H](CC(=O)O)NC(=O)CC[C@H](NC(=O)c6ccc(NCc7cnc8nc(N)[nH]c(=O)c8n7)cc6)C(=O)O)C(=O)O)C5=O)C(C)C)cc4OC)c(OC)cc3C(=O)N2C1]
(SEQ ID NO: 2 is included in the structure above)
282
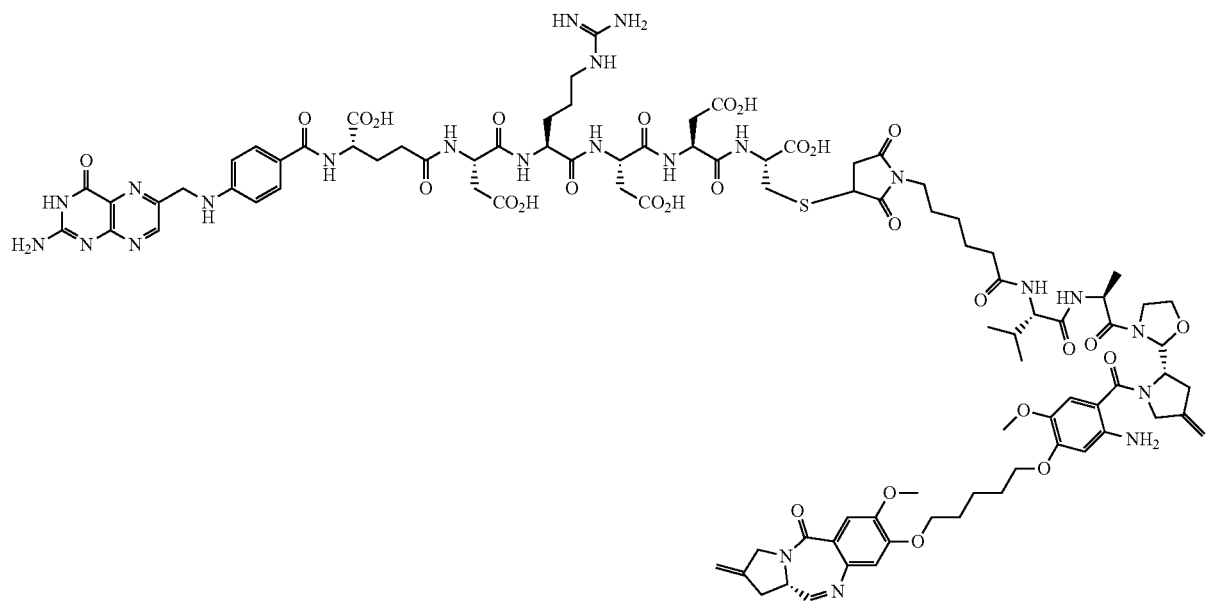 [SMILES: C=C1C[C@H]2C=Nc3cc(OCCCCCOc4cc(N)c(C(=O)N5CC(=C)C[C@H]5C5OCCN5C(=O)[C@H](C)NC(=O)[C@@H](NC(=O)CCCCCN5C(=O)CC(SC[C@H](NC(=O)[C@H](CC(=O)O)NC(=O)[C@H](CC(=O)O)NC(=O)[C@H](CCCNC(=N)N)NC(=O)[C@H](CC(=O)O)NC(=O)CC[C@H](NC(=O)c6ccc(NCc7cnc8nc(N)[nH]c(=O)c8n7)cc6)C(=O)O)C(=O)O)C5=O)C(C)C)cc4OC)c(OC)cc3C(=O)N2C1]
(SEQ ID NO: 2 is included in the structure above)

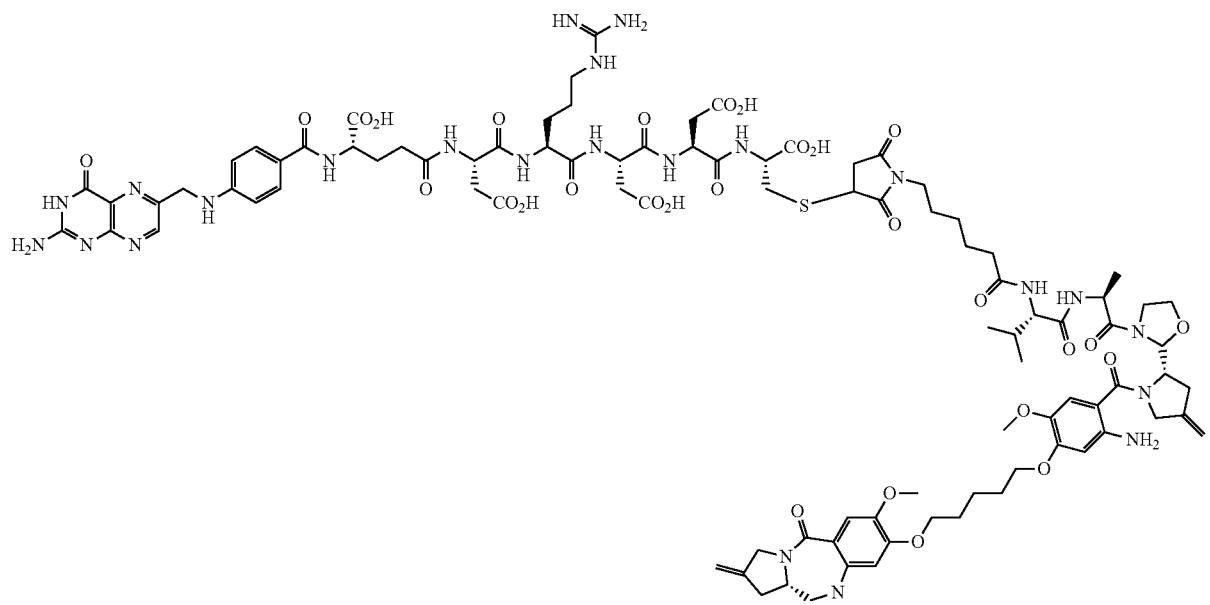 [SMILES: C=C1C[C@H]2CNc3cc(OCCCCCOc4cc(N)c(C(=O)N5CC(=C)C[C@H]5C5OCCN5C(=O)[C@H](C)NC(=O)[C@@H](NC(=O)CCCCCN5C(=O)CC(SC[C@H](NC(=O)[C@H](CC(=O)O)NC(=O)[C@H](CC(=O)O)NC(=O)[C@H](CCCNC(=N)N)NC(=O)[C@H](CC(=O)O)NC(=O)CC[C@H](NC(=O)c6ccc(NCc7cnc8nc(N)[nH]c(=O)c8n7)cc6)C(=O)O)C(=O)O)C5=O)C(C)C)cc4OC)c(OC)cc3C(=O)N2C1]

(SEQ ID NO: 2 is included in the structure above)

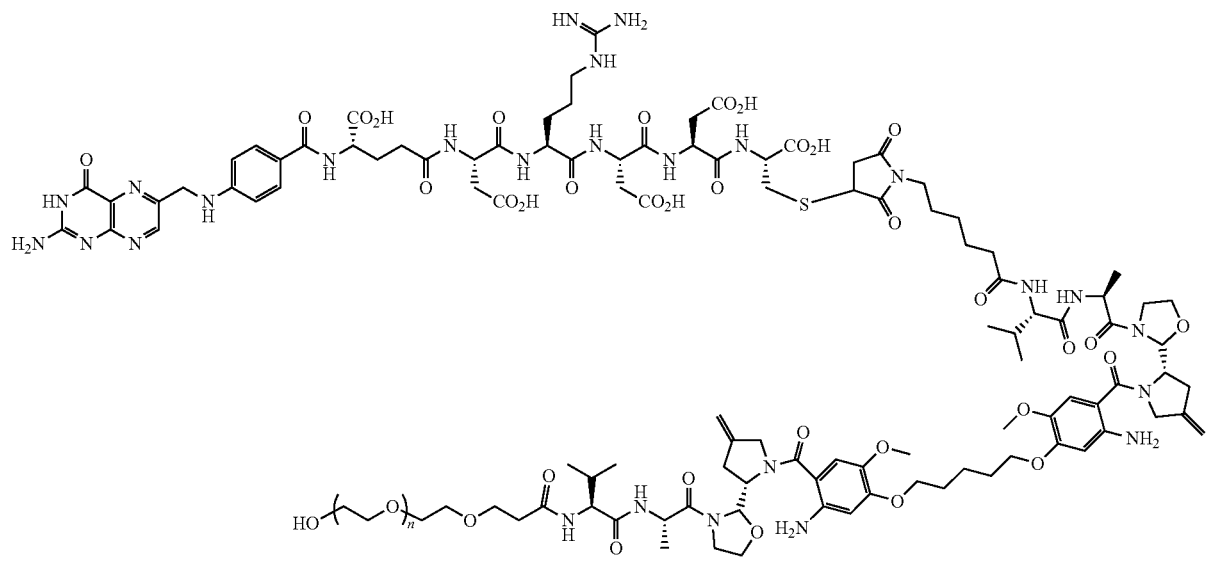

(SEQ ID NO: 2 is included in the structure above)

Method Examples

General. The following abbreviations are used herein: partial response (PR); complete response (CR), biweekly (M/F) (BIW), three times per week (M/W/F) (TIW). A PR is observed where tumor volume, as defined herein, decreases from a previous high during the observation period, though regrowth may occur. A CR is observed where tumor volume, as defined herein, decreases to zero during the observation period, though regrowth may occur. A cure is observed where tumor volume, as defined herein, decreases to zero, and does not regrow during the observation period.

METHOD. Relative Affinity Assay. The affinity for folate receptors (FRs) relative to folate was determined according to a previously described method (Westerhof, G. R., J. H. Schornagel, et al. (1995) Mol. Pharm. 48: 459-471) with slight modification. FR-positive KB cells were heavily seeded into 24-well cell culture plates and allowed to adhere to the plastic for 18 h. Spent incubation media was replaced in designated wells with folate-free RPMI (FFRPMI) supplemented with 100 nM $^3$H-folic acid in the absence and presence of increasing concentrations of test article or folic acid. Cells were incubated for 60 min at 37° C. and then rinsed 3 times with PBS, pH 7.4. Five hundred microliters of 1% SDS in PBS, pH 7.4, was added per well. Cell lysates were then collected and added to individual vials containing 5 mL of scintillation cocktail, and then counted for radioactivity. Negative control tubes contain only the $^3$H-folic acid in FFRPMI (no competitor). Positive control tubes contain a final concentration of 1 mM folic acid, and CPMs measured in these samples (representing non-specific binding of label) were subtracted from all samples. Relative affinities were defined as the inverse molar ratio of compound required to displace 50% of $^3$H-folic acid bound to the FR on KB cells, where the relative affinity of folic acid for the FR was set to 1.

EXAMPLE. The conjugates described herein show high binding affinities towards folate receptors as determined by an in vitro competitive binding assay that measures the ability of the ligand to compete against $^3$H-folic acid for binding to cell surface folate receptors (FR). Without being bound by theory, it is believed herein that the high binding affinity of the conjugates described herein allows for efficient cellular uptake via FR-mediated endocytosis.

METHOD. Inhibition of Cellular DNA Synthesis. The conjugates described herein were evaluated using an in vitro cytotoxicity assay that predicted the ability of the drug to inhibit the growth of the corresponding targeted cells, such as, but not limited to the following

| Cell Line | |
|---|---|
| KB | Human cervical carcinoma |
| NCI/ADR-RES-Cl$_2$ | Human ovarian carcinoma |
| IGROV1 | Human ovarian adenocarcinoma |
| MDA-MB-231 | Human breast adenocarcinoma (triple negative) |
| A549 | Human lung carcinoma |
| H23 | Human lung adenocarcinoma |
| HepG2 | Human hepatocellular carcinoma |
| AN3CA | Human endometrial adenocarcinoma |

It is to be understood that the choice of cell type can be made on the basis of the susceptibility of those selected cells to the drug that forms the conjugate, and the relative expression of the cell surface receptor or target antigen. The test conjugates were conjugates of a cell surface receptor or target antigen binding compound and PBD prodrugs, poly-PBD prodrugs, and mixed PBDs, as described herein. The test cells were exposed to varying concentrations of the conjugates, and optionally also in the absence or presence of at least a 100-fold excess of the unconjugated cell surface receptor or target antigen binding compound for competition studies to assess activity as being specific to the cell surface receptor or target antigen.

EXAMPLE. Conjugates of PBD prodrugs, poly-PBD prodrugs, and mixed PBDs described herein were active against KB cells. The activity was mediated by the folate receptor as indicated by competition experiments using co-administered folic acid. KB cells were exposed for up to 7 h at 37° C. to the indicated concentrations of folate-drug conjugate in the absence or presence of at least a 100-fold excess of folic acid. The cells were then rinsed once with fresh culture medium and incubated in fresh culture medium for 72 hours at 37° C. Cell viability was assessed using a $^3$H-thymidine incorporation assay. For conjugates described herein, dose-dependent cytotoxicity was generally measurable, and in most cases, the IC$_{50}$ values (concentration of drug conjugate required to reduce $^3$H-thymidine incorporation into newly synthesized DNA by 50%) were in the low nanomolar range. Though without being bound by theory, when the cytotoxicities of the conjugates were reduced in the presence of excess free folic acid, it is believed herein that such results indicate that the observed cell death was mediated by binding to the folate receptor.

| Example | IC$_{50}$ KB Cells (nM) |
|---|---|
| EC1628 | 383 |
| EC1628 + DTT [a] | 11 |
| EC1629 + DTT [a] | ≥10 |
| EC1630 | 2.7 |
| EC1673 | ≥1 μM |
| EC1695 | ≥100 |
| EC1695 + DTT [a] | 1 |
| EC1704 | 0.46 |
| EC1744 | 1.2 |
| EC1772 | 0.33 |
| EC1788 | 0.18 |
| EC1879 | 0.56 |
| EC1884 | 0.36 |
| EC1904 | ≥50 |
| EC1911 | 0.7 |
| EC1949 | 1.49 |
| EC2074 | 3.6 |
| EC2080 | 0.2 |
| EC2103 | 3.5 |
| EC2127 | 1.34 |

[a] Co-administered with dithiothreitol (DTT).

METHOD. In vitro activity against various cancer cell lines. IC$_{50}$ values were generated for various cell lines. Cells were heavily seeded in 24-well Falcon plates and allowed to form nearly confluent monolayers overnight. Thirty minutes prior to the addition of the test compound, spent medium was aspirated from all wells and replaced with fresh folate-deficient RPMI medium (FFRPMI). A subset of wells were designated to receive media containing 100 μM folic acid. The cells in the designated wells were used to determine the targeting specificity. Without being bound by theory it is believed herein that the cytotoxic activity produced by test compounds in the presence of excess folic acid, i.e. where there is competition for FR binding, corresponded to the portion of the total activity that was unrelated to FR-specific delivery. Following one rinse with 1 mL of fresh FFRPMI containing 10% heat-inactivated fetal calf serum, each well received 1 mL of medium containing increasing concentrations of test compound (4 wells per sample) in the presence or absence of 100 μM free folic acid as indicated. Treated cells were pulsed for 2 h at 37° C., rinsed 4 times with 0.5 mL of media, and then chased in 1 mL of fresh medium up to 70 h. Spent medium was aspirated from all wells and replaced with fresh medium containing 5 μCi/mL $^3$H-thymidine. Following a further 2 h 37° C. incubation, cells were washed 3 times with 0.5 mL of PBS and then treated with 0.5 mL of ice-cold 5% trichloroacetic acid per well. After 15 min, the trichloroacetic acid was aspirated and the cell material solubilized by the addition of 0.5 mL of 0.25 N sodium hydroxide for 15 min. A 450 μL aliquot of each solubilized sample was transferred to a scintillation vial containing 3 mL of Ecolume scintillation cocktail and then counted in a liquid scintillation counter. Final results were expressed as the percentage of $^3$H-thymidine incorporation relative to untreated controls.

METHOD. Inhibition of Tumor Growth in Mice. Four to seven week-old mice (Balb/c or nu/nu strains) were purchased from Harlan Sprague Dawley, Inc. (Indianapolis, Ind.). Normal rodent chow contains a high concentration of folic acid (6 mg/kg chow); accordingly, test animals were maintained on a folate-free diet (Harlan diet #TD00434) for about 1 week before tumor implantation to achieve serum folate concentrations close to the range of normal human serum, and during the Method. For tumor cell inoculation, 1×10$^6$ M109 cells (a syngeneic lung carcinoma) in Balb/c strain, or 1×10$^6$ KB cells in nu/nu strain, in 100 μL were injected in the subcutis of the dorsal medial area (right axilla). Tumors were measured in two perpendicular directions every 2-3 days using a caliper, and their volumes were calculated as $0.5 \times L \times W^2$, where L=measurement of longest axis in mm and W=measurement of axis perpendicular to L in mm. Log cell kill (LCK) and treated over control (T/C) values were then calculated according to published procedures (see, e.g., Lee et al., "BMS-247550: a novel epothilone analog with a mode of action similar to paclitaxel but possessing superior antitumor efficacy" *Clin Cancer Res* 7:1429-1437 (2001); Rose, "Taxol-based combination chemotherapy and other in vivo preclinical antitumor studies" *J Natl Cancer Inst Monogr* 47-53 (1993)).

Dosing was initiated when the s.c. tumors had an average volume between 50-100 mm$^3$ ($t_0$), typically 8 days post tumor inoculation (PTI) for KB tumors, and 11 days PTI for M109 tumors. Test animals (5/group) were injected intravenously, generally three times a week (TIW), for 3 weeks with varying doses, such as with 1 μmol/kg to 5 mol/kg, of the drug delivery conjugate or with an equivalent dose volume of PBS (control), unless otherwise indicated. Dosing solutions were prepared fresh each day in PBS and administered through the lateral tail vein of the mice.

METHOD. General 4T-1 Tumor Assay. Six to seven week-old mice (female Balb/c strain) were obtained from Harlan, Inc. (Indianapolis, Ind.). The mice were maintained on Harlan's folate-free chow for a total of three weeks prior to the onset of and during the method. Folate receptor-negative 4T-1 tumor cells ($1 \times 10^6$ cells per animal) were inoculated in the subcutis of the right axilla. Approximately 5 days post tumor inoculation when the 4T-1 tumor average volume was ~100 mm$^3$ ($t_0$), mice (5/group) were injected i.v. three times a week (TIW), for 3 weeks with varying doses, such as 3 μmol/kg, of drug delivery conjugate or with an equivalent dose volume of PBS (control), unless otherwise indicated herein. Tumor growth was measured using calipers at 2-day or 3-day intervals in each treatment group. Tumor volumes were calculated using the equation $V = a \times b^2/2$, where "a" was the length of the tumor and "b" was the width expressed in millimeters.

METHOD. Drug Toxicity. Persistent drug toxicity was assessed by collecting blood via cardiac puncture and submitting the serum for independent analysis of blood urea nitrogen (BUN), creatinine, total protein, AST-SGOT, ALT-SGPT plus a standard hematological cell panel at Ani-Lytics, Inc. (Gaithersburg, Md.). In addition, histopathologic evaluation of formalin-fixed heart, lungs, liver, spleen, kidney, intestine, skeletal muscle and bone (tibia/fibula) was conducted by board-certified pathologists at Animal Reference Pathology Laboratories (ARUP; Salt Lake City, Utah).

METHOD. Toxicity as Measured by Weight Loss. The percentage weight change of the test animals was determined on selected days post-tumor inoculation (PTI), and during dosing. The results were graphed.

EXAMPLE. In vivo activity against tumors. Conjugates described herein showed high potency and efficacy against KB tumors in nu/nu mice. Conjugates described herein showed specific activity against folate receptor expressing tumors, with low host animal toxicity.

EXAMPLE. EC1629 in vivo activity against tumors. As shown in FIG. 1, EC1629 (♦) dosed at 2 μmol/kg TIW for two weeks decreased KB tumors in test animals compared to untreated control (●). Toxicity was not observed, as evidenced by test animal total body weight.

Figure 2:
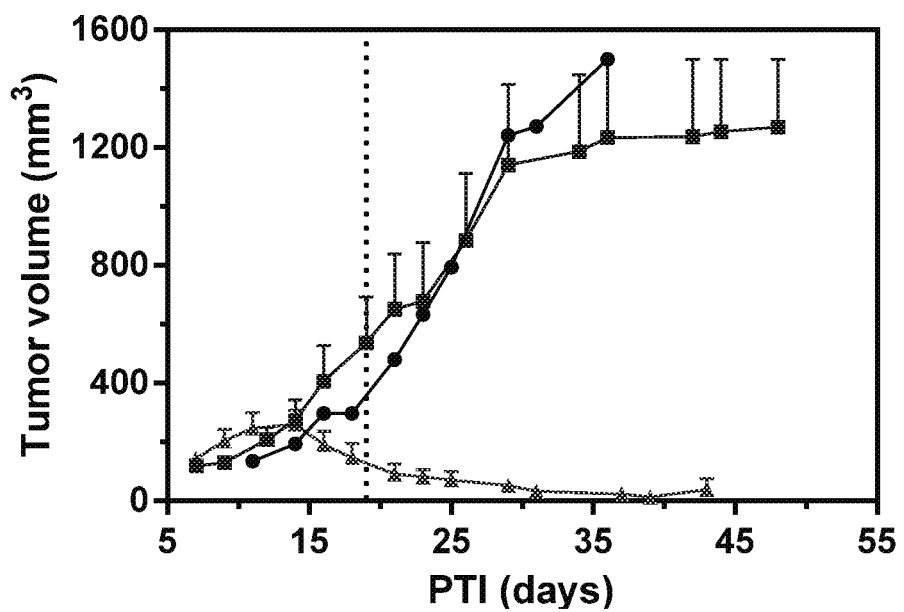
FIG. 2 shows that EC1744 (■) dosed at 2 µmol/kg TIW for two weeks decreases KB tumors in test animals compared to untreated control (●).

EXAMPLE. EC1744 and EC1788 in vivo activity against tumors. As shown in FIG. 2 EC1744 (■) dosed at 2 μmol/kg TIW for two weeks and EC1788 (▲) dosed at 0.2 μmol/kg TIW for two weeks decreases KB tumors in test animals compared to untreated control (●). Moreover, EC1788 gave a complete response. Toxicity was not observed for EC1744, as evidenced by test animal total body weight. Minor toxicity was observed for EC1788, as evidenced by test animal total body weight; however, test animal total body weight steadily increased after the last dosing day.

Figure 3:
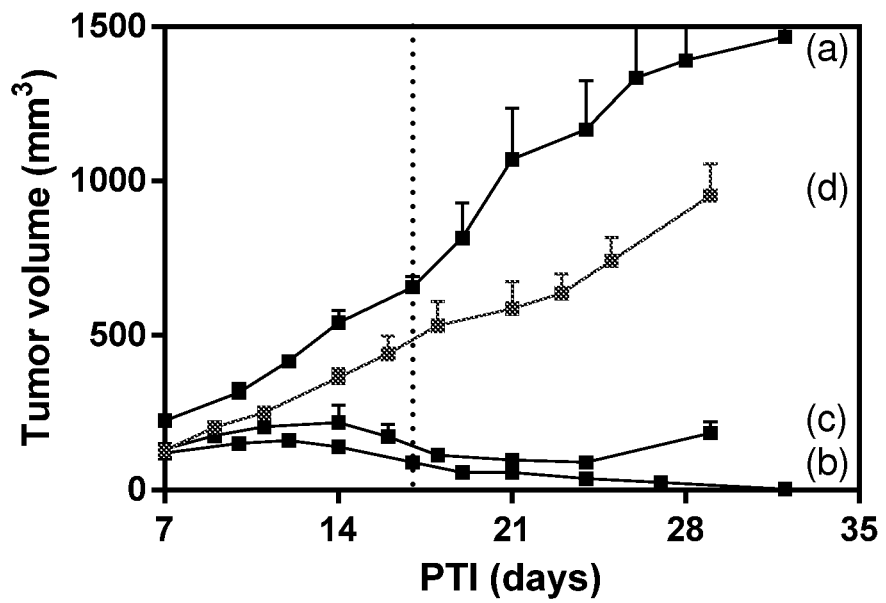
FIG. 3 shows that EC1884 (d) dosed at 2 µmol/kg TIW for two weeks decreases KB tumors in test animals compared to untreated control (a).

EXAMPLE. EC1884, EC1879, and EC1788 in vivo activity against tumors. As shown in FIG. 3, EC1884 (d) dosed at 2 μmol/kg TIW for two weeks decreases KB tumors in test animals compared to untreated control (a). Toxicity was not observed for EC1884, as evidenced by test animal total body weight. FIG. 3 also shows and that EC1879 (c) dosed at 2 μmol/kg TIW for 1 week decreased KB tumors in test animals compared to untreated control (a). Moreover, EC1879 gave a partial response. Minor toxicity was observed for EC1879, as evidenced by test animal total body weight. FIG. 3 also shows and that EC1788 (b) dosed at 0.4 μmol/kg BIW for 2 weeks decreases KB tumors in test animals compared to untreated control (a). Moreover, EC1788 gave a complete response, and cure. Minor toxicity was observed for EC1788, as evidenced by test animal total body weight; however, test animal total body weight increased after the last dosing day.

Figure 4:
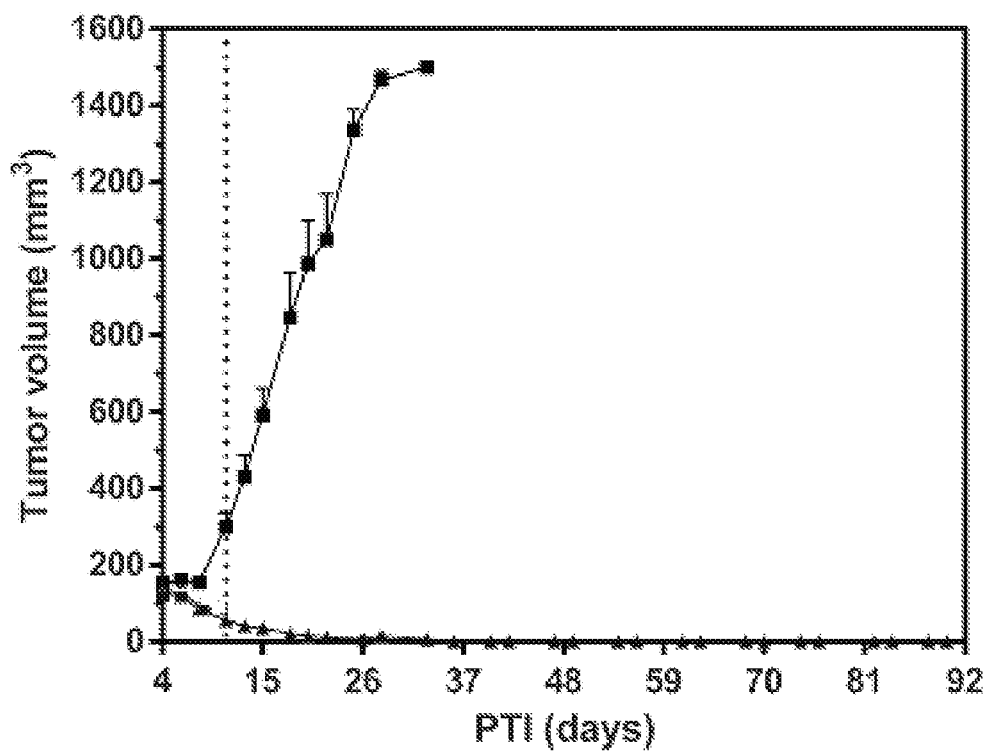
FIG. 4 shows that EC1879 (▲) dosed at 2 µmol/kg TIW for two weeks decreases KB tumors in test animals compared to untreated control (■), and that EC1879 gave a complete response in 5/5 test animals, and cure in 5/5 test animals. The dotted line indicates the last dosing day.

EXAMPLE. EC1879 in vivo activity against tumors. As shown in FIG. 4, EC1879 (▲) dosed at 2 μmol/kg TIW for two weeks decreases KB tumors in test animals compared to untreated control (■). Moreover, EC1879 gave a complete response in 5/5 test animals, and cure in 5/5 test animals. Toxicity was not observed for EC1879, as evidenced by test animal total body weight.

METHOD EXAMPLE. TNBC Tumor Assay. Triple negative breast cancer (TNBC) is a subtype characterized by lack of gene expression for estrogen, progesterone and Her2/neu. TNBC is difficult to treat, and the resulting death rate in patients is reportedly disproportionately higher than for any other subtype of breast cancer. A TNBC xenograft model was generated in an analogous way to the KB and M109 models described herein by implanting MDA-MB-231 breast cancer cells in nu/nu mice. Dosing was initiated when the s.c. tumors had an average volume between 110-150 (generally 130) mm$^3$ ($t_0$), typically 17 days post tumor inoculation (PTI). Test animals (5/group) were injected intravenously, generally three times a week (TIW), for 2-3 weeks with varying doses, such as with 1 μmol/kg to 5 μmol/kg, of the drug delivery conjugate or with an equivalent dose volume of PBS (control), unless otherwise indicated. Dosing solutions were prepared fresh each day in PBS and administered through the lateral tail vein of the mice.

Figure 5:
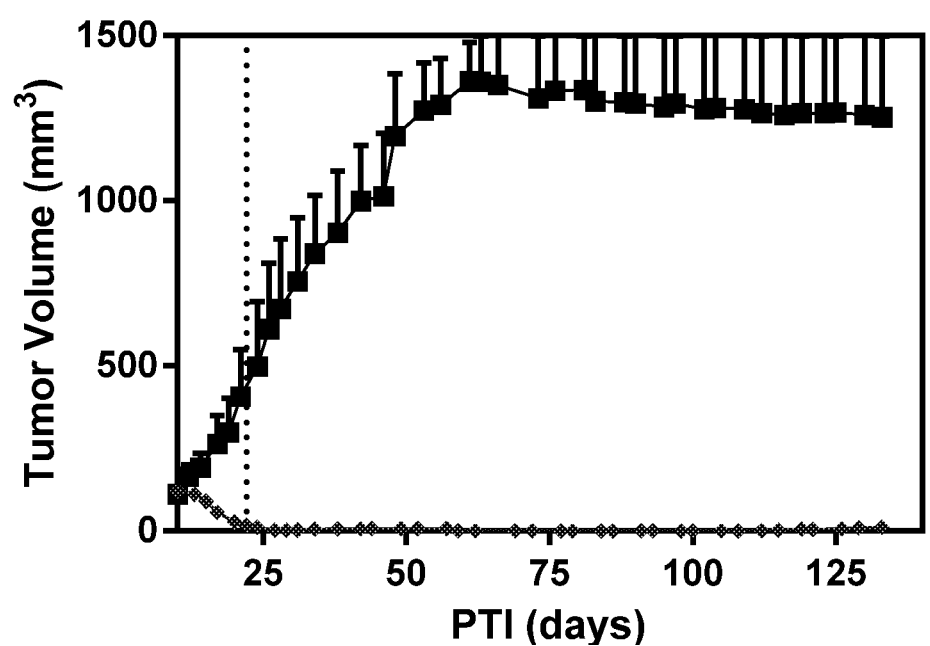
FIG. 5 shows that EC1744 (♦) dosed at 2 µmol/kg TIW for two weeks decreases MDA-MB-231 tumors in test animals compared to untreated control (■), and that EC1744 gave a complete response in 5/5 test animals, and cure in 4/5 test animals. The dotted line indicates the last dosing day.

EXAMPLE. EC1744 in vivo activity against tumors. As shown in FIG. 5, EC1744 (♦) dosed at 2 μmol/kg TIW for two weeks decreased triple negative breast cancer (TNBC) MDA-MB-231 tumors in test animals compared to untreated control (■). Moreover, EC1744 gave a complete response in 5/5 test animals, and cure in 4/5 test animals. Toxicity was not observed for EC1744, as evidenced by test animal total body weight.

METHOD. Human cisplatin-resistant cell line. A human cisplatin-resistant cell line was created by culturing FR-positive KB cells in the presence of increasing cisplatin concentrations (100→2000 nM; over a >12 month period). The cisplatin-resistant cells, labeled as KB-CR2000 cells, were found to be tumorigenic, and were found to retain their FR expression status in vivo. KB-CR2000 tumors were confirmed to be resistant to cisplatin therapy. Treatment with a high, toxic dose of cisplatin (average weight loss of 10.3%) did not produce even a single partial response (PR).

METHOD. Human serum stability. Conjugates described herein may be tested in human serum for stability using conventional protocols and methods. The test compound may be administered to the test animal, such as by subcutaneous injection. The plasma concentration of the conjugate, and optionally one or more metabolites, may be monitored over time. The results may be graphed to determine Cmax, Tmax, half-life, and AUC for the test compound and metabolites.

METHOD. Plasma clearance. In vivo studies include a minimum of 3 test animals, such as rats, per time point. Illustratively, female Lewis rats with jugular vein catheters (Harlan, regular rodent diet) may be given a single subcutaneous injection of test compound. Whole blood samples (300 µL) may collected at the following time points: 1 min, 10 min, 30 min, 1 h, 2 h, 3 h, 4 h, 8 h, and 12 h after injection. The blood samples may be placed into anti-coagulant tubes containing 1.7 mg/mL of $K_3$-EDTA and 0.35 mg/mL of N-maleoyl-beta-alanine (0.35 mg/mL) in a 0.15% acetic acid solution. Plasma samples may be obtained by centrifugation for 3 min at ~2,000 g and stored at −80° C. The amounts of test compound in the plasma and any metabolites were quantified by LC-MS/MS.

The invention claimed is:

1. A conjugate comprising a binding ligand, a linker and a drug, having the formula $B\text{-}(AA)_{z1}\text{-}L^2\text{-}(L^3)_{z2}\text{-}(AA)_{z3}\text{-}(L^1)_{z4}\text{-}(L^4)_{z5}\text{-}D^1\text{-}L^5\text{-}D^2$,
$B\text{-}(AA)_{z11}\text{-}L^2\text{-}D^1\text{-}L^5\text{-}D^1\text{-}L^2\text{-}(AA)_{z12}\text{-}B$ or
$B\text{-}L^1\text{-}AA\text{-}L^1\text{-}AA\text{-}L^1\text{-}L^2\text{-}(L^3)_{z6}\text{-}(L^4)_{z7}\text{-}(AA)_{z8}\text{-}(L^4)_{z9}\text{-}D^1\text{-}L^5\text{-}D^2$, wherein each $z1$, $z10$, $z11$ and $z12$ is each independently 2, 3, 4 or 5;
$z2$ is 0, 1 or 2;
$z3$ is 0, 1, 2, 3 or 4;
$z4$ is 0, 1 or 2; and
$z5$ is 0, 1 or 2
$z6$ is 0, 1 or 2;
$z7$ is 0, 1 or 2;
$z8$ is 0, 1, 2, 3 or 4;
$z9$ is 0, 1 or 2;
B is of the formula I

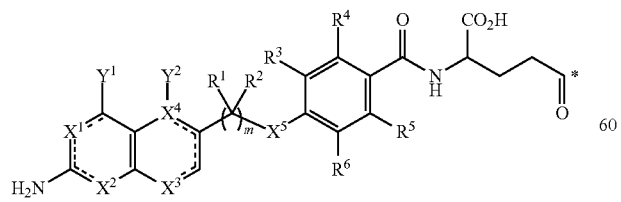

I wherein $R^1$ and $R^2$ in each instance are independently selected from the group consisting of H, deuterium, halogen, $C_1\text{-}C_6$ alkyl, $C_2\text{-}C_6$ alkenyl, $C_2\text{-}C_6$ alkynyl, —$OR^7$, —$SR^7$ and —$NR^7R^{7'}$, wherein each hydrogen atom in $C_1\text{-}C_6$ alkyl, $C_2\text{-}C_6$ alkenyl and $C_2\text{-}C_6$ alkynyl is independently optionally substituted by halogen, —$OR^8$, —$SR^8$, —$NR^8R^{8'}$, —$C(O)R^8$, —$C(O)OR^8$ or —$C(O)NR^8R^{8'}$;

$R^3$, $R^4$, $R^5$ and $R^6$ are each independently selected from the group consisting of H, deuterium, halogen, $C_1\text{-}C_6$ alkyl, $C_2\text{-}C_6$ alkenyl, $C_2\text{-}C_6$ alkynyl, —CN, —$NO_2$, —NCO, —$OR^9$, —$SR^9$, —$NR^9R^{9'}$, —$C(O)R^9$, —$C(O)OR^9$ and —$C(O)NR^9R^{9'}$, wherein each hydrogen atom in $C_1\text{-}C_6$ alkyl, $C_2\text{-}C_6$ alkenyl and $C_2\text{-}C_6$ alkynyl is independently optionally substituted by halogen, —$OR^{10}$, —$SR^{10}$, —$NR^{10}R^{10'}$, —$C(O)R^{10}$, —$C(O)OR^{10}$ or —$C(O)NR^{10}R^{10'}$;

each $R^7$, $R^{7'}$, $R^8$, $R^{8'}$, $R^9$, $R^{9'}$, $R^{10}$ and $R^{10'}$ is independently H, deuterium, $C_1\text{-}C_6$ alkyl, $C_2\text{-}C_6$ alkenyl or $C_2\text{-}C_6$ alkynyl;

$X^1$ is —$NR^{11}$—, =N—, —N=, —$C(R^{11})$= or =$C(R^{11})$—;

$X^2$ is —$NR^{11'}$— or =N—;

$X^3$ is —$NR^{11''}$—, —N= or —$C(R^{11'})$=;

$X^4$ is —N= or —C=;

$X^5$ is $NR^{12}$ or $CR^{12}R^{12'}$;

$Y^1$ is H, deuterium, —$OR^{13}$, —$SR^{13}$ or —$NR^{13}R^{13'}$ when $X^1$ is —N= or —$C(R^{11})$=, or $Y^1$ is =O when $X^1$ is —$NR^{11}$—, =N— or =$C(R^{11})$—;

$Y^2$ is H, deuterium, $C_1\text{-}C_6$ alkyl, $C_2\text{-}C_6$ alkenyl, —$C(O)R^{14}$, —$C(O)OR^{14}$, —$C(O)NR^{14}R^{14'}$ when $X^4$ is —C=, or $Y^2$ is absent when $X^4$ is —N=;

$R^{11}$, $R^{11'}R^{11''}$, $R^{12}$, $R^{12'}$, $R^{13}$, $R^{13'}$, $R^{14}$ and $R^{14'}$ are each independently selected from the group consisting of H, deuterium, $C_1\text{-}C_6$ alkyl, —$C(O)R^{15}$, —$C(O)OR^{15}$ and —$C(O)NR^{15}R^{15'}$;

$R^{15}$ and $R^{15'}$ are each independently H or $C_1\text{-}C_6$ alkyl;

m is 1, 2, 3 or 4;

AA is a naturally occurring amino acid or stereoisomer thereof;

$L^1$ is a linker of the formula II

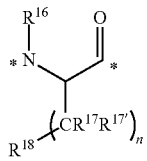

wherein $R^{16}$ is selected from the group consisting of H, deuterium, $C_1$-$C_6$ alkyl, $C_2$-$C_6$ alkenyl, $C_2$-$C_6$ alkynyl, —C(O)$R^{19}$, —C(O)O$R^{19}$ and —C(O)N$R^{19}R^{19'}$, wherein each hydrogen atom in $C_1$-$C_6$ alkyl, $C_2$-$C_6$ alkenyl and $C_2$-$C_6$ alkynyl is independently optionally substituted by halogen, $C_1$-$C_6$ alkyl, $C_2$-$C_6$ alkenyl, and $C_2$-$C_6$ alkynyl, —O$R^{20}$, —OC(O)$R^{20}$, —OC(O)N$R^{20}R^{20'}$, —OS(O)$R^{20}$, —OS(O)$_2R^{20}$, —S$R^{20}$, —S(O)$R^{20}$, —S(O)$_2R^{20}$, —S(O)N$R^{20}R^{20'}$, —S(O)$_2$N$R^{20}R^{20'}$, —OS(O)N$R^{20}R^{20'}$, —OS(O)$_2$N$R^{20}R^{20'}$, —N$R^{20}R^{20'}$, —N$R^{20}$C(O)$R^{21}$, —N$R^{20}$C(O)O$R^{21}$, —N$R^{20}$C(O)N$R^{21}R^{21'}$, —N$R^{20}$S(O)$R^{21}$, —N$R^{20}$S(O)$_2R^{21}$, —N$R^{20}$S(O)N$R^{21}R^{21'}$, —N$R^{20}$S(O)$_2$N$R^{21}R^{21'}$, —C(O)$R^{20}$, —C(O)O$R^{20}$ or —C(O)N$R^{20}R^{20'}$;

each $R^{17}$ and $R^{17'}$ is independently selected from the group consisting of H, deuterium, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{22}$, —OC(O)$R^{22}$, —OC(O)N$R^{22}R^{22'}$, —OS(O)$R^{22}$, —OS(O)$_2R^{22}$, —S$R^{22}$, —S(O)$R^{22}$, —S(O)$_2R^{22}$, —S(O)N$R^{22}R^{22'}$, —S(O)$_2$N$R^{22}R^{22'}$, —OS(O)N$R^{22}R^{22'}$, —OS(O)$_2$N$R^{22}R^{22'}$, —N$R^{22}R^{22'}$, —N$R^{22}$C(O)$R^{23}$, —N$R^{22}$C(O)O$R^{23}$, —N$R^{22}$C(O)N$R^{23}R^{23'}$, —N$R^{22}$S(O)$R^{23}$, —N$R^{22}$S(O)$_2R^{23}$, —N$R^{22}$S(O)N$R^{23}R^{23'}$, —N$R^{22}$S(O)$_2$N$R^{23}R^{23'}$, —C(O)$R^{22}$, —C(O)O$R^{22}$, and —C(O)N$R^{22}R^{22'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by halogen, $C_1$-$C_6$ alkyl, $C_2$-$C_6$ alkenyl, $C_2$-$C_6$ alkynyl, —O$R^{24}$, —OC(O)$R^{24}$, —OC(O)N$R^{24}R^{24'}$, —OS(O)$R^{24}$, —OS(O)$_2R^{24}$, —S$R^{24}$, —S(O)$R^{24}$, —S(O)$_2R^{24}$, —S(O)N$R^{24}R^{24'}$, —S(O)$_2$N$R^{24}R^{24'}$, —OS(O)N$R^{24}R^{24'}$, —OS(O)$_2$N$R^{24}R^{24'}$, —N$R^{24}R^{24'}$, —N$R^{24}$C(O)$R^{25}$, —N$R^{24}$C(O)O$R^{25}$, —N$R^{24}$C(O)N$R^{25}R^{25'}$, —N$R^{24}$S(O)$R^{25}$, —N$R^{24}$S(O)$_2R^{25}$, —N$R^{24}$S(O)N$R^{25}R^{25'}$, —N$R^{24}$S(O)$_2$N$R^{25}R^{25'}$, —C(O)$R^{24}$, —C(O)O$R^{24}$ or —C(O)N$R^{24}R^{24'}$; or $R^{17}$ and $R^{17'}$ may combine to form a $C_4$-$C_6$ cycloalkyl or a 4- to 6-membered heterocycle, wherein each hydrogen atom in $C_4$-$C_6$ cycloalkyl or 4- to 6-membered heterocycle is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{24}$, —OC(O)$R^{24}$, —OC(O)N$R^{24}R^{24'}$, —OS(O)$R^{24}$, —OS(O)$_2R^{24}$, —S$R^{24}$, —S(O)$R^{24}$, —S(O)$_2R^{24}$, —S(O)N$R^{24}R^{24'}$, —S(O)$_2$N$R^{24}R^{24'}$, —OS(O)N$R^{24}R^{24'}$, —OS(O)$_2$N$R^{24}R^{24'}$, —N$R^{24}R^{24'}$, —N$R^{24}$C(O)$R^{25}$, —N$R^{24}$C(O)O$R^{25}$, —N$R^{24}$C(O)N$R^{25}R^{25'}$, —N$R^{24}$S(O)$R^{25}$, —N$R^{24}$S(O)$_2R^{25}$, —N$R^{24}$S(O)N$R^{25}R^{25'}$, —N$R^{24}$S(O)$_2$N$R^{25}R^{25'}$, —C(O)$R^{24}$, —C(O)O$R^{24}$ or —C(O)N$R^{24}R^{24'}$;

$R^{18}$ is selected from the group consisting of H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —O$R^{26}$, —OC(O)$R^{26}$, —OC(O)N$R^{26}R^{26'}$, —OS(O)$R^{26}$, —OS(O)$_2R^{26}$, —S$R^{26}$, —S(O)$R^{26}$, —S(O)$_2R^{26}$, —S(O)N$R^{26}R^{26'}$, —S(O)$_2$N$R^{26}R^{26'}$, —OS(O)N$R^{26}R^{26'}$, —OS(O)$_2$N$R^{26}R^{26'}$, —N$R^{26}R^{26'}$, —N$R^{26}$C(O)$R^{27}$, —N$R^{26}$C(O)O$R^{27}$, —N$R^{26}$C(O)N$R^{27}R^{27'}$, —N$R^{26}$C(=N$R^{26''}$)N$R^{27}R^{27'}$, —N$R^{26}$S(O)$R^{27}$, —N$R^{26}$S(O)$_2R^{27}$, —N$R^{26}$S(O)N$R^{27}R^{27'}$, —N$R^{26}$S(O)$_2$N$R^{27}R^{27'}$, —C(O)$R^{26}$, —C(O)O$R^{26}$ and —C(O)N$R^{26}R^{26'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by halogen, $C_1$-$C_6$ alkyl, $C_2$-$C_6$ alkenyl, —(CH$_2$)$_p$O$R^{28}$, —(CH$_2$)$_p$(OCH$_2$)$_q$O$R^{28}$, —(CH$_2$)$_p$(OCH$_2$CH$_2$)$_q$O$R^{28}$, —O$R^{29}$, —OC(O)$R^{29}$, —OC(O)N$R^{29}R^{29'}$, —OS(O)$R^{29}$, —OS(O)$_2R^{29}$, —(CH$_2$)$_p$OS(O)$_2$O$R^{29}$, —OS(O)$_2$O$R^{29}$, —S$R^{29}$, —S(O)$R^{29}$, —S(O)$_2R^{29}$, —S(O)N$R^{29}R^{29'}$, —S(O)$_2$N$R^{29}R^{29'}$, —OS(O)N$R^{29}R^{29'}$, —OS(O)$_2$N$R^{29}R^{29'}$, —N$R^{29}R^{29'}$, —N$R^{29}$C(O)$R^{30}$, —N$R^{29}$C(O)O$R^{30}$, —N$R^{29}$C(O)N$R^{30}R^{30'}$, —N$R^{29}$S(O)$R^{30}$, —N$R^{29}$S(O)$_2R^{30}$, —N$R^{29}$S(O)N$R^{30}R^{30'}$, —N$R^{29}$S(O)$_2$N$R^{30}R^{30'}$, —C(O)$R^{29}$, —C(O)O$R^{29}$ or —C(O)N$R^{29}R^{29'}$;

each each $R^{19}$, $R^{19'}$, $R^{20}$, $R^{20'}$, $R^{21}$, $R^{21'}$, $R^{22}$, $R^{22'}$, $R^{23}$, $R^{23'}$, $R^{24}$, $R^{24'}$, $R^{25}$, $R^{25'}$, $R^{26}$, $R^{26'}$, $R^{26''}$, $R^{29}$, $R^{29'}$, $R^{30}$ and $R^{30'}$ is independently selected from the group consisting of H, deuterium, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, —OH, —SH, —NH$_2$ or —CO$_2$H;

$R^{27}$ and $R^{27'}$ are each independently selected from the group consisting of H, $C_1$-$C_9$ alkyl, $C_2$-$C_9$ alkenyl, $C_2$-$C_9$ alkynyl, $C_3$-$C_6$ cycloalkyl, —(CH$_2$)$_p$(sugar), —(CH$_2$)$_p$(OCH$_2$CH$_2$)$_q$—(sugar) and —(CH$_2$)$_p$(OCH$_2$CH$_2$CH$_2$)$_q$(sugar);

$R^{28}$ is a H, deuterium, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, 5- to 7-membered heteroaryl or sugar;

n is 1, 2, 3, 4 or 5;

p is 1, 2, 3, 4 or 5;

q is 1, 2, 3, 4 or 5;

$L^2$ is a releasable linker;

$L^3$ is selected from the group consisting of $C_1$-$C_6$ alkyl, —(C$R^{39}R^{39'}$)$_r$C(O)—, —(C$R^{39}R^{39'}$)$_r$OC(O)—, —N$R^{39}R^{39'}$C(O)(C$R^{39}R^{39'}$)$_r$—, —(CH$_2$)$_r$N$R^{39}$—, —(OC$R^{39}R^{39'}$C$R^{39}R^{39'}$)$_r$C(O), and —(OC$R^{39}R^{39'}$C$R^{39}R^{39'}$C$R^{39}R^{39'}$)—$_r$C(O)—, wherein each $R^{39}$ and $R^{39'}$ is independently selected from the group consisting of H, deuterium, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —OR$^{40}$, —OC(O)R$^{40}$, —OC(O)NR$^{40}$R$^{40'}$, —OS(O)R$^{40}$, —OS(O)$_2$R$^{40}$, —SR$^{40}$, —S(O)R$^{40}$, —S(O)$_2$R$^{40}$, —S(O)NR$^{40}$R$^{40'}$, —S(O)$_2$NR$^{40}$R$^{40'}$, —OS(O)NR$^{40}$R$^{40'}$, —OS(O)$_2$NR$^{40}$R$^{40'}$, —NR$^{40}$R$^{40'}$, —NR$^{40}$C(O)R$^{41}$, —NR$^{40}$C(O)OR$^{41}$, —NR$^{40}$C(O)NR$^{41}$R$^{41'}$, —NR$^{40}$S(O)R$^{41}$, —NR$^{40}$S(O)$_2$R$^{41}$, —NR$^{40}$S(O)NR$^{41}$R$^{41'}$, —NR$^{40}$S(O)$_2$NR$^{41}$R$^{41'}$, —C(O)R$^{40}$, —C(O)OR$^{40}$ and —C(O)NR$^{40}$R$^{40'}$;

$R^{40}$, $R^{40'}$, $R^{41}$ and $R^{41'}$ are each independently selected from the group consisting of H, deuterium, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl; and r in each instance is 1, 2, 3, 4, or 5;

$L^4$ is selected from the group consisting of —C(O)(CR$^{44}$R$^{44'}$)$_t$—, —NR$^{42}$CR$^{43}$R$^{43'}$CR$^{43}$R$^{43'}$(OCR$^{44}$R$^{44'}$CR$^{44}$R$^{44'}$)$_t$—, —NR$^{42}$CR$^{43}$R$^{43'}$CR$^{43}$R$^{43'}$(OCR$^{44}$R$^{44'}$CR$^{44}$R$^{44'}$)$_t$—, —NR$^{42}$CR$^{43}$R$^{43'}$CR$^{43}$R$^{43'}$ (OCR$^{44}$R$^{44'}$CR$^{44}$R$^{44'}$)$_t$C(O)—, —NR$^{42}$CR$^{43}$R$^{43'}$CR$^{43}$R$^{43'}$ (CR$^{44}$=CR$^{44'}$)$_t$—, and —NR$^{42}$C$_6$-$C_{10}$ aryl($C_1$-$C_6$ alkyl)OC(O)—;

wherein $R^{42}$ is selected from the group consisting of H, deuterium, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —OR$^{45}$, —OC(O)R$^{45}$, —OC(O)NR$^{45}$R$^{45'}$, —OS(O)R$^{45}$, —OS(O)$_2$R$^{45}$, —SR$^{45}$, —S(O)R$^{45}$, —S(O)$_2$R$^{45}$, —S(O)NR$^{45}$R$^{45'}$ —S(O)$_2$NR$^{45}$R$^{45'}$, —OS(O)NR$^{45}$R$^{45'}$, —OS(O)$_2$NR$^{45}$NR$^{45'}$, —NR$^{45}$R$^{45'}$, —NR$^{45}$C(O)R$^{46}$, —NR$^{45}$C(O)OR$^{46}$, —NR$^{45}$C(O)NR$^{46}$R$^{46'}$, —NR$^{45}$S(O)R$^{46}$, —NR$^{45}$S(O)$_2$R$^{46}$, —NR$^{45}$S(O)NR$^{46}$R$^{46''}$ —NR$^{45}$S(O)$_2$NR$^{46}$R$^{46'}$, —C(O)R$^{45}$, —C(O)OR$^{45}$ or —C(O)NR$^{45}$R$^{45'}$;

each $R^{43}$, $R^{43'}$, $R^{44}$ and $R^{44'}$ is independently selected from the group consisting of H, deuterium, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —OR$^{47}$, —OC(O)R$^{47}$, —OC(O)NR$^{47}$R$^{47'}$, —OS(O)R$^{47}$, —OS(O)$_2$R$^{47}$, —SR$^{47}$, —S(O)R$^{47}$, —S(O)$_2$R$^{47}$, —S(O)NR$^{47}$R$^{47'}$, —S(O)$_2$NR$^{47}$R$^{47'}$, —OS(O)NR$^{47}$R$^{47'}$, —OS(O)$_2$NR$^{47}$R$^{47'}$, —NR$^{47}$R$^{47'}$, —NR$^{47}$C(O)R$^{48}$, —NR$^{47}$C(O)OR$^{48}$, —NR$^{47}$C(O)NR$^{48}$R$^{48'}$, —NR$^{47}$S(O)R$^{48}$, —NR$^{47}$S(O)$_2$R$^{48}$, —NR$^{47}$S(O)NR$^{48}$R$^{48'}$, —NR$^{47}$S(O)$_2$NR$^{48}$R$^{48'}$, —C(O)R$^{47}$, —C(O)OR$^{47}$ or —C(O)NR$^{47}$R$^{47'}$;

$R^{45}$, $R^{45'}$, $R^{46}$, $R^{46'}$, $R^{47}$, $R^{47'}$, $R^{48}$ and $R^{48'}$ are each independently selected from the group consisting of H, deuterium, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl;

t is in each instance 1, 2, 3, 4, or 5;

$L^5$ is selected from the groups consisting of $C_1$-$C_{10}$ alkyl, —(CR$^{49}$=CR$^{49'}$)$_u$—, —(CR$^{49}$R$^{49'}$)$_u$C(O)—, —CH$_2$CH$_2$(OCR$^{49}$R$^{49'}$CR$^{49}$R$^{49'}$)$_u$—, —CH$_2$CH$_2$CH$_2$(OCR$^{49}$R$^{49'}$CR$^{49}$R$^{49'}$CR$^{49}$R$^{49'}$)$_u$—, —CH$_2$CH$_2$(OCR$^{49}$R$^{49'}$CR$^{49}$R$^{49'}$)$_u$C(O)— and —CH$_2$CH$_2$(OCR$^{49}$R$^{49'}$CR$^{49}$R$^{49'}$CR$^{49}$R$^{49'}$)$_u$C(O)—, wherein each $R^{49}$ and $R^{49'}$ is independently selected from the group consisting of H, deuterium, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —OR$^{50}$, —OC(O)R$^{50}$, —OC(O)NR$^{50}$R$^{50'}$, —OS(O)R$^{50}$, —OS(O)$_2$R$^{50}$, —SR$^{50}$, —S(O)R$^5$, —S(O)$_2$R$^{50}$, —S(O)NR$^{50}$R$^{50'}$, —S(O)$_2$NR$^{50}$R$^{50'}$, —OS(O)NR$^{50}$R$^{50'}$, —OS(O)$_2$NR$^{50}$R$^{50'}$, —NR$^{50}$R$^{50'}$, —NR$^{50}$C(O)R$^{51}$, —NR$^{50}$C(O)OR$^{51}$, —NR$^{50}$C(O)NR$^{51}$R$^{51'}$, —NR$^{50}$S(O)R$^{51}$, —NR$^{50}$S(O)$_2$R$^{51}$, —NR$^{50}$S(O)NR$^{51}$R$^{51'}$, —NR$^{50}$S(O)$_2$NR$^{51}$R$^{51'}$, —C(O)R$^{50}$, —C(O)OR$^{50}$ or —C(O)NR$^{50}$R$^{5'}$;

$R^{50}$, $R^{50'}$, $R^{51}$ and $R^{51'}$ are each independently selected from the group consisting of H, deuterium, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl;

u is in each instance 0, 1, 2, 3, 4 or 5;

$D^1$ is a PBD prodrug; and $D^2$ is a DNA binding agent;

or a pharmaceutically acceptable salt thereof.

2. The conjugate of claim 1, wherein $D^1$ is of the formula III

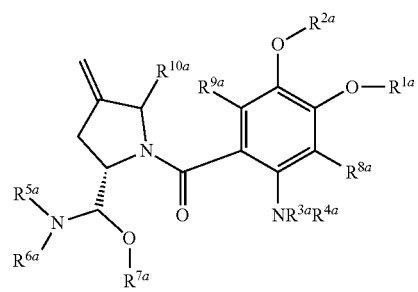

wherein $R^{1a}$, $R^{2a}$, $R^{3a}$ and $R^{4a}$ are each independently selected from the group consisting of H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —C(O)R$^{11a}$, —C(O)OR$^{11a}$, and —C(O)NR$^{11a}$R$^{11a'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —OR$^{11a}$, —OC(O)R$^{11a}$, —OC(O)NR$^{11a}$R$^{11a'}$, —OS(O)R$^{11a}$, —OS(O)$_2$R$^{11a}$, —SR$^{11a}$, —S(O)R$^{11a}$, —S(O)$_2$R$^{11a}$, —S(O)NR$^{11a}$R$^{11a'}$, —S(O)$_2$NR$^{11a}$R$^{11a'}$, —OS(O)NR$^{11a}$R$^{11a'}$, —OS(O)$_2$NR$^{11a}$R$^{11a'}$, —NR$^{11a}$R$^{11a'}$, —NR$^{11a}$C(O)R$^{12a}$, —NR$^{11a}$C(O)OR$^{12a}$, —NR$^{11a}$C(O)NR$^{12a}$R$^{12a'}$, —NR$^{11a}$S(O)R$^{12a}$, —NR$^{11a}$S(O)$_2$R$^{12a}$, —NR$^{11a}$S(O)NR$^{12a}$R$^{12a'}$, —NR$^{11a}$S(O)$_2$NR$^{12a}$R$^{12a'}$, —C(O)R$^{11a}$, —C(O)OR$^{11a}$ or —C(O)NR$^{11a}$R$^{11a'}$; or R$^{1a}$ is a bond; or R$^{4a}$ is a bond;

R$^{5a}$, R$^{6a}$ and R$^{7a}$ are each independently selected from the group consisting of H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —C(O)R$^{13a}$, —C(O)OR$^{13a}$ and —C(O)NR$^{13a}$R$^{13a'}$, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl is optionally substituted by C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{14a}$, —OC(O)R$^{14a}$, —OC(O)NR$^{14a}$R$^{14a'}$, —OS(O)R$^{14a}$, —OS(O)$_2$R$^{14a}$, —SR$^{14a}$, —S(O)R$^{14a}$, —S(O)$_2$R$^{14a}$, —S(O)NR$^{14a}$R$^{14a'}$, —S(O)$_2$NR$^{14a}$R$^{14a'}$, —OS(O)NR$^{14a}$R$^{14a'}$, —OS(O)$_2$NR$^{14a}$R$^{14a'}$, —NR$^{14a}$R$^{14a'}$, —NR$^{14a}$C(O)R$^{15a}$, —NR$^{14a}$C(O)OR$^{15a}$, —NR$^{14a}$C(O)NR$^{15a}$R$^{15a'}$, —NR$^{14a}$S(O)R$^{15a}$, —NR$^{14a}$S(O)$_2$R$^{15a}$, —NR$^{14a}$S(O)NR$^{15a}$R$^{15a'}$, —NR$^{14a}$S(O)$_2$NR$^{15a}$R$^{15a'}$, —C(O)R$^{14a}$, —C(O)OR$^{14a}$ or —C(O)NR$^{14a}$R$^{14a'}$; wherein R$^{6a}$ and R$^{7a}$ taken together with the atoms to which they are attached optionally combine to form a 3- to 7-membered heterocycloalkyl, or R$^{5a}$ and R$^{6a}$ taken together with the atoms to which they are attached optionally combine to form a 3- to 7-membered heterocycloalkyl or 5- to 7-membered heteroaryl, wherein each hydrogen atom in 3- to 7-membered heterocycloalkyl or 5- to 7-membered heteroaryl is independently optionally substituted by C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{16a}$, —OC(O)R$^{16a}$, —OC(O)NR$^{16a}$R$^{16a'}$, —OS(O)R$^{16a}$, —OS(O)$_2$R$^{16a}$, —SR$^{16a}$, —S(O)R$^{16a}$, —S(O)$_2$R$^{16a}$, —S(O)NR$^{16a}$R$^{16a'}$, —S(O)$_2$NR$^{16a}$R$^{16a'}$, —OS(O)NR$^{16a}$R$^{16a'}$, —OS(O)$_2$NR$^{16a}$R$^{16a'}$, —NR$^{16a}$R$^{16a'}$, —NR$^{16a}$C(O)R$^{17a}$, —NR$^{16a}$C(O)CH$_2$CH$_2$—, —NR$^{16a}$C(O)OR$^{17a}$, —NR$^{16a}$C(O)NR$^{17a}$R$^{17a'}$, —NR$^{16a}$S(O)R$^{17a}$, —NR$^{16a}$S(O)$_2$R$^{17a}$, —NR$^{16a}$S(O)NR$^{17a}$R$^{17a'}$, —NR$^{16a}$S(O)$_2$NR$^{17a}$R$^{17a'}$, —C(O)R$^{16a}$, —C(O)OR$^{16a}$ or —C(O)NR$^{16a}$R$^{16a'}$, and wherein one hydrogen atom in 5- to 7-membered heteroaryl is optionally a bond, or R$^{5a}$ is a bond;

R$^{8a}$ and R$^{9a}$ are each independently selected from the group consisting of H, deuterium, halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —CN, —NO$_2$, —NCO, —OR$^{18a}$, —OC(O)R$^{18a}$, —OC(O)NR$^{18a}$R$^{18a'}$, —OS(O)R$^{18a}$, —OS(O)$_2$R$^{18a}$, —SR$^{18a}$, —S(O)R$^{18a}$, —S(O)$_2$R$^{18a}$, —S(O)NR$^{18a}$R$^{18a'}$, —S(O)$_2$NR$^{18a}$R$^{18a'}$, —OS(O)NR$^{18a}$R$^{18a'}$, —OS(O)$_2$NR$^{18a}$R$^{18a'}$, —NR$^{18a}$R$^{18a'}$, —NR$^{18a}$C(O)R$^{19a}$, —NR$^{18a}$C(O)OR$^{19a}$, —NR$^{18a}$C(O)NR$^{19a}$R$^{19a'}$, —NR$^{18a}$S(O)R$^{19a}$, —NR$^{18a}$S(O)$_2$R$^{19a}$, —NR$^{18a}$S(O)NR$^{19a}$R$^{19a'}$, —NR$^{18a}$S(O)$_2$NR$^{19a}$R$^{19a'}$, —C(O)R$^{18a}$, —C(O)OR$^{18a}$ and —C(O)NR$^{18a}$R$^{18a'}$, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl is independently optionally substituted by C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{20a}$, —OC(O)R$^{20a}$, —OC(O)NR$^{20a}$R$^{20a'}$, —OS(O)R$^{20a}$, —OS(O)$_2$R$^{20a}$, —SR$^{20a}$, —S(O)R$^{20a}$, —S(O)$_2$R$^{20a}$, —S(O)NR$^{20a}$R$^{20a'}$, —S(O)$_2$NR$^{20a}$R$^{20a'}$, —OS(O)NR$^{20a}$R$^{20a'}$, —OS(O)$_2$NR$^{20a}$R$^{20a'}$, —NR$^{20a}$R$^{20a'}$, —NR$^{20a}$C(O)R$^{21a}$, —NR$^{20a}$C(O)OR$^{21a}$, —NR$^{20a}$C(O)NR$^{21a}$R$^{21a'}$, —NR$^{20a}$S(O)R$^{21a}$, —NR$^{20a}$S(O)$_2$R$^{21a}$, —NR$^{20a}$S(O)NR$^{21a}$R$^{21a'}$, —NR$^{20a}$S(O)$_2$NR$^{21a}$R$^{21a'}$, —C(O)R$^{20a}$, —C(O)OR$^{20a}$ or —C(O)NR$^{20a}$R$^{20a'}$;

R$^{10a}$ is selected from the group consisting of H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{22a}$, —OC(O)R$^{22a}$, —OC(O)NR$^{22a}$R$^{22a'}$, —OS(O)R$^{22a}$, —OS(O)$_2$R$^{22a}$, —SR$^{22a}$, —S(O)R$^{22a}$, —S(O)$_2$R$^{22a}$, —S(O)NR$^{22a}$R$^{22a'}$, —S(O)$_2$NR$^{22a}$R$^{22a'}$, —OS(O)NR$^{22a}$R$^{22a'}$, —OS(O)$_2$NR$^{22a}$R$^{22a'}$, —NR$^{22a}$R$^{22a'}$, —NR$^{22a}$C(O)R$^{23a}$, —NR$^{22a}$C(O)OR$^{23a}$, —NR$^{22a}$C(O)NR$^{23a}$R$^{23a'}$, —NR$^{22a}$S(O)R$^{23a}$, —NR$^{22a}$S(O)$_2$R$^{23a}$, —NR$^{22a}$S(O)NR$^{23a}$R$^{23a'}$, —NR$^{22a}$S(O)$_2$NR$^{23a}$R$^{23a'}$, —C(O)R$^{22a}$, —C(O)OR$^{23a}$ and —C(O)NR$^{22a}$R$^{22a'}$, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl is independently optionally substituted by C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{24a}$, —OC(O)R$^{24a}$, —OC(O)NR$^{24a}$R$^{24a'}$, —OS(O)R$^{24a}$, —OS(O)$_2$R$^{24a}$, —SR$^{24a}$, —S(O)R$^{24a}$, —S(O)$_2$R$^{24a}$, —S(O)NR$^{24a}$R$^{24a'}$, —S(O)$_2$NR$^{24a}$R$^{24a'}$, —OS(O)NR$^{24a}$R$^{24a'}$, —OS(O)$_2$NR$^{24a}$R$^{24a'}$, —NR$^{24a}$R$^{24a'}$, —NR$^{24a}$C(O)R$^{25a}$, —NR$^{24a}$C(O)OR$^{25a}$, —NR$^{24a}$C(O)NR$^{25a}$R$^{25a'}$, —NR$^{24a}$S(O)R$^{25a}$, —NR$^{24a}$S(O)$_2$R$^{25a}$, —NR$^{24a}$S(O)NR$^{25a}$R$^{25a'}$, —NR$^{24a}$S(O)$_2$NR$^{25a}$R$^{25a'}$, —C(O)R$^{24a}$, —C(O)OR$^{24a}$ or —C(O)NR$^{24a}$R$^{24a'}$; and each R$^{11a}$, R$^{11a'}$, R$^{12a}$, R$^{12a'}$, R$^{13a}$, R$^{13a'}$, R$^{14a}$, R$^{14a'}$, R$^{15a}$, R$^{15a'}$, R$^{16a}$, R$^{16a'}$, R$^{17a}$, R$^{17a'}$, R$^{18a}$, R$^{18a'}$, R$^{19a}$, R$^{19a'}$, R$^{20a}$, R$^{20a'}$, R$^{21a}$, R$^{21a'}$, R$^{22a}$, R$^{22a'}$, R$^{23a}$, R$^{23a'}$, R$^{24a}$, R$^{24a'}$, R$^{25a}$ and R$^{25a'}$ is independently selected from the group consisting of H, deuterium, C$_1$-C$_7$ alkyl, C$_2$-C$_7$ alkenyl, C$_2$-C$_7$ alkynyl, C$_3$-C$_{13}$ cycloalkyl, 3- to 7-membered heterocycloalkyl, C$_6$-C$_{10}$ aryl, and 5- to 7-membered heteroaryl;

provided that at least two of R$^{1a}$, R$^{4a}$ and R$^{5a}$ are a bond, or when R$^{5a}$ and R$^{6a}$ taken together with the atoms to which they are attached optionally combine to form a 3- to 7-membered heterocycloalkyl or 5- to 7-membered heteroaryl, one hydrogen atom in 5- to 7-membered heteroaryl is a bond and one of R$^{1a}$ or R$^{4a}$ is a bond; or a pharmaceutically acceptable salt thereof.

3. The conjugate of claim 1, wherein D$^2$ is a minor groove binding drug; or a pharmaceutically acceptable salt thereof.

4. The conjugate of claim 1, wherein D$^2$ is of the formula selected from the group consisting of

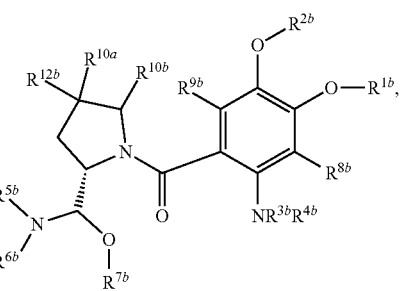

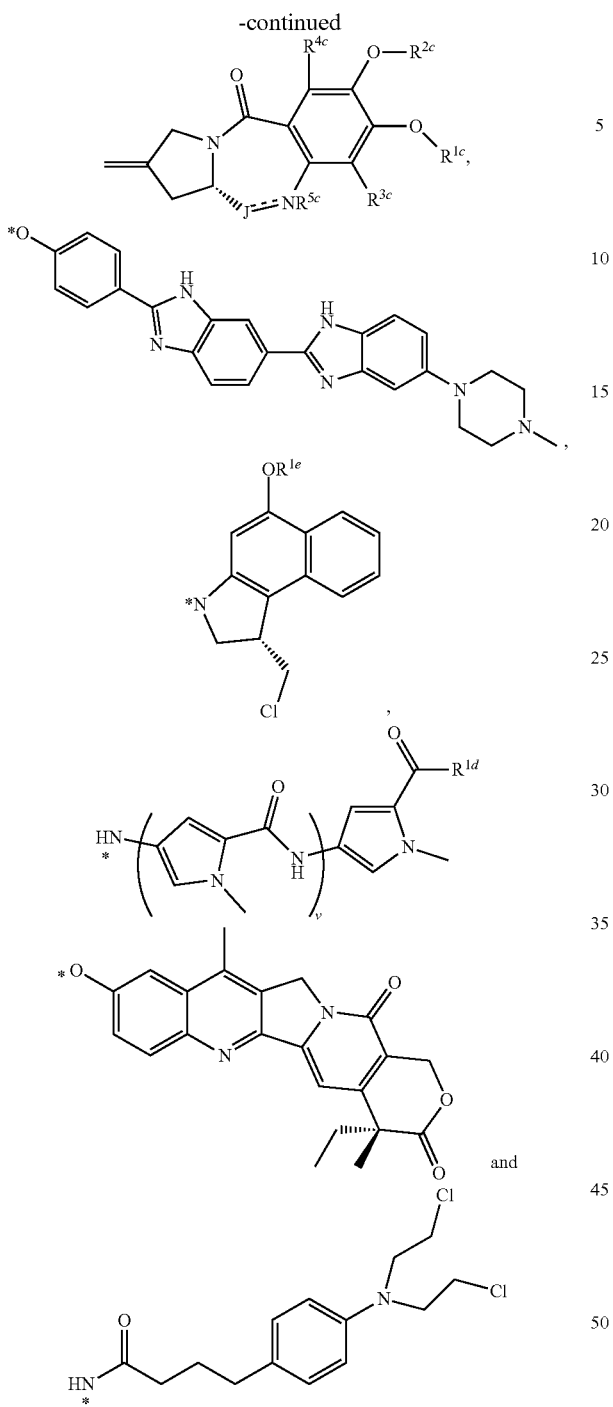

wherein

R$^{1b}$, R$^{2b}$, R$^{3b}$ and R$^{4b}$ are each independently selected from the group consisting of H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —C(O)R$^{13b}$, —C(O)OR$^{13b}$ and —C(O)NR$^{13b}$R$^{13b'}$, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl is independently optionally substituted by C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{13b}$, —OC(O)R$^{13b}$, —OC(O)NR$^{13b}$R$^{13b'}$, —OS(O)R$^{13b}$, —OS(O)$_2$R$^{13b}$, —SR$^{13b}$, —S(O)R$^{13b}$, —S(O)$_2$R$^{13b}$, —S(O)NR$^{13b}$R$^{13b'}$, —S(O)$_2$NR$^{13b}$R$^{13b'}$, —OS(O)NR$^{13b}$R$^{13b'}$, —OS(O)$_2$NR$^{13b}$R$^{13b'}$, —NR$^{13b}$R$^{13b'}$, —NR$^{13b}$C(O)R$^{14b}$, —NR$^{13b}$C(O)OR$^{14b}$, —NR$^{13b}$C(O)NR$^{14b}$R$^{14b'}$, —NR$^{13b}$S(O)R$^{14b}$, —NR$^{13b}$S(O)$_2$R$^{14b}$, —NR$^{13b}$S(O)NR$^{14b}$R$^{14b'}$, —NR$^{13b}$S(O)$_2$NR$^{14b}$R$^{14b'}$, —C(O)R$^{13b}$, —C(O)OR$^{13b}$ or —C(O)NR$^{13b}$R$^{13b'}$; or any one of R$^{1b}$, R$^{2b}$, R$^{3b}$ and R$^{4b}$ is a bond;

R$^{5b}$, R$^{6b}$ and R$^{7b}$ are each independently selected from the group consisting of H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —C(O)R$^{15b}$, —C(O)OR$^{15b}$ and —C(O)NR$^{15b}$R$^{15b'}$, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl is independently optionally substituted by C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, -L$^4$H, -L$^3$H, —OR$^{15b}$, —OC(O)R$^{15b}$, —OC(O)NR$^{15b}$R$^{15b'}$, —OS(O)R$^{15b}$, —OS(O)$_2$R$^{15b}$, —SR$^{15b}$, —S(O)R$^{15b}$, —S(O)$_2$R$^{15b}$, —S(O)NR$^{15b}$R$^{15b'}$, —S(O)$_2$NR$^{15b}$R$^{15b'}$, —OS(O)NR$^{15b}$R$^{15b'}$, —OS(O)$_2$NR$^{15b}$R$^{15b'}$, —NR$^{15b}$R$^{15b'}$, —NR$^{15b}$C(O)R$^{16b}$, —NR$^{15b}$C(O)OR$^{16b}$, —NR$^{15b}$C(O)NR$^{16b}$R$^{16b'}$, —NR$^{15b}$S(O)R$^{16b}$, —NR$^{15b}$S(O)$_2$R$^{16b}$, —NR$^{15b}$S(O)NR$^{16b}$R$^{16b'}$, —NR$^{15b}$S(O)$_2$NR$^{16b}$R$^{16b'}$, —C(O)R$^{15b}$, —C(O)OR$^{15b}$ or —C(O)NR$^{15b}$R$^{15b'}$; wherein R$^{6b}$ and R$^{7b}$ taken together with the atoms to which they are attached optionally combine to form a 3- to 7-membered heterocycloalkyl, or R$^{5b}$ and R$^{6b}$ taken together with the atoms to which they are attached optionally combine to form a 3- to 7-membered heterocycloalkyl or 5- to 7-membered heteroaryl, wherein each hydrogen atom in 3- to 7-membered heterocycloalkyl and 5- to 7-membered heteroaryl is independently optionally substituted by C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{17b}$, —OC(O)R$^{17b}$, —OC(O)NR$^{17b}$R$^{17b'}$, —OS(O)R$^{17b}$, —OS(O)$_2$R$^{17b}$, —SR$^{17b}$, —S(O)R$^{17b}$, —S(O)$_2$R$^{17b}$, —S(O)NR$^{17b}$R$^{17b'}$, —S(O)$_2$NR$^{17b}$R$^{17b'}$, —OS(O)NR$^{17b}$R$^{17b'}$, —OS(O)$_2$NR$^{17b}$R$^{17b'}$, —NR$^{17b}$R$^{17b'}$, —NR$^{17b}$C(O)R$^{18b}$, —NR$^{17b}$C(O)OR$^{18b}$, —NR$^{17b}$C(O)NR$^{18b}$R$^{18b'}$, —NR$^{17b}$S(O)R$^{18b}$, —NR$^{17b}$S(O)$_2$R$^{18b}$, —NR$^{17b}$S(O)NR$^{18b}$R$^{18b'}$, —NR$^{17b}$S(O)$_2$NR$^{18b}$R$^{18b'}$, —C(O)R$^{17b}$, —C(O)OR$^{17b}$ or —C(O)NR$^{17b}$R$^{17b'}$; or any one of R$^{5b}$, R$^{6b}$ or R$^{7b}$ is a bond;

R$^{8b}$ and R$^{9b}$ are each independently selected from the group consisting of H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —CN, —NO$_2$, —NCO, —OR$^{19b}$, —OC(O)R$^{19b}$, —OC(O)NR$^{19b}$R$^{19b'}$, —OS(O)R$^{19b}$, —OS(O)$_2$R$^{19b}$, —SR$^{19b}$, —S(O)R$^{19b}$, —S(O)$_2$R$^{19b}$, —S(O)NR$^{19b}$R$^{19b'}$, —S(O)$_2$NR$^{19b}$R$^{19b'}$, —OS(O)NR$^{19b}$R$^{19b'}$, —OS(O)$_2$NR$^{19b}$R$^{19b'}$, —NR$^{19b}$R$^{19b'}$, —NR$^{19b}$C(O)R$^{20b}$, —NR$^{19b}$C(O)OR$^{20b}$, —NR$^{19b}$C(O)NR$^{20b}$R$^{20b'}$, —NR$^{19b}$S(O)R$^{20b}$, —NR$^{19b}$S(O)$_2$R$^{20b}$, —NR$^{19b}$S(O)NR$^{20b}$R$^{20b'}$, —NR$^{19b}$S(O)$_2$NR$^{20b}$R$^{20b'}$, —C(O)R$^{19b}$, —C(O)OR$^{19b}$ and —C(O)NR$^{19b}$R$^{19b'}$, wherein each hydrogen atom in C$_1$-C$_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{21b}$, —$OC(O)R^{21b}$, —$OC(O)NR^{21b}R^{21b'}$, —$OS(O)R^{21b}$, —$OS(O)_2R^{21b}$, —$SR^{21b}$, —$S(O)R^{21b}$, —$S(O)_2R^{21b}$, —$S(O)NR^{21b}R^{21b'}$, —$S(O)_2NR^{21b}R^{21b'}$, —$OS(O)NR^{21b}R^{21b'}$, —$OS(O)_2NR^{21b}R^{21b'}$, —$NR^{21b}R^{21b'}$, —$NR^{21b}C(O)R^{22b}$, —$NR^{21b}C(O)OR^{22b}$, —$NR^{21b}C(O)NR^{22b}R^{22b'}$, —$NR^{21b}S(O)R^{22b}$, —$NR^{21b}S(O)_2R^{22b}$, —$NR^{21b}S(O)NR^{22b}R^{22b'}$, —$NR^{21b}S(O)_2NR^{22b}R^{22b'}$, —$C(O)R^{21b}$, —$C(O)OR^{21b}$ or —$C(O)NR^{21b}R^{21b'}$;

$R^{10b}$, $R^{11b}$ and $R^{12b}$ are each independently selected from the group consisting of H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{23b}$, —$OC(O)R^{23b}$, —$OC(O)NR^{23b}R^{23b'}$, —$OS(O)R^{23b}$, —$OS(O)_2R^{23b}$, —$SR^{23b}$, —$S(O)R^{23b}$, —$S(O)_2R^{23b}$, —$S(O)NR^{23b}R^{23b'}$, —$S(O)_2NR^{23b}R^{23b'}$, —$OS(O)NR^{23b}R^{23b'}$, —$OS(O)_2NR^{23b}R^{23b'}$, —$NR^{23b}R^{23b'}$, —$NR^{23b}C(O)R^{24b}$, —$NR^{23b}C(O)NR^{24b}R^{24b'}$, —$NR^{23b}C(O)OR^{24b}$, —$NR^{23b}S(O)R^{24b}$, —$NR^{23b}S(O)_2R^{24b}$, —$NR^{23b}S(O)NR^{24b}R^{24b'}$, $NR^{23b}S(O)_2NR^{24b}R^{24b'}$, —$C(O)R^{23b}$, —$C(O)OR^{23b}$ and —$C(O)NR^{23b}R^{23b'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{25b}$, —$OC(O)R^{25b}$, —$OC(O)NR^{25b}R^{25b'}$, —$OS(O)R^{25b}$, —$OS(O)_2R^{25b}$, —$SR^{25b}$, —$S(O)R^{25b}$, —$S(O)_2R^{25b}$, —$S(O)NR^{25b}R^{25b'}$, —$S(O)_2NR^{25b}R^{25b'}$, —$OS(O)NR^{25b}R^{25b'}$, —$OS(O)_2NR^{25b}R^{25b'}$, —$NR^{25b}R^{25b'}$, —$NR^{25b}C(O)R^{26b}$, —$NR^{25b}C(O)OR^{26b}$, —$NR^{25b}C(O)NR^{26b}R^{26b'}$, —$NR^{25b}S(O)R^{26b}$, —$NR^{25b}S(O)_2R^{26b}$, —$NR^{25b}S(O)NR^{26b}R^{26b'}$, —$NR^{25b}S(O)_2NR^{26b}R^{26b'}$, —$C(O)R^{25b}$, —$C(O)OR^{25b}$ or —$C(O)NR^{25b}R^{25b'}$, or $R^{10b}$ and $R^{11b}$ taken together with the carbon atoms to which they are attached optionally combine to form a $C_6$-$C_{10}$ aryl, or $R^{11b}$ and $R^{12b}$ taken together with the carbon atom to which they are attached optionally combine to form an exo-methylene; or $R^{12b}$ is absent;

each $R^{13b}$, $R^{13b'}$, $R^{14b}$, $R^{14b'}$, $R^{15b}$, $R^{15b'}$, $R^{16b}$, $R^{16b'}$, $R^{17b}$, $R^{17b'}$, $R^{18b}$, $R^{18b'}$, $R^{19b}$, $R^{19b'}$, $R^{20b}$, $R^{20b'}$, $R^{21b}$, $R^{21b'}$, $R^{22b}$, $R^{22b'}$, $R^{23b}$, $R^{23b'}$, $R^{24b}$, $R^{24b'}$, $R^{25b}$, $R^{25b'}$, $R^{26b}$ and $R^{26b'}$ is independently selected from the group consisting of H, deuterium, $C_1$-$C_7$ alkyl, $C_2$-$C_7$ alkenyl, $C_2$-$C_7$ alkynyl, $C_3$-$C_{13}$ cycloalkyl, 3- to 7-membered heterocycloalkyl, $C_6$-$C_{10}$ aryl, $C_1$-$C_6$ alkyl($C_6$-$C_{10}$ aryl) and 5- to 7-membered heteroaryl, wherein each hydrogen atom in $C_6$-$C_{10}$ aryl, $C_1$-$C_6$ alkyl($C_6$-$C_{10}$ aryl) and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —CN, —$NO_2$, —NCO, —OH, —SH, —$NH_2$, —$SO_3H$, —C(O)OH and —$C(O)NH_2$;

provided that one of $R^{1b}$, $R^{2b}$, $R^{3b}$, $R^{4b}$, $R^{5b}$, $R^{6b}$ and $R^{7b}$ is a bond;

$R^{1c}$, $R^{2c}$ and $R^{5c}$ are each independently selected from the group consisting of H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$C(O)R^{6c}$, —$C(O)OR^{6c}$ and —$C(O)NR^{6c}R^{6c'}$, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{7c}$, —$OC(O)R^{7c}$, —$OC(O)NR^{7c}R^{7c'}$, —$OS(O)R^{7c}$, —$OS(O)_2R^{7c}$, —$SR^{7c}$, —$S(O)R^{7c}$, —$S(O)_2R^{7c}$, —$S(O)_2OR^{7c}$, —$S(O)NR^{7c}R^{7c'}$, —$S(O)_2NR^{7c}R^{7c'}$, —$OS(O)NR^{7c}R^{7c'}$, —$OS(O)_2NR^{7c}R^{7c'}$, —$NR^{7c}R^{7c'}$, —$NR^{7c}C(O)R^{8c}$, —$NR^{7c}C(O)OR^{8c}$, —$NR^{7c}CC(O)NR^{8c}R^{8c'}$, —$NR^{7c}S(O)R^{8c}$, —$NR^{7c}S(O)_2R^{8c}$, —$NR^{7c}S(O)NR^{8c}R^{8c'}$, —$NR^{7c}S(O)_2NR^{8c}R^{8c'}$, —$C(O)R^{7c}$, —$C(O)OR^{7c}$ or —$C(O)NR^{7c}R^{7c'}$; or when J is —$CR^{13c}$=, $R^{5c}$ is absent; provided that one of $R^{1c}$ or $R^{2c}$ is a bond;

$R^{3c}$ and $R^{4c}$ are each independently selected from the group consisting of H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —CN, —$NO_2$, —NCO, —$OR^{9c}$, —$OC(O)R^{9c}$, —$OC(O)NR^{9c}R^{9c'}$, —$OS(O)R^{9c}$, —$OS(O)_2R^{9c}$, —$SR^{9c}$, —$S(O)R^{9c}$, —$S(O)_2R^{9c}$, —$S(O)NR^{9c}R^{9c'}$, —$S(O)_2NR^{9c}R^{9c'}$, —$OS(O)NR^{9c}CR^{9c'}$, —$OS(O)_2NR^9CR^{9c'}$, —$NR^9CR^{9c'}$, —$NR^{9c}C(O)Roc$, —$NR^{9c}C(O)OR^{10c}$, —$NR^{9c}C(O)NR^{10c}R^{10c'}$, —$NR^{9c}S(O)R^{10c}$, —$NR^{9c}S(O)_2R^{10c}$, —$NR^{9c}S(O)NR^{10c}R^{10c'}$, —$NR^{9c}S(O)_2NR^{10c}R^{10c'}$, —$C(O)R^{9c}$, —$C(O)OR^{9c}$ and —$C(O)NR^{9c}R^{9c'}$ wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is independently optionally substituted by $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{11c}$, —$OC(O)R^{11c}$, —$OC(O)NR^{11c}R^{11c'}$, —$OS(O)R^{11c}$, —$OS(O)_2R^{11c}$, —$SR^{11}$, —$S(O)R^{11c}$, —$S(O)_2R^{11c}$, —$S(O)NR^{11c}R^{11c'}$, —$S(O)_2NR^{11c}R^{11c'}$, —$OS(O)NR^{11c}R^{11c'}$, —$OS(O)_2NR^{11c}R^{11c'}$, —$NR^{11c}R^{11c'}$, —$NR^{11c}C(O)R^{12c}$, —$NR^{11c}C(O)OR^{12c}$, —$NR^{11c}C(O)NR^{12c}R^{12c'}$, —$NR^{11c}S(O)R^{12c}$, —$NR^{11}S(O)_2R^{12c}$, —$NR^{11c}S(O)NR^{12c}R^{12c'}$, —$NR^{11}CS(O)_2NR^{12c}R^{12c'}$, —$C(O)R^{11c}$, —$C(O)OR^{11c}$ or —$C(O)NR^{11c}R^{11c'}$;

J is —C(O)—, —$CR^{13c}$= or —($CR^{13c}R^{13c'}$)— each $R^{6c}$, $R^{6c'}$, $R^{7c}$, $R^{7c'}$, $R^{8c}$, $R^{8c'}$, $R^{9c}$, $R^{9c'}$, $R^{10c}$, $R^{10c'}$, $R^{11c}$, $R^{11c'}$, $R^{12c}$, $R^{12c'}$, $R^{13c}$ and $R^{13c'}$ is independently selected from the group consisting of H, deuterium, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl;

$R^{1d}$ is selected from the group consisting of H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{2d}$, —$SR^{2d}$ and —$NR^{2d}R^{2d'}$;

$R^{2d}$ and $R^{2d'}$ are each independently selected from the group consisting of H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl is optionally substituted by —OR$^{3d}$, —SR$^{3d}$, and —NR$^{3d}$R$^{3d'}$;

R$^{3d}$ and R$^{3d'}$ are each independently selected from the group consisting of H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl;

R$^{1e}$ is selected from the group consisting of H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl is independently optionally substituted by C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{2e}$, —OC(O)R$^{2e}$, —OC(O)NR$^{2e}$R$^{2e'}$, —OS(O)R$^{2e}$, —OS(O)$_2$R$^{2e}$, —SR$^{2e}$, —S(O)R$^{2e}$, —S(O)$_2$R$^{2e}$, —S(O)NR$^{2e}$R$^{2e'}$, —S(O)$_2$NR$^{2e}$R$^{2e'}$, —OS(O)NR$^{2e}$R$^{2e'}$, —OS(O)$_2$NR$^{2e}$R$^{2e'}$, —NR$^{2e}$R$^{2e'}$, —NR$^{2e}$C(O)R$^{3e}$, —NR$^{2e}$C(O)OR$^{3e}$, —NR$^{2e}$C(O)NR$^{3e}$R$^{3e'}$, —NR$^{2e}$S(O)R$^{3e}$, —NR$^{2e}$S(O)$_2$R$^{3e}$, —NR$^{2e}$S(O)NR$^{2e}$R$^{2e'}$, —NR$^{2e}$S(O)$_2$NR$^{3e}$R$^{3e'}$, —C(O)R$^{2e}$, —C(O)OR$^{2e}$ or —C(O)NR$^{2e}$R$^{2e}$;

each R$^{2e}$, R$^{2e'}$, R$^{3e}$ and R$^{3e'}$ is independently selected from the group consisting of H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl, wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl is optionally substituted by —OR$^{4e}$, —SR$^{4e}$ or —NR$^{4e}$R$^{4e'}$;

R$^{4e}$ and R$^{4e'}$ are independently selected from the group consisting of H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl and 5- to 7-membered heteroaryl;

v is 1, 2 or 3; and

* is a covalent bond;

or a pharmaceutically acceptable salt thereof.

5. The conjugate of claim 1, wherein each AA is independently selected from the group consisting of L-lysine, L-asparagine, L-threonine, L-serine, L-isoleucine, L-methionine, L-proline, L-histidine, L-glutamine, L-arginine, L-glycine, L-aspartic acid, L-glutamic acid, L-alanine, L-valine, L-phenylalanine, L-leucine, L-tyrosine, L-cysteine, L-tryptophan, L-phosphoserine, L-sulfo-cysteine, L-arginosuccinic acid, L-hydroxyproline, L-phosphoethanolamine, L-sarcosine, L-taurine, L-carnosine, L-citrulline, L-anserine, L-1,3-methyl-histidine, L-alpha-amino-adipic acid, D-lysine, D-asparagine, D-threonine, D-serine, D-isoleucine, D-methionine, D-proline, D-histidine, D-glutamine, D-arginine, D-glycine, D-aspartic acid, D-glutamic acid, D-alanine, D-valine, D-phenylalanine, D-leucine, D-tyrosine, D-cysteine, D-tryptophan, D-citrulline and D-carnosine, or a pharmaceutically acceptable salt thereof.

6. The conjugate of claim 1, wherein each L$^1$ is selected from the group consisting of

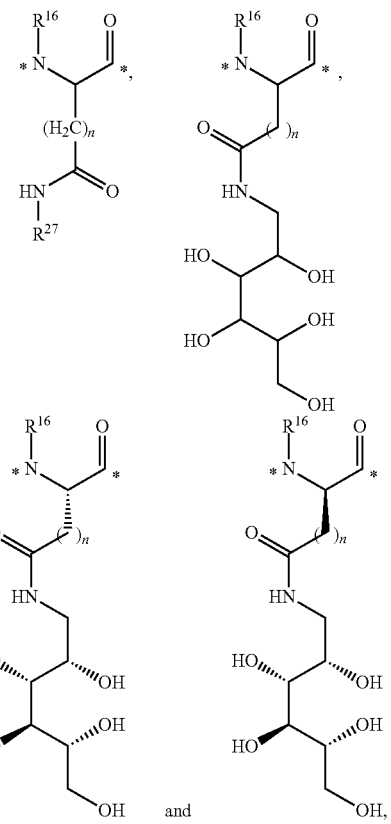

wherein R$^{16}$ is H, and * is a covalent bond; or a pharmaceutically acceptable salt thereof.

7. The conjugate of claim 1, wherein R$^1$ and R$^2$ in each instance are H; R$^3$, R$^4$, R$^5$ and R$^6$ are H; X$^1$ is —NR$^{11}$—; X$^2$ is =N—; X$^3$ is —N=; X$^4$ is —N=; X$^5$ is NR$^{12}$; Y$^1$ is is =O; Y$^2$ is absent; R$^{11}$ and R$^{12}$ are H; m is 1, 2, 3 or 4; and * is a covalent bond; or a pharmaceutically acceptable salt thereof.

8. The conjugate of claim 1, having the formula

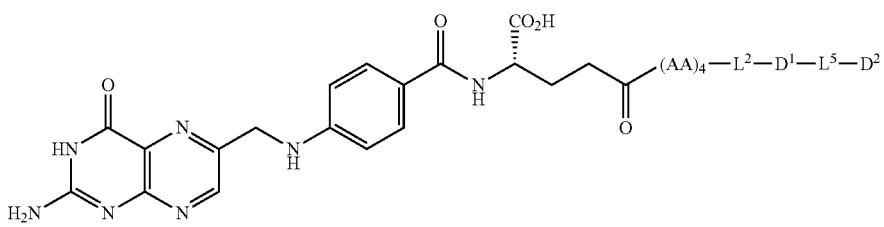

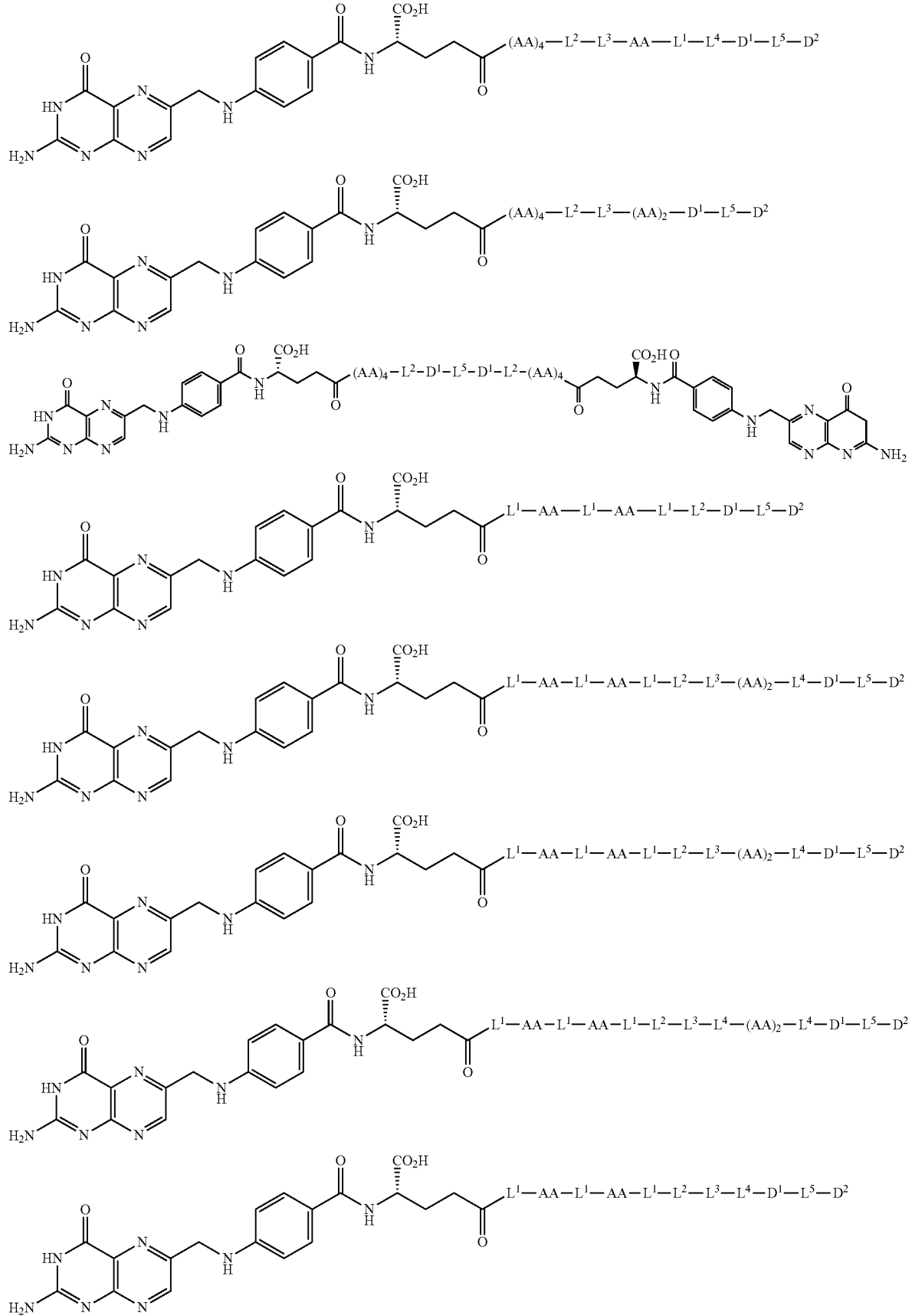

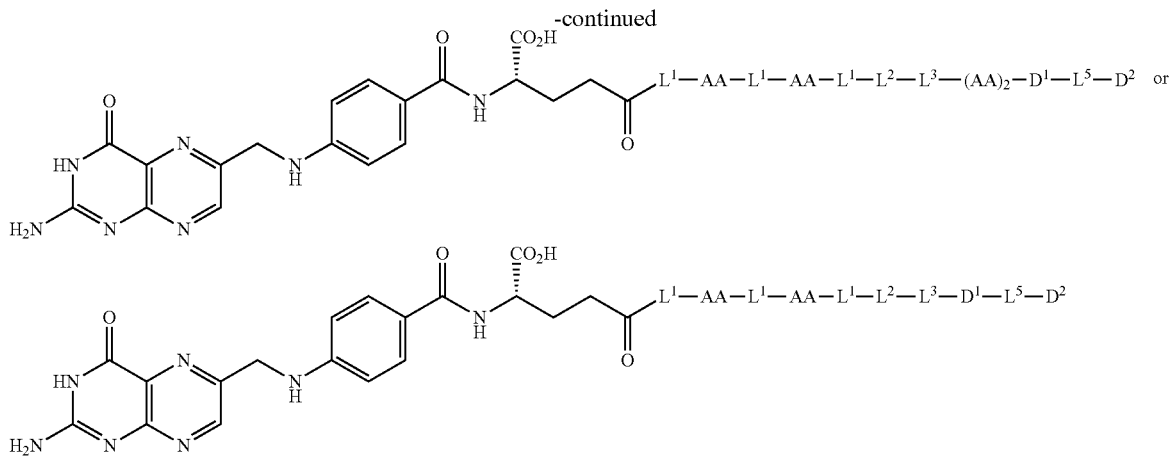

or a pharmaceutically acceptable salt thereof.

9. The conjugate of claim 1, wherein the sequence of -(AA)$_4$- is -Asp-Arg-Asp-Asp- (SEQ ID NO: 5); or a pharmaceutically acceptable salt thereof.

10. The conjugate of claim 1, wherein the sequence of -(AA)$_2$- is Val-CIT; or a pharmaceutically acceptable salt thereof.

11. The conjugate of claim 1, wherein L$^2$ is selected from the group consisting of

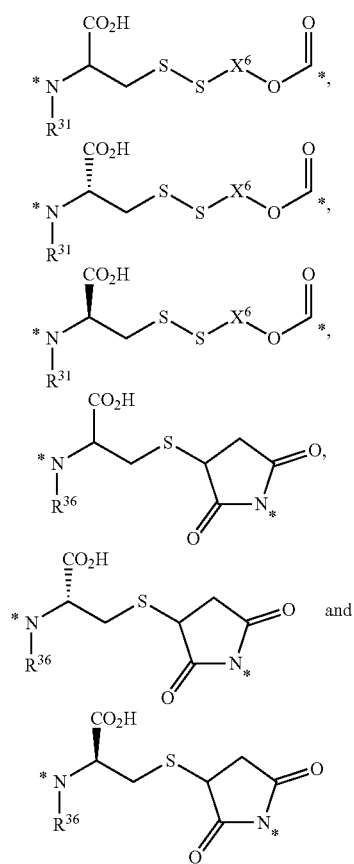

wherein
R$^{31}$ is selected from the group consisting of H, deuterium, C$_1$-C$_6$ alkyl, C$_2$-C$_6$ alkenyl, C$_2$-C$_6$ alkynyl and C$_3$-C$_6$ cycloalkyl, wherein each hydrogen atom in C$_1$-C$_6$ alkyl, C$_2$-C$_6$ alkenyl, C$_2$-C$_6$ alkynyl and C$_3$-C$_6$ cycloalkyl is independently optionally substituted by halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{32}$, —OC(O)R$^{32}$, —OC(O)NR$^{32}$R$^{32'}$, —OS(O)R$^{32}$, —OS(O)$_2$R$^{32}$, —SR$^{32}$, —S(O)R$^{32}$, —S(O)$_2$R$^{32}$, —S(O)NR$^{32}$R$^{32'}$, —S(O)$_2$NR$^{32}$R$^{32'}$, —OS(O)NR$^{32}$R$^{32'}$, —OS(O)$_2$NR$^{32}$R$^{32'}$, —NR$^{32}$R$^{32'}$, —NR$^{32}$C(O)R$^{33}$, —NR$^{32}$C(O)OR$^{33}$, —NR$^{32}$C(O)NR$^{33}$R$^{33'}$, —NR$^{32}$S(O)R$^{33}$, —NR$^{32}$S(O)$_2$R$^{33}$, —NR$^{32}$S(O)NR$^{33}$R$^{33'}$, —NR$^{32}$S(O)$_2$NR$^{33}$R$^{33'}$, —C(O)R$^{32}$, —C(O)OR$^{32}$ or —C(O)NR$^{32}$R$^{32'}$;

X$^6$ is C$_1$-C$_6$ alkyl or C$_6$-C$_{10}$ aryl(C$_1$-C$_6$ alkyl), wherein each hydrogen atom in C$_1$-C$_6$ alkyl and C$_6$-C$_{10}$ aryl (C$_1$-C$_6$ alkyl) is independently optionally substituted by halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{34}$, —OC(O)R$^{34}$, —OC(O)NR$^{34}$R$^{34'}$, —OS(O)R$^{34}$, —OS(O)$_2$R$^{34}$, —SR$^{34}$, —S(O)R$^{34}$, —S(O)$_2$R$^{34}$, —S(O)NR$^{34}$R$^{34'}$, —S(O)$_2$NR$^{34}$R$^{34'}$, —OS(O)NR$^{34}$R$^{34'}$, —OS(O)$_2$NR$^{34}$R$^{34'}$, —NR$^{34}$R$^{34'}$, —NR$^{34}$C(O)R$^{35}$, —NR$^{34}$C(O)OR$^{35}$, —NR$^{34}$C(O)NR$^{35}$R$^{35'}$, —NR$^{34}$S(O)R$^{35}$, —NR$^{34}$S(O)$_2$R$^{35}$, —NR$^{34}$S(O)NR$^{35}$R$^{35'}$, —NR$^{34}$S(O)$_2$NR$^{35}$R$^{35'}$, —C(O)R$^{34}$, —C(O)OR$^{34}$ or —C(O)NR$^{34}$R$^{34'}$;

each R$^{32}$, R$^{32'}$, R$^{33}$, R$^{33'}$, R$^{34}$, R$^{34'}$, R$^{35}$ and R$^{35'}$ are independently selected from the group consisting of H, deuterium, C$_1$-C$_7$ alkyl, C$_2$-C$_7$ alkenyl, C$_2$-C$_7$ alkynyl, C$_3$-C$_6$ cycloalkyl, 3- to 7-membered heterocycloalkyl, C$_6$-C$_{10}$ aryl, and 5- to 7-membered heteroaryl;

R$^{36}$ is independently selected from the group consisting of H, deuterium, C$_1$-C$_6$ alkyl, C$_2$-C$_6$ alkenyl, C$_2$-C$_6$ alkynyl and C$_3$-C$_6$ cycloalkyl, wherein each hydrogen atom in C$_1$-C$_6$ alkyl, C$_2$-C$_6$ alkenyl, C$_2$-C$_6$ alkynyl and C$_3$-C$_6$ cycloalkyl is independently optionally substituted by halogen, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, 5- to 7-membered heteroaryl, —OR$^{37}$, —OC(O)R$^{37}$, —OC(O)NR$^{37}$R$^{37'}$, —OS(O)R$^{37}$, —OS(O)$_2$R$^{37}$, —SR$^{37}$, —S(O)R$^{37}$, —S(O)$_2$R$^{37}$, —S(O)NR$^{37}$R$^{37'}$, —S(O)$_2$NR$^{37}$R$^{37'}$, —OS(O)NR$^{37}$R$^{37'}$, —OS(O)$_2$NR$^{37}$R$^{37'}$, —NR$^{37}$R$^{37'}$, —NR$^{37}$C(O)R$^{38}$, —NR$^{37}$C(O)OR$^{38}$, —NR$^{37}$C(O)NR$^{38}$R$^{38'}$, —NR$^{37}$S(O)R$^{38}$, —NR$^{37}$S(O)$_2$R$^{38}$, —NR$^{37}$S(O)NR$^{38}$R$^{38'}$, —NR³⁷S(O)₂NR³⁸R³⁸', —C(O)R³⁷, —C(O)OR³⁷ or —C(O)NR³⁷R³⁷';

R³⁷, R³⁷', R³⁸ and R³⁸' are each independently selected from the group consisting of H, deuterium, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl; and

* is a covalent bond;

or a pharmaceutically acceptable salt thereof.

12. The conjugate of claim 1, wherein the linker is of the formula

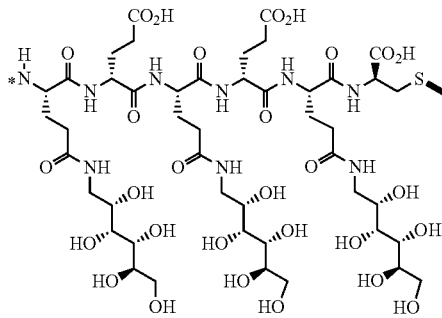
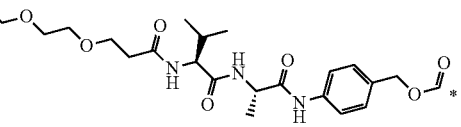

(SEQ ID NO 1 is included in the structure above),

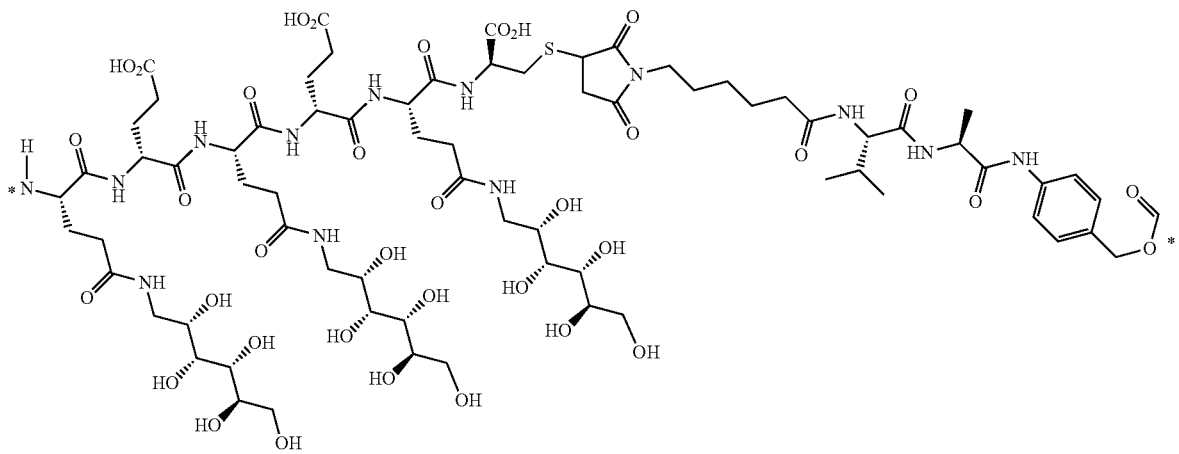 [SMILES: CC(C)[C@H](NC(=O)CCCCCN1C(=O)CC(SC[C@@H](NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)[C@@H](CCC(=O)O)NC(=O)[C@@H](N)CCC(=O)NC[C@H](O)[C@@H](O)[C@H](O)[C@H](O)CO)C(=O)O)C1=O)C(=O)N[C@@H](C)C(=O)Nc1ccc(COC=O)cc1]

(SEQ ID NO 1 is included in the structure above),

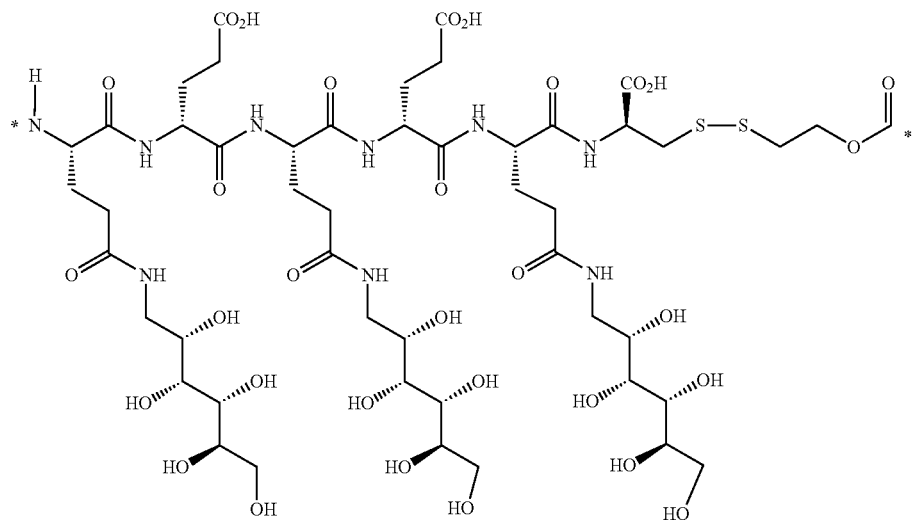 [SMILES: N[C@@H](CCC(=O)NC[C@H](O)[C@@H](O)[C@H](O)[C@H](O)CO)C(=O)N[C@H](CCC(=O)O)C(=O)N[C@@H](CCC(=O)NC[C@H](O)[C@@H](O)[C@H](O)[C@H](O)CO)C(=O)N[C@H](CCC(=O)O)C(=O)N[C@@H](CCC(=O)NC[C@H](O)[C@@H](O)[C@H](O)[C@H](O)CO)C(=O)N[C@H](CSSCCOC=O)C(=O)O]

(SEQ ID NO 1 is included in the structure above),

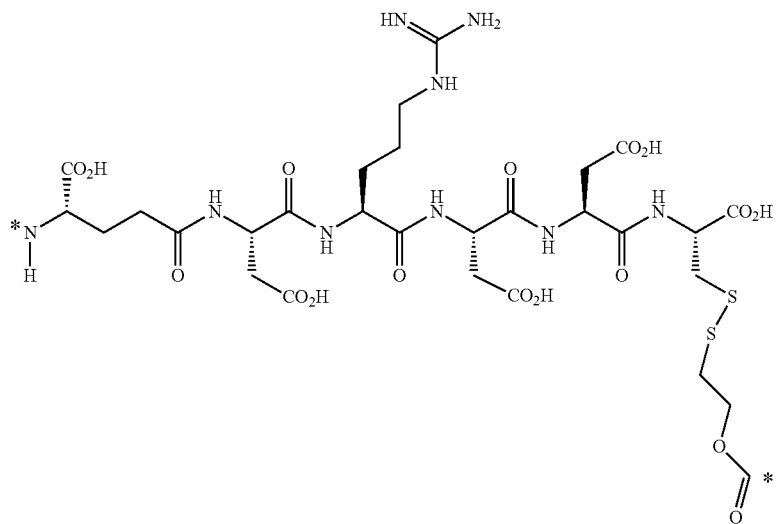 [SMILES: N=C(N)NCCC[C@H](NC(=O)[C@H](CC(=O)O)NC(=O)CC[C@H](N)C(=O)O)C(=O)N[C@@H](CC(=O)O)C(=O)N[C@@H](CC(=O)O)C(=O)N[C@@H](CSSCCOC=O)C(=O)O]
(SEQ ID NO 2 is included in the structure above), or
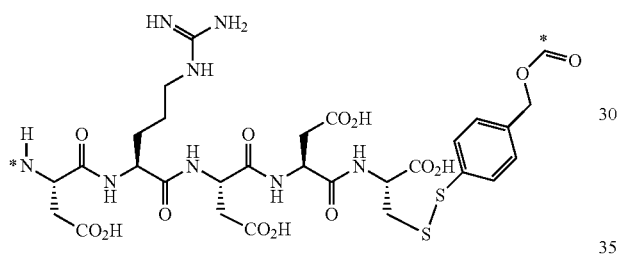
(SEQ ID NO 2 is included in the structure above),
wherein * is a bond; or a pharmaceutically acceptable salt thereof.
13. The conjugate of claim 1, wherein the linker is of the formula
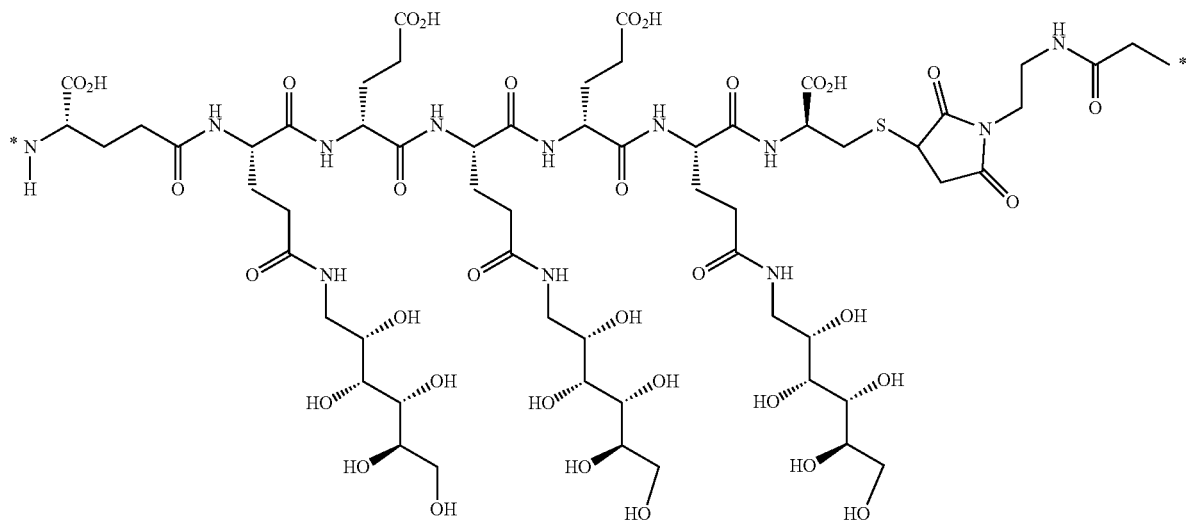 [SMILES: CCC(=O)NCCN1C(=O)CC(SC[C@@H](NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)[C@@H](CCC(=O)O)NC(=O)[C@H](CCC(=O)NC[C@H](O)[C@@H](O)[C@H](O)[C@H](O)CO)NC(=O)CC[C@H](N)C(=O)O)C(=O)O)C1=O]
(SEQ ID NO 1 is included in the structure above),

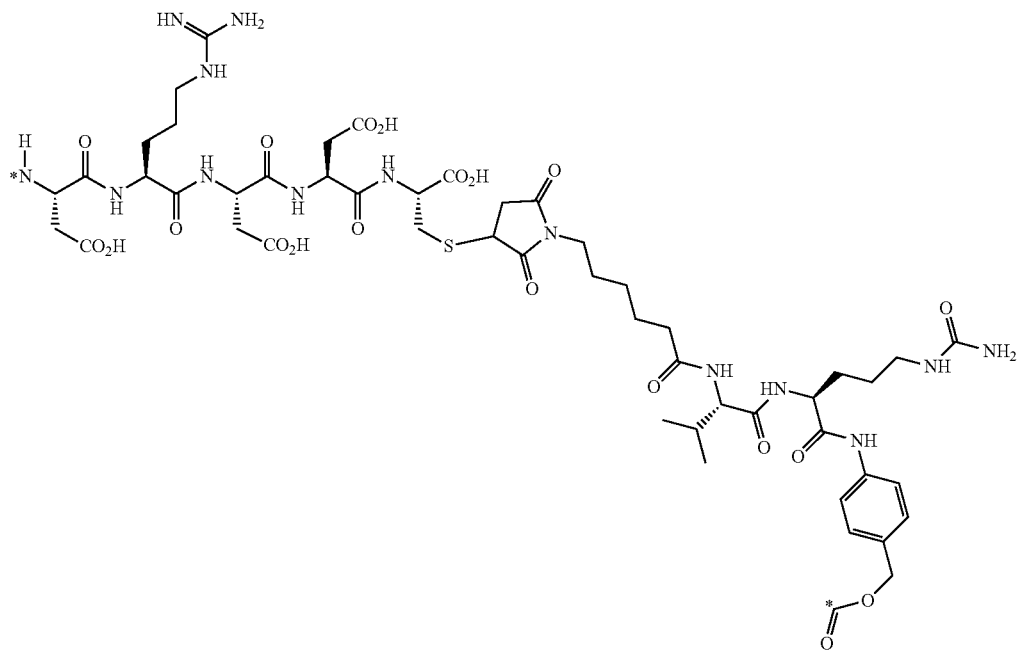 [SMILES: CC(C)[C@H](NC(=O)CCCCCN1C(=O)CC(SC[C@H](NC(=O)[C@H](CC(=O)O)NC(=O)[C@H](CC(=O)O)NC(=O)[C@H](CCCNC(=N)N)NC(=O)[C@@H](N)CC(=O)O)C(=O)O)C1=O)C(=O)N[C@@H](CCCNC(N)=O)C(=O)Nc1ccc(COC=O)cc1]
(SEQ ID NO 2 is included in the structure above),
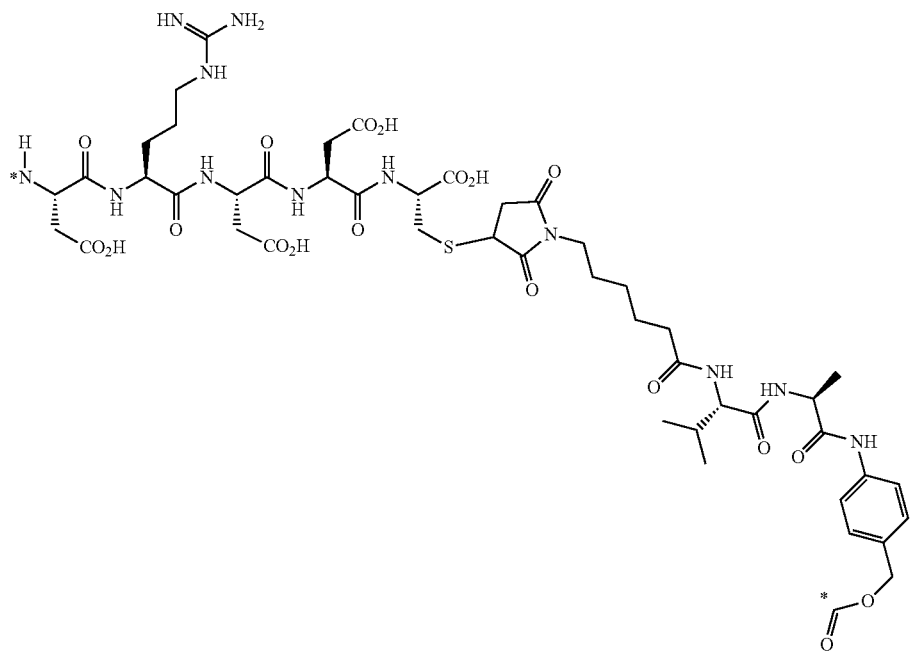 [SMILES: CC(C)[C@H](NC(=O)CCCCCN1C(=O)CC(SC[C@H](NC(=O)[C@H](CC(=O)O)NC(=O)[C@H](CC(=O)O)NC(=O)[C@H](CCCNC(=N)N)NC(=O)[C@@H](N)CC(=O)O)C(=O)O)C1=O)C(=O)N[C@@H](C)C(=O)Nc1ccc(COC=O)cc1]

(SEQ ID NO 2 is included in the structure above), or

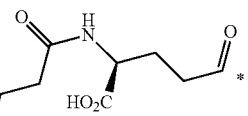
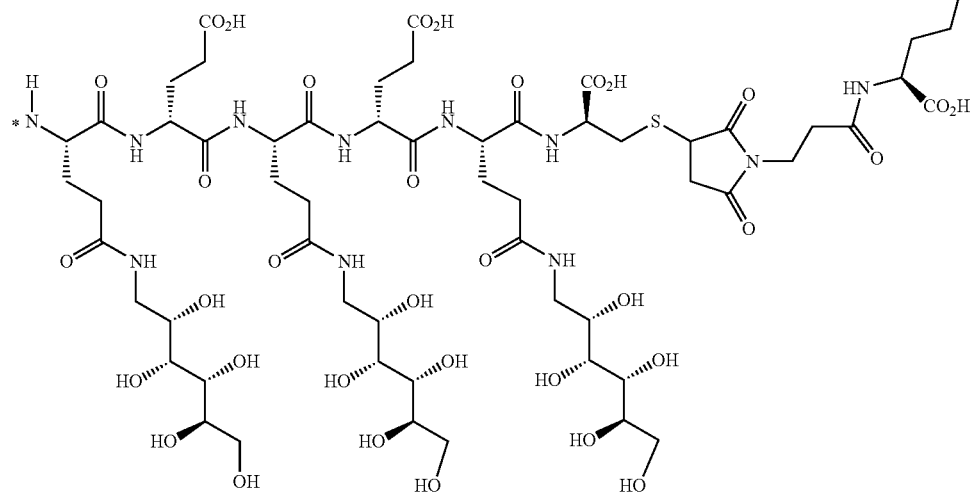

(SEQ ID NO 1 is included in the structure above),
wherein * is a bond; or a pharmaceutically acceptable salt thereof.

14. The conjugate of claim 1, wherein -$D^1$-$L^5$-$D^2$ is of the formula

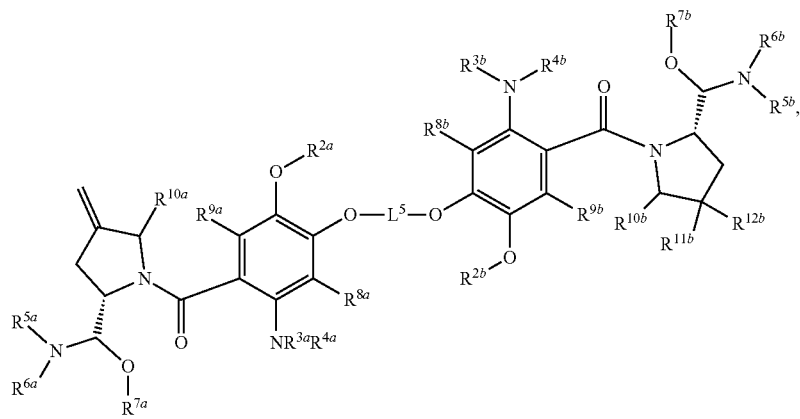

wherein $R^{3a}$, $R^{4a}$, $R^{8a}$, $R^{9a}$, $R^{10a}$, $R^{3b}$, $R^{4b}$, $R^{8b}$ and $R^{9b}$ are H; or a pharmaceutically acceptable salt thereof.

15. The conjugate of any of claim 14, wherein $L^5$ is $C_1$-$C_{10}$ alkyl or —$(CR^{49}R^{49'})_uC(O)$—, each $R^{49}$ and $R^{49'}$ is H, and u is 1, 2, 3, or 4; or a pharmaceutically acceptable salt thereof.

16. The conjugate of claim 1, wherein -$D^1$-$L^5$-$D^2$ is of the formula

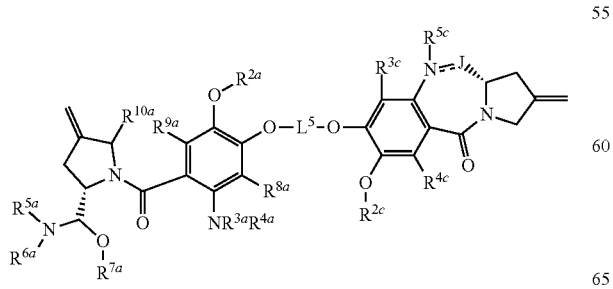

wherein $R^{3a}$, $R^{4a}$, $R^{8a}$, $R^{9a}$, $R^{10a}$, $R^{3c}$, $R^{4c}$, $R^5$ are H; or a pharmaceutically acceptable salt thereof.

17. The conjugate of any of claim 16, wherein, $L^5$ is $C_1$-$C_{10}$ alkyl or —$(CR^{49}R^{49'})_uC(O)$—, wherein each $R^{49}$ and $R^{49'}$ is H, and u is 1, 2, 3, 4 or 5; or a pharmaceutically acceptable salt thereof.

18. The conjugate of claim 1, wherein -$D^1$-$L^5$-$D^2$ is of the formula

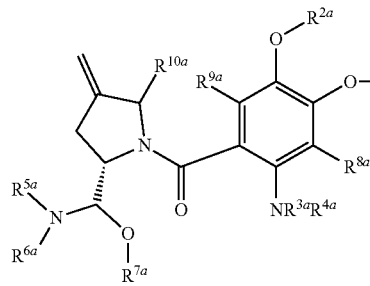

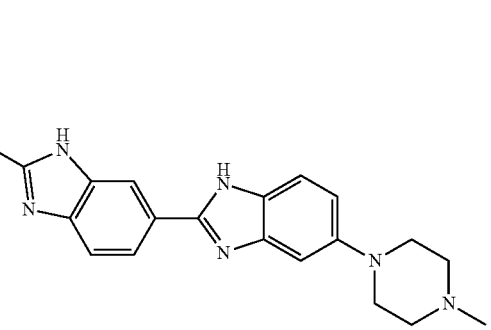

wherein, $R^{3a}$, $R^{4a}$, $R^{8a}$, $R^{9a}$ and $R^{10a}$ are H; or a pharmaceutically acceptable salt thereof.

19. The conjugate of claim 18, wherein $L^5$ is $C_1$-$C_{10}$ alkyl or —$(CR^{49}R^{49'})_uC(O)$—, wherein each $R^{49}$ and $R^{49'}$ is H, and u is 1, 2, 3, 4 or 5; or a pharmaceutically acceptable salt thereof.

20. The conjugate of claim 1, wherein -$D^1$-$L^5$-$D^2$ is of the formula

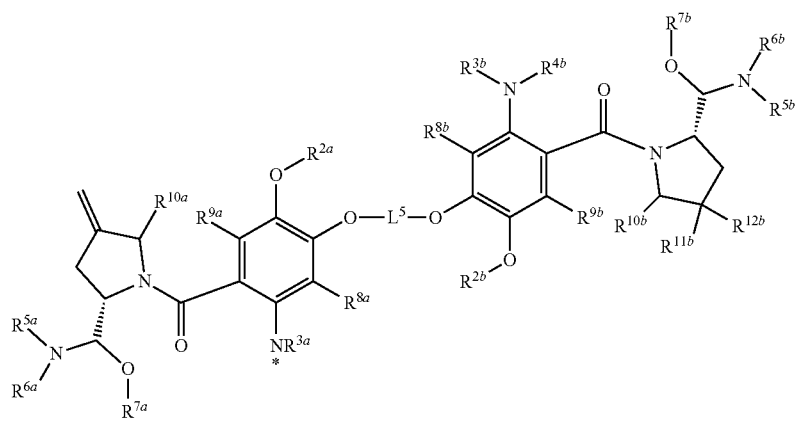

wherein $R^{3a}$, $R^{8a}$, $R^{9a}$, $R^{10a}$, $R^{3b}$, $R^{4b}$, $R^{8b}$, $R^{9b}$, $R^{10b}$, $R^{11b}$ and $R^{12b}$ are H; or a pharmaceutically acceptable salt thereof.

21. The conjugate of claim 20, wherein $L^5$ is $C_1$-$C_{10}$ alkyl or —$(CR^{49}R^{49'})_uC(O)$—, wherein each $R^{49}$ and $R^{49'}$ is H, and u is 1, 2, 3, 4 or 5; or a pharmaceutically acceptable salt thereof.

22. A pharmaceutical composition comprising a therapeutically effective amount of a conjugate according to claim 1, or a pharmaceutically acceptable salt thereof, and at least one excipient.

23. A method of treating abnormal cell growth in a mammal, including a human, the method comprising administering to the mammal a conjugate of claim 1.

24. The method of claim 23, wherein the abnormal cell growth is cancer.

25. The method of claim 24, wherein the cancer is lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers.

* * * * *